(12) United States Patent
Gonzalez et al.

(10) Patent No.: US 8,268,835 B2
(45) Date of Patent: *Sep. 18, 2012

(54) INHIBITORS OF HEPATITIS C VIRUS RNA-DEPENDENT RNA POLYMERASE, AND COMPOSITIONS AND TREATMENTS USING THE SAME

(75) Inventors: Javier Gonzalez, Oceanside, CA (US); Tanya Michelle Jewell, Encinitas, CA (US); Hui Li, Carslbad, CA (US); Angelica Linton, San Diego, CA (US); John Howard Tatlock, San Diego, CA (US)

(73) Assignee: Pfizer Inc., New York, NY (US)

( * ) Notice: Subject to any disclaimer, the term of this patent is extended or adjusted under 35 U.S.C. 154(b) by 266 days.

This patent is subject to a terminal disclaimer.

(21) Appl. No.: 12/503,286

(22) Filed: Jul. 15, 2009

(65) Prior Publication Data

US 2009/0281122 A1 Nov. 12, 2009

Related U.S. Application Data

(63) Continuation of application No. 11/470,540, filed on Sep. 6, 2006, now Pat. No. 7,622,605, which is a continuation of application No. 11/204,269, filed on Aug. 15, 2005, now Pat. No. 7,151,105.

(60) Provisional application No. 60/602,618, filed on Aug. 18, 2004.

(51) Int. Cl.
*A61K 31/519* (2006.01)
*C07D 487/04* (2006.01)
*A61P 31/12* (2006.01)

(52) U.S. Cl. .................................. 514/259.31; 544/263
(58) Field of Classification Search .................. 544/263; 514/259.31
See application file for complete search history.

(56) References Cited

U.S. PATENT DOCUMENTS 7,151,105 B2 * 12/2006 Gonzalez et al. ........ 514/259.31

* cited by examiner

*Primary Examiner* — Niloofar Rahmani
(74) *Attorney, Agent, or Firm* — James T. Wasicak

(57) ABSTRACT

The present invention provides compounds of formula (4), and their pharmaceutically acceptable salts and solvates, which are useful as inhibitors of the Hepatitis C virus (HCV) polymerase enzyme and are also useful for the treatment of HCV infections in HCV-infected mammals. The present invention also provides pharmaceutical compositions comprising compounds of formula (4), their pharmaceutically acceptable salts and solvates. Furthermore, the present invention provides intermediate compounds and methods useful in the preparation of compounds of formula (4).

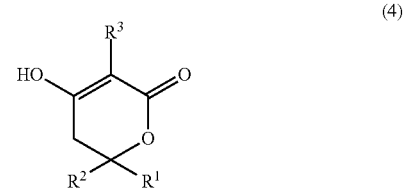

(4)

12 Claims, No Drawings

INHIBITORS OF HEPATITIS C VIRUS RNA-DEPENDENT RNA POLYMERASE, AND COMPOSITIONS AND TREATMENTS USING THE SAME

This application is a continuation of U.S. application Ser. No. 11/470,540, filed Sep. 6, 2006, which is a continuation of U.S. application Ser. No. 11/204,269, filed Aug. 15, 2005, which claims priority of U.S. Provisional Application Ser. No. 60/602,618, filed Aug. 15, 2004.

FIELD OF THE INVENTION

The present invention relates to compounds useful as inhibitors of the Hepatitis C virus (HCV) polymerase enzyme, pharmaceutical compositions comprising such compounds, methods of using such compounds and formulations in the treatment of HCV-infected mammals, such as humans, and methods and intermediates compounds useful in preparing such compounds.

BACKGROUND

The invention relates to agents that inhibit hepatitis C virus (HCV) RNA-dependent RNA polymerase (RdRp). The invention also relates to the use of such compounds in pharmaceutical compositions and therapeutic treatments useful for inhibition of HCV replication.

HCV is an enveloped RNA virus containing a single-stranded positive-sense RNA genome approximately 9.5 kb in length (Choo, et al., *Science* 244:359-362 (1989)). The RNA genome contains a 5'-nontranslated region (5' NTR) of 341 nucleotides (Brown, et al., *Nucl. Acids Res.* 20:5041-5045 (1992); Bukh, et al., *Proc. Natl. Acad. Sci. USA* 89:4942-4946 (1992)), a large open reading frame (ORF) encoding a single polypeptide of 3,010 to 3,040 amino acids (Choo, et al. (1989), supra;), and a 3'-nontranslated region (3'-NTR) of variable length of about 230 nucleotides (Kolykhalov, et al., *J. Virol.* 70:3363-3371 (1996); Tanaka, et al., *J. Virol.* 70:3307-3312 (1996)).

The 5' NTR is one of the most conserved regions of the viral genome and plays a pivotal role in the initiation of translation of the viral polyprotein. A single ORF encodes a polyprotein that is co- or post-translationally processed into structural (core, E1, and E2) and nonstructural (NS2, NS3, NS4A, NS4B, NS5A, and NS5B) viral proteins by either cellular or viral proteinases (Bartenschlager (1997), supra). The 3' NTR consists of three distinct regions: a variable region of about 38 nucleotides following the stop codon of the polyprotein, a polyuridine tract of variable length with interspersed substitutions of cystines, and 98 nucleotides (nt) at the very 3' end which are highly conserved among various HCV isolates. The order of the genes within the genome is: NH$_2$—C-E1-E2-p7-NS2-NS3-NS4A-NS4B-NS5A-NS5B—COOH (Grakoui, et al., *J. Virol.* 67:1385-1395 (1993)).

Hepatitis C virus (HCV) is a member of the hepacivirus genus in the family Flaviviridae. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. The persistent property of the HCV infection has been explained by its ability to escape from the host immune surveillance through hypermutability of the exposed regions in the envelope protein E2 (Weiner, et al., *Virology* 180:842-848 (1991); Weiner, et al. *Proc. Natl. Acad. Sci. USA* 89:3468-3472 (1992).

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2 (Hijikata, et al., *Proc. Natl. Acad. Sci. USA* 88:5547-5551 (1991); Lin, et al., *J. Virol.* 68:5063-5073 (1994)). The NS2-3 proteinase, which is a metalloprotease, then cleaves at the NS2/NS3 junction. The NS3/4A proteinase complex (NS3 serine protease/NS4A cofactor), then at all the remaining cleavage sites (Bartenschlager, et al., *J. Virol.* 67:3835-3844 (1993); Bartenschlager, (1997), supra). RNA helicase and NTPase activities have also been identified in the NS3 protein. The N-terminal one-third of the NS3 protein functions as a protease, and the remaining two-thirds of the molecule acts as a helicase/ATPase, which is thought to be involved in HCV replication (Bartenschlager, (1997), supra). NS5A may be phosphorylated and act as a putative cofactor of NS5B. The fourth viral enzyme, NS5B, is an RNA-dependent RNA polymerase (RdRp) and a key component responsible for replication of the viral RNA genome (Lohmann, et al., *J. Virol.* 71:8416-8428 (1997)).

Replication of HCV is thought to occur in membrane-associated replication complexes. Within these, the genomic plus-strand RNA is transcribed into minus-strand RNA, which in turn can be used as a template for synthesis of progeny genomic plus strands. Two viral proteins appear to be involved in this reaction: the NS3 protein, which carries in the carboxy terminal two-thirds a nucleoside triphosphatase/ RNA helicase, and the NS5B protein, which is a membrane-associated phosphoprotein with an RNA-dependent RNA polymerase activity (RdRp) (Hwang, et al., *J. Virol.* 227:439-446 (1997)). While the role of NS3 in RNA replication is less clear, NS5B apparently is the key enzyme responsible for synthesis of progeny RNA strands. Using recombinant baculoviruses to express NS5B in insect cells and a synthetic nonviral RNA as a substrate, two enzymatic activities have been identified as being associated with NS5B. The two activities include a primer-dependent RdRp and a terminal transferase (TNTase) activity. NS5B's activity was confirmed and further characterized through the use of the HCV RNA genome as a substrate (Lohmann, et al., *Virology* 249:108-118 (1998)). Recent studies have shown that NS5B with a C-terminal 21 amino-acid truncation expressed in *Escherichia coli* is also active for in vitro RNA synthesis (Ferrari, et al., *J. Virol.* 73:1649-1654 (1999); Yamashita, et al., *J. Biol. Chem.* 273:15479-15486 (1998)).

Since persistent infection of HCV is related to chronic hepatitis and eventually to hepatocarcinogenesis, HCV replication is one of the targets to eliminate HCV reproduction and to prevent hepatocellular carcinoma. Unfortunately, present treatment approaches for HCV infection are characterized by relatively poor efficacy and an unfavorable side-effect profile. Therefore, intensive effort is directed at the discovery of molecules to treat this disease, including the discovery of drugs designed to inhibit HC replication, as there is a persistent need for non-peptide, small-molecule compounds that are HCV RdRp inhibitors having desirable or improved physical and chemical properties appropriate for pharmaceutical applications.

SUMMARY OF THE INVENTION

The present invention relates to compounds of the formula 1

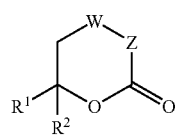

1 and to pharmaceutically acceptable salts, hydrates, metabolites, prodrugs and solvates thereof, wherein:

W—Z is —C(=O)—C(—$R^3$)(H)— or —C(—$OR^6$)=C(—$R^{3'}$)—, wherein when W—Z is —C(—$OR^6$)=C(—$R^{3'}$)—;

each $R^1$ is independently selected from hydrogen, $C_1$-$C_6$ alkyl, $C_2$-$C_6$ alkenyl, $C_2$-$C_6$ alkynyl, ($C_3$-$C_{10}$) cycloalkyl, 4- to 10-membered heterocyclic, and $C_6$-$C_{10}$ aryl, wherein the foregoing $R^1$ groups, except H, are optionally substituted by 1 to 4 substituents selected from $R^4$;

$R^2$ is selected from the group of $R^1$ substituents, —$(CR^8R^9)_t(C_6$-$C_{10}$ aryl), —$(CR^8R^9)_t$(4-10 membered heterocyclic), —$(CR^8R^9)_qC(O)(CR^8R^9)_t(C_6$-$C_{10}$ aryl), —$(CR^8R^9)_qC(O)(CR^8R^9)_t$(4-10 membered heterocyclic), —$(CR^8R^9)_tO(CR^8R^9)_q(C_6$-$C_{10}$ aryl), —$(CR^8R^9)_tO(CR^8R^9)_q$(4-10 membered heterocyclic), —$(CR^8R^9)_qSO_n(CR^8R^9)_t(C_6$-$C_{10}$ aryl), and —$(CR^8R^9)_qSO_n(CR^8R^9)_t$(4-10 membered heterocyclic), wherein q and t are each independently an integer from 0 to 5, n is an integer from 0 to 2, the alkyl, aryl and heterocyclic moieties of said $R^2$ groups are optionally substituted by 1 to 5 $R^4$ groups, and with the proviso that $R^2$ is not H;

$R^3$ is hydrogen, —$OR^6$, —$SR^6$, —$NR^6R^7$, and the group of $R^2$ substituents;

$R^{3'}$ is selected from the group of $R^3$ substituents except $R^{3'}$ is not H;

each $R^4$ is independently selected from halo, cyano, nitro, trifluoromethoxy, trifluoromethyl, azido, $C_1$-$C_{10}$ alkyl, $C_2$-$C_6$ alkenyl, $C_2$-$C_6$ alkynyl, —$C(O)R^6$, —$C(O)OR^6$, —$OC(O)R^6$, —$NR^6C(O)R^7$, —$NR^6C(O)NR^7$, —$C(O)NR^6R^7$, —$NR^6R^7$, —$NR^6OR^7$, —$SO_2NR^6R^7$, —$NR^6SO_2R^7$, —$(CR^8R^9)_t(C_6$-$C_{10}$ aryl) (wherein t is an integer from 0 to 5), —$(CR^8R^9)_t$(4-10 membered heterocyclic) (wherein t is an integer from 0 to 5), $C_3$-$C_{10}$ cycloalkyl, $R^6$—O—, $R^6$—$SO_n$— (wherein n is an integer from 0 to 2), and oxo (=O), and wherein the alkyl, aryl, and heterocyclic moieties of said $R^4$ groups are optionally substituted by 1 to 4 substituents selected from $R^5$;

each $R^5$ is independently selected from halo, trifluoromethyl, trifluoromethoxy, cyano, $C_1$-$C_6$ alkyl, $C_2$-$C_6$ alkenyl, $C_2$-$C_6$ alkynyl, —$OR^8$, $C_3$-$C_{10}$ cycloalkyl, $C_6$-$C_{10}$ aryl, 4- to 10-membered heterocyclic, oxo (=O), —$C(O)R^6$, —$C(O)OR^6$, —$OC(O)R^C(O)R^6$, (O)$NR^7$, —$C(O)NR^6R^7$, —$NR^6R^7$, —$NR^6OR^7$, —$NR^6SO_2R^7$ and —$SO_2NR^6R^7$, wherein the alkyl, aryl and heterocyclic moieties of the foregoing $R^5$ groups are optionally substituted by 1 to 3 $R^{10}$;

each $R^6$ and $R^7$ is independently selected from H, $C_1$-$C_6$ alkyl, $C_3$-$C_{10}$ cycloalkyl, —$(CR^8R^9)_t(C_6$-$C_{10}$ aryl), and —$(CR^8R^9)_t$(4-10 membered heterocyclic), wherein t is an integer from 0 to 5, 1 or 2 ring carbon atoms of the heterocyclic group are optionally substituted with an oxo (=O) moiety, and the alkyl, aryl and heterocyclic moieties of the foregoing $R^6$ and $R^7$ groups are optionally substituted with 1 to 3 halo, cyano, trifluoromethyl, trifluoromethoxy, $C_1$-$C_6$ alkyl, $C_1$-$C_6$ alkoxy, $C_2$-$C_6$ alkenyl, $C_2$-$C_6$ alkynyl, —$(CR^8R^9)_t(C_6$-$C_{11}$ aryl), and —$(CR^8R^9)_t$(4-10 membered heterocyclic), wherein t is an integer from 0 to 5;

each $R^8$ and $R^9$ is independently selected from H and $C_1$-$C_4$ alkyl; and each $R^{10}$ is independently selected from halo, cyano, trifluoromethyl, trifluoromethoxy, —$C(O)O$—$R^6$, —$OR^6$, —$C(O)(CR^8R^9)_pC(O)OR^6$, wherein p is an integer from 1 to 5, $C_1$-$C_6$ alkyl, $C_2$-$C_6$ alkenyl, $C_2$-$C_6$ alkynyl, and —$NR^6R^7$.

The present invention also relates to compounds of formula (I), wherein:

W—Z is —C(=O)—C(—$R^3$)(H)— or —C(—$OR^6$)=C(—$R^{3'}$)—;

each $R^1$ is independently selected from hydrogen, $C_1$-$C_6$ alkyl, $C_2$-$C_6$ alkenyl, $C_2$-$C_6$ alkynyl, ($C_3$-$C_{10}$) cycloalkyl, 4- to 10-membered heterocyclic, and $C_6$-$C_{10}$ aryl, wherein the foregoing $R^1$ groups, except H, are optionally substituted by 1 to 4 substituents selected from $R^4$;

$R^2$ is selected from the group of $R^1$ substituents, —$(CR^8R^9)_t(C_3$-$C_{10}$ cycloalkyl), —$(CR^6R^9)_t(C_6$-$C_{10}$ aryl), —$(CR^8R^9)_t$(4-10 membered heterocyclic), —$(CR^8R^9)_qC(O)(CR^8R^9)_t(C_6$-$C_{10}$ aryl), —$(CR^8R^9)_qC(O)(CR^8R^9)_t$(4-10 membered heterocyclic), —$(CR^6R^9)_tO(CR^8R^9)_q(C_6$-$C_{10}$ aryl), —$(CR^8R^9)_tO(CR^8R^9)_q$(4-10 membered heterocyclic), —$(CR^6R^9)_qSO_n(CR^8R^9)_t(C_6$-$C_{10}$ aryl), and —$(CR^8R^9)_qSO_n(CR^8R^9)_t$(4-10 membered heterocyclic), wherein q and t are each independently an integer from 0 to 5, n is an integer from 0 to 2, the alkyl, cycloalkyl, aryl and heterocyclic moieties of said $R^2$ groups are optionally substituted by 1 to 5 $R^4$ groups, and with the proviso that $R^2$ is not H;

$R^3$ is hydrogen, —$OR^6$, —$SR^6$, —$NR^6R^7$, and the group of $R^2$ substituents;

$R^{3'}$ is selected from the group of $R^3$ substituents;

each $R^4$ is independently selected from halo, cyano, nitro, trifluoromethoxy, trifluoromethyl, azido, $C_1$-$C_{10}$ alkyl, $C_2$-$C_6$ alkenyl, $C_2$-$C_6$ alkynyl, $C_3$-$C_{10}$ cycloalkyl, —$(CR^8R^9)_tN(R^5)_2$, —$(CR^8R^9)_tNR^6C(O)R^6$, —$(CR^8R^9)_tOR^6$, —$(CR^8R^9)_tC(O)R^6$, —$(CR^8R^9)_tC(O)OR^6$, —$(CR^8R^9)_tC(O)R^6$, —$(CR^8R^9)_t$ $NR^6C(O)R^7$, —$(CR^8R^9)_tNR^6C(O)OR^6$—$(CR^8R^9)_tNR^6C(O)NR^7$, —$(CR^8R^9)_tC(O)NR^6R^7$, —$(CR^8R^9)_tNR^6R^7$, —$(CR^8R^9)_tNR^6OR^7$, —$(CR^8R^9)_tSO_2NR^6R^7$, —$(CR^83R^9)_tNR^6SO_2R^7$, —$(CR^8R^9)_t(C_6$-$C_{10}$ aryl) (wherein t is an integer from 0 to 5), —$(CR^8R^9)_t$(4-10 membered heterocyclic) (wherein t is an integer from 0 to 5), $C_3$-$C_{10}$ cycloalkyl, $R^6$—O—, $R^6$—$SO_n$—$(CR^8R^9)_t$— (wherein n is an integer from 0 to 2), and oxo (=O), and wherein the alkyl, aryl, and heterocyclic moieties of said $R^4$ groups are optionally substituted by 1 to 4 substituents selected from $R^5$;

each $R^5$ is independently selected from halo, trifluoromethyl, trifluoromethoxy, cyano, $C_1$-$C_6$ alkyl, $C_2$-$C_6$ alkenyl, $C_2$-$C_6$ alkynyl, —$OR^8$, $C_3$-$C_{10}$ cycloalkyl, $C_6$-$C_{10}$ aryl, 4- to 1-membered heterocyclic, oxo (=O), —$C(O)R^6$, —$C(O)OR^6$, —$OC(O)R^6$, —$NR^6C(O)NR^6$, —$NR^6C(O)NR^7$, —$C(O)NR^6R^7$, —$NR^6R^7$, —$NR^6OR^7$, —$NR^6SO_2R^7$ and —$SO_2NR^6R^7$, wherein the alkyl, aryl and heterocyclic moieties of the foregoing $R^5$ groups are optionally substituted by 1 to 3 $R^{10}$;

each $R^6$ and $R^7$ is independently selected from H, cyano, $C_1$-$C_6$ alkyl, $C_3$-$C_{10}$ cycloalkyl, —$(CR^8R^9)_t(C_6$-$C_{10}$ aryl), and —$(CR^8R^9)_t$(4-10 membered heterocyclic), —$(CR^8R^9)_tC(O)R^8$ wherein t is an integer from 0 to 5, 1 or 2 ring carbon atoms of the heterocyclic group are optionally substituted with an oxo (=O) moiety, and the alkyl, aryl and heterocyclic moieties of the foregoing $R^6$ and $R^7$ groups are optionally substituted with 1 to 3 halo, cyano, $C_3$-$C_{10}$ cycloalkyl, —$C(O)OR^8$—$NR^8C(O)R^9$, —$(CR^8R^9)_tNR^8R^9$, —$OR^8$, —$NC(O)R^9$, trifluoromethyl, trifluoromethoxy, $C_1$-$C_6$ alkyl, $C_1$-$C_6$ alkoxy, $C_2$-$C_6$ alkenyl, $C_2$-$C_6$ alkynyl, —$(CR^8R^9)_t(C_6$-$C_{10}$ aryl), and —$(CR^8R^9)_t$(4-10 membered heterocyclic), wherein t is an integer from 0 to 5;

each $R^8$ and $R^9$ is independently selected from H and $C_1$-$C_4$ alkyl; and each $R^{10}$ is independently selected from halo, cyano, trifluoromethyl, trifluoromethoxy, —$C(O)OR^6$, —$C(O)O$—$R^5$, —$OR^6$, —$C(O)(CR^8R^9)_pC(O)OR^6$, wherein p is an integer from 1 to 5, $C_1$-$C_6$ alkyl, $C_2$-$C_6$ alkenyl, $C_2$-$C_6$ alkynyl, and —$NR^6R^7$.

The present further relates to a compound of the formula 2

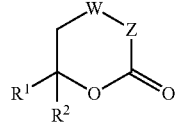

and pharmaceutically acceptable salts, solvates, metabolites, prodrugs and solvates thereof, wherein:

W—Z is —C(—OR$^6$)═C(—R$^{3'}$)—;

R$^1$ is cyclopentyl;

R$^2$ is —(CR$^8$R$^9$)$_t$(C$_6$-C$_{10}$ aryl) or —(CR$^6$R$^9$)$_t$(4-10 membered heterocyclic), wherein t is an integer from 0 to 5, and the aryl and heterocyclic moieties of said R$^2$ groups are optionally substituted by 1 to 5 R$^4$ groups, and with the proviso that R$^2$ is not H;

R$^3$ is hydrogen, —OR$^6$, —SR$^6$, —NR$^6$R$^7$, and the group of R$^2$ substituents;

each R$^4$ is independently selected from halo, cyano, nitro, trifluoromethoxy, trifluoromethyl, azido, C$_1$-C$_{10}$ alkyl, C$_2$-C$_6$ alkenyl, C$_2$-C$_6$ alkynyl, —C(O)R$^6$, —C(O)OR$^6$, —OC(O)R$^6$, —NR$^6$C(O)R$^7$, —NR$^6$C(O)NR$^7$, —C(O)NR$^6$R$^7$, —NR$^6$R$^7$, —NR$^6$OR$^7$, —SO$_2$NR$^6$R$^7$, —NR$^6$SO$_2$R$^7$, —(CR$^8$R$^9$)$_t$(C$_6$-C$_{10}$ aryl) (wherein t is an integer from 0 to 5), —(CR$^8$R$^9$)$_t$(4-10 membered heterocyclic) (wherein t is an integer from 0 to 5), C$_3$-C$_{10}$ cycloalkyl, R$^6$—O—, R$^6$—SO$_n$— (wherein n is an integer from 0 to 2), and oxo (═O), and wherein the alkyl, aryl, and heterocyclic moieties of said R$^4$ groups are optionally substituted by 1 to 4 substituents selected from R$^5$;

each R$^5$ is independently selected from halo, trifluoromethyl, trifluoromethoxy, cyano, C$_1$-C$_6$ alkyl, C$_2$-C$_6$ alkenyl, C$_2$-C$_6$ alkynyl, —OR$^8$, C$_3$-C$_{10}$ cycloalkyl, C$_6$-C$_{10}$ aryl, 4- to 10-membered heterocyclic, oxo (═O), —C(O)R$^6$, —C(O)OR$^6$, —OC(O)R$^6$, —NR$^6$C(O)R$^6$, —NR$^6$C(O)NR$^7$, —C(O)NR$^6$R$^7$, —NR$^6$R$^7$, —NR$^6$OR$^7$, —NR$^6$SO$_2$R$^7$ and —SO$_2$NR$^6$R$^7$, wherein the alkyl, aryl and heterocyclic moieties of the foregoing R$^5$ groups are optionally substituted by 1 to 3 R$^{10}$;

each R$^6$ and R$^7$ is independently selected from H, C$_1$-C$_6$ alkyl, C$_3$-C$_{10}$ cycloalkyl, —(CR$^8$R$^9$)$_t$(C$_6$-C$_{10}$ aryl), and —(CR$^8$R$^9$)$_t$(4-10 membered heterocyclic), wherein t is an integer from 0 to 5, 1 or 2 ring carbon atoms of the heterocyclic group are optionally substituted with an oxo (═O) moiety, and the alkyl, aryl and heterocyclic moieties of the foregoing R$^6$ and R$^7$ groups are optionally substituted with 1 to 3 halo, cyano, trifluoromethyl, trifluoromethoxy, C$_1$-C$_6$ alkyl, C$_1$-C$_6$ alkoxy, C$_2$-C$_6$ alkenyl, C$_2$-C$_6$ alkynyl, (CR$^8$R$^9$)$_t$(C$_6$-C$_{10}$ aryl), and —(CR$^8$R$^9$)$_t$(4-10 membered heterocyclic), wherein t is an integer from 0 to 5;

each R$^8$ and R$^9$ is independently selected from H and C$_1$-C$_4$ alkyl; and each R$^{10}$ is independently selected from halo, cyano, trifluoromethyl, trifluoromethoxy, —C(O)O—R$^6$, —OR$^6$, —C(O)(CR$^8$R$^9$)$_p$C(O)OR$^6$, wherein p is an integer from 1 to 5, C$_1$-C$_6$ alkyl, C$_2$-C$_6$ alkenyl, C$_2$-C$_6$ alkynyl, and NR$^6$R$^7$.

The present invention further relates to a compound of the formula (3)

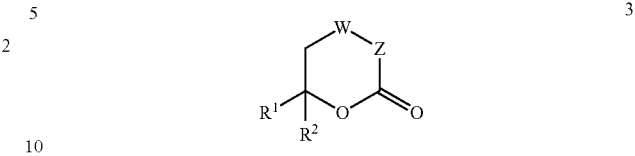

and to pharmaceutically acceptable salts, solvates, prodrugs, and metabolites thereof, wherein:

W—Z is —C(═O)—C(—R$^3$)(H)—;

R$^1$ is cyclopentyl;

R$^2$ is —(CR$^8$R$^9$)$_t$(C$_6$-C$_{10}$ aryl) or —(CR$^8$R$^9$)$_t$(4-10 membered heterocyclic), wherein t is an integer from 0 to 5, and the aryl and heterocyclic moieties of said R$^2$ groups are optionally substituted by 1 to 5 R$^4$ groups, and with the proviso that R$^2$ is not H;

R$^3$ is hydrogen;

each R$^4$ is independently selected from halo, cyano, nitro, trifluoromethoxy, trifluoromethyl, azido, C$_1$-C$_{10}$ alkyl, C$_2$-C$_6$ alkenyl, C$_2$-C$_6$ alkynyl, —C(O)R$^6$, —C(O)OR$^6$, —OC(O)R$^6$, —NR$^6$C(O)R$^7$, —NR$^6$C(O)NR$^7$, —C(O)NR$^6$R$^7$, —NR$^6$R$^7$, —NR$^6$OR$^7$, —SO$_2$NR$^6$R$^7$, —NR$^6$SO$_2$R$^7$, —(CR$^8$R$^9$)$_t$(C$_6$-C$_{10}$ aryl) (wherein t is an integer from 0 to 5), —(CR$^8$R$^9$)$_t$(4-10 membered heterocyclic) (wherein t is an integer from 0 to 5), C$_3$-C$_{10}$ cycloalkyl, R$^6$—O—, R$^6$—SO$_n$— (wherein n is an integer from 0 to 2), and oxo (═O), and wherein the alkyl, aryl, and heterocyclic moieties of said R$^4$ groups are optionally substituted by 1 to 4 substituents selected from R$^5$;

each R$^5$ is independently selected from halo, trifluoromethyl, trifluoromethoxy, cyano, C$_1$-C$_6$ alkyl, C$_2$-C$_6$ alkenyl, C$_2$-C$_6$ alkynyl, —OR$^8$, C$_3$-C$_{10}$ cycloalkyl, C$_6$-C$_{10}$ aryl, 4- to 10-membered heterocyclic, oxo (═O), —C(O)R$^6$, —C(O)OR$^6$, —OC(O)R$^6$, —NR$^6$C(O)R$^6$, —NR$^6$C(O)NR$^7$, —C(O)NR$^6$R$^7$, —NR$^6$R$^7$, —NR$^6$OR$^7$, —NR$^6$SO$_2$R$^7$ and —SO$_2$NR$^6$R$^7$, wherein the alkyl, aryl and heterocyclic moieties of the foregoing R$^5$ groups are optionally substituted by 1 to 3 R$^{10}$;

each R$^6$ and R$^7$ is independently selected from H, C$_1$-C$_6$ alkyl, C$_3$-C$_{10}$ cycloalkyl, —(CR$^8$R$^9$)$_t$(C$_6$-C$_{10}$ aryl), and —(CR$^8$R$^9$)$_t$(4-10 membered heterocyclic), wherein t is an integer from 0 to 5, 1 or 2 ring carbon atoms of the heterocyclic group are optionally substituted with an oxo (═O) moiety, and the alkyl, aryl and heterocyclic moieties of the foregoing R$^6$ and R$^7$ groups are optionally substituted with 1 to 3 halo, cyano, trifluoromethyl, trifluoromethoxy, C$_1$-C$_6$ alkyl, C$_1$-C$_6$ alkoxy, C$_2$-C$_6$ alkenyl, C$_2$-C$_6$ alkynyl, (CR$^8$R$^9$)$_t$(C$_6$-C$_{10}$ aryl), and —(CR$^8$R$^9$)$_t$(4-10 membered heterocyclic), wherein t is an integer from 0 to 5;

each R$^8$ and R$^9$ is independently selected from H and C$_1$-C$_4$ alkyl; and each R$^{10}$ is independently selected from halo, cyano, trifluoromethyl, trifluoromethoxy, —C(O)O—R$^6$, —OR$^6$, —C(O)(CR$^8$R$^9$)$_p$C(O)OR$^6$, wherein p is an integer from 1 to 5, C$_1$-C$_6$ alkyl, C$_2$-C$_6$ alkenyl, C$_2$-C$_6$ alkynyl, and NR$^6$R$^7$.

In a specific embodiment of the present invention, according to formula 1, R$^2$ is —(CR$^8$R$^9$)$_t$(C$_6$-C$_{10}$ aryl), wherein t is an integer from 2 to 5, and the aryl moiety of said R$^2$ group is optionally substituted by 1 to 5 R$^4$ groups, and with the proviso that R$^2$ is not H; optionally each R$^4$ is independently selected from halo, nitro, C$_1$-C$_{10}$ alkyl, —C(O)R$^6$, —C(O)OR$^6$, —OC(O)R$^6$, —C(O)NR$^6$R$^7$, —(CR$^8$R$^9$)$_t$(4-10 membered heterocyclic) (wherein t is an integer from 0 to 5), $C_3$-$C_{10}$ cycloalkyl, $R^6$—O—, and wherein the alkyl, aryl, and heterocyclic moieties of said $R^4$ groups are optionally substituted by 1 to 4 substituents selected from $R^5$, optionally each $R^5$ is independently selected from halo, trifluoromethyl, $C_1$-$C_6$ alkyl, —$OR^8$, $C_3$-$C_{10}$ cycloalkyl, $C_6$-$C_{10}$ aryl, oxo (═O), —C(O)$R^6$, —C(O)O$R^6$, —OC(O)$R^6$, —$NR^6$C(O)$R^6$, —$NR^6$C(O)$NR^7$, —C(O)$NR^6R^7$, —$NR^6R^7$, —$NR^6OR^7$, —$NR^6SO_2R^7$ and —$SO_2NR^6R^7$, wherein the alkyl and aryl moieties of the foregoing $R^5$ groups are optionally substituted by 1 to 3 $R^{10}$; optionally each $R^{10}$ is independently selected from halo, trifluoromethyl, —C(O)O—$R^6$, —$OR^6$, $C_1$-$C_6$ alkyl and $NR^6R^7$; optionally $R^3$ is —$OR^6$, —$SR^6$, —$NR^6R^7$, and —(CR^8R^9)$_t$($C_6$-$C_{10}$ aryl), wherein t is an integer from 2 to 5, and the aryl moiety of said $R^2$ group is optionally substituted by 1 to 5 $R^4$ groups.

In another aspect of the present invention are provided compounds of formula (4),

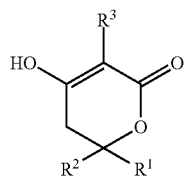

(4)

wherein any of the definitions of $R^1$, $R^2$ and $R^3$ below apply.

Also provided are compounds of formula (4a),

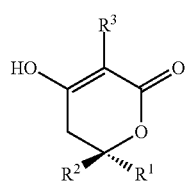

(4a)

wherein any of the definitions of $R^1$, $R^2$ and $R^3$ below apply.

Further provided are compounds of formula (4b),

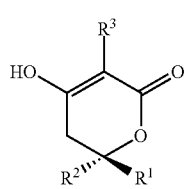

(4b)

wherein any of the definitions of $R^1$, $R^2$ and $R^3$ below apply.

It is specifically contemplated herein that compounds of formula (4) are meant to encompass both compounds of formulae (4a) and (4b), unless otherwise indicated.

In a further aspect are provided compounds of formula (4) wherein:

$R^1$ is cyclopentyl;
$R^2$ is —(CR^6R^7)$_n$(5-6 membered heterocyclic), wherein said 5-6 membered heterocyclic group is optionally substituted with at least one $R^4$ group;
$R^3$ is —(CR^6R^7)$_t$($C_6$-$C_{10}$ aryl) or —(CR^6R^7)$_t$(4-10 membered heterocyclic), wherein each of said $C_6$-$C_{10}$ aryl and 4-10 membered heterocyclic moieties of said $R^3$ groups are optionally substituted with at least one $R^5$ group;

each $R^4$ is independently selected from halo, —$OR^6$, oxo, —$NR^6R^7$, —$CF_3$, —CN, —C(O)$R^6$, —C(O)$OR^6$, —OC(O)$R^6$, —$NR^6C(O)R^7$, —$NR^6C(O)OR^7$, —$NR^6C(O)NR^6R^7$, —C(O)$NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;
each $R^5$ is independently selected from $C_1$-$C_6$ alkyl, halo, —$OR^6$, —$CF_3$, and —CN;
each $R^6$ and $R^7$ is independently selected from hydrogen and $C_1$-$C_6$ alkyl;
n is 0, 1, 2, 3, 4, or 5; and
t is 0, 1, 2, 3, 4, or 5; or
pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Still another aspect of the present invention provides compounds of formula (4), wherein:
$R^1$ is cyclopentyl;
$R^2$ is —(CR^6R^7)$_n$(5-6 membered heterocyclic), wherein said 5-6 membered heterocyclic group is optionally substituted with at least one $R^4$ group;
$R^3$ is —(CR^6R^7)$_t$($C_6$-$C_{10}$ aryl) or —(CR^6R^7)$_t$(4-10 membered heterocyclic), wherein said aryl and heterocyclic moieties of said $R^3$ groups are optionally substituted with at least one $R^5$ group;
each $R^4$ is independently selected from halo, —$OR^6$, oxo, —$NR^6R^7$, —$CF_3$, —CN, —C(O)$R^6$, —C(O)$OR^6$, —OC(O)$R^6$, —$NR^6C(O)R^7$, —$NR^6C(O)OR^7$, —$NR^6C(O)NR^6R^7$, —C(O)$NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;
each $R^5$ is independently selected from $C_1$-$C_6$ alkyl, halo, —$OR^6$, —$CF_3$, and —CN;
each $R^6$ and $R^7$ is independently selected from hydrogen and $C_1$-$C_6$ alkyl;
n is 1 or 2; and
t is 1 or 2; or
pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethyl pyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Further provided are compounds of formula (4), wherein:
$R^1$ is cyclopentyl;
$R^2$ is —(CR^6R^7)$_n$(5-6 membered heterocyclic), wherein said 5-6 membered heterocyclic group is optionally substituted with at least one $R^4$ group;
$R^3$ is —(CR^6R^7)$_t$($C_6$-$C_{10}$ aryl) or —(CR^6R^7)$_t$(4-10 membered heterocyclic), wherein said aryl and heterocyclic moieties of said $R^3$ groups are optionally substituted with at least one $R^5$ group;
each $R^4$ is independently selected from halo, —$OR^6$, oxo, —$NR^6R^7$, —$CF_3$, —CN, —C(O)$R^6$, —C(O)$OR^6$, —OC(O)

$R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN;

each $R^6$ and $R^7$ is independently selected from hydrogen and $C_1$-$C_6$ alkyl;

n is 2; and t is 1 or 2; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

In yet another aspect are afforded compounds of formula (4), wherein:

$R^1$ is cyclopentyl;

$R^2$ is —$(CR^6R^7)_n$(5-6 membered heterocyclic), wherein said 5-6 membered heterocyclic group is optionally substituted with at least one $R^4$ group;

$R^3$ is —$(CR^6R^7)_t$(4-10 membered heterocyclic), optionally substituted with at least one $R^5$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN;

each $R^6$ and $R^7$ is independently selected from hydrogen and $C_1$-$C_6$ alkyl;

n is 2; and t is 1 or 2; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Also provided herein are compounds of formula (4), wherein:

$R^1$ is cyclopentyl;

$R^2$ is —$(CR^6R^7)_n$(5-6 membered heterocyclic), wherein said 5-6 membered heterocyclic group is optionally substituted with at least one $R^4$ group;

$R^3$ is —$(CR^6R^7)_t$(4-10 membered heterocyclic), optionally substituted with at least one $R^5$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN;

each $R^6$ and $R^7$ is independently selected from hydrogen and $C_1$-$C_6$ alkyl;

n is 2; and t is 1; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Yet another aspect provides compounds of formula (4), wherein:

$R^1$ is cyclopentyl;

$R^2$ is a —$(CH_2)_2$(pyridyl), —$(CH_2)_2$(pyrazolyl), —$(CH_2)_2$(pyrrolyl), —$(CH_2)_2$(oxazolyl), —$(CH_2)_2$(thiazolyl), —$(CH_2)_2$(imidazolyl), —$(CH_2)_2$(isoxazolyl), —$(CH_2)_2$(isothiazolyl), —$(CH_2)_2$(1,2,3-triazolyl), —$(CH_2)_2$(1,3,4-triazolyl), —$(CH_2)_2$(1,3,4-thiadiazolyl), —$(CH_2)_2$(pyridazinyl), —$(CH_2)_2$(pyrimidinyl), —$(CH_2)_2$(pyrazinyl), or —$(CH_2)_2$(1,3,5-triazinyl) group, each of which is optionally substituted with at least one $R^4$ group;

$R^3$ is —$(CR^6R^7)_t$(4-10 membered heterocyclic), optionally substituted with at least one $R^5$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN;

each $R^6$ and $R^7$ is independently selected from hydrogen and $C_1$-$C_6$ alkyl; and t is 1 or 2; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Further provided are compounds of formula (4), wherein:

$R^1$ is cyclopentyl;

$R^2$ is a —$(CH_2)_2$(pyridyl), —$(CH_2)_2$(pyrazolyl), —$(CH_2)_2$(pyrrolyl), —$(CH_2)_2$(oxazolyl), —$(CH_2)_2$(thiazolyl), —$(CH_2)_2$(imidazolyl), —$(CH_2)_2$(isoxazolyl), —$(CH_2)_2$(isothiazolyl), —$(CH_2)_2$(1,2,3-triazolyl), —$(CH_2)_2$(1,3,4-triazolyl), —$(CH_2)_2$(1,3,4-thiadiazolyl), —$(CH_2)_2$(pyridazinyl), —$(CH_2)_2$(pyrimidinyl), —$(CH_2)_2$(pyrazinyl), or —$(CH_2)_2$(1,3,5-triazinyl) group, each of which is optionally substituted with at least one $R^4$ group;

$R^3$ is —$(CH_2)$(4-10 membered heterocyclic), optionally substituted with at least one $R^5$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN; and each $R^6$ and $R^7$ is independently selected from hydrogen and $C_1$-$C_6$ alkyl; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Still another aspect provides compounds of formula (4), wherein:

$R^1$ is cyclopentyl;

$R^2$ is a —$(CH_2)_2$(pyridyl), —$(CH_2)_2$(pyrazolyl), —$(CH_2)_2$(pyrrolyl), —$(CH_2)_2$(oxazolyl), —$(CH_2)_2$(thiazolyl), —$(CH_2)_2$(imidazolyl), —$(CH_2)_2$(isoxazolyl), —$(CH_2)_2$(isothiazolyl), —$(CH_2)_2$(1,2,3-triazolyl), —$(CH_2)_2$(1,3,4-triazolyl), —$(CH_2)_2$(1,3,4-thiadiazolyl), —$(CH_2)_2$(pyridazinyl), —$(CH_2)_2$(pyrimidinyl), —$(CH_2)_2$(pyrazinyl), or —$(CH_2)_2$(1,3,5-triazinyl) group, each of which is optionally substituted with at least one $R^4$ group;

$R^3$ is —$(CH_2)$([1,2,4]triazolo[1,5-a]pyrimidin-2-yl), optionally substituted with at least one $R^5$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN; and each $R^6$ and $R^7$ is independently selected from hydrogen and $C_1$-$C_6$ alkyl; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Yet another aspect affords compounds of formula (4), wherein:

$R^1$ is cyclopentyl;

$R^2$ is a —$(CH_2)_2$(pyridyl), —$(CH_2)_2$(pyrazolyl), —$(CH_2)_2$(pyrrolyl), —$(CH_2)_2$(oxazolyl), —$(CH_2)_2$(thiazolyl), —$(CH_2)_2$(imidazolyl), —$(CH_2)_2$(isoxazolyl), —$(CH_2)_2$(isothiazolyl), —$(CH_2)_2$(1,2,3-triazolyl), —$(CH_2)_2$(1,3,4-triazolyl), —$(CH_2)_2$(1,3,4-thiadiazolyl), —$(CH_2)_2$(pyridazinyl), —$(CH_2)_2$(pyrimidinyl), —$(CH_2)_2$(pyrazinyl), or —$(CH_2)_2$(1,3,5-triazinyl0 group, each of which is optionally substituted with at least one $R^4$ group;

$R^3$ is —$(CH_2)$([1,2,4]triazolo[1,5-a]pyrimidin-2-yl), optionally substituted with at least one $R^5$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN; and each $R^6$ and $R^7$ is independently selected from hydrogen and $C_1$-$C_6$ alkyl; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Further still are compounds of formula (4), wherein:

$R^1$ is cyclopentyl;

$R^2$ is —$(CH_2)_2$(pyridyl) or —$(CH_2)_2$(pyrazolyl), each of which is optionally substituted with at least one $R^4$ group;

$R^3$ is —$(CH_2)$([1,2,4]triazolo[1,5-a]pyrimidin-2-yl), optionally substituted with at least one $R^5$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

each $R^5$ is independently selected from $C_1$-$C_6$ alkyl, halo, —$OR^6$, —$CF_3$, and —CN; and each $R^6$ and $R^7$ is independently selected from hydrogen and $C_1$-$C_6$ alkyl; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

In still another aspect are compounds of formula (4), wherein:

$R^1$ is cyclopentyl;

$R^2$ is —$(CH_2)_2$(pyridyl) or —$(CH_2)_2$(pyrazolyl), each of which is optionally substituted with at least one substituent selected from halo, $C_1$-$C_6$ alkyl, —$OR^6$, and —$NR^6R^7$;

$R^3$ is —$(CH_2)$([1,2,4]triazolo[1,5-a]pyrimidin-2-yl), optionally substituted with at least one substituent selected from halo and $C_1$-$C_6$ alkyl; and each $R^6$ and $R^7$ is independently selected from hydrogen and $C_1$-$C_6$ alkyl; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Further still are provided compounds of formula (4), wherein:

R$^1$ is cyclopentyl;

R$^2$ is —(CH$_2$)$_2$(pyridyl) optionally substituted with at least one substituent selected from halo, C$_1$-C$_6$ alkyl, —OR$^6$, and —NR$^6$R$^7$;

R$^3$ is —(CH$_2$)([1,2,4]triazolo[1,5-a]pyrimidin-2-yl), optionally substituted with at least one substituent selected from halo and C$_1$-C$_6$ alkyl; and each R$^6$ and R$^7$ is independently selected from hydrogen and C$_1$-C$_6$ alkyl; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

Also provided are compounds of formula (4), wherein:

R$^1$ is cyclopentyl;

R$^2$ is —(CH$_2$)$_2$(pyrazolyl) optionally substituted with at least one substituent selected from halo, C$_1$-C$_6$ alkyl, —OR$^6$, and —NR$^6$R$^7$;

R$^3$ is —(CH$_2$)([1,2,4]triazolo[1,5-a]pyrimidin-2-yl), optionally substituted with at least one substituent selected from halo and C$_1$-C$_6$ alkyl; and each R$^6$ and R$^7$ is independently selected from hydrogen and C$_1$-C$_6$ alkyl; or pharmaceutically acceptable salts or solvates thereof, with the proviso that the compound of formula (4) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

In yet another aspect are compounds selected from:

6-[2-(6-amino-5-ethyl-2-methylpyridin-3-yl)ethyl]-6-cyclopentyl-3-[(5,7-dimethyl[1,2,4]triazolo[1,5-a]pyrimidin-2-yl)methyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-[2-(4-ethylpyridin-2-yl)ethyl]-4-hydroxy-5,6-dihydro-2H-pyran-2-one;

6-cyclopentyl-6-[2-(4-ethylpyridin-2-yl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one;

6-cyclopentyl-6-[2-(2,6-dimethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-[2-(2-isopropylpyridin-4-yl)ethyl]-5,6-dihydro-2H-pyran-2-one;

6-cyclopentyl-3-[(5,7-dimethyl[1,2,4]triazolo[1,5-a]pyrimidin-2-yl)methyl]-6-[2-(2-ethyl-6-isopropylpyridin-4-yl)ethyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-[2-(2-ethyl-6-methylpyridin-4-yl)ethyl]-4-hydroxy-5,6-dihydro-2H-pyran-2-one;

6-cyclopentyl-6-[2-(2,6-diethylpyridin-4-yl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-6-[2-(2-ethyl-5-methoxypyridin-4-yl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one;

6-cyclopentyl-6-[2-(5-ethoxy-2-ethylpyridin-4-yl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-6-[2-(2-ethyl-5-propoxypyridin-4-yl)ethyl]-4-hydroxy-3-[(6-methyl[1,2,4]triazolo[1,5-a]pyrimidin-2-yl)methyl]-5,6-dihydro-2H-pyran-2-one;

6-{2-[2,6-bis(2,2,2-trifluoroethyl)pyridin-4-yl]ethyl}-6-cyclopentyl-4-hydroxy-3-[(6-methyl[1,2,4]triazolo[1,5-a]pyrimidin-2-yl)methyl]-5,6-dihydro-2H-pyran-2-one;

6-cyclopentyl-3-[(5,7-dimethyl[1,2,4]triazolo[1,5-a]pyrimidin-2-yl)methyl]-6-[2-(6-ethyl-3-methoxypyridin-2-yl)ethyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-[2-(1-ethyl-1H-pyrazol-4-yl)ethyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-[2-(1-isopropyl-1H-pyrazol-4-yl)ethyl]-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-[2-(5-methoxy-2-methylpyridin-4-yl)ethyl]-5,6-dihydro-2H-pyran-2-one;

6-{2-[2,6-bis(2,2,2-trifluoroethyl)pyridin-4-yl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

5-bromo-1-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2(1H)-one;

1-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-5-ethylpyridin-2(1H)-one;

2-[3-chloro-5-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2-yl]-2-methylpropanenitrile;

(+)-6-{2-[2,6-bis(2,2,2-trifluoroethyl)pyridin-4-yl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

(−)-6-{2-[2,6-bis(2,2,2-trifluoroethyl)pyridin-4-yl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

(+)-6-cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one;

(−)-6-cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one;

(+)-6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one;

(−)-6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one;

(+)-6-cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one;

(−)-6-cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one;

(+)-6-cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one;

(−)-6-cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one;

(+)-6-cyclopentyl-6-[2-(5-ethoxy-2-ethylpyridin-4-yl)ethyl]-4-hydroxy-3-[(6-methyl[1,2,4]triazolo[1,5-a]pyrimidin-2-yl)methyl]-5,6-dihydro-2H-pyran-2-one; and (−)-6-cyclopentyl-6-[2-(5-ethoxy-2-ethylpyridin-4-yl)ethyl]-4-hydroxy-3-[(6-methyl[1,2,4]triazolo[1,5-a]pyrimidin-2-yl)methyl]-5,6-dihydro-2H-pyran-2-one; or pharmaceutically acceptable salts or solvates thereof.

A further aspect of the present invention provides compounds of formula (4), wherein:

$R^1$ is cyclopentyl;

$R^2$ is —$(CR^6R^7)_n(C_6-C_{10}$ aryl) or —$(CR^6R^7)_n$(4-10 membered heterocyclic), wherein each of said $C_6-C_{10}$ aryl and 4-10 membered heterocyclic groups is optionally substituted with at least one $R^4$ group;

$R^3$ is —$(CR^6R^7)_t$(4-10 membered heterocyclic) substituted with at least one $R^5$, and further optionally substituted with at least one $C_1-C_6$ alkyl;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1-C_6$ alkyl, $C_2-C_6$ alkenyl, and $C_2-C_6$ alkynyl, wherein said $C_1-C_6$ alkyl, $C_2-C_6$ alkenyl, and $C_2-C_6$ alkynyl groups are optionally substituted with at least one $R^5$;

$R^5$ is halogen, oxo, $C_3-C_8$ cycloalkyl, $C_6-C_{10}$ aryl, —$OR^6$, —$C(O)OR^6$, —$NR^6R^7$, and 4-10 membered heterocyclic substituted with $R^6$;

each $R^6$ and $R^7$ is independently selected from hydrogen and $C_1-C_6$ alkyl;

n is 0, 1, 2, 3, 4, or 5; and t is 0, 1, 2, 3, 4, or 5; or pharmaceutically acceptable salts or solvates thereof, with the proviso that the compound of formula (4) is not 6-{2-[4-(benzyloxy)phenyl]ethyl}-6-cyclopentyl-3-[(2-cyclopropyl-6-hydroxypyrimidin-4-yl)methyl]dihydro-2H-pyran-2,4(3H)-dione, methyl {5-[(6-cyclopentyl-6-{2-[4-(difluoromethyl)-3-fluorophenyl]ethyl}-2,4-dioxotetrahydro-2H-pyran-3-yl)methyl]isoxazol-3-yl}carbamate; or 6-[2-(5-chloro-2,4-dimethoxyphenyl)ethyl]-6-cyclopentyl-3-[(3-pyridin-2-yl-1,2,4-oxadiazol-5-yl)methyl]dihydro-2H-pyran-2,4(3H)-dione.

In yet another aspect are compounds of formula (4), wherein:

$R^1$ is cyclopentyl;

$R^2$ is —$(CR^6R^7)_n(C_6-C_{10}$ aryl) or —$(CR^6R^7)_n$(4-10 membered heterocyclic), wherein each of said $C_6-C_{10}$ aryl and 4-10 membered heterocyclic groups is optionally substituted with at least one $R^4$ group;

$R^3$ is —$(CH_2)$(4-10 membered heterocyclic) substituted with at least one $R^5$, and further optionally substituted with at least one $C_1-C_6$ alkyl;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1-C_6$ alkyl, $C_2-C_6$ alkenyl, and $C_2-C_6$ alkynyl, wherein said $C_1-C_6$ alkyl, $C_2-C_6$ alkenyl, and $C_2-C_6$ alkynyl groups are optionally substituted with at least one $R^5$;

$R^5$ is halogen, oxo, $C_3-C_8$ cycloalkyl, $C_6-C_{10}$ aryl, —$OR^6$, —$C(O)OR^6$, —$NR^6R^7$, and 4-10 membered heterocyclic substituted with $R^6$;

each $R^6$ and $R^7$ is independently selected from hydrogen and $C_1-C_6$ alkyl;

n is 0, 1, 2, 3, 4, or 5; and t is 0, 1, 2, 3, 4, or 5; or pharmaceutically acceptable salts or solvates thereof, with the proviso that the compound of formula (4) is not 6-{2-[4-(benzyloxy)phenyl]ethyl}-6-cyclopentyl-3-[(2-cyclopropyl-6-hydroxypyrimidin-4-yl)methyl]dihydro-2H-pyran-2,4(3H)-dione, methyl {5-[(6-cyclopentyl-6-{2-[4-(difluoromethyl)-3-fluorophenyl]ethyl}-2,4-dioxotetrahydro-2H-pyran-3-yl)methyl]isoxazol-3-yl}carbamate; or 6-[2-(5-chloro-2,4-dimethoxyphenyl)ethyl]-6-cyclopentyl-3-[(3-pyridin-2-yl-1,2,4-oxadiazol-5-yl)methyl]dihydro-2H-pyran-2,4(3H)-dione.

Further provided are compounds of formula (4), wherein:

$R^1$ is cyclopentyl;

$R^2$ is —$(CH_2)_2(C_6-C_{10}$ aryl) or —$(CH_2)_2$(4-10 membered heterocyclic), wherein each of said $C_6-C_{10}$ aryl and 4-10 membered heterocyclic groups is optionally substituted with at least one $R^4$ group;

$R^3$ is —$(CH_2)$(4-10 membered heterocyclic) substituted with at least one $R^5$, and further optionally substituted with at least one $C_1-C_6$ alkyl;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1-C_6$ alkyl, $C_2-C_6$ alkenyl, and $C_2-C_6$ alkynyl, wherein said $C_1-C_6$ alkyl, $C_2-C_6$ alkenyl, and $C_2-C_6$ alkynyl groups are optionally substituted with at least one $R^5$;

$R^5$ is halogen, oxo, $C_3-C_8$ cycloalkyl, $C_6-C_{10}$ aryl, —$OR^6$, —$C(O)OR^6$, —$NR^6R^7$, and 4-10 membered heterocyclic substituted with $R^6$;

each $R^6$ and $R^7$ is independently selected from hydrogen and $C_1-C_6$ alkyl;

n is 0, 1, 2, 3, 4, or 5; and t is 0, 1, 2, 3, 4, or 5; or pharmaceutically acceptable salts or solvates thereof, with the proviso that the compound of formula (4) is not 6-{2-[4-(benzyloxy)phenyl]ethyl}-6-cyclopentyl-3-[(2-cyclopropyl-6-hydroxypyrimidin-4-yl)methyl]dihydro-2H-pyran-2,4(3H)-dione, methyl {5-[(6-cyclopentyl-6-{2-[4-(difluoromethyl)-3-fluorophenyl]ethyl}-2,4-dioxotetrahydro-2H-pyran-3-yl)methyl]isoxazol-3-yl}carbamate; or 6-[2-(5-chloro-2,4-dimethoxyphenyl)ethyl]-6-cyclopentyl-3-[(3-pyridin-2-yl-1,2,4-oxadiazol-5-yl)methyl]dihydro-2H-pyran-2,4(3H)-dione.

In addition, herein are provided compounds selected from:

2-[4-(2-{2-cyclopentyl-5-[(1,5-dimethyl-3-oxo-2-phenyl-2,3-dihydro-1H-pyrazol-4-yl)methyl]-4-hydroxy-6-oxo-3,6-dihydro-2H-pyran-2-yl}ethyl)-2-fluorophenyl]-2-methylpropanenitrile;

ethyl 2-[(6-{2-[3-chloro-4-(1-cyano-1-methylethyl)phenyl]ethyl}-6-cyclopentyl-4-hydroxy-2-oxo-5,6-dihydro-2H-pyran-3-yl)methyl][1,2,4]triazolo[1,5-a]pyrimidine-6-carboxylate;

6-[2-(5-chloro-2,4-dimethoxyphenyl)ethyl]-6-cyclopentyl-4-hydroxy-3-[(1-methyl-3-pyrazin-2-yl-1H-1,2,4-triazol-5-yl)methyl]-5,6-dihydro-2H-pyran-2-one;

6-[2-(5-chloro-2,4-dimethoxyphenyl)ethyl]-6-cyclopentyl-4-hydroxy-3-[(1-methyl-3-pyridin-2-yl-1H-1,2,4-triazol-5-yl)methyl]-5,6-dihydro-2H-pyran-2-one;

6-[2-(5-chloro-2,4-dimethoxyphenyl)ethyl]-6-cyclopentyl-4-hydroxy-3-[(1-methyl-3-phenyl-1H-1,2,4-triazol-5-yl)methyl]-5,6-dihydro-2H-pyran-2-one;

2-{4-[2-(2-cyclopentyl-4-hydroxy-5-{[1-methyl-3-(6-methylpyridin-2-yl)-1H-1,2,4-triazol-5-yl]methyl}-6-oxo-3,6-dihydro-2H-pyran-2-yl)ethyl]-2-fluorophenyl}-2-methylpropanenitrile;

2-{4-[2-(2-cyclopentyl-5-{[1,3-dimethyl-5-(4-methylpiperazin-1-yl)-1H-pyrazol-4-yl]methyl}-4-hydroxy-6-oxo-3,6-dihydro-2H-pyran-2-yl)ethyl]-2-fluorophenyl}-2-methylpropanenitrile;

2-[4-(2-{2-cyclopentyl-4-hydroxy-5-[(1-methyl-3-pyrazin-2-yl-1H-1,2,4-triazol-5-yl)methyl]-6-oxo-3,6-dihydro-2H-pyran-2-yl}ethyl)-2-fluorophenyl]-2-methylpropanenitrile;

2-[4-(2-{2-cyclopentyl-5-[(3-ethyl-1-methyl-5-morpholin-4-yl-1H-pyrazol-4-yl)methyl]-4-hydroxy-6-oxo-3,6-dihydro-2H-pyran-2-yl}ethyl)-2-fluorophenyl]-2-methylpropanenitrile;

2-[4-(2-{2-cyclopentyl-5-[(1,3-dimethyl-5-morpholin-4-yl-1H-pyrazol-4-yl)methyl]-4-hydroxy-6-oxo-3,6-dihydro-2H-pyran-2-yl}ethyl)-2-fluorophenyl]-2-methylpropanenitrile; and 2-{4-[2-(2-cyclopentyl-5-[([3-(difluoromethyl)-5-(dimethylamino)-1-methyl-1H-pyrazol-4-yl]methyl}-4-hydroxy-6-oxo-3,6-dihydro-2H-pyran-2-yl)ethyl]-2-fluorophenyl]-2-methylpropanenitrile; or pharmaceutically acceptable salts or solvates thereof.

In a still further aspect of the present invention are afforded compounds of formula (4), wherein:

$R^1$ is cyclopentyl;

$R^2$ is —(CR$^6$R$^7$)$_n$(C$_6$-C$_{10}$ aryl), wherein said C$_6$-C$_{10}$ aryl group is substituted with at least one R$^{4a}$ group, and is optionally substituted with at least one R$^{4b}$ group;

$R^3$ is —(CR$^6$R$^7$)$_t$(C$_6$-C$_{10}$ aryl) or —(CR$^6$R$^7$)$_t$(4-10 membered heterocyclic), wherein said aryl and heterocyclic moieties of said R$^3$ groups are optionally substituted with at least one R$^5$ group;

each R$^{4a}$ is independently selected from —O(4-10 membered heterocyclic), —S(4-10 membered heterocyclic), and —(CR$^6$R$^7$)$_t$(4-10 membered heterocyclic);

each R$^{4b}$ is independently selected from halo, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;

each R$^5$ is independently selected from C$_1$-C$_6$ alkyl, halo, —OR$^6$, —CF$_3$, and —CN;

each R$^6$ and R$^7$ is independently selected from hydrogen and C$_1$-C$_6$ alkyl;

n is 0, 1, 2, 3, 4, or 5; and t is 0, 1, 2, 3, 4, or 5; or pharmaceutically acceptable salts or solvates thereof.

Another aspect provides compounds of formula (4), wherein:

$R^1$ is cyclopentyl;

$R^2$ is —(CH$_2$)$_2$(C$_6$-C$_{10}$ aryl), wherein said C$_6$-C$_{10}$ aryl group is substituted with at least one R$^{4a}$ group, and is optionally substituted with at least one R$^{4b}$ group;

$R^3$ is —(CR$^6$R$^7$)$_t$(C$_6$-C$_{10}$ aryl) or —(CR$^6$R$^7$)$_t$(4-10 membered heterocyclic), wherein said aryl and heterocyclic moieties of said R$^3$ groups are optionally substituted with at least one R$^5$ group;

each R$^{4a}$ is independently selected from —O(4-10 membered heterocyclic), —S(4-10 membered heterocyclic), and —(CR$^6$R$^7$)$_t$(4-10 membered heterocyclic);

each R$^{4b}$ is independently selected from halo, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;

each R$^5$ is independently selected from C$_1$-C$_6$ alkyl, halo, —OR$^6$, —CF$_3$, and —CN;

each R$^6$ and R$^7$ is independently selected from hydrogen and C$_1$-C$_6$ alkyl; and t is 0, 1, 2, 3, 4, or 5; or pharmaceutically acceptable salts or solvates thereof.

Also provided herein are compounds of formula (4), wherein:

$R^1$ is cyclopentyl;

$R^2$ is —(CH$_2$)$_2$(C$_6$-C$_{10}$ aryl), wherein said C$_6$-C$_{10}$ aryl group is substituted with at least one R$^{4a}$ group, and is optionally substituted with at least one R$^{4b}$ group;

$R^3$ is —(CH$_2$)(C$_6$-C$_{10}$ aryl) or —(CH$_2$)(4-10 membered heterocyclic), wherein said aryl and heterocyclic moieties of said R$^3$ groups are optionally substituted with at least one R$^5$ group;

each R$^{4a}$ is independently selected from —O(4-10 membered heterocyclic), —S(4-10 membered heterocyclic), and —(CR$^6$R$^7$)$_t$(4-10 membered heterocyclic);

each R$^{4b}$ is independently selected from halo, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;

each R$^5$ is independently selected from C$_1$-C$_6$ alkyl, halo, —OR$^6$, —CF$_3$, and —CN;

each R$^6$ and R$^7$ is independently selected from hydrogen and C$_1$-C$_6$ alkyl; and t is 0 or 1; or pharmaceutically acceptable salts or solvates thereof.

Further still, provided herein are compounds of formula (4), wherein:

$R^1$ is cyclopentyl;

$R^2$ is —(CH$_2$)$_2$(C$_6$-C$_{10}$ aryl), wherein said C$_6$-C$_{10}$ aryl group is substituted with at least one R$^{4a}$ group, and is optionally substituted with at least one R$^{4b}$ group;

$R^3$ is —(CH$_2$)(4-10 membered heterocyclic), wherein said aryl and heterocyclic moieties of said R$^3$ groups are optionally substituted with at least one R$^5$ group;

each R$^{4a}$ is independently selected from —O(4-10 membered heterocyclic), —S(4-10 membered heterocyclic), and —(CR$^6$R$^7$)$_t$(4-10 membered heterocyclic);

each R$^{4b}$ is independently selected from halo, oxo, —NR$^6$R$^7$, —CF$_3$, —CN, —C(O)R$^5$, —C(O)OR$^6$, —OC(O)R$^7$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;

each R$^5$ is independently selected from C$_1$-C$_6$ alkyl, halo, —OR$^6$, —CF$_3$, and —CN;

each $R^6$ and $R^7$ is independently selected from hydrogen and $C_1$-$C_6$ alkyl; and t is 0 or 1; or pharmaceutically acceptable salts or solvates thereof.

In yet another aspect are compounds of formula (4), wherein:

$R^1$ is cyclopentyl;

$R^2$ is —(CH$_2$)$_2$(C$_6$-C$_{10}$ aryl), wherein said C$_6$-C$_{10}$ aryl group is substituted with at least one $R^{4a}$ group, and is optionally substituted with at least one $R^{4b}$ group;

$R^3$ is —(CH$_2$)([1,2,4]triazolo[1,5-a]pyrimidin-2-yl), optionally substituted with at least one substituent selected from halo and C$_1$-C$_6$ alkyl;

each $R^{4a}$ is independently selected from —O(4-10 membered heterocyclic), —S(4-10 membered heterocyclic), and —(CR$^6$R$^7$)$_t$(4-10 membered heterocyclic);

each $R^{4b}$ is independently selected from halo, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one $R^5$;

each $R^5$ is independently selected from C$_1$-C$_6$ alkyl, halo, —OR$^6$, —CF$_3$, and —CN;

each $R^6$ and $R^7$ is independently selected from hydrogen and C$_1$-C$_6$ alkyl; and t is 0 or 1; or pharmaceutically acceptable salts or solvates thereof.

Further still are compounds of formula (4), wherein:

$R^1$ is cyclopentyl;

$R^2$ is —(CH$_2$)$_2$(C$_6$-C$_{10}$ aryl), wherein said C$_6$-C$_{10}$ aryl group is substituted with at least one $R^{4a}$ group, and is optionally substituted with at least one $R^{4b}$ group;

$R^3$ is —(CH$_2$)([1,2,4]triazolo[1,5-a]pyrimidin-2-yl), substituted with at least one substituent selected from halo and C$_1$-C$_6$ alkyl;

each $R^{4a}$ is independently selected from —O(4-10 membered heterocyclic), —S(4-10 membered heterocyclic), and —(C R$^6$R$^7$)$_t$(4-10 membered heterocyclic);

each $R^{4b}$ is independently selected from halo, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one $R^5$;

each $R^5$ is independently selected from C$_1$-C$_6$ alkyl, halo, —OR$^6$, —CF$_3$, and —CN;

each $R^6$ and $R^7$ is independently selected from hydrogen and C$_1$-C$_6$ alkyl; and t is 0 or 1; or pharmaceutically acceptable salts or solvates thereof.

Also provided are compounds selected from:

6-cyclopentyl-3-[(5,7-dimethyl[1,2,4]triazolo[1,5-a]pyrimidin-2-yl)methyl]-6-{2-[3-ethyl-4-(1H-1,2,4-triazol-1-ylmethyl)phenyl]ethyl}-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-{2-[3-ethyl-4-(1H-pyrazol-1-ylmethyl)phenyl]ethyl}-4-hydroxy-5,6-dihydro-2H-pyran-2-one;

6-cyclopentyl-6-{2-[3-ethyl-4-(1H-pyrazol-1-ylmethyl)phenyl]ethyl}-4-hydroxy-3-[(6-methyl[1,2,4]triazolo[1,5-a]pyrimidin-2-yl)methyl]-5,6-dihydro-2H-pyran-2-one;

6-cyclopentyl-3-[(5,7-dimethyl[1,2,4]triazolo[1,5-a]pyrimidin-2-yl)methyl]-6-{2-[3-ethyl-4-(1,3-thiazol-2-yloxy)phenyl]ethyl}-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-{2-[3-ethyl-4-(morpholin-4-ylmethyl)phenyl]ethyl}-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one;

6-cyclopentyl-6-{2-[3-ethyl-4-(1,3-oxazol-2-yl)phenyl]ethyl}-4-hydroxy-3-([1,2,4]triazolo[1,5-a]pyrimidin-2-ylmethyl)-5,6-dihydro-2H-pyran-2-one;

6-cyclopentyl-6-{2-[3-ethyl-4-(1,3-oxazol-2-yl)phenyl]ethyl}-4-hydroxy-3-[(6-methyl[1,2,4]triazolo[1,5-a]pyrimidin-2-yl)methyl]-5,6-dihydro-2H-pyran-2-one;

(+)-6-cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one;

(−)-6-cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one; and 6-cyclopentyl-3-[(5,7-dimethyl[1,2,4]triazolo[1,5-a]pyrimidin-2-yl)methyl]-6-{2-[3-ethyl-4-(pyrrolidin-1-ylmethyl)phenyl]ethyl}-4-hydroxy-5,6-dihydro-2H-pyran-2-one; or pharmaceutically acceptable salts or solvates thereof.

In yet a further aspect of the present invention are provided compounds selected from:

6-cyclopentyl-3-[(5,7-dimethyl[1,2,4]triazolo[1,5-a]pyrimidin-2-yl)methyl]-6-[2-(5-ethyl-4-hydroxy-2-propoxyphenyl)ethyl]-4-hydroxy-5,6-dihydro-2H-pyran-2-one;

[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile;

6-cyclopentyl-3-[(5,7-dimethyl[1,2,4]triazolo[1,5-a]pyrimidin-2-yl)methyl]-6-[2-(3-ethyl-4-methylphenyl)ethyl]-4-hydroxy-5,6-dihydro-2H-pyran-2-one;

(6R)-6-cyclopentyl-6-[2-(5-ethyl-2,4-dihydroxyphenyl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-3-[(5,7-dimethyl[1,2,4]triazolo[1,5-a]pyrimidin-2-yl)methyl]-6-[2-(2-ethoxy-5-ethyl-4-hydroxyphenyl)ethyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-{2-[4-methoxy-3-(trifluoromethyl)phenyl]ethyl}-5,6-dihydro-2H-pyran-2-one;

6-cyclopentyl-3-[(5,7-dimethyl[1,2,4]triazolo[1,5-a]pyrimidin-2-yl)methyl]-6-[2-(5-ethyl-2,4-dimethoxyphenyl)ethyl]-4-hydroxy-5,6-dihydro-2H-pyran-2-one;

6-cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-3-[(5,7-dimethyl[1,2,4]triazolo[1,5-a]pyrimidin-2-yl)methyl]-6-[2-(5-ethyl-4-hydroxy-2-isopropoxyphenyl)ethyl]-4-hydroxy-5,6-dihydro-2H-pyran-2-one;

6-cyclopentyl-6-[2-(5-ethyl-4-hydroxy-2-propoxyphenyl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-3-[(5,7-dimethyl[1,2,4]triazolo[1,5-a]pyrimidin-2-yl)methyl]-6-[2-(5-ethyl-2-hydroxy-4-propoxyphenyl)ethyl]-4-hydroxy-5,6-dihydro-2H-pyran-2-one;

6-cyclopentyl-6-[2-(5-ethyl-2-hydroxy-4-propoxyphenyl)ethyl]-4-hydroxy-3-[(6-methyl[1,2,4]triazolo[1,5-a]pyrimidin-2-yl)methyl]-5,6-dihydro-2H-pyran-2-one;

6-cyclopentyl-3-[(5,7-dimethyl[1,2,4]triazolo[1,5-a]pyrimidin-2-yl)methyl]-6-[2-(5-ethyl-4-hydroxy-2-isobutoxyphenyl)ethyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-{2-[4-hydroxy-3-methyl-5-(2,2,2-trifluoroethyl)phenyl]ethyl}-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-{2-[4-hydroxy-2-propoxy-5-(2,2,2-trifluoroethyl)phenyl]ethyl}-5,6-dihydro-2H-pyran-2-one;

2-[4-(2-{2-cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-methylphenyl]-2-methylpropanenitrile;

2-[4-(2-{2-cyclopentyl-5-[(1,3-dimethyl-1H-1,2,4-triazol-5-yl)methyl]-4-hydroxy-6-oxo-3,6-dihydro-2H-pyran-2-yl}ethyl)-2-fluorophenyl]-2-methylpropanenitrile;

2-[4-(2-{2-cyclopentyl-5-[(1-ethyl-1H-pyrazol-4-yl)methyl]-4-hydroxy-6-oxo-3,6-dihydro-2H-pyran-2-yl}ethyl)-2-fluorophenyl]-2-methylpropanenitrile;

2-[4-(2-{2-cyclopentyl-4-hydroxy-5-[(1-methyl-1H-pyrazol-4-yl)methyl]-6-oxo-3,6-dihydro-2H-pyran-2-yl}ethyl)-2-fluorophenyl]-2-methylpropanenitrile;

2-[4-(2-{2-cyclopentyl-4-hydroxy-6-oxo-5-[(1,3,5-trimethyl-1H-pyrazol-4-yl)methyl]-3,6-dihydro-2H-pyran-2-yl}ethyl)-2-fluorophenyl]-2-methylpropanenitrile;

2-[4-(2-{2-cyclopentyl-5-[(1,5-dimethyl-1H-pyrazol-4-yl)methyl]-4-hydroxy-6-oxo-3,6-dihydro-2H-pyran-2-yl}ethyl)-2-fluorophenyl]-2-methylpropanenitrile;

2-[4-(2-{2-cyclopentyl-5-[(1-ethyl-3-methyl-1H-pyrazol-4-yl)methyl]-4-hydroxy-6-oxo-3,6-dihydro-2H-pyran-2-yl}ethyl)-2-fluorophenyl]-2-methylpropanenitrile;

2-[4-(2-{5-[(5-chloro-1,3-dimethyl-1H-pyrazol-4-yl)methyl]-2-cyclopentyl-4-hydroxy-6-oxo-3,6-dihydro-2H-pyran-2-yl}ethyl)-2-fluorophenyl]-2-methylpropanenitrile;

2-{4-[2-(5-{[5-chloro-1-methyl-3-(trifluoromethyl)-1H-pyrazol-4-yl]methyl}-2-cyclopentyl-4-hydroxy-6-oxo-3,6-dihydro-2H-pyran-2-yl)ethyl]-2-fluorophenyl}-2-methylpropanenitrile;

2-(2-chloro-4-{2-[2-cyclopentyl-4-hydroxy-5-(imidazo[1,2-b][1,2,4]triazin-6-ylmethyl)-6-oxo-3,6-dihydro-2H-pyran-2-yl]ethyl}phenyl)-2-methylpropanenitrile;

6-[2-(5-chloro-2,4-dimethoxyphenyl)ethyl]-6-cyclopentyl-3-[(1-ethyl-3,5-dimethyl-1H-pyrazol-4-yl)methyl]-4-hydroxy-5,6-dihydro-2H-pyran-2-one;

6-[2-(3-chloro-4-isopropoxyphenyl)ethyl]-6-cyclopentyl-3-[(1-ethyl-3,5-dimethyl-1H-pyrazol-4-yl)methyl]-4-hydroxy-5,6-dihydro-2H-pyran-2-one;

2-[4-(2-{2-cyclopentyl-5-[(2-ethyl-5-oxo-5H-[1,3,4]thiadiazolo[3,2-a]pyrimidin-7-yl)methyl]-4-hydroxy-6-oxo-3,6-dihydro-2H-pyran-2-yl}ethyl)-2-fluorophenyl]-2-methylpropanenitrile;

2-[2-chloro-4-(2-{2-cyclopentyl-5-[(1,3-dimethyl-1H-1,2,4-triazol-5-yl)methyl]-4-hydroxy-6-oxo-3,6-dihydro-2H-pyran-2-yl}ethyl)phenyl]-2-methylpropanenitrile;

2-[2-chloro-4-(2-{2-cyclopentyl-5-[(1-ethyl-1H-pyrazol-4-yl)methyl]-4-hydroxy-6-oxo-3,6-dihydro-2H-pyran-2-yl}ethyl)phenyl]-2-methylpropanenitrile;

2-[2-chloro-4-(2-{2-cyclopentyl-4-hydroxy-5-[(1-methyl-1H-pyrazol-4-yl)methyl]-6-oxo-3,6-dihydro-2H-pyran-2-yl}ethyl)phenyl]-2-methylpropanenitrile;

2-[2-chloro-4-(2-{2-cyclopentyl-4-hydroxy-6-oxo-5-[(1,3,5-trimethyl-1H-pyrazol-4-yl)methyl]-3,6-dihydro-2H-pyran-2-yl}ethyl)phenyl]-2-methylpropanenitrile;

2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-methylpropanenitrile;

6-cyclopentyl-3-[(5,7-dimethyl[1,2,4]triazolo[1,5-a]pyrimidin-2-yl)methyl]-4-hydroxy-6-{2-[4-hydroxy-3-(trifluoromethyl)phenyl]ethyl}-5,6-dihydro-2H-pyran-2-one;

2-[4-(2-{2-cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-fluoro-5-hydroxyphenyl]-2-methylpropanenitrile;

[4-(2-{2-cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-ethylphenyl]acetonitrile;

[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]acetonitrile;

2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-ethylbutanenitrile;

2-[4-(2-{2-cyclopentyl-5-[(3-ethyl-1-methyl-1H-1,2,4-triazol-5-yl)methyl]-4-hydroxy-6-oxo-3,6-dihydro-2H-pyran-2-yl}ethyl)-2-fluorophenyl]-2-methylpropanenitrile;

2-[4-(2-{2-cyclopentyl-5-[(1-ethyl-3,5-dimethyl-1H-pyrazol-4-yl)methyl]-4-hydroxy-6-oxo-3,6-dihydro-2H-pyran-2-yl}ethyl)-2-fluorophenyl]-2-methylpropanenitrile; and 2-[4-(2-{2-cyclopentyl-5-[(1-ethyl-5-methyl-1H-1,2,4-triazol-3-yl)methyl]-4-hydroxy-6-oxo-3,6-dihydro-2H-pyran-2-yl}ethyl)-2-fluorophenyl]-2-methylpropanenitrile;

or pharmaceutically acceptable salts or solvates thereof.

In yet another aspect of the present invention are afforded compounds selected from:

(+)-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile;

(−)-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile;

(+)-6-cyclopentyl-3-[(5,7-dimethyl[1,2,4]triazolo[1,5-a]pyrimidin-2-yl)methyl]-6-[2-(5-ethyl-4-hydroxy-2,3-dihydro-1-benzofuran-7-yl)ethyl]-4-hydroxy-5,6-dihydro-2H-pyran-2-one;

(−)-6-cyclopentyl-3-[(5,7-dimethyl[1,2,4]triazolo[1,5-a]pyrimidin-2-yl)methyl]-6-[2-(5-ethyl-4-hydroxy-2,3-dihydro-1-benzofuran-7-yl)ethyl]-4-hydroxy-5,6-dihydro-2H-pyran-2-one;

(+)-6-cyclopentyl-3-[(5,7-dimethyl[1,2,4]triazolo[1,5-a]pyrimidin-2-yl)methyl]-6-[2-(2-ethoxy-5-ethyl-4-hydroxyphenyl)ethyl]-4-hydroxy-5,6-dihydro-2H-pyran-2-one;

(−)-6-cyclopentyl-3-[(5,7-dimethyl[1,2,4]triazolo[1,5-a]pyrimidin-2-yl)methyl]-6-[2-(2-ethoxy-5-ethyl-4-hydroxyphenyl)ethyl]-4-hydroxy-5,6-dihydro-2H-pyran-2-one;

(+)-6-cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one;

(−)-6-cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one;

(+)-6-cyclopentyl-3-[(5,7-dimethyl[1,2,4]triazolo[1,5-a]pyrimidin-2-yl)methyl]-4-hydroxy-6-{2-[4-hydroxy-3-(2,2,2-trifluoroethyl)phenyl]ethyl}-5,6-dihydro-2H-pyran-2-one; and (−)-6-cyclopentyl-3-[(5,7-dimethyl[1,2,4]triazolo[1,5-a]pyrimidin-2-yl)methyl]-4-hydroxy-6-{2-[4-hydroxy-3-(2,2,2-trifluoroethyl)phenyl]ethyl}-5,6-dihydro-2H-pyran-2-one; or pharmaceutically acceptable salts or solvates thereof.

Furthermore, the present invention comprises compounds selected from:

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]methanesulfonamide;

N-[4-(2-{2-cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-ethylphenyl]methanesulfonamide;

N-(4-{2-[2-cyclopentyl-4-hydroxy-6-oxo-5-([1,2,4]triazolo[1,5-a]pyrimidin-2-ylmethyl)-3,6-dihydro-2H-pyran-2-yl]ethyl}-2-ethylphenyl)methanesulfonamide;

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]ethanesulfonamide;

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]propane-1-sulfonamide;

methyl 4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzoate;

6-cyclopentyl-6-(2-{4-[(dimethylamino)methyl]-3-ethylphenyl}ethyl)-3-[(5,7-dimethyl[1,2,4]triazolo[1,5-a]pyrimidin-2-yl)methyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-{2-[3-ethyl-4-(methoxymethyl)phenyl]ethyl}-4-hydroxy-5,6-dihydro-2H-pyran-2-one;

4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethyl-N-methylbenzamide;

6-{2-[4-(aminomethyl)-3-ethylphenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

tert-butyl 4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzylcarbamate;

6-cyclopentyl-6-[2-(4-{[(cyclopropylmethyl)amino]methyl}-3-ethylphenyl)ethyl]-3-[(5,7-dimethyl[1,2,4]triazolo[1,5-a]pyrimidin-2-yl)methyl]-4-hydroxy-5,6-dihydro-2H-pyran-2-one;

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide;

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]acetamide;

6-cyclopentyl-3-[(5,7-dimethyl[1,2,4]triazolo[1,5-a]pyrimidin-2-yl)methyl]-6-{2-[5-ethyl-2-(3-methoxypropyl)phenyl]ethyl}-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-{2-[3-ethyl-4-(3-methoxypropyl)phenyl]ethyl}-4-hydroxy-5,6-dihydro-2H-pyran-2-one;

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorobenzyl]acetamide;

N-{1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorophenyl]-1-methylethyl}methanesulfonamide;

6-cyclopentyl-3-[(5,7-dimethyl[1,2,4]triazolo[1,5-a]pyrimidin-2-yl)methyl]-6-{2-[4-(ethylsulfonyl)phenyl]ethyl}-4-hydroxy-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-(2-{4-[(trifluoromethyl)sulfonyl]phenyl}ethyl)-5,6-dihydro-2H-pyran-2-one;

tert-butyl 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethyl(methyl)carbamate;

tert-butyl 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethylcarbamate;

6-{2-[4-(2-aminoethoxy)-3-ethylphenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-(2-{3-ethyl-4-[2-(methylamino)ethoxy]phenyl}ethyl)-4-hydroxy-5,6-dihydro-2H-pyran-2-one;

6-cyclopentyl-3-[(5,7-dimethyl[1,2,4]triazolo[1,5-a]pyrimidin-2-yl)methyl]-6-{2-[5-fluoro-4-(hydroxymethyl)-2-methoxyphenyl]ethyl}-4-hydroxy-5,6-dihydro-2H-pyran-2-one;

N-{(1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethyl}ethanesulfonamide;

N-{(1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethyl}-2,2,2-trifluoroethanesulfonamide;

N-{(1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethyl}methanesulfonamide;

tert-butyl (1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethylcarbamate;

6-(2-{4-[(1R)-1-aminoethyl]phenyl}ethyl)-6-cyclopentyl-3-[(5,7-dimethyl[1,2,4]triazolo[1,5-a]pyrimidin-2-yl)methyl]-4-hydroxy-5,6-dihydro-2H-pyran-2-one;

6-[2-(5-acetyl-4-hydroxy-2-methoxyphenyl)ethyl]-6-cyclopentyl-3-[(5,7-dimethyl[1,2,4]triazolo[1,5-a]pyrimidin-2-yl)methyl]-4-hydroxy-5,6-dihydro-2H-pyran-2-one;

6-{2-[3-chloro-4-(methylsulfonyl)phenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorobenzoic acid;

2-chloro-4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)benzoic acid;

6-cyclopentyl-3-[(5,7-dimethyl[1,2,4]triazolo[1,5-a]pyrimidin-2-yl)methyl]-4-hydroxy-6-{2-[4-(1-hydroxy-1-methylethyl)-3-methylphenyl]ethyl}-5,6-dihydro-2H-pyran-2-one;

6-cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one;

6-{2-[3-chloro-4-(1-hydroxy-1-methylethyl)phenyl]ethyl}-6-cyclopentyl-4-hydroxy-3-([1,2,4]triazolo[1,5-a]pyrimidin-2-ylmethyl)-5,6-dihydro-2H-pyran-2-one;

6-{2-[3-chloro-4-(1-hydroxy-1-methylethyl)phenyl]ethyl}-6-cyclopentyl-4-hydroxy-3-[(6-methyl[1,2,4]triazolo[1,5-a]pyrimidin-2-yl)methyl]-5,6-dihydro-2H-pyran-2-one;

6-{2-[3-chloro-4-(1-hydroxy-1-methylethyl)phenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

6-{2-[3-chloro-4-(1-hydroxy-1-methylethyl)phenyl]ethyl}-3-[(6-chloro[1,2,4]triazolo[1,5-a]pyrimidin-2-yl)methyl]-6-cyclopentyl-4-hydroxy-5,6-dihydro-2H-pyran-2-one;

6-cyclopentyl-3-[(5,7-dimethyl[1,2,4]triazolo[1,5-a]pyrimidin-2-yl)methyl]-4-hydroxy-6-{2-[4-(methylsulfonyl)-3-(trifluoromethyl)phenyl]ethyl}-5,6-dihydro-2H-pyran-2-one;

methyl 4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorobenzoate; and methyl 2-chloro-4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)benzoate; or pharmaceutically acceptable salts or solvates thereof.

In still another aspect are compounds selected from:

(+)-6-cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one;

(−)-6-cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one;

(+)-N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide;

(−)-N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide;

(+)-N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethyl benzyl]acetamide;

(−)-N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]acetamide;

(+)-6-cyclopentyl-6-(2-{4-[(dimethylamino)methyl]-3-ethylphenyl}ethyl)-3-[(5,7-dimethyl[1,2,4]triazolo[1,5-a]pyrimidin-2-yl)methyl]-4-hydroxy-5,6-dihydro-2H-pyran-2-one; and (−)-6-cyclopentyl-6-(2-{4-[(dimethylamino)methyl]-3-ethylphenyl}ethyl)-3-[(5,7-dimethyl[1,2,4]triazolo[1,5-a]pyrimidin-2-yl)methyl]-4-hydroxy-5,6-dihydro-2H-pyran-2-one; or pharmaceutically acceptable salts or solvates thereof.

Further afforded are compounds selected from:

{4-[2-(2-cyclopentyl-4,6-dioxotetrahydro-2H-pyran-2-yl)ethyl]-2-ethyl phenyl}acetonitrile;

N-{4-[2-(2-cyclopentyl-4,6-dioxotetrahydro-2H-pyran-2-yl)ethyl]-2-ethylphenyl}methanesulfonamide;

6-cyclopentyl-6-{2-[3-ethyl-4-(1,3-oxazol-2-yl)phenyl]ethyl}dihydro-2H-pyran-2,4(3H)-dione;

N-((1R)-1-{4-[2-(2-cyclopentyl-4,6-dioxotetrahydro-2H-pyran-2-yl)ethyl]phenyl}ethyl)ethanesulfonamide;

6-cyclopentyl-6-{2-[3-fluoro-4-(methylsulfonyl)phenyl]ethyl}dihydro-2H-pyran-2,4(3H)-dione;

6-cyclopentyl-6-(2-{4-[(trifluoromethyl)sulfonyl]phenyl}ethyl)dihydro-2H-pyran-2,4(3H)-dione;

tert-butyl 2-{4-[2-(2-cyclopentyl-4,6-dioxotetrahydro-2H-pyran-2-yl)ethyl]-2-ethylphenoxy}ethyl(methyl)carbamate;

tert-butyl 2-{4-[2-(2-cyclopentyl-4,6-dioxotetrahydro-2H-pyran-2-yl)ethyl]-2-ethylphenoxy}ethylcarbamate;

tert-butyl 2-{4-[2-(2-cyclopentyl-4,6-dioxotetrahydro-2H-pyran-2-yl)ethyl]-2-ethyl-5-methoxyphenoxy}ethyl(methyl)carbamate;

N-((1R)-1-{4-[2-(2-cyclopentyl-4,6-dioxotetrahydro-2H-pyran-2-yl)ethyl]phenyl}ethyl)-2,2,2-trifluoroethanesulfonamide;

tert-butyl (1R)-1-{4-[2-(2-cyclopentyl-4,6-dioxotetrahydro-2H-pyran-2-yl)ethyl]phenyl}ethylcarbamate;

6-[2-(5-acetyl-4-hydroxy-2-methoxyphenyl)ethyl]-6-cyclopentyldihydro-2H-pyran-2,4(3H)-dione;

2-chloro-4-[2-(2-cyclopentyl-4,6-dioxotetrahydro-2H-pyran-2-yl)ethyl]benzoic acid;

6-{2-[3-chloro-4-(methylsulfonyl)phenyl]ethyl}-6-cyclopentyldihydro-2H-pyran-2,4(3H)-dione;

6-cyclopentyl-6-{2-[4-(methylsulfonyl)-3-(trifluoromethyl)phenyl]ethyl}dihydro-2H-pyran-2,4(3H)-dione;

6-cyclopentyl-6-{2-[3-ethyl-4-(hydroxymethyl)phenyl]ethyl}dihydro-2H-pyran-2,4(3H)-dione;

methyl 4-[2-(2-cyclopentyl-4,6-dioxotetrahydro-2H-pyran-2-yl)ethyl]-2-fluorobenzoate;

4-[2-(2-cyclopentyl-4,6-dioxotetrahydro-2H-pyran-2-yl)ethyl]-2-fluorobenzoic acid;

methyl 2-chloro-4-[2-(2-cyclopentyl-4,6-dioxotetrahydro-2H-pyran-2-yl)ethyl]benzoate;

2-[4-[2-(2-cyclopentyl-4,6-dioxotetrahydro-2H-pyran-2-yl)ethyl]-2-(trifluoromethyl)phenyl]-2-methylpropanenitrile;

[4-[2-(2-cyclopentyl-4,6-dioxotetrahydro-2H-pyran-2-yl)ethyl]-2-(trifluoromethyl)phenyl]acetonitrile;

1-[4-[2-(2-cyclopentyl-4,6-dioxotetrahydro-2H-pyran-2-yl)ethyl]-2-(trifluoromethyl)phenyl]cyclopropanecarbonitrile;

2-[4-[2-(2-cyclopentyl-4,6-dioxotetrahydro-2H-pyran-2-yl)ethyl]-2-(trifluoromethyl)phenyl]-2-ethylbutanenitrile;

tert-butyl 4-[4-(2-cyclopentyl-4,6-dioxotetrahydro-2H-pyran-2-yl) butyl]piperidine-1-carboxylate;

6-cyclopentyl-6-[2-(2-ethyl-5-methoxypyridin-4-yl)ethyl]dihydro-2H-pyran-2,4(3H)-dione;

6-cyclopentyl-6-[2-(6-ethyl-3-methoxypyridin-2-yl)ethyl]dihydro-2H-pyran-2,4(3H)-dione;

6-cyclopentyl-6-[2-(5-methoxy-2-methylpyridin-4-yl)ethyl]dihydro-2H-pyran-2,4(3H)-dione; and 2-{3-chloro-5-[2-(2-cyclopentyl-4,6-dioxotetrahydro-2H-pyran-2-yl)ethyl]pyridin-2-yl}-2-methylpropanenitrile; or pharmaceutically acceptable salts or solvates thereof.

The present invention also affords compounds selected from:

6-cyclopentyl-6-{2-[2-(cyclopropylmethoxy)-5-ethyl-4-hydroxyphenyl]ethyl}-3-[(5,7-dimethyl[1,2,4]triazolo[1,5-a]pyrimidin-2-yl)methyl]-4-hydroxy-5,6-dihydro-2H-pyran-2-one;

6-{2-[2-(cyclobutylmethoxy)-5-ethyl-4-hydroxyphenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one;

1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]cyclopropanecarbonitrile 3-[(2-amino-7H-purin-6-yl)thio]-6-[2-(5-chloro-2,4-dimethoxyphenyl)ethyl]-6-cyclopentyldihydro-2H-pyran-2,4(3H)-dione;

2-[2-chloro-4-(2-{2-cyclopentyl-5-[(5,7-dimethyl[1,2,4]triazolo[1,5-a]pyrimidin-2-yl)(methyl)amino]-4,6-dioxotetrahydro-2H-pyran-2-yl}ethyl)phenyl]-2-methylpropanenitrile;

2-[2-chloro-4-(2-{2-cyclopentyl-5-[(5,7-dimethyl[1,2,4]triazolo[1,5-a]pyrimidin-2-yl)oxy]-4,6-dioxotetrahydro-2H-pyran-2-yl}ethyl)phenyl]-2-methylpropanenitrile;

1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]cyclopropanecarbonitrile;

tert-butyl 4-(4-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}butyl)piperidine-1-carboxylate; and 6-cyclopentyl-3-[(5,7-dimethyl[1,2,4]triazolo[1,5-a]pyrimidin-2-yl)methyl]-4-hydroxy-6-(4-piperidin-4-ylbutyl)-5,6-dihydro-2H-pyran-2-one; or pharmaceutically acceptable salts or solvates thereof.

The invention also relates to a method for the treatment of Hepatitis C virus (HCV) in a mammal, such as a human, comprising administering to said mammal an amount of a compound of the present invention or a salt or solvate thereof that is effective in treating HCV.

In a further aspect of the present invention are provided methods for the treatment of a mammal, such as a human, suffering from infection with Hepatitis C virus, comprising administering to said mammal a Hepatitis C virus-inhibiting amount of a compound of the present invention, or a pharmaceutically acceptable salt, prodrug, pharmaceutically active metabolite, or solvate thereof.

The present invention also relates to a method of inhibiting Hepatitis C polymerase, comprising contacting said polymerase with a polymerase-inhibiting amount of a compound of the present invention, or a pharmaceutically acceptable salt, prodrug, pharmaceutically active metabolite, or solvate thereof.

The present invention is also directed to a pharmaceutical composition for the treatment of Hepatitis C virus (HCV) in a mammal, such as a human, comprising an amount of a compound the present invention, or a pharmaceutically acceptable salt, prodrug, pharmaceutically active metabolite, or solvate thereof, that is effective in treating Hepatitis C virus in an infected mammal, and a pharmaceutically acceptable carrier.

The present invention is also directed to inhibition of Hepatitis C virus replication in a mammal, such as a human, comprising administering to said mammal a Hepatitis C virus replication-inhibiting amount of a compound of the present invention.

The present invention is further directed to a method of inhibiting Hepatitis C virus RdRp protein activity, comprising contacting the protein with an effective amount of a compound of the present invention, or a pharmaceutically acceptable salt, prodrug, pharmaceutically active metabolite, or solvate thereof. For Example, HCV activity may be inhibited in mammalian tissue by administering an HCV-inhibiting agent according to the invention.

The present invention also relates to the use of the compounds of the invention in the preparation of a medicament for the treatment of a mammal suffering from infection with Hepatitis C virus. The medicament may comprise a Hepatitis C virus-inhibiting amount of a compound or compounds of the invention and a pharmaceutically acceptable carrier or carriers.

In a further aspect of the present invention are provided compounds of formula (7),

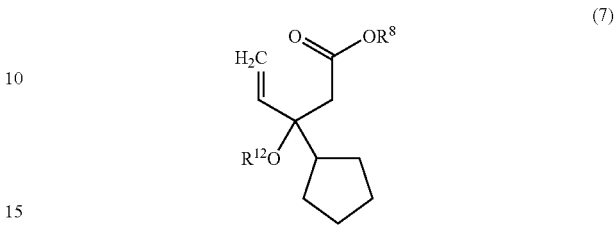

(7)

wherein:
$R^8$ is hydrogen or $C_1$-$C_6$ alkyl;
$R^{12}$ is hydrogen or —C(O)$R^{13}$; and
$R^{13}$ is $C_1$-$C_6$ alkyl or —(CH$_2$)(C$_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N(C$_1$-$C_6$ alkyl)$_2$;
or a salt thereof.

Also provided herein are compounds of formula (7a),

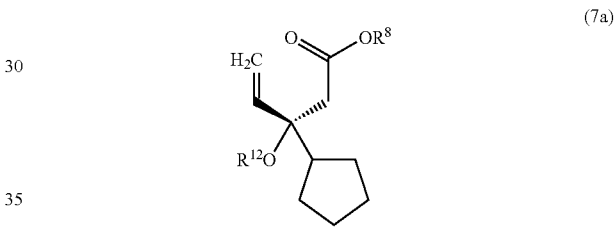

(7a)

$R^8$ is hydrogen or $C_1$-$C_6$ alkyl;
$R^{12}$ is hydrogen or —C(O)$R^{13}$; and
$R^{13}$ is $C_1$-$C_6$ alkyl or —(CH$_2$)(C$_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N(C$_1$-$C_6$ alkyl)$_2$;
or a salt thereof.

In yet another aspect are compounds of formula (7b),

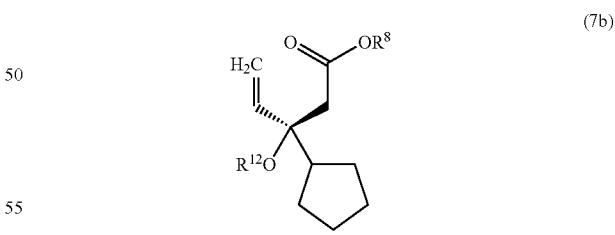

(7b)

$R^8$ is hydrogen or $C_1$-$C_6$ alkyl;
$R^{12}$ is hydrogen or —C(O)$R^{13}$; and
$R^{13}$ is $C_1$-$C_6$ alkyl or —(CH$_2$)(C$_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N(C$_1$-$C_6$ alkyl)$_2$;
or a salt thereof.

Still further are provided any of the above compounds of formula (7), (7a), or (7b), wherein $R^8$ is hydrogen or any of the compounds wherein $R^8$ is $C_1$-$C_6$ alkyl.

Further provided herein are compounds of formula (8),

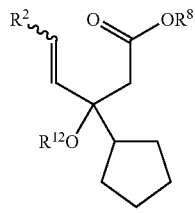

(8)

wherein:

R² is —(CR⁶R⁷)ₙC₆-C₁₀ aryl or —(CR⁶R⁷)ₙ(5-6 membered heterocyclic), wherein said C₆-C₁₀ aryl or 5-6 membered heterocyclic group is optionally substituted with at least one R⁴ group;

each R⁴ is independently selected from halo, —OR⁶, oxo, —NR⁶R⁷, —CF₃, —CN, —C(O)R⁶, —C(O)OR⁶, —OC(O)R⁶, —NR⁶C(O)R⁷, —NR⁶C(O)OR⁷, —NR⁶C(O)NR⁶R⁷, —C(O)NR⁶R⁷, —SO₂NR⁶R⁷, —NR⁶SO₂R⁷, C₁-C₆ alkyl, C₂-C₆ alkenyl, and C₂-C₆ alkynyl, wherein said C₁-C₆ alkyl, C₂-C₆ alkenyl, and C₂-C₆ alkynyl groups are optionally substituted with at least one R⁵;

R⁵ is oxo, C₃-C₈ cycloalkyl, C₆-C₁₀ aryl, —OR⁶, —C(O)OR⁶, —NR⁶R⁷, —CN, and 4-10 membered heterocyclic substituted with R⁶;

each R⁶ and R⁷ is independently selected from hydrogen and C₁-C₆ alkyl;

R⁸ is hydrogen or C₁-C₆ alkyl;

R¹² is hydrogen or —C(O)R¹³;

R¹³ is C₁-C₆ alkyl or —(CH₂)(C₆-C₁₀ aryl), wherein said C₆-C₁₀ aryl group is optionally substituted with at least one substituent selected from halogen, C₁-C₆ alkyl, —OH, —OCH₃, and —N(C₁-C₆ alkyl)₂; and n is 0, 1, 2, 3, 4, or 5;

or a salt thereof.

In still another aspect are provided compounds of formula (8a),

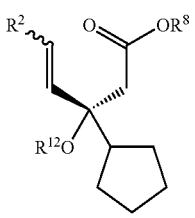

(8a)

wherein:

R² is —(CR⁶R⁷)ₙC₆-C₁₀ aryl or —(CR⁶R⁷) (5-6 membered heterocyclic), wherein said C₆-C₁₀ aryl or 5-6 membered heterocyclic group is optionally substituted with at least one R⁴ group;

each R⁴ is independently selected from halo, —OR⁶, oxo, —NR⁶R⁷, —CF₃, —CN, —C(O)R⁶, —C(O)OR⁶, —OC(O)R⁶, —NR⁶C(O)R⁷, —NR⁶C(O)OR⁷, —NR⁶C(O)NR⁶R⁷, —C(O)NR⁶R⁷, —SO₂NR⁶R⁷, —NR⁶SO₂R⁷, C₁-C₆ alkyl, C₂-C₆ alkenyl, and C₂-C₆ alkynyl, wherein said C₁-C₆ alkyl, C₂-C₆ alkenyl, and C₂-C₆ alkynyl groups are optionally substituted with at least one R⁵;

R⁵ is oxo, C₃-C₈ cycloalkyl, C₆-C₁₀ aryl, —OR⁶, —C(O)OR⁶, —NR⁶R⁷, —CN, and 4-10 membered heterocyclic substituted with R⁶;

each R⁶ and R⁷ is independently selected from hydrogen and C₁-C₆ alkyl;

R⁸ is hydrogen or C₁-C₆ alkyl;

R¹² is hydrogen or —C(O)R¹³;

R¹³ is C₁-C₆ alkyl or —(CH₂)(C₆-C₁₀ aryl), wherein said C₆-C₁₀ aryl group is optionally substituted with at least one substituent selected from halogen, C₁-C₆ alkyl, —OH, —OCH₃, and —N(C₁-C₆ alkyl)₂; and n is 0, 1, 2, 3, 4, or 5;

or a salt thereof.

Further provided herein are compounds of formula (8b),

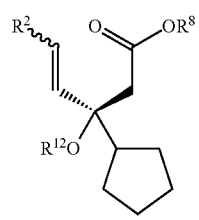

(8b)

wherein:

R² is —(CR⁶R⁷)ₙC₆-C₁₀ aryl or —(CR⁶R⁷)ₙ(5-6 membered heterocyclic), wherein said C₆-C₁₀ aryl or 5-6 membered heterocyclic group is optionally substituted with at least one R⁴ group;

each R⁴ is independently selected from halo, —OR⁶, oxo, —NR⁶R⁷, —CF₃, —CN, —C(O)R⁶, —C(O)OR⁶, —OC(O)R⁶, —NR⁶C(O)R⁷, —NR⁶C(O)OR⁷, —NR⁶C(O)NR⁶R⁷, —C(O)NR⁶R⁷, —SO₂NR⁶R⁷, —NR⁶SO₂R⁷, C₁-C₆ alkyl, C₂-C₆ alkenyl, and C₂-C₆ alkynyl, wherein said C₁-C₆ alkyl, C₂-C₆ alkenyl, and C₂-C₆ alkynyl groups are optionally substituted with at least one R⁵;

R⁵ is oxo, C₃-C₈ cycloalkyl, C₆-C₁₀ aryl, —OR⁶, —C(O)OR⁶, —NR⁶R⁷, —CN, and 4-10 membered heterocyclic substituted with R⁶;

each R⁶ and R⁷ is independently selected from hydrogen and C₁-C₆ alkyl;

R⁸ is hydrogen or C₁-C₆ alkyl; and

R¹² is hydrogen or —C(O)R¹³;

R¹³ is C₁-C₆ alkyl or —(CH₂)(C₆-C₁₀ aryl), wherein said C₆-C₁₀ aryl group is optionally substituted with at least one substituent selected from halogen, C₁-C₆ alkyl, —OH, —OCH₃, and —N(C₁-C₆ alkyl)₂; and n is 0, 1, 2, 3, 4, or 5;

or a salt thereof.

Still further included herein are any of the above of formula (8), (8a), or (8b), wherein:

R² is —(CR⁶R⁷)ₙC₆-C₁₀ aryl, optionally substituted with at least one R⁴ group;

each R⁴ is independently selected from halo, —OR⁶, oxo, —NR⁶R⁷, —CF₃, —CN, —C(O)R⁶, —C(O)OR⁶, —OC(O)R⁶, —NR⁶C(O)R⁷, —NR⁶C(O)OR⁷, —NR⁶C(O)NR⁶R⁷, —C(O)NR⁶R⁷, —SO₂NR⁶R⁷, —NR⁶SO₂R⁷, C₁-C₆ alkyl, C₂-C₆ alkenyl, and C₂-C₆ alkynyl, wherein said C₁-C₆ alkyl, C₂-C₆ alkenyl, and C₂-C₆ alkynyl groups are optionally substituted with at least one R⁵;

R⁵ is oxo, C₃-C₈ cycloalkyl, C₆-C₁₀ aryl, —OR⁶, —C(O)OR⁶, —NR⁶R⁷, —CN, and 4-10 membered heterocyclic substituted with R⁶;

each R⁶ and R⁷ is independently selected from hydrogen and C₁-C₆ alkyl;

R⁸ is hydrogen or C₁-C₆ alkyl; and

R¹² is hydrogen or —C(O)R¹³;

$R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl$)_2$; and n is 0, 1, 2, 3, 4, or 5;

or a salt thereof.

Still further included herein are any of the above of formula (8), (8a), or (8b), wherein:

$R^2$ is $C_6$-$C_{10}$ aryl substituted with at least one substituent selected from halo, —$OR^6$, —$CF_3$, —CN, and $C_1$-$C_6$ alkyl, wherein said $C_1$-$C_6$ alkyl is optionally substituted with at least one $R^5$;

$R^5$ is oxo, $C_3$-$C_8$ cycloalkyl, $C_6$-$C_{10}$ aryl, —$OR^6$, —$C(O)OR^6$, —$NR^6R^7$, —CN, and 4-10 membered heterocyclic substituted with $R^6$;

each $R^6$ and $R^7$ is independently selected from hydrogen and $C_1$-$C_6$ alkyl; and $R^8$ is hydrogen or $C_1$-$C_6$ alkyl;

$R^{12}$ is hydrogen or —$C(O)R^{13}$; and $R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl$)_2$;

or a salt thereof.

Still further included herein are any of the above of formula (8), (8a), or (8b), wherein:

$R^2$ is $C_6$-$C_{10}$ aryl substituted with halo and —$C(CH_3)_2CN$; and $R^8$ is hydrogen or $C_1$-$C_6$ alkyl; and $R^{12}$ is hydrogen;

or a salt thereof.

Still further included herein are any of the above of formula (8), (8a), or (8b), wherein:, wherein:

$R^2$ is $C_6$-$C_{10}$ aryl substituted with fluorine and —$C(CH_3)_2CN$; and $R^8$ is hydrogen or $C_1$-$C_6$ alkyl; and $R^{12}$ is hydrogen;

or a salt thereof.

Still further included herein are any of the above of formula (8), (8a), or (8b), wherein:

$R^2$ is $C_6$-$C_{10}$ aryl substituted with chlorine and —$C(CH_3)_2CN$; and $R^8$ is hydrogen or $C_1$-$C_6$ alkyl; and $R^{12}$ is hydrogen;

or a salt thereof.

The present invention also affords compounds of formula (8c),

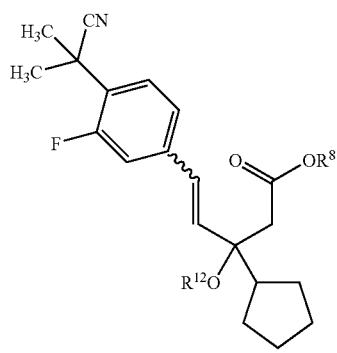

(8c)

wherein;

$R^8$ is hydrogen or $C_1$-$C_6$ alkyl;

$R^{12}$ is hydrogen or —$C(O)R^{13}$; and $R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl$)_2$;

or a salt thereof.

Further provided herein are compounds of formula (8c), wherein $R^{12}$ is hydrogen; or a salt thereof.

In another aspect of the present invention are provides compounds of formula (8d),

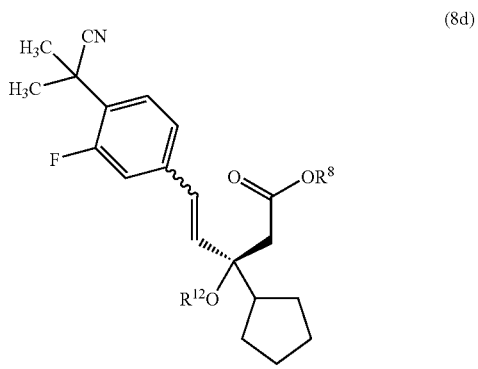

(8d)

wherein:

$R^8$ is hydrogen or $C_1$-$C_6$ alkyl;

$R^{12}$ is hydrogen or —$C(O)R^{13}$; and $R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl$)_2$;

or a salt thereof.

Also provided herein are compounds of formula (8d), wherein $R^{12}$ is hydrogen; or a salt thereof.

The present invention further provides compounds of formula (8e),

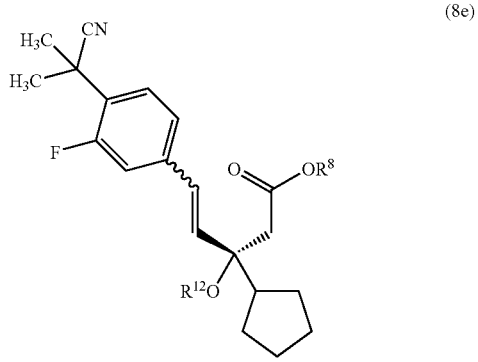

(8e)

wherein:

$R^8$ is hydrogen or $C_1$-$C_6$ alkyl;

$R^{12}$ is hydrogen or —$C(O)R^{13}$; and $R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl$)_2$;

or a salt thereof.

In an additional aspect are compounds of formula (8e), or a salt thereof, wherein $R^{12}$ is hydrogen.

In still an additional aspect of the present invention are afforded compounds of formula (8f),

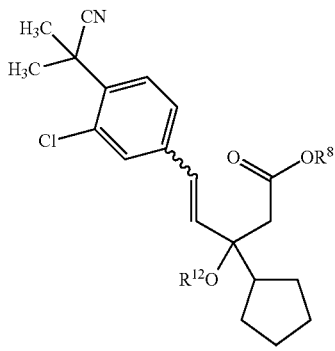

(8f)

wherein:
R[8] is hydrogen or $C_1$-$C_6$ alkyl;
R[12] is hydrogen or —C(O)R[13]; and
R[13] is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;
or a salt thereof.

Additionally provided are compounds of formula (8f), or a salt thereof, wherein R[12] is hydrogen.

In yet another aspect are provided compounds of formula (8g),

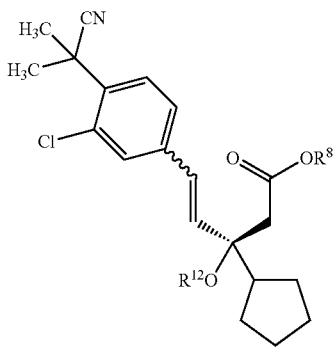

(8g)

wherein:
R[8] is hydrogen or $C_1$-$C_6$ alkyl;
R[12] is hydrogen or —C(O)R[13]; and
R[13] is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;
or a salt thereof.

Further still are compounds of formula (8g), or a salt thereof, wherein R[12] is hydrogen.

In a further aspect of the present invention are provided compounds of formula (8h),

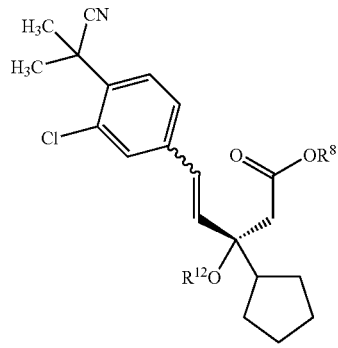

(8h)

wherein:
R[8] is hydrogen or $C_1$-$C_6$ alkyl;
R[12] is hydrogen or —C(O)R[13]; and
R[13] is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;
or a salt thereof.

In still another aspect are compounds of formula (8h), or a salt thereof, wherein R[12] is hydrogen.

The present invention also affords compounds according to any one of formula (8), (8a), (8b), (8c), (8d), (8e), (8f), (8g), and (8h), wherein R[8] is hydrogen, or any of those compounds wherein R[8] is $C_1$-$C_6$ alkyl.

Further provided herein are compounds of formula (8), (8a), or (8b), wherein:
R[2] is —(CR[6]R[7])$_n$(5-6 membered heterocyclic), optionally substituted with at least one R[4] group;
each R[4] is independently selected from halo, —OR[6], oxo, —NR[6]R[7], —CF$_3$, —CN, —C(O)R[6], —C(O)OR[6], —OC(O)R[6], —NR[6]C(O)R[7], —NR[6]C(O)OR[7], —NR[6]C(O)NR[6]R[7], —C(O)NR[6]R[7], —SO$_2$NR[6]R[7], —NR[6]SO$_2$R[7], $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one R[5];
R[5] is oxo, $C_3$-$C_8$ cycloalkyl, $C_6$-$C_{10}$ aryl, —OR[6], —C(O)OR[6], —NR[6]R[7], —CN, and 4-10 membered heterocyclic substituted with R[6];
each R[6] and R[7] is independently selected from hydrogen and $C_1$-$C_6$ alkyl;
R[8] is hydrogen or $C_1$-$C_6$ alkyl; and
n is 0, 1, 2, 3, 4, or 5.

Further provided herein are compounds of formula (8), (8a), or (8b), wherein:
R[2] is -(5-6 membered heterocyclic), optionally substituted with at least one R[4] group;
each R[4] is independently selected from halo, —OR[6], oxo, —NR[6]R[7], —CF$_3$, —CN, —C(O)R[6], —C(O)OR[6], —OC(O)R[6], —NR[6]C(O)R[7], —NR[6]C(O)OR[7], —NR[6]C(O)NR[6]R[7], —C(O)NR[6]R[7], —SO$_2$NR[6]R[7], —NR[6]SO$_2$R[7], $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one R[5];
R[5] is oxo, $C_3$-$C_8$ cycloalkyl, $C_6$-$C_{10}$ aryl, —OR[6], —C(O)OR[6], —NR[6]R[7], —CN, and 4-10 membered heterocyclic substituted with R[6];
each R[6] and R[7] is independently selected from hydrogen and $C_1$-$C_6$ alkyl; and
R[8] is hydrogen or $C_1$-$C_6$ alkyl.

Further provided herein are compounds of formula (8), (8a), or (8b), wherein:

$R^2$ is -(4-pyridyl), substituted with at least one $C_1$-$C_6$ alkyl; and $R^3$ is hydrogen or $C_1$-$C_6$ alkyl.

Also provided herein are compounds of formula (8i),

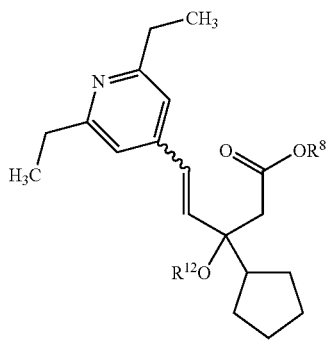

(8i)

wherein:

$R^8$ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)(C$_6$-C$_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Further provided herein are compounds of formula (8l), or a salt thereof, wherein $R^{12}$ is hydrogen.

In still a further aspect of the present invention are afforded compounds of formula (8j),

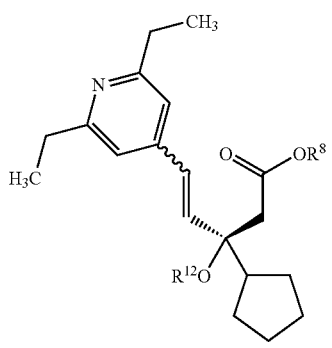

(8j)

wherein:

$R^8$ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)(C$_6$-C$_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Further afforded herein are compounds of formula (8j), or a salt thereof, wherein $R^{12}$ is hydrogen.

Another aspect of the present invention provides compounds of formula (8k),

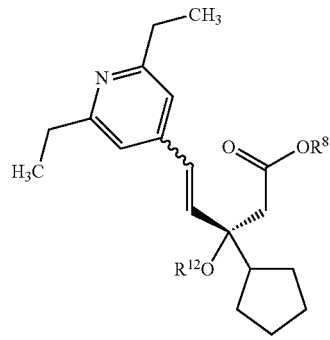

(8k)

wherein:

$R^8$ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)(C$_6$-C$_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Further provided herein are compounds of formula (8k), or a salt thereof, wherein $R^{12}$ is hydrogen.

Also provided herein are compounds according to any one of formula (8i), (8j), or (8k), wherein $R^8$ is hydrogen, or wherein $R^8$ is $C_1$-$C_6$ alkyl.

The present invention further provides compounds of formula (8l),

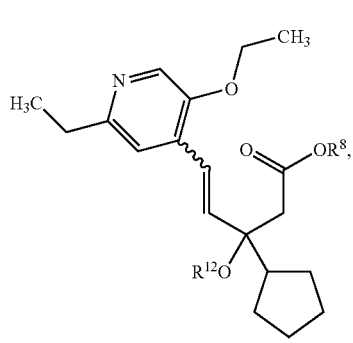

(8l)

wherein:

$R^8$ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)(C$_6$-C$_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Also afforded herein are compounds of formula (8l), or a salt thereof, wherein $R^{12}$ is hydrogen.

In yet a further aspect of the present invention are provided compounds of formula (8m),

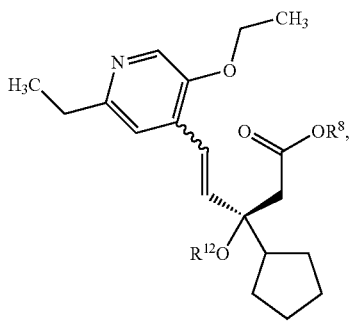

(8m)

wherein:

R⁸ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Further provided herein are compounds of formula (8m), or a salt thereof, wherein $R^{12}$ is hydrogen.

The present invention further affords compounds of formula (8n),

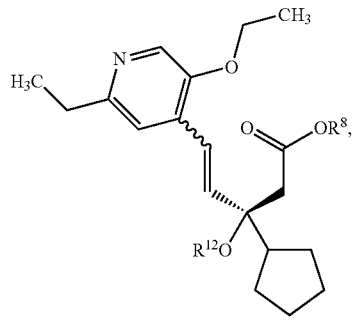

(8n)

wherein:

R⁸ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Also afforded herein are compounds of formula (8n), or a salt thereof, wherein $R^{12}$ is hydrogen.

Further provided herein are compounds according to any one of formula (8l), (8m), or (8n), wherein R⁸ is hydrogen, or wherein R⁸ is $C_1$-$C_6$ alkyl.

The present invention also provides compounds of formula (8o),

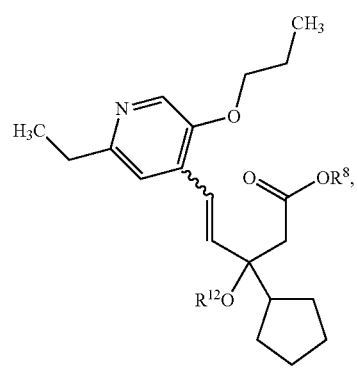

(8o)

wherein:

R⁸ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Further provided herein are compounds of formula (8o), or a salt thereof, wherein $R^{12}$ is hydrogen.

Also provided herein are compounds of formula (8p), (8p)

wherein:

R⁸ is hydrogen or $C_1$-$C_6$ alkyl;

$R^{12}$ is hydrogen or —C(O)$R^{13}$; and $R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

or a salt thereof.

Also afforded herein are compounds of formula (8p), or a salt thereof, wherein $R^{12}$ is hydrogen.

Further provided herein are compounds of formula (8q), (8q)

[Chemical structure of formula (8q): pyridine ring with CH3CH2- group, N, -OCH2CH2CH3, connected via vinyl to a carbon bearing cyclopentyl, OR12, and CH2C(O)OR8]

wherein:
R$^8$ is hydrogen or C$_1$-C$_6$ alkyl;
R$^{12}$ is hydrogen or —C(O)R$^{13}$; and
R$^{13}$ is C$_1$-C$_6$ alkyl or —(CH$_2$)(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$;
or a salt thereof.

Also afforded herein are compounds of formula (8q), or a salt thereof, wherein R$^{12}$ is hydrogen.

The present invention further provides methods of preparing compounds of formula (8), (8)

[Chemical structure of formula (8)]

wherein:
R$^2$ is —(CR$^6$R$^7$)$_n$C$_6$-C$_{10}$ aryl or —(CR$^6$R$^7$)$_n$(5-6 membered heterocyclic), wherein said C$_6$-C$_{10}$ aryl or 5-6 membered heterocyclic group is optionally substituted with at least one R$^4$ group;
each R$^4$ is independently selected from halo, —OR$^6$, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;
R$^5$ is oxo, C$_3$-C$_8$ cycloalkyl, C$_6$-C$_{10}$ aryl, —OR$^6$, —C(O)OR$^6$, —NR$^6$R$^7$, —CN, and 4-10 membered heterocyclic substituted with R$^6$;
each R$^6$ and R$^7$ is independently selected from hydrogen and C$_1$-C$_6$ alkyl;
R$^8$ is hydrogen or C$_1$-C$_6$ alkyl;
R$^{12}$ is hydrogen or —C(O)R$^{13}$;
R$^{13}$ is C$_1$-C$_6$ alkyl or —(CH$_2$)(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$;

n is 0, 1, 2, 3, 4, or 5; said method comprising:
a) treating a compound of formula (6), wherein R$^2$ is as hereinbefore defined and X is halogen or —OSO$_2$CF$_3$, with a compound of formula (7) in the presence of a catalyst, wherein R$^8$ is as hereinbefore defined,

[Reaction scheme: R$^2$—X (6) + compound (7) → compound (8)]

to afford the compound of formula (8).

Also afforded herein are methods of preparing compounds of formula (8a), (8a)

[Chemical structure of formula (8a)]

wherein:
R$^2$ is —(CR$^6$R$^7$)$_n$C$_6$-C$_{10}$ aryl or —(CR$^6$R$^7$) (5-6 membered heterocyclic), wherein said C$_6$-C$_{10}$ aryl or 5-6 membered heterocyclic group is optionally substituted with at least one R$^4$ group;
each R$^4$ is independently selected from halo, —OR$^6$, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;
R$^5$ is oxo, C$_3$-C$_8$ cycloalkyl, C$_6$-C$_{10}$ aryl, —OR$^6$, —C(O)OR$^6$, —NR$^6$R$^7$, —CN, and 4-10 membered heterocyclic substituted with R$^6$;
each R$^6$ and R$^7$ is independently selected from hydrogen and C$_1$-C$_6$ alkyl;
R$^8$ is hydrogen or C$_1$-C$_6$ alkyl;
R$^{12}$ is hydrogen or —C(O)R$^{13}$;
R$^{13}$ is C$_1$-C$_6$ alkyl or —(CH$_2$)(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$; and
n is 0, 1, 2, 3, 4, or 5;
said method comprising:
a) treating a compound of formula (6), wherein R$^2$ is as hereinbefore defined and X is halogen, —OSO$_2$CF$_3$, with a compound of formula (7a) in the presence of a catalyst, wherein R$^8$ is as hereinbefore defined,

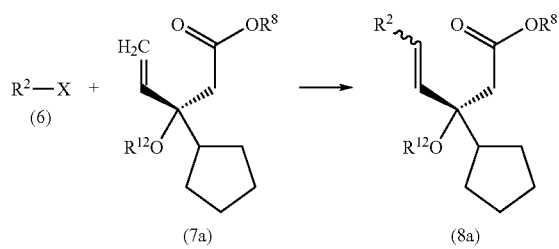 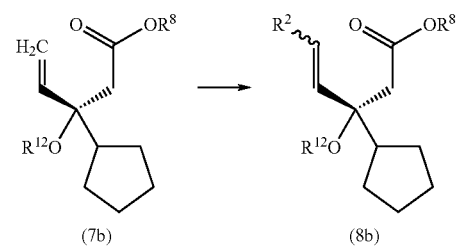

to afford the compound of formula (8a).

The present invention also affords methods of preparing compounds of formula (8b), to afford the compound of formula (8a).

Further provided herein are methods of preparing a compound of formula (9),

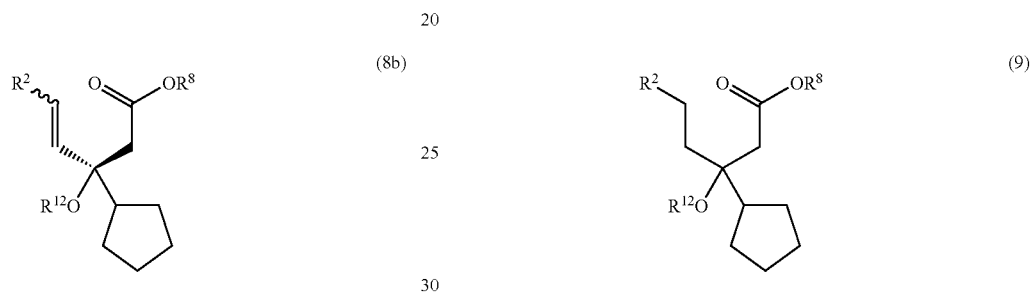

wherein:

$R^2$ is —$(CR^6R^7)_nC_6$-$C_{10}$ aryl or —$(CR^6R^7)_n$(5-6 membered heterocyclic), wherein said $C_6$-$C_{10}$ aryl or 5-6 membered heterocyclic group is optionally substituted with at least one $R^4$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

$R^5$ is oxo, $C_3$-$C_8$ cycloalkyl, $C_6$-$C_{10}$ aryl, —$OR^6$, —$C(O)OR^6$, —$NR^6R^7$, —CN, and 4-10 membered heterocyclic substituted with $R^6$;

each $R^6$ and $R^7$ is independently selected from hydrogen and $C_1$-$C_6$ alkyl;

$R^8$ is hydrogen or $C_1$-$C_6$ alkyl;

$R^{12}$ is hydrogen or —$C(O)R^{13}$;

$R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl)$_2$; and n is 0, 1, 2, 3, 4, or 5;

said method comprising:

a) treating a compound of formula (6), wherein $R^2$ is as hereinbefore defined and X is halogen or —$OSO_2CF_3$, with a compound of formula (7b) in the presence of a catalyst, wherein $R^8$ is as hereinbefore defined, wherein:

$R^2$ is —$(CR^6R^7)_nC_6$-$C_{10}$ aryl or —$(CR^6R^7)_n$(5-6 membered heterocyclic), wherein said $C_6$-$C_{10}$ aryl or 5-6 membered heterocyclic group is optionally substituted with at least one $R^4$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

$R^5$ is oxo, $C_3$-$C_8$ cycloalkyl, $C_6$-$C_{10}$ aryl, —$OR^6$, —$C(O)OR^6$, —$NR^6R^7$, —CN, and 4-10 membered heterocyclic substituted with $R^6$;

each $R^6$ and $R^7$ is independently selected from hydrogen and $C_1$-$C_6$ alkyl;

$R^8$ is hydrogen or $C_1$-$C_6$ alkyl;

$R^{12}$ is hydrogen or —$C(O)R^{13}$;

$R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl)$_2$; and n is 0, 1, 2, 3, 4, or 5;

said method comprising:

a) treating a compound of formula (8), wherein $R^2$ and $R^8$ are as defined herein, with a reducing agent in the presence of a catalyst,

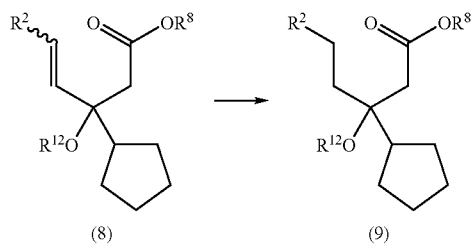

(8) → (9)

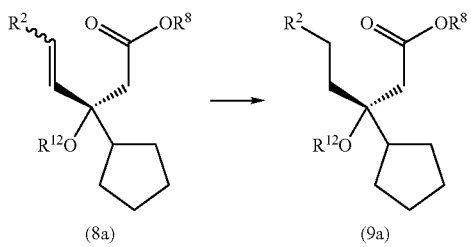

(8a) → (9a)

to afford the compound of formula (9).

Further provided herein are methods of preparing compounds of formula (9a), to afford the compound of formula (9a).

Further provided herein are methods of preparing compounds of formula (9b),

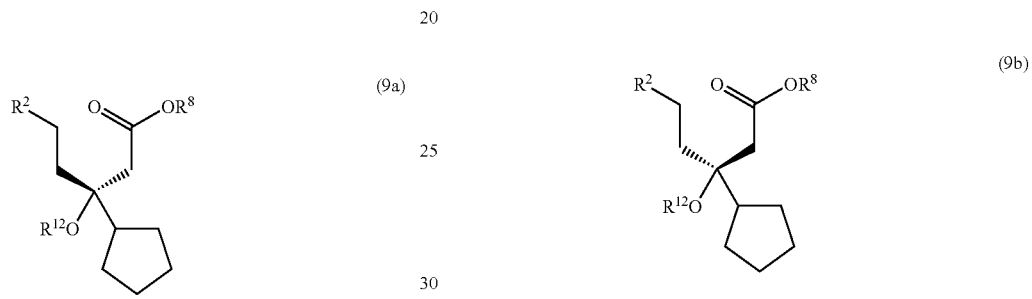

wherein:

$R^2$ is —$(CR^6R^7)_n C_6$-$C_{10}$ aryl or —$(CR^6R^7)_n$(5-6 membered heterocyclic), wherein said $C_6$-$C_{10}$ aryl or 5-6 membered heterocyclic group is optionally substituted with at least one $R^4$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

$R^5$ is oxo, $C_3$-$C_8$ cycloalkyl, $C_6$-$C_{10}$ aryl, —$OR^6$, —$C(O)OR^7$, —$NR^6R^7$, —CN, and 4-10 membered heterocyclic substituted with $R^6$;

each $R^6$ and $R^7$ is independently selected from hydrogen and $C_1$-$C_6$ alkyl;

$R^8$ is hydrogen or $C_1$-$C_6$ alkyl;

$R^{12}$ is hydrogen or —$C(O)R^{13}$;

$R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl)$_2$; and n is 0, 1, 2, 3, 4, or 5;

said method comprising:

a) treating a compound of formula (8a), wherein $R^2$ and $R^8$ are as defined herein, with a reducing agent in the presence of a catalyst, wherein:

$R^2$ is —$(CR^6R^7)_n C_6$-$C_{10}$ aryl or —$(CR^6R^7)_n$(5-6 membered heterocyclic), wherein said $C_6$-$C_{10}$ aryl or 5-6 membered heterocyclic group is optionally substituted with at least one $R^4$ group;

each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1$-$C_6$ alkyl, $C_2$-$C_6$ alkenyl, and $C_2$-$C_6$ alkynyl, wherein said $C_1$-$C_6$ alkyl, $C_2$-$C_6$ alkenyl, and $C_2$-$C_6$ alkynyl groups are optionally substituted with at least one $R^5$;

$R^5$ is oxo, $C_3$-$C_8$ cycloalkyl, $C_6$-$C_{10}$ aryl, —$OR^6$, —$C(O)OR^6$, —$NR^6R^7$, —CN, and 4-10 membered heterocyclic substituted with $R^6$;

each $R^6$ and $R^7$ is independently selected from hydrogen and $C_1$-$C_6$ alkyl;

$R^8$ is hydrogen or $C_1$-$C_6$ alkyl;

$R^{12}$ is hydrogen or —$C(O)R^{13}$;

$R^{13}$ is $C_1$-$C_6$ alkyl or —$(CH_2)(C_6$-$C_{10}$ aryl), wherein said $C_6$-$C_{10}$ aryl group is optionally substituted with at least one substituent selected from halogen, $C_1$-$C_6$ alkyl, —OH, —$OCH_3$, and —$N(C_1$-$C_6$ alkyl)$_2$; and n is 0, 1, 2, 3, 4, or 5;

said method comprising:

a) treating a compound of formula (8b), wherein $R^2$ and $R^8$ are as defined herein, with a reducing agent in the presence of a catalyst,

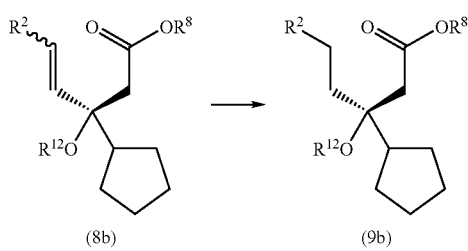

to afford the compound of formula (9b).

Further provided are such methods, wherein said catalyst is selected from palladium and platinum, and such methods wherein said reducing agent is hydrogen. Further provided are such methods, wherein said reducing agent is hydrogen and said catalyst is selected from palladium and platinum.

Also provided herein are methods of preparing stereoisomerically enriched compounds of formula (7), (7)

wherein:

$R^{12}$ is hydrogen or —C(O)$R^{13}$; and
$R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

said method comprising:

a) treating a compound of formula (7) with a chiral, non-racemic base to afford a mixture of diastereomeric salts;

b) separating said diastereomeric salts from each other to afford a stereoisomerically enriched diastereomeric salt; and c) converting said stereoisomerically enriched diastereomeric salt into a stereoisomerically enriched compound of formula (7).

Further provided herein are such methods, wherein said stereoisomerically enriched compound of formula (7) is (7a), (7a)

or is a compound of formula (7b), (7b)

In still another aspect are such above-described methods, wherein said chiral, non-racemic base is a chiral, non-racemic amine. Further provided are such methods wherein said chiral, non-racemic amine is selected from one enantiomer of 1,2,3,4-tetrahydro-1-napthylamine, 1,2,3,4-tetrahydro-1-napthylamine, 1-(2-napthyl)ethylamine, 1-(2-napthyl)ethylamine, and norephedrine. Additionally provided are such methods, wherein said chiral, non-racemic amine is (S)-1,2,3,4-tetrahydro-1-napthylamine.

Further provided herein are compounds of formula (7c), (7c)

wherein:

$R^{12}$ is hydrogen or —C(O)$R^{13}$;
$R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$; and A is a suitable counter-ion.

In an additional aspect of the present invention are provided compounds of formula (7d), (7d)

wherein:

$R^{12}$ is hydrogen or —C(O)$R^{13}$;
$R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$; and A is a suitable counter-ion.

Further provided herein are compounds of formula (7e),

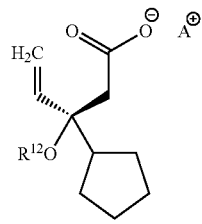
(7e)

wherein:
R$^{12}$ is hydrogen or —C(O)R$^{13}$;
R$^{13}$ is C$_1$-C$_6$ alkyl or —(CH$_2$)(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$; and
A is a suitable counter-ion.

In still another aspect of the present invention are provided compounds of formula (7c), (7d), and (7e), wherein said suitable counter-ion is derived from an amine. Also provided are such compounds, wherein said amine is chiral, non-racemic amine. Further provided are such compounds wherein said chiral, non-racemic amine is selected from one enantiomer of 1,2,3,4-tetrahydro-1-napthylamine, 1,2,3,4-tetrahydro-1-napthylamine, 1-(2-napthyl)ethylamine, norephedrine, norephedrine. Additionally provided are such methods, wherein said chiral, non-racemic amine is (S)-1,2,3,4-tetrahydro-1-napthylamine.

Also provided herein are compounds of formula (8c)

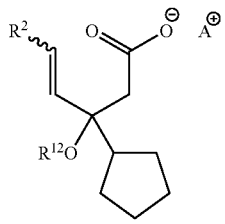
(8c)

wherein:
R$^2$ is —(CR$^6$R$^7$)$_n$C$_6$-C$_{10}$ aryl or —(CR$^6$R$^7$) (5-6 membered heterocyclic), wherein said C$_6$-C$_{10}$ aryl or 5-6 membered heterocyclic group is optionally substituted with at least one R$^4$ group;
each R$^4$ is independently selected from halo, —OR$^6$, oxo, —NR$^6$R$^7$, —CF$_3$, —CN, —C(O)R$^6$, —C(O)OR$^6$, —OC(O)R$^6$, —NR$^5$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;
R$^5$ is oxo, C$_3$-C$_8$ cycloalkyl, C$_6$-C$_{10}$ aryl, —OR$^6$, —C(O)OR$^7$, —NR$^6$R$^7$, —CN, and 4-10 membered heterocyclic substituted with R$^6$;
each R$^6$ and R$^7$ is independently selected from hydrogen and C$_1$-C$_6$ alkyl;
R$^{12}$ is hydrogen or —C(O)R$^{13}$;
R$^{13}$ is C$_1$-C$_6$ alkyl or —(CH$_2$)(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$;
n is 0, 1, 2, 3, 4, or 5; and
A is a suitable counter-ion.

The present invention further provides compounds of formula (8d)

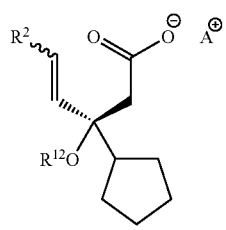
(8d)

wherein:
R$^2$ is —(CR$^6$R$^7$)$_n$C$_6$-C$_{10}$ aryl or —(CR$^6$R$^7$)$_n$(5-6 membered heterocyclic), wherein said C$_6$-C$_{10}$ aryl or 5-6 membered heterocyclic group is optionally substituted with at least one R$^4$ group;
each R$^4$ is independently selected from halo, —OR$^6$, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;
R$^5$ is oxo, C$_3$-C$_8$ cycloalkyl, C$_6$-C$_{10}$ aryl, —OR$^6$, —C(O)OR$^6$, —NR$^6$R$^7$, —CN, and 4-10 membered heterocyclic substituted with R$^6$;
each R$^6$ and R$^7$ is independently selected from hydrogen and C$_1$-C$_6$ alkyl;
R$^{12}$ is hydrogen or —C(O)R$^{13}$;
R$^{13}$ is C$_1$-C$_6$ alkyl or —(CH$_2$)(C$_6$-C$_{10}$ aryl), wherein said C$_6$-C$_{10}$ aryl group is optionally substituted with at least one substituent selected from halogen, C$_1$-C$_6$ alkyl, —OH, —OCH$_3$, and —N(C$_1$-C$_6$ alkyl)$_2$;
n is 0, 1, 2, 3, 4, or 5; and
A is a suitable counter-ion.

Also provided herein are compounds of formula (8e)

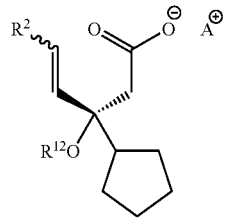
(8e)

wherein:
R$^2$ is —(CR$^6$R$^7$)$_n$C$_6$-C$_{10}$ aryl or —(CR$^6$R$^7$)$_n$(5-6 membered heterocyclic), wherein said C$_6$-C$_{10}$ aryl or 5-6 membered heterocyclic group is optionally substituted with at least one R$^4$ group;
each R$^4$ is independently selected from halo, —OR$^6$, oxo, —NR$^6$R$^7$, —CF$_3$, —CN, —C(O)R$^6$, —C(O)OR$^6$, —OC(O)R$^6$, —NR$^6$C(O)R$^7$, —NR$^6$C(O)OR$^7$, —NR$^6$C(O)NR$^6$R$^7$, —C(O)NR$^6$R$^7$, —SO$_2$NR$^6$R$^7$, —NR$^6$SO$_2$R$^7$, C$_1$-C$_6$ alkyl, C$_2$-C$_6$ alkenyl, and C$_2$-C$_6$ alkynyl, wherein said C$_1$-C$_6$ alkyl, C$_2$-C$_6$ alkenyl, and C$_2$-C$_6$ alkynyl groups are optionally substituted with at least one R$^5$;

$R^5$ is oxo, $C_3$-$C_8$ cycloalkyl, $C_6$-$C_{10}$ aryl, —$OR^6$, —C(O)$OR^6$, —$NR^6R^7$, —CN, and 4-10 membered heterocyclic substituted with $R^6$;

each $R^6$ and $R^7$ is independently selected from hydrogen and $C_1$-$C_6$ alkyl;

$R^{12}$ is hydrogen or —C(O)$R^{13}$;

$R^{13}$ is $C_1$-$C_6$ alkyl or —(CH$_2$)($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$;

n is 0, 1, 2, 3, 4, or 5; and

A is a suitable counter-ion.

Further provided herein are compounds of formula (8c), (8d), and (8e), wherein said suitable counter-ion is derived from an amine. Additionally provided are any of these compounds, wherein the amine is a chiral, non-racemic amine. Further provided are any of these compounds wherein the chiral, non-racemic amine is selected from one enantiomer of 1,2,3,4-tetrahydro-1-napthylamine, 1-(2-napthyl)ethylamine, and norephedrine.

As used herein, the terms "comprising" and "including" are used in their open, non-limiting sense.

The term "$C_1$-$C_6$ alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties, and containing from 1-6 carbon atoms. For an alkyl group to have cyclic moieties, the group must have at least three carbon atoms.

A "lower alkyl" is intended to mean an alkyl group having from 1 to 4 carbon atoms in its chain. The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary amines, alkyl sulfides and the like.

The term "$C_2$-$C_6$ alkenyl", as used herein, unless otherwise indicated, includes alkyl moieties having at least one carbon-carbon double bond wherein alkyl is as defined above and including E and Z isomers of said alkenyl moiety, and having from 2 to 6 carbon atoms.

The term "$C_2$-$C_6$ alkynyl", as used herein, unless otherwise indicated, includes alkyl moieties having at least one carbon-carbon triple bond wherein alkyl is as defined above, and containing from 2-6 carbon atoms.

The term "carbocycle" refers to a saturated, partially saturated, unsaturated, or aromatic, monocyclic or fused or non-fused polycyclic, ring structure having only carbon ring atoms (no heteroatoms, i.e., non-carbon ring atoms). Exemplary carbocycles include cycloalkyl, aryl, and cycloalkyl-aryl groups.

A "$C_3$-$C_{10}$ cycloalkyl group" is intended to mean a saturated or partially saturated, monocyclic, or fused or spiro polycyclic, ring structure having a total of from 3 to 10 carbon ring atoms (but no heteroatoms). Exemplary cycloalkyls include cyclopropyl, cyclobutyl, cyclopentyl, cyclopentenyl, cyclohexyl, cycloheptyl, adamantyl, and like groups.

A "heterocycloalkyl group" is intended to mean a monocyclic, or fused or spiro polycyclic, ring structure that is saturated or partially saturated, and has a total of from 3 to 18 ring atoms, including 1 to 5 heteroatoms selected from nitrogen, oxygen, and sulfur. Illustrative Examples of heterocycloalkyl groups include pyrrolidinyl, tetrahydrofuryl, piperidinyl, piperazinyl, morpholinyl, thiomorpholinyl, aziridinyl, and like groups.

The term "$C_6$-$C_{10}$ aryl", as used herein, unless otherwise indicated, includes an organic radical derived from an aromatic hydrocarbon by removal of one hydrogen, such as phenyl or naphthyl. The term "phenyl" and the symbol "Ph," as used herein, refer to a $C_6H_5$ group.

The term "4-10 membered heterocyclic", as used herein, unless otherwise indicated, includes aromatic and non-aromatic heterocyclic groups containing one to four heteroatoms each selected from O, S and N, wherein each heterocyclic group has from 4-10 atoms in its ring system, and with the proviso that the ring of said group does not contain two adjacent O or S atoms. Furthermore, the sulfur atoms contained in such heterocyclic groups may be oxidized with one or two sulfur atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

The term "5-6 membered heterocyclic" means aromatic and non-aromatic heterocyclic groups containing one to four heteroatoms each selected from O, S and N, and wherein each heterocyclic group has a total of from 5 to 6 atoms in its ring system, and with the proviso that the ring of said group does not contain two adjacent O or S atoms. The sulfur atoms contained in such heterocyclic groups may be oxidized with one or two sulfur atoms. Furthermore, any atom in the 5-6 membered heterocyclic group may be substituted with an oxo (=O) group, if such substitution would result in a stable compound. Examples of non-aromatic heterocyclic groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups include, but are not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, quinazolinyl, and quinoxalinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

A "heteroaryl group" is intended to mean a monocyclic or fused or spiro polycyclic, aromatic ring structure having from 4 to 18 ring atoms, including from 1 to 5 heteroatoms selected from nitrogen, oxygen, and sulfur. Illustrative Examples of heteroaryl groups include pyrrolyl, thienyl, oxazolyl, pyrazolyl, thiazolyl, furyl, pyridinyl, pyrazinyl, triazolyl, tetrazolyl, indolyl, quinolinyl, quinoxalinyl, benzthiazolyl, benzodioxinyl, benzodioxolyl, benzooxazolyl, and the like.

The term "alkoxy", as used herein, unless otherwise indicated, includes O-alkyl groups wherein alkyl is as defined above.

The term "amino" is intended to mean the $—NH_2$ radical.

The terms "halogen" and "halo," as used herein represent fluorine, chlorine, bromine or iodine.

The term "oxo," as used herein, means a group (=O). Such a group may be bonded to either a carbon atom or a heteroatom in the compounds of the present invention, if such substitution will result in a stable compound.

The term "trifluoromethyl," as used herein, is meant to represent a group $—CF_3$.

The term "trifluoromethoxy," as used herein, is meant to represent a group $—OCF_3$.

The term "cyano," as used herein, is meant to represent a group $—CN$.

The term "substituted" means that the specified group or moiety bears one or more substituents. The term "unsubstituted" means that the specified group bears no substituents. The term "optionally substituted" means that the specified group is unsubstituted or substituted by one or more substituents.

The term "HCV," as used herein, refers to Hepatitis C virus.

The terms "inhibiting Hepatitis C virus" and "inhibiting Hepatitis C virus replication" mean inhibiting Hepatitis C virus replication either in vitro or in vivo, such as in a mammal, such as a human, by contacting the Hepatitis C virus with an HCV-replication inhibiting amount of a compound of the present invention, or a pharmaceutically acceptable salt or solvate thereof. Such inhibition may take place in vivo, such as in a mammal, such as a human, by administering to the mammal a Hepatitis C virus-inhibiting amount of a compound of the present invention. The amount of a compound of the present invention necessary to inhibit replication of the HCV virus either in vitro or in vivo, such as in a mammal, such as a human, can be determined using methods known to those of ordinary skill in the art. For example, an amount of a compound of the invention may be administered to a mammal, either alone or as part of a pharmaceutically acceptable formulation. Blood samples may then be withdrawn from the mammal and the amount of Hepatitis C virus in the sample may be quantified using methods known to those of ordinary skill in the art. A reduction in the amount of Hepatitis C virus in the sample compared to the amount found in the blood before administration of a compound of the invention would represent inhibition of the replication of Hepatitis C virus in the mammal. The administration of a compound of the invention to the mammal may be in the form of single dose or a series of doses over successive days.

An "HCV-inhibiting agent" means a compound of the present invention or a pharmaceutically acceptable salt or solvate thereof.

The term "HCV-inhibiting amount," as used herein, refers to an amount of a compound of the present invention that is sufficient to inhibit the replication of the Hepatitis C virus when administered to a mammal, such as a human.

The term "HCV polymerase-inhibiting amount," as used herein, means an amount of a compound of the present invention that is sufficient to inhibit the function of the Hepatitis C virus polymerase enzyme when the compound is placed in contact with the enzyme.

A "solvate" is intended to mean a pharmaceutically acceptable solvate form of a specified compound that retains the biological effectiveness of such compound. Examples of solvates include compounds of the invention in combination with solvents such as, but not limited to, water, isopropanol, ethanol, methanol, DMSO, ethyl acetate, acetic acid, or ethanolamine. A "pharmaceutically acceptable salt" is intended to mean a salt that retains the biological effectiveness of the free acids and bases of the specified derivative and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "pharmaceutically acceptable salt(s)", as used herein, unless otherwise indicated, includes salts of acidic or basic groups, which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The phrases "therapeutically effective amount," "effective amount," and "HCV-inhibiting amount," are intended to mean the amount of an inventive agent that, when administered to a mammal in need of treatment, is sufficient to effect treatment for injury or disease conditions alleviated by the inhibition of HCV RNA replication such as for potentiation of anti-cancer therapies or inhibition of neurotoxicity consequent to stroke, head trauma, and neurodegenerative diseases.

The amount of a given HCV-inhibiting agent used in the method of the invention that will be therapeutically effective will vary depending upon factors such as the particular HCV-inhibiting agent, the disease condition and the severity thereof, the identity and characteristics of the mammal in need thereof, which amount may be routinely determined by artisans.

The term "6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one," as used herein, means a chemical compound with the structure:

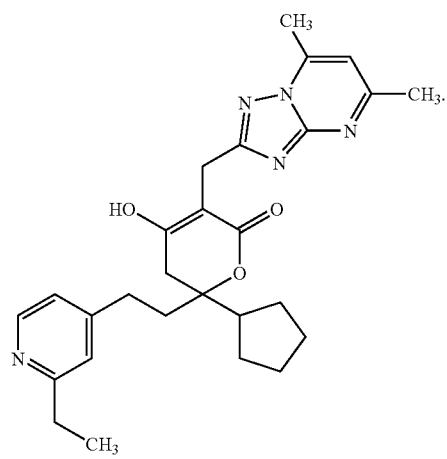

As used herein, the term "3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one" means a chemical compound with the structure:

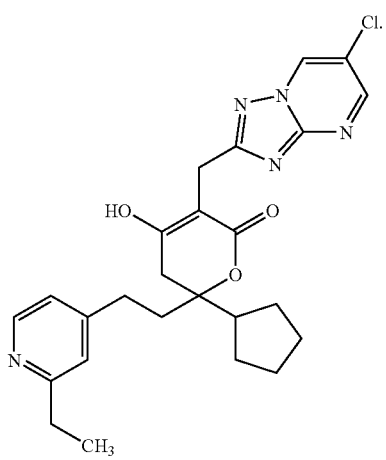

The term "6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one," as used herein, means a chemical compound with the structure:

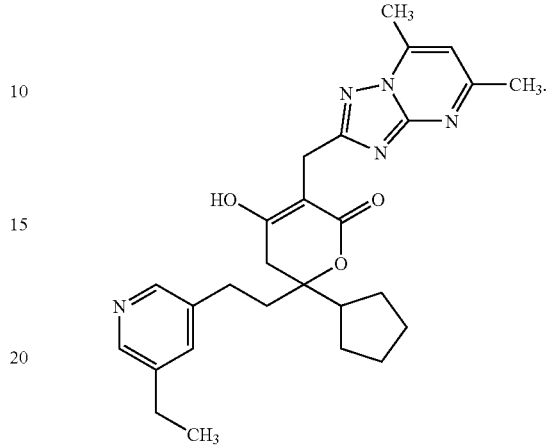

The term "treating," as used herein, refers to a chemical process or processes in which two or more reactants are allowed to come into contact with each other to effect a chemical change or transformation. For example, when reactant A and reactant B are allowed to come into contact with each other to afford a new chemical compound(s) C, A is said to have "reacted" with B to produce C.

As used herein, the term "catalyst" means a chemical element or compound that increases the rate of a chemical reaction by reducing the activation energy, but which is left unchanged by the reaction. Examples of catalysts include, but are not limited to, palladium (0) and platinum (0). It is specifically contemplated herein that such catalysts may be formed in situ during the course of a chemical reaction, from a so-called "pre-catalyst," but may never actually be observed or isolated. Such pre-catalysts are chemical compounds that are capable of being converted in situ during the course of a chemical reaction to a chemically and catalytically competent element or compound. Examples of suitable pre-catalysts include, but are not limited to, $PdCl_2$, $PdCl_2(PPh_3)_2$, $Pd(OH)_2$, $Pd(PPh_3)_4$, $Pt(OH)_2$, and $PtCl_2$.

The term "reducing agent," as used herein, means a chemical element or compound that provides electrons for another chemical element or compound in a reaction mixture. Alternatively, it means a chemical element or compound that is capable of affording a saturated chemical compound from an unsaturated chemical compound by the addition of hydrogen. For example, the addition of hydrogen to an alkene of the present invention to afford a saturated alkane is termed "reduction." A reducing agent is a chemical element or compound that is capable of affecting such a reduction, usually in the presence of a catalyst. Examples of reducing agents include, but are not limited to hydrogen, formic acid, and formic acid salts, such as ammonium formate.

The term "protecting," as used herein, refers to a process in which a functional group in a chemical compound is selectively masked by a non-reactive functional group in order to allow a selective reaction(s) to occur elsewhere on said chemical compound. Such non-reactive functional groups are herein termed "protecting groups." For example, the term "hydroxyl protecting group," as used herein refers to those groups that are capable of selectively masking the reactivity of a hydroxyl (—OH) group. The term "suitable protecting group," as used herein refers to those protecting groups that are useful in the preparation of the compounds of the present invention. Such groups are generally able to be selectively introduced and removed using mild reaction conditions that do not interfere with other portions of the subject compounds. Protecting groups that are suitable for use in the processes and methods of the present invention are known to those of ordinary skill in the art. The chemical properties of such protecting groups, methods for their introduction, and their removal can be found, for example, in T. Greene and P. Wuts, *Protective Groups in Organic Synthesis* (3$^{rd}$ ed.), John Wiley & Sons, NY (1999). The terms "deprotecting," "deprotected," or "deprotect," as used herein, are meant to refer to the process of removing a protecting group from a compound.

The terms "hydrolyze," "hydrolyzing," "hydrolysis," and "hydrolyzed," as used herein, all mean and refer to a chemical reaction in which an ester, an amide, or both are converted into their corresponding carboxylic acid derivatives, usually through the action of hydroxyl anion (—OH), such as would be present in a basic, aqueous solution.

The term "leaving group," as used herein, refers to a chemical functional group that generally allows a nucleophilic substitution reaction to take place at the atom to which it is attached. For example, in acid chlorides of the formula Cl—C(O)R, wherein R is alkyl, aryl, or heterocyclic, the —Cl group is generally referred to as a leaving group because it allows nucleophilic substitution reactions to take place at the carbonyl carbon to which it is attached. Suitable leaving groups are known to those of ordinary skill in the art and can include halides, aromatic heterocycles, cyano, amino groups (generally under acidic conditions), ammonium groups, alkoxide groups, carbonate groups, formates, and hydroxy groups that have been activated by reaction with compounds such as carbodiimides. For example, suitable leaving groups can include, but are not limited to, chloride, bromide, iodide, cyano, imidazole, and hydroxy groups that have been allowed to react with a carbodiimide such as dicyclohexylcarbodiimide (optionally in the presence of an additive such as hydroxybenzotriazole) or a carbodiimide derivative.

The term "combination of reagents," means a chemical reagent, or more than one reagent when necessary, that can be used to affect a desired chemical reaction. The choice of a particular reagent, or combination or reagents, will depend on factors that are familiar to those of ordinary skill in the art and include, but are not limited to, the identity of the reactants, the presence of other functional groups in the reactants, the solvent or solvents used in a particular chemical reaction, the temperature at which the chemical reaction will be performed, and the method or methods of purification of the desired chemical reaction product. The choice of a reagent, or combination of reagents, required to affect a particular chemical reaction are within the knowledge of one of ordinary skill in the art and such a choice can be made without undue experimentation.

The term "base," as used herein, means a so-called Bronsted-Lowry base. A Bronsted-Lowry base is a reagent that is capable of accepting a proton (H$^+$) from an acid present in a reaction mixture. Examples of Bronsted-Lowry bases include, but are not limited to, inorganic bases such as sodium carbonate, sodium bicarbonate, sodium hydroxide, potassium carbonate, potassium bicarbonate, potassium hydroxide, and cesium carbonate, inorganic bases such as triethylamine, diisopropylethylamine, diisopropylamine, dicyclohexylamine, morpholine, pyrrolidone, piperidine, pyridine, 4-N,N-dimethylaminopyridine (DMAP), and imidazole.

The term "chiral, non-racemic base," as used herein, means a basic compound that can exist in an enantiomeric form and is not present in an equal amount with its corresponding opposite enantiomer. For example, the compound 2-phenylglycinol exists as two enantiomers of opposite configuration, the so-called (R)- and (S)-enantiomers. If the (R)- and the (S)-enantiomers are present in equal amounts, such a mixture is said to be "racemic." If, however, one enantiomer is present in an amount greater than the other, the mixture is said to be "non-racemic."

The term "stereoisomers" refers to compounds that have identical chemical constitution, but differ with regard to the arrangement of their atoms or groups in space. In particular, the term "enantiomers" refers to two stereoisomers of a compound that are non-superimposable mirror images of one another. The terms "racemic" or "racemic mixture," as used herein, refer to a 1:1 mixture of enantiomers of a particular compound. The term "diastereomers", on the other hand, refers to the relationship between a pair of stereoisomers that comprise two or more asymmetric centers and are not mirror images of one another.

The term "stereochemically-enriched" product, when used herein, refers to a reaction product wherein a particular stereoisomer is present in a statistically significant greater amount relative to the other possible stereoisomeric products. For example, a product that comprises more of one enantiomer than the other would constitute a stereochemically enriched product. Similarly, a product that comprises more of one diastereoisomer than others would also constitute a stereochemically enriched product. The methods and processes contained herein are said to afford a "stereochemically enriched" product. In such cases, the methods and processes contained herein begin with a mixture of stereoisomeric compounds in which all possible stereoisomers are present in about an equal amount and afford a product in which at least one stereoisomer is present in a statistically significant greater amount than the others.

The term "diastereomeric," as used herein refers to the relationship between a pair of stereoisomers that comprise two or more asymmetric centers and are non-superimposable mirror images of one another. The phrases "diastereomeric salt," or "diastereomeric salts," as used herein means a salt of a diastereomeric compound, wherein "diastereomer" is as defined herein.

The term "racemic," as used herein, means a composition comprising a 1:1 ratio of enantiomers. The term "scalemic," as used herein, means a composition comprising an unequal amount of enantiomers. For example, a composition comprising a 1:1 mixture of the (R)- and (S)-enantiomers of a compound of the present invention is termed a racemic composition or mixture. As an additional example, a composition comprising a 2:1 mixture of (R)- and (S)-enantiomers of a compound of the present invention is termed a scalemic composition or mixture. It is specifically contemplated that the methods of the present invention may be advantageously used to prepare a scalemic compound of the present invention from a racemic compound of the present invention.

The terms "resolution" and "resolving" mean a method of physically separating stereoisomeric compounds from a mixture of stereoisomers, such as a racemic mixture comprising two enantiomers of a particular compound. As used herein, "resolution" and "resolving" are meant to include both partial and complete resolution.

The terms "separating" or "separated," as used herein, mean a process of physically isolating at least two different chemical compounds from each other. For example, if a chemical reaction takes place and produces at least two products, (A) and (B), the process of isolating both (A) and (B) from each other is termed "separating" (A) and (B). It is specifically contemplated that the separations of the present invention may be partial or complete as determined by analytical techniques known to those of ordinary skill in the art and those described herein.

The term "converting," as used herein, means allowing a chemical reaction to take place with a starting material or materials to produce a different chemical product. For example, if chemical reactants (A) and (B) are allowed to react with each other to produce product (C), starting materials (A) and (B) can be said to have "converted" to product (C), or it can be said that (A) was "converted" to (C), or that (B) was "converted" to (C).

The term "suitable counter-ion," as used herein, means an ion or ions opposite in charge to the ion present in the compound or compounds of the invention such that the overall complex or salt has a neutral charge. For example, if the compound of the present invention contains an overall negative one (−1) charge, a suitable counter ion would be one with an overall positive one (+1) charge that would afford an overall neutral charge for the complex or salt. Examples of suitable positive (+) counter-ions include, but are not limited to, sodium ion ($Na^+$), potassium ion ($K^+$), cesium ion ($Cs^+$), and protonated amines (such as protonated triethylamine, protonated dicyclohexylamine, protonated morpholine, or protonated pyridine). Alternatively, if the compound of the invention contains an overall positive one (+1) charge, a suitable counter-ion would be one with an overall negative one (−1) charge that would afford an overall neutral charge for the complex or salt. Examples of suitable negative (−) counter-ions include, but are not limited to, fluoride ($F^-$), chloride ($Cl^-$), bromide ($Br^-$), iodide ($I^-$), hydroxide ($^-OH$), and acetate ($^-O-C(O)CH_3$). It is also possible that the suitable counter-ion in the compounds of the present invention, including the compounds used in the methods of the present invention, may have more than a single charge associated with them. For example, if the compound of the invention contains a negative one (−1) charge, the suitable counter-ion may contain a plus two (+2) charge, such that two compounds of the invention with negative one charges are associated with one suitable counter-ion. Examples, of suitable counter-ions with more than one positive charge include, but are not limited to calcium ($Ca^{2+}$). Finally, it is also contemplated that the compounds of the present invention may contain more than one charge, such that more than one suitable counter-ion may be required to afford an overall neutral complex or salt. For example, the compound of the present invention may contain more than one negative one (−1) charges, such that two suitable counter-ions, each with a plus one (+1) charge, are required to afford an overall neutral complex or salt.

The term "substituted," means that the specified group or moiety bears one or more substituents. The term "unsubstituted," means that the specified group bears no substituents.

The term "optionally substituted" means that the specified group is unsubstituted or substituted by one or more substituents.

DETAILED DESCRIPTION

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

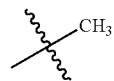

represents a methyl group,

represents an ethyl group,

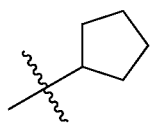

represents a cyclopentyl group, etc.

With respect to compounds of the invention that are alkenes, the symbol "⁓" denotes that either the E- or Z-isomer, or mixtures of the E- and Z-isomers, may be present. For example, in the structure below, the use of the symbol "⁓" for the bond from the $R^2$ group to the alkene,

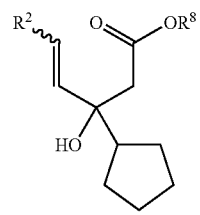

denotes that either the E- or Z-isomer, or mixtures of the E- and Z-isomers, are meant to be represented.

The compounds of the present invention may exist in several tautomeric forms. For example, a compound of the invention may exist in a form in which two ketones are present on a ring of the compound, as shown in (A) below. Alternatively, the compounds of the present invention may exist in at least two different enol forms, as shown in compounds (B) and (C)

below. These three forms may be in equilibrium and the compounds of the invention may exist in more than one of these forms at the same time. For example, in a particular compound of the invention, a certain percentage of the molecules may be present in form (A) while the remainder are present in form (B) or form (C). Which form predominates in a particular compound of the invention depends on several factors that include, but are not limited to, whether the compound is in solid, liquid, or crystalline form, whether the compound is dissolved in a solvent and the identity of the solvent, the environmental temperature, and the relative humidity. It is specifically contemplated that when the compounds of the present invention are drawn in a particular form, form (A) for example, all the tautomeric forms, forms (B) and (C) for example, are included as well.

enriched form by asymmetric synthesis. Asymmetric synthesis may be performed using techniques known to those of skill in the art, such as the use of asymmetric starting materials that are commercially available or readily prepared using methods known to those of ordinary skill in the art, the use of asymmetric auxiliaries that may be removed at the completion of the synthesis, or the resolution of intermediate compounds using enzymatic methods. The choice of such a method will depend on factors that include, but are not limited to, the availability of starting materials, the relative efficiency of a method, and whether such methods are useful for the compounds of the invention containing particular functional groups. Such choices are within the knowledge of one of ordinary skill in the art.

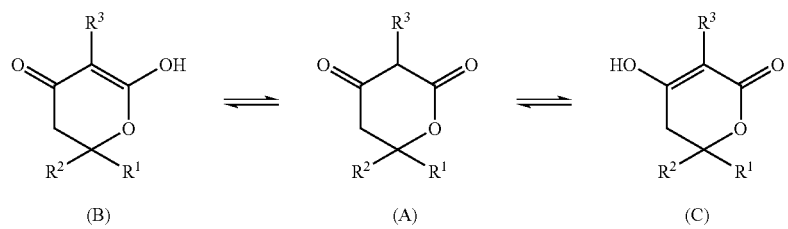

(B)　　　　　　(A)　　　　　　(C)

The compounds of the present invention may have asymmetric carbon atoms. The carbon-carbon bonds of the compounds of the present invention may be depicted herein using a solid line (——), a solid wedge (◄──), or a dotted wedge (·······). The use of a solid line to depict bonds to asymmetric carbon atoms is meant to indicate that all possible stereoisomers at that carbon atom are included. The use of either a solid or dotted wedge to depict bonds to asymmetric carbon atoms is meant to indicate that only the stereoisomer shown is meant to be included. It is possible that compounds of the invention may contain more than one asymmetric carbon atom. In those compounds, the use of a solid line to depict bonds to asymmetric carbon atoms is meant to indicate that all possible stereoisomers are meant to be included. The use of a solid line to depict bonds to one or more asymmetric carbon atoms in a compound of the invention and the use of a solid or dotted wedge to depict bonds to other asymmetric carbon atoms in the same compound is meant to indicate that a mixture of diastereomers is present.

Solutions of individual stereoisomeric compounds of the present invention may rotate plane-polarized light. The use of either a "(+)" or "(−)" symbol in the name of a compound of the invention indicates that a solution of a particular stereoisomer rotates plane-polarized light in the (+) or (−) direction, as measured using techniques known to those of ordinary skill in the art.

Diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

Alternatively, individual stereoisomeric compounds of the present invention may be prepared in enantiomerically When the compounds of the present invention contain asymmetric carbon atoms, the derivative salts, prodrugs and solvates may exist as single stereoisomers, racemates, and/or mixtures of enantiomers and/or diastereomers. All such single stereoisomers, racemates, and mixtures thereof are intended to be within the scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacological pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

If a derivative used in the method of the invention is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If a derivative used in the method of the invention is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative Examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of derivatives, prodrugs, salts, or solvates that are solids, it is understood by those skilled in the art that the derivatives, prodrugs, salts, and solvates used in the method of the invention, may exist in different polymorph or crystal forms, all of which are intended to be within the scope of the present invention and specified formulas. In addition, the derivative, salts, prodrugs and solvates used in the method of the invention may exist as tautomers, all of which are intended to be within the broad scope of the present invention.

The compounds of the present invention that are basic in nature are capable of forming a wide variety of different salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the present invention that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds as inhibitors of HCV activity may be measured by any of the suitable methods available in the art, including in vivo and in vitro assays. An Example of a suitable assay for activity measurements is the HCV replicon assay described herein.

Administration of the compounds and their pharmaceutically acceptable prodrugs, salts, active metabolites, and solvates may be performed according to any of the accepted modes of administration available to those skilled in the art. Illustrative Examples of suitable modes of administration include oral, nasal, parenteral, topical, transdermal, and rectal. Oral and intravenous deliveries are preferred.

An HCV-inhibiting agent of the present invention may be administered as a pharmaceutical composition in any suitable pharmaceutical form. Suitable pharmaceutical forms include solid, semisolid, liquid, or lypholized formulations, such as tablets, powders, capsules, suppositories, suspensions, liposomes, and aerosols. The HCV-inhibiting agent may be prepared as a solution using any of a variety of methodologies. For Example, the HCV-inhibiting agent can be dissolved with acid (e.g., 1 M HCl) and diluted with a sufficient volume of a solution of 5% dextrose in water (D5W) to yield the desired final concentration of HCV-inhibiting agent (e.g., about 15 mM). Alternatively, a solution of D5W containing about 15 mM HCl can be used to provide a solution of the HCV-inhibiting agent at the appropriate concentration. Further, the HCV-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For Example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition may contain at least a therapeutically effective amount of an HCV-inhibiting agent and preferably is made up of one or more pharmaceutical dosage units. The selected dose may be administered to a mammal, for example, a human, in need of treatment mediated by inhibition of HCV activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion. When the composition is administered in conjunction with a cytotoxic drug, the composition can be administered before, with, and/or after introduction of the cytotoxic drug. However, when the composition is administered in conjunction with radiotherapy, the composition is preferably introduced before radiotherapy is commenced.

Methods of preparing various pharmaceutical compositions with a specific amount of active compound are known, or will be apparent, to those skilled in this art. For examples, see *Remington's Pharmaceutical Sciences*, Mack Publishing Company, Easton, Pa., 15$^{th}$ Ed. (1975).

It will be appreciated that the actual dosages of the HCV-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.001 to about 1000 mg/kg body weight, or from about 0.1 to about 100 mg/kg body weight, or from about 1 to about 50 mg/kg body weight, or from about 0.1 to about 1 mg/kg body weight, with courses of treatment repeated at appropriate intervals. The dosage forms of the pharmaceutical formulations described herein may contain an amount of a compound of the present invention, or a pharmaceutically acceptable salt of solvate thereof, deemed appropriate by one of ordinary skill in the art. For example, such dosage forms may contain from about 1 mg to about 1500 mg of a compound of the present invention, or may contain from about 5 mg to about 1500 mg, or from about 5 mg to about 1250 mg, or from about 10 mg to about 1250 mg, or from about 25 mg to about 1250 mg, or from about 25 mg to about 1000 mg, or from about 50 mg to about 1000 mg, or from about 50 mg to about 750 mg, or from about 75 mg to about 750 mg, or from about 100 mg to about 750 mg, or from about 125 mg to about 750 mg, or from about 150 mg to about 750 mg, or from about 150 mg to about 500 mg of a compound of the present invention, or a pharmaceutically acceptable salt or solvate thereof.

The subject invention also includes isotopically-labelled compounds, which are identical to those recited in the compounds of the present invention, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^5$N, $^{18}$O, $^{17}$O, $^{31}$P, $^{32}$P, $^{35}$S, $^{18}$F, and $^{35}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of the present invention and prodrugs thereof can generally be prepared by carrying out the procedures disclosed in the Schemes and/or in the Examples and Preparations below, by substituting a readily available isotopically labelled reagent for a non-isotopically labelled reagent.

The compounds of the present invention are potent inhibitors of Hepatitis C virus, in particular HCV replication, and even in more particular, HCV RNA-dependent RNA-polymerase. The compounds are all adapted to therapeutic use as anti-HCV agents in mammals, particularly in humans.

The active compound may be applied as a sole therapy or may involve one or more other antiviral substances, for example those selected from, for example, HCV inhibitors such as interferon alphacon-1, natural interferon, interferon beta-1a, interferon omega, interferon gamma-1b, interleukin-10, BILN 2061 (serine protease), amantadine (Symmetrel), thymozine alpha-1, viramidine; HIV inhibitors such as nelfinavir, delavirdine, indinavir, nevirapine, saquinavir, and tenofovir. Such conjoint treatment may be achieved by way of the simultaneous, sequential or separate dosing of the individual components of the treatment.

In general, the compounds of the present invention may be prepared according to the methods described herein as well as methods known to those of ordinary skill in the art. The methods described herein are not meant to, and should not be construed to, limit the scope of the present invention in any way.

The compounds of formula (4) may be prepared by reaction of a compound of formula (II), wherein $R^1$ and $R^2$ are as hereinbefore defined, with a compound of formula (12), wherein $R^3$ is as hereinbefore defined.

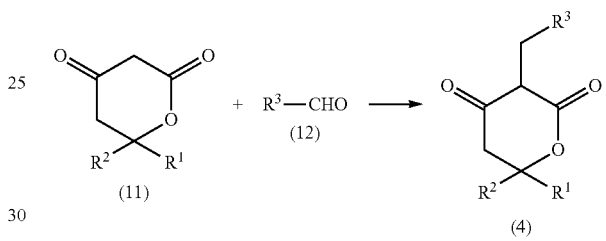

These reactions are generally performed in the presence of a reducing agent, such as a borane source or hydrogen in the presence of suitable catalyst. Suitable borane sources include, but are not limited to, borane-trimethylamine complex, borane-dimethylamine complex, borane t-butyl amine complex, and borane-pyridine complex. Suitable catalysts for use in the presence of a reducing agent such as hydrogen include, but are not limited to, nickel, palladium, rhodium and ruthenium. Furthermore, such reactions are performed in a solvent or mixture of solvents that will not interfere with desired chemical reaction. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 75° C., preferably in the range of from about 0° C. to about 32° C., most preferably at room or ambient temperature. The choice of a particular reducing agent, solvent, and temperature will depend on several factors including, but not limited to, the identity of the particular reactants and the functional groups present in such reactants. Such choices are within the knowledge of one of ordinary skill in the art and can be made without undue experimentation.

Alternatively, compounds of formula (4) may be prepared by reaction of a compound of formula (II) with a compound of formula (24), wherein X is a suitable leaving group. Suitable leaving groups include, but are not limited to, halides (such as chloride, bromide, and iodide), and activated esters (such as methanesulfonate, trifluoromethane sulfonate, and tosyl esters). Such reactions can be performed in the presence of a suitable base. Suitable bases include, but are not limited to, sodium carbonate, sodium bicarbonate, potassium carbonate, cesium carbonate, sodium hydroxide, potassium hydroxide, sodium hydride, lithium hydride, potassium hydride, and lithium diisopropylamide. Furthermore, appropriate solvents include those that are known to those of skill in the art to be compatible with the reaction conditions and include alkyl, heterocyclic, and aryl ethers, hydrocarbons, alkyl and aryl halogenated compounds, alkyl or aryl nitriles, and non-protic heterocyclic solvents. For example, suitable solvents include, but are not limited to, dimethoxyethane, diisopropyl ether, chlorobenzene, dimethyl formamide, dimethyl acetamide, propionitrile, butyronitrile, diethyl ether, methyl-t-butyl ether, diphenyl ether, methylphenyl ether, tetrahydrofuran, 2-methyltetrahydrofuran, 1,4-dioxane, pentane, hexane, heptane, acetonitrile, benzonitrile, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 150° C., preferably in the range of from about 0° C. to about 32° C., most preferably at room or ambient temperature. The choice of a particular reducing agent, solvent, and temperature will depend on several factors including, but not limited to, the identity of the particular reactants and the functional groups present in such reactants. Such choices are within the knowledge of one of ordinary skill in the art and can be made without undue experimentation.

Suitable bases for use in these reactions include inorganic bases and organic bases. Suitable inorganic bases include, but are not limited to, sodium carbonate, sodium bicarbonate, potassium carbonate, potassium bicarbonate, sodium hydroxide, sodium hydride, potassium hydride, and cesium carbonate. Preferably, the base is potassium carbonate. Suitable organic bases include, but are not limited to, pyridine, triethylamine, tributylamine, triethanolamine, N-methylmorpholine, N-ethyl-N,N-diisopropylamine, DBU, and 4-N,N-dimethylaminopyridine. These reactions can also be performed in the presence of a catalytic amount of a suitable acid. Suitable acids include both Bronsted-Lowry and Lewis acids. Furthermore, these reactions are generally performed in a solvent or mixture of solvents that will not interfere with desired chemical reaction. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 100° C., or in the range of from about 25° C. to about 100° C., or in the range of from about 35° C. to about 75° C., or in the range of from about 45° C. to about 55° C., or at about 50° C. The choice of a particular reducing agent, solvent, and temperature will depend on several factors including, but not limited to, the identity of the particular reactants and the functional groups present in such reactants. Such choices are within the knowledge of one of ordinary skill in the art and can be made without undue experimentation.

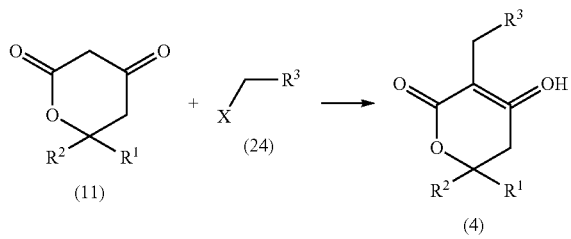

Compounds of formula (II), wherein $R^1$ and $R^2$ are as hereinbefore defined, can be prepared from compounds of formula (25), by reaction with a suitable acid or base.

Alternatively, the compounds of formula (II), wherein $R^1$ and $R^2$ are as hereinbefore defined, can be prepared from compounds of formula (25), wherein $R^{14}$ is hydrogen, by reaction with a suitable reagent, or a combination of suitable reagents, to affect cyclization. Such reactions may be performed in the presence of a reagent or combination of reagents that will convert the carboxylic —OH group into a suitable leaving group, such as chlorine or an imidazole group, for example. The term "a suitable leaving group" means a chemical group that is capable of being displaced when a suitable nucleophilic group, such as a hydroxyl group, reacts with the carbonyl carbon in the carboxyl group in the compounds of formula (25). Such suitable leaving groups can be introduced in the compounds of formula (25) wherein $R^{14}$ is hydrogen, by reaction of the compound of formula (25) with a suitable reagent or combination of reagents known to those of ordinary skill in the art. For example, a compound of formula (25), wherein $R^{14}$ is hydrogen, may be allowed to react with phosgene (ClC(O)Cl) or triphosgene (((Cl)$_3$C(O)C(Cl)$_3$) to afford a so-called acid chloride, that is where the carboxy hydroxyl group has been replaced with a chlorine

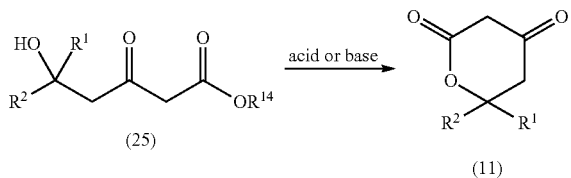

atom. Furthermore, the compounds of formula (25) may be converted to compounds wherein the carboxy hydroxyl group is replaced by another type of suitable leaving group, such as an imidazole group. Such compounds can be prepared using a suitable reagent or combination of reagents such as carbonyl diimidazole. These types of reactions may be performed in the presence of a suitable base, such as triethylamine for example, and in an aprotic solvent that will not interfere with the desired chemical reaction, chloroform or dichloromethane for example. Furthermore, such reactions may be performed at a temperature in the range from about −78° C. to about 75° C., or in the range of from about 0° C. to about 50° C., or from about 0° C. to about 25° C. The choice of a suitable reagent to convert the carboxyl group into an acid chloride, for example, a suitable solvent, and a suitable temperature are all choices within the knowledge of one of ordinary skill in the art and can be made without undue experimentation.

The compounds of formula (25), wherein the carboxy hydroxyl group has been converted to an appropriate leaving group, an acid chloride for example, may then be converted to compounds of formula (11) by reaction in the presence of a suitable base. Suitable bases include, but are not limited to, inorganic bases and organic bases. Suitable inorganic bases include, but are not limited to, sodium carbonate, sodium bicarbonate, potassium carbonate, potassium bicarbonate, and cesium carbonate. Suitable organic bases include, but are not limited to, pyridine and 4-N,N-dimethylaminopyridine. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. The particular choices of activating agent, solvent, base, and temperature to affect the desired transformation are all choices within the knowledge of one of ordinary skill in the art and can be made without undue experimentation.

Compounds of formula (25), wherein $R^1$ and $R^2$ are as hereinbefore defined, $P^1$ is hydrogen or a suitable protecting group, and $R^{14}$ is $C_1$-$C_6$ alkyl, —Si($C_1$-$C_6$ alkyl)$_3$, or —CH$_2$ ($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, can be prepared from compounds of formula (9), wherein $R^1$ and $R^2$ are as hereinbefore defined, $R^{12}$ is hydrogen or —C(O)$R^{13}$, and $R^{13}$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, or from compounds of formula (9a), wherein $R^1$, $R^2$, and $R^{12}$ are as hereinbefore defined, and L is a suitable leaving group, as shown below.

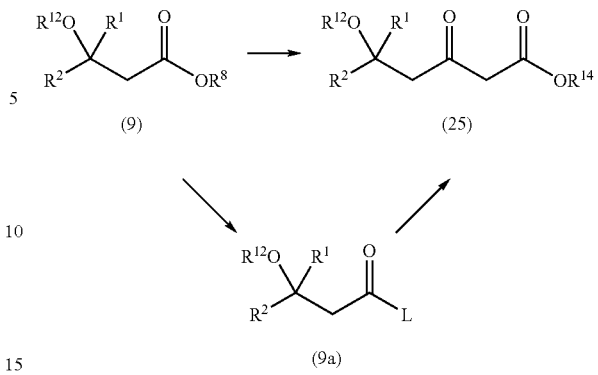

The compound of formula (9) wherein $R^8$ is hydrogen may be allowed to react with a reagent or combination of reagents that will convert the carboxy hydroxyl group to a suitable leaving group —OA. Such groups include activated esters, such as various benzoyl esters, such as a 2,6-dinitrobenzoyl ester or a perfluorobenzoyl ester, mixed anhydrides, or an intermediate derived from reaction of the caboxy group with a carbodiimide, such as diethyl carbodiimide or diisopropyl carbodiimide. These intermediate compounds can be prepared by reaction of the carboxy group with a suitable reagent, such as a carbodiimide, in a solvent that will not interfere with the desired chemical reaction, such as chloroform, dichloromethane, or tetrahydrofuran, and at a temperature of from about −78° C. to about 100° C., or in the range of from about 0° C. to about 75° C., or in the range of from about 0° C. to about 50° C. The compound of formula (9) containing the suitable leaving group —OA can be isolated or can be allowed to react in the next step without any further purification. The compound containing the suitable leaving group —OA can then be allowed to react with a reagent or combination of reagents to provide the compound of formula (25). Such suitable reagents include, but are not limited to, malonate anions derived from deprotonation of a malonate derivative with a suitable base, and magnesium malonate esters, such as methyl magnesium malonate and ethyl magnesium malonate. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Furthermore, they are performed at a temperature in the range of from about 0° C. to about 150° C., or in the range of from about 0° C. to about 75° C., or in the range of from about 20° C. to about 75° C., or in the range of from about 25° C. to about 50° C., or at about 40° C. The particular choice of reagent or combination or reagents, solvent or solvents, and temperature are within the knowledge of one of ordinary skill in the art and can be made without undue experimentation.

Alternatively, the compounds of formula (25) can be prepared from compounds of formula (9), wherein $R^8$ is $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, by reaction with a reagent or combination of reagents to provide the compound of formula (III). Such suitable reagents include, but are not limited to magnesium malonate esters, such as methyl magnesium malonate and ethyl magnesium malonate. Such suitable reagents include, but are not limited to, malonate anions derived from deprotonation of a malonate derivative with a suitable base, and magnesium malonate esters, such as methyl magnesium malonate and ethyl magnesium malonate. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Furthermore, they are performed at a temperature in the range of from about 0° C. to about 150° C., or in the range of from about 0° C. to about 75° C., or in the range of from about 20° C. to about 75° C., or in the range of from about 25° C. to about 50° C., or at about 40° C. The particular choice of reagent or combination or reagents, solvent or solvents, and temperature are within the knowledge of one of ordinary skill in the art and can be made without undue experimentation.

Additionally, the compounds of formula (25) can be prepared from compounds of formula (9a), wherein $R^1$, $R^2$, and $R^{12}$ are as hereinbefore defined, and L is a suitable leaving group, by reaction with a reagent or combination of reagents to provide the compound of formula (25). Suitable leaving groups include, but are not limited to, chloride, bromide, iodide, and imidazole. Compounds with suitable leaving groups can be prepared from compounds of formula (9) wherein $R^8$ is —OH by reaction with an activating reagent or combination of activating reagents capable of replacing the carboxy hydroxyl group with L. Such activating reagents include, but are not limited to, thionyl chloride (SOCl$_2$), phosgene, triphosgene, and carbonyldiimidazole. These reactions are typically performed in the presence of a base that will not interfere with the desired chemical reaction, such as triethylamine, ethyldiisopropylamine, pyridine, or 4-N,N,-dimethylaminopyridine. Furthermore, the reactions are performed in an aprotic solvent that will not interfere with the desired chemical reaction such as tetrahydrofuran, methylbutyl ether, diisopropyl ether, diethyl ether, toluene, chloroform, dichloromethane, or 1,2-dichloroethane, for example. Furthermore, such reactions are performed at a temperature in the range of from about −78° C. to about 100° C., or in the range of from about −50° C. to about 100° C., or in the range of from about 0° C. to about 75° C., or in the range of from about 0° C. to about 50° C., or in the range of from about 0° C. to about 25° C. After conversion of a compound of formula (9) to a compound of formula (9a), the compound of formula (9a) may be allowed to react with a reagent or combination of reagents capable of converting the compound of formula (9a) to one of formula (25). Such suitable reagents include, but are not limited to magnesium malonate esters, such as methyl magnesium malonate and ethyl magnesium malonate. These reactions are performed in a solvent or mixture of solvents that will not interfere with the desired chemical reaction, such as diethyl ether, methyl t-butyl ether, and tetrahydrofuran, or mixtures thereof. Furthermore, they are performed at a temperature in the range of from about 0° C. to about 100° C., or in the range of from about 0° C. to about 75° C., or in the range of from about 20° C. to about 75° C., or in the range of from about 25° C. to about 50° C., or at about 40° C. The particular choice of reagent or combination or reagents, solvent or solvents, and temperature are within the knowledge of one of ordinary skill in the art and can be made without undue experimentation.

The reaction of compounds of formula (9), (9a), or suitably activated derivatives thereof, with a reagent or combination or reagents to afford a compound of formula (25) may require the introduction of a suitable protecting group for the tertiary hydroxyl group in the compounds of formula (9). Such protecting groups should be capable of being introduced into the compound of formula (9) under conditions that will selectively protect such hydroxyl group. Such reagents and conditions are well-known to those of ordinary skill in the art and can be found, for example, in T. Greene and P. Wuts, *Protective Groups in Organic Synthesis* (3rd ed.), John Wiley & Sons, NY (1999). For example, a silyl protecting group, such as a triisopropyl silyl group, can be introduced into the compound of formula (9) to selectively protect the tertiary hydroxyl group. Such a group can be introduced using an activated silane reagent, such as triisopropyl silyl chloride for example, in the presence of a base, such as triethylamine for example, and in an aprotic solvent, chloroform for example. The protected compound of formula (9) may then be allowed to react as described above to afford a compound of formula (25) in protected form. The protected compound (25) can then be deprotected using conditions known to those of ordinary skill in the art. For example, if the tertiary hydroxyl group in the compound of formula (25) is protected with as a silyl ether, for example, it can be deprotected using a fluoride source, tetrabutylammonium fluoride for example, in a solvent such as THF and at a temperature in the range of from about 0° C. to about 100° C., or in the range of from about 0° C. to about 25° C. Whether the tertiary hydroxyl group in the compound of formula (9) requires protection prior to conversion to the compound of formula (25) is within the knowledge of one of ordinary skill in the art and such a choice can be made without undue experimentation.

Reagents such as magnesium malonate esters, methyl magnesium malonate or ethyl magnesium malonate for example, are either commercially available or can be prepared using methods known to those of ordinary skill in the art. For example, ethyl magnesium malonate can be prepared by reaction of magnesium ethoxide with ethyl malonic acid, as shown below.

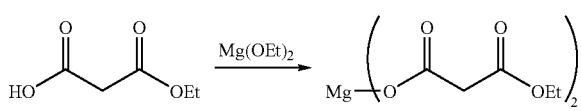

Compounds of formula (9), wherein $R^1$, $R^2$, and $R^{12}$, are as hereinbefore defined, and $R^8$ is hydrogen, can be prepared from compounds of formula (9),

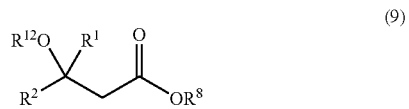

wherein $R^8$ is $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, by hydrolysis with a suitable acid or base in an aqueous solvent. Suitable bases include, but are not limited to, lithium hydroxide, sodium hydroxide, potassium hydroxide, sodium carbonate, and potassium carbonate. Suitable acids include, but are not limited to, hydrochloric acid, hydrobromic acid, hydroiodic acid, and sulfuric acid. These reactions can be performed in a solvent or mixture of solvents that will not interfere with the desired chemical reaction including, but not limited to, diethyl ether, methyl tert-butyl ether, tetrahydrofuran, methyl alcohol, ethyl alcohol, iso-propyl alcohol, n-propyl alcohol, and tert-butyl alcohol. Water may be advantageously used as a co-solvent in these reactions. Furthermore, these reactions are typically performed at a temperature in the range from about −78° C. to about 50° C., or in the range from about −35° C. to about 50° C., or in the range of from about −35° C. to about 25° C.

Compounds of formula (9), wherein $R^1$, $R^2$, and $R^{12}$ are as hereinbefore defined, and $R^8$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, can be prepared by reaction of a compound of formula (26), wherein $R^1$ and $R^2$ are as hereinbefore defined, with a compound of formula (14), wherein $R^8$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH$_3$, and —N($C_1$-$C_6$ alkyl)$_2$, as shown below.

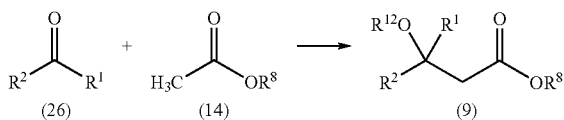

These reactions can be performed in the presence of strong base to first react with the compound of formula (14) to afford an anion. Suitable strong bases for such reactions include lithium hexamethyl disilylazide (LiHMDS), sodium hexamethyl disilazide, potassium hexamethyl disilazide, lithium diisopropyl amide, and magnesium diisopropylamide. Furthermore, such reactions can be performed in the presence of a solvent that will not interfere with the desired chemical reaction. Suitable solvents include, but are not limited to, neat solutions of the compound of formula (14), diethyl ether, methyl tert-butyl ether, and tetrahydrofuran. Additionally, such reactions can be performed at a temperature in the range of from about −78° C. to about 25° C., or in the range of from about −50° C. to about 25° C., or from about −35° C. to about 25° C., or in the range of from about −35° C. to about 0° C.

Alternatively, compounds of formula (9) can be prepared by reaction of a compound of formula (26) with a silylketene acetal as shown below, wherein R is, for example, a $C_1$-$C_6$ alkyl group, and $R^8$ is as hereinbefore defined. These reactions can be performed in the presence of a catalytic or stoichiometric amount of a suitable Lewis acid that include, but are not limited to, aluminum (III) chloride, titanium (II) chloride, titanium (IV) chloride, tin (II) chloride, and tin (IV) chloride. Furthermore, such reactions can be performed in the presence of a solvent that will not interfere with the desired chemical reaction. Suitable solvents include, but are not limited to, diethyl ether, methyl tert-butyl ether, and tetrahydrofuran. Additionally, such reactions can be performed at a temperature in the range of from about −78° C. to about 25° C., or in the range of from about −50° C. to about 25° C., or from about −35° C. to about 25° C., or in the range of from about −35° C. to about 0° C.

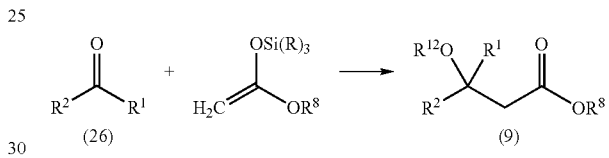

The compounds of formula (9), wherein $R^1$, $R^2$, and $R^{12}$ are as hereinbefore defined, and $R^8$ is hydrogen can be resolved or stereoisomerically enriched. Such compounds can be stereoisomerically enriched by allowing them to react with a chiral, non-racemic base to form a mixture of diastereomeric salts. Such diastereomeric salts can then be separated using techniques well-known to those of ordinary skill in the art, such as fractional crystallization. For example, a mixture of the diastereomeric salts can be dissolved in a suitable solvent and one diastereomeric salt may then crystallize from the solution after which time it may be collected, washed and dried. Suitable chiral, non-racemic bases include amine bases include, but are not limited to, one enantiomer of cis-1-amino-2-indanol, cinchonidine, 1-aminoindane, tert-leucinol, 2-amino-1,2-diphenylethanol, and alpha-methylbenzylamine. For example, a compound of formula (9), wherein $R^1$, $R^2$, and $R^{12}$ are as hereinbefore defined, and $R^8$ is hydrogen, may be allowed to react with (1R,2S)-(+)-cis-1-amino-2-indanol in a suitable solvent, such as tetrahydrofuran to afford a mixture of diastereomeric salts. The solution containing the mixture of diastereomeric salts can then be allowed to slowly cool so that only one of the diastereomeric salts is appreciably soluble in the cooled solvent. The remaining diastereomeric salt may then precipitate out of the solution in the form of a crystalline solid comprising one diastereomeric salt in substantially pure form. The desired stereoisomerically enriched compound of formula (9) may then be obtained from either the precipitated diastereomeric salt or from the diastereomeric salt that remained in solution. The compound of formula (9), wherein $R^8$ is hydrogen, may then be obtained from the substantially pure diastereomeric salt by reaction with a suitable acidic compound, such as citric acid.

Compounds of formula (14), wherein $R^8$ is hydrogen, $C_1$-$C_6$ alkyl, —Si($C_1$-$C_6$ alkyl)$_3$, or —CH$_2$($C_6$-$C_{10}$ aryl), wherein said $C_6$-$C_{10}$ aryl group is optionally substituted with at least one substituent selected from halogen, $C_1$-$C_6$ alkyl, —OH, —OCH₃, and —N(C₁-C₆ alkyl)₂, are either commercially available or can be prepared according to methods known to those of ordinary skill in the art.

Compounds of formula (26) can be prepared via a so-called Heck-type reaction. For example, the compound of formula (26), wherein R¹ is as hereinbefore defined and R² is —(CH₂)₂Ph, can be prepared from reaction of compounds of formula (27) with a compound of formula (28), wherein X is a group suitable for use in a palladium-catalyzed (Pd-catalyzed) Heck-type coupling reaction. Heck-type coupling reactions can be performed using a palladium based catalyst. Suitable catalysts include, but are not limited to, Pd(OAc)₂, PdCl₂, and Pd(PPh₃)₄. Furthermore, such reactions can be performed in the presence of a base, such as triethylamine, sodium acetate, lithium acetate, potassium acetate, sodium carbonate, potassium carbonate, or cesium carbonate. These reactions may be performed in a solvent that will not interfere with the desired chemical reaction. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, amides, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, N-methylpyrrolidinone, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Next, these reactions can be performed at a temperature in the range from about 0° C. to about 150° C., or in the range of from about 25° C. to about 150° C., or in the range of from about 25° C. to about 100° C., or in the range of from about 45° C. to about 100° C., or in the range of from about 45° C. to about 75° C. Last, in the compounds of formula (28), X is a group that is suitable for use in Heck-type reactions. Suitable groups include chloride, bromide, iodide, and triflate (—OSO₂CF₃).

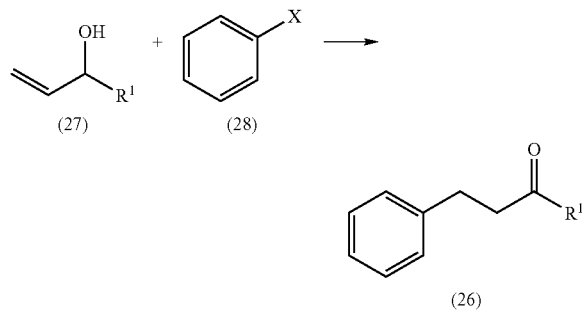

Compounds of formula (28) are either commercially available or can be prepared by methods known to those of ordinary skill in the art. For example, 2-(4-bromo-2-fluorophenyl)-2-methylpropanenitrile, compound (28a) can be prepared from (4-bromo-2-fluorophenyl)acetonitrile, compound (28b), by reaction with an alkylating agent, methyl tosylate for example, in the presence of a base, sodium t-butoxide for example, as shown below.

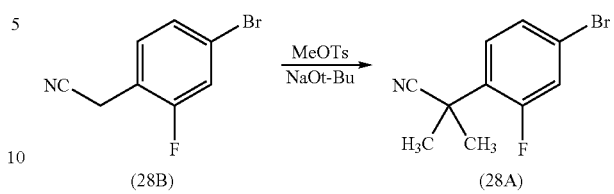

Furthermore, (4-bromo-2-fluorophenyl)acetonitrile can be prepared from 4-bromo-1-(bromomethyl)-2-fluorobenzene by reaction with a cyanide salt, sodium cyanide for example, as shown below.

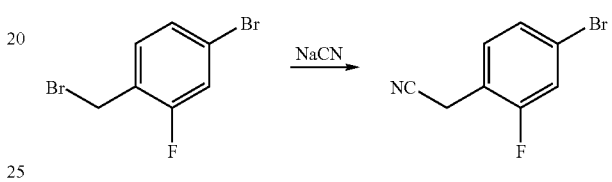

Compounds of formula (27), wherein R¹ is as hereinbefore defined, can be prepared by reaction of compounds of formula (29), wherein R¹ is as hereinbefore defined, and a compound of formula (30),

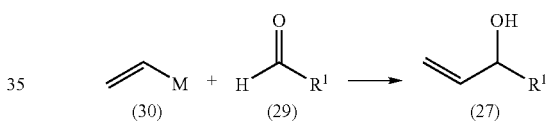

wherein M is a suitable metal, as shown. In the compounds of formula (30), M is chosen from a suitable metal, such as a magnesium derivative, such as magnesium bromide, or lithium. These reactions can be performed in an aprotic solvent, such as diethyl ether, methyl tert-butyl ether, or tetrahydrofuran for example. Additionally, these reactions can be performed at a temperature in the range of from about –78° C. to about 50° C., or in the range of from about –78° C. to about 25° C., or in the range of from about –78° C. to about 0° C.

Compounds of formula (30), wherein M is a suitable metal group, are either commercially available or can be prepared by methods known to those of ordinary skill in the art. For example, the compound of formula (30) wherein M is —MgBr can be prepared from vinyl bromide and a suitable magnesium precursor, such as magnesium metal or activated Reike magnesium. These reactions are can be performed in an aprotic solvent such as diethyl ether, methyl tert-butyl ether, or tetrahydrofuran, and at a temperature in the range of from about 0° C. to about 25° C. Compounds of formula (30) wherein M is Li can be prepared from vinyl halides, such as vinyl bromide or iodide and a suitable alkyl lithium reagent, such as butyl lithium or tert-butyl lithium. These reactions can be performed in an aprotic solvent such as diethyl ether, methyl tert-butyl ether, or tetrahydrofuran, and at a temperature in the range of from about 0° C. to about 25° C.

Compounds of formula (29), wherein R¹ is as hereinbefore defined, are either commercially available or can be prepared by reaction of a compound of formula (31), wherein L is a suitable leaving group, with a compound of formula (32), R¹ is as hereinbefore defined and M is a suitable metal. In the compounds of formula (31), L is a suitable leaving group, such a —N(CH$_3$)$_2$ group. In the compounds of formula (32), M is a suitable metal such as —MgBr or Li. These reactions are can be performed in an aprotic solvent such as diethyl ether, methyl tert-butyl ether, or tetrahydrofuran, and at a temperature in the range of from about 0° C. to about 25° C.

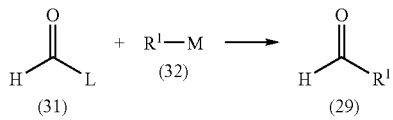

Compounds of formula (31) are either commercially available or can be prepared by methods known to those of ordinary skill in the art.

Compounds of formula (32) wherein M is a suitable metal are either commercially available or can be prepared by methods known to those of ordinary skill in the art. For example, the compound of formula (32) wherein M is —MgBr can be prepared from vinyl bromide and a suitable magnesium precursor, such as magnesium metal or activated Rieke magnesium. These reactions are can be performed in an aprotic solvent such as diethyl ether, methyl tert-butyl ether, or tetrahydrofuran, and at a temperature in the range of from about 0° C. to about 25° C. Compounds of formula (32) wherein M is Li can be prepared from a suitable halide, such as a bromide or iodide and a suitable alkyl lithium reagent, such as butyl lithium or tert-butyl lithium. These reactions can be performed in an aprotic solvent such as diethyl ether, methyl tert-butyl ether, or tetrahydrofuran, and at a temperature in the range of from about 0° C. to about 25° C.

Compounds of formula (24), such as (24a) below, are either commercially available or can be prepared using methods known to those of ordinary skill in the art. For example, the compound of formula (24a) was prepared by reaction of glycolic acid with aminoguanidine bicarbonate to afford (5-amino-1H-1,2,4-triazol-3-yl)methanol. The product was then allowed to react with 2,4-pentanedione to provide (5,7-dimethyl[1,2,4]triazolo[1,5-a]pyrimidin-2-yl)methanol, which was then oxidized using 2,2,6,6-tetramethyl-1-piperidinyloxy and iodobenzene diacetate to afford 5,7-dimethyl[1,2,4]triazolo[1,5-a]pyrimidine-2-carbaldehyde.

Compounds of formula (11), wherein R$^1$ is as hereinbefore defined and R$^2$ is an optionally substituted C$_6$-C$_{10}$ aryl or an optionally substituted 4-10 membered heterocycle, can be prepared from compounds of formula (17) by reaction with a suitable base in a suitable solvent.

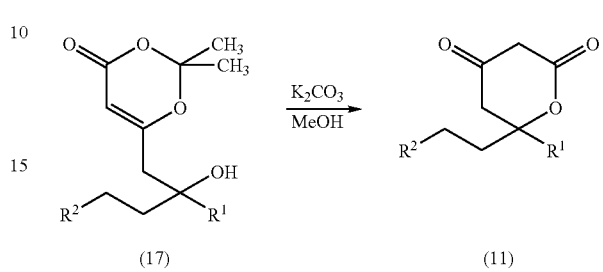

Such reactions may be performed using a suitable base in a suitable solvent. Suitable bases include, but are not limited to, potassium carbonate, sodium carbonate, potassium bicarbonate, sodium bicarbonate, potassium hydroxide, and sodium hydroxide. Solvents that may be used include, but are not limited to, methyl alcohol, ethyl alcohol, iso-propyl alcohol, n-propyl alcohol, acetonitrile, and DMF, or a mixture of them. Additionally, water may be used as a cosolvent if necessary. These reactions may be performed at a temperature of from about 0° C. to about 150° C. The particular choice of a base or combination of bases, solvent or combination of solvents, and reaction temperature will depend on the particular starting material being used and such choices are within the knowledge of one of ordinary skill in the art and can be made without undue experimentation.

Compounds of formula (17), wherein R$^1$ is as hereinbefore defined and R$^2$ is an optionally substituted C$_6$-C$_{10}$ aryl or an optionally substituted 4-10 membered heterocycle, can be prepared from compounds of formula (18) by reaction with a reducing agent in the presence of a catalyst.

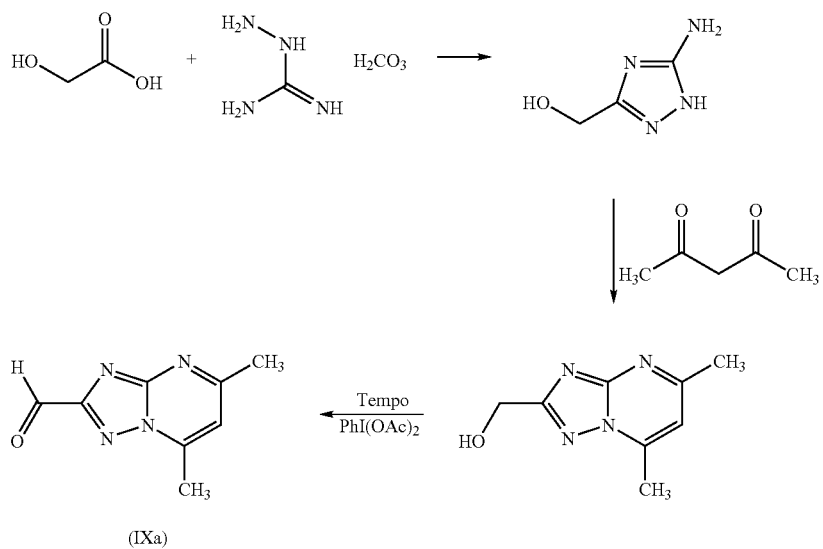

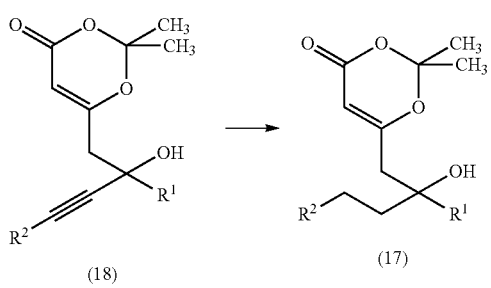

(18) → (17)

These reactions are typically performed in the presence of a metal catalyst, such as a palladium catalyst, a reducing agent, such as hydrogen, and in a solvent. Furthermore, these reactions may be performed at a temperature of from about 25° C. to about 150° C., depending on the substrate, the catalyst, the reducing agent, and the solvent. Catalysts useful in such reactions include, but are not limited to, Pd on carbon (5% w/w and 10% w/w, for example), Pt on carbon (5% w/w and 10% w/w, for example), palladium hydroxide, and Raney nickel. Suitable reducing agents that may be used include, but are not limited to, hydrogen and ammonium formate. When hydrogen is used as the reducing agent, it is advantageous to pressurize the reaction vessel with at least one atmosphere of hydrogen gas. Solvents that may be used include, but are not limited to, protic solvents, such as methyl and ethyl alcohol, and aprotic solvents such as acetonitrile, DMF, ethyl acetate, acetone, chloroform, and dichloromethane. The particular choice of a catalyst, reducing agent, solvent, and temperature will depend on the particular substrate being used and such choices are within the knowledge of one of ordinary skill in the art and can be made without undue experimentation.

Compounds of formula (18), wherein $R^1$ is as hereinbefore defined and $R^2$ is an optionally substituted $C_6$-$C_{10}$ aryl or an optionally substituted 4-10 membered heterocycle, can be prepared from compounds of formula (19) by reaction with a compound of formula (20), wherein $R^2$ is an optionally substituted $C_6$-$C_{10}$ aryl or an optionally substituted 4-10 membered heterocycle and X is a halogen (such as bromine or iodine) or —$OSO_2CF_3$, in the presence of a suitable catalyst.

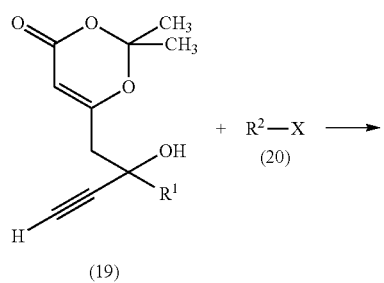

(19) + $R^2$—X (20) →

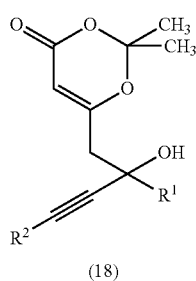

(18)

These reactions can be performed using a compound of formula (19), a compound of formula (20), a suitable catalyst, and a suitable copper compound (such as copper (I) iodide. These reactions are also performed in the presence of a base, such as diisopropyl amine, and in a solvent, such as dimethylformamide (DMF). These reactions may be performed at a temperature from 25° C. to 150° C., depending on the particular substrates, the catalyst, and the solvents. Suitable catalysts include, but are not limited to, $PdCl_2(PPh_3)_2$, $PdCl_2$, and $Pd(PPh_3)_4$. Suitable bases include, but are not limited to, triethylamine, diethylamine, and diethylisopropyl amine. Solvents that may be used include, but are not limited to, acetonitrile, dimethylformamide (DMF), ethyl acetate, 1,2-dichloroethane, and chloroform. The particular choice of palladium catalyst, base, solvent, and temperature will depend on the particular substrates being used and such choices are within the knowledge of one of ordinary skill in the art and can be made without undue experimentation.

Compounds of formula (20), wherein $R^2$ is an optionally substituted $C_6$-$C_{10}$ aryl or an optionally substituted 4-10 membered heterocycle, and X is a halogen (such as bromine or iodine) or —$SO_2CF_3$, are either commercially available or can be prepared using methods known to those of ordinary skill in the art.

Compounds of formula (19), wherein $R^1$ is as hereinbefore defined, can be prepared from compounds of formula (21), wherein $R^1$ is as hereinbefore defined, with a suitable reagent or combination of reagents that will cleave the silyl group in compound (21).

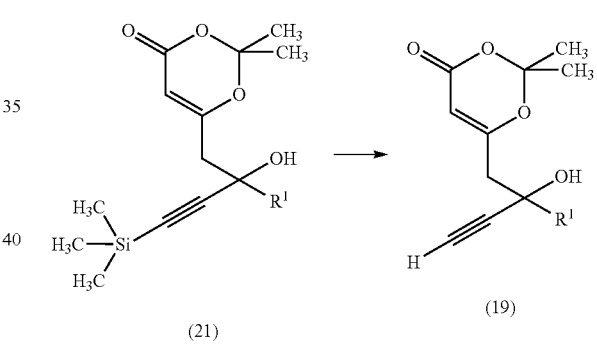

(21) → (19)

Suitable reagents or combinations of reagents that will cleave the silyl group in the compound of formula (21) include, but are not limited to, strong bases, such as sodium hydroxide and potassium hydroxide, and fluoride ion ($F^-$). Suitable sources of fluoride ion include, but are not limited to, ammonium fluoride salts such as tetrabutyl ammonium fluoride. These reactions can be performed in a solvent or mixture of solvents that will not interfere with the desired chemical reaction. Suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 100° C., or in the range of from about 0° C. to about 75° C., or in the range of from about 0° C. to about 50° C., or in the range of from 25° C. to about 50° C. The particular choice of a deprotecting reagent or combination of reagents, solvent, and temperature are within the knowledge of one of ordinary skill in the art and can be made without undue experimentation.

Compounds of formula (21), wherein $R^1$ is as hereinbefore defined, can be prepared from compounds of formula (22), wherein $R^1$ is as hereinbefore defined, by reaction with 2,2,6-trimethyl-[1,3]-dioxin-4-one.

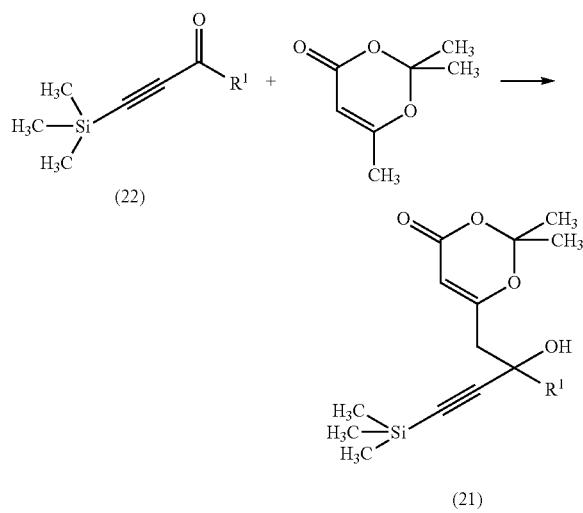

These reactions can be performed in the presence of base that will deprotonate the 2,2,6-trimethyl-[1,3]-dioxin-4-one. Suitable bases include, but are not limited to, lithium diisopropyl amide, tert-butyl lithium, and n-butyl lithium. Bases such as lithium diisopropyl amide can be generated in situ by reaction with diisopropyl amine and an alkyl lithium reagent, such as tert-butyl lithium or n-butyl lithium, and can be used without isolation or further purification. These reactions can also be performed in a solvent that will not interfere with the desired chemical reaction. Suitable solvents include, but are not limited to, aprotic solvents such as diethyl ether, methyl tert-butyl ether, and tetrahydrofuran. Last, these reactions can be performed at a temperature in the range from about −78° C. to about ambient or room temperature, or in the range from about −78° C. to about 0° C., or in the range from about −78° C. to about −30° C. The choice of a particular base, solvent, and temperature are within the knowledge of one of ordinary skill in the art and such choices can be made without undue experimentation.

Compounds of formula (22), wherein $R^1$ is as hereinbefore defined, are either commercially available or can be prepared using methods known to those of ordinary skill the art, such as those found in *Journal of Organic Chemistry*, 1984, 4786-4800.

The compounds of formula (4) can be prepared in stereoisomerically enriched form by reaction of a compound of formula (11), which is stereoisomerically enriched with a compound of formula (12).

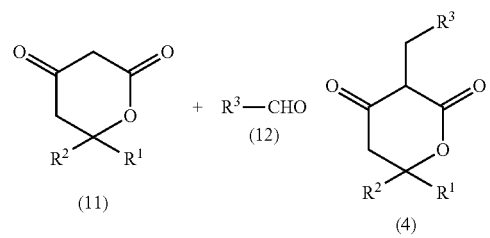

These reactions are generally performed in the presence of a reducing agent, such as a borane source or hydrogen in the presence of suitable catalyst. Suitable borane sources include, but are not limited to, borane-trimethylamine complex, borane-dimethylamine complex, borane t-butyl amine complex, and borane-pyridine complex. Suitable catalysts for use in the presence of a reducing agent such as hydrogen include, but are not limited to, nickel, palladium, rhodium and ruthenium. Furthermore, such reactions are performed in a solvent or mixture of solvents that will not interfere with desired chemical reaction. Furthermore, appropriate solvents include those that are known to those of skill in the art to be compatible with the reaction conditions and include alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 75° C., preferably in the range of from about 0° C. to about 32° C., most preferably at room or ambient temperature. The choice of a particular reducing agent, solvent, and temperature will depend on several factors including, but not limited to, the identity of the particular reactants and the functional groups present in such reactants. Such choices are within the knowledge of one of ordinary skill in the art and can be made without undue experimentation.

Compounds of formula (9), wherein $R^1$, $R^2$, and $R^8$ are as hereinbefore defined, can be prepared from compounds of formula (8), wherein $R^1$, $R^2$, and $R^8$ are as hereinbefore defined, with a reducing agent in the presence of a catalyst.

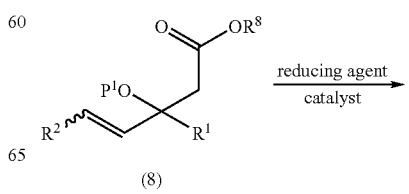

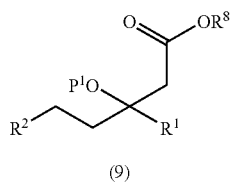

(9)

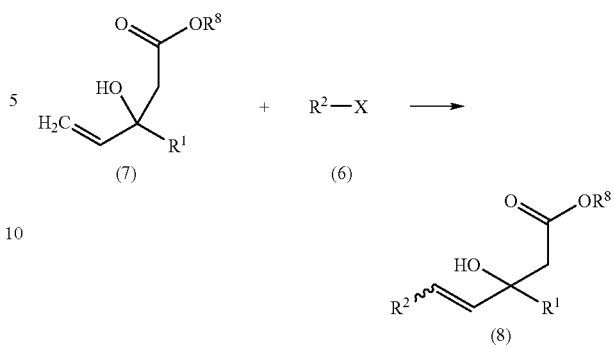

Suitable reducing agents for this reaction are those that are capable of transferring hydrogen ($H_2$) to the alkene to afford the desired alkane, compound (9). Suitable reducing agents include, but are not limited to hydrogen gas, formic acid, and formic acid salts, such as ammonium formate. When hydrogen gas is used as the reducing agent, the reaction vessel is usually pressurized with hydrogen gas. Suitable catalysts for this reaction include those that are capable of reducing the alkene in compound (8) to afford alkane (9) in the presence of the suitable reducing agents described above. Suitable catalysts include, but are not limited to, Pd (0), Pt (0), and Ni (0). These catalysts may be prepared in situ from suitable pre-catalysts that may be more shelf-stable. Suitable pre-catalysts include, but are not limited to, palladium on carbon (5 w/w % and 10 w/w %, for example), $PdCl_2$, $Pd(OH)_2$, $PdCl_2(PPh_3)_2$, $Pd(PPh_3)_4$, $PtCl_2$, $Pt(OH)_2$, and Raney Nickel. Furthermore, these reactions can be performed in a solvent or mixture of solvents that will not interfere with the desired chemical reaction. Suitable solvents include, but are not limited to, alkyl esters and aryl esters, alkyl, heterocyclic, and aryl ethers, hydrocarbons, alkyl and aryl alcohols, alkyl and aryl halogenated compounds, alkyl or aryl nitriles, alkyl and aryl ketones, and non-protic heterocyclic solvents. For example, suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent if it will not interfere with the desired transformation. Finally, such reactions can be performed at a temperature in the range of from about 0° C. to about 100° C., or in the range of from about 0° C. to about 75° C., or in the range of from about 0° C. to about 50° C., or in the range of from 25° C. to about 50° C. The choice of a particular reducing agent, catalyst, solvent, and temperature will depend on a number of factors including, but not limited to, the identity of the reactants and the presence or absence of other functional groups. Such choices are within the knowledge of one of ordinary skill in the art and can be made without undue experimentation.

Compounds of formula (8), wherein $R^1$, $R^2$, and $R^8$ are as hereinbefore defined, can be prepared from compounds of formula (7), wherein $R^1$ and $R^8$ are as hereinbefore defined, by reaction with a compound of formula (6), wherein X is a halogen or $-OSO_2CF_3$, and $R^2$ is as hereinbefore defined, in the presence of a suitable catalyst.

These reactions can be performed in the presence of a catalyst that is chemically and catalytically competent to perform a so-called Heck-type reaction. Suitable catalysts include Pd(0) species, either bound or unbound to an appropriate number of ligands. Such catalysts can be generated in situ from a suitable pre-catalyst in the presence of an appropriate ligand. Suitable pre-catalysts include, but are not limited to, $PdCl_2$, $PdCl_2(PPh_3)_2$, and $Pd(PPh_3)_4$. The amount of catalyst or pre-catalyst used in these reactions will depend on the particular reaction substrates, the temperature at which the reaction is performed, and the solvent in which the reaction is performed. Catalyst loadings may be in the range of from about 0.01 mol % (based on the amount of either compound (7) or (6)) to about 99 mol %, or in the range of from about 0.01 mol % to about 50 mol %, or in the range of from about 0.01 mol % to about 25 mol %, or in the range of from about 0.01 mol % to about 10 mol %, or in the range of from about 0.01 mol % to about 5 mol %. These reactions can also be performed in the presence of a base. Suitable bases include, but are not limited to, organic bases, such as triethylamine and sodium acetate, and inorganic bases, such as sodium carbonate, sodium bicarbonate, potassium carbonate, potassium bicarbonate, and cesium carbonate. These reactions can be performed in a solvent that will not interfere with the desired chemical reaction. Suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, 1-methyl-2-pyrrolidinone, and pyridine, or any mixture of the above solvents. Additionally, water may be used as a co-solvent if it will not interfere with the desired transformation. Finally, these reactions can be performed at a temperature in the range of from about 0° C. to about 150° C., or in the range of from about 25° C. to about 150° C., or in the range of from about 25° C. to about 100° C. The particular choice of a catalyst, base, solvent, and temperature are all within the knowledge of one of ordinary skill in the art and can be made without undue experimentation.

Compounds of formula (6), wherein X is a halogen or $-OSO_2CF_3$, and $R^2$ is as hereinbefore defined are either commercially available or can be prepared according to methods known to those of ordinary skill in the art.

Compounds of formula (7), wherein $R^1$ and $R^8$ are as hereinbefore defined, can be prepared from compounds of formula (13), wherein $R^1$ is as hereinbefore defined, by reaction with a compound of formula (14), wherein $R^8$ is $C_1$-$C_6$ alkyl.

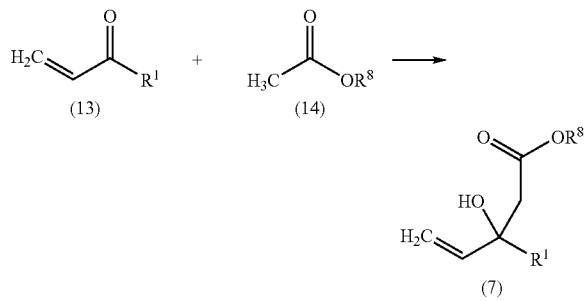

These reactions can be performed in the presence of a suitably basic compound that is capable of deprotonating the compound of formula (14). Suitable bases include, but are not limited to, lithium hexamethyldisilazide (LiHMDS), and lithium diisopropyl amide (LDA). Furthermore, these reactions can be performed in the presence of a solvent that will not interfere with the desired chemical reaction. Suitable solvents include, but are not limited to, dimethoxyethane, diisopropyl ether, chlorobenzene, diethyl ether, methyl-t-butyl ether, diphenyl ether, methylphenyl ether, tetrahydrofuran, 2-methyltetrahydrofuran, 1,4-dioxane, pentane, hexane, heptane, benzene, toluene, anisole, xylenes, and pyridine, or any mixture of the above solvents. Last, these reactions can be performed at a temperature in the range of from about −78° C. to about 25° C., or in the range of from about −78° C. to about 0° C. The particular choice of a base, solvent, and temperature are within the knowledge of one of ordinary skill in the art and can be made without undue experimentation.

Compounds of formula (7), wherein $R^1$ is as hereinbefore defined and $R^8$ is hydrogen, can be prepared in stereoisomerically enriched form from a racemic or scalemic compound of formula (7), wherein $R^1$ is as hereinbefore defined and $R^8$ is hydrogen, by: a) reaction with a chiral, non-racemic base to afford a mixture of diastereomeric salts; b) separation of the diastereomeric salts from each other; and 3) conversion to the compound of formula (7) by reaction with a suitable acidic compound. Suitable chiral, non-racemic bases include chiral, non-racemic amines. Useful chiral, non-racemic amines include, but are not limited to, (S)-1,2,3,4-tetrahydro-1-napthylamine, (R)-1,2,3,4-tetrahydro-1-napthylamine, (S)-(−)-1-(2-napthyl)ethylamine, (R)-(−)-1-(2-napthyl)ethylamine, (1R,2S)-(−)-norephedrine, (1S,2R)-(−)-norephedrine. These reactions can be performed in a solvent that will not interfere with the desired chemical reaction. Suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, t-amyl alcohol, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, methanol, ethanol, 1-propanol, 2-propanol, t-butanol, n-butanol, 2-butanol, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent if it will not interfere with the desired transformation. Finally, these reactions can be performed at a temperature in the range of from about 0° C. to about 150° C., or in the range of from about 25° C. to about 150° C., or in the range of from about 25° C. to about 100° C., or at ambient temperature. The solvent can be chosen such that one of the diastereomeric salts is appreciably soluble in the solvent while the other diastereomeric salt is appreciably insoluble in the solvent. Such a difference in solubilities can be used to affect separation of the diastereomeric salts from each other by the precipitation of one of the diastereomeric salts in stereoisomerically enriched form. After precipitation of substantially one diastereomeric salt, the stereoisomeric purity of the salt can be further increased by repeated recrystallization from an appropriate solvent or mixture of solvents. Conversion of a stereoisomerically enriched diastereomeric salt can be performed by reaction of the salt with a suitable acidic compound. Suitable acids include, but are not limited to inorganic acids (such as hydrochloric acid, hydrobromic acid, hydroiodic acid, sulfuric acid, nitric acid, and phosphoric acid) and organic acids (such as acetic acid, formic acid, and citric acid).

Alternatively, the compound of formula 7, wherein $R^1$ is as hereinbefore defined and $R^8$ is hydrogen, can be obtained in stereoisomerically enriched form by reaction with a chiral, non-racemic alcohol, to afford a mixture of diastereomeric esters. The diastereomeric esters can be obtained by reaction of the compound of formula (7) with the desired alcohol in the presence of a suitable activating agent or mixture of activating agents. Suitable activating agents include, but are not limited to, carbodiimides (such as diethylcarbodiimide), diethyldiazodicarboxylate, thionyl chloride, phosgene, and triphosgene. Reaction of the desired chiral, non-racemic alcohol with the activated compound of formula (7) can be performed in the presence of a suitable base. Suitable bases include, but are not limited to, organic bases such as triethylamine, diethylisopropylamine, pyridine, and 4,4-N,N-dimethylaminopyridine. Once obtained, the diastereomeric ester compounds of formula (7) can be separated from each other using methods known to those of ordinary skill in the art, including, but not limited to, chromatography and fractional crystallization. The choice of a suitable chiral, non-racemic alcohol and conditions for the separation of the mixture of diastereomeric esters are within the knowledge of one of ordinary skill in the art and can be made without undue experimentation.

Compounds of formula (14) are either commercially available or can be prepared using methods known to those of ordinary skill in the art.

Compounds of formula (13), wherein $R^1$ is as hereinbefore defined, can be prepared from compounds of formula (15), wherein $R^1$ is as hereinbefore defined and $R^{10}$ is a suitable leaving group, with a compound of formula (16), wherein M is a group capable of transferring the vinyl group of compound (16) to the compound of formula (15).

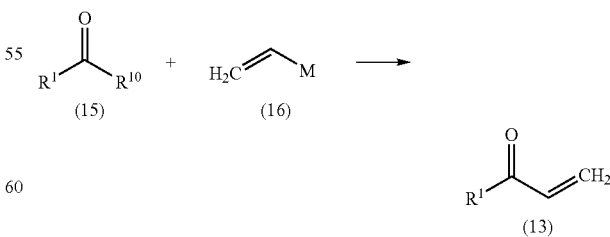

These reactions can be performed with a compound of formula (16), wherein M is a magnesium derivative, such as magnesium chloride or magnesium bromide, with a compound of formula (15), wherein $R^{10}$ is a group —N(OCH$_3$)

$CH_3$. These reactions can be performed in an aprotic solvent that will not interfere with desired chemical reaction. Suitable solvents include, but are not limited to, diethyl ether, tert-butyl methyl ether, diisopropyl ether, and tetrahydrofuran. Furthermore, such reactions can be performed at a temperature in the range of from about −78° C. to about 25° C., or in the range of from about −78° C. to about 0° C. The choice of a particular solvent and temperature are within the knowledge of one of ordinary skill in the art and can be made without undue experimentation.

Alternatively, compounds of formula (13) can be prepared by reaction of compounds of formula (15), wherein $R^1$ is as hereinbefore defined and $R^{10}$ is a suitable leaving group, such as chloride, by reaction with a compound of formula (16), wherein M is a suitable group such as —$Si(CH_3)_3$. The compound of formula (15) wherein $R^{10}$ is a suitable leaving group, such as chlorine, can be prepared from compounds of formula (15) wherein $R^{10}$ is —OH by reaction with an activating agent. Suitable activating agents include, but are not limited to, oxalyl chloride, thionyl chloride, phosgene, and triphosgene. These reactions can be performed in a solvent that will not interfere with the desired chemical reaction. Suitable solvents include, but are not limited to, aprotic solvents such as dichloromethane, chloroform, 1,2-dichloroethane, and N,N-dimethylformamide (DMF). Reaction of the compound of formula (15) wherein $R^{10}$ is a suitable leaving group, such as chlorine, with the compound of formula (16), wherein M is a suitable group such as —$Si(CH_3)_3$, can be performed in a solvent that will not interfere with the desired chemical reaction. Suitable solvents include, but are not limited to, aprotic solvents such as dichloromethane, chloroform, 1,2-dichloroethane, and N,N-dimethylformamide (DMF). Furthermore, such reactions can be performed in the presence of a Lewis acid to assist in the displacement of the leaving group by the vinyl group. Suitable Lewis acids include, but are not limited to, aluminum chloride, tin (IV) chloride, tin (II) chloride, and titanium tetrachloride. The amount of a particular Lewis acid required may vary from about 1 mol % to about 125 mol % (based on the vinyl silane reaction partner) and will depend on the identity of the Lewis acid used, the identity of the reaction partners, the solvent used, and the temperature at which the reaction is performed. Finally, these reactions can be performed at a temperature in the range from about −78° C. to about 100° C., or in the range of from about −78° C. to about 25° C., or preferably in the range of from about −78° C. to about 0° C.

Compounds of formula (15) wherein $R^{10}$ is a group —$N(OCH_3)CH_3$ can be prepared from compounds of formula (15) wherein $R^{10}$ is a suitable leaving group, such as —Cl, by reaction N,O-dimethylhydroxylamine. These reactions are performed in the presence of a suitable base. Suitable bases include, but are not limited to, organic bases (such as triethylamine, pyridine, and N,N-4-dimethylaminopyridine) and inorganic bases (such as sodium carbonate, sodium bicarbonate, potassium carbonate, potassium bicarbonate, and cesium carbonate). Furthermore, these reactions can be performed in a solvent that will not interfere with the desired chemical reaction. Suitable solvents include, but are not limited to, ethyl acetate, isobutyl acetate, isopropyl acetate, n-butyl acetate, methyl isobutyl ketone, dimethoxyethane, diisopropyl ether, chlorobenzene, dimethyl formamide, dimethyl acetamide, propionitrile, butyronitrile, acetic acid, diethyl ether, methyl-t-butyl ether, diphenyl ether, methylphenyl ether, tetrahydrofuran, 2-methyltetrahydrofuran, 1,4-dioxane, pentane, hexane, heptane, dichloromethane, chloroform, 1,2-dichloroethane, acetonitrile, benzonitrile, acetone, 2-butanone, benzene, toluene, anisole, xylenes, and pyridine, or any mixture of the above solvents. Additionally, water may be used as a co-solvent if it will not interfere with the desired transformation.

Compounds of formula (15) wherein $R^{10}$ is —OH are commercially available or can be prepared by methods known to those of ordinary skill in the art.

Compounds of formula (16) wherein M is a magnesium derivative, such as —MgBr or —MgCl, are either commercially available or can be prepared from compounds of formula (16) wherein M is a halogen, preferably bromine or iodine, by reaction with a suitable magnesium reagent. Suitable magnesium reagents include, but are not limited to, magnesium (0) and Rieke magnesium. These reagents are usually formed in situ in the reaction mixture and are used without isolation or further purification.

Compounds of formula (16) wherein M is —$Si(CH_3)_3$ are commercially available or can be prepared from compounds of formula (16) is a magnesium derivative, such as —MgBr or —MgCl by reaction with $XSi(CH_3)_3$, wherein X is chlorine, bromine, or iodine. These compounds are usually formed in situ in the reaction mixture and are used without further purification or isolation.

The following Examples are meant to illustrate particular embodiments of the present invention only and are not intended to limit its scope in any manner.

Unless otherwise indicated, all numbers expressing quantities of ingredients, properties such as molecular weight, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EXAMPLES

In the examples described below, unless otherwise indicated, all temperatures in the following description are in degrees Celsius (° C.) and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated.

The reactions set forth below were performed under a positive pressure of nitrogen, argon or with a drying tube, at ambient temperature (unless otherwise stated), in anhydrous solvents. Analytical thin-layer chromatography was performed on glass-backed silica gel 60° F. 254 plates (Analtech (0.25 mm)) and eluted with the appropriate solvent ratios (v/v). The reactions were assayed by high-pressure liquid chromatography (HPLC) or thin-layer chromatography (TLC) and terminated as judged by the consumption of starting material. The TLC plates were visualized by UV, phosphomolybdic acid stain, or iodine stain.

$^1$H-NMR spectra were recorded on a Bruker instrument operating at 300 MHz or 400 MHz and $^{13}$C-NMR spectra were recorded at 75 MHz. NMR spectra are obtained as DMSO-$d_6$ or CDCl$_3$ solutions (reported in ppm), using chloroform as the reference standard (7.25 ppm and 77.00 ppm) or DMSO-$d_6$ (2.50 ppm and 39.52 ppm). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Infrared spectra were recorded on a Perkin-Elmer FT-IR Spectrometer as neat oils, as KBr pellets, or as CDCl$_3$ solutions, and when reported are in wave numbers (cm$^{-1}$). The mass spectra were obtained using LC/MS or APCI. All melting points are uncorrected.

All final products had greater than 95% purity (by HPLC at wavelengths of 220 nm and 254 nm).

In the following examples and preparations, "Et" means ethyl, "Ac" means acetyl, "Me" means methyl, "Ph" means phenyl, "(PhO)$_2$POCl" means chlorodiphenylphosphate, "HCl" means hydrochloric acid, "EtOAc" means ethyl acetate, "Na$_2$CO$_3$" means sodium carbonate, "NaOH" means sodium hydroxide, "NaCl" means sodium chloride, "NEt$_3$" means triethylamine, "THF" means tetrahydrofuran, "DIC" means diisopropylcarbodiimide, "HOBt" means hydroxy benzotriazole, "H$_2$O" means water, "NaHCO$_3$" means sodium hydrogen carbonate, "K$_2$CO$_3$" means potassium carbonate, "MeOH" means methanol, "i-PrOAc" means isopropyl acetate, "MgSO$_4$" means magnesium sulfate, "DMSO" means dimethylsulfoxide, "AcCl" means acetyl chloride, "CH$_2$Cl$_2$" means methylene chloride, "MTBE" means methyl t-butyl ether, "DMF" means dimethyl formamide, "SOCl$_2$" means thionyl chloride, "H$_3$PO$_4$" means phosphoric acid, "CH$_3$SO$_3$H" means methanesulfonic acid, "Ac$_2$O" means acetic anhydride, "CH$_3$CN" means acetonitrile, "KOH" means potassium hydroxide, "CDI" means carbonyl diimidazole, "DABCO" means 1,4-diazabicyclo[2.2.2]octane, "IPE" means isopropyl ether, "MTBE" means methyl tert-butyl ether, "Et$_2$O" means diethylether, "Na$_2$SO$_4$" means sodium sulfate, "NBS" means N-bromosuccinimide, "TEA" means triethylamine, "DCM" means dichloromethane, "TBAB" means tetrabutylammonium bromide, "HMPA" means hexamethylphosphoramide, "NMP" means 1-methyl-2-pyrrolidinone, "DMAC" means N,N-dimethylacetamide, "h" means hours, "min" means minutes, "mol" means moles, and "rt" means room temperature.

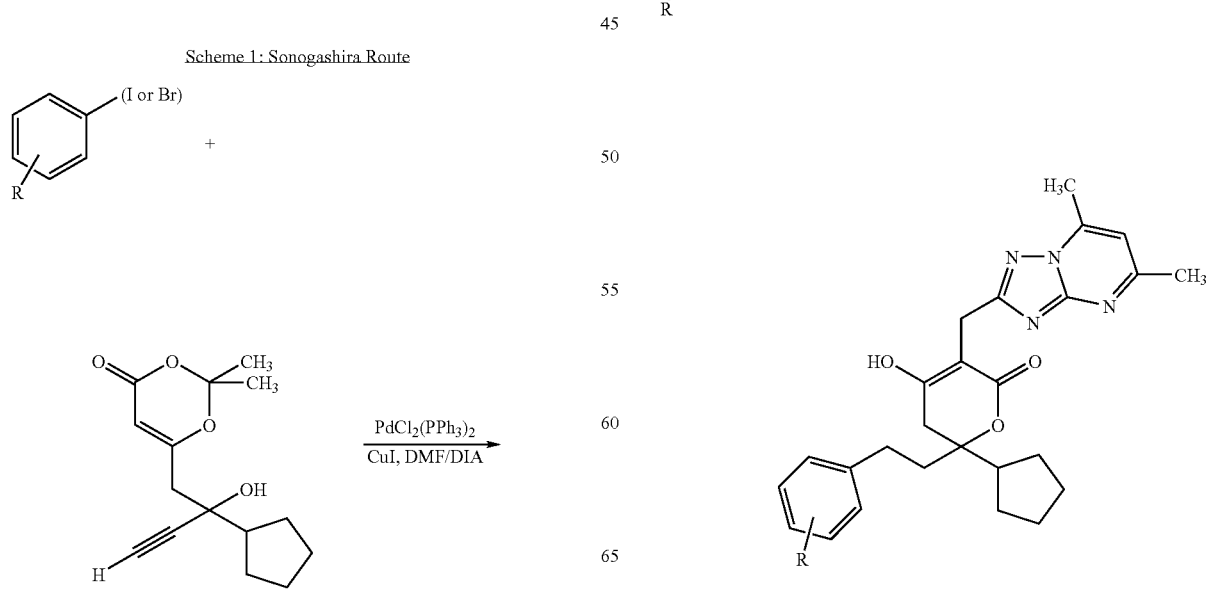

Example A(1)

6-Cyclopentyl-3-[(5,7-dimethyl[1,2,4]triazolo[1,5-a]pyrimidin-2-yl)methyl]-6-[2-(5-ethyl-4-hydroxy-2-propoxyphenyl)ethyl]-4-hydroxy-5,6-dihydro-2H-pyran-2-one

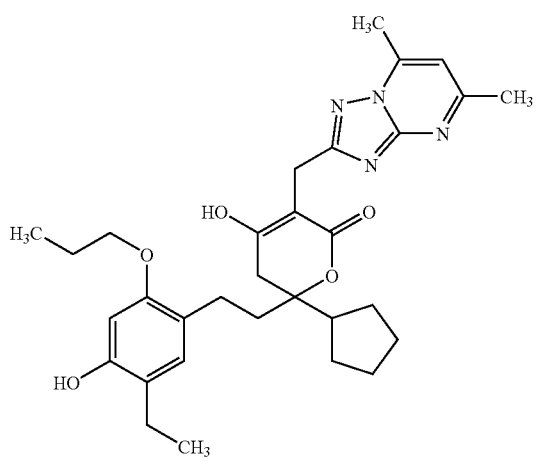

5,7-Dimethyl-[1,2,4]triazolo[1,5-a]pyrimidine-2-carbaldehyde (0.24 g, 1.4 mmol, from step 8 below) was added to a solution of 6-cyclopentyl-6-[2-(5-ethyl-4-hydroxy-2-propoxy-phenyl)-ethyl]-dihydro-pyran-2,4-dione (0.45 g, 1.2 mmol, from step 5 below) in MeOH (15 mL). The reaction mixture was stirred for 15 mins and then treated with borane-dimethylamine complex (100 mg, 1.7 mmoL). After 15 hours the reaction mixture was filtered through a glass frit washing with MeOH. The filtrate was concentrated to a yellow oil. Purification by prep HPLC gave the product as a white powder (230 mg, 36%). $^1$H NMR (400 MHz, DMSO-$d_6$): δ 0.84 (t, J=7.3 Hz, 3 H), 0.92 (t, J=7.6 Hz, 3H), 1.32-1.69 (m, 10 H), 1.82 (m, 1 H), 1.96 (m, 1 H), 2.28-2.47 (m, 11 H), 2.49 (d, J=17.5 Hz, 1 H), 2.67 (d, J=17.5 Hz, 1 H), 3.61-3.73 (m, 4 H), 6.26 (s, 1 H), 6.63 (s, 1 H), 6.95 (s, 1 H), 8.87 (s, 1 H), 10.72 (s, 1 H). Anal. Calcd. For $C_{31}H_{40}N_4O_5$: C, 67.86; H, 7.25; N, 10.21. Found: C, 67.69; H, 7.40; N, 10.04.

Step 1: 2-Ethyl-5-propoxy-phenol

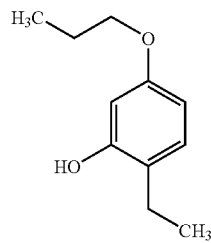

Potassium carbonate (54 g, 0.39 mol) followed by 1-iodopropane (11.5 mL, 0.12 mol) were added to a solution of 2',4'-dihydroxyacetophenone (20 g, 0.13 mol) in DMF (150 mL). The mixture was stirred for 5 hours and then partitioned between $H_2O$ and EtOAc. The organic layer was washed with satd $NaHCO_3$, brine, dried over $Na_2SO_4$ and concentrated to a clear oil (21.1 g, 91%).

The oil was dissolved in MeOH (100 mL), treated with 10 wt % Pd/C (6 g, Degussa type) and stirred under a balloon of $H_2$ for 24 hours. The reaction mixture was filtered through a pad of celite washing with EtOAc. The filtrate was concentrated and purified by flash column chromatography (0% to 20% EtOAc in hexanes) to give an orange oil (15 g, 93%). $^1$H NMR (400 MHz, $CDCl_3$): δ 1.01 (t, J=7.3 Hz, 3 H), 1.20 (t, J=7.6 Hz, 3 H), 1.78 (m, 2 H), 2.56 (q, J=7.6 Hz, 2 H), 3.86 (t, J=6.8 Hz, 2 H), 4.90 (s, 1 H), 6.37 (d, J=2.5 Hz, 1 H), 6.44 (dd, J=8.1, 2.5 Hz, 1 H), 7.01 (d, J=8.3 Hz, 1 H).

Step 2: 2-Benzyloxy-1-ethyl-4-propoxy-benzene

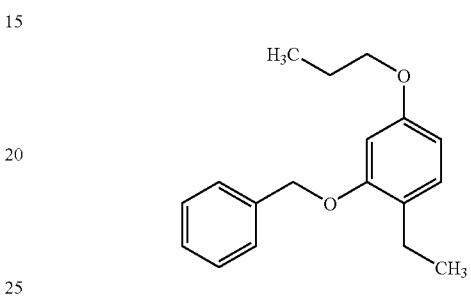

Potassium carbonate (17.8 g, 0.13 mol) followed by benzyl bromide (5.12 mL, 42.9 mmol) were added to a solution of 2-ethyl-5-propoxy-phenol (7.74 g, 42.9 mmol) in DMF (60 mL). The mixture was stirred at 45° C. for 15 hours and then partitioned between $H_2O$ and EtOAc. The organic layer was washed with 1N HCl, brine, dried over $Na_2SO_4$ and concentrated to a brown oil. Purification by flash column chromatography (0% to 20% EtOAc in hexanes) gave the product as a clear oil (6.1 g, 55%). $^1$H NMR (400 MHz, $CDCl_3$): δ 1.02 (t, J=7.6 Hz, 3 H), 1.19 (t, J=7.6 Hz, 3 H), 1.78 (q, J=7.6 Hz, 2 H), 2.63 (q, J=7.6 Hz, 2 H), 3.88 (t, J=6.6 Hz, 2 H), 5.05 (s, 2 H), 6.44 (dd, J=8.1, 2.3 Hz, 1 H), 6.51 (dd, J=2.3 Hz, 1 H), 7.05 (d, J=8.3 Hz, 1 H), 7.31 (m, 1 H), 7.38 (m, 2 H), 7.44 (m, 2 H).

Step 3: 1-Benzyloxy-2-ethyl-4-iodo-5-propoxy-benzene

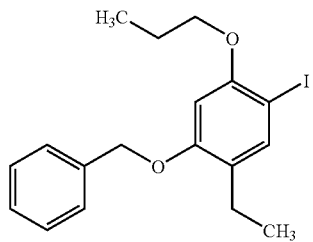

A solution of iodine (2.82 g, 11.1 mmol) dissolved in $CHCl_3$ (80 mL) was added dropwise to a stirred mixture of 2-benzyloxy-1-ethyl-4-propoxy-benzene (3 g, 11.1 mmol), silver trifluoroacetate (2.45 g, 11.1 mmol) in $CHCl_3$ (20 mL). After the addition was complete the reaction mixture was stirred for 1 hour. The mixture was filtered through a pad of celite washing with $CH_2Cl_2$. The filtrate was washed with satd $Na_2S_2O_3$, brine, dried over $Na_2SO_4$ and concentrated to a pale yellow solid (4.04 g, 92%). $^1$H NMR (400 MHz, $CDCl_3$): δ 1.07 (t, J=7.3 Hz, 3 H), 1.17 (t, J=7.6 Hz, 3 H), 1.81

(m, 2 H), 2.59 (q, J=7.6 Hz, 2 H), 3.90 (t, J=6.3 Hz, 2 H), 5.05 (s, 2 H), 6.43 (s, 1 H), 7.31-7.45 (m, 5 H), 7.49 9s, 1 H).

Step 4: 6-[2-Cyclopentyl-4-(5-ethyl-4-hydroxy-2-propoxy-phenyl)-2-hydroxy-butyl]-2,2-dimethyl-[1,3]dioxin-4-one

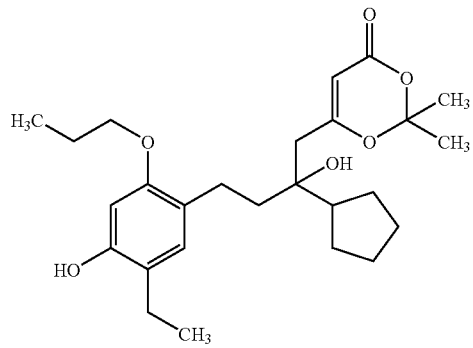

A mixture of 1-benzyloxy-2-ethyl-4-iodo-5-propoxy-benzene (4.0 g, 10.1 mmol), 6-(2-cyclopentyl-2-hydroxybut-3-ynyl)-2,2-dimethyl-4H-1,3-dioxin-4-one (2.42 g, 19.2 mmol, from step 11 below), PdCl$_2$(PPh$_3$)$_2$ (0.26 g, 4 mol %) and CuI (53 mg, 3 mol %). in diisopropylamine (12 mL) and DMF (12 mL) was heated at 90° C. for 90 min. The reaction mixture was cooled to room temperature and partitioned between 1N HCl and EtOAc. The organic layer was washed with brine, dried over Na$_2$SO$_4$ and concentrated to a black oil. Flash column chromatography (0% to 40% EtOAc in hexanes) gave a brown oil.

The oil was dissolved in EtOH (30 mL) and treated with Pd(OH)$_2$ (1 g, 20 wt %, Degussa type). The mixture was stirred under a balloon of hydrogen for 4 hours. The reaction mixture was filtered through a pad of celite washing with EtOAc. The filtrate was concentrated to an orange oil and purified by flash column chromatography to give the product as a yellow solid (0.83 g, 18%). $^1$H NMR (400 MHz, CDCl$_3$): δ 1.03 (t, J=7.3 Hz, 3 H), 1.20 (t, J=7.6 Hz, 3 H), 1.38-1.86 (br m, 19 H), 2.10 (m, 1 H), 2.44-2.65 (m, 6 H), 3.87 (t, J=6.6 Hz, 2 H), 4.60 (s, 1 H), 5.36 (s, 1 H), 6.35 (s, 1 H), 6.83 (s, 1H).

Step 5: 6-Cyclopentyl-6-[2-(5-ethyl-4-hydroxy-2-propoxy-phenyl)-ethyl]-dihydro-pyran-2,4-dione

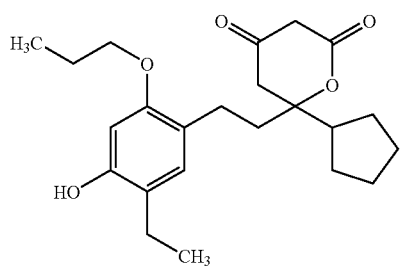

6-[2-Cyclopentyl-4-(5-ethyl-4-hydroxy-2-propoxy-phenyl)-2-hydroxy-butyl]-2,2-dimethyl-[1,3]dioxin-4-one (0.8 g, 1.8 mmol,) was dissolved in methanol (15 mL), treated with potassium carbonate (0.74 g, 5.4 mmol) and heated at 45° C. under N$_2$ for 90 mins. The reaction mixture was partitioned between H$_2$O and IPE. The aqueous layer was made acidic with 1N HCl and extracted with EtOAc. The organic layers were washed with brine, dried over Na$_2$SO$_4$ and concentrated to give the product as a yellow foam (0.5 g, 72% yield). $^1$H NMR (400 MHz, CDCl$_3$): δ 1.02 (t, J=7.3 Hz, 3 H), 1.19 (t, J=7.6 Hz, 3 H), 1.41-1.87 (br m, 11 H), 1.95 (m, 1 H), 2.32 (m, 1 H), 2.49-2.80 (m, 6H), 3.41 (m, 2 H), 3.85 (m, 2 H), 4.62 (s, 1 H), 6.33 (s, 1 H), 6.80 (s, 1 H).

Step 6: (5-Amino-1H-[1,2,4]triazol-3-yl)-methanol

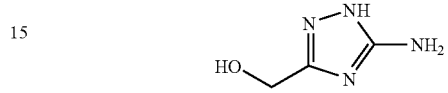

A solution of glycolic acid (70% in water, 70 mL, 805 mmol) was added to aminoguanidine bicarbonate (55.12 g, 405 mmol) carefully. After foaming subsided, concentrated nitric acid (0.5 mL) was added and the entire reaction was refluxed for 40 hours. The reaction was cooled to 5° C. for 30 minutes, and the solids were filtered. The solids were then triturated with EtOH for 1 hour. The product was then filtered and dried under nitrogen (40.36 g, 52% yield). MS (ESI): 115 (M+H).

Step 7: (5,7-Dimethyl-[1,2,4]triazolo[1,5-a]pyrimidin-2-yl)-methanol

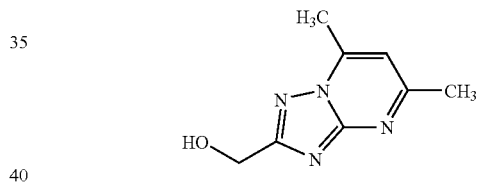

To a slurry of (5-amino-1H-[1,2,4]triazol-3-yl)-methanol (9.5 g, 50 mmol) from step 6 above in acetic acid (200 mL) was added 2,4-pentanedione (5.13 mL, 50 mmol). The mixture was heated to reflux for 4 hours, and then cooled to room temperature. The product was isolated by removing the solvent by rotary evaporation (8.5 g, 95% yield). MS (ESI): 179 (M+H).

Step 8: 5,7-Dimethyl-[1,2,4]triazolo[1,5-a]pyrimidine-2-carbaldehyde

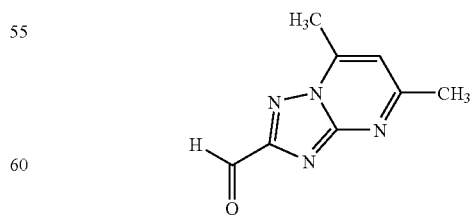

A slurry of 5,7-dimethyl-[1,2,4]triazolo[1,5-a]pyrimidin-2-yl)-methanol (0.3 g, 1.7 mmol) from step 7 above and IBX (1.4 g, 5.0 mmol) in 1,2-dichloroethane (22 mL) was stirred at 80° C. for 18 hours. The reaction was cooled to room temperature, and diluted with 100 mL CH$_2$Cl$_2$. After the solids were removed by filtration, the solvent was removed by rotary evaporation to give a yellow solid. The solid was purified by flash chromatography to give the desired product (229 mg, 77% yield). $^1$H NMR (CDCl$_3$) δ: 2.72 (s, 3 H), 2.86 (s, 3 H), 6.96 (s, 1 H), 10.24 (s, 1 H).

Step 9:
1-Cyclopentyl-3-(trimethylsilyl)prop-2-yn-1-one

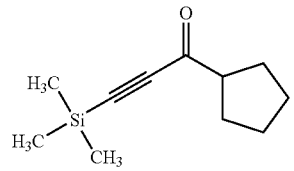

The title compound was prepared as described in the following reference: *Journal of Organic Chemistry* 1984, 106, 4786-4800. $^1$H NMR (CDCl$_3$) δ: 0.24 (s, 9 H), 1.63 (m, 4 H), 1.90 (m, 4 H), 2.92 (pentet, 1 H, J=7.6 Hz).

Step 10: 6-[2-Cyclopentyl-2-hydroxy-4-(trimethylsilyl)but-3-yn-1-yl]-2,2-dimethyl-4H-1,3-dioxin-4-one

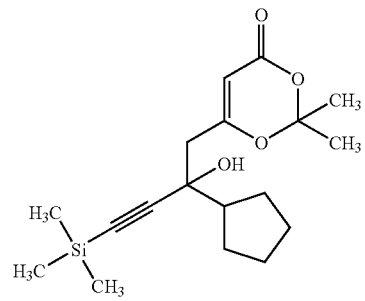

A solution of diisopropylamine (3.85 mL, 27.5 mmol) dissolved in THF (100 mL) was cooled to −78° C., where BuLi (11 mL, 27.5 mmol, 2.5 M in hexanes) was added dropwise over 10 minutes. After stirring at this temperature for 5 minutes the mixture was warmed to room temperature for 5 minutes, then cooled back to −78° C., where 2,2,6-trimethyl-[1,3]dioxin-4-one (3.6 mL, 27.5 mmol) was added dropwise over the 5 minutes, then stirred an additional 30 minutes at −78° C. To this solution was added 1-cyclopentyl-3-(trimethylsilyl)prop-2-yn-1-one (4.85 g, 25 mmol, from step 9) over 5 minutes. The resulting mixture was stirred at −78° C. for 1 hour, then slowly warmed to −30° C. and quenched with 0.5 N citric acid. The mixture was diluted with ether, washed with 1 N NaHCO$_3$, brine, dried with MgSO$_4$ and concentrated to give the crude product (9.4 g) contaminated with unreacted 2,2,6-trimethyl-[1,3]dioxin-4-one. ESIMS (M+Na$^+$): 359.1.

Step 11: 6-(2-Cyclopentyl-2-hydroxybut-3-ynyl)-2,2-dimethyl-4H-1,3-dioxin-4-one

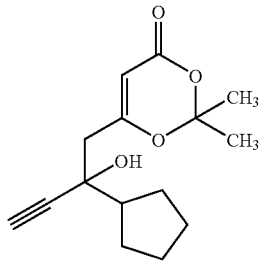

A solution of crude 6-[2-cyclopentyl-2-hydroxy-4-(trimethylsilyl)but-3-yn-1-yl]-2,2-dimethyl-4H-1,3-dioxin-4-one (25 mmol), ceasium fluoride (7.6 g, 50 mmol) dissolved in MeOH (75 mL) was stirred over night. The solvent was removed and the residue was diluted with EtOAc, washed with 0.5 N citric acid, 1 N NaHCO$_3$, brine, dried over MgSO$_4$ and concentrated. Purification by flash column chromatography (20% to 30% EtOAc in hexanes) gave the product (3.6 g, 54%). $^1$H NMR (300 MHz, CDCl$_3$) □: 1.45-1.80 (m, 8 H), 1.72 (s, 3H), 1.74 (s, 3 H), 2.13-2.18 (m, 1 H), 2.49 (s, 1 H), 2.56 (s, 1 H), 2.58 (s, 2 H), 5.43 (s, 1 H).

Example A(2)

6-Cyclopentyl-6-[2-(2-ethyl-5-methoxypyridin-4-yl)ethyl]dihydro-2H-pyran-2,4(3H)-dione

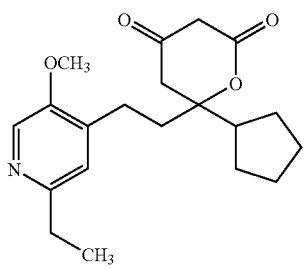

6-[2-Cyclopentyl-4-(2-ethyl-5-methoxy-pyridin-4-yl)-2-hydroxy-but-3-ynyl]-2,2-dimethyl-[1,3]dioxin-4-one (1.6 g, 4 mmol, from step 6 below) was dissolved in EtOH (15 mL) and treated with Pd(OH)$_2$ (0.5 g, 20 wt % Degussa type). The mixture was stirred under a balloon of hydrogen for 2 hours. The reaction mixture was filtered through a pad of celite washing with EtOAc. The filtrate was concentrated to a pale yellow solid.

The solid was dissolved in methanol (10 mL), treated with potassium carbonate (1.28 g, 9.3 mmol) and heated at 45° C. under N$_2$ for 60 mins. The reaction mixture was partitioned between H$_2$O and IPE. The aqueous layer was made neutral with 1N HCl and extracted with EtOAc. The organic layers were washed with brine, dried over Na$_2$SO$_4$ and concentrated to give the product as a yellow solid (0.71 g, 51% yield). $^1$H NMR (400 MHz, CDCl$_3$): δ 1.26 (t, J=7.6 Hz, 3 H), 1.41-1.95

(br m, 8H), 2.34 (m, 1 H), 2.63-2.76 (m, 6 H), 3.43 (m, 2 H), 3.88 (m, 5 H), 6.90 (s, 1 H), 8.09 (s, 1 H). Anal. Calcd. For C$_{20}$H$_{27}$NO$_4$: C, 69.54; H, 7.88; N, 4.05. Found: C, 69.33; H, 7.88; N, 3.99.

Step 1: 5-Methoxy-2-methyl-pyridine

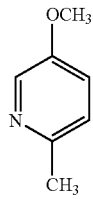

5-Hydroxy-2-methylpyridine (15 g, 0.14 mol) was added to a stirred suspension of KOH (31 g, 0.55 mol) in DMSO (150 mL). The mixture was stirred for 1 hour and then treated with methyl iodide (9.8 mL, 0.15 mol). After 20 mins the reaction mixture was poured into H$_2$O and extracted with ether. The ether extracts were dried over MgSO$_4$ and concentrated to a red oil. Purification by flash column chromatography (0% to 50% EtOAc in hexanes) gave the product as a clear oil (10.1 g, 59%). $^1$H NMR (400 MHz, CDCl$_3$): δ 2.49 (s, 3 H), 3.83 (s, 3 H), 7.06 (d, J=8.6 Hz, 1 H), 7.12 (d, J=8.3 Hz, 1 H), 8.19 (d, J=2.8 Hz, 1 H).

Step 2: 2-Ethyl-5-methoxy-pyridine

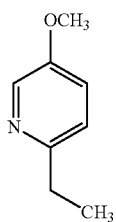

5-Methoxy-2-methyl-pyridine (9.5 g, 77 mmol) was added to a cooled −78° C. solution of LDA prepared from n-BuLi (37 mL, 93 mmol, 2.5 M in hexanes) and diisopropylamine (13 mL, 93 mmol) dissolved in THF (100 mL). The deep red reaction mixture was stirred for 30 mins and then treated with methyl iodide (5.4 mL, 85 mmol). After 2 hours the mixture was quenched with conc NH$_4$OH (15 mL). The mixture was poured into H$_2$O and extracted with EtOAc. The organic extracts were washed with brine, drived over Na$_2$SO$_4$ and concentrated to a red oil. Purification by flash column chromatography (0% to 40% EtOAc in hexanes) gave the product as a clear oil (2.5 g, 24%) and unreacted starting material (3.8 g, 40%). $^1$H NMR (400 MHz, CDCl$_3$): δ 1.28 (t, J=7.3 Hz, 3 H), 2.76 (q, J=7.3 Hz, 2 H), 3.84 (s, 3 H), 7.08 (d, J=8.3 Hz, 1 H), 7.14 (d, J=8.3 Hz, 1 H), 8.23 (s, 1 H).

Step 3: 2-Ethyl-5-methoxy-pyridine 1-oxide

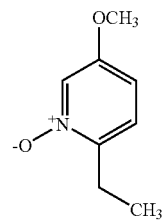

3-Chloroperoxybenzoic acid (5.66 g, 32.8 mmol) was added to a stirred solution of 2-ethyl-5-methoxy-pyridine (3 g, 22 mmol) dissolved in CHCl$_3$ (100 mL). The reaction was stirred at room temperature for 3 hours and then quenched with satd Na$_2$SO$_3$. The reaction mixture was partitioned between H$_2$O and CH$_2$Cl$_2$. The organic layer was washed with 1N NaOH, dried over Na$_2$SO$_4$ and concentrated to an oil (3.3 g, 99%). $^1$H NMR (400 MHz, CDCl$_3$): δ 1.29 (t, J=7.5 Hz, 3 H), 2.89 (q, J=7.5 Hz, 2 H), 3.82 (s, 3 H), 6.86 (d, J=8.4 Hz, 1 H), 7.11 (d, J=8.3 Hz, 1 H), 8.04 (s, 1 H).

Step 4: 2-Bromo-6-ethyl-3-methoxy-pyridine 1-oxide (A) and 4-Bromo-2-ethyl-5-methoxy-pyridine 1-oxide (B)

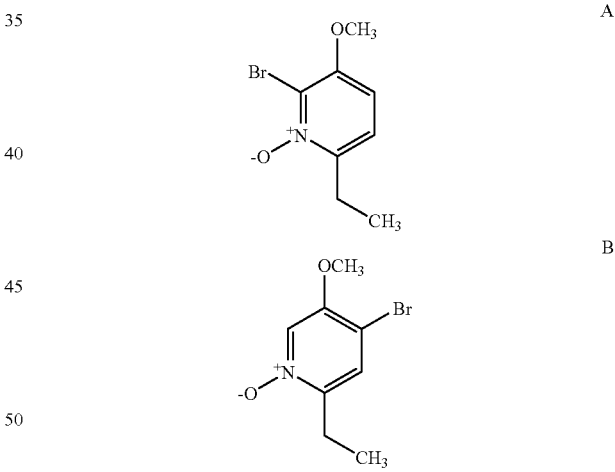

Nitric acid (6 mL) was slowly added to a cooled 0° C. solution of 2-ethyl-5-methoxy-pyridine 1-oxide (3.4 g, 22.2 mmol) dissolved in sulfuric acid (8 mL). The mixture was heated to 90° C. for 5 hours. The mixture was poured into ice, made basic with 15% NaOH and extracted with EtOAc. The organic extracts were washed with brine, dried over Na$_2$SO$_4$ and concentrated to a yellow soil. Purification by flash column chromatography (0% to 50% gave a mixture of nitro isomers as a yellow solid (1.58 g, 36%)

The solid was dissolved in acetic acid (30 mL) and treated with acetyl bromide (18 mL). The mixture was heated to 80° C. for 5 hours. The mixture was poured into ice, made basic with NaOH pellets and extracted with EtOAc. The organic layers were dried over Na$_2$SO$_4$ and concentrated to a yellow solid. Flash column chromatography (0% to 80% EtOAc in hexanes) gave 2-bromo-6-ethyl-3-methoxy-pyridine 1-oxide (0.32 g, 18%). Further elution with 5% MeOH in CH$_2$Cl$_2$ gave 4-bromo-2-ethyl-5-methoxy-pyridine 1-oxide (1.31 g, 74%). A: $^1$H NMR (400 MHz, CDCl$_3$): δ 1.30 (t, J=7.3 Hz, 3H), 2.95 (q, J=7.3 Hz, 2 H), 3.94 (s, 3 H), 6.79 (d, J=8.8 Hz, 1 H), 7.11 (d, J=8.8 Hz, 1 H). B: $^1$H NMR (400 MHz, CDCl$_3$): δ 1.29 (t, J=7.3 Hz, 3 H), 2.86 (q, J=7.3 Hz, 2 H), 3.90 (s, 3 H), 7.36 (s, 1H), 7.98 (s, 1 H)

Step 5: 4-Bromo-2-ethyl-5-methoxy-pyridine

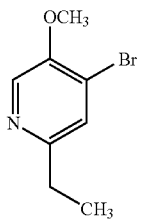

Phosphorous tribromide (5.5 mL) was added to a solution of 4-bromo-2-ethyl-5-methoxy-pyridine 1-oxide (1.25 g, 5.4 mmol) dissolved in CH$_2$Cl$_2$ (40 mL). The reaction mixture was heated to 50° C. for 1 hour. After cooling to room temperature the mixture was poured into ice and made basic with 15% NaOH and extracted with CH$_2$Cl$_2$. The organic extracts were dried over Na$_2$SO$_4$ and concentrated to a clear oil (1.13 g, 97%). $^1$H NMR (400 MHz, CDCl$_3$): δ 1.28 (t, J=7.6 Hz, 3 H), 2.75 (q, J=7.6 Hz, 2 H), 3.97 (s, 3 H), 7.37 (s, 1 H), 8.13 (s, 1 H)

Step 6: 6-[2-Cyclopentyl-4-(2-ethyl-5-methoxy-pyridin-4-yl)-2-hydroxy-but-3-ynyl]-2,2-dimethyl-[1,3]dioxin-4-one

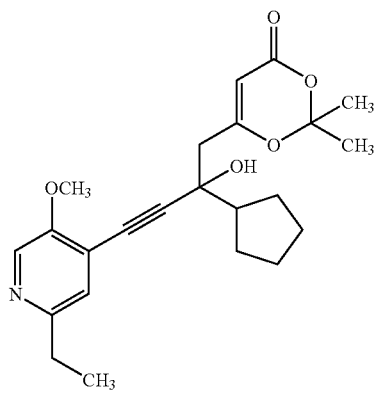

A mixture of 4-bromo-2-ethyl-5-methoxy-pyridine (1.1 g, 5.1 mmol), 6-(2-cyclopentyl-2-hydroxybut-3-ynyl)-2,2-dimethyl-4H-1,3-dioxin-4-one (1.22 g, 4.6 mmol), PdCl$_2$(PPh$_3$)$_2$ (0.13 g, 4 mol %) and CuI (27 mg, 3 mol %) in diisopropylamine (6 mL) and DMF (6 mL) was heated at 90° C. for 30 min. The reaction mixture was cooled to room temperature and partitioned between satd NaHCO$_3$ and EtOAc. The organic layer was washed with H$_2$O, brine, dried over Na$_2$SO$_4$ and concentrated to a brown oil. Flash column chromatography (0% to 60% EtOAc in hexanes) gave the product as a yellow oil (1.62, 89%). $^1$H NMR (400 MHz, CDCl$_3$): δ 1.26 (t, J=7.6 Hz, 3 H), 1.60-1.84 (br m, 14 H), 2.26 (m, 1H), 2.71 (m, 5 H), 3.91 (s, 3 H), 5.54 (s, 1 H), 7.05 (s, 1 H), 8.19 (s, 1 H).

Example A(3)

6-Cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one

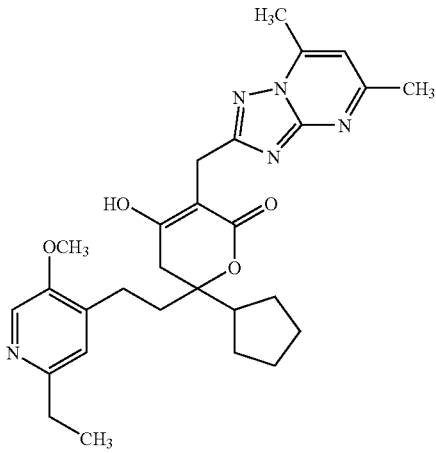

The title compound was prepared analogously to example A(1) where 6-cyclopentyl-6-[2-(2-ethyl-5-methoxypyridin-4-yl)ethyl]dihydro-2H-pyran-2,4(3H)-dione (example A(2)) was substituted in place of 6-cyclopentyl-6-[2-(5-ethyl-4-hydroxy-2-propoxy-phenyl)-ethyl]-dihydro-pyran-2,4-dione. $^1$H NMR (400 MHz, DMSO-d$_6$): δ 0.94 (t, J=7.58 Hz, 3H), 1.19-1.53 (m, 8H), 1.83 (m, 1H), 1.91 (m, 1H), 2.20 (m, 4 H), 2.29-2.37 (m, 6H), 2.43 (q, J=7.58 Hz, 2H), 2.59 (d, J=17.2 Hz, 1H), 3.50 (d, J=16.2 Hz, 1H), 3.56 (s, 3H), 3.61 (d, J=16.2 Hz, 1H), 6.83 (s, 1 H), 6.85 (s, 1 H), 7.88 (s, 1 H), 10.82 (s, 1 H). Anal. Calcd. For C$_{28}$H$_{35}$N$_5$O$_4$.0.5 AcOH: C, 65.03; H, 6.96; N, 13.08. Found: C, 65.15; H, 7.05; N, 12.79.

Example A(4)

6-Cyclopentyl-6-[2-(2-ethyl-5-methoxypyridin-4-yl)ethyl]-4-hydroxy-3-[(6-methyl[1,2,4]triazolo[1,5-a]pyrimidin-2-yl)methyl]-5,6-dihydro-2H-pyran-2-one

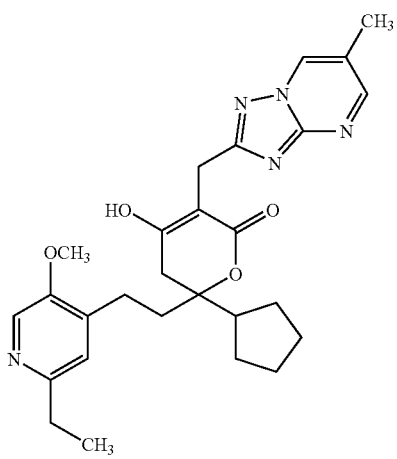

6-Methyl-[1,2,4]triazolo[1,5-a]pyrimidine-2-carbaldehyde (0.13 g, 0.82 mmol, from step 2 below) was added to a solution of 6-cyclopentyl-6-[2-(2-ethyl-5-methoxypyridin-4-yl)ethyl]dihydro-2H-pyran-2,4(3H)-dione (0.23 g, 0.68 mmol, example A(2)) in MeOH (7 mL). The reaction mixture was stirred for 10 mins and then treated with borane-dimethylamine complex (60 mg, 0.68 mmol.). After 15 hours the reaction mixture was filtered through a glass frit washing with MeOH. The filtrate was concentrated to a yellow oil. Purification by prep HPLC gave the product as a white powder (58 mg, 17%). $^1$H NMR (400 MHz, DMSO-$d_6$): δ 1.22 (t, J=7.6 Hz, 3H), 1.42-1.75 (m, 8H), 2.11 (m, 2 H), 2.41 (s, 3 H), 2.46-2.65 (m, 4 H), 2.70 (q, J=7.6 Hz, 2H), 2.83 (d, J=17.7 Hz, 1H), 3.85 (m, 5 H), 7.13 (s, 1 H), 8.16 (s, 1 H) 8.74 (s, 1 H), 8.93 (s, 1 H), 11.04 (s, 1 H). MS (ESI): 492.10 (M+H)$^+$.

Step 1: (6-Methyl[1,2,4]triazolo[1,5-a]pyrimidin-2-yl)methanol

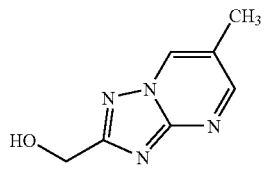

To a slurry of (5-amino-1H-[1,2,4]triazol-3-yl)-methanol (16.6 g, 87.6 mmol) from step 6 of example A(1) in acetic acid was added 3-ethoxymethacrolein (10 g, 87.6 mmol). The mixture was heated to 80° C. for 4 hours. Upon cooling of the reaction, the product cyrstallized out of solution. The collected product was a white solid (14 g, 92%). $^1$H NMR (300 MHz, DMSO-$d_6$): δ 2.38 (s, 3 H), 4.63 (s, 2 H), 5.52 (s, 1 H), 8.75 (s, 1 H), 9.21 (s, 1 H).

Step 2: 6-Methyl[1,2,4]triazolo[1,5-a]pyrimidine-2-carbaldehyde

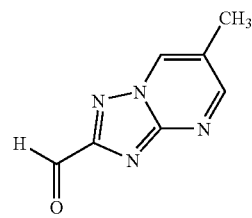

A slurry of (6-methyl[1,2,4]triazolo[1,5-a]pyrimidin-2-yl)methanol (15.7 g, 95.6 mmol) from step 1 above, TEMPO (112 mg, 7.2 mmol), iodobenzene diacetate (33.9 g, 105.2 mmol) in CH$_2$Cl$_2$ (100 mL) was stirred at room temperature for 2 hours. Once the reaction was deemed complete, methyl tert-butyl ether (50 mL) was added slowly to precipitate the product. The concentrated mother liquor was introduced into a silica gel column and eluted with 2% MeOH/CH$_2$Cl$_2$ to give an additional amount of the aldehyde product as a white solid (12 g, 80%). $^1$H NMR (CDCl$_3$) □: 2.54 (s, 3 H), 8.73 (s, 1 H), 8.85 (s, 1 H), 10.23 (s, 1 H).

Example A(5)

6-Cyclopentyl-6-[2-(6-ethyl-3-methoxypyridin-2-yl)ethyl]dihydro-2H-pyran-2,4(3H)-dione

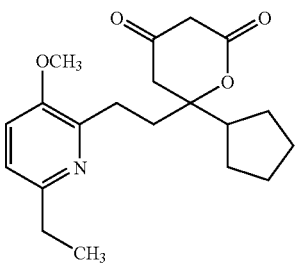

The title compound was prepared analogously to example A(2) where 2-bromo-6-ethyl-3-methoxy-pyridine from step 1 below was substituted in place of 4-bromo-2-ethyl-5-methoxy-pyridine in step 6 of that example. $^1$H NMR (400 MHz, CDCl$_3$): δ 1.24 (t, J=7.6 Hz, 3 H), 1.41-1.84 (br m, 8H), 2.12 (m, 2 H), 2.37 (m, 1 H), 2.72 (m, 4 H), 2.89 (m, 2 H), 3.42 (m, 2 H), 3.79 (s, 3 H), 6.96 (d, J=8.3 Hz, 1 H), 7.03 (d, J=8.3 Hz, 1H). MS (ESI): 346.10 (M+H)$^+$ Step 1: 2-Bromo-6-ethyl-3-methoxy-pyridine

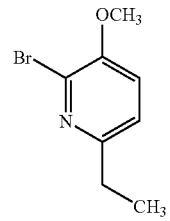

Phosphorous tribromide (1.3 mL) was added to a solution of 2-bromo-6-ethyl-3-methoxy-pyridine 1-oxide (0.3 g, 1.3 mmol, from step 4 of example A(2)) dissolved in CH$_2$Cl$_2$ (10 mL). The reaction mixture was heated to 50° C. for 1 hour. After cooling to room temperature the mixture was poured into ice and made basic with 15% NaOH and extracted with CH$_2$Cl$_2$. The organic extracts were dried over Na$_2$SO$_4$ and concentrated to a clear oil (0.28 g, 99%). $^1$H NMR (400 MHz, CDCl₃): δ 1.27 (t, J=7.6 Hz, 3 H), 2.76 (d, J=7.6 Hz, 2 H), 3.89 (s, 3 H), 7.06 (d, J=8.1 Hz, 1 H), 7.09 (d, J=8.1 Hz, 1 H).

Example A(6)

6-Cyclopentyl-3-[(5,7-dimethyl[1,2,4]triazolo[1,5-a]pyrimidin-2-yl)methyl]-6-[2-(6-ethyl-3-methoxypyridin-2-yl)ethyl]-4-hydroxy-5,6-dihydro-2H-pyran-2-one

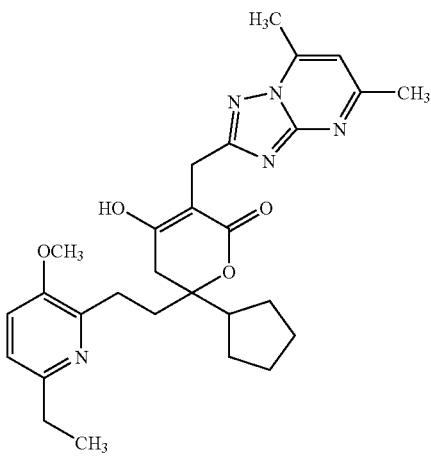

The title compound was prepared analogously to example A(1) where 6-cyclopentyl-6-[2-(6-ethyl-3-methoxypyridin-2-yl)ethyl]dihydro-2H-pyran-2,4(3H)-dione (example A(5)) was substituted in place of 6-cyclopentyl-6-[2-(5-ethyl-4-hydroxy-2-propoxy-phenyl)-ethyl]-dihydro-pyran-2,4-dione. ¹H NMR (400 MHz, DMSO-d₆): δ 1.15 (t, J=7.58 Hz, 3H), 1.42-1.75 (m, 8H), 2.11 (s, 1 H), 2.22 (s, 1 H), 2.34-2.65 (m, 11 H), 2.74 (m, 2 H), 3.71 (s, 3 H), 3.73 (d, J=16.4 Hz, 1H), 3.79 (d, J=16.4 Hz, 1H), 7.02 (s, 1 H), 7.04 (d, J=8.6 Hz, 1H), 8.59 (d, J=8.6 Hz, 1H), 10.91 (s, 1 H). MS (ESI): 506.10 (M+H)⁺

Example A(7)

6-Cyclopentyl-6-[2-(5-methoxy-2-methylpyridin-4-yl)ethyl]dihydro-2H-pyran-2,4(3H)-dione

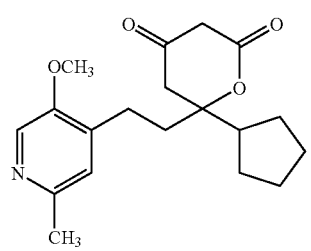

The title compound was prepared analogously to example A(2) where 5-methoxy-2-methyl-pyridine from step 1 of example A(2) was substituted in place of 2-ethyl-5-methoxy-pyridine in step 3 of that example. ¹H NMR (400 MHz, CDCl₃): δ 1.41-1.84 (br m, 8 H), 2.31 (m, 1 H), 2.46 (s, 3 H), 2.67-2.76 (m, 4 H), 3.42 (s, 2 H), 3.88 (m, 5 H), 6.91 (s, 1 H), 8.04 (s, 1 H). Anal. Calcd. For C₁₉H₂₅NO₄: C, 68.86; H, 7.60; N, 4.23. Found: C, 68.92; H, 7.75; N, 4.26.

Example A(8)

6-Cyclopentyl-3-[(5,7-dimethyl[1,2,4]triazolo[1,5-a]pyrimidin-2-yl)methyl]-4-hydroxy-6-[2-(5-methoxy-2-methylpyridin-4-yl)ethyl]-5,6-dihydro-2H-pyran-2-one

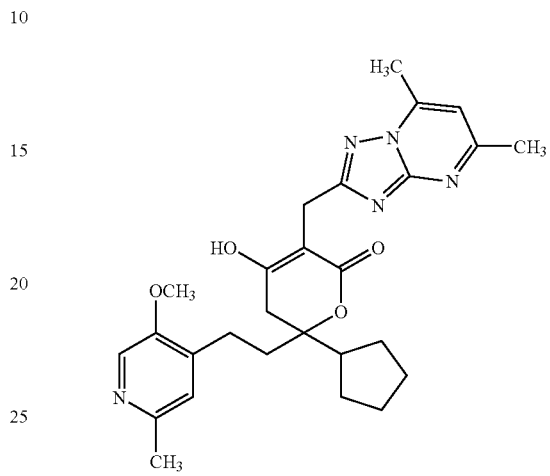

The title compound was prepared analogously to example A(1) where 6-cyclopentyl-6-[2-(5-methoxy-2-methylpyridin-4-yl)ethyl]dihydro-2H-pyran-2,4(3H)-dione (example A(7)) was substituted in place of 6-cyclopentyl-6-[2-(5-ethyl-4-hydroxy-2-propoxy-phenyl)-ethyl]-dihydro-pyran-2,4-dione. ¹H NMR (400 MHz, DMSO-d₆): δ 1.45-1.78 (m, 8H), 2.11 (s, 1 H), 2.19 (s, 1 H), 2.41 (s, 3 H), 2.48 (m, 4H), 2.56-2.62 (m, 6 H), 2.84 (d, J=17.4 Hz, 1H), 3.76 (d, J=16.0 Hz, 1H), 3.82 (s, 3 H), 3.88 (d, J=16.0 Hz, 1H), 7.10 (s, 1 H), 7.12 (s, 1 H), 8.11 (s, 1 H), 11.15 (s, 1 H). Anal. Calcd. For C₂₇H₃₃N₅O₄·0.5 AcOH: C, 64.47; H, 6.76; N, 13.43. Found: C, 64.42; H, 6.78; N, 13.39.

Example A(9)

6-{2-[2,6-Bis(2,2,2-trifluoroethyl)pyridin-4-yl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one

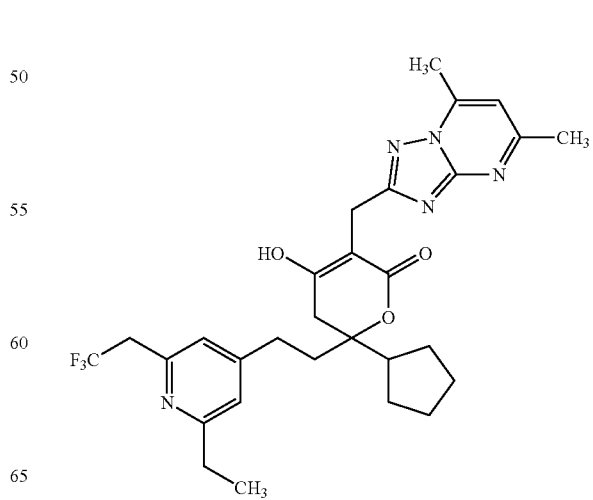

The title compound was prepared analogously to example A(1) where 4-bromo-2,6-bis-(2,2,2-trifluoro-ethyl)-pyridine from step 5 below was substituted in place of 1-benzyloxy-2-ethyl-4-iodo-5-propoxy-benzene in step 4 of that example. $^1$H NMR (400 MHz, DMSO-d$_6$): δ 1.19-1.53 (m, 8H), 1.98 (m, 2H), 2.14-2.37 (m, 8H), 2.52 (m, 2H), 2.59 (d, J=17.4 Hz, 1H), 3.50-3.67 (m, 6 H), 6.86 (s, 1 H), 7.20 (s, 2 H), 10.79 (s, 1 H). MS (ESI): 612.15 (M+H)$^+$.

Step 1: 2,6-Bis-(2,2,2-trifluoro-ethyl)-pyridine

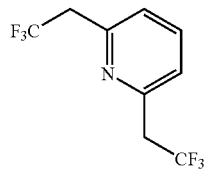

Trimethyl(trifluoromethyl)silane (11.8 mL, 75.5 mmol) was added to a stirred mixture of 2,6-bis(bromomethyl)pyridine (8 g, 30.2 mmol), KF (4.4 g, 75.5 mmol), CuI (17.3 g, 90.6 mmol) in DMF (40 mL) and NMP (40 mL). The reaction mixture was heated to 55° C. under N$_2$ for 15 hours. The mixture was poured into water, made basic with 1N NaOH and extracted with EtOAc. The organic layers were washed with brine, dried over Na$_2$SO$_4$ and concentrated to a black oil. Flash column chromatography (0% to 30% EtOAc in hexanes) gave the product as a yellow oil (4.3 g, 54%). $^1$H NMR (400 MHz, CDCl$_3$): δ 3.61 (q, J=10.6 Hz, 4 H), 7.32 (d, J=7.6 Hz, 2 H), 7.71 (d, J=7.6 Hz, 1H).

Step 2: 2,6-Bis-(2,2,2-trifluoro-ethyl)-pyridine 1-oxide

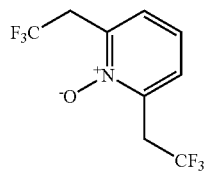

3-Chloroperoxybenzoic acid (4.52 g, 26.2 mmol) was added to a solution of 2,6-bis-(2,2,2-trifluoro-ethyl)-pyridine (4.25 g, 17.5 mmol) in CHCl$_3$ (70 mL). The reaction was stirred at room temperature for 4 hours and then quenched with satd Na$_2$SO$_3$. The layers were separated and the aqueous layer was extracted with CH$_2$Cl$_2$. The organic layers were washed with 1 N NaOH, brine, dried over Na$_2$SO$_4$ and concentrated to a yellow oil. Purification by flash column chromatography (0% to 50% EtOAc in hexanes) gave the product as a yellow solid (2.65 g, 58%). $^1$H NMR (400 MHz, CDCl$_3$): δ 3.96 (q, J=10.4 Hz, 4 H), 7.27 (t, J=8.1 Hz, 1 H), 7.47 (d, J=8.1 Hz, 2H).

Step 3: 4-Nitro-2,6-bis-(2,2,2-trifluoro-ethyl)-pyridine 1-oxide

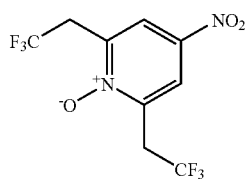

2,6-Bis-(2,2,2-trifluoro-ethyl)-pyridine 1-oxide (2.65 g, 10.22 mmol) was dissolved in H$_2$SO$_4$ (4 mL) and cooled to 0° C. HNO$_3$ (3.2 mL) was added slowly and after the addition was complete the reaction mixture was heated to 90° C. for 2 hours. The mixture was poured into ice, made basic with 15% NaOH and extracted with CH$_2$Cl$_2$. The organic layers were washed with brine, dried over Na$_2$SO$_4$ and concentrated to a red oil (2.72 g, 81%). $^1$H NMR (400 MHz, CDCl$_3$): δ 3.95 (t, J=10.1 Hz, 4 H), 8.31 (s, 2 H).

Step 4: 4-Bromo-2,6-bis-(2,2,2-trifluoro-ethyl)-pyridine 1-oxide

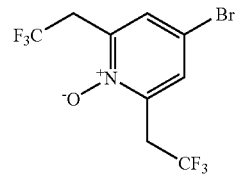

Acetyl bromide (14 mL) was added to a solution of 4-nitro-2,6-bis-(2,2,2-trifluoro-ethyl)-pyridine 1-oxide (2.7 g, 8.9 mmol) dissolved in AcOH (25 mL). The reaction mixture was heated to 90° C. for 5 hours. The reaction was cooled to room temperature, poured into ice, made basic with NaOH pellets and extracted with EtOAc. The organic layers were washed with brine, dried over Na$_2$SO$_4$ and concentrated to a red oil. Purification by flash column chromatography (0% to 30%

EtOAc in hexanes) gave the product as a yellow oil (2.18 g, 72%). ¹H NMR (400 MHz, CDCl₃): δ 3.92 (t, J=10.1 Hz, 4 H), 7.59 (s, 2 H).

Step 5: 4-Bromo-2,6-bis-(2,2,2-trifluoro-ethyl)-pyridine

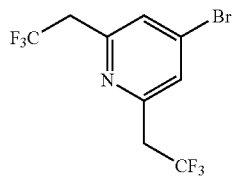

A solution of 4-bromo-2,6-bis-(2,2,2-trifluoro-ethyl)-pyridine 1-oxide (2.1 g, 6.2 mmol) and PBr₃ (1 mL) in CH₂Cl₂ (15 mL) was stirred at room temperature for 4 hours. The reaction mixture was poured into ice, made basic with 15% NaOH and extracted with EtOAc. The organic layers were washed with brine, dried over Na₂SO₄ and concentrated to a pale yellow solid (1.77 g, 89%). ¹H NMR (400 MHz, CDCl₃): δ 3.59 (t, J=10.4 Hz, 4 H), 7.51 (s, 2 H).

Example A(10)

Enantiomer 1 of 6-{2-[2,6-Bis(2,2,2-trifluoroethyl) pyridin-4-yl]ethyl}-6-cyclopentyl-3-[(5,7-dimethyl [1,2,4]triazolo[1,5-a]pyrimidin-2-yl)methyl]-4-hydroxy-5,6-dihydro-2H-pyran-2-one

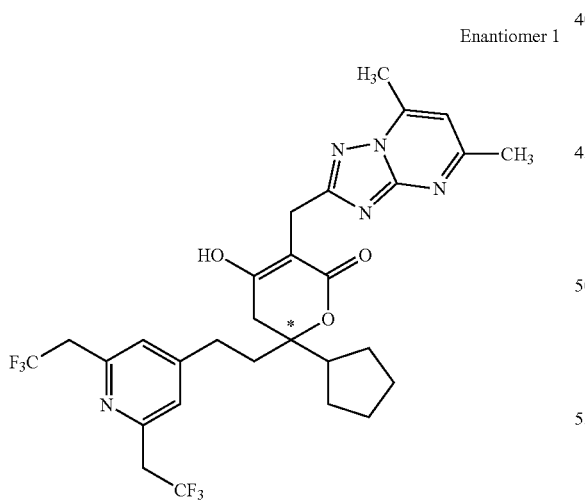

Enantiomer 1

The title compound was separated from racemic 6-{2-[2,6-Bis(2,2,2-trifluoroethyl)pyridin-4-yl]ethyl}-6-cyclopentyl-3-[(5,7-dimethyl[1,2,4]triazolo[1,5-a]pyrimidin-2-yl) methyl]-4-hydroxy-5,6-dihydro-2H-pyran-2-one (65 mg, Example A(9)) using chiral HPLC (Chiralpak AS-H, 100 bar, 30% MeOH). (27 mg, 1.975 min retention time, 100% ee)

Example A(11)

Enantiomer 2 of 6-{2-[2,6-Bis(2,2,2-trifluoroethyl) pyridin-4-yl]ethyl}-6-cyclopentyl-3-[(5,7-dimethyl [1,2,4]triazolo[1,5-a]pyrimidin-2-yl)methyl]-4-hydroxy-5,6-dihydro-2H-pyran-2-one

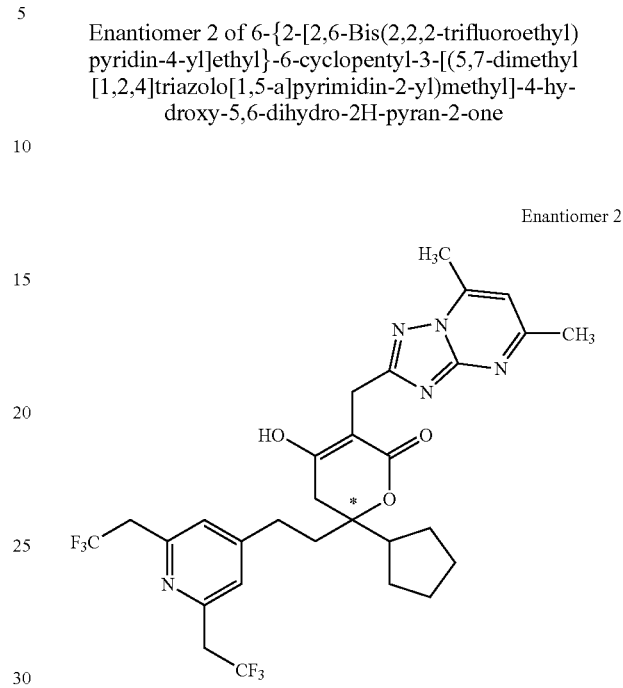

Enantiomer 2

The title compound was separated from racemic 6-{2-[2,6-bis(2,2,2-trifluoroethyl)pyridin-4-yl]ethyl}-6-cyclopentyl-3-[(5,7-dimethyl[1,2,4]triazolo[1,5-a]pyrimidin-2-yl) methyl]-4-hydroxy-5,6-dihydro-2H-pyran-2-one (65 mg, Example A(9)) using chiral HPLC (Chiralpak AS-H, 100 bar, 30% MeOH). (29 mg, 3.203 min retention time, 100% ee)

Example A(12)

Enantiomer 1 of 6-Cyclopentyl-3-[(5,7-dimethyl[1,2, 4]triazolo[1,5-a]pyrimidin-2-yl)methyl]-6-[2-(5-ethyl-4-hydroxy-2,3-dihydro-1-benzofuran-7-yl) ethyl]-4-hydroxy-5,6-dihydro-2H-pyran-2-one

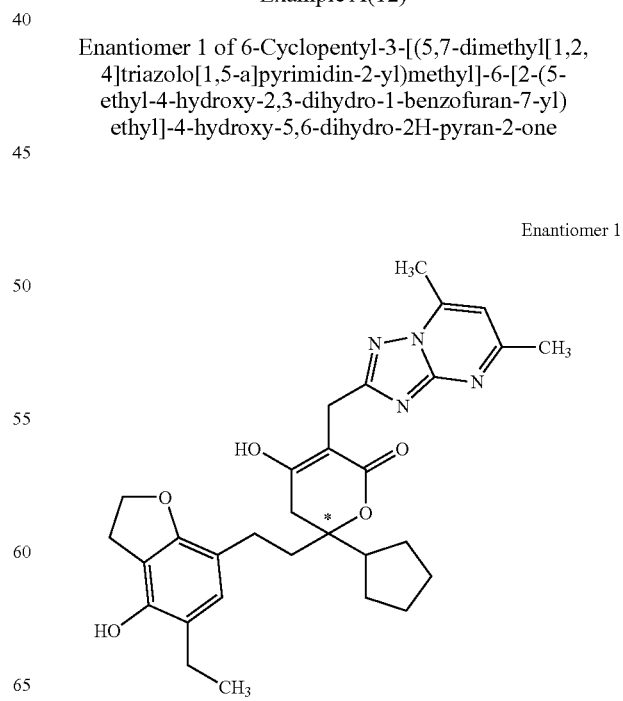

Enantiomer 1

The title compound was separated from racemic 6-cyclopentyl-3-[(5,7-dimethyl[1,2,4]triazolo[1,5-a]pyrimidin-2-yl)methyl]-6-[2-(5-ethyl-4-hydroxy-2,3-dihydro-1-benzofuran-7-yl)ethyl]-4-hydroxy-5,6-dihydro-2H-pyran-2-one (280 mg, from step 1 below) using chiral HPLC (Chiralpak AS-H, 140 bar, 40% MeOH). (113 mg, 5.140 min retention time, 100% ee)

Step 1: 6-Cyclopentyl-3-[(5,7-dimethyl[1,2,4]triazolo[1,5-a]pyrimidin-2-yl)methyl]-6-[2-(5-ethyl-4-hydroxy-2,3-dihydro-1-benzofuran-7-yl)ethyl]-4-hydroxy-5,6-dihydro-2H-pyran-2-one

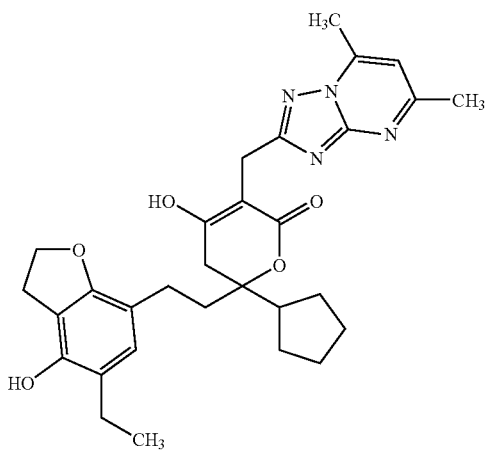

The title compound was prepared analogously to example X(x) where 1-(4-hydroxy-benzofuran-5-yl)-ethanone from step 1 below was substituted in place of 1-(4-ethoxy-2-hydroxy-phenyl)-ethanone in step 2 of that example.

$^1$H NMR (400 MHz, DMSO-$d_6$) δ: 1.08 (t, J=7.3 Hz, 3 H), 1.45-1.75 (br m, 8 H), 2.01 (m, 1 H), 2.15 (m, 1 H), 2.39-2.65 (m, 12 H), 2.80 (d, J=17.4 Hz, 1 H), 3.09 (t, J=8.8 Hz, 2 H), 3.77 (d, J=15.9 Hz, 1H), 3.85 (d, J=15.9 Hz, 1 H), 4.47 (t, J=11.4 Hz, 2 H), 6.64 (s, 1 H), 7.09 (s, 1 H), 8.58 (s, 1 H), 10.89 (s, 1 H). Anal. Calcd. For $C_{30}H_{36}N_4O_5 \cdot 0.4H_2O$: C, 66.74; H, 6.87; N, 10.38. Found: C, 66.71; H, 6.65; N, 10.21.

Step 1: 1-(4-Hydroxy-benzofuran-5-yl)-ethanone

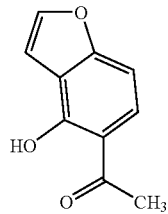

The title compound was prepared as described in the following reference: *Tetrahedron* 1995, 51, 4909-4922. $^1$H NMR (400 MHz, CDCl$_3$): δ 1.58 (s, 3 H), 7.00 (dd, J=2.0, 1.0 Hz, 1 H), 7.05 (dd, J=8.8, 1.0 Hz, 1 H), 7.57 (d, J=2.0 Hz, 1 H), 7.66 (d, J=8.8 Hz, 1 H), 13.3 (s, 1 H).

Example A(13)

Enantiomer 2 of 6-Cyclopentyl-3-[(5,7-dimethyl[1,2,4]triazolo[1,5-a]pyrimidin-2-yl)methyl]-6-[2-(5-ethyl-4-hydroxy-2,3-dihydro-1-benzofuran-7-yl)ethyl]-4-hydroxy-5,6-dihydro-2H-pyran-2-one

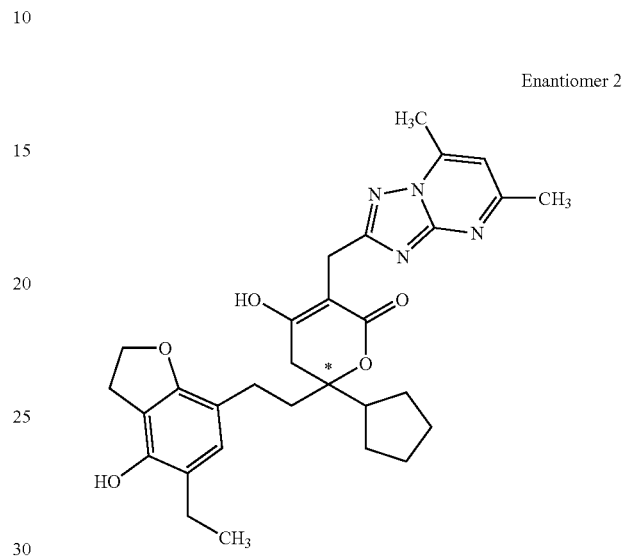

Enantiomer 2

The title compound was separated from racemic 6-cyclopentyl-3-[(5,7-dimethyl[1,2,4]triazolo[1,5-a]pyrimidin-2-yl)methyl]-6-[2-(5-ethyl-4-hydroxy-2,3-dihydro-1-benzofuran-7-yl)ethyl]-4-hydroxy-5,6-dihydro-2H-pyran-2-one (280 mg, from step 1 of example A(12)) using chiral HPLC (Chiralpak AS-H, 140 bar, 40% MeOH). (106 mg, 8.992 min retention time, 100% ee)

Example A(14)

6-Cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one

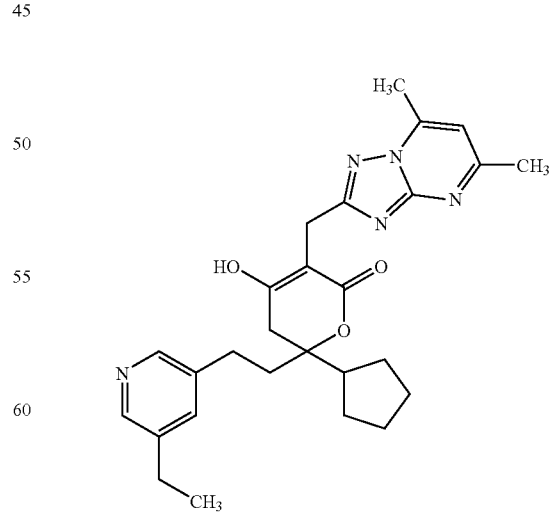

The title compound was prepared analogously to example A(1) where 3-bromo-5-ethyl-pyridine from step 1 below was substituted in place of 1-benzyloxy-2-ethyl-4-iodo-5-propoxy-benzene in step 4 of that example. $^1$H NMR (400 MHz, DMSO-d$_6$) δ: 1.14 (t, J=7.6 Hz, 3 H), 1.40-1.70 (br m, 8 H), 2.14 (m, 2 H), 2.44-2.65 (m, 12 H), 2.79 (d, J=17.6 Hz, 1 H), 3.72 (d, J=16.4 Hz, 1 H), 3.83 (d, J=16.4 Hz, 1 H), 7.04 (s, 1 H), 7.50 (s, 1 H), 8.24 (s, 1 H), 8.26 (s 1 H), 10.90 (s, 1 H). MS (ESI): 476.10 (M+H)$^+$ Step 1: 3-Bromo-5-ethyl-pyridine

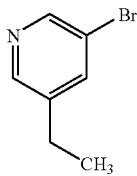

A mixture of NaOH (10 g, 0.25 mol), hydrazine monohydrate (10 mL) and 3-acetyl-5-bromopyridine (5 g, 25 mmol) suspended in diethylene glycol (18 mL) was heated to 140° C. for 6 hours. The mixture was cooled to room temperature and partitioned between H$_2$O and ether. The ether extracts were dried over MgSO$_4$ and concentrated to a clear oil. Flash column chromatography (0% to 15% EtOAc in hexanes) gave the product as a clear oil (2.9 g, 58%). $^1$H NMR (400 MHz, CDCl$_3$): δ 1.26 (t, J=7.6 Hz, 3 H), 2.65 (d, J=7.6 Hz, 2 H), 7.67 (t, J=2.0 Hz, 1 H), 8.37 (d, J=1.8 Hz, 1 H), 8.51 (d, J=2.0 Hz, 1 H).

Example A(15)

6-Cyclopentyl-3-[(5,7-dimethyl[1,2,4]triazolo[1,5-a]pyrimidin-2-yl)methyl]-6-[2-(4-ethylpyridin-2-yl)ethyl]-4-hydroxy-5,6-dihydro-2H-pyran-2-one

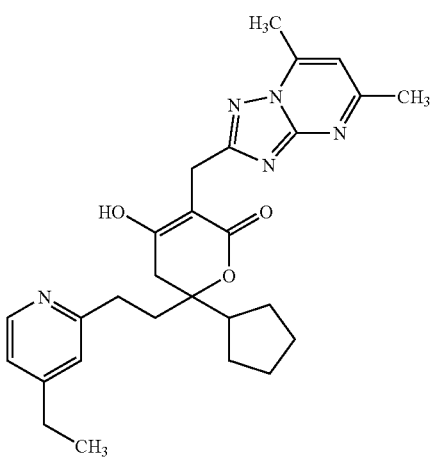

The title compound was prepared analogously to example A(1) where 2-bromo-4-ethyl-pyridine was substituted in place of 1-benzyloxy-2-ethyl-4-iodo-5-propoxy-benzene in step 4 of that example. $^1$H NMR (400 MHz, DMSO-d$_6$) δ: 0.99 (t, J=7.6 Hz, 3 H), 1.22-1.53 (br m, 8 H), 2.06 (m, 2H), 2.24-2.44 (m, 10 H), 2.59 (m, 3 H), 3.56 (d, J=16.2 Hz, 1 H), 3.65 (d, J=16.2 Hz, 1 H), 6.87 (s, 1H), 6.90 (d, J=5.0 Hz, 1 H), 6.97 (s, 1 H), 8.16 (d, J=5.0 Hz, 1 H), 10.77 (s, 1 H). Anal. Calcd. For C$_{27}$H$_{33}$N$_5$O$_3$.0.25 AcOH: C, 67.32; H, 6.99; N, 14.28. Found: C, 67.31; H, 7.02; N, 13.92.

Example A(16)

6-Cyclopentyl-6-[2-(4-ethylpyridin-2-yl)ethyl]-4-hydroxy-3-[(6-methyl[1,2,4]triazolo[1,5-a]pyrimidin-2-yl)methyl]-5,6-dihydro-2H-pyran-2-one

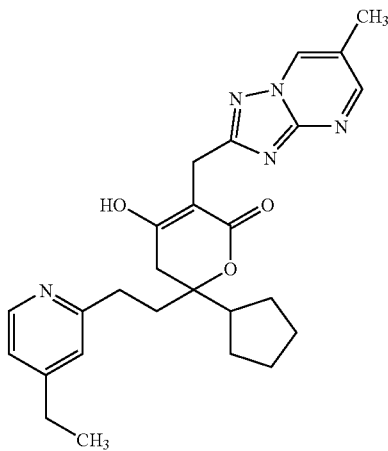

The title compound was prepared analogously to example A(4) where 6-cyclopentyl-6-[2-(4-ethyl-pyridin-2-yl)-ethyl]-dihydro-pyran-2,4-dione (from step 1 below) was substituted in place of 6-cyclopentyl-6-[2-(2-ethyl-5-methoxy-pyridin-4-yl)-ethyl]-dihydro-pyran-2,4-dione. $^1$H NMR (400 MHz, DMSO-d$_6$) δ: 1.07 (t, J=7.6 Hz, 3 H), 1.29-1.59 (br m, 8 H), 2.09 (m, 2 H), 2.26-2.52 (m, 6 H), 2.66 (m, 4 H), 3.64 (d, J=16.2 Hz, 1 H), 3.70 (d, J=15.9 Hz, 1 H), 6.97 (d, J=5.0 Hz, 1 H), 7.05 (s, 1 H), 8.24 (d, J=5.0 Hz, 1 H), 8.59 (s, 1 H), 8.86 (s, 1 H), 10.82 (s, 1 H). Anal. Calcd. For C$_{26}$H$_{31}$N$_5$O$_3$.0.3 AcOH: C, 66.62; H, 6.77; N, 14.60. Found: C, 66.63; H, 6.86; N, 14.24.

Step 1: 6-Cyclopentyl-6-[2-(4-ethyl-pyridin-2-yl)-ethyl]-dihydro-pyran-2,4-dione

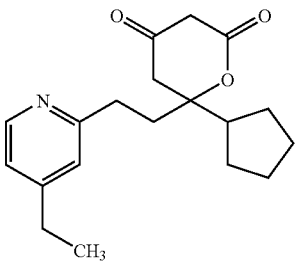

The title compound was prepared analogously to example A(2) where 2-bromo-4-ethyl-pyridine was substituted in place of 4-bromo-2-ethyl-5-methoxy-pyridine in step 6 of that example. $^1$H NMR (400 MHz, CDCl$_3$): δ 1.25 (t, J=7.6 Hz, 3 H), 1.41-1.82 (br m, 8 H), 2.14 (m, 2 H), 2.30 (m, 1H), 2.63 (q, J=7.6 Hz, 2 H), 2.75 (m, 2 H), 2.86 (m, 2 H), 3.47 (m, 2 H), 7.01 (m, 2 H), 8.37 (s, 1 H). MS (ESI): 316.10 (M+H)+

Example A(17)

6-Cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one

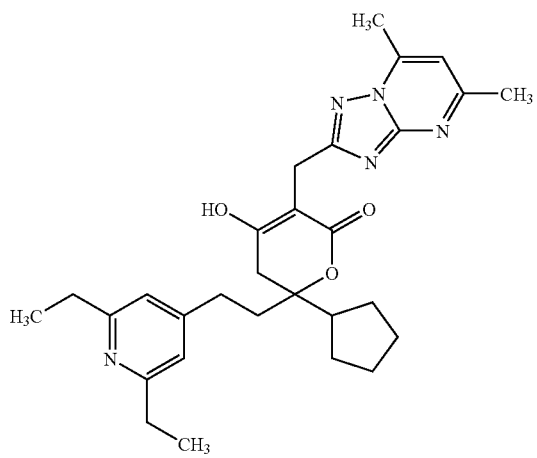

The title compound was prepared analogously to example A(9) where 2,6-diethyl-pyridine from step 1 below was substituted in place of 2,6-bis-(2,2,2-trifluoro-ethyl)-pyridine in step 2 of that example. $^1$H NMR (400 MHz, DMSO-d$_6$) δ: 1.16 (t, J=7.6 Hz, 6 H), 1.40-1.72 (br m, 8 H), 2.13 (m, 2H), 2.41-2.67 (m, 14 H), 2.78 (d, J=17.1 Hz, 1 H), 3.70 (d, J=16.4 Hz, 1 H), 3.83 (d, J=16.4 Hz, 1H), 6.91 (s, 2 H), 7.05 (s, 1 H), 10.93 (s, 1 H). Anal. Calcd. For C$_{29}$H$_{37}$N$_5$O$_3$·0.5 AcOH: C, 67.52; H, 7.37; N, 13.12. Found: C, 67.70; H, 7.60; N, 12.91.

Step 1: 2,6-diethyl-pyridine

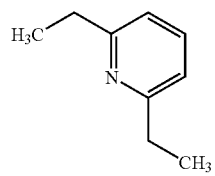

A mixture of NaOH (14.7 g, 0.37 mol), hydrazine monohydrate (15 mL) and 2,6-diacetylpyridine (6 g, 36.8 mmol) suspended in diethylene glycol (27 mL) was cautiously heated to 120° C. for 16 hours. The mixture was cooled to room temperature and partitioned between H$_2$O and ether. The ether extracts were washed with 1 N NaOH, dried over MgSO$_4$ and concentrated to a clear oil. Flash column chromatography (0% to 15% EtOAc in hexanes) gave the product as a clear oil (2.9 g, 58%). $^1$H NMR (400 MHz, CDCl$_3$): δ 1.29 (t, J=7.8 Hz, 3 H), 2.80 (d, J=7.8 Hz, 2 H), 6.97 (d, J=2.0 Hz, 2 H), 7.51 (t, J=7.6 Hz, 1 H).

2,6-Diethyl-pyridine has also been prepared as follows:

A solution of ethylmagnesium bromide in ethyl ether [prepared from Mg (16.5 g, 0.68 mol) and ethyl bromide (50 mL, 0.68 mol) in 500 mL of ether] was added dropwise to a mixture of 2,6-dichloropyridine (50 g, 0.34 mol) and NiCl$_2$(dppp) (1.0 g, 2 mol) in anhydrous ethyl ether (500 mL) at 0° C. under N$_2$ atmosphere. After addition, the resulting mixture was stirred at ambient temperature overnight, was then heated to reflux for about 3 hours. The suspension was poured into crushed ice (200 g) and the mixture was saturated with NH$_4$Cl. The organic layer was separated and the aqueous phase was extracted with ether (200 mL×3). The combined organic layers were washed with water, brine, dried over Na$_2$SO$_4$ and concentrated to give the product (41.1 g, 89%).

Example A(18)

6-Cyclopentyl-6-[2-(2,6-dimethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one

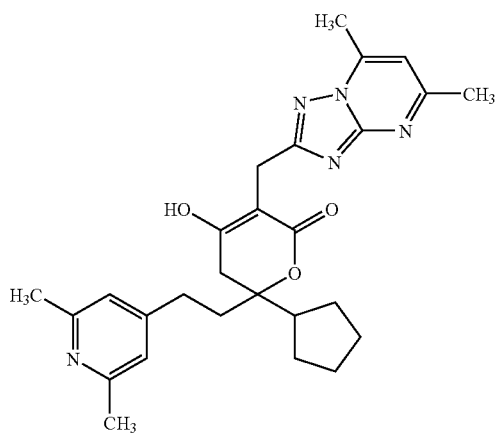

The title compound was prepared analogously to example A(9) where 2,6-lutidine N-oxide was substituted in place of 2,6-Bis-(2,2,2-trifluoro-ethyl)-pyridine 1-oxide in step 3 of that example. $^1$H NMR (400 MHz, DMSO-d$_6$) δ: 1.44-1.75 (br m, 8 H), 2.19 (m, 2 H), 2.42-2.63 (m, 16 H), 2.85 (d, J=17.7 Hz, 1 H), 3.77 (d, J=16.1 Hz, 1 H), 3.89 (d, J=16.9 Hz, 1 H), 6.97 (s, 2 H), 7.12 (s, 1 H), 11.05 (s, 1 H). MS (ESI): 476.20 (M+H)+

Example A(19)

6-Cyclopentyl-3-[(5,7-dimethyl[1,2,4]triazolo[1,5-a]pyrimidin-2-yl)methyl]-6-{2-[5-ethyl-2-(3-methoxypropyl)phenyl]ethyl}-4-hydroxy-5,6-dihydro-2H-pyran-2-one

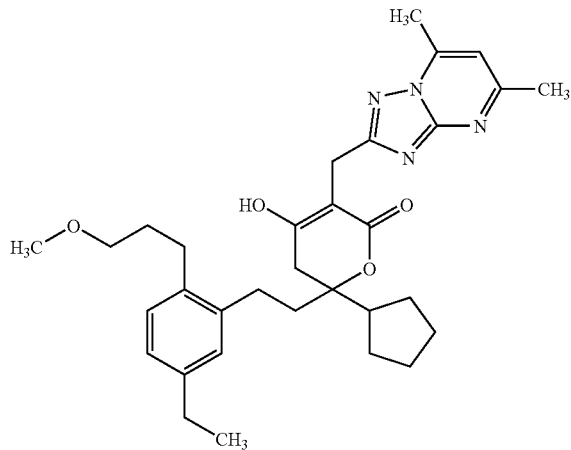

The title compound was prepared analogously to example A(1) where trifluoro-methanesulfonic acid 5-ethyl-2-(3-methoxy-propyl)-phenyl ester from step 5 below was substituted in place of 1-benzyloxy-2-ethyl-4-iodo-5-propoxy-benzene in step 4 of that example. ¹H NMR (400 MHz, DMSO-d₆) δ: 1.08 (d, J=7.6 Hz, 3 H), 1.40-1.73 (br m, 10 H), 1.99 (s, 1 H), 2.18 (m, 1 H), 2.33 (s, 3H), 2.40-2.57 (m, 11 H), 2.79 (d, J=117.4 Hz, 1 H), 3.16 (s, 3 H), 3.17 (d, J=7.6 Hz, 2 H), 3.70 (d, J=15.9 Hz, 1 H), 3.81 (d, J=15.9 Hz, 1 H), 6.94 (m, 3 H), 7.01 (s, 1 H), 10.95 (s, 1 H). MS (ESI): 546.72 (M+H)+

Step 1: 4-Ethyl-2-hydroxy-benzaldehyde (A) and 2-Ethyl-4-hydroxy-benzaldehyde (B)

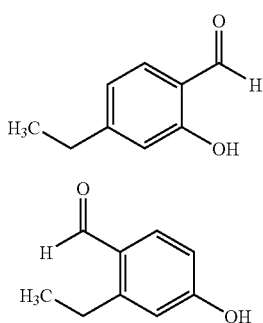

Titanium(IV) chloride (100 mL, 100 mmol, 1M in CH₂Cl₂) followed by dichloromethyl methyl ether (7.47 mL, 82.5 mmol) was added to a cooled 0° C. solution of 3-ethylphenol (6.11 g, 50 mmol). The reaction mixture was stirred for 45 mins. The mixture was poured into ice and extracted with EtOAc. The organic layers were washed with brine, dried over Na₂SO₄ and concentrated to a bright pink oil. Purification by flash column chromatography (0% to 10% EtOAc in hexanes) gave 4-ethyl-2-hydroxy-benzaldehyde (4.9 g, 65%) followed by 2-ethyl-4-hydroxy-benzaldehyde (1.32 g, 18%). A: ¹H NMR (400 MHz, CDCl₃): δ 1.25 (t, J=7.6 Hz, 3 H), 2.67 (d, J=7.6 Hz, 2 H), 6.82 (s, 1 H), 6.85 (d, J=8.0 Hz, 1 H), 7.46 (t, J=8.0 Hz, 1 H), 9.83 (s, 1 H), 11.05 (s, 1 H). B: ¹H NMR (400 MHz, CDCl₃): δ 1.27 (t, J=7.6 Hz, 3 H), 3.03 (d, J=7.6 Hz, 2 H), 6.68 (s, 1 H), 6.78 (s, 1 H), 6.82 (d, J=8.3 Hz, 1 H), 7.77 (t, J=8.3 Hz, 1 H), 10.10 (s, 1 H).

Step 2: 3-(2-Benzyloxy-4-ethyl-phenyl)-acrylic acid ethyl ester

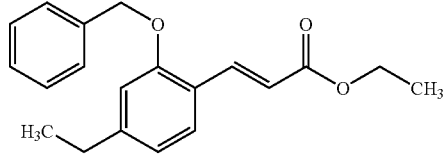

Potassium carbonate (8.84 g, 64 mmol) followed by benzyl bromide (3.8 mL, 32 mmol) was added to a solution of 4-ethyl-2-hydroxy-benzaldehyde (4.8 g, 32 mmol) in DMF (50 mL). The mixture was stirred for 15 hours and then partitioned between 1N HCl and EtOAc. The organic layer was washed with brine, dried over Na₂SO₄ and concentrated to a brown oil. Purification by flash column chromatography (0% to 10% EtOAc in hexanes) gave the product as a yellow oil (6.1 g, 84%).

The oil was dissolved in THF (40 mL) and treated with (carbethoxymethylene)triphenylphosphorane (3.5 g, 9.99 mmol). The reaction mixture was heated at 70° C. for 5 days. The reaction mixture was concentrated and purified by flash column chromatography (0% to 15% EtOAc in hexanes) to give the product (2.93 g, 95%). ¹H NMR (400 MHz, CDCl₃): δ 1.21 (t, J=7.6 Hz, 3 H), 1.32 (t, J=7.3 Hz, 3 H), 2.63 (d, J=7.6 Hz, 2 H), 4.24 (q, J=7.1 Hz, 2 H), 5.15 (s, 2 H), 6.49 (d, J=16.2 Hz, 1 H), 6.80 (m, 2 H), 7.33-7.47 (m, 6 H), 8.05 (d, J=16.2 Hz, 1 H).

Step 3: 3-(2-Benzyloxy-4-ethyl-phenyl)-prop-2-en-1-ol

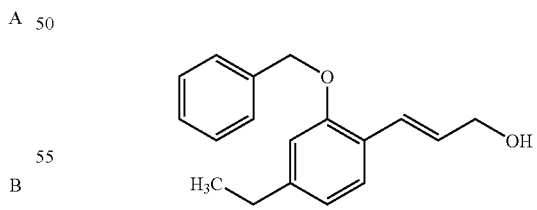

A solution of 3-(2-benzyloxy-4-ethyl-phenyl)-acrylic acid ethyl ester (2.9 g, 9.3 mmol) dissolved in ether (7 mL) was added to a cooled 0° C. suspension of lithium aluminium hydride (0.89 g, 23.4 mmol) in ether (20 mL). The reaction mixture was stirred for 4 hours, quenched with H₂O (3.6 mL) and 15% NaOH (0.9 mL) and then filtered through glass frit washing with ether. The filtrate was concentrated to a clear oil and purified by flash column chromatography (0% to 30% EtOAc in hexanes) to give the product (1.78 g, 71%). ¹H NMR (400 MHz, CDCl$_3$): δ 1.22 (t, J=7.6 Hz, 3 H), 2.62 (q, J=7.6 Hz, 2 H), 4.29 (m, 2 H), 5.10 (s, 2 H), 6.35 (dt, J=16.2, 7.6 Hz, 1 H), 6.78 (s, 1 H), 6.80 (d, J=7.1 Hz, 1 H), 6.95 (d, J=16.2 Hz, 1 H), 7.32-7.45 (m, 6 H).

Step 4: 5-Ethyl-2-(3-methoxy-propyl)-phenol

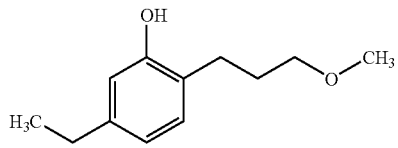

Potassium hydroxide (1.17 g, 20.9 mmol) followed by methyl iodide (0.5 mL, 7.8 mmol) were added to a solution of 3-(2-benzyloxy-4-ethyl-phenyl)-prop-2-en-1-ol (1.4 g, 5.2 mmol) in DMSO (20 mL). The mixture was stirred for 15 hours and then partitioned between 1 N HCl and EtOAc. The organic layer was washed with brine, dried over Na$_2$SO$_4$ and concentrated to a brown oil. Purification by flash column chromatography (0% to 30% EtOAc in hexanes) gave a clear oil (1.0 g, 68%).

The oil was dissolved in EtOH (10 mL) and treated with Pd(OH)$_2$ (0.25 g, 20 wt %, Degussa type). The mixture was stirred under a balloon of hydrogen for 6 hours. The reaction mixture was filtered through a pad of celite washing with EtOAc. The filtrate was concentrated and purified by flash column chromatography to give the product (0.48 g, 65%). $^1$H NMR (400 MHz, CDCl$_3$): δ 1.22 (t, J=7.6 Hz, 3 H), 1.87 (m, 2 H), 2.58 (d, J=7.6 Hz, 2 H), 2.69 (d, J=6.6 Hz, 2 H), 3.37 (t, J=5.8 Hz, 2H), 3.41 (s, 3 H), 6.70 (d, J=9.1 Hz, 1 H), 6.73 (s, 1 H), 6.98 (m, 2 H).

Step 5: Trifluoro-methanesulfonic acid 5-ethyl-2-(3-methoxy-propyl)-phenyl ester

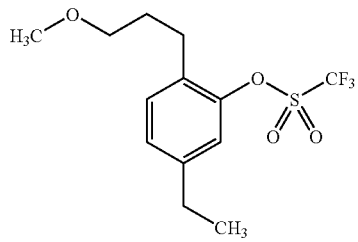

Trifluoromethanesulfonic anhydride (0.47 mL, 2.8 mmol) followed by triethylamine (0.42 mL, 3 mmol) was added to a cooled 0° C. solution of 5-ethyl-2-(3-methoxy-propyl)-phenol (0.45 g, 2.3 mmol). The reaction was stirred for 1 hour and then warmed to room temperature. The reaction was partitioned between 1 N HCl and EtOAc. The organic extracts were washed with bring, dried over Na2SO4 and concentrated to a black oil. $^1$H NMR (400 MHz, CDCl$_3$): δ 1.24 (t, J=7.6 Hz, 3 H), 1.89 (m, 2 H), 2.65 (d, J=7.6 Hz, 2 H), 2.75 (t, J=7.6 Hz, 2 H), 3.35 (s, 3 H), 3.40 (t, J=7.6 Hz, 2 H), 7.07 (s, 1 H), 7.14 (d, J=8.0 Hz, 1 H), 7.23 (d, J=8.0 Hz, 1 H).

Example A(20)

6-Cyclopentyl-3-[(5,7-dimethyl[1,2,4]triazolo[1,5-a]pyrimidin-2-yl)methyl]-6-{2-[3-ethyl-4-(3-methoxypropyl)phenyl]ethyl}-4-hydroxy-5,6-dihydro-2H-pyran-2-one

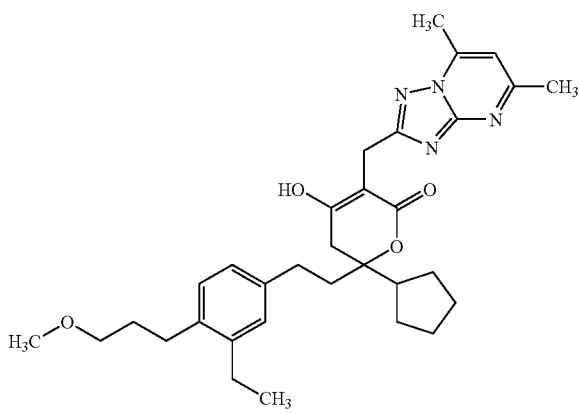

The title compound was prepared analogously to example A(19) where 2-ethyl-4-hydroxy-benzaldehyde from step 1 of example A(19) was substituted in place of 4-ethyl-2-hydroxy-benzaldehyde in step 2 of that example. $^1$H NMR (400 MHz, DMSO-d$_6$) δ: 0.97 (t, J=7.6 Hz, 3 H), 1.28-1.60 (br m, 10 H), 1.98 (m, 2 H), 2.31-2.45 (m, 14 H), 2.66 (d, J=17.7 Hz, 1 H), 3.14 (s, 3 H), 3.23 (t, J=7.6 Hz, 2 H), 3.58 (d, J=16.9 Hz, 1 H), 3.71 (d, J=16.9 Hz, 1 H), 6.88 (m, 4 H), 10.98 (s, 1H). MS (ESI): 547.20 (M+H)$^+$ Example A(21)

(6R)-6-cyclopentyl-6-[2-(5-ethyl-2,4-dihydroxyphenyl)ethyl]-4-hydroxy-3-[(6-methyl[1,2,4]triazolo[1,5-a]pyrimidin-2-yl)methyl]-5,6-dihydro-2H-pyran-2-one

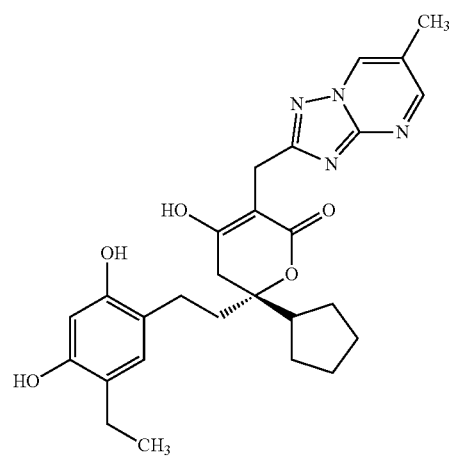

Boron tribromide (0.82 mL, 1M in $CH_2Cl_2$) was added to a cooled −78° C. of 6-cyclopentyl-6-[2-(5-ethyl-4-hydroxy-2-methoxy-phenyl)-ethyl]-4-hydroxy-3-(6-methyl-[1,2,4]triazolo[1,5-a]pyrimidin-2-ylmethyl)-5,6-dihydro-pyran-2-one (70 mg, 0.14 mmol, from step 3 below) dissolved in $CH_2Cl_2$ (5 mL). The reaction was stirred for 15 hours. 1 N HCl was added and the reaction was stirred for 10 mins. The mixture was extracted with 10% MeOH in EtOAc. The organic layers were washed with brine, dried over $Na_2SO_4$ and concentrated to brown solid residue. Purification by prep HPLC gave the product as a brown solid (27 mg, 40%). $^1$H NMR (400 MHz, DMSO-$d_6$) δ: 1.04 (t, J=7.3 Hz, 3 H), 1.40-1.75 (br m, 8 H), 1.98 (m, 2 H), 2.37-2.45 (m, 8 H), 2.57 (d, J=17.4 Hz, 1 H), 2.74 (d, J=17.4 Hz, 1 H), 3.78 (d, J=16.1 Hz, 1 H), 3.79 (d, J=16.1 Hz, 1 H), 6.33 (s, 1 H), 6.68 (s, 1 H), 8.69 (s, 1 H), 8.84 (m, 3 H), 10.90 (s, 1 H). MS (ESI): 492.55 $(M+H)^+$ Step 1: Acetic acid 4-bromo-2-ethyl-5-methoxy-phenyl ester

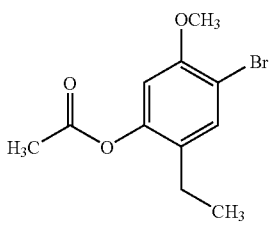

The title compound was prepared analogously to step 4 of example A(22) where methyl iodide was substituted in place of ethyl iodide in step 1 of that example. $^1$H NMR (400 MHz, CDCl$_3$): δ 1.16 (t, J=7.4 Hz, 3 H), 2.32 (s, 3 H), 2.45 (q, J=7.4 Hz, 2 H), 3.85 (s, 3 H), 6.59 (s, 1 H), 7.42 (s, 1H).

Step 2: 6-Cyclopentyl-6-[2-(5-ethyl-4-hydroxy-2-methoxy-phenyl)-ethyl]-dihydro-pyran-2,4-dione

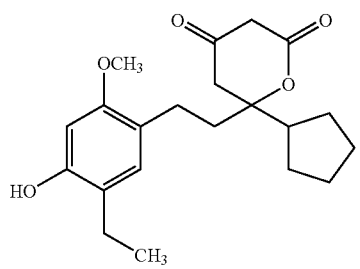

The title compound was prepared analogously to example A(2) where acetic acid 4-bromo-2-ethyl-5-methoxy-phenyl ester was substituted in place of 4-bromo-2-ethyl-5-methoxy-pyridine in step 6 of that example. $^1$H NMR (400 MHz, CDCl$_3$): δ 1.20 (t, J=7.4 Hz, 3 H), 1.41-1.86 (m, 9 H), 1.94 (m, 1 H), 2.34 (m, 1 H), 2.52 (m, 3 H), 2.62 (m, 1 H), 2.73 (d, J=16.4 Hz, 1 H), 2.78 (d, J=16.4 Hz, 1H), 3.41 (s, 2 H), 3.75 (s, 3 H), 4.58 (s, 1 H), 6.35 (s, 1 H), 6.80 (s, 1 H).

Step 3: 6-Cyclopentyl-6-[2-(5-ethyl-4-hydroxy-2-methoxy-phenyl)-ethyl]-4-hydroxy-3-(6-methyl-[1,2,4]triazolo[1,5-a]pyrimidin-2-ylmethyl)-5,6-dihydro-pyran-2-one

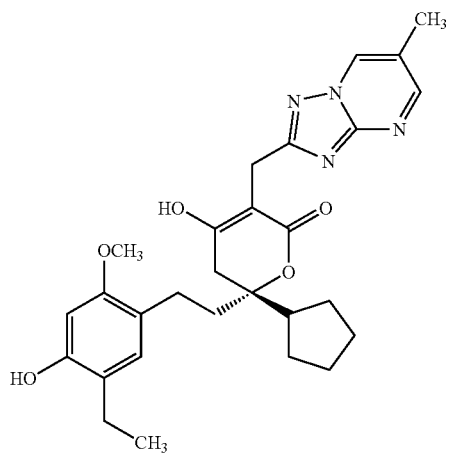

Racemic 6-cyclopentyl-6-[2-(5-ethyl-4-hydroxy-2-methoxy-phenyl)-4-hydroxy-3-(6-methyl-[1,2,4]triazolo[1,5-a]pyrimidin-2-ylmethyl)-5,6-dihydro-pyran-2-one was prepared analogously to example A(4) where 6-cyclopentyl-6-[2-(5-ethyl-4-hydroxy-2-methoxy-phenyl)-ethyl]-dihydro-pyran-2,4-dione from step 2 above was substituted in place of 6-cyclopentyl-6-[2-(2-ethyl-5-methoxypyridin-4-yl)ethyl]dihydro-2H-pyran-2,4(3H)-dione.

The title compound was separated from racemic 6-cyclopentyl-6-[2-(5-ethyl-4-hydroxy-2-methoxy-phenyl)-ethyl]-4-hydroxy-3-(6-methyl-[1,2,4]triazolo[1,5-a]pyrimidin-2-ylmethyl)-5,6-dihydro-pyran-2-one using chiral HPLC (Chiralpak AS-H, 140 bar, 40% MeOH). (5.65 min retention time). $^1$H NMR (400 MHz, DMSO-$d_6$) δ: 1.10 (t, J=7.6 Hz, 3 H), 1.44-1.76 (br m, 8 H), 2.04 (m, 2 H), 2.41-2.62 (m, 9 H), 2.81 (d, J=17.4 Hz, 1 H), 3.69 (s, 3 H), 3.79 (d, J=16.2 Hz, 1 H), 3.85 (d, J=16.2 Hz, 1 H), 6.44 (s, 1 H), 6.82 (s, 1 H), 8.74 (s, 1 H), 8.88 (s, 1 H), 9.10 (s, 1 H), 10.95 (s, 1 H).

Example A(22)

6-Cyclopentyl-3-[(5,7-dimethyl[1,2,4]triazolo[1,5-a]pyrimidin-2-yl)methyl]-6-[2-(2-ethoxy-5-ethyl-4-hydroxyphenyl)ethyl]-4-hydroxy-5,6-dihydro-2H-pyran-2-one

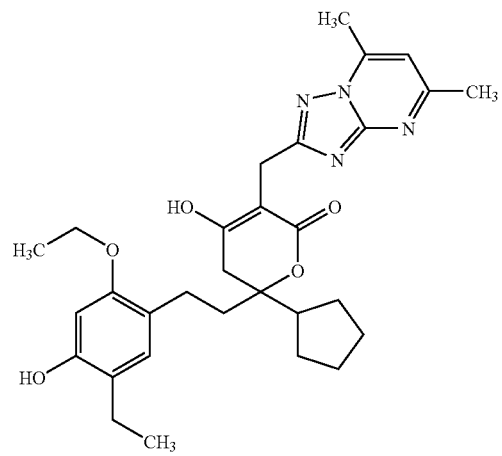

The title compound was prepared analogously to example A(1) where acetic acid 4-bromo-5-ethoxy-2-ethyl-phenyl ester from step 4 below was substituted in place of 1-benzyloxy-2-ethyl-4-iodo-5-propoxy-benzene in step 4 of that example. $^1$H NMR (400 MHz, DMSO-d$_6$) δ: 0.80 (t, J=7.3 Hz, 3H), 1.03 (t, J=6.8 Hz, 3 H), 1.24-1.52 (br m, 8 H), 1.70 (m, 1 H), 1.85 (m, 1 H), 2.12-2.32 (m, 11 H), 2.37 (d, J=17.4 Hz, 1 H), 2.55 (d, J=17.4 Hz, 1 H), 3.51 (d, J=16.2 Hz, 1 H), 3.61 (m, 3 H), 6.13 (s, 1H), 6.51 (s, 1 H), 6.83 (s, 1 H), 8.76 (s, 1 H), 10.61 (s, 1 H). MS (ESI): 536.20 (M+H)$^+$ Step 1: 144-Ethoxy-2-hydroxy-phenyl)-ethanone

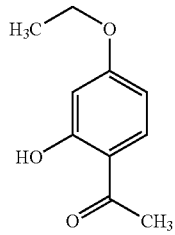

Potassium carbonate (13.6 g, 99 mmol) followed by ethyl iodide (2.4 mL, 29.6 mmol) were added to a solution of 2',4'-dihydroxyacetophenone (5 g, 33 mmol) in DMF (50 mL). The mixture was stirred for 4 hours and then partitioned between H$_2$O and EtOAc. The organic layer was washed with satd NaHCO$_3$, brine, dried over Na$_2$SO$_4$ and concentrated to a clear oil. Purification by column chromatography gave the product as a white solid (3.7 g, 63%). $^1$H NMR (400 MHz, CDCl$_3$): δ 1.43 (t, J=6.8 Hz, 3 H), 2.55 (s, 3 H), 4.07 (d, J=7.1 Hz, 2 H), 6.40 (s, 1 H), 6.43 (d, J=8.8 Hz, 1 H), 7.62 (d, J=8.8 Hz, 1 H), 12.74 (s, 1 H).

Step 2: 5-Ethoxy-2-ethyl-phenol

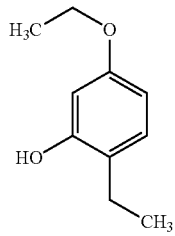

1-(4-Ethoxy-2-hydroxy-phenyl)-ethanone was dissolved in MeOH (40 mL), treated with 10 wt % Pd/C (1.4 g, Degussa type) and stirred under a balloon of H$_2$ for 24 hours. The reaction mixture was filtered through a pad of celite washing with EtOAc. The filtrate was concentrated to give the product as an oil (3.12 g, 97%). $^1$H NMR (400 MHz, CDCl$_3$): δ 1.21 (t, J=7.6 Hz, 3 H), 1.39 (t, J=7.1 Hz, 3 H), 2.56 (d, J=7.6 Hz, 2 H), 3.98 (d, J=7.1 Hz, 2 H), 4.79 (s, 1 H), 6.37 (d, J=2.5 Hz, 1 H), 6.44 (dd, J=8.3, 2.5 Hz, 1 H), 7.01 (d, J=8.3 Hz, 1 H).

Step 3: 4-Bromo-5-ethoxy-2-ethyl-phenol

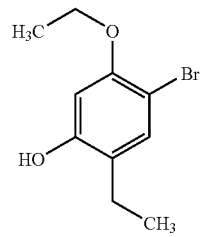

A solution of tetrabutyl ammonium tribromide (9.9 g, 20.5 mmol) in CHCl$_3$ (60 mL) was added to a stirred solution of 5-ethoxy-2-ethyl-phenol (3.1 g, 18.6 mmol) dissolved in CHCl$_3$ (90 mL). The reaction mixture was stirred for 30 mins and then quenched with 5% solution of sodium thiosulfate (30 mL). The biphasic mixture was stirred for 30 mins and then the layers were separated. The organic layer was washed with 1 N HCl, brine, dried over Na$_2$SO$_4$ and concentrated to a red oil. Purification by flash column chromatography (0% to 15% EtOAc in hexanes) gave the product as an oil (2.6 g, 58%). $^1$H NMR (400 MHz, CDCl$_3$): δ 1.20 (t, J=7.6 Hz, 3 H), 1.44 (t, J=7.1 Hz, 3 H), 2.53 (q, J=7.6 Hz, 2H), 4.03 (q, J=7.1 Hz, 2 H), 4.85 (s, 1 H), 6.41 (s, 1 H), 7.25 (s, 1 H).

Step 4: Acetic acid 4-bromo-5-ethoxy-2-ethyl-phenyl ester

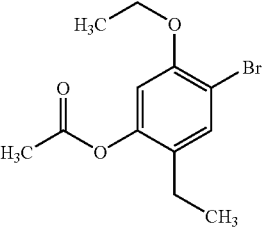

Acetyl chloride (0.91 mL, 12.8 mmol) followed by triethylamine (1.8 mL, 12.8 mmol) were added to a stirred solution of 4-bromo-5-ethoxy-2-ethyl-phenol (2.6 g, 10.7 mmol) dissolved in CH$_2$Cl$_2$ (20 mL). The reaction was stirred for 45 mins and then partitioned between 1N HCl and EtOAc. The organic layer was washed with saturated NaHCO$_3$, brine dried over Na$_2$SO$_4$ and concentrated. Purification by flash column chromatography (0% to 20% EtOAc in hexanes) gave the product as a clear oil (1.64 g, 53%). $^1$H NMR (400 MHz, CDCl$_3$): δ 1.16 (t, J=7.6 Hz, 3 H), 1.45 (t, J=7.1 Hz, 3 H), 2.31 (s, 3 H), 2.45 (q, J=7.6 Hz, 2 H), 4.05 (q, J=7.1 Hz, 2 H), 6.58 (s, 1 H), 7.41 (s, 1 H).

Example A(23)

6-Cyclopentyl-3-[(5,7-dimethyl[1,2,4]triazolo[1,5-a]pyrimidin-2-yl)methyl]-4-hydroxy-6-{2-[4-methoxy-3-(trifluoromethyl)phenyl]ethyl}-5,6-dihydro-2H-pyran-2-one

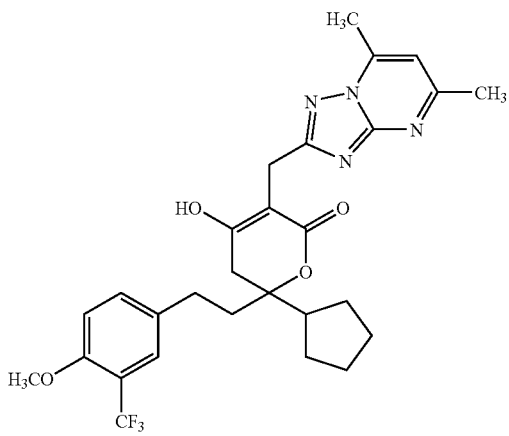

The title compound was prepared analogously to example A(1) where 4-bromo-2-(trifluoromethyl)anisole was substituted in place of 1-benzyloxy-2-ethyl-4-iodo-5-propoxy-benzene in step 4 of that example. $^1$H NMR (400 MHz, DMSO-$d_6$) δ: 1.19-1.51 (br m, 8 H), 1.93 (m, 2 H), 2.21-2.46 (m, 10 H), 2.60 (d, J=17.4 Hz, 1 H), 3.53 (d, J=16.2 Hz, 1 H), 3.64 (d, J=16.2 Hz, 1 H), 3.67 (s, 3 H), 6.87 (s, 1 H), 7.00 (d, J=8.6 Hz, 1 H), 7.22 (d, J=2.0 Hz, 1 H), 7.40 (d, J=17.4 Hz, 1 H), 10.76 (s, 1 H). MS (ESI): 545.10 (M+H)$^+$

Example A(24)

6-Cyclopentyl-3-[(5,7-dimethyl[1,2,4]triazolo[1,5-a]pyrimidin-2-yl)methyl]-6-[2-(5-ethyl-2,4-dimethoxyphenyl)ethyl]-4-hydroxy-5,6-dihydro-2H-pyran-2-one

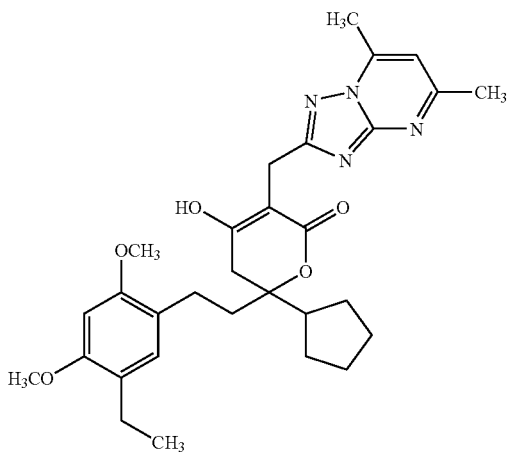

The title compound was prepared analogously to Example A(1) where 1-bromo-5-ethyl-2,4-dimethoxy-benzene from step 1 below was substituted in place of 1-benzyloxy-2-ethyl-4-iodo-5-propoxy-benzene in step 4 of that example. $^1$H NMR (400 MHz, DMSO-$d_6$) δ: 0.82 (d, J=7.6 Hz, 3H), 1.22-1.52 (br m, 8 H), 1.72 (m, 1 H), 1.88 (m, 1 H), 2.20-2.40 (m, 12 H), 2.56 (d, J=17.9 Hz, 1 H), 3.43 (s, 3 H), 3.52 (d, J=18.1 Hz, 1 H), 3.58 (s, 3 H), 3.61 (d, J=18.1 Hz, 1 H), 6.32 (s, 1 H), 6.63 (s, 1 H), 6.84 (s, 1 H), 10.70 (s, 1 H). MS (ESI): 535.20 (M+H)$^+$ Step 1: 1-Bromo-5-ethyl-2,4-dimethoxy-benzene

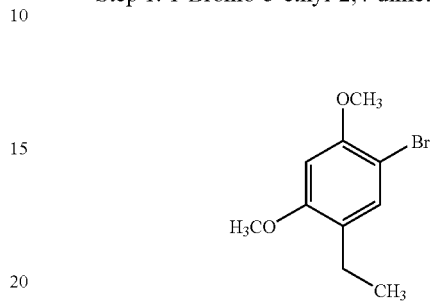

A solution of tetrabutyl ammonium tribromide (15.4 g, 31.8 mmol) in CHCl$_3$ (100 mL) was added to a stirred solution of 4-ethyl resorcinol (4 g, 29 mmol) dissolved in CHCl$_3$ (50 mL). The reaction mixture was stirred for 2 hours and then quenched with 5% solution of sodium thiosulfate (30 mL). The biphasic mixture was stirred for 30 mins and then the layers were separated. The organic layer was washed with 1 N HCl, brine, dried over Na$_2$SO$_4$ and concentrated to yellow oil. The oil was dissolved in DMF (60 mL) and treated with K$_2$CO$_3$ (12.7 g, 92 mmol), followed by methyl iodide (2.9 mL, 46 mmol). The mixture was stirred for 15 hours and then partitioned between H$_2$O and EtOAc. The organic layers were washed with 1 N HCl, brine, dried over Na$_2$SO$_4$ and concentrated to a dark red oil. Purification by flash column chromatography (0% to 10% EtOAc in hexanes) gave the product as a yellow oil (2.8 g, 39%). $^1$H NMR (400 MHz, CDCl$_3$): δ 1.15 (t, J=7.6 Hz, 3 H), 2.54 (q, J=7.6 Hz, 2 H), 3.83 (s, 3 H), 3.89 (s, 3 H), 6.46 (s, 1 H), 7.26 (s, 1 H).

Example A(25)

N-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorobenzyl]acetamide

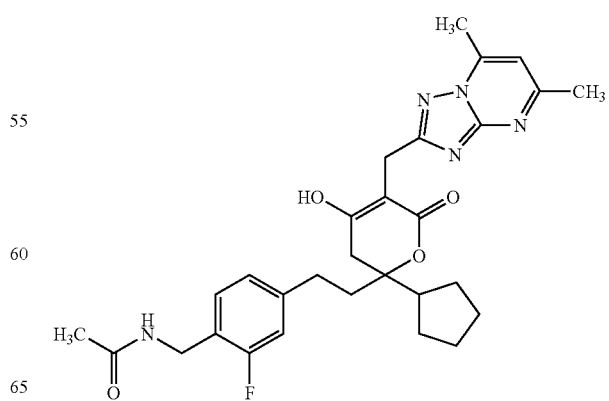

The title compound was prepared analogously to example A(1) where 4-bromo-2-(trifluoromethyl)anisole was substituted in place of 1-benzyloxy-2-ethyl-4-iodo-5-propoxy-benzene in step 4 of that example. $^1$H NMR (400 MHz, DMSO-d$_6$) δ: 1.38-1.69 (br m, 8 H), 1.86 (s, 3 H), 2.12 (m, 2 H), 2.39-2.63 (m, 10 H), 2.77 (d, J=17.2 Hz, 1 H), 3.71 (d, J=16.2 Hz, 1 H), 3.83 (d, J=16.2 Hz, 1 H), 4.23 (d, J=5.8 Hz, 2 H), 7.04 (m, 3 H), 7.21 (t, J=7.8 Hz, 1 H), 8.29 (t, J=5.8 Hz, 1 H), 10.99 (s, 1 H). MS (ESI): 536.20 (M+H)$^+$ Step 1: N-(4-Bromo-2-fluoro-benzyl)-acetamide

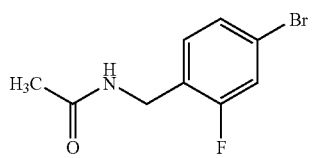

Acetyl chloride (0.7 mL, 9.9 mmol) followed by triethylamine (2.8 mL, 19.9 mmol) were added to a suspension of 4-bromo-2-fluorobenzylamine hydrochloride (2 g, 8.3 mmol) in CH$_2$Cl$_2$ (20 mL). The mixture was stirred for 90 mins and then partitioned between 1 N HCl and EtOAc. The organic layers were brine, dried over Na$_2$SO$_4$ and concentrated. Purification by flash column chromatography (0% to 60% EtOAc in hexanes) gave the product as a clear oil (1.5 g, 74%). MS (ESI): 246.10, 248.10 (M+H)$^+$ Example A(26)

6-Cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one

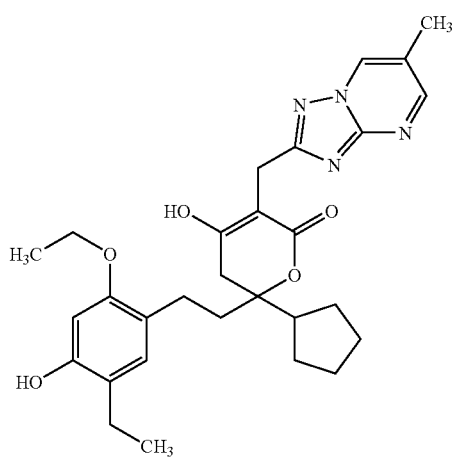

The title compound was prepared analogously to example A(4) where 6-cyclopentyl-6-[2-(2-ethoxy-5-ethyl-4-hydroxy-phenyl)-ethyl]-dihydro-pyran-2,4-dione from step 1 below was substituted in place of 6-cyclopentyl-6-[2-(2-ethyl-5-methoxy-pyridin-4-yl)-ethyl]-dihydro-pyran-2,4-dione. $^1$H NMR (400 MHz, DMSO-d$_6$) δ: 1.08 (t, J=7.3 Hz, 3 H), 1.32 (t, J=6.8 Hz, 3 H), 1.46-1.77 (br m, 8 H), 2.03 (m, 2 H), 2.40 (s, 3 H), 2.44-2.56 (m, 6 H), 2.80 (d, J=17.2 Hz, 1 H), 3.78 (d, J=15.7 Hz, 1 H), 3.83 (d, J=15.7 Hz, 1 H), 3.91 (q, J=7.1 Hz, 2 H), 6.42 (s, 1 H), 6.80 (s, 1 H), 8.73 (s, 1 H), 8.90 (s, 1 H), 9.04 (s, 1 H), 10.98 (s, 1 H). Anal. Calcd. For C$_{29}$H$_{36}$N$_4$O$_5$·0.25H$_2$O: C, 66.33; H, 7.01; N, 10.67. Found: C, 66.57; H, 7.07; N, 10.28.

Step 1: 6-Cyclopentyl-6-[2-(2-ethoxy-S-ethyl-4-hydroxy-phenyl)-ethyl]-dihydro-pyran-2,4-dione

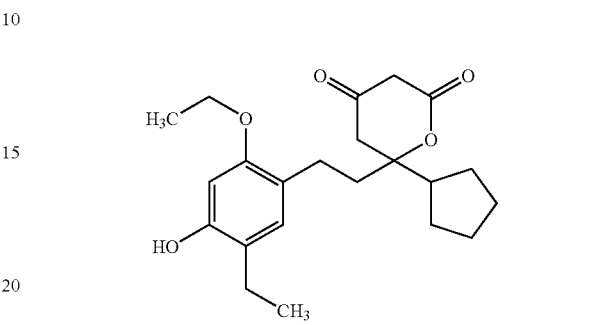

The title compound was prepared analogously to step 5 of example A(1) where acetic acid 4-bromo-5-ethoxy-2-ethyl-phenyl ester from step 4 of example A(22) was substituted in place of 1-benzyloxy-2-ethyl-4-iodo-5-propoxy-benzene in step 4 of example A(1). $^1$H NMR (400 MHz, CDCl$_3$): δ 1.19 (t, J=7.6 Hz, 3 H), 1.38 (t, J=6.8 Hz, 3 H), 1.62-1.85 (br m, 9 H), 1.98 (m, 1 H), 2.33 (m, 1 H), 2.51 (m, 3 H), 2.62 (m, 1 H), 2.73 (d, J=16.2 Hz, 1 H), 2.78 (d, J=16.2 Hz, 1 H), 3.42 (m, 2 H), 3.95 (q, J=7.1 Hz, 2 H), 4.98 (br s, 1 H), 6.33 (s, 1 H), 6.79 (s, 1 H).

Example A(27)

6-Cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one

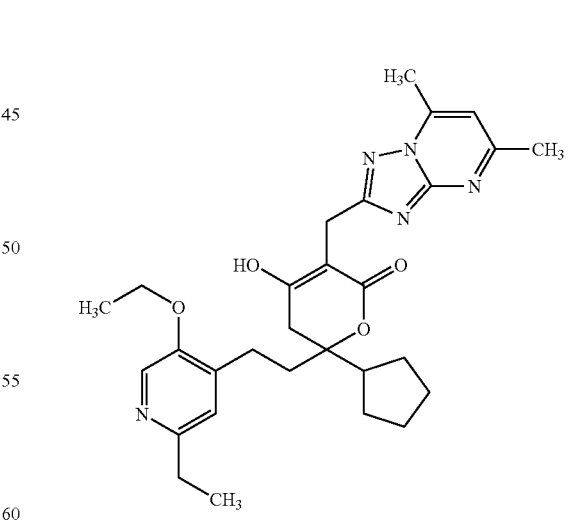

The title compound was prepared analogously to example A(1) where 6-cyclopentyl-6-[2-(5-ethoxy-2-ethyl-pyridin-4-yl)-ethyl]-dihydro-pyran-2,4-dione from step 1 below was substituted in place of 6-cyclopentyl-6-[2-(5-ethyl-4-hydroxy-2-propoxy-phenyl)-ethyl]-dihydro-pyran-2,4-dione. $^1$H NMR (400 MHz, DMSO-d$_6$) δ: 1.19 (t, J=7.6 Hz, 3 H), 1.31 (t, J=6.8 Hz, 3 H), 1.40-1.78 (br m, 8H), 2.03-217 (m, 2 H), 2.48-2.72 (m, 12 H), 2.85 (d, J=17.4 Hz, 1 H), 3.76 (d, J=16.4 Hz, 1 H), 3.87 (d, J=16.2 Hz, 1 H), 4.08 (m, 2 H), 7.09 (m, 2 H), 8.13 (s, 1 H), 10.96 (s, 1 H). MS (ESI): 520.20 (M+H)$^+$ Step 1: 6-Cyclopentyl-6-[2-(S-ethoxy-2-ethyl-pyridin-4-yl)-ethyl]-dihydro-pyran-2,4-dione

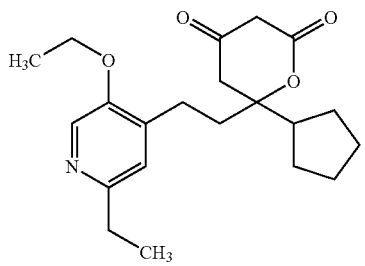

The title compound was prepared analogously to example A(2) where ethyl iodide was substituted in place of methyl iodide in step 1 of that example. $^1$H NMR (400 MHz, CDCl$_3$): δ 1.26 (t, J=7.6 Hz, 3 H), 1.43 (t, J=6.8 Hz, 3 H), 1.50-2.05 (br m, 9 H), 2.34 (m, 2 H), 2.62-2.77 (m, 6 H), 3.44 (m, 2 H), 4.11 (q, J=6.8 Hz, 2 H), 6.90 (s, 1 H), 8.08 (s, 1 H).

Example A(28)

6-Cyclopentyl-3-[(5,7-dimethyl[1,2,4]triazolo[1,5-a]pyrimidin-2-yl)methyl]-4-hydroxy-6-{2-[4-hydroxy-3-(trifluoromethyl)phenyl]ethyl}-5,6-dihydro-2H-pyran-2-one

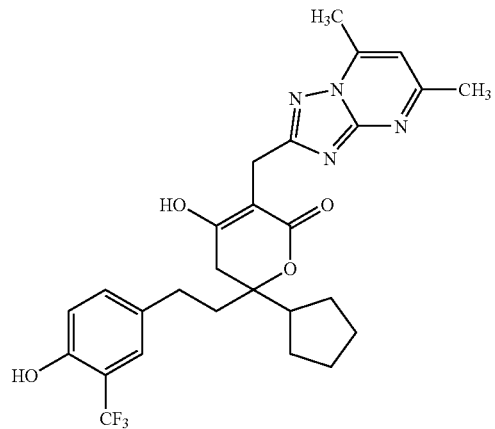

The title compound was prepared analogously to example A(22) where 2-hydroxybenzotrifluoride was substituted in place of 5-ethoxy-2-ethyl-phenol in step 3 of that example. $^1$H NMR (400 MHz, DMSO-d$_6$) δ: 1.39-1.71 (br m, 8 H), 2.09 (m, 2 H), 2.39-2.60 (m, 10 H), 2.77 (d, J=17.7 Hz, 1 H), 3.71 (d, J=16.2 Hz, 1 H), 3.83 (d, J=16.2 Hz, 1 H), 6.96 (d, J=8.6 Hz, 1 H), 7.06 (s, 1 H), 7.29 (s, 1 H), 7.38 (d, J=9.8 Hz, 1 H), 10.29 (s, 1 H), 10.95 (s, 1 H). Anal. Calcd. For C$_{27}$H$_{29}$N$_4$O$_4$F$_3$.1.0 AcOH: C, 58.87; H, 5.63; N, 9.49. Found: C, 59.13; H, 5.89; N, 9.44.

Example A(29)

N-{1-[4-(2-{2-cyclopentyl-5-[(5,7-dimethyl[1,2,4]triazolo[1,5-a]pyrimidin-2-yl)methyl-4-hydroxy-6-oxo-3,6-dihydro-2H-pyran-2-yl}ethyl)-2-fluorophenyl]-methylethyl}methanesulfonamide

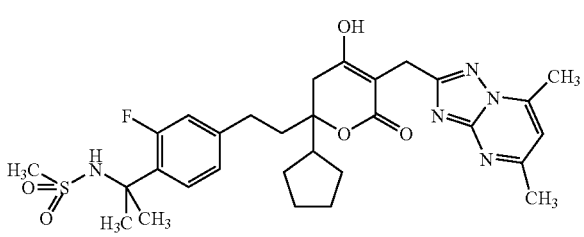

The title compound was prepared analogously to example A(1) where N-[1-(4-bromo-2-fluoro-phenyl)-1-methylethyl]-methanesulfonamide from step 2 below was substituted in place of 1-benzyloxy-2-ethyl-4-iodo-5-propoxybenzene in that example. $^1$H NMR (300 MHz, CDCl$_3$): δ ppm 1.31-1.41 (m, 1 H) 1.54 (s, 3 H) 1.55-1.70 (m, 5 H) 1.73 (s, 6 H) 1.98 (dd, J=9.98, 7.16 Hz, 2 H) 2.29-2.39 (m, 1 H) 2.55-2.69 (m, 9 H) 2.73-2.81 (m, 4 H) 4.05 (s, 2 H) 5.03 (s, 1 H) 6.84 (t, J=6.69 Hz, 2 H) 6.90 (d, J=8.10 Hz, 1 H) 7.25 (d, J=16.77 Hz, 1 H). MS (ESI): 600 (M+H)$^+$ Step 1:
1-(4-Bromo-2-fluoro-phenyl)-1-methyl-ethylamine

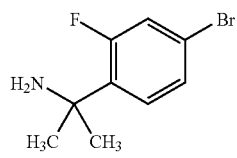

CeCl$_3$·7H$_2$O (29.7 g, 80 mmol) was dehydrated for 2 h under vacuum at 150° C. After cooling to 0° C., THF (anhydrous, 640 mL) was added at, and the suspension was stirred for 2 h at room temperature. The suspension was cooled to −78° C. and MeLi (1.6M in diethylether, 50 mL) was added. The mixture was stirred 30 min, then 4-bromo-2-fluorobenzonitrile (4 g, 20 mmol) was added and stirred at that temperature for 5 h. The temperature was raised to 0° C., concentrated NH$_4$OH (50 mL) was added slowly, and the suspension was filtered though Celite. The aqueous layer was acidified with 1N HCl (aq) and washed with ethyl acetate. The aqueous layer was basified with 3N NaOH (aq) and extracted with dichloromethane. The synthesis and workup were repeated and lots were combined, dried (Na$_2$SO$_4$), filtered, and concentrated in vacuo to give a colorless oil (1.25 g, 14%). $^1$H NMR (300 MHz, CDCl$_3$): δ ppm 1.51 (s, 6 H) 1.66 (s, 2 H) 7.17-7.24 (m, 2 H) 7.30-7.37 (m, 1 H).

Step 2: N-[1-(4-Bromo-2-fluoro-phenyl)-1-methyl-ethyl]-methanesulfonamide

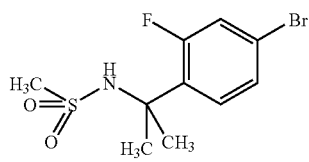

To 1-(4-bromo-2-fluoro-phenyl)-1-methyl-ethylamine (1.2 g, 5.4 mmol) and triethylamine (900 μL, 6.5 mmol) in dichloromethane (10 mL) at room temperature was added methanesulfonyl chloride (500 μL, 6.5 mmol). The solution was stirred 16 h, diluted in 1N HCl(aq) and extracted with ethyl acetate. The organic layer was washed with saturated sodium bicarbonate, then saturated sodium chloride, dried (Na$_2$SO$_4$), filtered, and concentrated in vacuo to an off-white solid. Flash chromatography (SiO$_2$, 40% ethyl acetate/hexane) gave a white solid (950 mg, 57%). $^1$H NMR (300 MHz, CDCl$_3$): δ ppm 1.76 (s, 6 H) 2.74 (s, 3 H) 4.88 (s, 1 H) 7.24 (d, J=1.51 Hz, 1 H) 7.27-7.30 (m, 2 H)

Example A(30)

Enantiomer 1 of 6-Cyclopentyl-3-[(5,7-dimethyl[1,2,4]triazolo[1,5-a]pyrimidin-2-yl)methyl]-6-[2-(2-ethoxy-5-ethyl-4-hydroxyphenyl)ethyl]-4-hydroxy-5,6-dihydro-2H-pyran-2-one

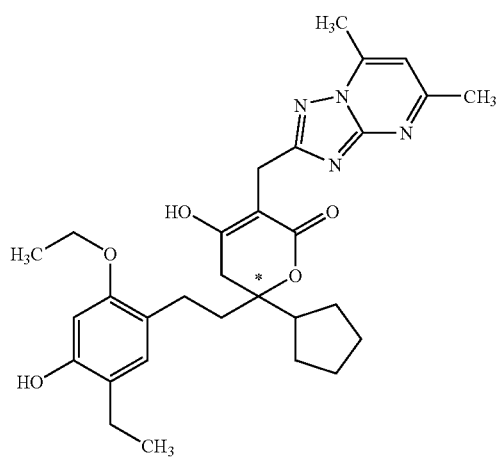

Enantiomer 1

The title compound was separated from racemic 6-cyclopentyl-3-[(5,7-dimethyl[1,2,4]triazolo[1,5-a]pyrimidin-2-yl)methyl]-6-[2-(2-ethoxy-5-ethyl-4-hydroxyphenyl)ethyl]-4-hydroxy-5,6-dihydro-2H-pyran-2-one (120 mg, Example A(22)) using chiral HPLC (Chiralpak AS-H, 115 bar, 55% MeOH). (47 mg, 1.89 min retention time, 100% ee)

Example A(31)

Enantiomer 2 of 6-Cyclopentyl-3-[(5,7-dimethyl[1,2,4]triazolo[1,5-a]pyrimidin-2-yl)methyl]-6-[2-(2-ethoxy-S-ethyl-4-hydroxyphenyl)ethyl]-4-hydroxy-6,6-dihydro-2H-pyran-2-one

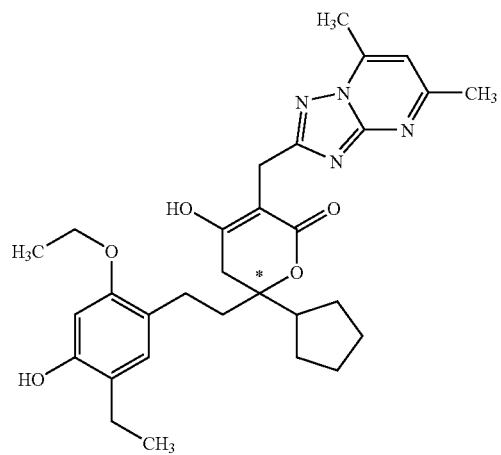

Enantiomer 2

The title compound was separated from racemic 6-cyclopentyl-3-[(5,7-dimethyl[1,2,4]triazolo[1,5-a]pyrimidin-2-yl)methyl]-6-[2-(2-ethoxy-5-ethyl-4-hydroxyphenyl)ethyl]-4-hydroxy-5,6-dihydro-2H-pyran-2-one (120 mg, Example A(22)) using chiral HPLC (Chiralpak AS-H, 115 bar, 55% MeOH). (43 mg, 3.429 min retention time, 99% ee)

Example A(32)

6-Cyclopentyl-6-{2-[2-(cyclopropylmethoxy)-5-ethyl-4-hydroxyphenyl]ethyl}-3-[(5,7-dimethyl[1,2,4]triazolo[1,5-a]pyrimidin-2-yl)methyl]-4-hydroxy-5,6-dihydro-2H-pyran-2-one

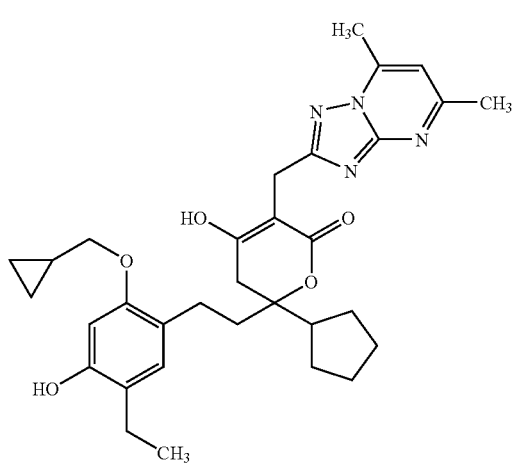

The title compound was prepared analogously to example A(22) where (bromomethyl)-cyclopropane was substituted in place of ethyl iodide in step 1 of that example. $^1$H NMR (400 MHz, DMSO-d$_6$) δ: 0.02 (d, J=4.8 Hz, 2 H), 0.28 (d, J=8.6 Hz, 2 H), 0.75 (t, J=7.6 Hz, 3 H), 0.80 (m, 1 H), 1.18-1.51 (br m, 8 H), 1.72 (m, 1 H), 1.82 (m, 1 H), 2.09-2.52 (m, 13 H), 3.41 (d, J=6.8 Hz, 2 H), 3.47 (d, J=15.9 Hz, 1 H), 3.55 (d, J=15.9 Hz, 1 H), 6.08 (s, 1 H), 6.47 (s, 1 H), 6.79 (s, 1 H), 8.70 (s, 1 H), 10.56 (s, 1 H). MS (ESI): 561.25 (M+H)$^+$

Example A(33)

6-Cyclopentyl-3-[(5,7-dimethyl[1,2,4]triazolo[1,5-a]pyrimidin-2-yl)methyl]-4-hydroxy-6-[2-(2-isopropylpyridin-4-yl)ethyl]-5,6-dihydro-2H-pyran-2-one

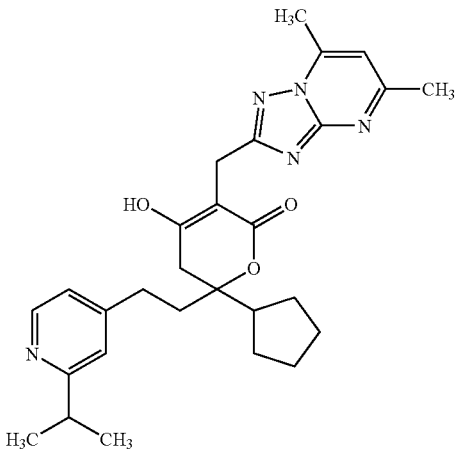

The title compound was prepared analogously to example A(10) where 2-isopropylpyridine was substituted in place of 2,6-bis-(2,2,2-trifluoro-ethyl)-pyridine in step 2 of that example. $^1$H NMR (400 MHz, DMSO-d$_6$) δ: 1.10 (d, J=6.8 Hz, 6 H), 1.28-1.59 (br m, 8 H), 2.03 (m, 2 H), 2.31-2.54 (m, 10 H), 2.67 (d, J=17.4 Hz, 1 H), 2.67 (m, 1 H), 3.60 (d, J=16.2 Hz, 1 H), 3.73 (d, J=16.2 Hz, 1 H), 6.95 (s, 1 H), 7.01 (s, 2 H), 8.25 (d, J=5.8 Hz, 1 H), 10.85 (s, 1 H). Anal. Calcd. For C$_{28}$H$_{35}$N$_5$O$_3$.0.7EtOAc: C, 67.10; H, 7.42; N, 12.70. Found: C, 67.24; H, 7.61; N, 12.68.

Example A(34)

6-Cyclopentyl-3-[(5,7-dimethyl[1,2,4]triazolo[1,5-a]pyrimidin-2-yl)methyl]-6-[2-(2-ethyl-6-isopropylpyridin-4-yl)ethyl]-4-hydroxy-5,6-dihydro-2H-pyran-2-one

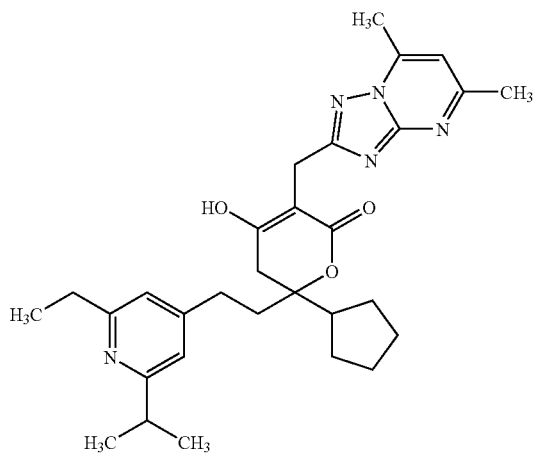

The title compound was prepared analogously to example A(9) where 2-ethyl-6-isopropylpyridine was substituted in place of 2,6-bis-(2,2,2-trifluoro-ethyl)-pyridine in step 2 of that example. $^1$H NMR (400 MHz, DMSO-d$_6$) δ: 1.03 (m, 9 H), 1.24-1.55 (br m, 8 H), 2.00 (m, 2 H), 2.28-2.55 (m, 12 H), 2.63 (d, J=17.4 Hz, 1 H), 2.79 (m, 1 H), 3.57 (d, J=16.2 Hz, 1 H), 3.69 (d, J=16.2 Hz, 1 H), 6.77 (s, 2 H), 6.91 (s, 1 H), 10.79 (s, 1 H). Anal. Calcd. For C$_{30}$H$_{39}$N$_5$O$_3$.0.5AcOH: C, 67.98; H, 7.55; N, 12.79. Found: C, 68.01; H, 7.74; N, 12.77.

Example A(35)

6-Cyclopentyl-3-[(5,7-dimethyl[1,2,4]triazolo[1,5-a]pyrimidin-2-yl)methyl]-6-[2-(2-ethyl-6-methylpyridin-4-yl)ethyl]-4-hydroxy-5,6-dihydro-2H-pyran-2-one

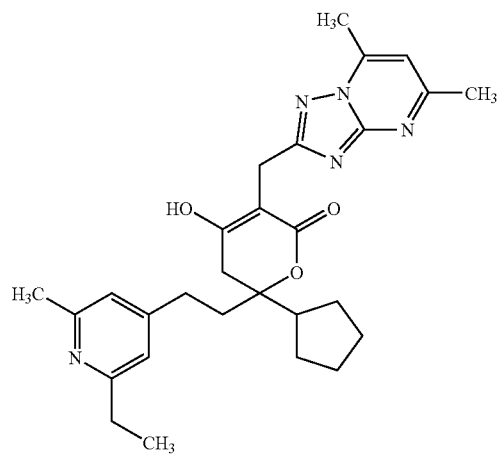

The title compound was prepared analogously to example A(9) where 2-ethyl-6-methylpyridine was substituted in place of 2,6-bis-(2,2,2-trifluoro-ethyl)-pyridine in step 2 of that example. $^1$H NMR (400 MHz, DMSO-d$_6$) δ: 0.93 (d, J=7.3 Hz, 3 H), 1.18-1.47 (br m, 8 H), 1.90 (m, 2H), 2.15 (s, 3 H), 2.23-2.46 (m, 12 H), 2.56 (d, J=16.9 Hz, 1 H), 3.48 (d, J=16.4 Hz, 1 H), 3.61 (d, J=16.2 Hz, 1 H), 6.68 (s, 1 H), 6.69 (s, 1 H), 6.83 (s, 1 H), 10.67 (s, 1 H). MS (ESI): 490.20 (M+H)$^+$

Example A(36)

6-Cyclopentyl-6-[2-(2,6-diethylpyridin-4-yl)ethyl]-4-hydroxy-3-[(6-methyl[1,2,4]triazolo[1,5-a]pyrimidin-2-yl)methyl]-5,6-dihydro-2H-pyran-2-one

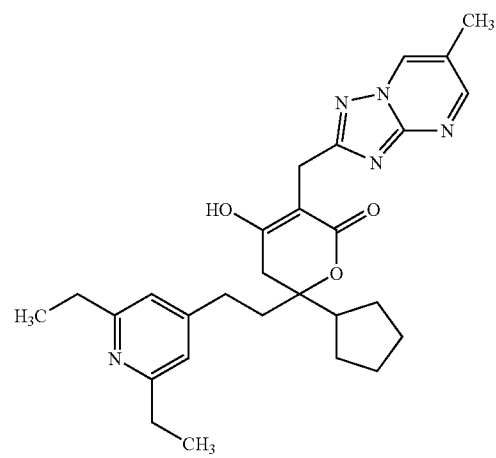

The title compound was prepared analogously to example A(4) where 6-cyclopentyl-6-[2-(2-ethoxy-5-ethyl-4-hydroxy-phenyl)-ethyl]-dihydro-pyran-2,4-dione from step 1 below was substituted in place of 6-cyclopentyl-6-[2-(2-ethyl-5-methoxy-pyridin-4-yl)-ethyl]-dihydro-pyran-2,4-dione. $^1$H NMR (400 MHz, DMSO-$d_6$) δ: 0.93 (d, J=7.3 Hz, 6 H), 1.11-1.46 (br m, 8 H), 1.87 (m, 2 H), 2.11 (s, 3 H), 2.21-2.33 (m, 4 H), 2.41 (d, J=7.6 Hz, 4 H), 2.55 (d, J=17.7 Hz, 1 H), 3.48 (d, J=16.2 Hz, 1 H), 3.58 (d, J=16.2 Hz, 1 H), 6.68 (s, 2 H), 8.44 (s, 1 H), 8.61 (s, 1 H), 10.67 (s, 1 H). Anal. Calcd. For $C_{28}H_{35}N_5O_3 \cdot 0.5$AcOH: C, 67.03; H, 7.18; N, 13.48. Found: C, 67.09; H, 7.25; N, 13.41.

Step 1: 6-Cyclopentyl-6-[2-(2,6-diethyl-pyridin-4-yl)-ethyl]-dihydro-pyran-2,4-dione

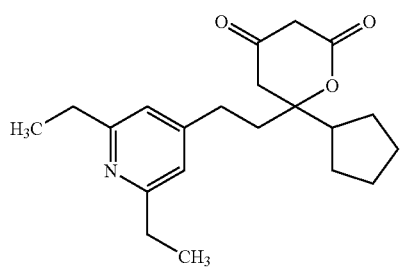

The title compound was prepared analogously to example A(2) where 2,6-diethyl-pyridine from step 1 of example A(17) was substituted in place 4-bromo-2-ethyl-5-methoxy-pyridine in step 6 of example A(2). $^1$H NMR (400 MHz, CDCl$_3$): δ 1.28 (t, J=7.6 Hz, 6 H), 1.45-1.78 (br m, 10 H), 1.96 (m, 1 H), 2.28 (m, 2 H), 2.65 (m, 2 H), 2.79 (q, J=7.6 Hz, 4 H), 3.45 (m, 2 H), 6.81 (s, 2 H).

Example A(37)

6-Cyclopentyl-3-[(5,7-dimethyl[1,2,4]triazolo[1,5-a]pyrimidin-2-yl)methyl]-6-[2-(5-ethyl-4-hydroxy-2-isopropoxyphenyl)ethyl]-4-hydroxy-5,6-dihydro-2H-pyran-2-one

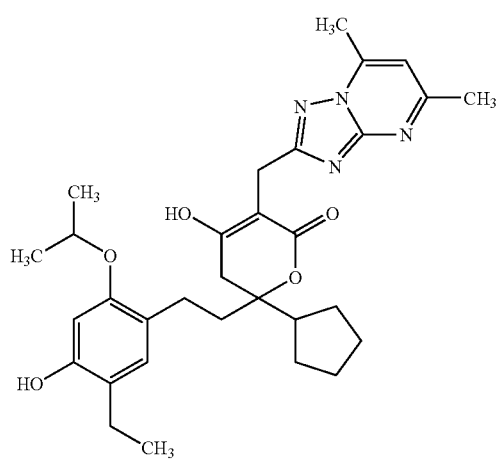

The title compound was prepared analogously to example A(22) where 2-iodopropane was substituted in place of ethyl iodide in step 1 of that example. $^1$H NMR (400 MHz, DMSO-$d_6$) δ: 1.06 (t, J=7.3 Hz, 3 H), 1.23 (t, J=6.1 Hz, 3 H), 1.28 (t, J=6.1 Hz, 3 H), 1.46-1.95 (br m, 8 H), 1.95 (m, 1 H), 2.11 (m, 1 H), 2.39-2.64 (m, 12 H), 2.80 (d, J=17.4 Hz, 1 H), 3.76 (d, J=15.9 Hz, 1 H), 3.85 (d, J=15.9 Hz, 1 H), 4.40 (m, 1 H), 6.44 (s, 1 H), 6.77 (s, 1 H), 7.09 (s, 1 H), 8.99 (s, 1 H), 10.95 (s, 1 H). Anal. Calcd. For $C_{31}H_{40}N_4O_5 \cdot 0.3$EtOAc: C, 67.25; H, 7.43; N, 9.74. Found: C, 67.00; H, 7.44; N, 9.72.

Example A(38)

Enantiomer 1 of 6-Cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one

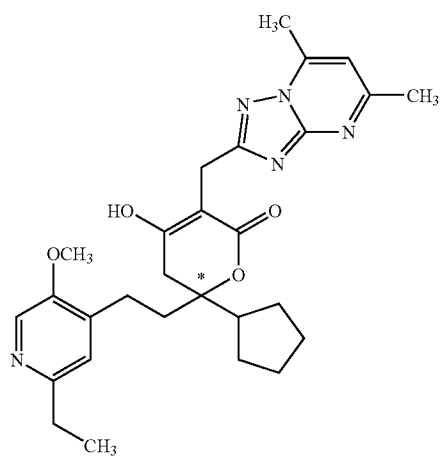

Enantiomer 1

The title compound was separated from racemic 6-cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one (75 mg, Example A(3)) using chiral HPLC (Chiralpak AD-H, 140 bar, 35% MeOH). (21 mg, 3.758 min retention time, 100% ee)

Example A(39)

Enantiomer 2 6-Cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one

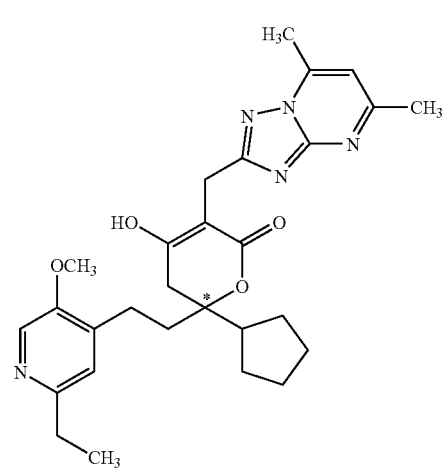

Enantiomer 2

The title compound was separated from racemic 6-cyclopentyl-3-[(5,7-dimethyl[1,2,4]triazolo[1,5-a]pyrimidin-2-yl)methyl]-6-[2-(2-ethyl-5-methoxypyridin-4-yl)ethyl]-4-hydroxy-5,6-dihydro-2H-pyran-2-one (75 mg, Example A(3)) using chiral HPLC (Chiralpak AD-H, 140 bar, 35% MeOH). (21 mg, 6.142 min retention time, 100% ee)

Example A(40)

Enantiomer 1 of 6-Cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one Enantiomer 1

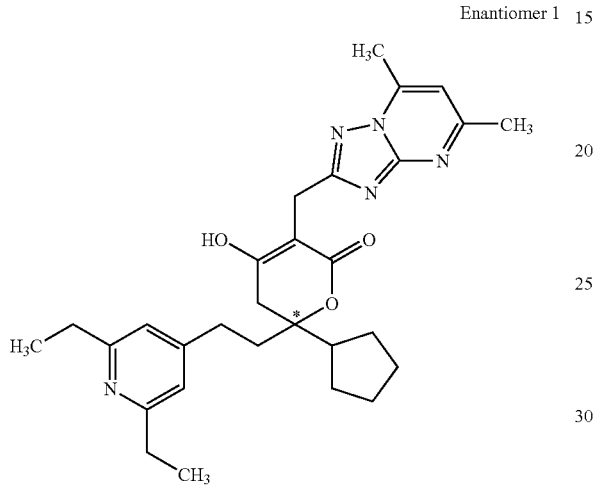

The title compound was separated from racemic 6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one (60 mg, Example A(17)) using chiral HPLC (Chiralpak AD-H, 140 bar, 35% MeOH). (12 mg, 3.23 min retention time, 100% ee)

Example A(41)

Enantiomer 2 of 6-Cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one Enantiomer 2

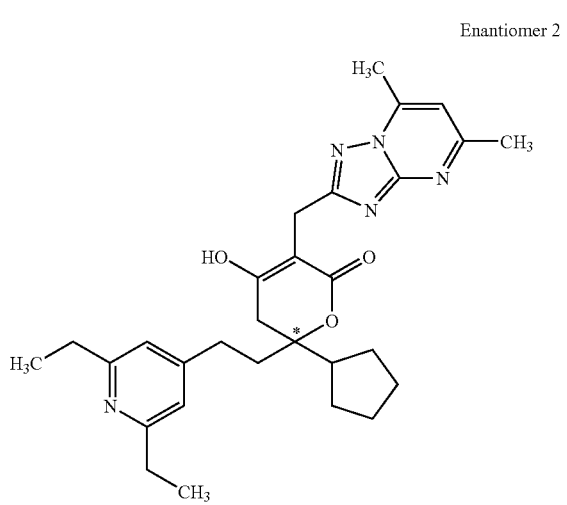

The title compound was separated from racemic 6-cyclopentyl-6-[2-(2,6-diethylpyridin-4-yl)ethyl]-3-[(5,7-dimethyl[1,2,4]triazolo[1,5-a]pyrimidin-2-yl)methyl]-4-hydroxy-5,6-dihydro-2H-pyran-2-one (60 mg, Example A(17)) using chiral HPLC (Chiralpak AD-H, 140 bar, 35% MeOH). (9 mg, 6.46 min retention time, 100% ee)

Example A(42)

6-Cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one

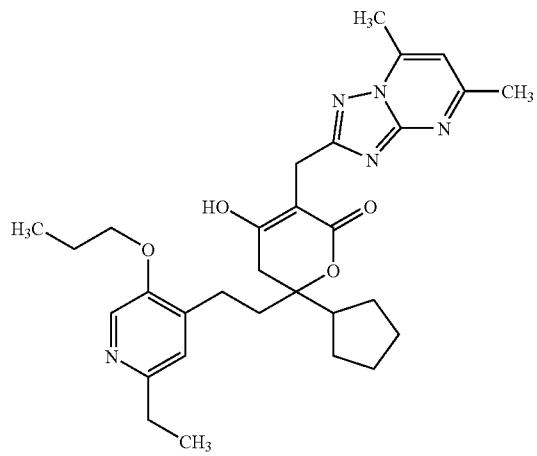

The title compound was prepared analogously to example A(1) where 6-cyclopentyl-6-[2-(2-ethyl-5-propoxy-pyridin-4-yl)-ethyl]-dihydro-pyran-2,4-dione from step 1 below was substituted in place of 6-cyclopentyl-6-[2-(5-ethyl-4-hydroxy-2-propoxy-phenyl)-ethyl]-dihydro-pyran-2,4-dione.

$^1$H NMR (400 MHz, DMSO-d$_6$) δ: 1.06 (t, J=7.3 Hz, 3 H), 1.26 (t, J=7.6 Hz, 3 H), 1.51-1.87 (br m, 10H), 2.25 (m, 2 H), 2.52-2.91 (m, 13 H), 3.84 (d, J=16.2 Hz, 1 H), 3.94 (d, J=16.2 Hz, 1 H), 4.06 (t, J=6.3 Hz, 2 H), 7.17 (s, 1 H), 8.21 (s, 1 H), 10.96 (s, 1 H), 12.02 (s, 1 H). Anal. Calcd. For $C_{30}H_{39}N_5O_4 \cdot 0.8H_2O$: C, 65.74; H, 7.47; N, 12.78. Found: C, 65.68; H, 7.27; N, 12.80.

Step 1: 6-Cyclopentyl-6-[2-(2-ethyl-5-propoxy-pyridin-4-yl)-ethyl]-dihydro-pyran-2,4-dione

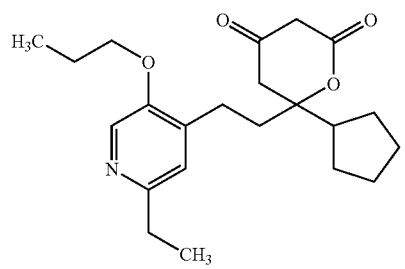

135

The title compound was prepared analogously to example A(2) where 1-iodopropane was substituted in place of methyl iodide in step 1 of that example.

$^1$H NMR (400 MHz, CDCl$_3$): δ 1.05 (t, J=7.3 Hz, 3 H), 1.26 (t, J=7.6 Hz, 3 H), 1.45-1.99 (br m, 12 H), 2.33 (m, 1 H), 2.62-2.76 (m, 6 H), 3.43 (s, 2 H), 3.99 (t, J=6.6 Hz, 2 H), 6.90 (s, 1 H), 8.06 (s, 1 H). Anal. Calcd. For C$_{22}$H$_{31}$NO$_4$.0.2H$_2$O: C, 70.07; H, 8.39; N, 3.71. Found: C, 70.10; H, 8.36; N, 3.34.

Example A(43)

6-Cyclopentyl-6-[2-(5-ethoxy-2-ethylpyridin-4-yl) ethyl]-4-hydroxy-3-[(6-methyl[1,2,4]triazolo[1,5-a] pyrimidin-2-yl)methyl]-5,6-dihydro-2H-pyran-2-one

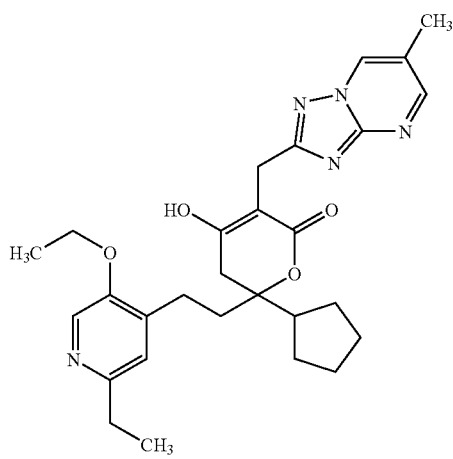

The title compound was prepared analogously to example A(4) where 6-cyclopentyl-6-[2-(5-ethoxy-2-ethyl-pyridin-4-yl)-ethyl]-dihydro-pyran-2,4-dione from step 1 of example A(27) was substituted in place of 6-cyclopentyl-6-[2-(2-ethyl-5-methoxy-pyridin-4-yl)-ethyl]-dihydro-pyran-2,4-dione. $^1$H NMR (400 MHz, DMSO-d$_6$) δ: 1.21 (t, J=7.3 Hz, 3 H), 1.34 (t, J=7.6 Hz, 3 H), 1.42-1.79 (br m, 8H), 2.09 (m, 2 H), 2.41-2.85 (m, 10 H), 3.78 (d, J=16.2 Hz, 1 H), 3.85 (d, J=16.2 Hz, 1 H), 4.11 (q, J=7.6 Hz, 2 H), 7.12 (s, 1 H), 8.15 (s, 1 H), 8.74 (s, 1 H), 8.96 (s, 1 H), 10.94 (s, 1 H). MS (ESI): 506.20 (M+H)$^+$

136

Example A(44)

Enantiomer 1 of 6-Cyclopentyl-3-[(5,7-dimethyl[1,2, 4]triazolo[1,5-a]pyrimidin-2-yl)methyl]-6-[2-(2-ethylpyridin-4-yl)ethyl]-4-hydroxy-5,6-dihydro-2H-pyran-2-one

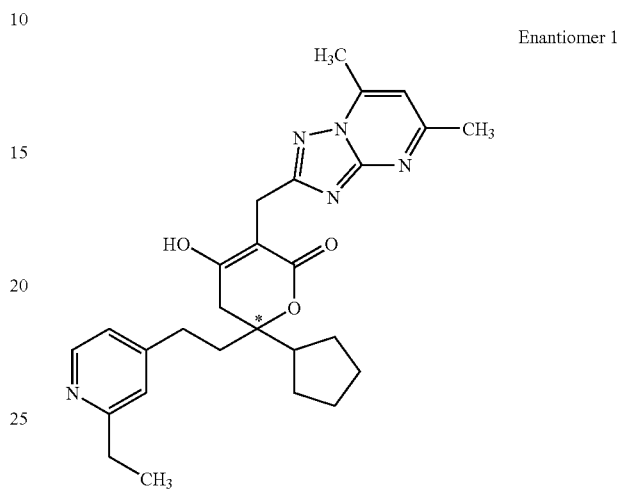

The title compound was separated from racemic 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one (60 mg, from step 1 below) using chiral HPLC (Chiralpak AS-H, 100 bar, 60% MeOH). (28 mg, 1.48 min retention time, 100% ee)

Step 1: 6-Cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one

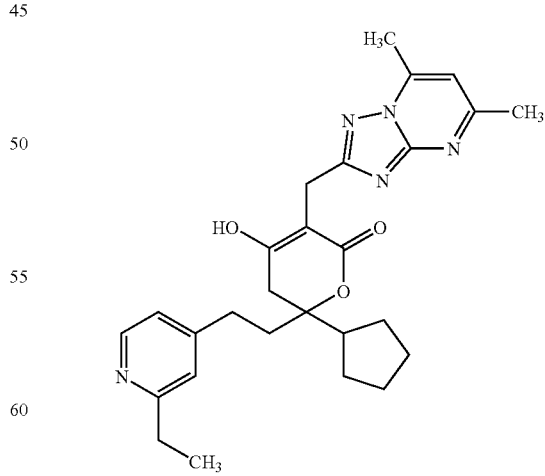

The title compound was prepared analogously to example A(9) where 2-ethylpyridine was substituted in place of 2,6-bis-(2,2,2-trifluoro-ethyl)-pyridine in step 2 of that example.

$^1$H NMR (400 MHz, DMSO-d$_6$) δ: 1.24 (t, J=7.6 Hz, 3 H), 1.44-1.75 (br m, 8 H), 2.2 (m, 2 H), 2.50-2.86 (m, 13 H), 3.76 (d, J=16.0 Hz, 1 H), 3.89 (d, J=16.0 Hz, 1 H), 7.11 (s, 1 H), 7.18 (s, 2 H), 8.39 (s, 1 H), 11.12 (s, 1 H). MS (ESI): 476.25 (M+H$^+$)

Example A(45)

Enantiomer 2 of 6-Cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one

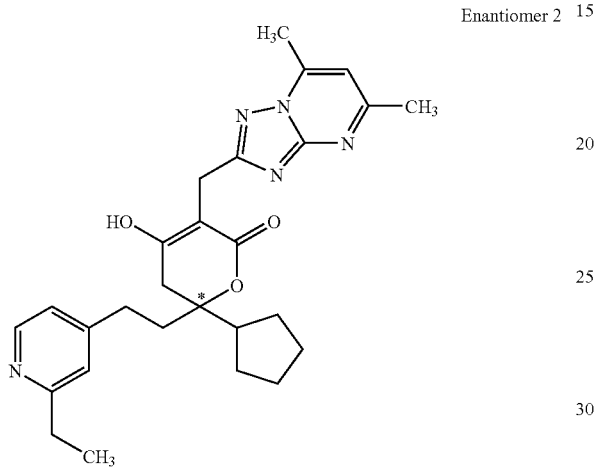

Enantiomer 2

The title compound was separated from racemic 6-Cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one (60 mg, from step 1 of example A(44)) using chiral HPLC (Chiralpak AS-H, 100 bar, 60% MeOH). (21 mg, 1.83 min retention time, 98.4% ee)

Example A(46)

6-Cyclopentyl-6-[2-(2-ethyl-5-propoxypyridin-4-yl)ethyl]-4-hydroxy-3-[(6-methyl[1,2,4]triazolo[1,5-a]pyrimidin-2-yl)methyl]-5,6-dihydro-2H-pyran-2-one

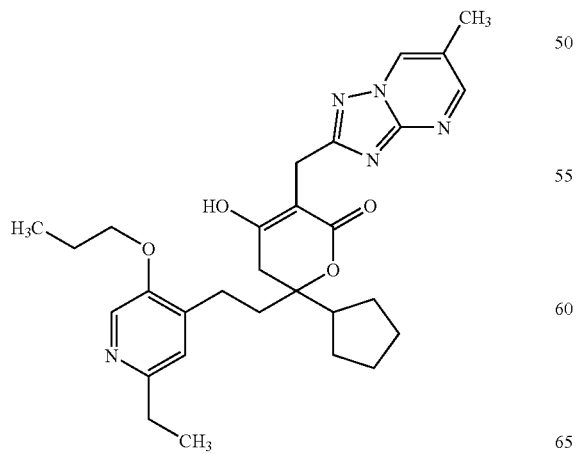

The title compound was prepared analogously to example A(4) where 6-cyclopentyl-6-[2-(2-ethyl-5-propoxy-pyridin-4-yl)-ethyl]-dihydro-pyran-2,4-dione from step 1 of example A(42) was substituted in place of 6-cyclopentyl-6-[2-(2-ethyl-5-methoxypyridin-4-yl)ethyl]dihydro-2H-pyran-2,4(3 H)-dione.

$^1$H NMR (400 MHz, DMSO-d$_6$) δ: 1.20 (t, J=7.3 Hz, 3 H), 1.40 (t, J=7.3 Hz, 3 H), 1.61-1.96 (br m, 10H), 2.29 (m, 2 H), 2.59 (s, 3 H), 2.60-2.90 (m, 6 H), 3.02 (d, J=17.4 Hz, 1 H), 3.97 (d, J=15.9 Hz, 1H), 4.04 (d, J=15.9 Hz, 1 H), 4.20 (d, J=6.3 Hz, 2 H), 7.30 (s, 1 H), 8.34 (s, 1 H), 8.93 (s, 1 H), 9.14 (s, 1 H), 11.16 (s, 1 H). MS (ESI): 520.20 (M+H)$^+$

Example A(47)

6-Cyclopentyl-6-[2-(5-ethyl-4-hydroxy-2-propoxyphenyl)ethyl]-4-hydroxy-3-[(6-methyl[1,2,4]triazolo[1,5-a]pyrimidin-2-yl)methyl]-5,6-dihydro-2H-pyran-2-one

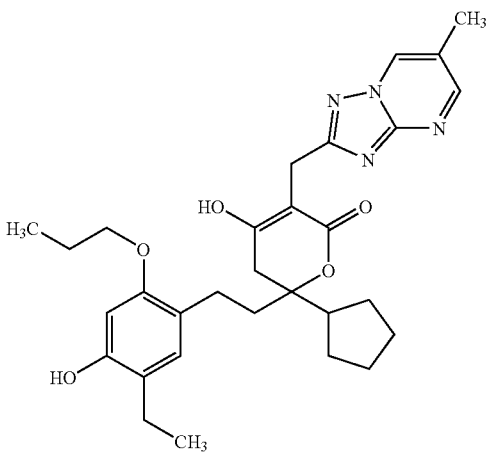

The title compound was prepared analogously to example A(4) where 6-cyclopentyl-6-[2-(5-ethyl-4-hydroxy-2-propoxy-phenyl)-ethyl]-dihydro-pyran-2,4-dione from step 5 of example A(1) below was substituted in place of 6-cyclopentyl-6-[2-(2-ethyl-5-methoxypyridin-4-yl)ethyl]dihydro-2H-pyran-2,4(3 H)-dione. $^1$H NMR (400 MHz, DMSO-d$_6$): δ 0.85 (t, J=7.3 Hz, 3 H), 0.92 (t, J=7.6 Hz, 3 H), 1.27-1.60 (m, 10 H), 1.88 (m, 2 H), 2.25-2.44 (m, 9 H), 2.64 (d, J=17.7 Hz, 1 H), 3.66 (m, 4 H), 6.27 (s, 1H), 6.64 (s, 1 H), 8.58 (s, 1 H), 8.74 (s, 1 H), 8.89 (s, 1 H), 10.82 (s, 1 H). Anal. Calcd. For C$_{30}$H$_{38}$N$_4$O$_5$·0.3H$_2$O: C, 66.72; H, 7.20; N, 10.37. Found: C, 66.55; H, 7.14; N, 10.39.

Example A(48)

6-{2-[2,6-Bis(2,2,2-trifluoroethyl)pyridin-4-yl]ethyl}-6-cyclopentyl-4-hydroxy-3-[(6-methyl[1,2,4]triazolo[1,5-a]pyrimidin-2-yl)methyl]-5,6-dihydro-2H-pyran-2-one

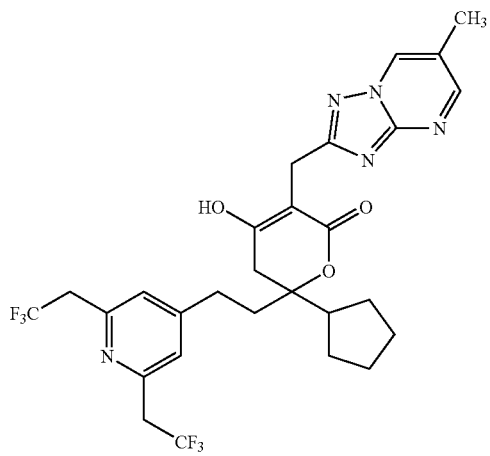

The title compound was prepared analogously to example A(4) where 6-cyclopentyl-6-[2-(5-ethyl-4-hydroxy-2-propoxy-phenyl)-ethyl]-dihydro-pyran-2,4-dione from step 1 below was substituted in place of 6-cyclopentyl-6-[2-(2-ethyl-5-methoxypyridin-4-yl)ethyl]dihydro-2H-pyran-2,4(3H)-dione. $^1$H NMR (400 MHz, DMSO-$d_6$) δ: 1.21-1.56 (br m, 8 H), 1.93 (m, 1 H), 2.08 (m, 1 H), 2.21 (s, 3 H), 2.24-2.58 (m, 4 H), 2.67 (d, J=14.6 Hz, 1 H), 3.56-3.72 (m, 6 H), 7.26 (s, 2 H), 8.53 (s, 1 H), 8.81 (s, 1 H), 10.83 (s, 1 H). MS (ESI): 598.10 (M+H)$^+$ Step 1: 6-{2-[2,6-Bis-(2,2,2-trifluoro-ethyl)-pyridin-4-yl]-ethyl}-6-cyclopentyl-dihydro-pyran-2,4-dione

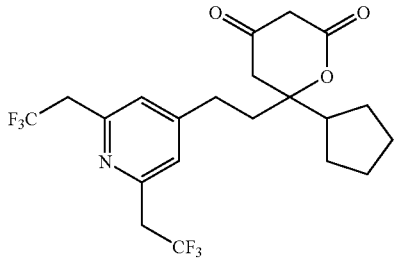

The title compound was prepared analogously to example A(2) where 4-bromo-2,6-bis-(2,2,2-trifluoro-ethyl)-pyridine from step 5 of example A(9) was substituted in place of 4-bromo-2-ethyl-5-methoxy-pyridine in step 6 of that example. $^1$H NMR (400 MHz, CDCl$_3$): δ 1.41-1.75 (br m, 8 H), 1.96 (m, 2 H), 2.28 (m, 1 H), 2.70 (m, 4 H), 3.44-3.61 (m, 6 H), 7.10 (s, 2 H).

Example A(49)

6-Cyclopentyl-3-[(5,7-dimethyl[1,2,4]triazolo[1,5-a]pyrimidin-2-yl)methyl]-6-[2-(5-ethyl-2-hydroxy-4-propoxyphenyl)ethyl]-4-hydroxy-5,6-dihydro-2H-pyran-2-one The title compound was prepared analogously to example A(1) where 6-cyclopentyl-6-[2-(5-ethyl-2-hydroxy-4-propoxy-phenyl)-ethyl]-dihydro-pyran-2,4-dione from step 3 below was substituted in place of 6-cyclopentyl-6-[2-(5-ethyl-4-hydroxy-2-propoxy-phenyl)-ethyl]-dihydro-pyran-2,4-dione. $^1$H NMR (400 MHz, DMSO-$d_6$): δ 1.01 (m, 6 H), 1.42-1.77 (m, 10 H), 1.95 (m, 1 H), 2.15 (m, 1 H), 2.39-2.82 (m, 13 H), 3.70-3.84 (m, 4 H), 6.38 (s, 1 H), 6.75 (s, 1 H), 7.06 (s, 1 H), 9.04 (s, 1 H), 10.13 (s, 1H). MS (ESI): 549.20 (M+H)$^+$ Step 1: 1-(4-Benzyloxy-2-hydroxy-phenyl)-ethanone

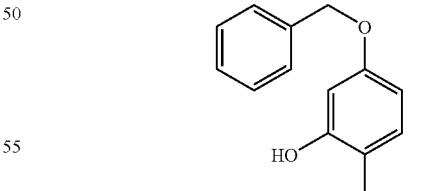

Potassium carbonate (54 g, 0.39 mol) followed by benzyl bromide (13.9 mL, 0.12 mol) were added to a solution of 2',4'-dihydroxyacetophenone (20 g, 0.13 mol) in DMF (180 mL). The mixture was stirred for 5 hours and then partitioned between H$_2$O and EtOAc. The organic layer was washed with satd NaHCO$_3$, 1N HCl, brine, dried over Na$_2$SO$_4$ and concentrated to a clear oil (23.7 g, 81%). $^1$H NMR (400 MHz, CDCl$_3$): δ 2.56 (s, 3 H), 5.02 (s, 2 H), 6.51 (m, 2 H), 7.33-7.43 (m, 5 H), 7.64 (d, J=8.3 Hz, 1 H), 12.73 (s, 1 H).

Step 2: 4-Benzyloxy-1-ethyl-2-propoxy-benzene

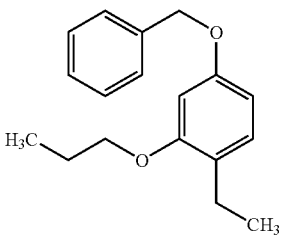

Potassium carbonate (5.14 g, 12.4 mmol) followed by 1-iodopropane (1.33 mL, 13.6 mmol) were added to a solution of 1-(4-benzyloxy-2-hydroxy-phenyl)-ethanone (3 g, 12.4 mmol) in DMF (30 mL). The mixture was stirred for 15 hours and then partitioned between H$_2$O and EtOAc. The organic layer was washed with 1 N HCl, brine, dried over Na$_2$SO$_4$ and concentrated to a pink oil. Purification by flash column chromatography (0% to 20% EtOAc in hexanes) gave a white solid (3.5 g, 99%).

The solid was suspended in triethylene glycol (15 mL) and treated with NaOH (1.23 g, 31 mmol) followed by hydrazine monohydrate (1.79 mL, 37 mmol). The mixture was heated to 160 for 16 hours. The reaction mixture was poured into 1 N HCl and extracted with EtOAc. The organic extracts were washed with brine, dried over Na$_2$SO$_4$ and concentrated to a clear oil. Purification by flash column chromatography (0% to 10% EtOAc in hexanes) gave the title compound as a clear oil (2.5 g, 76%). $^1$H NMR (400 MHz, CDCl$_3$): δ 1.04 (t, J=7.3 Hz, 3 H), 1.16 (t, J=7.6 Hz, 3 H), 1.80 (m, 2 H), 2.58 (q, J=7.6 Hz, 2 H), 3.88 (t, J=6.3 Hz, 2 H), 5.03 (s, 2 H), 6.48 (dd, J=8.1, 2.5 Hz, 1 H), 6.51 (d, J=2.3 Hz, 1 H), 7.03 (d, J=8.1 Hz, 1 H), 7.30-7.44 (m, 5 H).

Step 3: 6-Cyclopentyl-6-[2-(5-ethyl-2-hydroxy-4-propoxy-phenyl)-ethyl]-dihydro-pyran-2,4-dione

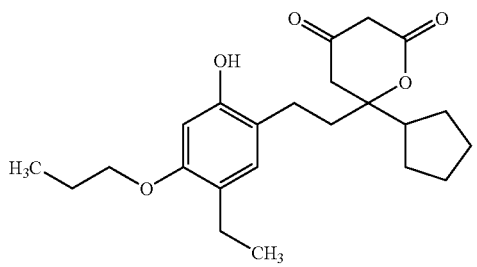

The title compound was prepared analogously to example A(2) where 4-benzyloxy-1-ethyl-2-propoxy-benzene was substituted in place of 2-benzyloxy-1-ethyl-4-propoxy-benzene in step 3 of that example. $^1$H NMR (400 MHz, CDCl$_3$): δ 1.03 (t, J=7.6 Hz, 3 H), 1.18 (m, 6 H), 1.43-2.05 (m, 10 H), 2.50-2.82 (m, 6 H), 3.44 (m, 2 H), 3.84 (m, 2 H), 4.90 (s, 1 H), 6.27 (s, 1 H), 6.79 (s, 1 H).

Example A(50)

6-Cyclopentyl-6-[2-(5-ethyl-2-hydroxy-4-propoxyphenyl)ethyl]-4-hydroxy-3-[(6-methyl[1,2,4]triazolo[1,5-a]pyrimidin-2-yl)methyl]-5,6-dihydro-2H-pyran-2-one

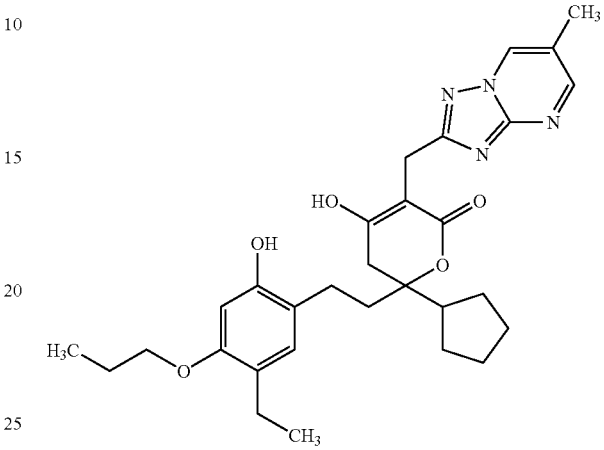

The title compound was prepared analogously to example A(4) where 6-cyclopentyl-6-[2-(5-ethyl-4-hydroxy-2-propoxy-phenyl)-ethyl]-dihydro-pyran-2,4-dione from step 3 of example A(49) was substituted in place of 6-cyclopentyl-6-[2-(2-ethyl-5-methoxypyridin-4-yl)ethyl]dihydro-2H-pyran-2,4(3H)-dione. $^1$H NMR (400 MHz, DMSO-d$_6$): δ 0.85 (m, 6H), 1.25-1.62 (m, 10 H), 1.83 (m, 2 H), 2.19 (s, 3H), 2.25-2.65 (m, 7H), 3.61 (m, 2 H), 3.67 (t, J=7.6 Hz, 2 H), 6.23 (s, 1 H), 6.61 (s, 1 H), 8.53 (s, 1H), 8.70 (s, 1 H), 8.90 (s, 1 H), 10.70 (s, 1 H). MS (ESI): 535.20 (M+H)$^+$ Example A(51)

Enantiomer 1 of 6-Cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one Enantiomer 1

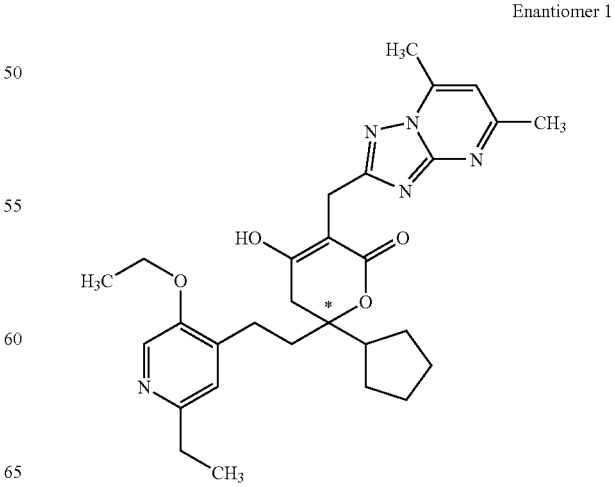

The title compound was separated from racemic 6-cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one (85 mg, Example A(27)) using chiral HPLC (Chiralpak AD-H, 140 bar, 30% MeOH). (22 mg, 5.38 min retention time, 100% ee)

Example A(52)

Enantiomer 2 of 6-cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one The title compound was separated from racemic 6-cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one (80 mg, Example A(42)) using chiral HPLC (Chiralpak AD-H, 140 bar, 25% MeOH w/0.1% isopropylamine). (27 mg, 6.91 min retention time, 100% ee)

Example A(54)

Enantiomer 2 of 6-Cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one

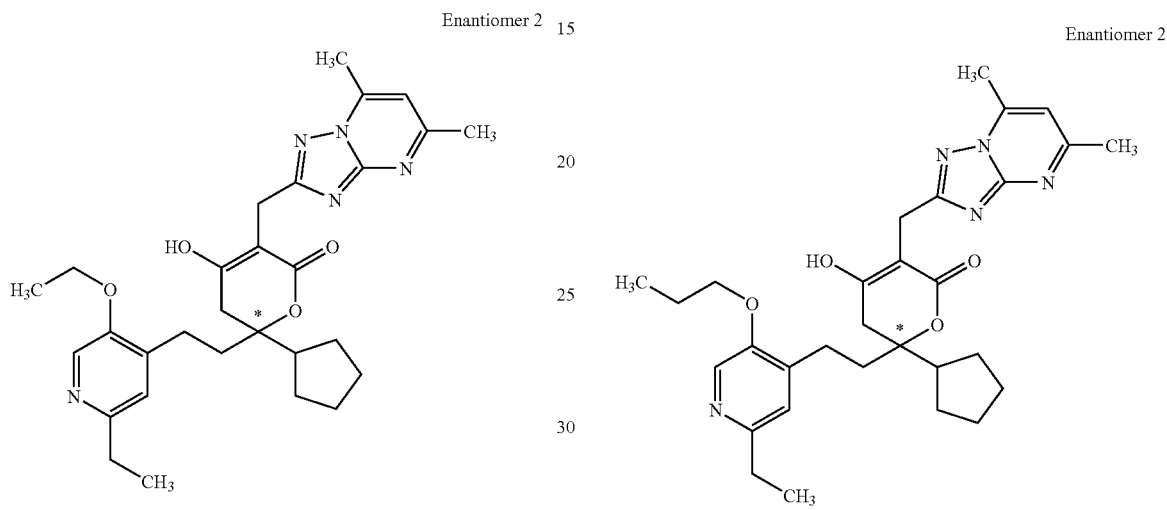

The title compound was separated from racemic 6-cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one (85 mg, Example A(27)) using chiral HPLC (Chiralpak AD-H, 140 bar, 30% MeOH). (16 mg, 7.21 min retention time, 100% ee)

Example A(53)

Enantiomer 1 of 6-Cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one The title compound was separated from racemic 6-cyclopentyl-3-[(5,7-dimethyl[1,2,4]triazolo[1,5-a]pyrimidin-2-yl)methyl]-6-[2-(2-ethyl-5-propoxypyridin-4-yl)ethyl]-4-hydroxy-5,6-dihydro-2H-pyran-2-one (80 mg, Example A(42)) using chiral HPLC (Chiralpak AD-H, 140 bar, 25% MeOH w/0.1% isopropylamine). (12.3 mg, 8.91 min retention time, 100% ee)

Example A(55)

Enantiomer 1 of 6-Cyclopentyl-6-[2-(5-ethoxy-2-ethylpyridin-4-yl)ethyl]-4-hydroxy-3-[(6-methyl[1,2,4]triazolo[1,5-a]pyrimidin-2-yl)methyl]-5,6-dihydro-2H-pyran-2-one

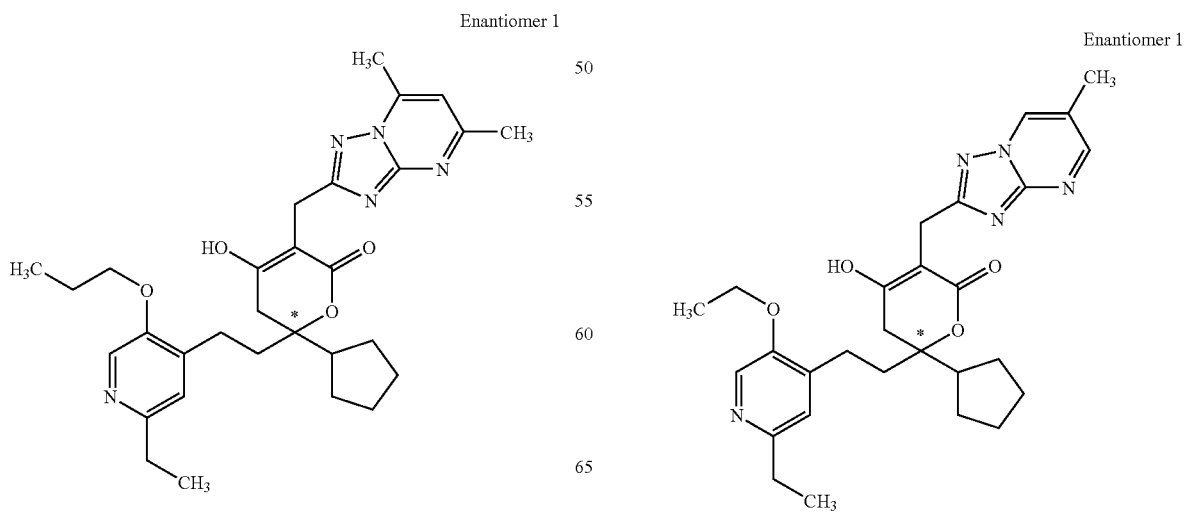

The title compound was separated from racemic 6-cyclopentyl-6-[2-(5-ethoxy-2-ethylpyridin-4-yl)ethyl]-4-hydroxy-3-[(6-methyl[1,2,4]triazolo[1,5-a]pyrimidin-2-yl)methyl]-5,6-dihydro-2H-pyran-2-one (33 mg, Example A(43)) using chiral HPLC (Chiralpak AD-H, 140 bar, 30% MeOH). (9 mg, 5.49 min retention time, 100% ee).

Example A(56)

Enantiomer 2 of 6-Cyclopentyl-6-[2-(5-ethoxy-2-ethylpyridin-4-yl)ethyl]-4-hydroxy-3-[(6-methyl[1,2,4]triazolo[1,5-a]pyrimidin-2-yl)methyl]-5,6-dihydro-2H-pyran-2-one

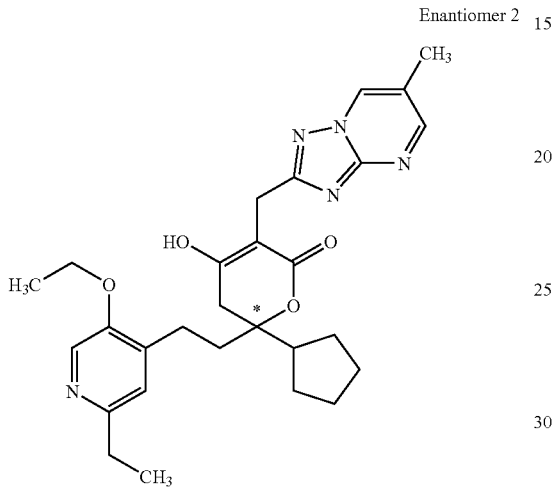

Enantiomer 2

The title compound was separated from racemic 6-cyclopentyl-6-[2-(5-ethoxy-2-ethylpyridin-4-yl)ethyl]-4-hydroxy-3-[(6-methyl[1,2,4]triazolo[1,5-a]pyrimidin-2-yl)methyl]-5,6-dihydro-2H-pyran-2-one (33 mg, Example A(43)) using chiral HPLC (Chiralpak AD-H, 140 bar, 30% MeOH). (9.5 mg, 6.79 min retention time, 100% ee).

Example A(57)

Enantiomer 1 of 6-Cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one

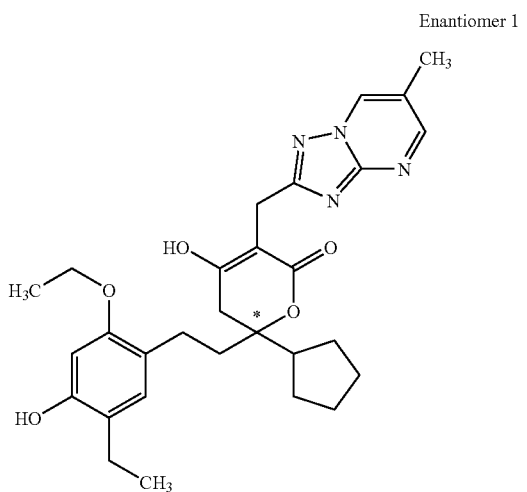

Enantiomer 1

The title compound was separated from racemic 6-cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one (70 mg, Example A(26)) using chiral HPLC (Chiralpak AS-H, 140 bar, 40% MeOH w/0.1% isopropylamine). (26 mg, 1.73 min retention time, 100% ee).

Example A(58)

Enantiomer 2 of 6-Cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one

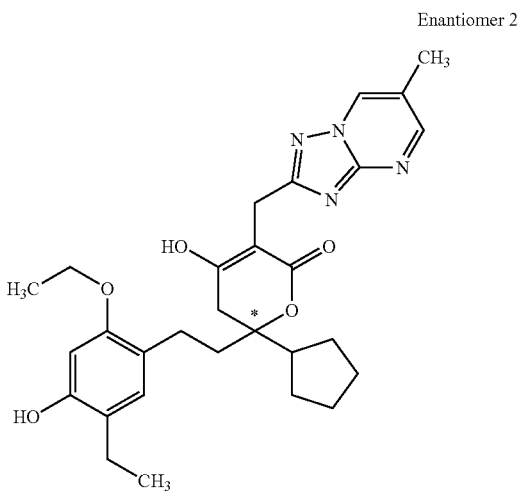

Enantiomer 2

The title compound was separated from racemic 6-cyclopentyl-6-[2-(2-ethoxy-5-ethyl-4-hydroxyphenyl)ethyl]-4-hydroxy-3-[(6-methyl[1,2,4]triazolo[1,5-a]pyrimidin-2-yl)methyl]-5,6-dihydro-2H-pyran-2-one (70 mg, Example A(26)) using chiral HPLC (Chiralpak AS-H, 140 bar, 40% MeOH w/0.1% isopropylamine). (27 mg, 9.35 min retention time, 100% ee).

Example A(59)

6-Cyclopentyl-3-[(5,7-dimethyl[1,2,4]triazolo[1,5-a]pyrimidin-2-yl)methyl]-6-[2-(5-ethyl-4-hydroxy-2-isobutoxyphenyl)ethyl]-4-hydroxy-5,6-dihydro-2H-pyran-2-one

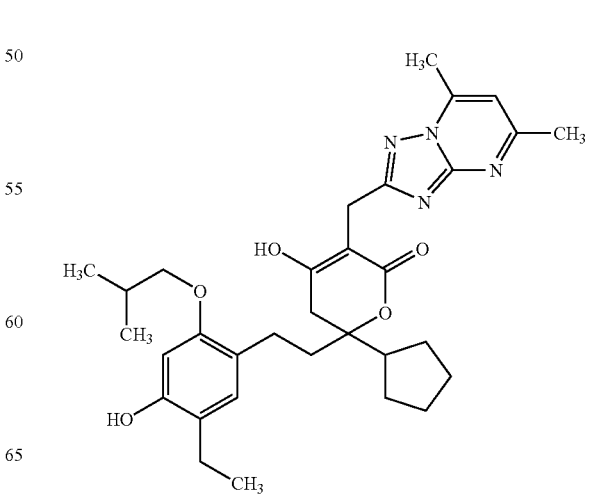

147

The title compound was prepared analogously to example A(1), where 1-Iodo-2-methyl-propane was substituted in place of 1-Iodopropane in step 1 of that example. ¹H NMR (400 MHz, CDCl₃): δ 1.00 (d, J=6.8 Hz, 6 H), 1.17 (t, J=7.6 Hz, 3 H), 1.35-1.78 (m, 12 H), 1.97 (t, J=8.5 Hz, 2 H), 2.07 (m, 1 H), 2.35-2.77 (m, 10 H), 3.61 (d, J=6.3 Hz, 2 H), 4.04 (d, J=15.4 Hz, 1 H), 4.13 (d, J=15.4 Hz, 1 H), 6.30 (s, 1 H), 6.82 (s, 1 H), 6.84 (s, 1 H), 10.72 (s, 1 H).

Example A(60)

6-{2-[2-(Cyclobutylmethoxy)-5-ethyl-4-hydroxyphenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one

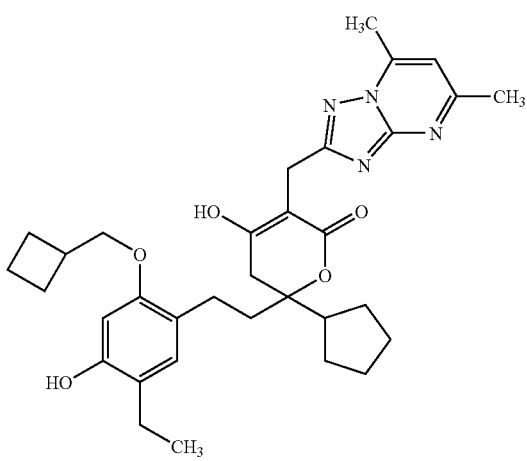

The title compound was prepared analogously to example A(1), where iodomethyl-cyclobutane was substituted in place of 1-Iodopropane in step 1 of that example. ¹H NMR (400 MHz, CDCl₃): δ 1.16 (t, J=7.6 Hz, 3 H), 1.35-2.45 (m, 21 H), 2.36-2.78 (m, 10 H), 3.83 (d, J=6.5 Hz, 2 H), 4.07 (d, J=15.4 Hz, 1 H), 4.12 (d, J=15.4 Hz, 1 H), 6.31 (s, 1 H), 6.81 (s, 1 H), 6.84 (s, 1 H), 10.72 (s, 1 H).

148

Example A(61)

6-Cyclopentyl-3-[(5,7-dimethyl[1,2,4]triazolo[1,5-a]pyrimidin-2-yl)methyl]-6-[2-(1-ethyl-1H-pyrazol-4-yl)ethyl]-4-hydroxy-5,6-dihydro-2H-pyran-2-one

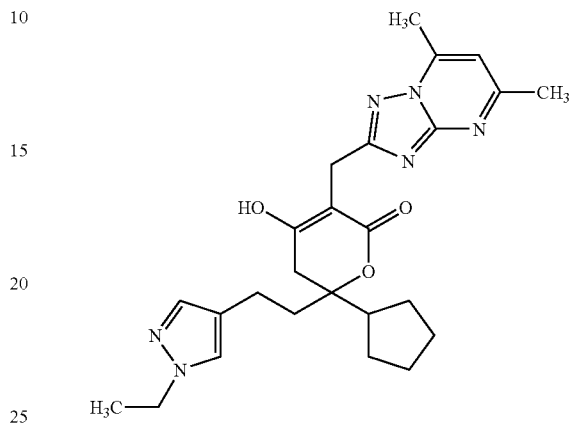

The title compound was prepared analogously to example A(1), where 1-ethyl-4-iodo-1H-pyrazole (ref: Trofimenko, S. J. Am. Chem. Soc 88, 558, 1966) was substituted in place of 1-benzyloxy-2-ethyl-4-iodo-5-propoxy-benzene in step 4 of that example. ¹H NMR (400 MHz, DMSO-d₆): δ 1.36 (t, J=7.4 Hz, 3 H), 1.57-1.69 (m 6 H), 2.10-2.16 (m, 2 H), 2.39-2.79 (m, 11 H), 3.34 (brm, 2 H), 3.74 (d, J=16.5 Hz, 1 H), 3.85 (d, J=16.5 Hz, 1 H), 4.01-4.12 (m, 1 H), 7.02 (s, 1 H), 7.24 (s, 1 H), 7.59 (s, 1 H), 8.26 (s, 1 H), 10.76 (s, 1 H).

Example A(62)

6-Cyclopentyl-3-[(5,7-dimethyl[1,2,4]triazolo[1,5-a]pyrimidin-2-yl)methyl]-4-hydroxy-6-[2-(1-isopropyl-1H-pyrazol-4-yl)ethyl]-5,6-dihydro-2H-pyran-2-one

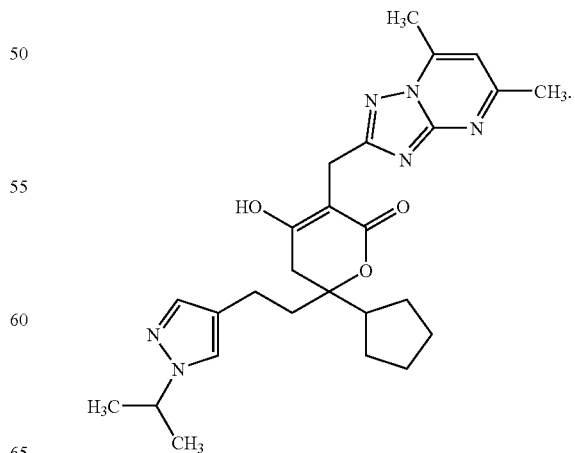

The title compound was prepared analogously to example A(1)$_b$, where 4-iodo-1-isopropyl-1H-pyrazole (ref: Trofimenko, S. *J. Am. Chem. Soc* 88, 558, 1966) was substituted in place of 1-benzyloxy-2-ethyl-4-iodo-5-propoxy-benzene in step 4 of that example. $^1$H NMR (400 MHz, DMSO-d$_6$): δ 1.39 (d, J=6.6 Hz, 6 H), 1.57-1.72 (m, 6 H), 2.10-2.17 (m, 3 H), 2.39-2.79 (m, 11 H), 3.74 (d, J=16.2 Hz, 1 H), 3.86 (d, J=16.2 Hz, 1 H), 4.42-4.48 (m, 1 H), 7.00 (s, 1 H), 7.23 (s, 1 H), 7.56 (s, 1 H), 8.23 (s, 1 H), 10.74 (s, 1 H).

Example A(63)

6-Cyclopentyl-6-{2-[3-fluoro-4-(methylsulfonyl)phenyl]ethyl}dihydro-2H-pyran-2,4(3H)-dione

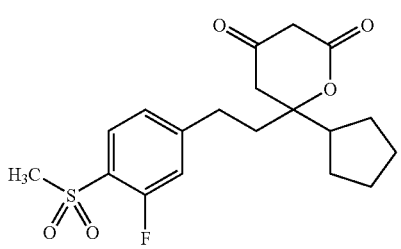

The title compound was prepared analogously to example A(2), where 4-bromo-2-fluoro-1-methanesulfonyl-benzene from step 1 below was substituted in place of 4-bromo-2-ethyl-5-methoxy-pyridine in step 6 of that example. $^1$H NMR (CDCl$_3$): δ 1.42-1.85 (brm, 8H), 1.97 (m, 2H), 2.29 (t, J=7.6 Hz, 1H), 2.79 (m, 4H), 3.44 (s, 3H), 3.45 (s, 2H), 7.11 (s, 1 H), 7.44 (m, 2 H)

Step 1:
4-Bromo-2-fluoro-1-methanesulfonyl-benzene

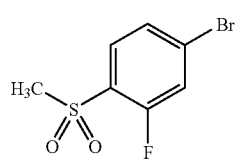

The title compound was prepared analogously to step 1 of example B(2), where 4-bromo-2-fluorobenzenesulfonyl chloride was used in place of 4-bromo-2-chlorobenzenesulfonyl chloride. $^1$H NMR (300 MHz, CDCl$_3$): δ 3.34 (s, 3 H), 7.57 (d, J=8.5, 2 H), 7.76 (d J=8.52 H), 8.14 (s, 1 H)

Example A(64)

6-Cyclopentyl-3-[(5,7-dimethyl[1,2,4]triazolo[1,5-a]pyrimidin-2-yl)methyl]-6-{2-[4-(ethylsulfonyl)phenyl]ethyl}-4-hydroxy-5,6-dihydro-2H-pyran-2-one

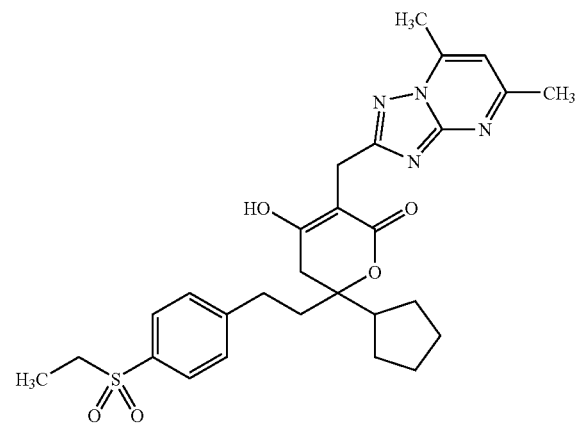

The title compound was prepared analogously to example A(1), where 1-bromo-4-ethanesulfonyl-benzene from step 1 below was substituted in place of 1-benzyloxy-2-ethyl-4-iodo-5-propoxy-benzene in step 4 of that example. $^1$H NMR (300 MHz, CDCl$_3$): δ 1.37 (t, J=7.5 Hz, 3 H) 1.40-2.19 (m, 13 H), 2.58 (s, 3 H), 2.73 2.99 (m, 7 H), 3.02 (q, J=12.57 Hz, 2 H), 6.99 (s, 1 H), 7.36 (dd, J=3.56 Hz, 2 H), 7.70 (dd, J=3.06 Hz, 1 H). Anal. Calcd. For C$_{28}$H$_{34}$N$_4$O$_5$S: C, 62.43; H, 6.36; N, 10.40. Found: C, 62.25; H, 6.40; N, 10.34.

Step 1: Bromo-4-ethanesulfonyl-benzene

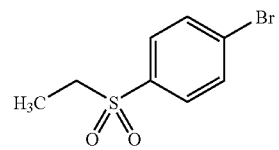

1-Bromo-4-ethylsulfanyl-benzene (5.0 g) was dissolved in acetic acid and potassium permanganate as a 3% solution in water (8 mL) was added. The reaction mixture was heated to 90° C. for 3 hrs, after which time the reaction was cooled to room temperature and partitioned between ethyl acetate and 2N NaOH solution (500 m) each. The organics were separated and washed with water (100 mL), dried over sodium sulfate and purified on biotage eluting with 90:10 hexanes:ethyl acetate to afford the title compound as a clear oil (2.70 g). ¹H NMR (300 MHz, CDCl₃): δ 1.30 (t, J=7.85 Hz, 3 H) 3.02 (q, J=7.54 Hz, 2 H), 7.40 (m, 4 H).

Example A(65)

6-Cyclopentyl-3-[(5,7-dimethyl[1,2,4]triazolo[1,5-a]pyrimidin-2-yl)methyl]-4-hydroxy-6-(2-{4-[(trifluoromethyl)sulfonyl]phenyl}ethyl)-5,6-dihydro-2H-pyran-2-one

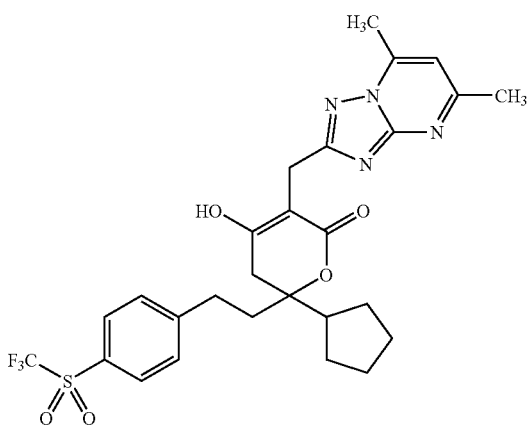

The title compound was prepared analogously to example A(1), where 6-cyclopentyl-6-(2-{4-[(trifluoromethyl)sulfonyl]phenyl}ethyl)dihydro-2H-pyran-2,4(3H)-dione (Example A(66) was substituted in place of 6-cyclopentyl-6-[2-(5-ethyl-4-hydroxy-2-propoxy-phenyl)-ethyl]-dihydro-pyran-2,4-dione in that example. ¹H NMR (300 MHz, CDCl₃): δ 1.35-2.23 (m, 11 H), 2.58 (s, 3 H), 2.73-2.89 (m, 7 H), 3.03 (t, J=8.57 Hz, 2 H), 6.99 (s, 1 H), 7.78 (d, J=2.56 Hz, 2 H), 8.10 (dd, J=2.36 Hz, 2 H) Anal. Calcd. For C₂₇H₂₉N₄O₅S: C, 56.04; H, 5.05; N, 9.68. Found: C, 56.35; H, 5.20; N, 9.34.

Example A(66)

6-Cyclopentyl-6-(2-{4-[(trifluoromethyl)sulfonyl]phenyl}ethyl)dihydro-2H-pyran-2,4(3H)-dione

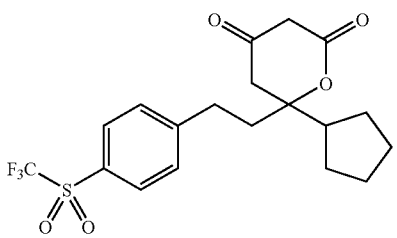

The title compound was prepared analogously to example A(2), where 1-bromo-4-trifluoromethanesulfonyl-benzene from step 1 below was substituted in place of (4-bromo-2-ethyl-5-methoxy-pyridine in step 6 of that example. ¹H NMR (300 MHz, CDCl₃): δ 1.35-2.33 (m, 11 H), 2.80-3.15 (m, 6 H), 7.75 (d, J=1.56 Hz, 2 H), 8.10 (d, J=1.56 Hz, 2 H).

Step 1: 1-Bromo-4-trifluoromethanesulfonyl-benzene

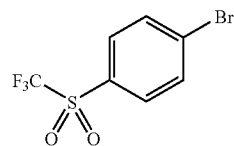

The title compound was prepared analogously to step 1 from example A(64), where 1-bromo-4-trifluoromethylsulfanyl-benzene was substituted in place of 1-bromo-4-ethylsulfanyl-benzene in step 1 of that example. ¹H NMR (300 MHz, CDCl₃): δ 7.80-7.93 (m, 4H).

Example A(67)

tert-Butyl 2-{4-[2-(2-cyclopentyl-4,6-dioxotetrahydro-2H-pyran-2-yl)ethyl]-2-ethylphenoxy}ethyl(methyl)carbamate

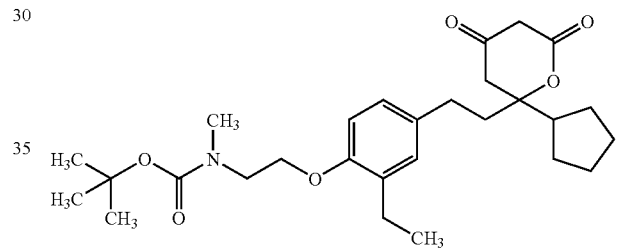

The title compound was prepared analogously to example A(2), where [2-(4-bromo-2-ethyl-phenoxy)-ethyl]-methyl-carbamic acid tert-butyl ester from step 3 below was substituted in place of 4-bromo-2-ethyl-5-methoxy-pyridine in step 6 of that example. ¹H NMR (300 MHz, CDCl₃): δ 1.16 (t, J=7.56 Hz, 3 H) 1.40-2.25 (m, 20 H), 2.62-3.13 (m, 14 H), 3.42 (q, J=8.54 Hz, 2 H), 3.84 (t, J=7.54 Hz, 2 H), 6.58 (d, J=2.06 Hz, 1 H), 6.66 (d, J=1.58 Hz, 1 H), 6.94 (s, 1 H).

Step 1: 4-Bromo-2-ethyl-phenol

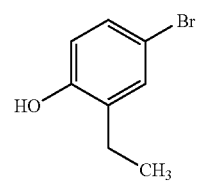

A solution of tetrabutyl ammonium tribromide (39.56 g, 0.08 mol) in CHCl₃ (100 mL) was added to a stirred solution of 2-ethyl-phenol (10.0 g, 0.08 mol) dissolved in CHCl₃ (100 mL). The reaction mixture was stirred for 2 hrs and then quenched with 5% solution of sodium thiosulfate (100 mL). The biphasic mixture was stirred for 30 mins and then the layers were separated. The organic layer was washed with 1 N HCl, brine, dried over Na₂SO₄ and concentrated to a red oil. Purification by flash column chromatography (0% to 15% EtOAc in hexanes) gave the product as an oil (14 g.). LCMS APCI−VE=200 M/E.

Step 2:
[2-(4-Bromo-2-ethyl-phenoxy)-ethyl]-carbamic acid tert!-butyl ester

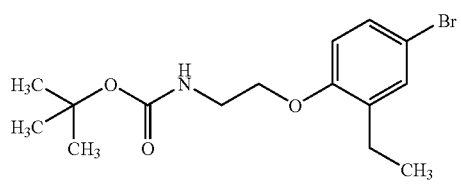

4-Bromo-2-ethyl-phenol (1.75 g, 8.70 mmol) from step 1 above was dissolved in acetonitrile (10 ml) and ceasium carbonate (2.83 g, 8.70 mmol) was added followed by (2-Bromo-ethyl)-carbamic acid tert-butyl ester (1.95 g, 8.70 mmol). The reaction was stirred at room temperature for 18 hrs. The mixture was partitioned between ethyl acetate (200 ml) and water (200 ml), the organics were separated and dried over magnesium sulfate and concentrated to a oil. Purification by flash column chromatography (0% to 30% EtOAc in hexanes) gave the product as an oil (1.0 g.). LCMS: APCI+ VE=244 M/E, mass-BOC.

Step 3: [2-(4-Bromo-2-ethyl-phenoxy)-ethyl]-methyl-carbamic acid tert!-butyl ester

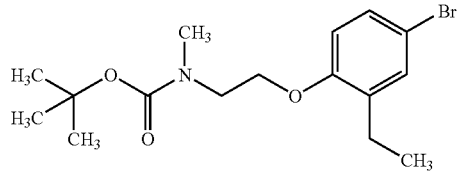

2-(4-Bromo-2-ethyl-phenoxy)-ethyl]-carbamic acid tert!-butyl ester (1.0 g, 2.90 mmol) was dissolved in THF (50 ml) and 60% NaH (128 mg, 3.19 mmol) was added followed by methyl iodide (0.2 ml, 3.19 mmol). The reaction was stirred at room temperature for 18 hrs. The mixture was partitioned between ethyl acetate (100 ml) and water (100 ml), the organics were separated and dried over magnesium sulfate and concentrated to a clear oil. (1.3 g). LCMS: electrospray+ VE=380 M/E, mass+sodium.

Example A(68)

tert-Butyl 2-{4-[2-(2-cyclopentyl-4,6-dioxotetrahydro-2H-pyran-2-yl)ethyl]-2-ethylphenoxy}ethylcarbamate

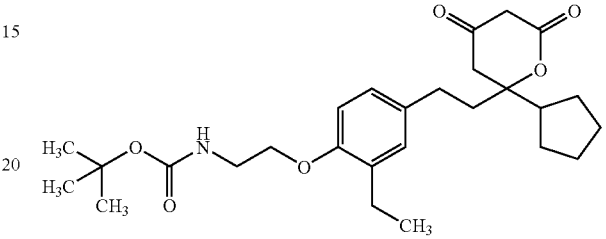

The title compound was prepared analogously to example A(2), where [2-(4-bromo-2-ethyl-phenoxy)-ethyl]carbamic acid tert-butyl ester from step 2 of example A(67) was substituted in place of 4-bromo-2-ethyl-5-methoxy-pyridinein step 6 of that example. ¹H NMR (300 MHz, CDCl₃): δ 1.16 (t, J=7.56 Hz, 3 H) 1.40-2.22 (m, 20 H), 2.60-3.10 (m, 11 H), 3.39 (q, J=8.54 Hz, 2 H), 3.84 (t, J=7.54 Hz, 2 H), 6.56 (d, J=2.06 Hz, 1 H), 6.64 (d, J=1.58 Hz, 1 H), 6.94 (s, 1 H).

Example A(69)

tert-Butyl 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethyl(methyl)carbamate

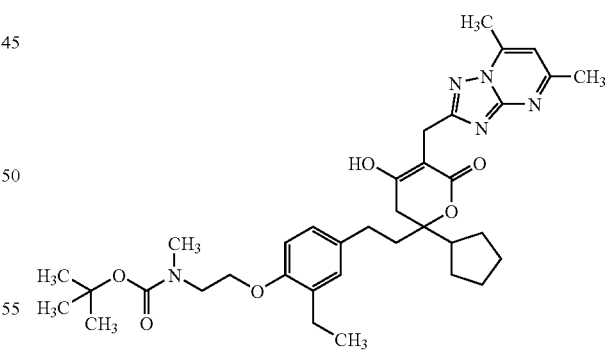

The title compound was prepared analogously to example A(1), where tert-butyl 2-{4-[2-(2-cyclopentyl-4,6-dioxotetrahydro-2H-pyran-2-yl)ethyl]-2-ethylphenoxy}ethyl(methyl)carbamate (Example A(67)) was substituted in place of 6-cyclopentyl-6-[2-(5-ethyl-4-hydroxy-2-propoxy-phenyl)-ethyl]-dihydro-pyran-2,4-dione in that example. ¹H NMR (300 MHz, CDCl₃): δ 1.20 (t, J=8.56 Hz, 3 H) 1.40-2.30 (m, 20 H), 2.55-2.99 (m, 17 H), 3.35 (q, J=9.54 Hz, 2 H), 3.90 (t, J=7.54 Hz, 3 H), 6.60 (d, J=1.56 Hz, 1 H), 6.67 (d, J=1.58 Hz, 1 H), 7.00 (m, 2 H). Anal. Calcd. For $C_{36}H_{49}N_5O_6$: C, 66.74; H, 7.62; N, 10.81. Found: C, 66.50; H, 7.40; N, 10.84.

Example A(70)

tert-Butyl 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethylcarbamate

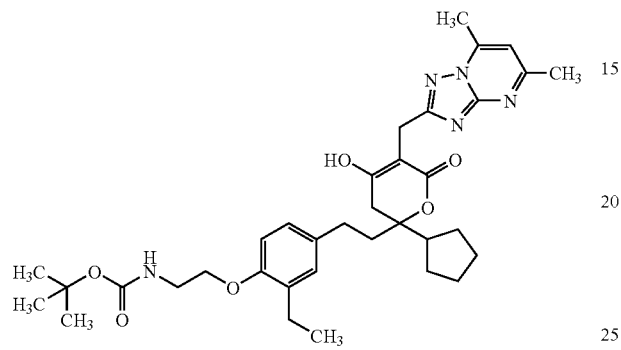

The title compound was prepared analogously to example A(1), where tert-butyl 2-{4-[2-(2-cyclopentyl-4,6-dioxotetrahydro-2H-pyran-2-yl)ethyl]-2-ethylphenoxy}ethylcarbamate (Example A(68)) was substituted in place of 6-cyclopentyl-6-[2-(5-ethyl-4-hydroxy-2-propoxy-phenyl)-ethyl]-dihydro-pyran-2,4-dione in that example. $^1$H NMR (300 MHz, CDCl$_3$): δ 1.20 (t, J=8.56 Hz, 3 H) 1.40-2.30 (m, 20 H), 2.55-2.99 (m, 15 H), 3.35 (q, J=9.54 Hz, 2 H), 3.90 (t, J=7.54 Hz, 3 H), 6.60 (d, J=1.56 Hz, 1H), 6.67 (d, J=1.58 Hz, 1 H), 7.00 (m, 2 H). Anal. Calcd. For $C_{35}H_{47}N_5O_6$: C, 66.33; H, 7.47; N, 11.05. Found: C, 66.30; H, 7.40; N, 11.10.

Example A(71)

6-{2-[4-(2-Aminoethoxy)-3-ethylphenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one

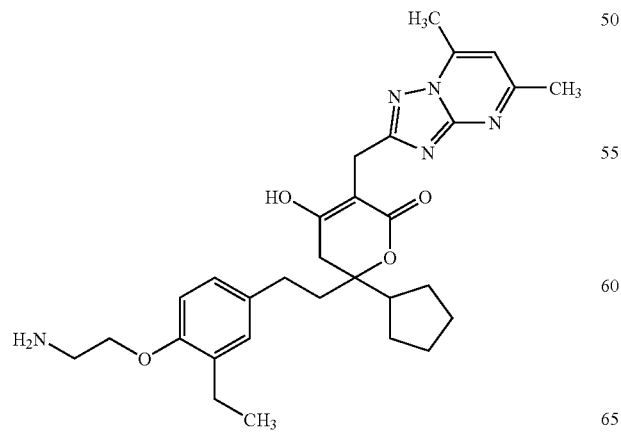

tert-Butyl 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethylcarbamate (Example A(70)) (250 mg) was dissolved in 4N HCl in dioxane (10 ml) and stirred at room temperature for 12 hrs. Upon completion the mixture was concentrated and azeotroped several times with dichloromethane to afford the title compound as a white solid (235 mg). $^1$H NMR (300 MHz, MeOD): δ 1.18 (t, J=7.56 Hz, 3 H) 1.32-2.35 (m, 11 H), 2.59-2.85 (m, 15 H), 2.92 (dd, J=116.54 Hz, 1 H), 4.05 (t, J=7.54 Hz, 2 H), 6.55 (d, J=1.56 Hz, 1 H), 6.65 (d, J=1.56 Hz, 1 H), 6.95 (s, 1 H), 6.99 (s, 1 H).

Example A(72)

6-Cyclopentyl-3-[(5,7-dimethyl[1,2,4]triazolo[1,5-a]pyrimidin-2-yl)methyl]-6-(2-{3-ethyl-4-[2-(methylamino)ethoxy]phenyl}ethyl)-4-hydroxy-5,6-dihydro-2H-pyran-2-one

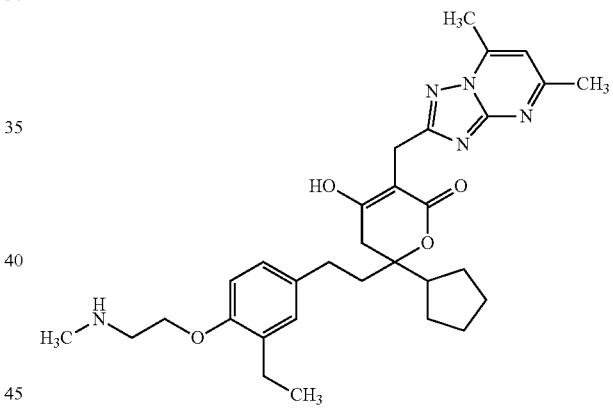

The title compound was prepared analogously to example A(71) where tert-butyl 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethyl(methyl)carbamate (Example A(69)) was substituted in place of tert-butyl 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenoxy]ethylcarbamate in that example. $^1$H NMR (300 MHz, MeOD): δ 1.16 (t, J=8.54 Hz, 3 H) 1.32-2.35 (m, 11 H), 2.40 (s, 3 H), 2.59-2.75 (m, 14 H), 2.92 (t, J=16.54 Hz, 2 H),

Example A(73)

tert-Butyl 2-{4-[2-(2-cyclopentyl-4,6-dioxotetrahydro-2H-pyran-2-yl)ethyl]-2-ethyl-5-methoxyphenoxy}ethyl(methyl)carbamate

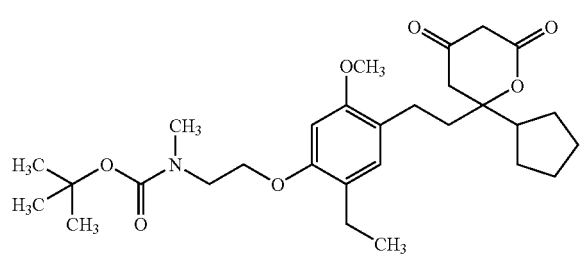

The title compound was prepared analogously to example A(2), where [2-(4-bromo-5-methoxy-2-ethyl-phenoxy)-ethyl]carbamic acid tert!-butyl ester from step 5 below was substituted in place of 4-bromo-2-ethyl-5-methoxy-pyridinein step 6 of that example. $^1$H NMR (300 MHz, CDCl$_3$): δ 1.16 (t, J=7.56 Hz, 3 H) 1.40-2.25 (m, 20 H), 2.62-3.13 (m, 14 H), 3.42 (q, J=8.54 Hz, 2 H), 3.84 (t, J=7.54 Hz, 2 H), 4.00 (s, 3 H) 6.26 (s, 1 H), 6.96 (s, 1 H).

Step 1: 144-Methoxy-2-hydroxy-phenyl)-ethanone

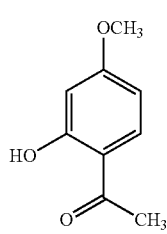

Potassium carbonate (27.2 g, 197 mmol) followed by methyl iodide (4.1 mL, 65.7 mmol) were added to a solution of 2',4'-dihydroxyacetophenone (10.0 g, 65.7 mmol) in DMF (100 mL). The mixture was stirred for 4 hours and then partitioned between H$_2$O and EtOAc. The organic layer was washed with satd NaHCO$_3$, brine, dried over Na$_2$SO$_4$ and concentrated to a clear oil (11.0 g). $^1$H NMR (300 MHz, CDCl$_3$): δ 2.60-(s, 3 H), 3.80 (s, 3 H), 6.40 (s, 1 H) 6.51 (d, J=2.45 Hz, 1 H), 7.62 (d, J=8.67 Hz, 1 H), 12.90 (s, 1 H).

Step 2: 5-Methoxy-2-ethyl-phenol

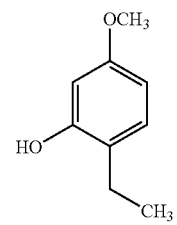

1-(4-Methoxy-2-hydroxy-phenyl)-ethanone (11.0 g) was dissolved in MeOH (100 mL), treated with 10 wt % Pd/C (4.0 g, Degussa type) and stirred under a balloon of H$_2$ for 24 hours. The reaction mixture was filtered through a pad of celite washing with EtOAc. The filtrate was concentrated to give the product as an oil (10.0 g). $^1$H NMR (300 MHz, CDCl$_3$): δ 1.20 (t, J=7.85 Hz, 3 H) 2.60-(q, J=6.22 Hz 2 H), 3.75 (s, 3 H), 6.40 (dd, J=9.04 Hz, 2.64 Hz, 1 H), 6.45 (d, J=2.64 Hz, 1 H) 7.00 (d, J=8.29 Hz, 1 H), 12.90 (s, 1 H).

Step 3: 4-Bromo-5-methoxy-2-ethyl-phenol

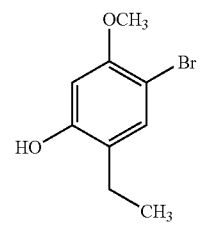

A solution of tetrabutyl ammonium tribromide (38.10 g, 79 mmol) in CHCl$_3$ (100 mL) was added to a stirred solution of 5-methoxy-2-ethyl-phenol (12.0 g, 79 mmol) dissolved in CHCl$_3$ (90 mL). The reaction mixture was stirred for 4 hrs and then quenched with 5% solution of sodium thiosulfate (90 mL). The biphasic mixture was stirred for 30 mins and then the layers were separated. The organic layer was washed with 1 N HCl, brine, dried over Na$_2$SO$_4$ and concentrated to a red oil. Purification by flash column chromatography (0% to 60% EtOAc in hexanes) gave the product as an oil (19 g). LCMS: APCI–VE=230 M/E.

Step 4: [2-(4-Bromo-5-methoxy-2-ethyl-phenoxy)-ethyl]-carbamic acid tert!-butyl ester

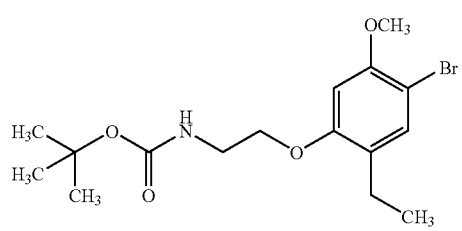

4 Bromo-5-methoxy-2-ethyl-phenol (10.0 g, 43 mmol) from step 3 above was dissolved in DMF (100 ml) and ceasium carbonate (21.17 g, 65 mmol) was added followed by (2-bromo-ethyl)-carbamic acid tert!-butyl ester (21.17 g, 65 mmol). The reaction was stirred at room temperature for 18 hrs. The mixture was partitioned between ethyl acetate (200 ml) and 10% citric acid (200 ml), the organics were separated and dried over magnesium sulfate and concentrated to a oil. Purification by flash column chromatography (0% to 30% EtOAc in hexanes) gave the product as an oil (10.0 g.). LCMS: APCI+VE=375 M/E.

Step 5: [2-(4-Bromo-5-methoxy-2-ethyl-phenoxy)-ethyl]-methyl-carbamic acid tert-butyl ester

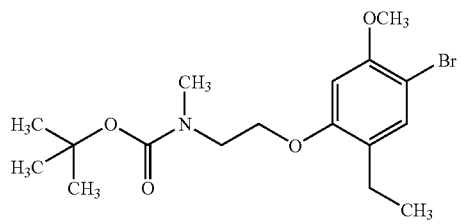

2-(4-Bromo-5-methoxy-2-ethyl-phenoxy)-ethyl]-carbamic acid tert-butyl ester (5.0 g, 13.4 mmol) was dissolved in THF (50 ml) and 60% NaH (804 mg, 20.1 mmol) was added followed by methyl iodide (1.3 ml, 20.1 mmol). The reaction was stirred at room temperature for 18 hrs. The mixture was partitioned between ethyl acetate (100 ml) and 1N citric acid (100 ml), the organics were separated and dried over magnesium sulfate and concentrated to a clean oil. (6.0 g). LCMS: APCI+VE=389 M/E.

Example A(74)

Enantiomer 1 of 6-Cyclopentyl-3-[(5,7-dimethyl[1,2,4]triazolo[1,5-a]pyrimidin-2-yl)methyl]-4-hydroxy-6-[(2-[4-hydroxy-3-(2,2,2-trifluoroethyl)phenyl]ethyl]-5,6-dihydro-2H-pyran-2-one

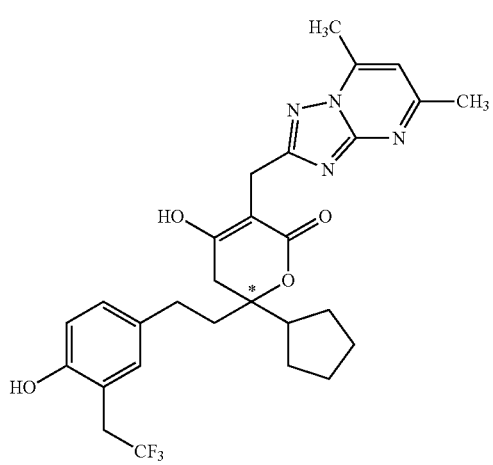

Enantiomer 1

The title compound was separated from racemic 6-cyclopentyl-3-[(5,7-dimethyl[1,2,4]triazolo[1,5-a]pyrimidin-2-yl)methyl]-4-hydroxy-6-{2-[4-hydroxy-3-(2,2,2-trifluoroethyl)phenyl]ethyl}-5,6-dihydro-2H-pyran-2-one (100 mg, from step 9 below) using chiral HPLC (Chiralpak AS-H, 100 bar, 30% MeOH). (26 mg, 1.677 min retention time, 100% ee)

Step 1: 2,2,2-trifluoro-1-(2-methoxyphenyl)ethanone

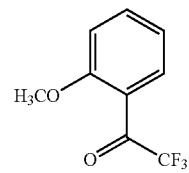

2 Methoxy phenyl magnesium bromide (35 ml) was added slowly to a solution of methyl trifluoroacetate (5.0 g) in diethyl ether (100 ml) at −78° C. The reaction mixture was warmed to room temperature over 12 hrs and the quenched with saturated ammonium chloride solution (100 ml). The mixture was then partitioned between ethyl acetate (500 ml) and water (250 ml) The organics were separated and dried over magnesium sulfate filtered and concentrated in vacuo. The crude residue was purified by column chromatography on silica gel eluting with 100% hexanes, 90:10 and 80:20, hexanes:ethyl acetate, to afford title compound as a yellow oil. (4.0 g). $^1$H NMR (CDCl$_3$): δ 3.57 (s, 3H), 7.00 (m, 2H), 7.35 (m, 1H), 7.63, (d, J=2.54 Hz 2H).

Step 2: 2,2,2-trifluoro-1-(2-methoxyphenyl)ethanol

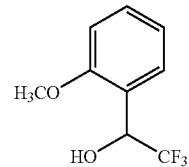

10% Palladium on carbon (1.5 g) was added to a solution of 2,2,2-trifluoro-1-(2-methoxyphenyl)ethanone (3.0 g) in methanol (50 ml). The resultant was hydrogenated at room temperature for 12 hrs. After which time the catalyst was filtered off through a plug of celite and the solvent concentrated in vacuo. The crude was purified by column chromatography on silica gel eluting with 100% hexanes the 80:20 hexanes:ethylacetate to afford the title compound as a yellow oil (3.0 g). $^1$H NMR (CDCl$_3$): δ3.75 (d, J=2.56 Hz, 1H), 3.96 (s, 3H), 5.35 (m, 1H), 7.05 (m, 2H), 7.50 (m, 2H).

Step 3: 2-(2,2,2-trifluoro-1-hydroxyethyl)phenol

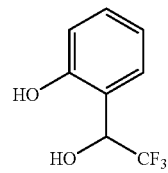

Boron tribromide (10 ml) (1M soln in DCM) was added to a solution of 2,2,2-trifluoro-1-(2-methoxyphenyl)ethanol (1.5 g) in dichloromethane (20 ml). The reaction mixture was stirred at room temperature under a atmosphere of nitrogen for 56 hrs. The mixture was then partitioned between DCM (100 ml) and 1N HCl (100 ml), organics washed with water (100 ml), dried over magnesium sulfate, filtered and solvent removed in vacuo to afford the title compound as a clear yellow oil (1.5 g). $^1$H NMR (CDCl$_3$): δ 3.50 (bs, 1H), 5.25 (m, 1H), 6.73 (bs, 1H), 7.00 (m, 2H), 7.32 (d, J=2.56 Hz, 1H), 7.45 (m, 1H).

Step 4: 2-(1-chloro-2,2,2-trifluoroethyl)phenol

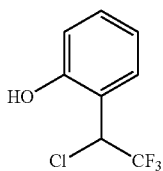

Thionyl chloride (2.28 ml) was added to a solution of 2-(2,2,2-trifluoro-1-hydroxyethyl)phenol (3.0 g) and pyridine (1.23 ml) in toluene (50 ml). The reaction was stirred at room temperature for 1 hr, after which time the toluene was removed in vacuo and the residue partitioned between ethyl acetate (100 ml) and 1N HCl (100 ml). The organics were separated and dried over magnesium sulfate, filtered and solvent removed in vacuo to afford the title compound as a clear oil (3.0 g). $^1$H NMR (CDCl$_3$): δ 5.93 (m, 1H), 6.90 (d, J=4.52 Hz, 1H), 7.10 (m, 1H), 7.35 (m, 1H), 7.69 (m, 1H).

Step 5: 2-(2,2,2-trifluoroethyl)phenol

Sodium borohydride (0.930 g) was added to a solution of 2-(1-chloro-2,2,2-trifluoroethyl)phenol (2.6 g) in THF (30 ml). The reaction mixture was then stirred for 14 hrs at room temperature under an atmosphere of nitrogen, after which time the reaction was quenched with 1N HCl (50 ml) and partitioned between 1N HCl (100 ml) and ethyl acetate (200 ml), the organics were separated and dried over magnesium sulfate, filtered and solvent evaporated in vacuo to afford title compound as a semi solid (2.4 g). $^1$H NMR (CDCl$_3$): δ 3.50 (q, J=21.06 Hz 2H), 6.80 (m, 1H), 7.00 (m, 1H), 7.25 (m, 2H).

Step 6: 4-bromo-2-(2,2,2-trifluoroethyl)phenol

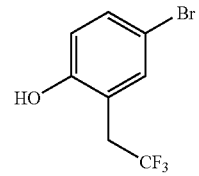

Tetrabutylammonium tribromide (6.56 g) was dissolved in chloroform (50 ml) and added dropwise to a solution of 2-(2,2,2-trifluoroethyl)phenol (2.4 g) in chloroform (50 ml). The reaction mixture was stirred at room temperature for 2 hrs, after which time 5% sodium thiosulfate solution (100 ml) was added and the resultant stirred for 30 mins. The mixture was then partitioned between dichloromethane (100 ml) and 1N HCl (200 ml). The organics were separated and dried over magnesium sulfate. The solvent was then removed in vacuo, the crude residue was then purified by column chromatography on silica gel eluting with 90:10 hexanes:ethyl acetate to afford the title compound as a yellow oil (3.24 g). $^1$H NMR (CDCl$_3$): δ 3.50 (q, J=21.48 Hz 2H), 6.70 (d, J=2.54 Hz, 1H), 7.32 (d, J=2.54 Hz, 1H), 7.45 (s, 1H).

Step 7: Acetic acid 4-bromo-2-(2,2,2-trifluoro-ethyl)-phenyl ester

Acetyl chloride (0.91 mL, 12.8 mmol) followed by triethylamine (1.8 mL, 12.8 mmol) were added to a stirred solution of 4-bromo-2-(2,2,2-trifluoroethyl)phenol (2.55 g, 10.7 mmol) dissolved in CH$_2$Cl$_3$ (20 mL). The reaction was stirred for 45 mins and then partitioned between 1N HCl and EtOAc. The organic layer was washed with saturated NaHCO$_3$, brine dried over Na$_2$SO$_4$ and concentrated. Purification by flash column chromatography (0% to 20% EtOAc in hexanes) gave the product as a clear oil (2.50 g). LCMS: apci 297 MH+

Step 8: 6-Cyclopentyl-6-{2-[4-hydroxy-3-(2,2,2-trifluoroethyl)phenyl]ethyl}dihydro-2H-pyran-2,4(3H)-dione

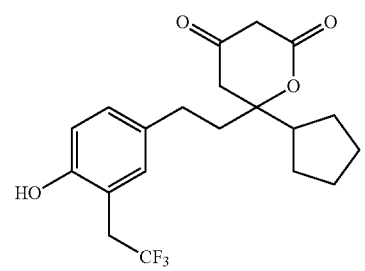

The title compound was prepared analogously to example A(2) where acetic acid 4-bromo-2-(2,2,2-trifluoro-ethyl)-phenyl ester from step 7 above was substituted in place of 4-bromo-2-ethyl-5-methoxy-pyridine in step 6 of that example. $^1$H NMR (CDCl$_3$): δ 1.35-1.70 (brm, 6H), 1.93, (brm, 2H), 2.04-2.21 (brm, 3H), 2.83-3.12 (brm, 8H), 6.78 (dd, J=2.81 Hz 2H), 6.99 (s, 1H). MS (APCI): 385 (M–H).

Step 9: 6-Cyclopentyl-3-[(5,7-dimethyl[1,2,4]triazolo[1,5-a]pyrimidin-2-yl)methyl]-4-hydroxy-6-{2-[4-hydroxy-3-(2,2,2-trifluoroethyl)phenyl]ethyl}-5,6-dihydro-2H-pyran-2-one

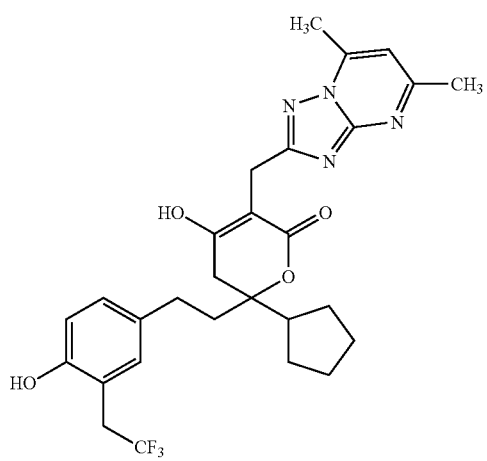

The title compound was prepared analogously to example A(1) where 6-cyclopentyl-6-{2-[4-hydroxy-3-(2,2,2-trifluoroethyl)phenyl]ethyl}dihydro-2H-pyran-2,4(3H)-dione was substituted in place of 6-cyclopentyl-6-[2-(5-ethyl-4-hydroxy-2-propoxy-phenyl)-ethyl]-dihydro-pyran-2,4-dione in that example. $^1$H NMR (DMSO): δ 1.40-1.90 (brm, 8H), 1.99-2.28 (brm, 3H), 2.58 (s, 3H), 2.73 (m, 5H), 3.00 (m, 2H); 3.10 (m, 2H), 3.47 (m, 3H), 6.79 (m, 2H), 7.05 (m, 2H), 8.83 (bs, 1H), 10.0 (bs, 1H). Anal. Calcd. For C$_{28}$H$_{31}$O$_4$N$_4$F$_3$: C, 61.76; H, 5.74; N, 10.29. Found: C, 61.50; H, 5.50; N, 10.14.

Example A(75)

Enantiomer 2 of 6-cyclopentyl-3-[(5,7-dimethyl[1,2,4]triazolo[1,5-a]pyrimidin-2-yl)methyl]-4-hydroxy-6-{2-[4-hydroxy-3-(2,2,2-trifluoroethyl)phenyl]ethyl}-5,6-dihydro-2H-pyran-2-one

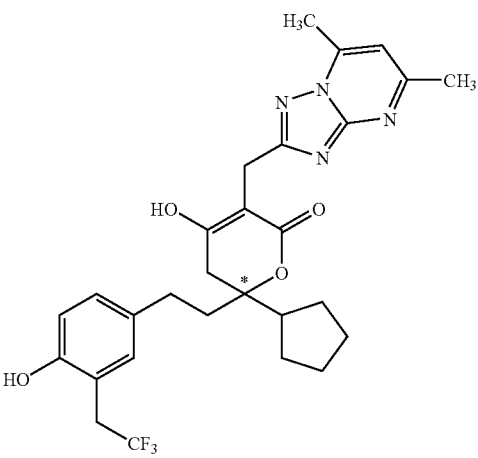

Enantiomer 2

The title compound was separated from racemic 6-cyclopentyl-3-[(5,7-dimethyl[1,2,4]triazolo[1,5-a]pyrimidin-2-yl)methyl]-4-hydroxy-6-{2-[4-hydroxy-3-(2,2,2-trifluoroethyl)phenyl]ethyl}-5,6-dihydro-2H-pyran-2-one (100 mg, from step 9 of example A(74) using chiral HPLC (Chiralpak AS-H, 100 bar, 30% MeOH). (27 mg, 3.566 min retention time, 100% ee)

Example A(76)

) 6-Cyclopentyl-3-[(5,7-dimethyl[1,2,4]triazolo[1,5-a]pyrimidin-2-yl)methyl]-4-hydroxy-6-{2-[4-hydroxy-3-methyl-5-(2,2,2-trifluoroethyl)phenyl]ethyl}-5,6-dihydro-2H-pyran-2-one

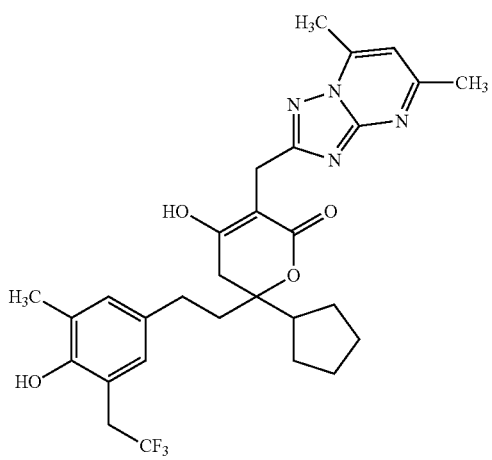

The title compound was prepared analogously to example A(1) where 2-benzyloxy-5-iodo-1-methyl-3-(2,2,2-trifluoro-ethyl)-benzene from step 5 below was substituted in place of 1-benzyloxy-2-ethyl-4-iodo-5-propoxy-benzene in step 4 of that example. $^1$H NMR (300 MHz, CDCl$_3$): δ 1.35-1.80 (m, 8 H), 2.00-2.40 (m, 6 H), 2.58 (s, 3 H), 2.80 (m, 7 H), 3.10 (t, J=7.06 Hz, 2 H), 3.20 (q, J=10.47 Hz, 2 H) 6.52 (s, 1 H), 6.81 (s, 1 H), 6.99 (s, 1 H), 8.82 (s, 2H). Anal. Calcd. For C$_{29}$H$_{33}$F$_3$N$_4$O$_4$: C, 62.36; H, 5.95; N, 10.03. Found: C, 62.30; H, 5.83; N, 10.16.

Step 1:
1-Bromomethyl-2-methoxy-3-methyl-benzene

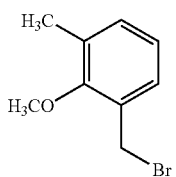

2-5-Dimethylanisole (10.0 g, 73 mmol) was dissolved in CCl$_4$ (100 ml) and NBS (26.26 g, 147 mmol) followed by benzoyl peroxide (884 mg 5 mol %) were added. The reaction was heated to reflux and stirred as such for 48 hrs, after which time the mixture was cooled to room temperature and filtered. The filtrate was concentrated and purified by flash column chromatography (0% to 30% EtOAc in hexanes) to give the product as a white solid (19.3 g.). LCMS: APCI–VE=213

Step 2: 2-Methoxy-1-methyl-3-(2,2,2-trifluoro-ethyl)-benzene

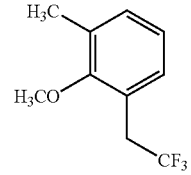

Trimethyl(trifluoromethyl)silane (25.39 mL, 162.5 mmol) was added to a stirred mixture of 1-bromomethyl-2-methoxy-3-methyl-benzene (19 g, 65 mmol), KF (9.44 g, 162.5 mmol), CuI (37.10 g, 195 mmol) in DMF (75 mL) and NMP (75 mL). The reaction mixture was heated to 55° C. under N$_2$ for 15 hours. The mixture was poured into water, made basic with 1N NaOH and extracted with EtOAc. The organic layers were washed with brine, dried over Na$_2$SO$_4$ and concentrated to a black oil. Flash column chromatography (0% to 60% EtOAc in hexanes) gave the product as a yellow oil (12.0 g). LCMS: APCI–VE=203

Step 3: 2-Methyl-6-(2,2,2-trifluoro-ethyl)-phenol

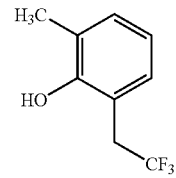

2-Methoxy-1-methyl-3-(2,2,2-trifluoro-ethyl)-benzene (6.0 g) was dissolved in dichloromethane (100 ml) and BBr$_3$ (100 ml) added. The reaction was allowed to stir at room temperature for 12 hrs, after which time it was quenched slowly with cHCl. The mixture was then made basic with 2N NaOH solution and the organics discarded. The aqueous was acidified with 1N HCl and the product extracted with ethyl acetate to afford the title compound as a brown oil (4.43 g). LCMS: APCI–VE=189

Step 4: 2-Benzyloxy-1-methyl-3-(2,2,2-trifluoro-ethyl)-benzene

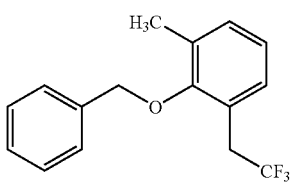

Potassium carbonate (953 mg, 6.89 mmol) followed by benzyl bromide (0.8 mL, 6.89 mmol) were added to a solution of 2-methyl-6-(2,2,2-trifluoro-ethyl)-phenol (1.78 g, 6.89 mmol) in DMF (20 mL). The mixture was stirred at room temperature for 15 hours and then partitioned between H₂O and EtOAc. The organic layer was washed with 1N HCl, brine, dried over Na₂SO₄ and concentrated to a brown oil. Purification by flash column chromatography (0% to 20% EtOAc in hexanes) gave the product as a clear oil (2.1 g). LCMS: APCI−VE=279

Step 5: 2-Benzyloxy-5-iodo-1-methyl-3-(2,2,2-trifluoro-ethyl)-benzene

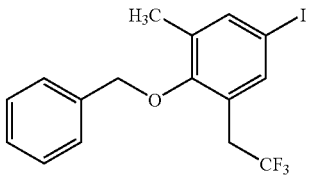

A solution of iodine (1.52 g, 6.0 mmol) dissolved in CHCl₃ (80 mL) was added dropwise to a stirred mixture of 2-benzyloxy-1-methyl-3-(2,2,2-trifluoro-ethyl)-benzene (2.1 g, 6.0 mmol), silver trifluoroacetate (1.33 g, 6.0 mmol) in CHCl₃ (20 mL). After the addition was complete the reaction mixture was stirred for 1 hour. The mixture was filtered through a pad of celite washing with CH₂Cl₂. The filtrate was washed with satd Na₂S₂O₃, brine, dried over Na₂SO₄ and concentrated to a pale yellow solid (1.68 g). LCMS: APCI−VE=405

Example A(77)

6-Cyclopentyl-3-[(5,7-dimethyl[1,2,4]triazolo[1,5-a]pyrimidin-2-yl)methyl]-4-hydroxy-6-{2-[4-hydroxy-2-propoxy-5-(2,2,2-trifluoroethyl)phenyl]ethyl}-5,6-dihydro-2H-pyran-2-one

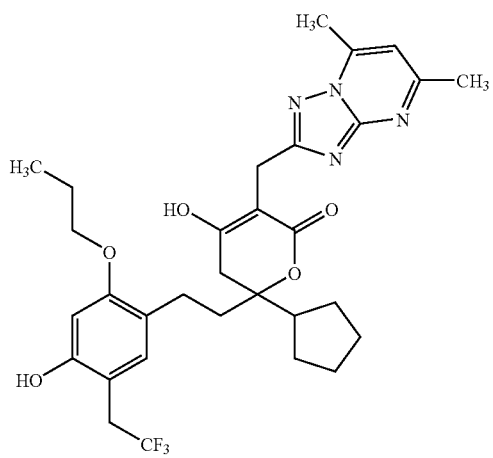

The title compound was prepared analogously to example A(1), where 1-benzyloxy-4-iodo-5-propoxy-2-(2,2,2-trifluoro-ethyl)-benzene from step 4 below was substituted in place of 1-benzyloxy-2-ethyl-4-iodo-5-propoxy-benzene in step 4 of that example. ¹H NMR (300 MHz, CDCl₃): δ0.98 (t, J=6.79 Hz, 3 H) 1.40-2.40 (m, 10 H), 2.50-2.75 (m, 10 H), 3.10 (q, J=10.06 Hz, 2 H), 3.78 (t, J=8.56 Hz, 2 H) 6.12 (s, 1 H), 6.99 (m, 2 H), 10.12 (bs, 1H). Anal. Calcd. For C₃₁H₃₇F₃N₄O₅: C, 61.73; H, 6.19; N, 9.29. Found: C, 61.60; H, 6.24; N, 9.39.

Step 1: 1-Methyl-2-nitro-4-propoxy-benzene

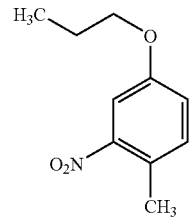

Potassium carbonate (13.5 g, 0.098 mol) followed by 1-iodopropane (9.56 mL, 0.098 mol) were added to a solution of 4-methyl-3-nitro-phenol (15 g, 0.098 mol) in DMF (100 mL). The mixture was stirred for 5 hours and then partitioned between H₂O and EtOAc. The organic layer was washed with satd NaHCO₃, brine, dried over Na₂SO₄ and concentrated to a clear oil (17.5 g).

Step 2: 2-Nitro-4-propoxy-1-(2,2,2-trifluoro-ethyl)-benzene

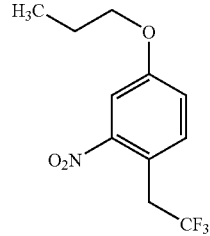

1-Methyl-2-nitro-4-propoxy-benzene (17.0 g, 87 mmol) was dissolved in CCl₄ (100 ml) and NBS (15.58 g, 87 mmol) followed by benzoyl peroxide (1.0 mg 5 mol %) were added. The reaction was heated to reflux and stirred as such for 24 hrs, after which time the mixture was cooled to room temperature and filtered. The filtrate was concentrated and purified by flash column chromatography (0% to 5% EtOAc in hexanes) to give the bromide as a white solid (7.0 g). Trimethyl(trifluoromethyl)silane (4.8 mL, 31.9 mmol) was added to a stirred mixture of the bromide (7.0 g, 25.5 mmol), KF (1.85 g, 31.90 mmol), CuI (7.28 g, 38.25 mmol) in DMF (50 mL) and NMP (50 mL). The reaction mixture was heated to 55° C. under N₂ for 15 hours. The mixture was poured into water, made basic with 1N NaOH and extracted with EtOAc. The organic layers were washed with brine, dried over Na₂SO₄ and concentrated to a black oil, and purified by flash column chromatography (0% to 10% EtOAc in hexanes) to give the product as a yellow oil (3.0 g). ¹H NMR (300 MHz, CDCl₃): δ 1.06 (t, J=6.79 Hz, 3 H) 1.80 (m, 2 H), 3.68 (q, J=10.47 Hz, 2 H), 3.78 (t, J=8.56 Hz, 2 H) 6.76 (d, J=2.33 Hz, 1 H) 7.33 (d, J=2.33 Hz, 1 H), 7.69 (s, 1 H).

Step 3: 5-Propoxy-2-(2,2,2-trifluoroethyl)-phenol

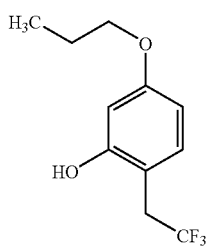

2-Nitro-4-propoxy-1-(2,2,2-trifluoro-ethyl)-benzene (3.0 g) was dissolved in ethanol (50 ml) and 10% palladium on carbon (1.0 g) was added. The mixture was hydrogenated by use of balloon for 5 hrs, after which time the catalyst was filtered off through a plug of celite. The filtrate was concentrated and purified by flash column chromatography (0% to 60% EtOAc in hexanes) to give the aniline as a yellow oil (2.5 g). This aniline was suspended in $H_2SO_4$ (2.05 ml in 5 ml water) and cooled to −5° C. Sodium nitrite (814 mg in water 5 ml) was added dropwise. The mixture was stirred at 0° C. for a further 30 mins and then the mixture was added to a solution of sulfuric acid (19 ml in water 100 ml). The mixture was heated to 80° C. for 1 hr. The reaction mixture was cooled to room temperature and the product was extracted using ethyl acetate. The organics were separated and dried over magnesium sulfate and the solvent was concentrated. The residue was purified flash column chromatography (0% to 60% EtOAc in hexanes) to afford the product as a red solid (500 mg). $^1$H NMR (300 MHz, $CDCl_3$): δ 1.06 (t, J=6.79 Hz, 3 H) 1.80 (m, 2 H), 3.46 (q, J=10.33 Hz, 2 H), 3.92 (t, J=8.86 Hz, 2 H) 6.26 (d, J=2.33 Hz, 1 H) 6.48 (s, 1 H) 7.10 (d, J=2.33 Hz, 1 H), 8.40 (bs, 1 H).

Step 4: 1-Benzyloxy-4-iodo-5-propoxy-2-(2,2,2-trifluoro-ethyl)-benzene

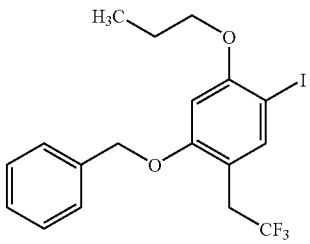

The title compound was prepared analogously to example A(76) where 5-propoxy-2-(2,2,2-trifluoro-ethyl)-phenol from step 3 above was substituted in place of 2-methyl-6-(2,2,2-trifluoro-ethyl)-phenol in step 4 of that example. $^1$H NMR (300 MHz, $CDCl_3$): δ 1.06 (t, J=6.79 Hz, 3 H) 1.80 (m, 2 H), 3.46 (q, J=10.56 Hz, 2 H), 4.00 (t, J=8.56 Hz, 2 H) 4.99 (s, 2 H), 6.65 (s, 1 H) 7.26-7.42 (m, 6 H).

Example A(78)

2-[4-(2-{2-Cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-methylphenyl]-2-methylpropanenitrile

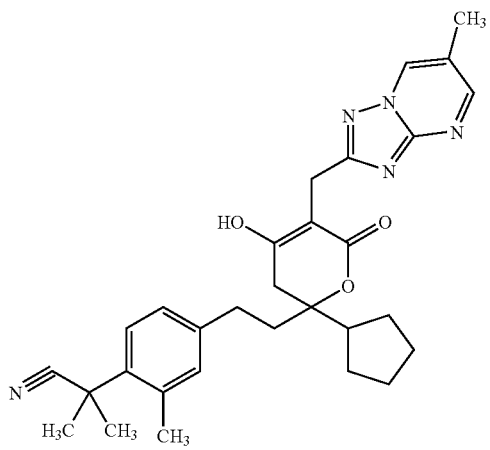

6-Methyl-[1,2,4]triazolo[1,5-a]pyrimidine-2-carbaldehyde (0.11 g, 0.7 mmol) was added to a solution of 2-{4-[2-(2-cyclopentyl-4-hydroxy-6-oxo-3,6-dihydro-2H-pyran-2-yl)-ethyl]-2-methyl-phenyl}-2-methyl-propionitrile (0.16 g, 0.5 mmol, from step 5 below) in MeOH (4 mL). The reaction mixture was stirred for 15 mins and then treated with borane-dimethylamine complex (34 mg, 0.6 mmol). After 15 hours the reaction mixture was filtered through a glass frit washing with MeOH. The filtrate was concentrated to a yellow oil. Purification by prep HPLC gave the product as a white powder (32 mg, 14% yield). $^1$H NMR (400 MHz, DMSO-$d_6$): 1.35-1.46 (2 H, m) 1.75 (6 H, s) 1.77-1.81 (2 H, m) 1.93-2.04 (3 H, m) 2.35-2.46 (2 H, m) 2.48 (3 H, s) 2.52-2.56 (2 H, m) 2.59 (3 H, s) 2.61-2.78 (4 H, m) 4.10 (2 H, d, J=8.08 Hz) 6.96-7.02 (2 H, m) 7.15-7.23 (1 H, m) 8.57-8.63 (1 H, m) 8.69 (1 H, d, J=2.53 Hz). MS (ESI): 512 (M−H).

Step 1: (4-Bromo-2-methyl-phenyl)-methanol

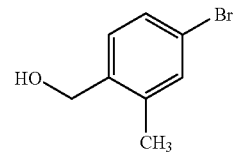

4-Bromo-2-methyl-benzoic acid (9.88 g, 45.9 mmol) was dissolved in THF (100 ml), and the solution was cooled to 0° C. To this solution, a solution of 1M $BH_3$.THF (91.89 ml, 91.89 mmol) was added at 0° C., and the solution was vigorously stirred for 3 hours at room temperature. The reaction mixture was diluted with cold water (20 mL), washed with a saturated solution of $NaHCO_3$, then extracted with ether 3 times (300 mL). The combined organic ether was washed with brine (250 mL), dried over MgSO$_4$, and concentrated in Vacuo. The residue was purified via flash column chromatography (25% to 55% EtOAc in Hexane) to give white solid (8.24 g, 90% yield). $^1$H NMR (400 MHz, CDCl$_3$) δ: 2.32 (2 H, s) 4.64 (1 H, d, J=5.81 Hz) 7.20-7.26 (2 H, m) 7.30-7.36 (1 H, m).

Step 2: 4-Bromo-1-bromomethyl-2-methyl-benzene

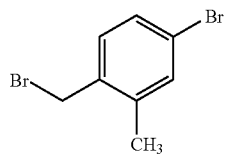

Triphenylphosphine (11.35 g, 43.27 mmol) followed by carbon tetrabromide (14.35 g, 43.27 mmol) were added to a solution of (4-bromo-2-methyl-phenyl)-methanol (7.25 g, 36 mmol) in CH$_2$Cl$_2$ (200 mL). The mixture was stirred at room temperature for 5 hours. The solution was concentrated to 15 mL. The residue was purified by flash column chromotography (1% to 10% EtOAc in Hexane) gave the product as brown oil (9.25 g, 81% yield). $^1$H NMR (400 MHz, CDCl$_3$) δ: 2.39 (3 H, s) 4.45 (2 H, s) 7.17 (1 H, d, J=8.08 Hz) 7.29 (2 H, m) 7.30 (1 H, dd, J=8.08, 2.02 Hz) 7.34 (1 H, s).

Step 3: (4-Bromo-2-methyl-phenyl)-acetonitrile

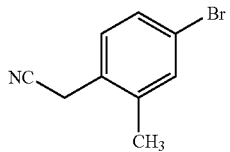

To a solution of 4-bromo-1-bromomethyl-2-methyl-benzene (3.96 g, 15 mmol) dissolved in DMF (16 mL) were added sodium cyanide (0.85 g, 17.25 mmol) and water (1.8 mL). The reaction was stirred for overnight at room temperature. To the reaction was added 100 mL water; 80 mL saturated NaHCO$_3$, and 100 mL EtOAc. The layers were separated, and the aqueous layer was extracted with 3×100 mL EtOAc. The combined organics were washed with 100 mL water, and then dried over Na$_2$SO$_4$. After filtering off the solids, the mother liquor was concentrated to the desired product by rotary evaporation (2.92 g, 92.7% yield). $^1$H NMR (400 MHz, CDCl$_3$): δ 2.32 (2H, s), 3.62 (1 H, s), 7.20-7.27 (1 H, m), 7.32-7.41 (1 H, m).

Step 4:
2-(4-Bromo-2-methyl-phenyl)-2-methyl-propionitrile

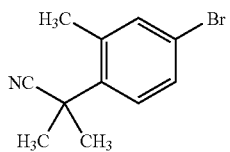

To a solution of (4-bromo-2-methyl-phenyl)-acetonitrile (1.26 g, 6 mmol) from step 3 above in DMF (15 mL) cooled to −10° C. was added a potassium t-butoxide (1.62 g, 14.4 mmol). The reaction was stirred for 15 minutes, iodomethane (0.86 mL, 13.8 mmol) was added slowly. The reaction was stirred for 2 hours then quenched with HOAc (0.51 mL, 9 mmol). The reaction mixture stirred for 20 minutes and mixed with IPE (250 mL) and water (200 mL). The layers were separated, and the aqueous layer was extracted with 3×100 mL IPE. The combined organics were washed with 200 mL water, and then dried over MgSO$_4$. After filtering off the solids, the mother liquor was concentrated to the crude product by rotary evaporation. The residue was purified by flash column chromatography (0% to 75% EtOAc in Hexane) to give the desired product. Yield: 1.28 g, 89%. $^1$H NMR (400 MHz, CDCl$_3$): δ 1.77 (6 H, s) 2.62 (3 H, s) 7.16 (1 H, d, J=8.59 Hz) 7.31-7.40 (2 H, m).

Step 5: 2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-methyl-phenyl)-2-methyl-propionitrile

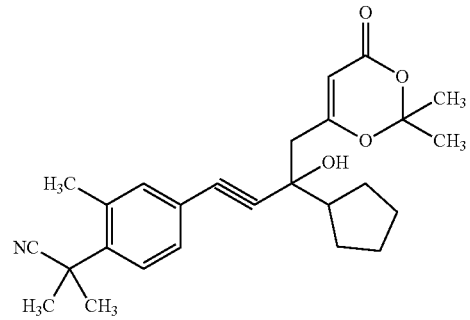

A mixture of 2-(4-bromo-2-methyl-phenyl)-2-methyl-propionitrile (1.24 g, 5.2 mmol), 6-(2-cyclopentyl-2-hydroxy-but-3-ynyl)-2,2-dimethyl-4H-1,3-dioxin-4-one (1.37 g, 5.2 mmol), PdCl$_2$(PPh$_3$)$_2$ (0.13 g, 4 mol %) and CuI (7.9 mg, 8 mol %). in diisopropylamine (4 mL) and DMF (8 mL) was heated at 90° C. for 40 min. The reaction mixture was cooled to room temperature and diluted with EtOAc (250 mL), then washed with aqueous NH$_4$Cl, brine and dried over Na$_2$SO$_4$. The solvent was removed in vacuo and the residue was purified by flash column chromatography to give the desired product. Yield: 1.28 g, 57%. $^1$H NMR (400 MHz, CDCl$_3$) δ: 1.38-1.40 (1 H, m) 1.52-1.62 (6 H, m) 1.65-1.71 (7 H, m)

1.92-1.99 (2 H, m) 2.33-2.42 (2 H, m) 2.53 (3 H, s) 2.56-2.67 (3 H, m) 5.43 (1 H, s) 6.95-7.04 (2 H, m) 7.22 (1 H, d, J=8.08 Hz). MS (ESI): 420 (M−H).

Step 6: 6-Cyclopentyl-6-[2-(5-ethyl-4-hydroxy-2-propoxy-phenyl)-ethyl]-dihydro-pyran-2,4-dione

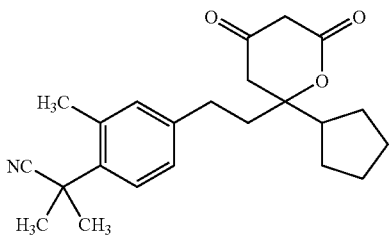

2-{4-[3-Cyclopentyl-4-(2,2-dimethyl-6-oxo-6H-[1,3]dioxin-4-yl)-3-hydroxy-but-1-ynyl]-2-methyl-phenyl}-2-methyl-propionitrile (1.28 g, 3.0 mmol, from step 5 above was dissolved in and treated with Pd(OH)$_2$ (0.38 g, 20 wt % Degussa type). The mixture was stirred under a balloon of hydrogen overnight. The reaction mixture was filtered through a celite pad, followed by washing with EtOAc. The filtrate was concentrated to a pale yellow solid. The solid was dissolved in NaOH (0.3 M in MeOH, 15 mL, 4.5 mmol). The reaction was stirred at room temperature for 3 hours then quenched with 75 mL saturated NH$_4$Cl and 3 mL 1 N HCl. To this solution was added 100 mL CH$_2$Cl$_2$ and the layers were separated. The aqueous layer was extracted with 2×75 mL CH$_2$Cl$_2$ and the organic layers were combined. After drying the organic layer with MgSO$_4$, and filtering to remove the solids, the solvent was removed by rotary evaporation. The remaining oil was purified by flash chromatography to yield the desired product (0.52 g, 47% yield). $^1$H NMR (400 MHz, CDCl$_3$): δ: 1.38-1.40 (1 H, m) 1.52-1.62 (6 H, m) 1.65-1.71 (7 H, m) 1.92-1.99 (2 H, m) 2.33-2.42 (2 H, m) 2.53 (3 H, s) 2.56-2.67 (3 H, m) 5.43 (1 H, s) 6.95-7.04 (2 H, m) 7.22 (1 H, d, J=8.08 Hz). MS (ESI): 366 (M−H).

Example A(79)

2-[4-(2-{2-Cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-fluoro-5-hydroxyphenyl]-2-methylpropanenitrile

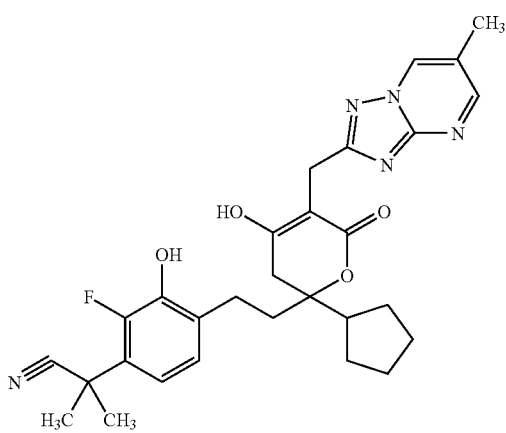

2-(4-{2-[1-Cyclopentyl-3-hydroxy-4-(6-methyl-[1,2,4]triazolo[1,5-a]pyrimidin-2-ylmethyl)-5-oxo-cyclohex-3-enyl]-ethyl}-2-fluoro-5-methoxy-phenyl)-2-methyl-propionitrile from step 2 below (168 mg, 0.3 mmol) in CH$_2$Cl$_2$ was cooled to −78° C. 1M boron tribromide (3.06 mL, 3.1 mmol) was slowly added at −78° C. The reaction mixture was then stirred for 0.5 hr at −78° C., and at room temperature for an additional 2.5 hrs. Ice water (6 mL), followed by concentrated HCl (0.5 mL), were slowly added to the reaction mixture. The resulting mixture was stirred for another 0.5 hr then extracted 3 times with CH$_2$Cl$_2$ (3×75 mL). The combined organic CH$_2$Cl$_2$ layer was washed with brine (75 mL), dried over MgSO$_4$, and concentrated in vacuo. The residue was purified via flash column chromatography to give the desired product (25 mg, 15% yield). $^1$H NMR (400 MHz, CDCl$_3$) δ: 1.69-1.79 (10 H, m) 1.90-1.98 (3 H, m) 2.33-2.43 (2 H, m) 2.45-2.53 (6 H, m) 2.58-2.69 (4 H, m) 4.02-4.16 (2 H, m) 6.78 (1 H, d, J=11.87 Hz) 6.91 (1 H, d, J=6.82 Hz) 8.62 (1 H, s) 8.70 (1 H, s). MS (ESI): 532 (M−H).

Step 1:
(4-Bromo-2-fluoro-5-methoxy-phenyl)-methanol

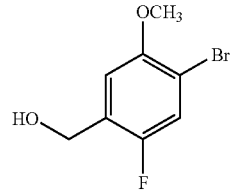

Bromine (15 mL, 0.3 mol) was added slowly to a solution of 2-fluoro-5-methoxy-benzaldehyde (23.1 g, 0.15 mol) in chloroform (500 mL) and the mixture was stirred at room temperature for 5 days. The mixture was poured into water (200 ml) and extracted with chloroform (2×200 mL). The organics were washed with water, brine, dried over MgSO$_4$, filtered and concentrated. The residue was purified by flash column chromatography (2-16% EtOAc in hexanes to give 4-bromo-2-fluoro-methoxy-benzaldehyde (20.7 g, 60%). To a solution of 4-bromo-2-fluoro-5-methoxy-benzaldehyde (4.0 g, 17.3 mmol) in MeOH at 0° C. was added NaBH$_4$ (0.65 g, 17.3 mmol). After the reaction mixture was stirred at 0° C. for 2 hours, it was allowed to warm to room temperature. The organic layer was taked up in ethyl ether washed with water and dried over MgSO$_4$, filtered and concentrated. The residue was purified by flash chromatography (25-45% EtOAc in hexanes) to give the product. (3.9 g, 99%). $^1$H NMR (300 MHz, CDCl$_3$): δ 3.90 (s, 3 H), 4.74 (d, J=6.02 Hz, 2 H), 6.82 (q, J=6.1 Hz, 1 H), 7.29 (d, J=10.58 Hz, 1 H).

Step 2: 2-(4-{2-[2-Cyclopentyl-4-hydroxy-5-(6-methyl-[1,2,4]triazolo[1,5-a]pyrimidin-2-ylmethyl)-6-oxo-3,6-dihydro-2H-pyran-2-yl]-ethyl}-2-fluoro-5-methoxy-phenyl)-2-methyl-propionitrile

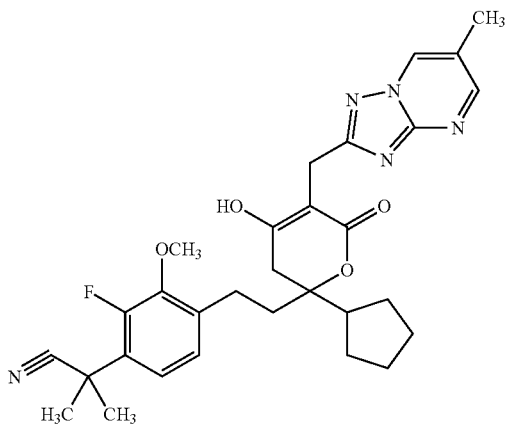

The title compound was prepared analogously to example A(78) where 4-bromo-2-fluoro-5-methoxy-phenyl)-methanol was substituted in place of (4-bromo-2-methyl-phenyl)-methanol in step 1 of that example. MS (ESI): 546 (M−1)

Example A(80)

6-Cyclopentyl-3-[(5,7-dimethyl[1,2,4]triazolo[1,5-a]pyrimidin-2-yl)methyl]-6-{2-[5-fluoro-4-(hydroxymethyl)-2-methoxyphenyl]ethyl}-4-hydroxy-5,6-dihydro-2H-pyran-2-one

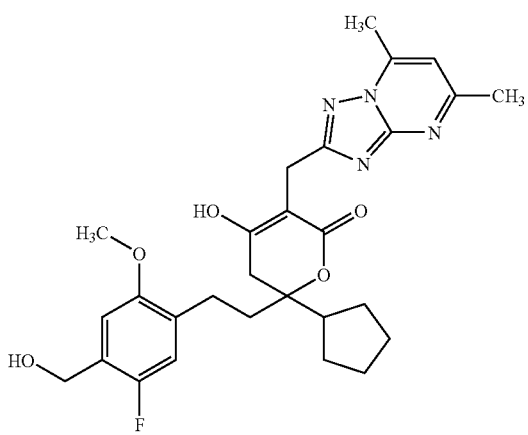

The desired product was prepared analogously to example A(1) substituting 6-cyclopentyl-6-[2-(5-fluoro-4-hydroxymethyl-2-methoxy-phenyl)-ethyl]-dihydro-pyran-2,4-dione (364 mg, 1.0 mmol) from step 2 below in place of 6-cyclopentyl-6-[2-(5-ethyl-4-hydroxy-2-propoxy-phenyl)-ethyl]-dihydro-pyran-2,4-dione. Yield: 52 mg, 12%. $^1$H NMR (400 MHz, CDCl$_3$) δ: 1.53-1.57 (2 H, m) 1.92-2.00 (3 H, m) 2.56-2.75 (12 H, m) 2.79 (3 H, s) 3.78 (3 H, s) 4.12 (2 H, s) 4.68-4.72 (3 H, m) 6.76 (1 H, d, J=10.11 Hz) 6.81 (1 H, d, J=5.81 Hz) 9.93 (1 H, s). MS (ESI): 523 (M−H).

Step 1: 6-[2-Cyclopentyl-4-(S-fluoro-4-hydroxymethyl-2-methoxy-phenyl)-2-hydroxy-but-3-ynyl]-2,2-dimethyl-[1,3]dioxin-4-one

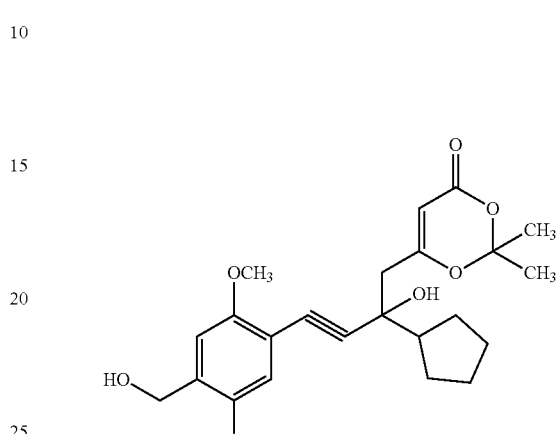

The desired product was prepared analogously to step 5 of example A(78), substituting (4-bromo-2-fluoro-5-methoxy-phenyl)-methanol (2.35 g, 10.0 mmol) from step 1 of A(79) in place of 2-(4-bromo-2-methyl-phenyl)-2-methyl-propionitrile. Yield: 4.4 g, 98%. $^1$H NMR (400 MHz, CDCl$_3$) δ: 1.33-1.45 (1 H, m) 1.52-1.64 (3 H, m) 1.65-1.76 (6 H, m) 1.76-1.85 (2 H, m) 2.18-2.27 (1 H, m) 2.37-2.49 (1 H, m) 2.55-2.66 (3 H, m) 3.82 (3 H, s) 4.73 (2 H, s) 5.53 (1 H, s) 6.91-7.01 (2 H, m). MS (ESI): 417 (M−H).

Step 2: 6-Cyclopentyl-6-[2-(5-fluoro-4-hydroxymethyl-2-methoxy-phenyl)-ethyl]-dihydro-pyran-2,4-dione

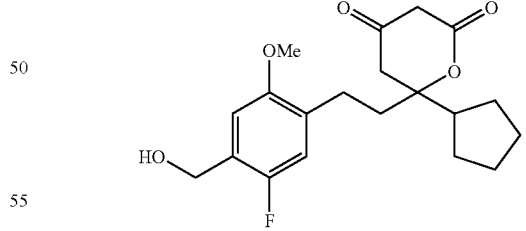

The desired product was prepared analogously to example A(2), where 6-[2-cyclopentyl-4-(5-fluoro-4-hydroxymethyl-2-methoxy-phenyl)-2-hydroxy-but-3-ynyl]-2,2 dimethyl-[1,3]dioxin-4-one (1.28 g, 3.03 mmol) was substituted in place 6-[2-Cyclopentyl-4-(2-ethyl-5-methoxy-pyridin-4-yl)-2-hydroxy-but-3-ynyl]-2,2-dimethyl-[1,3]dioxin-4-one. Yield: 1.4 g, 38%. $^1$H NMR (400 MHz, CDCl$_3$) δ: 1.37-1.49 (1 H, m) 1.53-1.97 (9 H, m) 2.53-2.6 (1 H, m) 2.64-2.7 (1 H, m) 2.75 (2 H, s) 3.41 (2H, s) 3.79 (3 H, s) 4.71 (2 H, s) 6.79 (1 H, d, J=9.85 HZ) 6.87 (1 H, d, J=5.81 Hz). MS (ESI): 363 (M−H).

Example A(81)

N-{(1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethyl}ethanesulfonamide

Example A(82)

N-{(1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethyl}-2,2,2-trifluoroethanesulfonamide

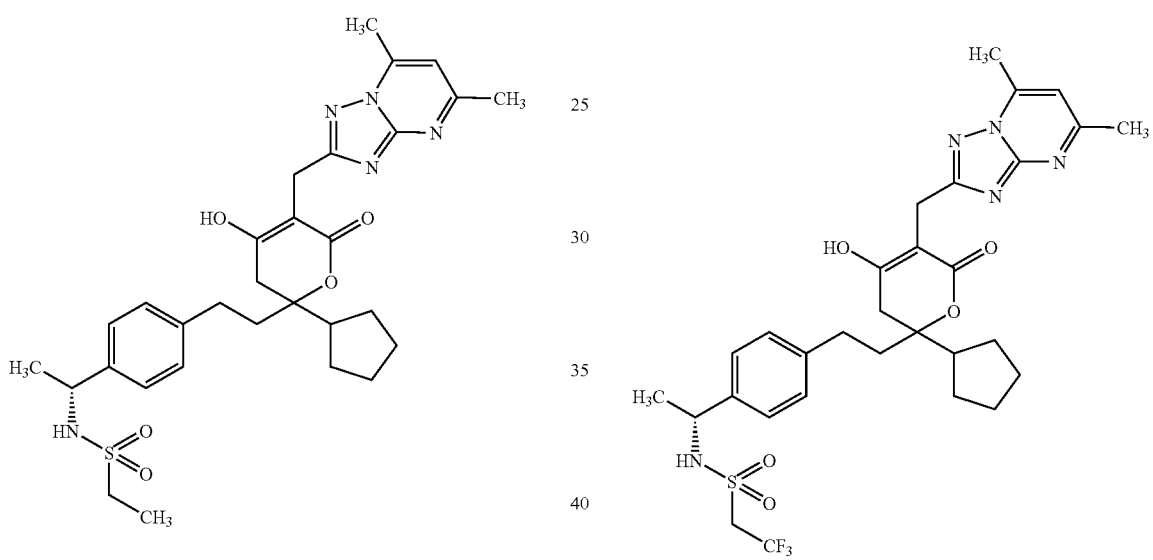

The title compound was prepared analogously to example A(1) where N-((1R)-1-{4-[2-(2-cyclopentyl-4,6-dioxotetrahydro-2H-pyran-2-yl)ethyl]phenyl}ethyl)ethanesulfonamide (Example A(87) was substituted in place of 6-cyclopentyl-6-[2-(5-ethyl-4-hydroxy-2-propoxy-phenyl)-ethyl]-dihydro-pyran-2,4-dione of that example. $^1$H NMR (300 MHz, DMSO-$d_6$): δ 1.07 (t, J=7.3 Hz, 3 H), 1.4 (d, J=6.9 Hz, 3 H), 1.5-1.8 (m, 9 H), 2.11-2.16 (m, 2 H), 2.48-2.59 (m, 7 H), 2.78-2.83 (m, 3 H), 3.71 (d, J=16 Hz, 1 H), 3.85 (d, J=16 Hz, 1 H), 4.03 (t, J=14, 7.3 Hz, 2 H), 4.39-4.45 (m, 1 H), 7.06 (s, 1 H), 7.21-7.31 (m, 4 H), 7.66 (d, J=8.3 Hz, 1 H), 10.9 (s, 1 H). Anal. Calcd. For $C_{30}H_{39}N_5O_5S$: C, 61.94; H, 6.76; N, 12.04. Found: C, 61.80; H, 6.87; N, 12.20. ESIMS (MH+): 582.

The title compound was prepared analogously to example A(1) where N-((1R)-1-{4-[2-(2-cyclopentyl-4,6-dioxotetrahydro-2H-pyran-2-yl)ethyl]phenyl}ethyl)-2,2,2-trifluoroethanesulfonamide (Example A(88))was substituted in place of 6-cyclopentyl-6-[2-(5-ethyl-4-hydroxy-2-propoxy-phenyl)-ethyl]-dihydro-pyran-2,4-dione of that example. $^1$H NMR (300 MHz, DMSO-$d_6$): δ 1.46 (d, J=6.6 Hz, 3H), 1.55-1.81 (m, 11 H), 2.16-2.20 (m, 2 H), 2.52-2.63 (m, 7 H), 2.81 (d, J=17 Hz, 1 H), 3.77 (d, J=16 Hz, 1 H), 3.9 (d, J=16 Hz, 1 H), 4.22-4.33 (m, 2 H), 4.56-4.63 (m, 1 H), 7.09 (s, 1 H), 7.27-7.34 (m, 4H), 8.41 (d, J=8.3 Hz, 1 H), 11 (s, 1 H). Anal.

Calcd. For C₃₀H₃₆F₃N₅O₅S. 0.5H₂O: C, 55.89; H, 5.78; N, 10.86. Found: C, 56.01; H, 5.80; N, 10.94. ESIMS (MH+): 636.

Example A(83)

N-{(1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethyl}methanesulfonamide

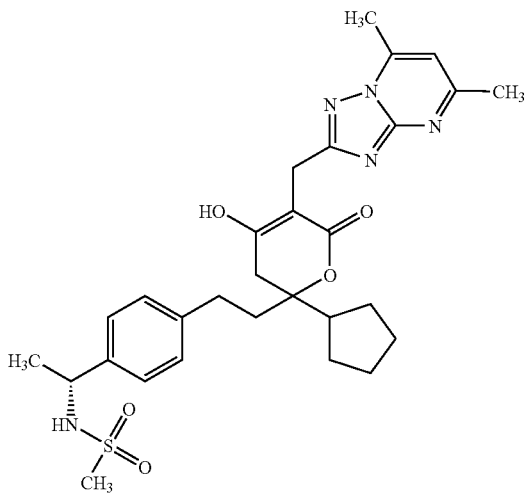

The title compound was prepared analogously to example A(1) where N-(1-{4-[2-(2-cyclopentyl-4,6-dioxo-tetrahydro-pyran-2-yl)-ethyl]-phenyl}-ethyl)-methanesulfonamide from step 2 below was substituted in place of 6-cyclopentyl-6-[2-(5-ethyl-4-hydroxy-2-propoxy-phenyl)-ethyl]-dihydro-pyran-2,4-dione of that example. ¹H NMR (300 MHz, DMSO-d₆): δ 1.4 (d, J=6.8 Hz, 3 H), 1.5-1.8 (m, 9 H), 2.10-2.13 (m, 2 H), 2.48-2.64 (m, 10 H), 2.82 (d, J=17 Hz, 1 H), 3.35 (s, 2 H), 3.71-3.88 (m, 2 H), 4.43-4.48 (m, 1 H), 7.06 (s, 1 H), 7.22-7.31 (m, 4 H), 7.64 (d, J=8.3 Hz, 1 H), 10.88 (s, 1 H). Anal. Calcd. For C₂₉H₃₇N₅O₅S: C, 61.36; H, 6.57; N, 12.34. Found: C, 61.47; H, 6.80; N, 12.30.

Step 1: (R) N-[1-(4-Bromo-phenyl)-ethyl]-methanesulfonamide

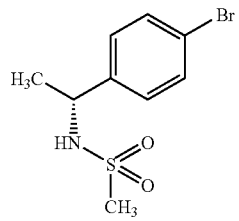

To a stirred solution of (R)-(+)-1-(4-bromophenyl)ethylamine (0.5 g, 2.49 mmol), in anhydrous CH₂Cl₂ (5 mL) under argon were added methane sulfonyl chloride (0.23 mL, 2.99 mmol) and pyridine (0.30 mL, 3.73 mmol). The resulting solution was stirred at 25° C. for 3 hrs. The reaction mixture was quenched with 1N HCl and extracted with EtOAc (30 mL). The organic phase was washed with brine (50 mL), dried over Na₂SO₄ and evaporated. The residue was purified by flash column chromatography (80% EtOAc in hexanes) to give the product (0.40 g, 58%) as a white solid. ¹H NMR (CDCl₃) δ: 1.52 (d, J=6.8 Hz, 3 H), 2.67 (s, 3 H), 4.61-4.72 (m, 2 H), 7.24 (d, J=8.3 Hz, 2 H), 7.51 (d, J=8.3 Hz, 2 H). ESIMS (MNa+): 279.

Step 2: N-(1-{4-[2-(2-Cyclopentyl-4,6-dioxo-tetrahydro-pyran-2-yl)-ethyl]-phenyl}-ethyl)-methanesulfonamide

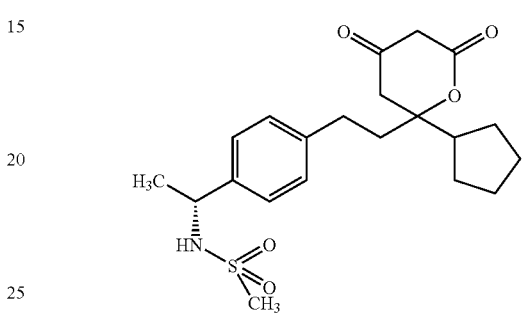

The title compound was prepared analogously to example A(2) where N-[1-(4-bromo-phenyl)-ethyl]-methanesulfonamide from step 1 above was substituted in place of 4-bromo-2-ethyl-5-methoxy-pyridine in step 6 of that example. ¹H NMR (300 MHz, CDCl₃): δ 1.52 (d, J=7.2 Hz, 3 H), 1.58-1.72 (m, 8 H), 1.93-2.05 (m, 2 H), 2.27-2.30 (m, 2 H), 2.66 (s, 3 H), 2.45-2.46 (m, 1 H), 2.78 (s, 2 H), 3.42 (d, J=2.7 Hz, 2 H), 4.54 (d, J=3.0 Hz, 1 H), 4.60-4.65 (m, 1 H), 7.15 (d, J=8.3 Hz, 2 H), 7.26 (d, J=8.3 Hz, 2 H). Anal. Calcd. For C₂₁H₂₉NO₅S: C, 61.89; H, 7.17; N, 3.44. Found: C, 61.94; H, 7.40; N, 3.59. ESIMS (MH−): 406.

Example A(84)

2-[4-(2-{2-Cyclopentyl-5-[(1,3-dimethyl-1H-1,2,4-triazol-5-yl)methyl]-4-hydroxy-6-oxo-3,6-dihydro-2H-pyran-2-yl}ethyl)-2-fluorophenyl]-2-methylpropanenitrile

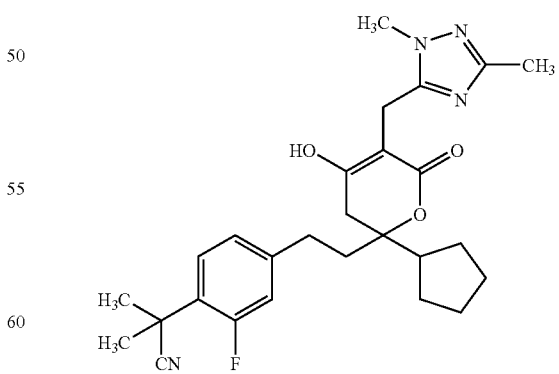

The title compound was prepared analogously to example A(1), where 2-{4-[2-(2-Cyclopentyl-4,6-dioxo-tetrahydro-pyran-2-yl)-ethyl]-2-fluoro-phenyl}-2-methyl-propionitrile from step 3 below, was substituted in place of 6-[2-(3-Chloro- 5-ethyl-4-methoxy-phenyl)-ethyl]-6-cyclopentyl-dihydro-pyran-2,4-dione and 2,5-Dimethyl-2H-[1,2,4]triazole-3-carbaldehyde was substituted instead of 5,7-Dimethyl-[1,2,4]triazolo[1,5-a]pyrimidine-2-carbaldehyde in that example. $^1$H NMR (300 MHz, DMSO-d$_6$): δ 1.49-1.69 (m, 8 H), 1.72 (s, 6 H), 2.06 (s, 3 H), 2.11 (s, 3 H), 2.12-2.13 (m, 2 H), 2.34-2.42 (m, 1H), 2.55-2.66 (m, 3H), 2.80 (d, J=17 Hz, 1 H), 3.42-3.65 (m, 2 H), 7.08-7.18 (m, 2 H), 7.35-7.40 (m, 1 H). Anal. Calcd. For C$_{27}$H$_{33}$FN$_4$O$_3$.0.25H$_2$O: C, 66.85; H, 6.96; N, 11.55. Found: C, 66.88; H, 6.99; N, 11.60. ESIMS (MH+): 481.

Step 1: (4-Bromo-2-fluoro-phenyl)-acetonitrile

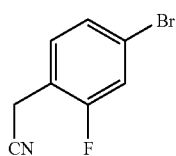

To a solution of 4-bromo-1-bromomethyl-2-fluoro-benzene (8.15 g, 30.4 mmol) dissolved in DMF (16 mL) were added sodium cyanide (2.24 g, 45.6 mmol) and water (2 mL). The reaction was stirred for one hour at 70° C. To the reaction was added 130 mL water; 120 mL saturated NaHCO$_3$, and 100 mL EtOAc. The layers were separated, and the aqueous layer was extracted with 3×100 mL EtOAc. The combined organics were washed with 100 mL water, and then dried over Na$_2$SO$_4$. After filtering off the solids, the mother liquor was concentrated to the desired product by rotary evaporation (6.5 g, 99% yield). MS (APCI): 240 (M+H), 242 (M+2+H).

Step 2:
2-(4-Bromo-2-fluoro-phenyl)-2-methyl-propionitrile

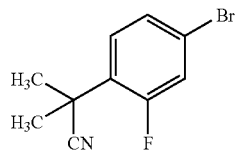

To a slurry of sodium hydride (60% dispersion in mineral oil, 0.82 g, 20.6 mmol) in DMF (20 mL) cooled to 0° C. was added a solution of (4-bromo-2-fluoro-phenyl)-acetonitrile (2.0 g, 9.35 mmol) from Step 1 above, dissolved in THF (10 mL). The reaction was stirred till gas evolution ceased, and then iodomethane (1.3 mL, 20.6 mmol) was added slowly. The reaction was stirred for 30 minutes, and then diluted with 100 mL EtOAc. The solids were removed by filtration, and the organic layer was washed with 100 mL water. The organic layer was dried over MgSO$_4$, and then filtered. The mother liquor was concentrated by rotary evaporation, and the product was distilled under high vacuum (0.3 torr, 45° C.). Yield: 2.25 g, 99%. %. $^1$H NMR (CDCl$_3$) δ: 2.81 (s, 3H), 2.88 (s, 3H), 7.20-7.25 (m, 3H).

Step 3: 2-{4-[2-(2-Cyclopentyl-4,6-dioxo-tetrahydro-pyran-2-yl)-ethyl]-2-fluoro-phenyl}-2-methyl-propionitrile

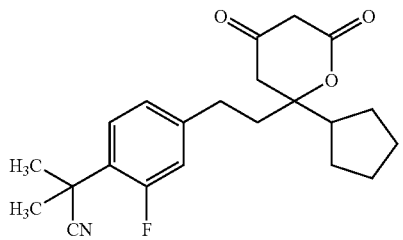

The title compound was prepared analogously to example A(2) where 2-(4-bromo-2-fluoro-phenyl)-2-methyl-propionitrile from step 2 above was substituted in place of 4-bromo-2-ethyl-5-methoxy-pyridine in step 6 of that example. $^1$H NMR (CDCl$_3$) δ: 1.60-1.73 (m, 6 H), 1.92-1.98 (m, 2 H), 2.22-2.30 (m, 1 H), 2.65-2.71 (m, 2 H), 2.75-2.80 (m, 2 H), 6.88-6.96 (m, 2 H), 7.37-7.43 (m, 1H).

Example A(85)

2-[4-(2-{2-Cyclopentyl-5-[(1-ethyl-1H-pyrazol-4-yl)methyl]-4-hydroxy-6-oxo-3,6-dihydro-2H-pyran-2-yl}ethyl)-2-fluorophenyl]-2-methylpropanenitrile

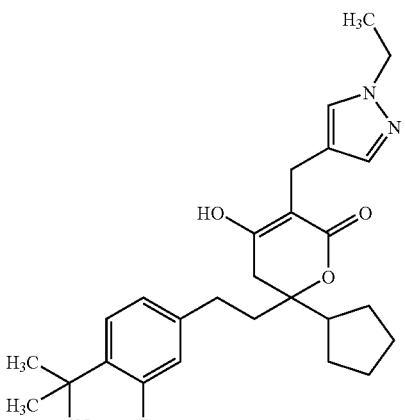

The title compound was prepared analogously to example A(84) where 1-ethyl-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.19 (t, J=7.4 Hz, 3 H), 1.31-1.52 (m, 8 H), 1.70 (s, 6 H), 1.77-1.98 (m, 2 H), 2.55-2.72 (m, 4H), 3.15-3.19 (m, 2H), 3.84 (m, 2 H), 3.98-4.07 (m, 2 H), 6.66-6.91 (m, 2 H), 7.15-

Example A(86)

2-[4-(2-{2-Cyclopentyl-4-hydroxy-5-[(1-methyl-1H-pyrazol-4-yl)methyl]-6-oxo-3,6-dihydro-2H-pyran-2-yl}ethyl)-2-fluorophenyl]-2-methylpropanenitrile

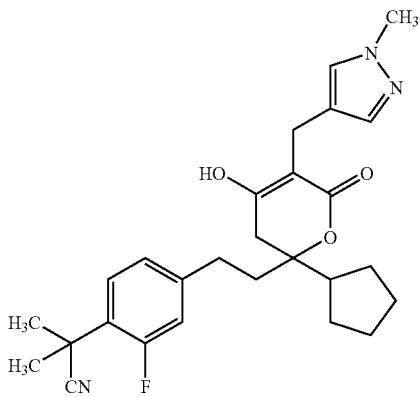

The title compound was prepared analogously to example A(84) where 1-methyl-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.44-1.62 (m, 8 H), 1.72 (s, 6 H), 1.86-1.91 (m, 2H), 2.30-2.36 (m, 2 H), 2.54-2.62 (m, 3 H), 2.72 (d, J=17 Hz, 1 H), 3.29-3.30 (m, 2 H), 3.73 (s, 3H), 6.99-7.17 (m, 4 H), 7.33-7.45 (m, 1 H). Anal. Calcd. For $C_{27}H_{32}FN_3O_3.1.0H_2O$: C, 67.06; H, 7.09; N, 8.69. Found: C, 67.20; H, 6.76; N, 8.65. ESIMS (MH+): 466.

Example A(87)

N-((1R)-1-{4-[2-(2-cyclopentyl-4,6-dioxotetrahydro-2H-pyran-2-yl)ethyl]phenyl}ethyl)ethanesulfonamide

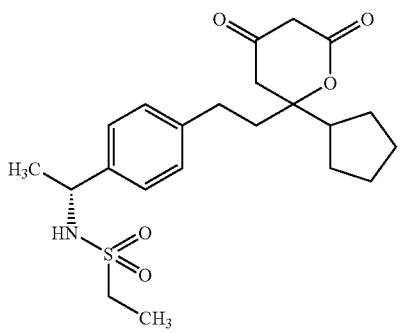

The title compound was prepared analogously to example A(2) where (R)-ethanesulfonic acid [1-(4-bromo-phenyl)-ethyl]-amide from step 1 below was substituted in place of 4-bromo-2-ethyl-5-methoxy-pyridine in step 6 of that example. $^1$H NMR (300 MHz, CDCl3): □ 1.22 (t, J=7.5 Hz, 3H), 1.53 (d, J=6.9 Hz, 3 H), 1.54-1.6 (m, 8 H), 1.93-2.05 (m, 2 H), 2.27-2.30 (m, 2 H), 2.46-2.48 (m, 1 H), 2.65-2.72 (m, 4 H), 2.77 (s, 2 H), 2.83 (d, J=17 Hz, 1 H), 4.57-4.64 (m, 1 H), 7.13-7.15 (m, 2H), 7.24-7.26 (m, 2 H). ESIMS (MH-): 420.

Step 1: (R)-Ethanesulfonic acid [1-(4-bromo-phenyl)-ethyl]-amide

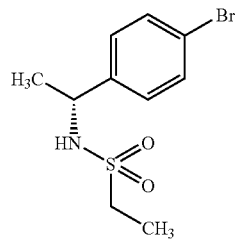

To a stirred solution of (R)-(+)-1-(4-bromophenyl)ethylamine (1 g, 5 mmol), in anhydrous CH$_2$Cl$_2$ (10 mL) under argon were added ethane sulfonyl chloride (0.57 mL, 5.99 mmol) and Pyridine (0.60 mL, 7.5 mmol). The resulting solution was stirred at 25° C. for 3 hrs. The reaction mixture was quenched with 1N HCl and extracted with EtOAc (3×10 mL). The organic phase was washed with brine (50 mL), dried over Na$_2$SO$_4$ and evaporated. The residue was purified by flash column chromatography (80% EtOAc in hexanes) to give the product (0.40 g, 58%) as a white solid. $^1$H NMR (CDCl$_3$) δ: 1.23 (t, J=7.5 Hz, 3 H), 1.52 (d, J=6.8 Hz, 3 H), 2.77 (q, J=14, 7.5 Hz, 2 H), 4.61-4.72 (m, 2 H), 7.24 (d, J=8.3 Hz, 2 H), 7.51 (d, J=8.3 Hz, 2 H). ESIMS (MH+): 293.

Example A(88)

N-((1R)-1-{4-[2-(2-cyclopentyl-4,6-dioxotetrahydro-2H-pyran-2-yl)ethyl]phenyl}ethyl)-2,2,2-trifluoroethanesulfonamide

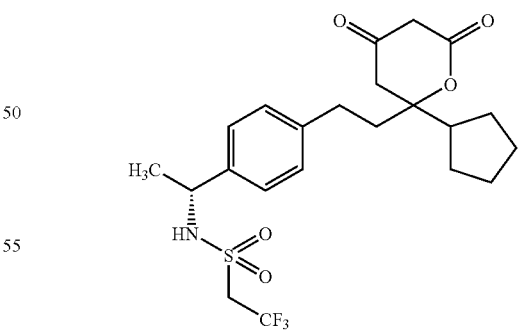

The title compound was prepared analogously to example A(1) where (R) 2,2,2-trifluoro-ethanesulfonic acid [1-(4-bromo-phenyl)-ethyl]-amide. from step 1 below was substituted in place of 1-benzyloxy-2-ethyl-4-iodo-5-propoxy-benzene in step 4 of that example. $^1$H NMR (300 MHz, CDCl$_3$): δ 1.17-1.21 (m, 3 H), 1.51-1.6 (m, 8 H), 1.93-2.0 (m, 2 H), 2.27-2.30 (m, 2 H), 2.67-2.70 (m, 2 H), 2.77 (s, 2 H), 3.71-3.74 (m, 2 H), 3.80-3.83 (m, 1 H), 4.63-4.72 (m, 1 H), 7.16-7.29 (m, 5 H). ESIMS (MH−): 474.

Step 1: (R)-2,2,2-Trifluoro-ethanesulfonic acid [1-(4-bromo-phenyl)-ethyl]-amide

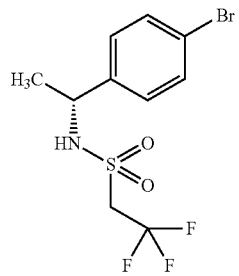

The title compound was prepared analogously to step 1 from example A(81) where 2,2,2'-trifluoroethanesulfonyl chloride was substituted in place of ethane sulfonyl chloride of that example. $^1$H NMR (CDCl$_3$) δ: 1.53 (d, J=6.8 Hz, 3 H), 2.70-2.8 (m, 2 H), 4.61-4.72 (m, 2 H), 7.24 (d, J=8.3 Hz, 2 H), 7.51 (d, J=8.3 Hz, 2 H). ESIMS (MH+): 345

Example A(89)

2-[4-(2-{2-Cyclopentyl-4-hydroxy-6-oxo-5-[(1,3,5-trimethyl-1H-pyrazol-4-yl)methyl]-3,6-dihydro-2H-pyran-2-yl}ethyl)-2-fluorophenyl]-2-methylpropanenitrile

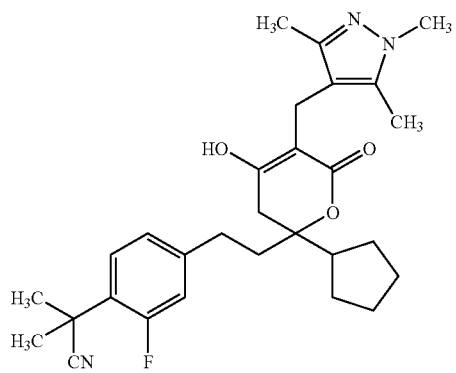

The title compound was prepared analogously to example A(84) where 1,3,5-trimethyl-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.45-1.69 (m, 8 H), 1.72 (s, 6 H), 1.82-1.88 (m, 2H), 2.03 (s, 3 H), 2.12 (s, 3 H), 2.26-2.31 (m, 1 H), 2.49-2.58 (m, 3 H), 2.71 (d, J=17 Hz, 1 H), 3.12 (d, J=14 Hz, 1 H), 3.24 (d, J=14 Hz, 1 H), 3.54 (s, 3 H), 6.94 (dd, J=8.4, 1.6 Hz, 1 H), 7.04 (dd, J=13, 1.6 Hz, 1 H), 7.36 (t, J=8.4 Hz 1 H), 10.68 (s, 1H).

Anal. Calcd. For C$_{29}$H$_{36}$FN$_3$O$_3$: C, 70.56; H, 7.35; N, 8.51. Found: C, 70.70; H, 7.45; N, 8.50. ESIMS (MH+): 494.

Example A(90)

tert-Butyl (1R)-1-{4-[2-(2-cyclopentyl-4,6-dioxotetrahydro-2H-pyran-2-yl)ethyl]phenyl}ethylcarbamate

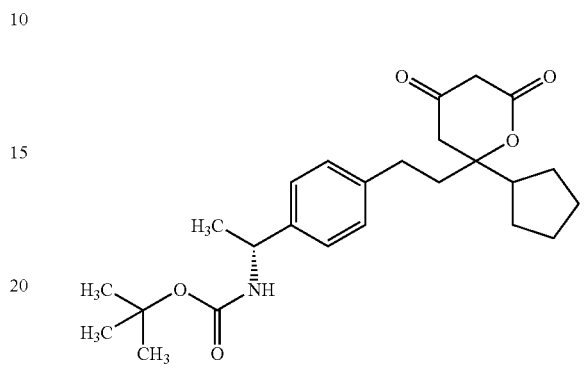

The title compound was prepared analogously to example A(2) where (R)-[1-(4-bromo-phenyl)-ethyl]-carbamic acid tert-butyl ester from step 1 below was substituted in place of 4-bromo-2-ethyl-5-methoxy-pyridine in step 6 of that example. $^1$H NMR (300 MHz, DMSO-d$_6$): δ 1.18 (d, J=6.6 Hz, 3 H), 1.35-1.69 (m, 17 H), 1.94-1.98 (m, 2H), 2.27-2.31 (m, 1 H), 2.63-2.69 (m, 2 H), 2.77 (s, 2H), 3.42 (s, 2 H), 3.81-3.88 (m, 1 H), 4.76 (brs, 1 H), 7.10 (d, J=8.1 Hz, 2 H), 7.23 (d, J=8.1 Hz, 2H). ESIMS (MH+): 430.

Step 1: (R)-[1-(4-Bromo-phenyl)-ethyl]-carbamic acid tert-butyl ester

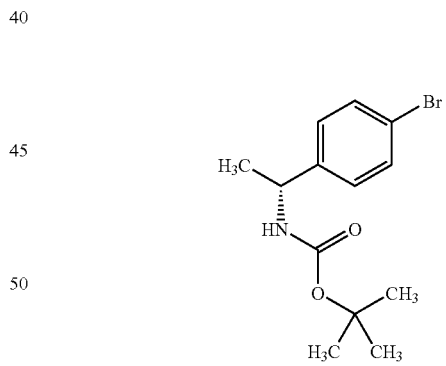

To a stirred solution of (R)-(+)-1-(4-bromophenyl)ethylamine (5 g, 24.99 mmol), in dioxane (50 mL) under argon were added di-tert-butyl dicarbonate (6 g, 27.5 mmol) and NaOH 0.5 M (50 mL). The resulting solution was stirred at 25° C. overnight. The reaction mixture was partitioned between ethyl acetate and 10% citric acid and extracted with ethyl acetate (3×100 mL). The organic phase was washed with brine (50 mL), dried over Na$_2$SO$_4$ and evaporated. The residue solidified to a white solid and was used without further purification. (7 g, 93%). $^1$H NMR (CDCl$_3$) δ: 1.32-1.34 (m, 12 H), 4.68-4.71 (m, 2 H), 7.29-7.12 (m, 2H), 7.36-7.39 (m, 2H). ESIMS (MH+): 302.

Example A(91)

tert-Butyl (1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl) phenyl]ethylcarbamate

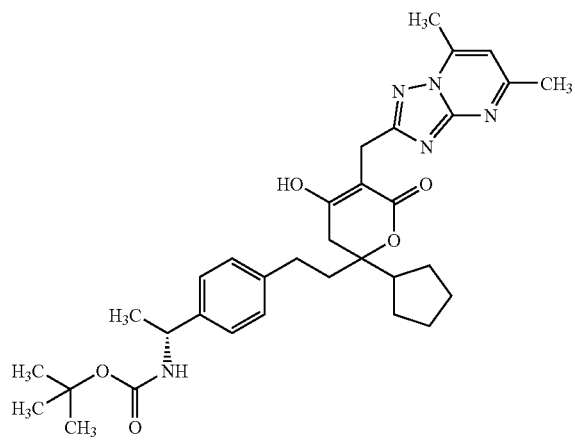

The title compound was prepared analogously to example A(1) where tert-butyl (1R)-1-{4-[2-(2-cyclopentyl-4,6-dioxotetrahydro-2H-pyran-2-yl)ethyl]phenyl}ethylcarbamate (Example A(90) was substituted in place of 6-cyclopentyl-6-[2-(5-ethyl-4-hydroxy-2-propoxy-phenyl)-ethyl]-dihydropyran-2,4-dione of that example. $^1$H NMR (300 MHz, DMSO-d$_6$): δ 1.24-1.66 (m, 21 H), 2.06-2.08 (m, 2H), 2.42-2.61 (m, 9 H), 2.77 (d, J=16 Hz, 1 H), 3.73 (d, J=16 Hz, 1 H), 3.82 (d, J=16 Hz, 1 H), 4.33-4.55 (m, 1 H), 7.05-7.08 (m, 1 H), 7.29-7.40 (m, 4 H), 8.35 (s, 1 H), 11 (s, 1 H). ESIMS (MH+): 590.

Example A(92)

6-(2-{4-[(1R)-1-Aminoethyl]phenyl}ethyl)-6-cyclopentyl-3-[(5,7-dimethyl[1,2,4]triazolo[1,5-]pyrimidin-2-yl)methyl]-4-hydroxy-5,6-dihydro-2H-pyran-2-one

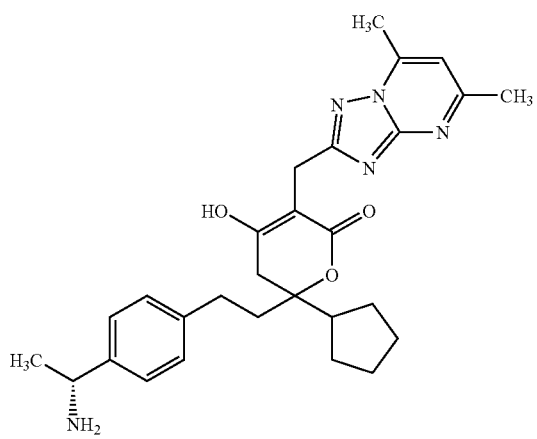

To a stirred solution of tert-butyl (1R)-1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]ethylcarbamate (0.589, 0.98 mmol, example A(91)) in dioxane (2 mL) under argon was added 4 N HCl in dioxane (2 mL). The resulting solution was stirred at 25° C. for 30 minutes. The solvents were completely evaporated and the resultant white solid was recrystallized from ethyl acetate to give the product (0.40 g, 80%) as a white solid. $^1$H NMR (300 MHz, DMSO-d$_6$): δ 1.56-1.77 (m, 11 H), 2.14-2.18 (m, 2 H), 2.57-2.86 (m, 10 H), 3.77-3.94 (m, 2 H), 4.40-4.43 (m, 1 H), 6.6 (brs, 2 H), 7.21 (s, 1 H), 7.38 (d, J=7.9 Hz, 2H), 7.48 (d, J=7.9 Hz, 2 H), 8.56 (s, 1 H), 11.2 (s, 1H). Anal. Calcd. For C$_{28}$H$_{35}$N$_5$O$_3$.1.0HCl. 1.0H20: C, 63.74; H, 7.26; N, 13.27. Found: C, 63.60; H, 7.48; N, 13.20. ESIMS (MH+): 527.

Example A(93)

1-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)phenyl]cyclopropanecarbonitrile

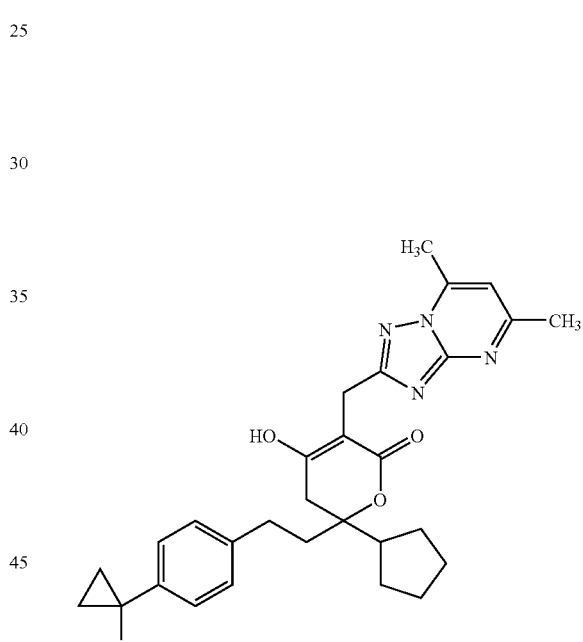

The title compound was prepared analogously to example A(1) where 1-(4-bromophenyl)cyclopropanecarbonitrile was substituted in place of 1-benzyloxy-2-ethyl-4-iodo-5-propoxy-benzene in step 4 of that example. $^1$H NMR (400 MHz, DMSO-d$_6$): δ 1.44-1.48 (m, 2 H), 1.5-1.7 (m, 8H), 1.73-1.77 (m, 2 H), 2.10-2.15 (m, 2H), 2.50-2.60 (m, 11H), 2.82 (d, J=16 Hz, 1H), 3.73 (d, J=16 Hz, 1H), 3.85 (d, J=16 Hz, 1H), 7.08 (s, 1H), 7.23-7.32 (m, 4H), 10.87 (s, 1H). ESIMS (MH+): 512.

Example A(94)

2-[4-(2-{2-Cyclopentyl-5-[(1,5-dimethyl-1H-pyrazol-4-yl)methyl]-4-hydroxy-6-oxo-3,6-dihydro-2H-pyran-2-yl}ethyl)-2-fluorophenyl]-2-methylpropanenitrile

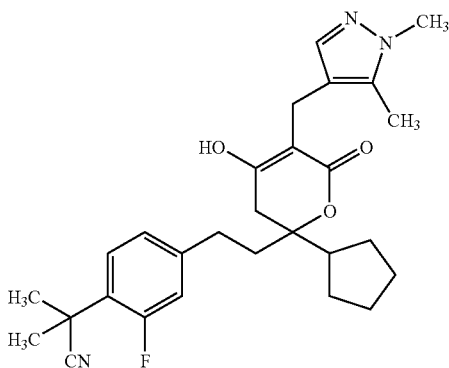

The title compound was prepared analogously to example A(84) where 1,5-dimethyl-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.47-1.66 (m, 8 H), 1.72 (s, 6 H), 1.82-1.89 (m, 2H), 2.11 (s, 3 H), 2.18 (s, 3 H), 2.29-2.32 (m, 1 H), 2.49-2.56 (m, 3 H), 2.70 (d, J=16 Hz, 1 H), 3.16-3.28 (m, 2 H), 6.96-7.09 (m, 3 H). 7.33-7.39 (m, 1 H), 10.7 (s, 1 H). Anal. Calcd. For C$_{28}$H$_{34}$FN$_3$O$_3$·0.5H$_2$O: C, 68.83; H, 7.22; N, 8.60. Found: C, 68.96; H, 7.23; N, 8.60. ESIMS (MH+): 480.

Example A(95)

2-[4-(2-{2-Cyclopentyl-5-[(1-ethyl-3-methyl-1H-pyrazol-4-yl)methyl]-4-hydroxy-6-oxo-3,6-dihydro-2H-pyran-2-yl}ethyl)-2-fluorophenyl]-2-methylpropanenitrile

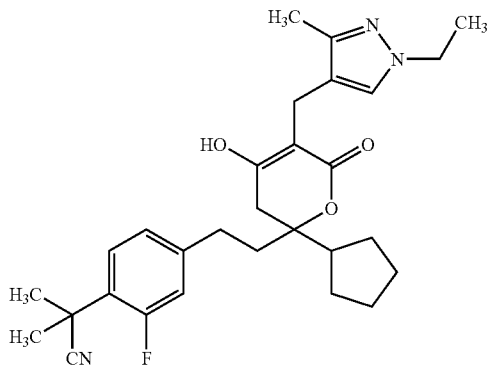

The title compound was prepared analogously to example A(84) where 1-ethyl-3-methyl-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.22 (t, J=7.2 Hz, 3 H), 1.45-1.67 (m, 8 H), 1.72 (s, 6 H), 1.88-1.93 (m, 2H), 2.10 (s, 3 H), 2.19-2.31 (m, 1 H), 2.53-2.61 (m, 2 H), 2.72 (d, J=16 Hz, 1 H), 3.17 (d, J=17 Hz, 1 H), 3.25 (d, J=17 Hz, 1 H), 3.90 (q, J=14, 7.2 Hz, 2 H), 6.98-7.01 (m, 1H), 7.00 (dd, J=8, 1.6 Hz, 1 H), 7.10 (dd, J=13, 1.6 Hz, 1 H), 7.16 (s, 1 H), 7.36 (t, J=8 Hz, 1 H), 10.8 (s, 1 H). Anal. Calcd. For C$_{29}$H$_{36}$FN$_3$O$_3$·0.5H$_2$O: C, 69.30; H, 7.42; N, 8.36. Found: C, 69.38; H, 7.43; N, 8.39. ESIMS (MH+): 494.

Example A(96)

2-[4-(2-{5-[(5-Chloro-1,3-dimethyl-1H-pyrazol-4-yl)methyl]-2-cyclopentyl-4-hydroxy-6-oxo-3,6-dihydro-2H-pyran-2-yl}ethyl)-2-fluorophenyl]-2-methylpropanenitrile

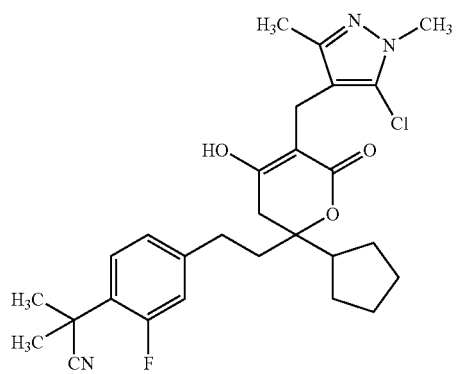

The title compound was prepared analogously to example A(84) where 5-chloro-1,3-dimethyl-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.42-1.67 (m, 8 H), 1.73 (s, 6 H), 1.88-1.93 (m, 2 H), 2.08 (s, 3 H), 2.11 (s, 3 H), 2.28-2.31 (m, 1 H), 2.51-2.61 (m, 3 H), 2.70 (d, J=17 Hz, 1 H), 3.20 (d, J=14 Hz, 1 H), 3.28 (d, J=14 Hz, 1 H), 7.00 (dd, J=8.2, 1.7 Hz, 1 H), 7.08 (dd, J=13, 1.7 Hz, 1 H), 7.36 (t, J=8.2 Hz 1 H), 10.8 (s, 1H). Anal. Calcd. For C$_{28}$H$_{33}$FClN$_3$O$_3$·0.25H$_2$O: C, 64.86; H, 6.51; N, 8.10. Found: C, 64.73; H, 6.42; N, 8.08. ESIMS (MH+): 515.

Example A(97)

2-{4-[2-(5-{[5-Chloro-1-methyl-3-(trifluoromethyl)-1H-pyrazol-4-yl]methyl}-2-cyclopentyl-4-hydroxy-6-oxo-3,6-dihydro-2H-pyran-2-yl)ethyl]-2-fluorophenyl}-2-methylpropanenitrile

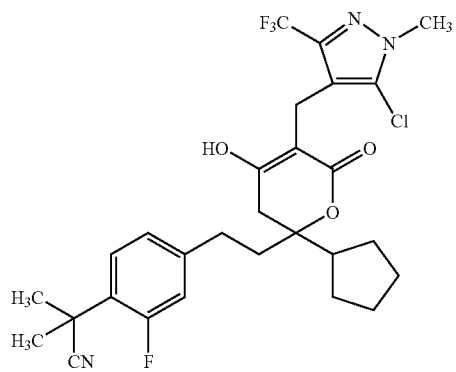

191

The title compound was prepared analogously to example A(84) where 5-chloro-1-methyl-3-trifluoromethyl-1H-pyrazole-4-carbaldehyde was substituted instead of 2,5-dimethyl-2H-[1,2,4]triazole-3-carbaldehyde in that example. $^1$H NMR (300 MHz, DMSO-$d_6$): δ 1.48-1.67 (m, 8 H), 1.76 (s, 6 H), 1.95-1.98 (m, 2 H), 2.38-2.40 (s, 1 H), 2.56-2.72 (m, 4 H), 3.39-3.48 (m, 2 H), 3.86 (s, 3H), 7.06-7.16 (m, 2 H), 7.37-7.43 (m, 1 H), 11 (s, 1 H). Anal. Calcd. For $C_{28}H_{30}F_4ClN_3O_3$: C, 59.21; H, 5.32; N, 7.40. Found: C, 59.04; H, 5.31; N, 7.32. ESIMS (MH+): 569.

Example A(98)

6-[2-(5-Acetyl-4-hydroxy-2-methoxyphenyl)ethyl]-6-cyclopentyl-3-[(5,7-dimethyl[1,2,4]triazolo[1,5-a]pyrimidin-2-yl)methyl]-4-hydroxy-5,6-dihydro-2H-pyran-2-one

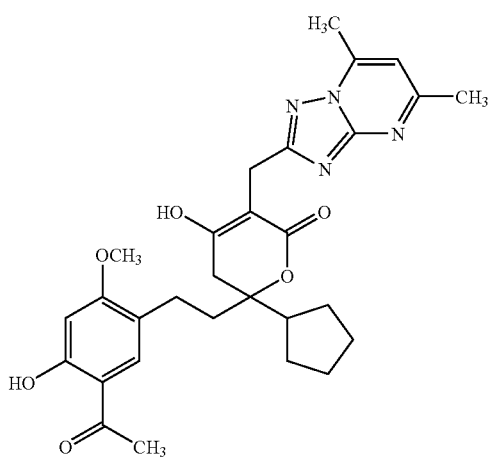

The title compound was prepared analogously to example A(1) where 6-[2-(5-acetyl-4-hydroxy-2-methoxyphenyl)ethyl]-6-cyclopentyldihydro-2H-pyran-2,4(3H)-dione (Example A(99)was substituted in place of 6-cyclopentyl-6-[2-(5-ethyl-4-hydroxy-2-propoxy-phenyl)-ethyl]-dihydro-pyran-2,4-dione of that example. $^1$H NMR (300 MHz, DMSO-$d_6$): δ 1.34-1.66 (m, 8 H), 1.8-2.06 (m, 3 H), 2.32-2.49 (m, 12 H), 2.65 (d, J=17 Hz, 1 H), 3.57-3.72 (m, 6 H), 6.31 (s, 1 H), 6.90 (s, 1 H), 7.46 (s, 1 H), 12.52 (s, 1 H). Anal. Calcd. For $C_{29}H_{34}N_4O_6$·0.25$H_2O$: C, 64.61; H, 6.45; N, 10.39. Found: C, 64.57; H, 6.39; N, 10.22. ESIMS (MH+): 535.

192

Example A(99)

6-[2-(5-Acetyl-4-hydroxy-2-methoxyphenyl)ethyl]-6-cyclopentyldihydro-2H-pyran-2,4(3H)-dione

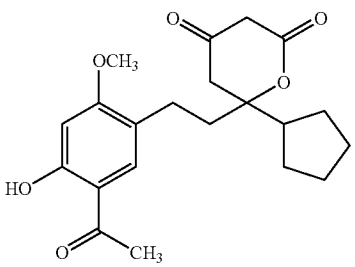

The title compound was prepared analogously to example A(2) where 1-(5-bromo-2-hydroxy-4-methoxy-phenyl)-ethanone from step 1 below was substituted in place of 4-bromo-2-ethyl-5-methoxy-pyridine in step 6 of that example. $^1$H NMR (300 MHz, CDCl$_3$): δ 1.51-1.54 (m, 8H), 1.80-1.95 (m, 2H), 2.29-2.36 (m, 1H), 2.57 (s, 3H), 2.57-2.67 (m, 2H), 2.75 (s, 2H), 3.41 (s, 2H), 3.74 (s, 3H), 6.45 (s, 1H), 7.87 (s, 1H), 12.60 (s, 1H). ESIMS (MH−): 374.

Step 1:
1-(5-Bromo-2-hydroxy-4-methoxy-phenyl)-ethanone

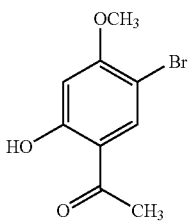

The title compound was prepared analogously to step 3 from example A(22) where 2'-hydroxy-4'-methoxyacetophenone was substituted in place of 5-ethoxy-2-ethyl-phenol of that example. $^1$H NMR (300 MHz, CDCl$_3$): δ 2.56 (s, 3H), 3.93 (s, 3H), 6.46 (s, 1H), 7.87 (s, 1H), 12.67 (s, 1H). ESIMS (MH−): 244.

Example A(100)

2-[4-(2-{2-Cyclopentyl-5-[(1,5-dimethyl-3-oxo-2-phenyl-2,3-dihydro-1H-pyrazol-4-yl)methyl]-4-hydroxy-6-oxo-3,6-dihydro-2H-pyran-2-yl}ethyl)-2-fluorophenyl]-2-methylpropanenitrile

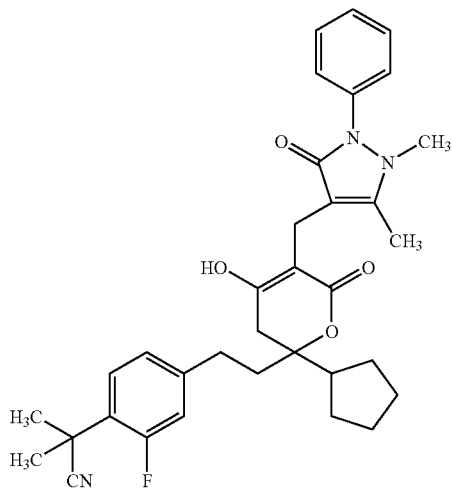

The title compound was prepared analogously to example A(84) where 1,5-dimethyl-3-oxo-2-phenyl-2,3-dihydro-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.45-1.67 (m, 8 H), 1.71 (s, 6 H), 1.88-1.94 (m, 2 H), 2.27-2.30 (m, 1 H), 2.37 (s, 3 H), 2.53-2.65 (m, 4 H), 3.12 (s, 3 H), 3.13-3.18 (m, 2 H), 7.05-7.17 (m,2 H), 7.34-7.41 (m, 5 H), 7.51-7.56 (m, 1 H), 12.3 (s, 1 H). ESIMS (MH+): 572.

Example A(101)

[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile

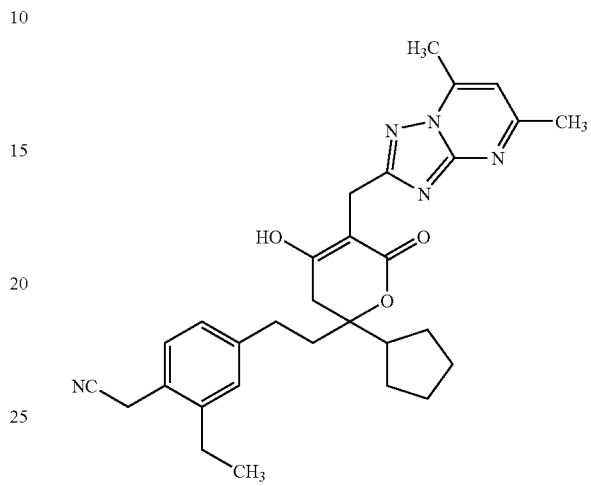

To a solution of {4-[2-(2-cyclopentyl-4,6-dioxotetrahydro-2H-pyran-2-yl)ethyl]-2-ethylphenyl}acetonitrile (200 mg, 0.57 mmol, example A(102)) in anhydrous MeOH (6 mL) at room temperature was added 5,7-dimethyl[1,2,4]triazolo[1,5-a]pyrimidine-2-carbaldehyde (120 mg, 0.68 mmol). The mixture was stirred for 5 min before borane-dimethylamine complex (37 mg, 0.62 mmol) was added. The reaction was stirred at that temperature for 15 hours before it was quenched by the addition of 1.0 N HCl. The solvent was removed and the residue was purified by HPLC to obtain the desired product (60 mg, 21% yield). $^1$H NMR (300 MHz, DMSO-d$_6$): δ 1.03 (t, J=7.5 Hz, 3 H), 1.32-1.64 (m, 8 H), 2.06 (m, 2 H), 2.36-2.55 (m, 12 H), 2.73 (d, J=17.9 Hz, 1 H), 3.64 (d, J=16.1 Hz, 1 H), 3.77 (d, J=16.4 Hz, 1 H), 3.89 (s, 2 H), 6.95 (s, 1 H), 7.00 (s, 1 H), 7.04 (d, J=7.7 Hz, 1 H), 7.17 (d, J=7.7 Hz, 1 H), 10.81 (s, 1 H).

Example A(102)

{4-[2-(2-Cyclopentyl-4,6-dioxotetrahydro-2H-pyran-2-yl)ethyl]-2-ethylphenyl}acetonitrile

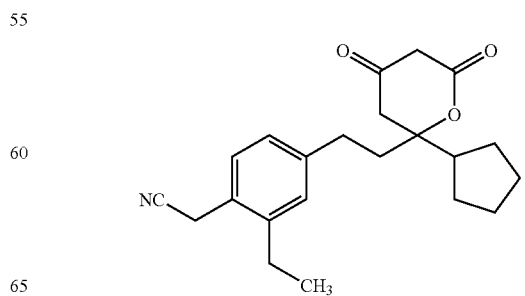

The title compound was prepared analogously to example A(2), where (4-bromo-2-ethyl-phenyl)-acetonitrile (step 4 below) was substituted in place of 4-bromo-2-ethyl-5-methoxy-pyridine (step 6). $^1$H NMR (300 MHz, CDCl$_3$): δ 1.25 (t, J=7.5 Hz, 3 H), 1.41-1.83 (m, 8H), 1.97 (m, 2 H), 2.27 (m, 1 H), 2.65 (m, 4 H), 2.78 (s, 2 H), 3.43 (s, 2 H), 3.67 (s, 2 H), 7.01 (m, 2 H), 7.29 (d, J=8.3 Hz, 1 H).

Step 1: 4-Bromo-2-ethyl-benzoic acid (4641-144)

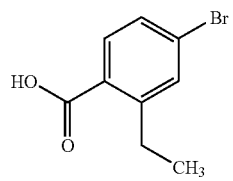

The title compound was prepared according to literature procedure. *J. Med. Chem.*, 1997, 40, 2017-2034.

Step 2: (4-Bromo-2-ethyl-phenyl)-methanol

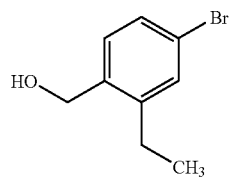

To a solution of 4-bromo-2-ethyl-benzoic acid (115 mmol) in anhydrous THF (380 mL) at 0° C. was added BH$_3$.THF complex (1.0 N solution in THF, 230 mL) over 30 min. The resulting mixture was slowly warmed up to room temperature and the stirred for 15 hours. The reaction was carefully quenched with slow addition of water. The solvent was removed and the residue was taken up in EtOAc. The organic layer was washed with 1.0 N HCl, H$_2$O, brine and dried over MgSO$_4$. The solvent was removed to afford the desired product. (22 g, 89% yield). $^1$H NMR (300 MHz, CDCl$_3$): δ 1.23 (t, J=7.5 Hz, 3 H), 2.64-3.01 (m, 2H), 4.68 (s, 2H), 7.24-7.26 (m, 1H), 7.32-7.36 (m, 2H).

Step 3: 4-Bromo-1-bromomethyl-2-ethyl-benzene

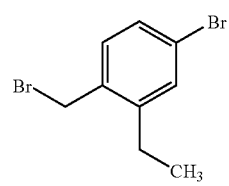

To a solution of (4-bromo-2-ethyl-phenyl)-methanol (7.9 g, 36.7 mmol) in anhydrous CHCl$_3$ (122 mL) was added PBr$_3$(4.2 mL, 44.1 mmol). The resulting mixture was stirred at room temperature for 2 hours before it was quenched by the addition of water. The organic layer was washed with NaHCO$_3$, brine and dried over MgSO$_4$. The solvent was removed in vacuo and the residue was filtered through a pad of silica gel with 20% EtOAc in hexanes. The solvent was removed in vacuo to afford the desired product (8.4 g, 83%). $^1$H NMR (300 MHz, CDCl$_3$): δ 1.29 (t, J=7.5 Hz, 3 H), 2.71-2.78 (m, 2H), 4.48 (s, 2H), 7.17-7.20 (m, 1H), 7.29-7.32 (m, 1 H), 7.36-7.38 (m, 1H).

Step 4: (4-Bromo-2-ethyl-phenyl)-acetonitrile

To a solution of 4-bromo-1-bromomethyl-2-ethyl-benzene (2.0 g, 7.25 mmol) in DMF/H$_2$O (30 mL/6 mL) was added potassium cyanide (471 mg, 7.25 mmol). The reaction mixture was heated to 45° C. for 3 hours before it was cooled to room temperature. The mixture was diluted with Et$_2$O and washed with H$_2$O, brine and dried over MgSO$_4$. The solvent was removed in vacuo to obtain the desired product (1.33 g, 80% yield). $^1$H NMR (300 MHz, CDCl$_3$): δ 1.26 (t, J=7.5 Hz, 3 H), 2.60-2.67 (m, 2 H), 3.66 (s, 2H), 7.23-7.26 (m, 1H), 7.35-7.36 (m, 1 H), 7.38-7.40 (m, 1H).

Example A(103)

[4-(2-{2-cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-ethylphenyl]acetonitrile

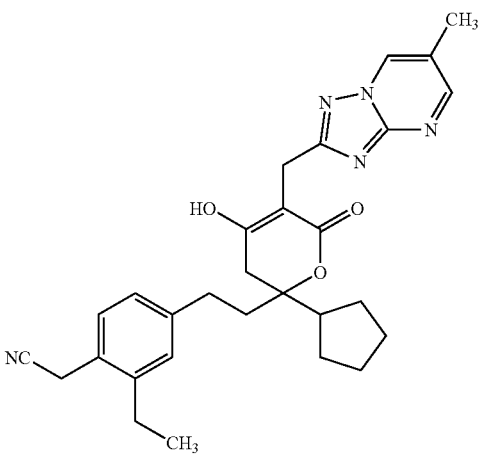

The title compound was prepared analogously to example A(101), where 6-methyl[1,2,4]triazolo[1,5-a]pyrimidine-2-carbaldehyde was substituted in place of 5,7-dimethyl[1,2,4]triazolo[1,5-a]pyrimidine-2-carbaldehyde. $^1$H NMR (300 MHz, DMSO-d$_6$): δ 1.15 (t, J=7.5 Hz, 3 H), 1.38-1.71 (m, 8 H), 2.11 (m, 2 H), 2.38 (s, 3 H), 2.42-2.66 (m, 6 H), 2.82 (d, J=18.2 Hz, 1 H), 3.76 (d, J=16.2 Hz, 1 H), 3.84 (d, J=16.1 Hz, 1 H), 3.98 (s, 2 H), 7.11 (m, 2 H), 7.27 (d, J=8.3 Hz, 1 H), 8.71 (s, 1 H), 8.96 (s, 1 H), 10.88 (s, 1 H).

Example A(104)

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]methanesulfonamide

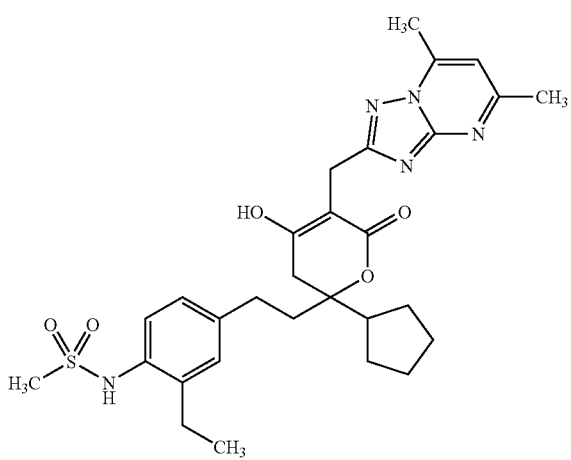

The title compound was prepared analogously to example A(101) where N-{4-[2-(2-cyclopentyl-4,6-dioxo-tetrahydropyran-2-yl)-ethyl]-2-ethyl-phenyl}-methanesulfonamide was substituted in place of {4-[2-(2-cyclopentyl-4,6-dioxotetrahydro-2H-pyran-2-yl)ethyl]-2-ethylphenyl}acetonitrile. $^1$H NMR (300 MHz, DMSO-d$_6$): δ 1.11 (t, J=7.5 Hz, 3 H), 1.41-174 (m, 8 H), 2.13 (m, 2 H), 2.47 (s, 3 H), 2.51-2.70 (m, 9 H), 2.83 (d, J=17.7 Hz, 1 H), 2.98 (s, 3 H), 3.74 (d, J=16.4 Hz, 1 H), 3.85 (d, J=16.2 Hz, 1 H), 7.04 (s, 1 H), 7.11 (m, 2 H), 7.20 (d, J=8.6 Hz, 1 H), 8.94 (s, 1 H), 10.86 (s, 1 H).

Example A(105)

N-{4-[2-(2-cyclopentyl-4,6-dioxotetrahydro-2H-pyran-2-yl)ethyl]-2-ethylphenyl}methanesulfonamide

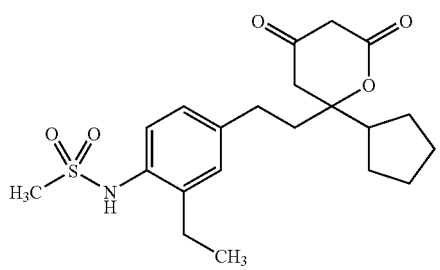

The title compound was prepared analogously to example A(2), where N-(4-bromo-2-ethyl-phenyl)-methanesulfonamide was substituted in place of 4-bromo-2-ethyl-5-methoxy-pyridine (step 6). $^1$H NMR (300 MHz, DMSO): δ 1.07 (t, J=7.5 Hz, 3 H), 1.46-1.70 (m, 8H), 1.89-1.95 (m, 2 H), 2.27-2.38 (m, 1 H), 2.56-2.73 (m, 4 H), 2.96 (s, 3 H), 3.42-3.49 (m, 4 H), 4.99 (s, 1H), 7.00-7.03 (m, 1H), 7.09-7.11 (m, 1 H), 7.17-7.19 (m, 1 H). MS (ESI) (M+Na$^+$): calcd for C$_{21}$H$_{29}$NO$_5$S: 430, found 430.

Step 1:
N-(4-Bromo-2-ethyl-phenyl)-methanesulfonamide

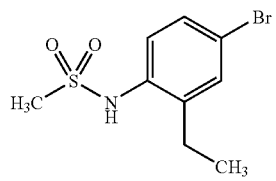

4-Bromo-2-ethyl-aniline (2 mL, 14 mmol) dissolved in anhydrous pyridine (35 mL) at room temperature was treated with methylsulfonyl chloride (1.3 mL, 16.8 mmol). The reaction was stirred at that temperature for 15 hours before it was diluted with EtOAc. The mixture was washed with H$_2$O, brine and dried over MgSO$_4$. The solvent was removed in vacuo and the residue was purified with flash chromatography (SiO$_2$, 5-30% EtOAc in hexanes) to afford the desired product (3.1 g, 81% yield). $^1$H NMR (300 MHz, CDCl$_3$): δ 1.25 (t, J=7.5 Hz, 3 H), 2.61-2.68 (m, 2 H), 3.02 (s, 3 H), 6.36 (s, 1 H), 7.36-7.39 (m, 3 H).

Example A(106)

N-[4-(2-{2-cyclopentyl-4-hydroxy-5-[(6-methyl[1,2,4]triazolo[1,5-a]pyrimidin-2-yl)methyl]-6-oxo-3,6-dihydro-2H-pyran-2-yl}ethyl)-2-ethylphenyl]methanesulfonamide

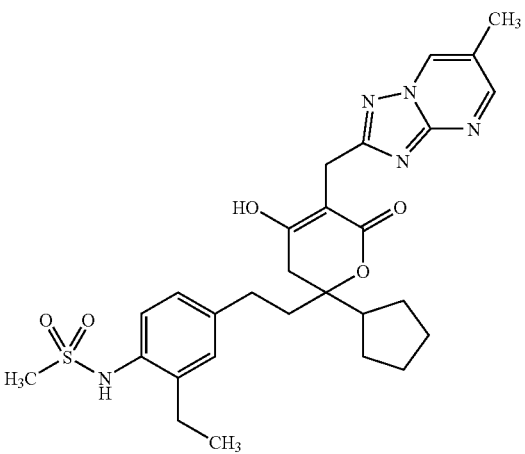

The title compound was prepared analogously to example A(104), where 6-methyl[1,2,4]triazolo[1,5-a]pyrimidine-2-carbaldehyde was substituted in place of 5,7-dimethyl[1,2,4]triazolo[1,5-a]pyrimidine-2-carbaldehyde. $^1$H NMR (300 MHz, DMSO-d$_6$): δ 0.93 (t, J=7.3 Hz, 3 H), 1.19-1.54 (m, 8 H), 1.88 (m, 2 H), 2.18 9s, 3 H), 2.28-2.55 (m, 6 H), 2.62 (d, J=17.0 Hz, 1 H), 2.79 (s, 3 H), 3.56 (d, J=15.8 Hz, 1 H), 3.65

(d, J=16.1 Hz, 1 H), 6.90 (d, J=7.54 Hz, 1 H), 6.93 (s, 1 H), 7.01 (d, J=7.9 Hz, 1 H), 8.51 (d, J=2.4 Hz, 1 H), 8.75 (s, 1 H), 6.79 (s, 1 H), 10.69 (s, 1H).

Example A(107)

N-(4-{2-[2-cyclopentyl-4-hydroxy-6-oxo-5-([1,2,4] triazolo[1,5-a]pyrimidin-2-ylmethyl)-3,6-dihydro-2H-pyran-2-yl]ethyl}-2-ethylphenyl)methane-sulfonamide

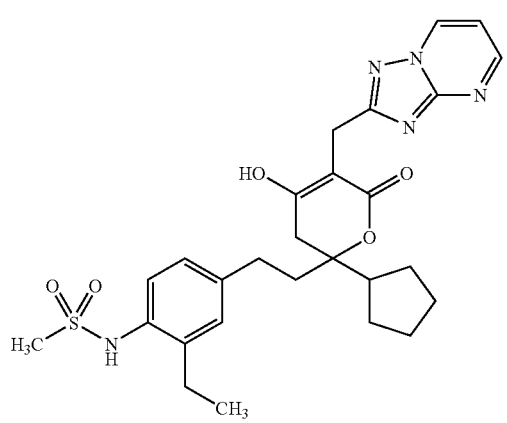

The title compound was prepared analogously to example A(104) where [1,2,4]triazolo[1,5-a]pyrimidine-2-carbaldehyde from step 2 below was substituted in place of 5,7-dimethyl[1,2,4]triazolo[1,5-a]pyrimidine-2-carbaldehyde. $^1$H NMR (300 MHz, DMSO-d$_6$): δ 1.08 (t, J=7.2 Hz, 3 H), 1.27-1.71 (m, 8 H), 2.11 (m 2 H), 2.48-2.75 (m, 6 H), 2.83 (d, J=17.1 Hz, 1 H), 2.99 (s, 3 H), 3.78 (d, J=15.8 Hz, 1 H), 3.87 (d, J=16.2 Hz, 1 H), 7.08 (d, J=6.2 Hz, 1 H), 7.13 (s, 1 H), 7.21 (d, J=8.3 Hz, 1 H), 7.27 (dd, J=6.6, 4.3 Hz, 1 H), 8.81 (d, J=4.3, 1.9 Hz, 1 H), 8.95 (s, 1 H), 9.07 (dd, J=6.8, 1.9 Hz, 1 H), 10.9 (s, 1 H).

Step 1: [1,2,4]Triazolo[1,5-a]pyrimidin-2-ylmethanol

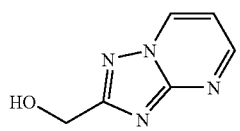

The title compound was prepared analogously to step 7 of example A(1) where malonaldehyde bis(dimethylacetal) was substituted in place of 2,4-pentanedione.

Step 2: [1,2,4]Triazolo[1,5-a]pyrimidine-2-carbaldehyde

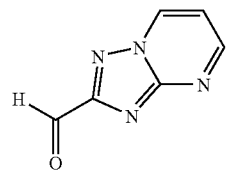

The title compound was prepared analogously to step 8 of example A(1) where [1,2,4]triazolo[1,5-a]pyrimidin-2-yl-methanol was substituted in place of 5,7-dimethyl-[1,2,4]triazolo[1,5-a]pyrimidin-2-yl)-methanol.

Example A(108)

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl] ethanesulfonamide The title compound was prepared analogously to example A(104) where ethanesulfonic acid (4-bromo-2-ethyl-phenyl)-amide was substituted in place of methanesulfonic acid (4-bromo-2-ethyl-phenyl)-amide. $^1$H NMR (300 MHz, DMSO-d$_6$): δ 1.02 (t, J=7.5 Hz, 3 H), 1.05 (t, J=7.5 Hz, 3 H), 1.29-1.67 (m, 9 H), 2.02-2.09 (m, 2 H), 2.38 (s, 3 H), 2.48 (s, 3 H), 2.51-2.56 (m, 2 H), 2.57-2.64 (m, 2H), 2.71-2.77 (m, 1

H), 2.95-3.02 (m, 2 H), 3.62-3.80 (m, 4 H), 6.95-6.96 (m, 1 H), 7.00-7.04 (m, 2H), 7.06-7.09 (m, 1 H).

Step 1: Ethanesulfonic acid (4-bromo-2-ethyl-phenyl)-amide

The title compound was prepared analogously to step 1 of example A(105), where ethylsulfonyl chloride was substituted in place of methylsulfonyl chloride. $^1$H NMR (400 MHz, CDCl$_3$): δ 1.26 (t, J=8.0 Hz, 3 H), 1.39 (t, J=8.0 Hz, 3 H), 2.60-2.66 (m, 2 H), 3.12-3.18 (m, 2 H), 7.32-7.37 (m, 3 H).

Example A(109)

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]propane-1-sulfonamide

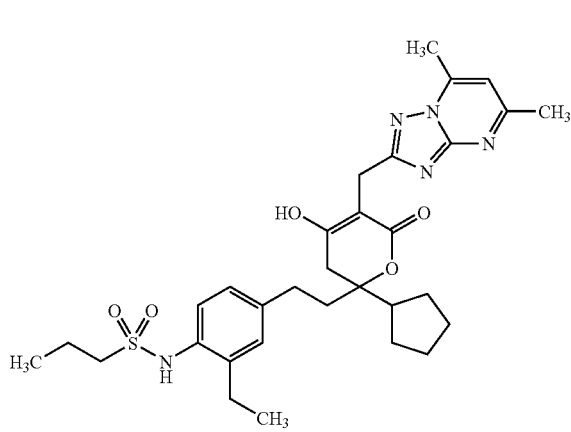

The title compound was prepared analogously to example A(104), where propanesulfonic acid (4-bromo-2-ethyl-phenyl)-amide was substituted in place of methanesulfonic acid (4-bromo-2-ethyl-phenyl)-amide. $^1$H NMR (300 MHz, DMSO-d$_6$): δ 1.00 (t, J=7.5 Hz, 3 H), 1.11 (t, J=7.5 Hz, 3H), 1.55-1.81 (m, 11H), 2.11-2.17 (m, 2 H), 2.47 (s, 3 H), 2.57 (s, 3 H), 2.62-2.72 (m, 6 H), 3.02-3.07 (m, 2 H), 3.71-3.88 (m, 2 H), 7.04 (s, 1 H), 7.10-7.18 (m, 3 H).

Step 1: Propane-1-sulfonic acid (4-bromo-2-ethyl-phenyl)-amide

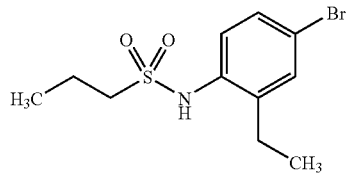

The title compound was prepared analogously to step 1 of example A(105), where propane-1-sulfonyl chloride was substituted in place of methylsulfonyl chloride. $^1$H NMR (400 MHz, CDCl$_3$): δ 1.04 (t, J=8.0 Hz, 3 H), 1.25 (t, J=8.0 Hz, 3 H), 1.81-1.91 (m, 2 H), 2.60-2.66 (m, 2 H), 3.07-3.10 (m, 2 H), 6.29 (s, 1 H), 7.32-7.37 (m, 3 H).

Example A(110)

6-Cyclopentyl-3-[(5,7-dimethyl[1,2,4]triazolo[1,5-a]pyrimidin-2-yl)methyl]-6-{2-[3-ethyl-4-(1H-1,2,4-triazol-1-ylmethyl)phenyl]ethyl}-4-hydroxy-5,6-dihydro-2H-pyran-2-one

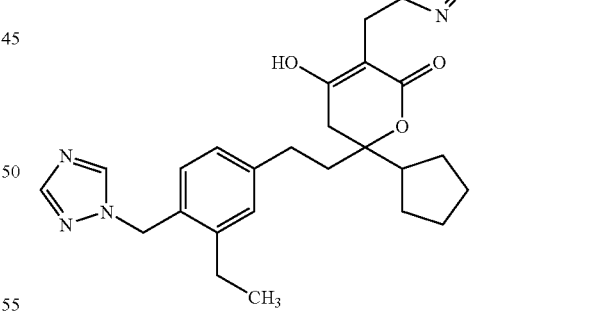

The title compound was prepared analogously to example A(101) where 1-(4-bromo-2-ethyl-benzyl)-1H-[1,2,4]triazole was substituted in place of {4-[2-(2-cyclopentyl-4,6-dioxo-tetrahydro-pyran-2-yl)-ethyl]-2-ethyl-phenyl}-acetonitrile. $^1$H NMR (300 MHz, DMSO-d$_6$): δ 0.95 (t, J=7.5 Hz, 3 H), 1.31-1.62 (m, 8 H), 2.03 (m 2 H), 2.31 (s, 3 H), 2.35-2.62 (m, 9 H), 2.74 (d, J=19.8 Hz, 1 H), 3.64 (d, J=16.6 Hz, 1 H), 3.76 (d, J=17.5 Hz, 1 H), 5.33 (s, 2 H), 6.92 (d, J=8.5 Hz, 1 H), 6.94 (s, 1 H), 6.98 (s, 1 H), 6.99 (d, J=9.2 Hz, 1 H), 7.93 (s, 1 H), 8.54 (s, 1 H), 10.77 (s, 1 H).

Step 1:
1-(4-Bromo-2-ethyl-benzyl)-1H-[1,2,4]triazole

Triazole (275 mg, 3.99 mmol) dissolved in anhydrous DMF (15 mL) was treated with NaH (60%, 153 mg). After 5 min, 4-bromo-1-bromomethyl-2-ethyl-benzene was added. The reaction mixture was heated to 75° C. for 5 hours before it was cooled to room temperature. The mixture was diluted with Et$_2$O and washed with H$_2$O, brine, dried over MgSO$_4$. The solvent was removed in vacuo to afford the desired product (580 mg, 55% yield). $^1$H NMR (300 MHz, CDCl$_3$): δ 1.10 (t, J=7.5 Hz, 3H), 2.68-2.73 (m, 2 H), 5.46 (s, 2 H), 7.01-7.04 (m, 1 H), 7.38-7.46 (m, 2 H), 7.97-8.01 (m, 2 H).

Example A(111)

6-Cyclopentyl-3-[(5,7-dimethyl[1,2,4]triazolo[1,5-a]pyrimidin-2-yl)methyl]-6-[2-(3-ethyl-4-methylphenyl)ethyl]-4-hydroxy-5,6-dihydro-2H-pyran-2-one

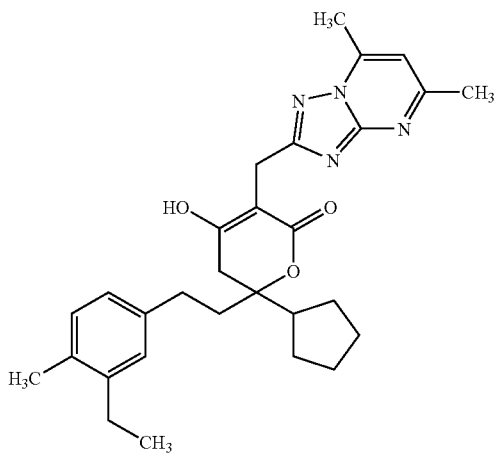

To a solution of 6-[2-cyclopentyl-4-(3-ethyl-4-methylphenyl)-2-hydroxy-butyl]-2,2-dimethyl-[1,3]dioxin-4-one (1.0 g, 1.94 mmol) K$_2$CO$_3$ (1.07 g, 7.75 mmol) was added. The mixture was heated to 45° C. for 45 min before it was cooled down to room temperature. The reaction was diluted with H$_2$O and washed with isopropyl ether. The aqueous was acidified to pH 1 with 1.0 N HCl and extracted with EtOAc. The organic layer was washed with H$_2$O, brine, dried over MgSO$_4$ and concentrated under reduced pressure to afford the desired product. (0.63 g, 71% yield). $^1$H NMR (300 MHz, DMSO-d$_6$): δ 0.98 (t, J=7.5 Hz, 3 H), 1.32-1.64 (m, 8 H), 2.04 (m, 2 H), 2.12 (s, 3 H), 2.33-2.51 (m, 12 H), 2.71 (d, J=17.5 Hz, 1 H), 3.64 (d, J=16.0 Hz, 1 H), 3.74 (d, J=16.2 Hz, 1 H), 6.83 (d, J=7.7 Hz, 1 H), 6.84 (s, 1 H), 6.92 (d, J=7.3 Hz, 1 H), 6.96 (s, 1 H), 10.75 (s, 1 H).

Step 1: (4-Bromo-2-ethyl-benzyloxy)-tert-butyl-dimethyl-silane

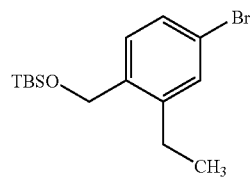

To a solution of (4-bromo-2-ethyl-phenyl)-methanol in anhydrous DMF was added TBSCl (1.5 eq.) and imidazole (1.5 eq). The mixture was stirred at that temperature for 12 hours before it was diluted with water. The mixture was extracted with Et$_2$O and the combined organic layers were washed with H$_2$O, brine, dried over MgSO$_4$ The solvent was removed in vacuo to give the desired product. (93% yield). $^1$H NMR (300 MHz, CDCl$_3$): δ 0.09 (s, 6 H), 0.92 (s, 9 H), 1.20 (t, J=7.5 Hz, 3H), 2.57 (q, J=7.5 Hz, 2 H), 4.67 (s, 2 H), 7.29 (s, 3 H).

Step 2: 6-{4-[4-(tert-Butyl-dimethyl-silanyloxymethyl)-3-ethyl-phenyl]-2-cyclopentyl-2-hydroxy-but-3-ynyl}-2,2-dimethyl-[1,3]dioxin-4-one

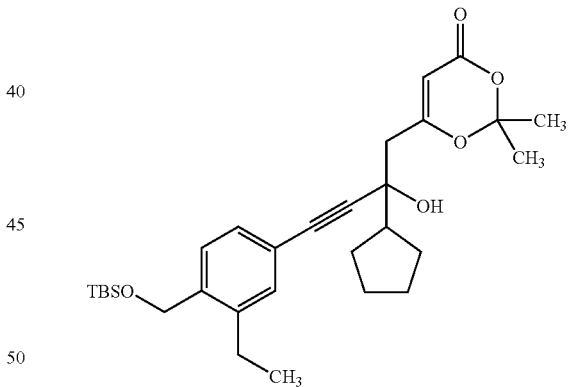

To a solution of (4-bromo-2-ethyl-benzyloxy)-tert-butyl-dimethyl-silane (1.0 g, 3.05 mmol) and 6-(2-cyclopentyl-2-hydroxybut-3-ynyl)-2,2-dimethyl-4H-1,3-dioxin-4-one (671 mg, 2.54 mmol) diisopropylamine (7 mL) and DMF (7 mL) was added PdCl$_2$(PPh$_3$)$_2$ (71 mg, 4 mol %) and CuI (14 mg, 3 mol %). The mixture was purged with Ar and heated to 90° C. for 30 min before it was cooled down to room temperature. The reaction was diluted with H$_2$O and extracted with EtOAc. The combined organic layers were washed with H$_2$O, brine, dried over MgSO$_4$ and concentrated in vacuo. The residue was purified by column flash chromatography (SiO$_2$, 5-30% EtOAc in hexanes) to afford the desired product (1.0 g, 60% yield). $^1$H NMR (300 MHz, CDCl$_3$): δ −0.10 (s, 3 H), 0.00 (s, 3 H), 0.83 (s, 9 H), 1.11 (t, J=7.5 Hz, 3 H), 1.49-1.74 (m, 8 H), 1.62 (s, 3 H), 1.64 (s, 3 H), 2.11-2.18 (m, 1 H), 2.44-2.62 (m, 4 H), 4.63 (s, 2 H), 5.37 (s, 1 H), 7.08-7.13 (m, 2 H), 7.28-7.31 (m, 1 H).

Step 3: 6-[2-Cyclopentyl-4-(3-ethyl-4-methyl-phenyl)-2-hydroxy-butyl]-2,2-dimethyl-[1,3]dioxin-4-one

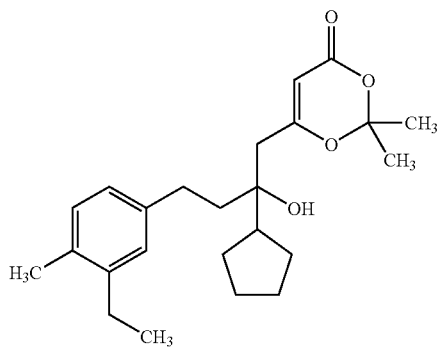

To a solution of 6-{4-[4-(tert-butyl-dimethyl-silanyloxymethyl)-3-ethyl-phenyl]-2-cyclopentyl-2-hydroxy-but-3-ynyl}-2,2-dimethyl-[1,3]dioxin-4-one (1.0 g) in EtOH (50 mL) was added Pd(OH)$_2$ (20 wt %, 100 mg). The reaction was stirred under H2 atmosphere for 15 hours. The reaction was filtered through a pad of celite and the solvent was removed under reduced pressure to afford the desired product. $^1$H NMR (300 MHz, CDCl$_3$): δ 1.19 (t, J=7.5 Hz, 3 H), 1.43-1.69 (m, 8 H), 1.71 (s, 6 H), 1.79-1.85 (m, 2 H), 2.05-2.16 (m, 1 H), 2.27 (s, 3 H), 2.44-2.66 (m, 6 H), 5.37 (s, 1 H), 6.89-6.95 (m, 2 H), 7.04-7.08 (m, 1 H).

Example A(112)

6-Cyclopentyl-3-[(5,7-dimethyl[1,2,4]triazolo[1,5-a]pyrimidin-2-yl)methyl]-6-{2-[3-ethyl-4-(1H-pyrazol-1-ylmethyl)phenyl]ethyl}-4-hydroxy-5,6-dihydro-2H-pyran-2-one

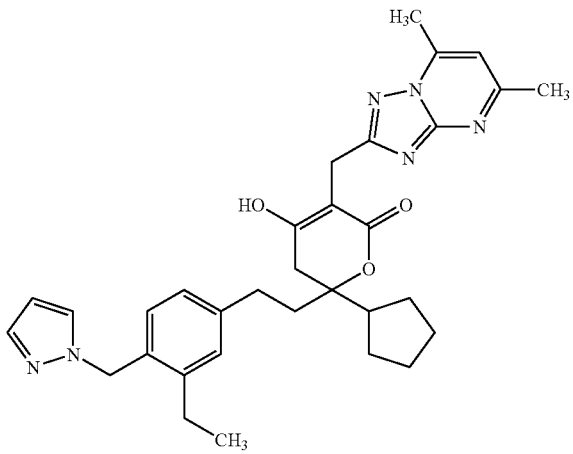

The title compound was prepared analogously to example A(1), where 1-(4-bromo-2-ethyl-benzyl)-1H-pyrazole from step 1 below was substituted in place of 1-benzyloxy-2-ethyl-4-iodo-5-propoxy-benzene in step 4 of that example. $^1$H NMR (400 MHz, DMSO-d$_6$): δ 1.11 (t, J=7.3 Hz, 3 H), 1.48-1.80 (m, 8 H), 2.18 (m, 2 H), 2.46 (s, 3 H), 2.51-2.74 μm, 9 H), 2.89 (d, J=17.4 Hz, 1 H), 3.81 (d, J=15.9 Hz, 1 H), 3.92 (d, J=16.1 Hz, 1 H), 5.41 (s, 2 H), 6.36 (t, J=2.0 Hz, 1 H), 6.98 (d, J=8.3 Hz, 1H), 7.11 (m, 3 H), 7.56 (s, 1 H), 7.79 (d, J=2.1 Hz, 1 H), 10.95 (s, 1 H).

Step 1: 1-(4-Bromo-2-ethyl-benzyl)-1H-pyrazole

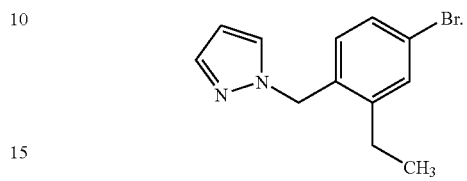

A solution of pyrazole (616 mg, 9.1 mmol) in anhydrous DMF (30 mL) was treated with naH (60%, 362 mg). 4-Bromo-1-bromomethyl-2-ethyl-benzene (2.5 g, 9.1 mmol) was added and the resulting solution was stirred at 80° C. for 13 hours before it was cooled down to room temperature. The mixture was diluted with H$_2$O, extracted with Et$_2$O. The combined organic extracts were washed with H$_2$O, brine, dried over MgSO$_4$ and concentrated under reduced pressure. The residue was purified by flash column chromatography to afford the desired product (1.92 g, 80% yield). $^1$H NMR (300 MHz, CDCl$_3$): δ 1.15 (t, J=7.5 Hz, 3 H), 2.59-2.66 (m, 2 H), 5.30 (s, 2 H), 6.26-6.28 (m, 1 H), 6.86-6.88 (m, 1 H), 7.29-7.32 (m, 2 H), 7.37-7.38 (m, 1 H), 7.54-7.55 (m, 1 H).

Example A(113)

6-Cyclopentyl-6-{2-[3-ethyl-4-(1H-pyrazol-1-ylmethyl)phenyl]ethyl}-4-hydroxy-3-[(6-methyl[1,2,4]triazolo[1,5-a]pyrimidin-2-yl)methyl]-5,6-dihydro-2H-pyran-2-one

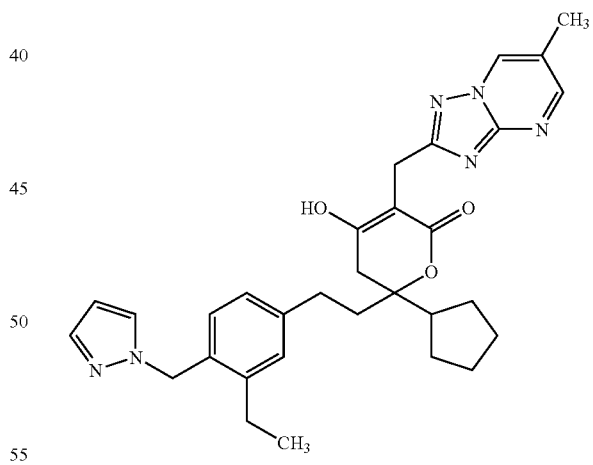

The title compound was prepared analogously to example A(112) where 6-methyl[1,2,4]triazolo[1,5-a]pyrimidine-2-carbaldehyde was substituted in place of 5,7-dimethyl[1,2,4]triazolo[1,5-a]pyrimidine-2-carbaldehyde. $^1$H NMR (400 MHz, DMSO-d$_6$): δ 0.89 (t, J=7.6 Hz, 3 H), 1.41-1.54 (m, 8 H), 1.89 (m, 2 H), 2.21 (s, 3 H), 2.27-2.52 (m, 6 H), 2.64 (d, J=17.7 Hz, 1 H), 3.59 (d, J=15.9 Hz, 1 H), 3.67 (d, J=15.6 Hz, 1 H), 5.17 (s, 2 H), 6.12 (t, J=15.9 Hz, 1 H), 6.74 (d, J=7.6 Hz, 1 H), 6.87 (d, J=7.8 Hz, 1 H), 6.90 (d, 1 H), 7.31 (s, 1 H), 7.54 (d, J=2.2 Hz, 1 H), 8.53 (d, J=2.2 Hz, 1 H), 8.80 (s, 1 H), 10.72 (s, 1 H).

Example A(114)

Enantiomer 1 of 6-cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one Enantiomer 1

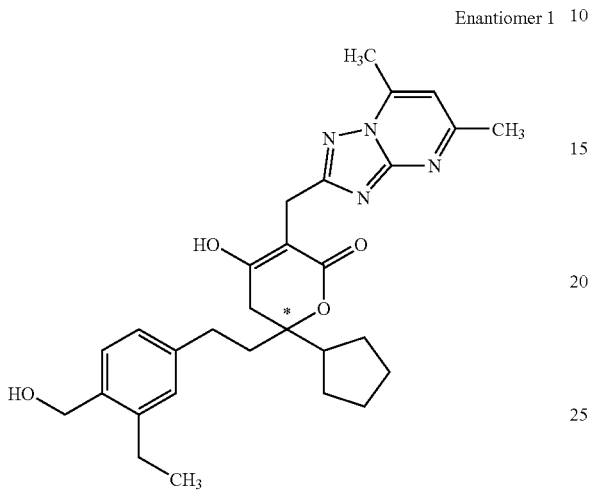

The title compound was separated from racemic 6-cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one (Example B(33)) (by chiral HPLC (ChiralPac OJ-H, 100 bar, 30% MeOH). r.t.=2.7 min, 100% ee.

Example A(115)

Enantiomer 2 6-cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one Enantiomer 2

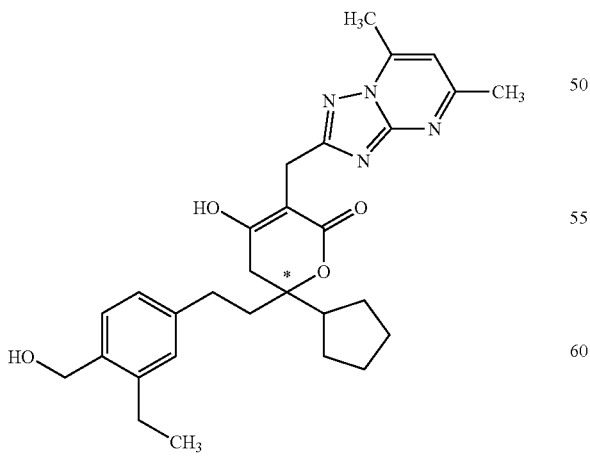

The title compound was separated from racemic 6-cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one (Example B(33)) by chiral HPLC (ChiralPac OJ-H, 100 bar, 30% MeOH). r.t.=3.9 min, 100% ee.

Example A(116)

Enantiomer 1 of [4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile Enantiomer 1

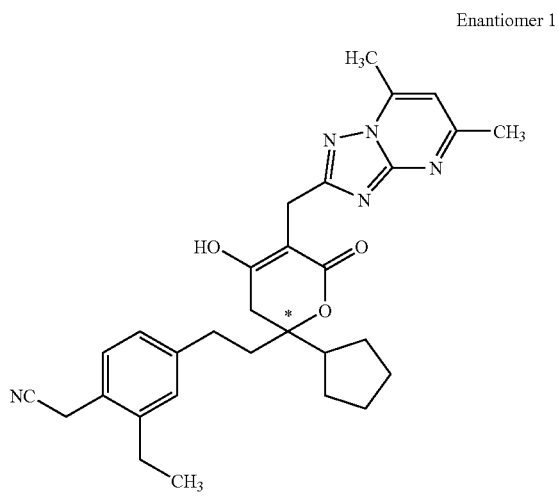

The title compound was separated from racemic [4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile (Example A(101)) by chiral HPLC (ChiralPac AD-H, 140 bar, 50% MeOH). r.t.=3.4 min, 100% ee.

Example A(117)

Enantiomer 2 of [4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile Enantiomer 2

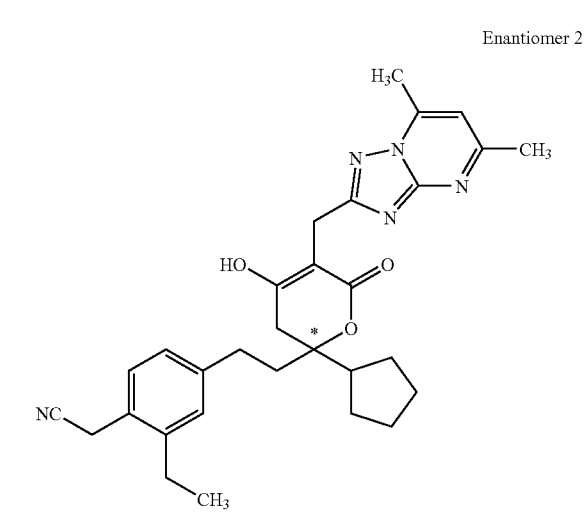

The title compound was separated from racemic [4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylphenyl]acetonitrile (Example A(101)) by chiral HPLC (ChiralPac AD-H, 140 bar, 50% MeOH) r.t.=4.7 min, 100% ee.

Example A(118)

Methyl 4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzoate

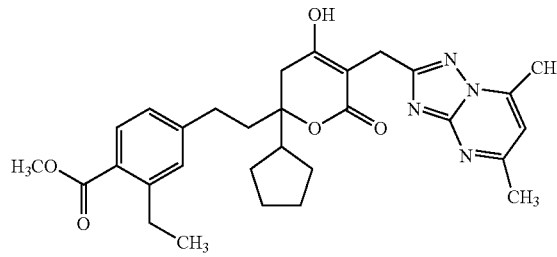

The title compound was prepared analogously to example A(1) where 4-bromo-2-ethyl-benzoic acid methyl ester from step 1 below was substituted in place of 1-benzyloxy-2-ethyl-4-iodo-5-propoxy-benzene in step 4 of that example. $^1$H NMR (300 MHz, CDCl$_3$): δ 1.18 (t, J=7.5 Hz, 3 H), 1.38 (s, 1 H), 1.63 (m, 10 H), 2.00 (m, 2 H), 2.37 (m, 1 H), 2.66 (s, 3 H), 2.72 (m, 2 H), 2.78 (s, 3 H), 2.92 (q, J=7.4 Hz, 2 H), 3.85 (s, 3 H), 4.08 (d, J=2.8 Hz, 2 H), 6.83 (s, 1 H), 7.00 (m, 2 H), 7.75 (d, J=7.7 Hz, 1 H). HRMS calcd for C$_{30}$H$_{36}$N$_4$O$_5$ (M+H)$^+$: 533.2759, found 533.2774.

Step 1: 4-Bromo-2-ethyl-benzoic acid methyl ester

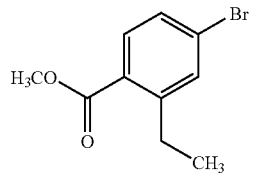

To a solution of 4-bromo-2-ethyl-benzoic acid (1.35 g, 5.89 mmol) in MeOH (40 mL) was added H$_2$SO$_4$ (1 drop). The mixture was stirred at 90° C. for 48 hours, at which time the volatiles were removed in vacuo. The residue was dissolved in Et$_2$O, washed with satd NaHCO$_3$ and brine, dried over MgSO$_4$, and concentrated to a clear oil (1.01 g, 70%). $^1$H NMR (300 MHz, CDCl$_3$): δ 1.22 (t, J=7.5 Hz, 3 H), 2.95 (q, J=7.5 Hz, 2 H), 3.87 (s, 3 H), 7.36 (dd, J=8.3, 2.1 Hz, 1 H), 7.42 (d, J=2.1 Hz, 1 H), 7.72 (d, J=8.3 Hz, 1 H).

Example A(119)

6-Cyclopentyl-6-(2-{4-[(dimethylamino)methyl]-3-ethylphenyl}ethyl)-3-[(5,7-dimethyl[1,2,4]triazolo[1,5-a]pyrimidin-2-yl)methyl]-4-hydroxy-5,6-dihydro-2H-pyran-2-one

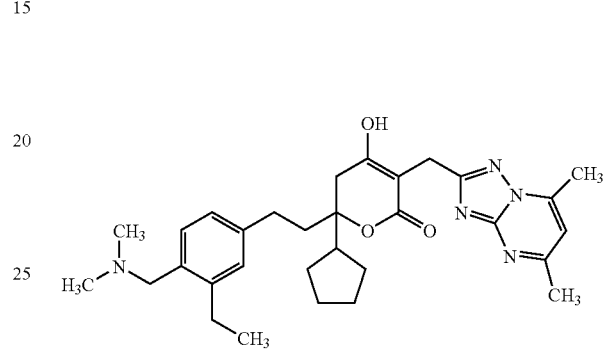

The title compound was prepared analogously to example A(1) where (4-bromo-2-ethyl-benzyl)-dimethyl-amine from step 1 below was substituted in place of 1-benzyloxy-2-ethyl-4-iodo-5-propoxy-benzene in step 4 of that example. $^1$H NMR (300 MHz, CDCl$_3$): δ 1.09 (t, J=7.5 Hz, 3 H), 1.38 (s, 1 H), 1.55 (s, 5 H), 1.69 (s, 2 H), 2.10 (s, 2 H), 2.49 (m, 7 H), 2.54 (s, 3 H), 2.65 (dd, J=15.7, 8.2 Hz, 4 H), 2.74 (s, 3 H), 2.76 (s, 3 H), 3.74 (q, J=14.8 Hz, 2 H), 4.27 (d, J=5.5 Hz, 2 H), 7.04 (s, 1H), 7.19 (m, 2 H), 7.35 (d, J=7.7 Hz, 1 H). Anal. Calcd. For C$_{31}$H$_{41}$N$_5$O$_3$.2.7 TFA: C, 52.07; H, 5.25; N, 8.34. Found: C, 51.73; H, 5.56; N, 8.20.

Step 1: (4-Bromo-2-ethyl-benzyl)-dimethyl-amine

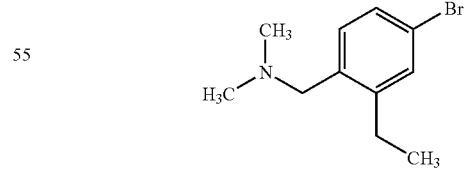

To a solution of 4-bromo-1-bromomethyl-2-ethyl-benzene (1.12 g, 4.03 mmol) in MeOH (20 mL) was added dimethylamine (2.5 mL, 40% solution in water). The mixture was stirred for 1 hour, at which time the volatiles were removed in vacuo. The residue was dissolved in EtOAc, washed with H$_2$O, dried over MgSO$_4$, and concentrated to a clear oil (0.910 g, 93%). ¹H NMR (300 MHz, CDCl₃): δ 1.19 (t, J=7.5 Hz, 3 H), 2.21 (s, 6 H), 2.69 (q, J=7.5 Hz, 2 H), 3.32 (s, 2 H), 7.14 (m, 1 H), 7.28 (m, 2 H).

Example A(120)

6-Cyclopentyl-3-[(5,7-dimethyl[1,2,4]triazolo[1,5-a]pyrimidin-2-yl)methyl]-6-{2-[3-ethyl-4-(methoxymethyl)phenyl]ethyl}-4-hydroxy-5,6-dihydro-2H-pyran-2-one

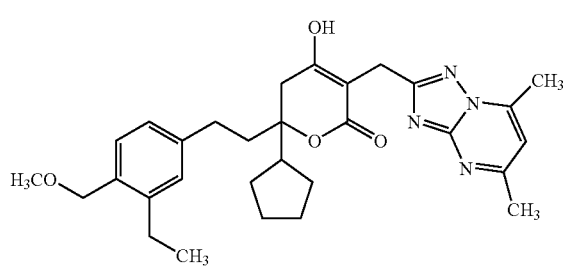

The title compound was prepared analogously to example A(1) where 4-bromo-2-ethyl-1-methoxymethyl-benzene from step 1 below was substituted in place of 1-benzyloxy-2-ethyl-4-iodo-5-propoxy-benzene in step 4 of that example. ¹H NMR (300 MHz, DMSO): δ 1.15 (t, J=7.5 Hz, 3 H), 1.45 (s, 1 H), 1.63 (s, 5 H), 1.78 (s, 2 H), 2.05 (s, 6 H), 2.60 (m, 10 H), 3.35 (s, 3 H), 3.88 (q, J=16.2 Hz, 2 H), 4.44 (s, 2 H), 5.82 (s, 1 H), 7.09 (d, J=8.1 Hz, 2 H), 7.24 (d, J=7.7 Hz, 1 H). Anal. Calcd. For C₃₀H₃₈N₄O₄·0.2 TFA: C, 67.43; H, 7.11; N, 10.35. Found: C, 67.73; H, 7.18; N, 10.46.

Step 1: 4-Bromo-2-ethyl-1-methoxymethyl-benzene

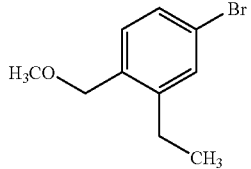

To a solution of (4-bromo-2-ethyl-phenyl)-methanol (0.700 g, 3.25 mmol) in DMF (30 mL) was added NaH (0.156 g, 60% dispersion in mineral oil, 3.90 mmol) followed by MeI (0.22 mL, 3.58 mmol). The mixture was stirred for 16 hours and then partitioned between H₂O and EtOAc. The aqueous layer was extracted with EtOAc, and the organic layer was washed with brine, dried over Na₂SO₄, and concentrated to a yellow oil. Purification by flash column chromatography (0% to 4% EtOAc in hexanes) gave the product as a clear oil (0.51 g, 69%). ¹H NMR (300 MHz, CDCl₃): δ 1.15 (t, J=7.6 Hz, 3 H), 2.58 (q, J=7.5 Hz, 2 H), 3.32 (s, 3 H), 4.35 (s, 2 H), 7.12 (m, 1 H), 7.24 (m, 1 H), 7.27 (d, J=2.1 Hz, 1 H).

Example A(121)

4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethyl-N-methylbenzamide

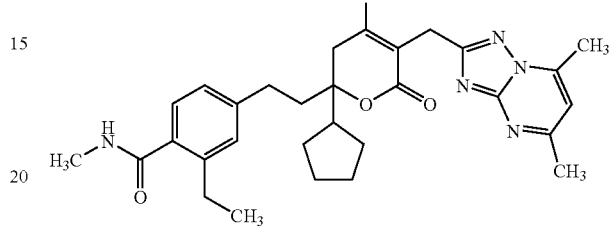

The title compound was prepared analogously to example A(1), where 4-bromo-2-ethyl-N-methyl-benzamide from step 2 below was substituted in place of 1-benzyloxy-2-ethyl-4-iodo-5-propoxy-benzene in step 4 of that example. ¹H NMR (300 MHz, DMSO): δ 1.09 (t, J=7.4 Hz, 3 H), 1.41 (s, 1 H), 1.58 (s, 6 H), 1.72 (s, 2 H), 2.12 (d, J=7.0 Hz, 2 H), 2.48 (m, 2H), 2.55 (s, 3 H), 2.65 (m, 5 H), 2.75 (d, J=4.3 Hz, 3 H), 2.82 (m, 1 H), 3.18 (s, 2 H), 3.80 (q, J=17.3 Hz, 2 H), 7.05 (s, 1 H), 7.11 (m, 2 H), 7.21 (m, 1 H), 8.10 (d, J=4.5 Hz, 1 H). Anal. Calcd. For C₃₀H₃₇N₅O₄·1.5 TFA: C, 56.40; H, 5.52; N, 9.97. Found: C, 56.68; H, 5.57; N, 9.97.

Step 1: 4-Bromo-2-ethyl-benzoyl chloride

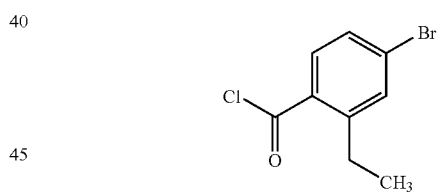

A solution of 4-bromo-2-ethyl-benzoic acid (1.72 g, 7.51 mmol) in SOCl₂ (50 mL) was heated to 90° C. and stirred for 2 hours. The volatiles were removed in vacuo to yield a brown solid (1.80 g, 96%). ¹H NMR (300 MHz, CDCl₃): δ 1.22 (t, J=7.4 Hz, 3 H), 2.89 (q, J=7.5 Hz, 2 H), 7.49 (m, 2 H), 8.03 (d, J=9.0 Hz, 1 H).

Step 2: 4-Bromo-2-ethyl-N-methyl-benzamide

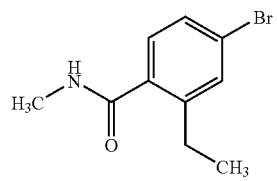

To a solution of 4-bromo-2-ethyl-benzoyl chloride (1.00 g, 4.04 mmol) in $CH_2Cl_2$ (20 mL) was added methylamine (0.70 mL, 40% solution in water, 8.08 mmol). The mixture was stirred for 3 hours, at which time the volatiles were removed in vacuo. The residue was dissolved in EtOAc, washed with $H_2O$, dried over $MgSO_4$, and concentrated to a brown oil (0.857 g, 88%). $^1H$ NMR (300 MHz, $CDCl_3$): δ 1.21 (t, J=7.4 Hz, 3 H), 2.75 (q, J=7.5 Hz, 2 H), 2.97 (d, J=4.9 Hz, 3 H), 5.74 (s, 1H), 7.17 (d, J=8.1 Hz, 1 H), 7.32 (d, J=8.1 Hz, 1 H), 7.39 (s, 1 H).

Example A(122)

6-Cyclopentyl-3-[(5,7-dimethyl[1,2,4]triazolo[1,5-a]pyrimidin-2-yl)methyl]-6-{2-[3-ethyl-4-(1,3-thiazol-2-yloxy)phenyl]ethyl}-4-hydroxy-5,6-dihydro-2H-pyran-2-one

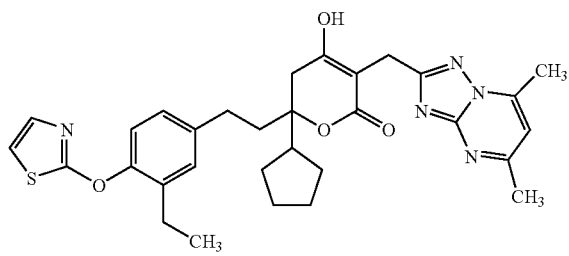

The title compound was prepared analogously to example A(1), where 2-(4-bromo-2-ethyl-phenoxy)-thiazole from step 2 below was substituted in place of 1-benzyloxy-2-ethyl-4-iodo-5-propoxy-benzene in step 4 of that example. $^1H$ NMR (300 MHz, DMSO): δ 1.06 (t, J=7.4 Hz, 3 H), 1.38 (s, 1 H), 1.56 (m, J=3.4 Hz, 5 H), 1.70 (s, 2 H), 2.15 (dd, J=11.2, 5.0 Hz, 2 H), 2.50 (m, 10 H), 2.64 (m, 3 H), 2.81 (m, 1 H), 3.79 (q, J=7.4, 2 H), 7.04 (s, 1 H), 7.19 (m, 5 H). Anal. Calcd. For $C_{31}H_{35}N_4O_4S \cdot 1.4TFA$: C, 55.36; H, 5.00; N, 9.55. Found: C, 55.12; H, 5.11; N, 9.39.

Step 1: 4-Bromo-2-ethyl-phenol

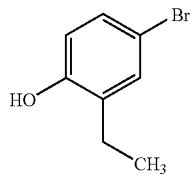

To a solution of 2-ethylphenol (2.00 g, 16.4 mmol) in $CHCl_3$ (60 mL) was added $TBABr_3$ (7.91 g, 16.4 mmol). The mixture was stirred for 20 min, at which time satd $NaHCO_3$ and satd $Na_2O_3S_2$ were added. The organic layer was washed with brine, dried over $Na_2SO_4$ and concentrated. Filtration through $SiO_2$ plug (100% $CH_2Cl_2$) gave the product as a clear oil (2.3 g, 72%). $^1H$ NMR (300 MHz, $CDCl_3$): δ 1.22 (t, J=7.5 Hz, 3 H), 2.60 (q, J=7.5 Hz, 2 H), 4.71 (s, 1 H), 6.64 (d, J=8.5 Hz, 1 H), 7.17 (dd, J=8.5, 2.4 Hz, 1 H), 7.25 (m, 1 H).

Step 2: 2-(4-Bromo-2-ethyl-phenoxy)-thiazole

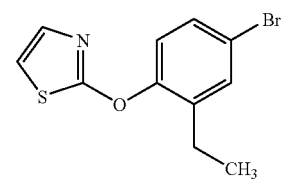

To a solution of 4-bromo-2-ethyl-phenol (1.00 g, 4.97 mmol) in DMF (40 mL) was added 2-bromothiazole (0.341 mL, 3.82 mmol) and finely crushed $K_2CO_3$ (3.17 g, 22.9 mmol). The mixture was stirred at 150° C. for 15 hours, at which time the hot solution was filtered through filter paper. The filtrate was diluted with $CH_2Cl_2$ and $H_2O$ and then brought to pH 6.0 with 6.0N HCl. The aqueous layer was extracted with $CH_2Cl_2$ and the organic layer was washed with $H_2O$ and brine. The organic layer was dried over $Na_2SO_4$ and concentrated to yield a yellow oil (1.0 g, 92%). $^1H$ NMR (300 MHz, $CDCl_3$): δ 1.19 (t, J=7.6 Hz, 3 H), 2.62 (q, J=7.5 Hz, 2 H), 6.79 (d, J=3.8 Hz, 1 H), 7.10 (d, J=8.5 Hz, 1 H), 7.19 (d, J=3.8 Hz, 1 H), 7.35 (dd, J=8.7, 2.4 Hz, 1 H), 7.43 (d, J=2.4 Hz, 1 H).

Example A(123)

6-Cyclopentyl-3-[(5,7-dimethyl[1,2,4]triazolo[1,5-a]pyrimidin-2-yl)methyl]-6-{2-[3-ethyl-4-(morpholin-4-ylmethyl)phenyl]ethyl}-4-hydroxy-5,6-dihydro-2H-pyran-2-one The title compound was prepared analogously to example A(1), where 4-(4-bromo-2-ethyl-benzyl)-morpholine from step 1 below was substituted in place of 1-benzyloxy-2-ethyl-4-iodo-5-propoxy-benzene in step 4 of that example. $^1H$ NMR (300 MHz, DMSO): δ 1.09 (t, J=7.4 Hz, 3 H), 1.39 (s, 1 H), 1.55 (s, 5 H), 1.69 (s, 2 H), 2.10 (m, 2 H), 2.49 (s, 7 H), 2.54 (s, 3 H), 2.63 (s, 2 H), 2.75 (m, 3 H), 3.25 (s, 4 H), 3.65 (s, 1 H), 3.74 (m, 2 H), 3.94 (d, J=10.9 Hz, 2 H), 4.33 (s, 2 H), 7.04 (s, 1 H), 7.19 (m, 2 H), 7.39 (d, J=7.7 Hz, 1 H). Anal.

Calcd. For $C_{33}H_{43}N_5O_4 \cdot 2.2$ TFA: C, 54.47; H, 5.53; N, 8.49. Found: C, 54.45; H, 5.67; N, 8.46.

Step 1: 4-(4-Bromo-2-ethyl-benzyl)-morpholine

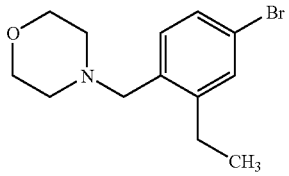

To a solution of 4-bromo-1-bromomethyl-2-ethyl-benzene (3.67 g, 13.2 mmol) in $CH_3CN$ (66 mL) was added triethylamine (2.76 mL, 19.8 mmol) and morpholine (1.38 mL, 15.8 mmol). The mixture was stirred for 1.5 hours, at which time the volatiles were removed in vacuo to yield a pale yellow solid (3.7 g, 97%). $^1$H NMR (300 MHz, $CDCl_3$): δ 1.19 (t, J=7.5 Hz, 3 H), 2.40 (m, 4 H), 2.68 (q, J=7.7 Hz, 2 H), 3.40 (s, 2 H), 3.65 (m, 4 H), 7.13 (m, 1 H), 7.22 (d, J=2.1 Hz, 1 H), 7.30 (d, J=2.1 Hz, 1 H).

Example A(124)

6-[2-(6-Amino-5-ethyl-2-methylpyridin-3-yl)ethyl]-6-cyclopentyl-3-[(5,7-dimethyl[1,2,4]triazolo[1,5-a]pyrimidin-2-yl)methyl]-4-hydroxy-5,6-dihydro-2H-pyran-2-one

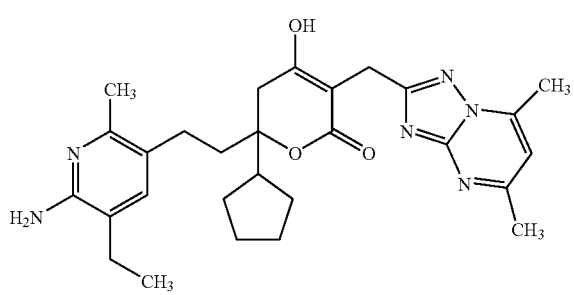

The title compound was prepared analogously to example A(1), where 3-ethyl-5-iodo-6-methyl-pyridin-2-ylamine from step 1 below was substituted in place of 1-benzyloxy-2-ethyl-4-iodo-5-propoxy-benzene in step 4 of that example. $^1$H NMR (300 MHz, DMSO): δ 1.06 (t, J=7.3 Hz, 3 H), 1.36 (s, 1 H), 1.56 (s, 5 H), 1.72 (s, 2 H), 2.03 (m, 2 H), 2.27 (s, 3 H), 2.49 (m, 8 H), 2.52 (d, J=1.5 Hz, 6 H), 3.73 (q, J=16.2, 2 H), 7.04 (s, 1 H), 7.46 (s, 2 H), 7.62 (s, 1 H). HRMS calcd for $C_{28}H_{36}N_6O_3$ (M+H)$^+$: 505.2922, found 505.2936.

Step 1: 3-Ethyl-5-iodo-6-methyl-pyridin-2-ylamine

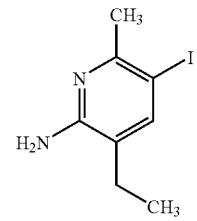

To a solution of 2-amino-3-ethyl-6-methylpyridine (3.00 g, 21.6 mmol) in DMF (100 mL) was added N-iodosuccinimide (4.86 g, 21.6 mmol). The mixture was stirred in the dark for 15 hours and then partitioned between $Et_2O$ and $H_2O$. The organic layer was washed with brine, dried over $MgSO_4$, and concentrated to yield a brown solid (4.6 g, 79%). $^1$H NMR (300 MHz, $CDCl_3$): δ 1.19 (t, J=7.5 Hz, 3 H), 2.35 (q, J=7.4 Hz, 2 H), 2.49 (s, 3 H), 4.44 (s, 2 H), 7.52 (s, 1 H).

Example A(125)

6-{2-[4-(Aminomethyl)-3-ethylphenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one hydrochloride

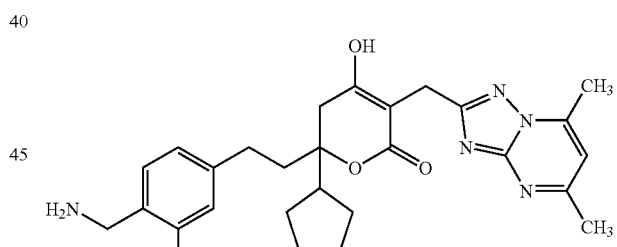

tert-Butyl 4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzylcarbamate (35 mg, 0.06 mmol, example A(126)) was dissolved in dichloromethane (1 mL) and 4N HCl in dioxane (0.5 mL) and stirred at room temperature 2 h. The solution was concentrated to give an off-white solid (30 mg, 96%). $^1$H NMR (300 MHz, $CDCl_3$): δ ppm 1.14 (t, J=7.54 Hz, 3 H) 1.37-1.49 (m, 1 H) 1.52-1.66 (m, 6 H) 1.67-1.77 (m, 2 H) 2.05-2.16 (m, 2 H) 2.58 (s, 4 H) 2.60-2.70 (m, 6 H) 2.74-2.80 (m, 1 H) 3.80 (d, J=14.51 Hz, 2 H) 4.02 (q, J=5.78 Hz, 2 H) 7.07 (s, 1 H) 7.13 (s, 1 H) 7.16-7.21 (m, 1 H) 7.32 (d, J=7.72 Hz, 1 H) 8.15 (s, 3 H). MS (ESI): 504 (M+H)⁺.

Example A(126)

tert-Butyl 4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzylcarbamate

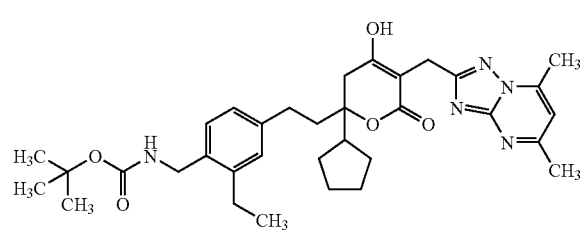

The title compound was prepared analogously to example A(1) where (4-bromo-2-ethyl-benzyl)-carbamic acid tert-butyl ester from step 1 below was substituted in place of 1-benzyloxy-2-ethyl-4-iodo-5-propoxy-benzene in that example except during workup where HCl(aq) treatments were dilute (0.1N). ¹H NMR (300 MHz, CDCl₃): δ ppm 1.20 (t, 3 H) 1.40 (d, J=6.78 Hz, 2 H) 1.45 (s, 9 H) 1.59 (d, J=3.20 Hz, 2 H) 1.60-1.71 (m, 10 H) 1.88-1.99 (m, 2 H) 2.27 (d, J=3.20 Hz, 2 H) 2.57-2.69 (m, 4 H) 2.72-2.80 (m, 2 H) 3.39-3.50 (m, 2 H) 4.30 (d, J=4.52 Hz, 2 H) 4.59-4.73 (m, 1 H) 6.88-7.01 (m, 3 H) 7.16 (d, J=5.84 Hz, 1 H). MS (ESI): 582 (M+H)⁺.

Step 1: (4-Bromo-2-ethyl-benzyl)-carbamic acid tert-butyl ester

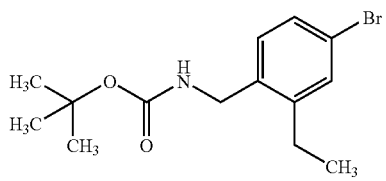

To a solution of 4-bromo-2-ethyl-benzylamine (830 mg, 3.9 mmol, from step 2 of example A(131)) and triethylamine (815 μL, 5.8 mmol) in THF (5 mL) at room temperature was added di-tert-butyl dicarbonate (1.26 g, 5.8 mmol). The solution was stirred 3 h, diluted in water and extracted with ethyl acetate. The organic layer was washed with saturated sodium bicarbonate, then saturated sodium chloride, dried (Na₂SO₄), filtered, and concentrated in vacuo to crude off-white solid (1.4 g). ¹H NMR (300 MHz, CDCl₃): δ ppm 1.22 (t, J=7.63 Hz, 3 H) 1.45 (s, 9 H) 2.64 (q, J=7.54 Hz, 2 H) 4.29 (d, J=5.65 Hz, 2 H) 4.67 (s, 1 H) 7.12 (d, J=8.10 Hz, 1 H) 7.28-7.32 (m, 1 H) 7.33 (d, J=1.88 Hz, 1 H).

Example A(127)

6-Cyclopentyl-6-[2-(4-{[(cyclopropylmethyl)amino]methyl}-3-ethylphenyl)ethyl]-3-[(5,7-dimethyl[1,2,4]triazolo[1,5-a]pyrimidin-2-yl)methyl]-4-hydroxy-5,6-dihydro-2H-pyran-2-one

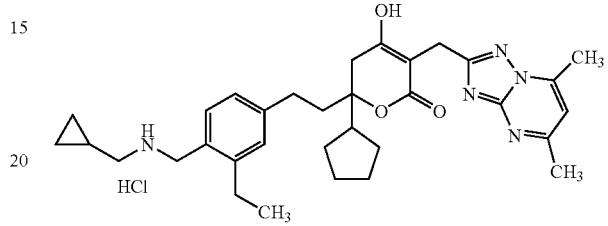

The title compound was prepared analogously to example A(1) where crude (4-bromo-2-ethyl-benzyl)-cyclopropylmethyl-carbamic acid tert-butyl ester from step 2 below was substituted in place of 1-benzyloxy-2-ethyl-4-iodo-5-propoxy-benzene in that example. ¹H NMR (300 MHz, MeOH): δ ppm 0.40-0.48 (m, 2 H) 0.70-0.78 (m, 2 H) 1.22 (t, J=7.54 Hz, 3 H) 1.45-1.57 (m, J=7.35 Hz, 1H) 1.58-1.70 (m, 5 H) 1.73-1.80 (m, J=12.06, 4.14 Hz, 2 H) 2.06-2.18 (m, 2 H) 2.50 (s, 1 H) 2.69-2.78 (m, 12 H) 3.00 (d, J=7.54 Hz, 2 H) 3.61-3.68 (m, 1 H) 4.02 (d, J=3.20 Hz, 2 H) 4.24 (s, 2 H) 7.13-7.20 (m, 2 H) 7.36 (d, J=7.91 Hz, 1 H) 7.42 (s, 1 H). MS (ESI): 558 (M+H)⁺.

Step 1: 4-Bromo-2-ethyl-benzaldehyde

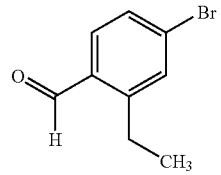

Morpholine-N-oxide (5.0 g, 43 mmol) was stirred in dichloromethane (30 mL) over 3A sieves 30 min under N₂ atmosphere. (4-Bromo-2-ethyl-phenyl)-methanol (3.1 g, 14.4 mmol), then tetrapropylammonium perruthenate (250 mg, 0.72 mmol) was added. The solution was stirred 2 h then filtered through a plug of silica. The silica was washed with 30% ethyl acetate in hexanes, and the organics were pooled. The solution was concentrated in vacuo to give a light yellow oil (3.4 g). ¹H NMR (300 MHz, CDCl₃): δ ppm 1.28 (t, J=7.54

Hz, 3 H) 3.04 (q, J=7.54 Hz, 2 H) 7.47 (d, J=1.70 Hz, 1 H) 7.49-7.53 (m, 1 H) 7.69 (d, J=8.29 Hz, 1 H) 10.23 (s, 1 H).

Step 2: ((4-Bromo-2-ethyl-benzyl)-cyclopropylmethyl-carbamic acid tert-butyl ester

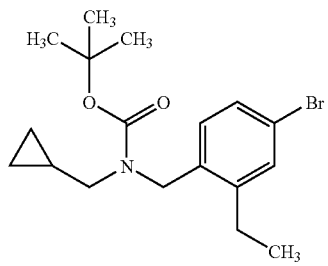

To 4-bromo-2-ethyl-benzaldehyde (3.0 g, 13.4 mmol) and cyclopropyl methylamine (1.0 g, 14.1 mmol) in dichloromethane (150 mL) was added magnesium sulfate (anhydrous, 200 mg) then sodium cyanoborohydride (2.2 g, 35 mmol). The mixture was stirred at room temperature 16 h. The mixture was diluted in water and partitioned. The organic layer was washed with saturated sodium chloride, dried ($MgSO_4$), filtered, and concentrated in vacuo to a crude colorless oil (3.44 g). The residue was redissolved in dichloromethane (100 mL) and triethylamine (3.6 mL, 26 mmol) then di-tert-butyl dicarbonate (3.5 g, 16.25 mmol) was added. The solution was stirred at room temperature for 2 h, then was diluted in water and extracted with ethyl acetate. The organic layer was washed with saturated sodium bicarbonate, then saturated sodium chloride, dried ($Na_2SO_4$), filtered, and concentrated in vacuo to give (4-bromo-2-ethyl-benzyl)-cyclopropylmethyl-carbamic acid tert-butyl ester (3.6 g) as a crude oil.

Example A(128)

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide

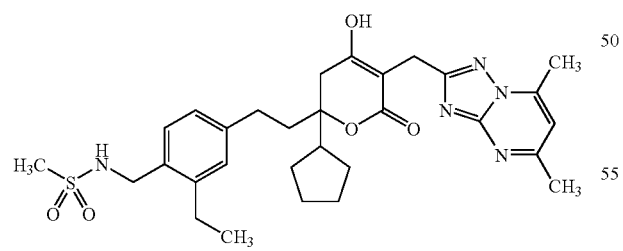

The title compound was prepared analogously to example A(1) where N-(4-bromo-2-ethyl-benzyl)-methanesulfonamide from step 1 below was substituted in place of 1-benzyloxy-2-ethyl-4-iodo-5-propoxy-benzene in that example. $^1$H NMR (300 MHz, $CDCl_3$): δ ppm 1.21 (t, J=7.54 Hz, 3 H) 1.36-1.46 (m, 1 H) 1.52-1.67 (m, 7 H) 1.96-2.06 (m, 2 H) 2.38 (s, 1 H) 2.48-2.57 (m, 1 H) 2.62-2.73 (m, 8 H) 2.79 (s, 3 H) 2.89 (s, 3 H) 4.02-4.15 (m, 2 H) 4.27-4.32 (m, 2 H) 4.32-4.40 (m, 1 H) 5.30 (s, 1 H) 6.85 (s, 1 H) 6.96-7.03 (m, 2 H) 7.19 (d, J=7.72 Hz, 1 H). MS (ESI): 582 (M+H)$^+$.

Step 1:
N-(4-Bromo-2-ethyl-benzyl)-methanesulfonamide

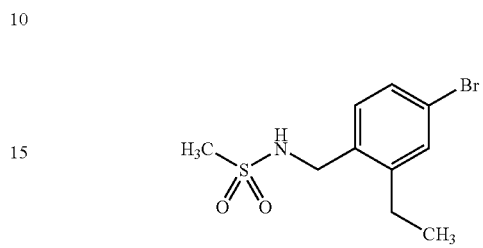

To 4-bromo-2-ethyl-benzylamine (650 mg, 3 mmol) and triethylamine (500 μL, 3.6 mmol) in dichloromethane (5 mL) at room temperature was added methanesulfonyl chloride (283 μL, 3.6 mmol). The solution was stirred 1 h, diluted in water and extracted with ethyl acetate. The organic layer was washed with saturated sodium bicarbonate, then saturated sodium chloride, dried ($Na_2SO_4$), filtered, and concentrated in vacuo to an off-white solid (880 mg, 100%). $^1$H NMR (300 MHz, $CDCl_3$): δ ppm 1.25 (t, J=7.54 Hz, 3 H) 2.69 (q, J=7.54 Hz, 2 H) 2.90 (s, 3 H) 4.27-4.31 (m, 2H) 4.40-4.50 (m, 1 H) 7.21 (d, J=8.10 Hz, 1 H) 7.32-7.40 (m, 2 H).

Example A(129)

Enantiomer 1 of N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide

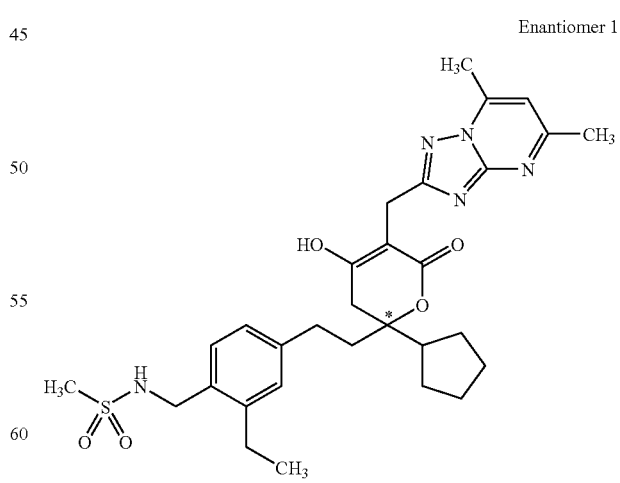

The title compound was separated from racemic N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide

Example A(130)

Enantiomer 2 of N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide

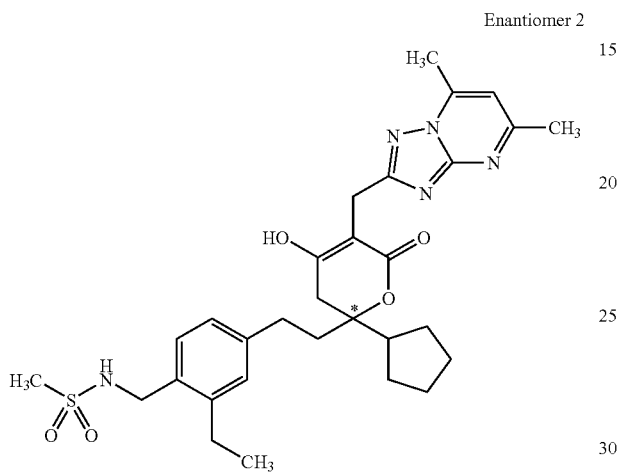

The title compound was separated from racemic N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]methanesulfonamide (Example A(128)) using chiral HPLC (Chiralpak OJ-H, 120 bar, 25% MeOH). (6.413 min retention time, 100% ee)

Example A(131)

N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]acetamide

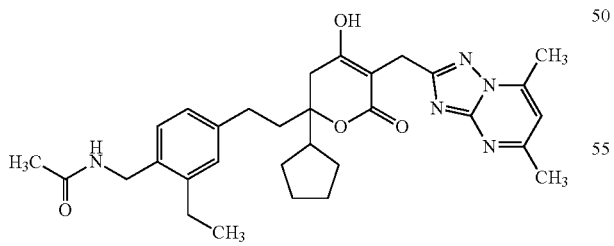

The title compound was prepared analogously to example A(1) where N-(4-bromo-2-ethyl-benzyl)-acetamide from step 3 below was substituted in place of 1-benzyloxy-2-ethyl-4-iodo-5-propoxy-benzene in that example. $^1$H NMR (300 MHz, CDCl$_3$): δ ppm 1.18 (t, J=7.54 Hz, 3 H) 1.40 (dd, J=8.19, 6.12 Hz, 1 H) 1.51-1.67 (m, 7 H) 1.97-2.05 (m, 6 H) 2.32-2.44 (m, 1 H) 2.56 (d, J=3.58 Hz, 1 H) 2.58-2.73 (m, 8 H) 2.79 (s, 3 H) 4.02-4.15 (m, 2 H) 4.40 (d, J=5.09 Hz, 2 H) 5.51 (s, 1 H) 6.85 (s, 1 H) 6.94-7.02 (m, 2 H) 7.12 (d, J=7.72 Hz, 1 H). MS (ESI): 546 (M+H)$^+$.

Step 1:
2-(4-Bromo-2-ethyl-benzyl)-isoindole-1,3-dione

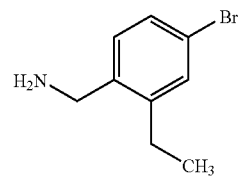

To 4-bromo-1-bromomethyl-2-ethyl-benzene (4.0 g, 14.2 mmol) in dimethylformamide (100 mL) at room temperature was added potassium phthalimide (2.9 g, 15.6 mmol), and the solution was heated at 80° C. for 5 h. The solution was cooled to room temperature and poured into water. The aqueous solution was extracted with ethyl acetate. The pooled organics were washed with saturated sodium chloride, dried (Na$_2$SO$_4$), filtered, and concentrated in vacuo to a yellow solid (4.0 g, 82%). $^1$H NMR (300 MHz, CDCl$_3$): δ ppm 1.27 (t, J=7.54 Hz, 3 H) 2.85 (q, J=7.60 Hz, 2 H) 4.84 (s, 2 H) 7.14-7.18 (m, 1 H) 7.24-7.27 (m, 1 H) 7.34 (d, J=2.07 Hz, 1 H) 7.73 (dd, J=5.46, 3.01 Hz, 2 H) 7.86 (dd, J=5.56, 3.11 Hz, 2 H).

Step 2: 4-Bromo-2-ethyl-benzylamine 2-(4-Bromo-2-ethyl-benzyl)-isoindole-1,3-dione (4 g, 11.7 mmol) and hydrazine (1.8 mL, 58.3 mmol) in chloroform:ethanol (1:1.5, 250 mL) were refluxed for 4 h. The mixture was cooled to room temperature and filtered through a pad of celite. The solution was diluted in water and partitioned. The organic layer was washed with water, saturated sodium bicarbonate, then saturated sodium chloride, dried (Na$_2$SO$_4$), filtered, and then concentrated in vacuo to a yellow oil (2.2 g, 88%). $^1$H NMR (300 MHz, CDCl$_3$): δ ppm 1.23 (t, J=7.54 Hz, 3 H) 1.65 (s, 2 H) 2.66 (q, J=7.60 Hz, 2 H) 3.84 (s, 2 H) 7.19-7.23 (m, 1 H) 7.30-7.34 (m, 2 H).

Step 3: N-(4-Bromo-2-ethyl-benzyl)-acetamide

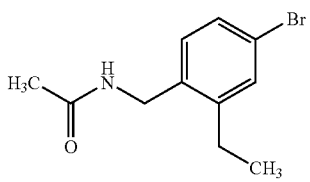

To 4-bromo-2-ethyl-benzylamine (700 mg, 3.3 mmol) and triethylamine (600 μL, 4.3 mmol) in dichloromethane (5 mL) at room temperature was added acetyl chloride (310 μL, 4.5 mmol). The solution was stirred for 1 h, diluted in water and extracted with ethyl acetate. The organic layer was washed with saturated sodium bicarbonate, then saturated sodium chloride, dried (Na$_2$SO$_4$), filtered, and concentrated in vacuo to an off-white solid (820 mg, 97%). $^1$H NMR (300 MHz, CDCl$_3$): δ 1.20 (t, J=7.54 Hz, 3 H) 2.00 (s, 3 H) 2.62 (q, J=7.54 Hz, 2 H) 4.38 (d, J=5.46 Hz, 2 H) 5.59 (s, 1 H) 7.09 (d, J=8.10 Hz, 1 H) 7.26-7.31 (m, 1 H) 7.34 (d, J=1.88 Hz, 1 H).

Example A(132)

Enantiomer 1 of N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]acetamide

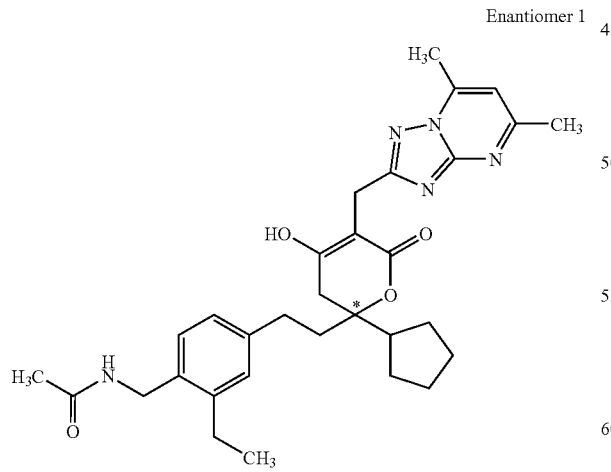

The title compound was separated from racemic N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]acetamide (Example A(131)) using chiral HPLC (Chiralpak AS-H, 140 bar, 50% MeOH). (4.924 min retention time, 100% ee).

Example A(133)

Enantiomer 2 of N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]acetamide

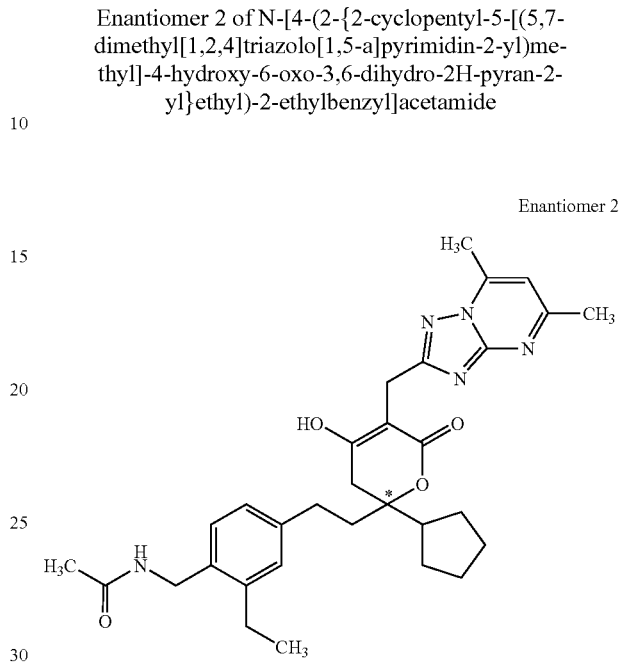

The title compound was separated from racemic N-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-ethylbenzyl]acetamide (Example A(131)) using chiral HPLC (Chiralpak AS-H, 140 bar, 50% MeOH). (6.947 min retention time, 100% ee).

Example A(134)

6-cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one

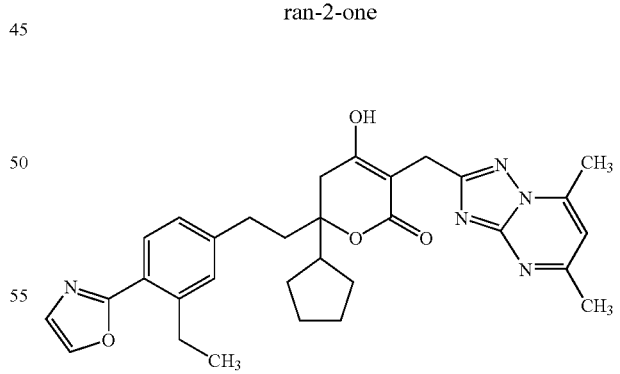

The title compound was prepared analogously to example A(1) where 6-cyclopentyl-6-{2-[3-ethyl-4-(1,3-oxazol-2-yl)phenyl]ethyl}dihydro-2H-pyran-2,4(3H)-dione (Example A(135)) was substituted in place of 6-cyclopentyl-6-[2-(5-ethyl-4-hydroxy-2-propoxy-phenyl)-ethyl]-dihydro-pyran-2,4-dione in that example. Yield (35 mg, 8%). $^1$H NMR (300 MHz, CDCl$_3$): δ ppm 1.19 (t, J=7.44 Hz, 3H) 1.50-1.57 (m, 3 H) 1.57-1.64 (m, J=8.29 Hz, 2 H) 1.65-1.77 (m, 3 H) 1.99-

2.07 (m, J=17.33 Hz, 1 H) 2.33-2.44 (m, 1 H) 2.51-2.59 (m, 1 H) 2.65 (s, 3 H) 2.68-2.80 (m, 7 H) 3.03 (q, J=7.41 Hz, 2 H) 4.09 (s, 2 H) 6.83 (s, 1 H) 7.03-7.09 (m, 2 H) 7.23 (s, 1 H) 7.69 (s, 1 H) 7.80 (d, J=7.91 Hz, 1 H). MS (ESI): 542 (M+H)$^+$.

Example A(135)

6-Cyclopentyl-6-{2-[3-ethyl-4-(1,3-oxazol-2-yl)phenyl]ethyl}dihydro-2H-pyran-2,4(3H)-dione

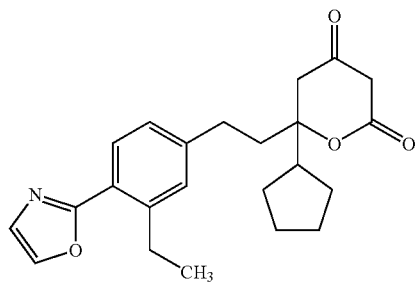

The title compound was prepared analogously to example A(2) where 2-(4-bromo-2-ethyl-phenyl)-oxazole from step 1 below was substituted in place of 4-bromo-2-ethyl-5-methoxy-pyridine in step 6 of that example. $^1$H NMR (300 MHz, CDCl$_3$): δ ppm 1.21 (t, J=7.44 Hz, 3 H) 1.42-1.57 (m, 2H) 1.58-1.74 (m, 6 H) 1.96-2.04 (m, 1 H) 2.14-2.22 (m, 1 H) 2.24-2.35 (m, 1 H) 2.67-2.78 (m, 2H) 2.80 (s, 2 H) 2.89-2.98 (m, 2 H) 3.46 (s, 2 H) 7.11-7.17 (m, 2 H) 7.44-7.53 (m, 1 H) 7.77 (d, J=8.29 Hz, 1 H) 7.84 (s, 1 H). MS (ESI): 382 (M+H)$^+$.

Step 1: 2-(4-Bromo-2-ethyl-phenyl)-oxazole

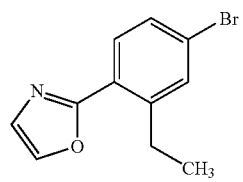

4-Bromo-2-ethyl-benzoic acid (6.8 g, 30 mmol), diisopropylethylamine (7.8 mL, 44.7 mmol), O-(7-azabenzotriazol-1-yl)-N,N,N',N'-tetramethyluronium hexafluorophosphate (HATU, 14 g, 37 mmol), and aminoacetaldehyde dimethyl ether (4 mL, 37 mmol) in 2:1 dichlormethane/dimethylformamide (120 mL) 5 h at room temperature. The solution was washed with several portions of water, then 1N HCl(aq) and saturated sodium chloride, dried (Na$_2$SO$_4$), filtered, and concentrated in vacuo to a crude light yellow oil. The residue was redissolved in Eaton's reagent (P$_2$O$_5$ in methanesulfonic acid, 100 mL), and the solution was heated at 135° C. under argon for 6 h. The solution was cooled to room temperature and carefully poured onto ice. The mixture was extracted with dichloromethane, and the organic layer was backwashed with saturated sodium chloride, dried (Na$_2$SO$_4$), filtered, and concentrated in vacuo to a crude oil. The residue was redissolved in ethyl acetate and washed with saturated sodium bicarbonate, then saturated sodium chloride, dried (Na$_2$SO$_4$), filtered, and concentrated in vacuo to pure brown liquid (3.16 g, 44%) $^1$H NMR (300 MHz, CDCl$_3$): δ ppm 1.24 (t, J=7.54 Hz, 3 H) 3.09 (q, J=7.54 Hz, 2 H) 7.27 (s, 1 H) 7.42 (dd, J=8.38, 1.98 Hz, 1 H) 7.48 (d, J=2.07 Hz, 1 H) 7.74 (s, 1 H) 7.81 (d, J=8.48 Hz, 1 H).

Example A(136)

6-Cyclopentyl-6-{2-[3-ethyl-4-(1,3-oxazol-2-yl)phenyl]ethyl}-4-hydroxy-3-([1,2,4]triazolo[1,5-a]pyrimidin-2-ylmethyl)-5,6-dihydro-2H-pyran-2-one

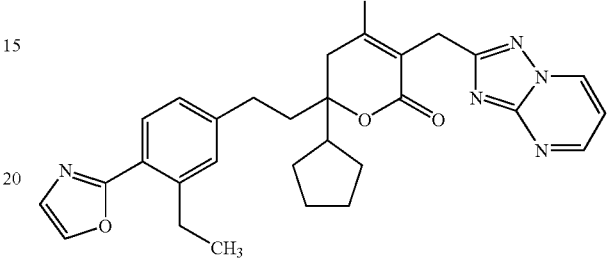

The title compound was prepared analogously to Example A(1) where 6-cyclopentyl-6-{2-[3-ethyl-4-(1,3-oxazol-2-yl)phenyl]ethyl}dihydro-2H-pyran-2,4(3H)-dione (Example A(135)) was substituted in place of 6-cyclopentyl-6-[2-(5-ethyl-4-hydroxy-2-propoxy-phenyl)-ethyl]-dihydro-pyran-2,4-dione in that example and methoxy-[1,2,4]triazolo[1,5-a]pyrimidin-2-yl-methanol was substituted in place of 5,7-dimethyl-[1,2,4]triazolo[1,5-a]pyrimidine-2-carbaldehyde. Yield (57 mg, 11%). $^1$H NMR (300 MHz, CDCl$_3$): δ ppm 1.20 (t, J=7.44 Hz, 3 H) 1.53-1.67 (m, 8 H) 2.00-2.11 (m, 2 H) 2.35-2.47 (m, 1 H) 2.51-2.63 (m, 1 H) 2.65-2.72 (m, 2 H) 2.72-2.83 (m, 2 H) 3.04 (q, J=7.54 Hz, 2 H) 4.14 (d, J=3.77 Hz, 2 H) 7.04-7.10 (m, 2 H) 7.14-7.20 (m, 1 H) 7.25 (s, 1 H) 7.71 (s, 1 H) 7.82 (d, J=7.91 Hz, 1 H) 8.84 (d, J=5.46 Hz, 2 H). MS (ESI): 514 (M+H)$^+$.

Example A(137)

6-Cyclopentyl-6-{2-[3-ethyl-4-(1,3-oxazol-2-yl)phenyl]ethyl}-4-hydroxy-3-[(6-methyl[1,2,4]triazolo[1,5-a]pyrimidin-2-yl)methyl]-5,6-dihydro-2H-pyran-2-one

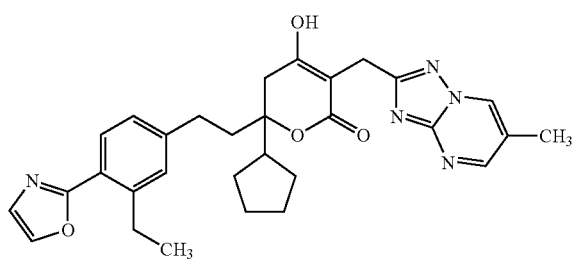

The title compound was prepared analogously to example A(1) where 6-cyclopentyl-6-{2-[3-ethyl-4-(1,3-oxazol-2-yl)phenyl]ethyl}dihydro-2H-pyran-2,4(3H)-dione (Example A(135))was substituted in place of 6-cyclopentyl-6-[2-(5-ethyl-4-hydroxy-2-propoxy-phenyl)-ethyl]-dihydro-pyran-2,4-dione in that example and 6-methyl-[1,2,4]triazolo[1,5-a]pyrimidine-2-carbaldehyde was substituted in place of 5,7- dimethyl-[1,2,4]triazolo[1,5-a]pyrimidine-2-carbaldehyde. Yield (58 mg, 11%). ¹H NMR (300 MHz, CDCl₃): δ ppm 1.19 (t, J=7.44 Hz, 3 H) 1.40 (d, J=4.33 Hz, 1 H) 1.53-1.67 (m, 8H) 2.01-2.10 (m, 2 H) 2.39 (s, 1 H) 2.45-2.49 (m, 3 H) 2.54-2.64 (m, 1 H) 2.71 (dd, J=11.87, 5.46 Hz, 2 H) 2.76-2.85 (m, 1 H) 3.01 (q, J=7.47 Hz, 2 H) 4.10 (s, 2 H) 7.05-7.11 (m, 2 H) 7.29 (s, 1 H) 7.73 (s, 1 H) 7.78 (d, J=7.91 Hz, 1 H) 8.61 (s, 1 H) 8.68 (d, J=2.07 Hz, 1 H). MS (ESI): 528 (M+H)⁺.

Example A(138)

Enantiomer 1 of 6-Cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one

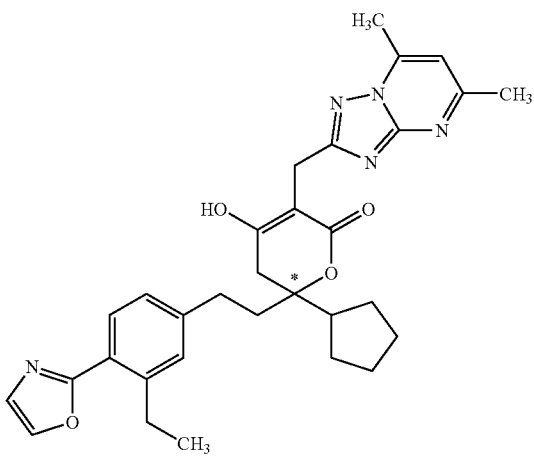

Enantiomer 1

The title compound was separated from racemic 6-cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one (Example A(134)) using chiral HPLC (Chiralpak AS-H, 140 bar, 50% MeOH). (1.968 min retention time, 100% ee).

Example A(139)

Enantiomer 2 of 6-Cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one

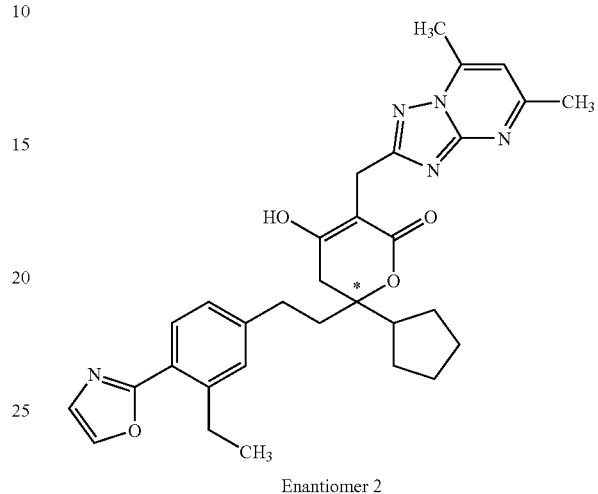

Enantiomer 2

The title compound was separated from racemic 6-cyclopentyl-3-[(5,7-dimethyl[1,2,4]triazolo[1,5-a]pyrimidin-2-yl)methyl]-6-{2-[3-ethyl-4-(1,3-oxazol-2-yl)phenyl]ethyl}-4-hydroxy-5,6-dihydro-2H-pyran-2-one (Example A(134)) using chiral HPLC (Chiralpak AS-H, 140 bar, 50% MeOH). (3.537 min retention time, 95% ee).

Example A(140)

6-Cyclopentyl-3-[(5,7-dimethyl[1,2,4]triazolo[1,5-a]pyrimidin-2-yl)methyl]-6-{2-[3-ethyl-4-(pyrrolidin-1-ylmethyl)phenyl]ethyl}-4-hydroxy-5,6-dihydro-2H-pyran-2-one

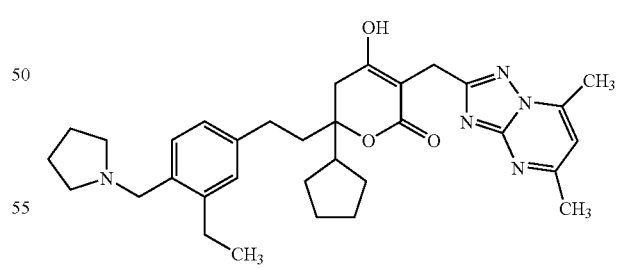

The title compound was prepared analogously to example A(1) where 1-(4-bromo-2-ethyl-benzyl)-pyrrolidine from step 1 below was substituted in place of 1-benzyloxy-2-ethyl-4-iodo-5-propoxy-benzene in step 4 of that example. ¹H NMR (300 MHz, DMSO): δ 1.05 (t, J=7.3 Hz, 3 H), 1.34 (s, 1 H), 1.50 (s, 5 H), 1.66 (m, 2 H), 1.81 (m, 2 H), 2.02 (m, 4 H), 2.44 (m, 7 H), 2.62 (m, 7 H), 3.07 (m, 2 H), 3.37 (m, 2 H), 3.75 (q, J=16.2 Hz, 2 H), 4.30 (d, J=5.3 Hz, 2 H), 6.99 (s, 1 H), 7.12

(m, 2 H), 7.33 (d, J=7.7 Hz, 1 H). HRMS calcd for C$_{33}$H$_{43}$N$_5$O$_3$ (M+H)$^+$: 558.3439, found 558.3446.

Step 1: 1-(4-Bromo-2-ethyl-benzyl)-pyrrolidine

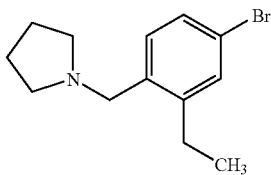

To a solution of 4-bromo-1-bromomethyl-2-ethyl-benzene (2.00 g, 7.19 mmol) in CH$_2$Cl$_2$ (30 mL) was added dropwise pyrrolidine (1.19 mL, 14.4 mmol). The mixture was stirred for 15 hours, and then partitioned between Et$_2$O and H$_2$O. The organic layer was washed with brine, dried over MgSO$_4$, and concentrated to yield a yellow oil (1.3 g, 68%). $^1$H NMR (300 MHz, CDCl$_3$): δ 1.19 (t, J=7.5 Hz, 3 H), 1.76 (m, 4 H), 2.47 (m, 4 H), 2.69 (q, J=7.5 Hz, 2 H), 3.54 (s, 2 H), 7.19 (m, 1 H), 7.25 (m, 1 H), 7.29 (d, J=1.9 Hz, 1 H).

Example A(141)

2-[4-[2-(2-Cyclopentyl-4,6-dioxotetrahydro-2H-pyran-2-yl)ethyl]-2-(trifluoromethyl)phenyl]-2-methylpropanenitrile

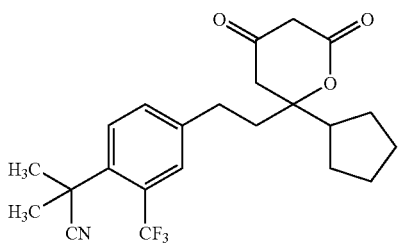

The title compound was prepared analogously to example A(2) where 2-(4-bromo-2-trifluoromethyl-phenyl)-2-methyl-propionitrile from step 3 below was substituted in place of 4-bromo-2-ethyl-5-methoxy-pyridine in step 6 of that example. $^1$H NMR (400 MHz, DMSO-d$_6$) δ: 1.50-1.86 (m, 14 H), 1.94-1.98 (m, 2H), 2.27-2.30 (m, 1H), 2.73-2.80 (m, 4H), 3.44 (d, J=4.3 Hz, 2 H), 7.36 (dd, J=8.2, 1.6 Hz, 1 H), 7.54 (d, J=1.6 Hz, 1 H), 7.65 (d, J=8.2 Hz, 1 H). (M+H)+MS (ESI): 422 (M+H)$^+$ Step 1: 4-Bromo-1-bromomethyl-2-trifluoromethyl-benzene

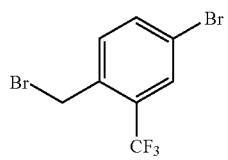

A mixture of 4-methyl-3-trifluorobromobenzene (25 g, 104.59 mmol), N-bromosuccinimde (18.62 g, 104.59 mmol) and benzoyl peroxide (1.27 g, 5.23 mmol) in CCl$_4$ (35 mL) was heated at 90° C. for 4 hours. The reaction mixture was cooled to 0° C. and then filtered through a glass frit washing with CH$_2$Cl$_2$. The filtrate was concentrated and then purified by flash column chromatography (0% to 5% EtOAc in hexanes) to give the product as a clear oil that crystallized on standing (33.26 g, 100%). $^1$H NMR (400 MHz, CDCl$_3$) δ 4.57 (s, 2H), 7.46 (d, J=8.3 Hz, 1 H), 7.67 (d, J=8.3 Hz, 1 H), 7.78 (s, 1H).

Step 2: (4-Bromo-2-trifluoromethyl-phenyl)-acetonitrile

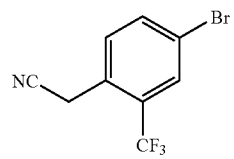

A mixture of 4-methyl-3-trifluorobromobenzene (33.26 g, 104.261 mmol) from step 1 above, KCN (20.43 g, 313.67 mmol) and tetrabutylammonium bromide (3.37 g, 10.45 mmol) in CH$_2$Cl$_2$/H$_2$O 1:1 (300 mL) was stirred at room temperature for 4 hours. The layers were separated and the organic layer washed with H$_2$O (100 mL) 1N HCl (100 mL), brine, dried over Na$_2$SO$_4$ and then concentrated to a brown oil which was purified by flash column chromatography (0% to 20% EtOAc in hexanes) to give the product as a clear oil (14.9 g, 54%). $^1$H NMR (400 MHz, CDCl$_3$) δ 3.91 (s, 2H), 7.57 (d, J=8.3 Hz, 1 H), 7.75 (dd, J=8.3, 2 Hz, 1 H), 7.84 (d, J=2 Hz, 1 H).

Step 3: 244-Bromo-2-trifluoromethyl-phenyl)-2-methyl-propionitrile

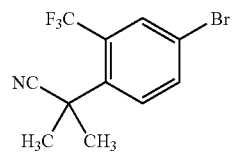

NaH 95% (2.28 g, 94.7 mmol) was suspended in DMF (25 mL) and cooled to 0° C. (4-Bromo-2-trifluoromethyl-phenyl)-acetonitrile (5 g, 18.94 mmol) from step 2 above, was dissolved in THF (35 mL) and slowly added via cannula to the NaH suspension. The reaction mixture was stirred for 20 min. Methyl iodide (11.79 mL, 189.36 mmol) was added and the resulting mixture was stirred overnight at room temperature. Reaction was quenched with H$_2$O (100 mL). Solvents were removed in vacuo and residue partitioned between EtOAc and 1N HCl (100 mL). The organic phase was dried over Na$_2$SO$_4$ and evaporated. The crude organic product was purified by flash column chromatography (5% EtOAc in hexanes) to give the product (4.14 g, 75%) as a clear oil. ¹H NMR (400 MHz, CDCl₃) δ 1.6 (s, 6H), 7.46 (d, J=8.3 Hz, 1 H), 7.67 (d, J=8.3 Hz, 1 H), 7.78 (s, 1H).

Example A(142)

[4-[2-(2-Cyclopentyl-4,6-dioxotetrahydro-2H-pyran-2-yl)ethyl]-2-(trifluoromethyl)phenyl]acetonitrile

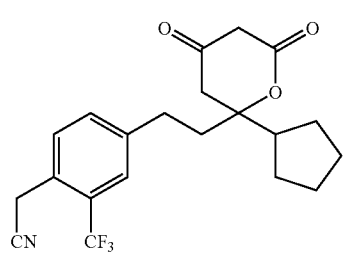

The title compound was prepared analogously to example A(2) where 4-bromo-1-bromomethyl-2-trifluoromethyl-benzene from step 2 of example A(141) was substituted in place of 4-bromo-2-ethyl-5-methoxy-pyridine in step 6 of that example. ¹H NMR (400 MHz, CDCl₃) δ: 1.48-1.82 (br m, 8 H), 1.94-1.97 (m, 2H), 2.24-2.30 (m, 1 H), 2.69-2.84 (m, 4 H), 3.44 (d, J=4.04 Hz, 2 H), 3.92 (s, 2H), 7.40 (d, J=8.08 Hz, 1 H), 7.47 (s, 1 H), 7.60-7.62 (m, 1H). MS (ESI): 394 (M+H)⁺

Example A(143)

[4-(2-{2Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]acetonitrile

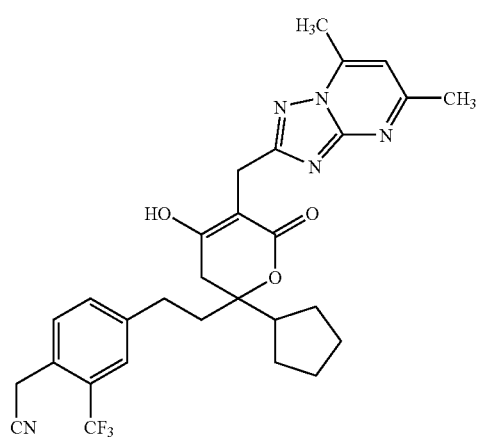

The title compound was prepared analogously to example A(1) where [4-[2-(2-cyclopentyl-4,6-dioxotetrahydro-2H-pyran-2-yl)ethyl]-2-(trifluoromethyl)phenyl]acetonitrile (example A(142)) was substituted in place of 6-cyclopentyl-6-[2-(5-ethyl-4-hydroxy-2-propoxy-phenyl)-ethyl]-dihydro-pyran-2,4-dione of that example. ¹H NMR (400 MHz, DMSO-d₆) δ: 1.38-1.74 (br m, 10 H), 2.13-2.23 (m, 1 H), 2.49-2.58 (m, 7 H), 2.73-2.87 (m, 3H), 3.76 (d, J=16 Hz, 1 H), 3.85 (d, J=16 Hz, 1 H), 4.16 (s, 2H), 7.06 (s, 1 H), 7.64-7.77 (m, 3H), 10.87 (s, 1 H). Anal. Calcd. For C₂₉H₃₀F₃N₅O₃·0.5H₂O: C, 61.91; H, 5.55; N, 12.45. Found: C, 62.00; H, 5.85; N, 12.65. MS (ESI): 554.1 (M+H)⁺

Example A(144)

1-[4-[2-(2-Cyclopentyl-4,6-dioxotetrahydro-2H-pyran-2-yl)ethyl]-2-(trifluoromethyl)phenyl]cyclopropanecarbonitrile

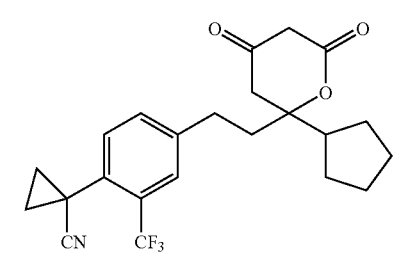

The title compound was prepared analogously to example A(2) where 1-(4-bromo-2-trifluoromethyl-phenyl)-cyclopropanecarbonitrile from step 1 below was substituted in place of 4-bromo-2-ethyl-5-methoxy-pyridine in step 6 of that example. ¹H NMR (400 MHz, CDCl₃) δ: 1.41-1.43 (m, 2H), 1.53-1.77 (m, 10 H), 1.93-1.97 (m, 2H), 2.25-2.30 (m, 1 H), 2.72-2.80 (m, 4H), 3.44 (d, J=4.8 Hz, 2 H), 7.33-7.35 (m, 1 H), 7.47-7.49 (m, 2 H). MS (ESI): 420 (M+H)⁺.

Step 1: 1-(4-Bromo-2-trifluoromethyl-phenyl)-cyclopropanecarbonitrile

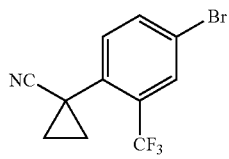

To a stirred solution of (4-bromo-2-trifluoromethyl-phenyl)-acetonitrile (3.33 g, 12.61 mmol) from step 2 of example A(141), benzyltriethylammonium chloride (0.057 g, 0.25 mmol) and 1-bromo-2-chloroethane (1.57 g, 10.94 mmol), was added dropwise a solution of NaOH 40% (3 mL). The reaction mixture was stirred 6 hours at 50° C. After this time the reaction was quenched with 1N HCl (30 mL) and extracted with EtOAC (3×30 mL). The organic phase was dried over Na₂SO₄ and evaporated. The crude organic product was purified by flash column chromatography (10% EtOAc in hexanes) to give the product (3.1 g, 86%) as a clear oil. $^1$H NMR (400 MHz, CDCl$_3$) δ 1.4-1.44 (m, 2H), 1.76-1.80 (m, 2H), 7.44 (d, J=8.3 Hz, 1 H), 7.69 (dd, J=8.3, 2 Hz, 1 H), 7.84 (d, J=2 Hz, 1 H).

Example A(145)

1-[4-(2-{2Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]cyclopropanecarbonitrile

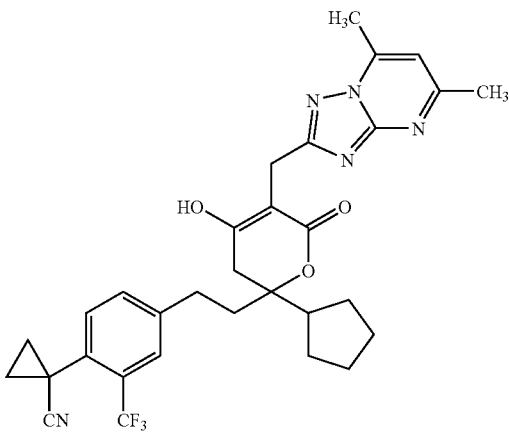

The title compound was prepared analogously to example A(1) where 1-[4-[2-(2-cyclopentyl-4,6-dioxotetrahydro-2H-pyran-2-yl)ethyl]-2-(trifluoromethyl)phenyl]cyclopropanecarbonitrile (example A(144)) was substituted in place of 6-cyclopentyl-6-[2-(5-ethyl-4-hydroxy-2-propoxy-phenyl)-ethyl]-dihydro-pyran-2,4-dione of that example. $^1$H NMR (400 MHz, DMSO-d$_6$) δ: 0.86-0.90 (m, 2H), 1.27-1.79 (m, 12 H), 2.11-2.16 (m, 1H), 2.48-2.59 (m, 7H), 2.76-2.80 (m, 3H), 3.75 (d, J=16 Hz, 1 H), 3.86 (d, J=16 Hz, 1 H), 7.07 (s, 1 H), 7.65-7.70 (m, 3H), 10.87 (s, 1 H). Anal. Calcd. For C$_{31}$H$_{32}$F$_3$N$_5$O$_3$.1.0H$_2$O: C, 62.30; H, 5.73; N, 11.72. Found: C, 62.40; H, 5.85; N, 11.90. MS (ESI): 580.1 (M+H)$^+$ Example A(146)

2-[4-[2-(2Cyclopentyl-4,6-dioxotetrahydro-2H-pyran-2-yl)ethyl]-2-(trifluoromethyl)phenyl]-2-ethylbutanenitrile

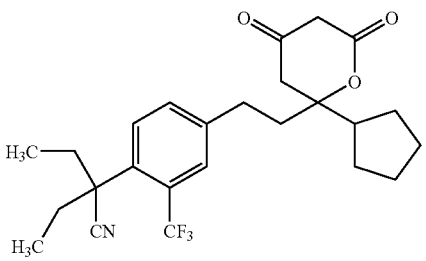

The title compound was prepared analogously to example A(2) where 2-(4-bromo-2-trifluoromethyl-phenyl)-2-ethyl-butyronitrile from step 1 below was substituted in place of 4-bromo-2-ethyl-5-methoxy-pyridine in step 6 of that example. $^1$H NMR (400 MHz, CDCl$_3$) δ: 0.95 (t, J=7.2 Hz, 6 H), 1.45-1.78 (m, 8 H), 1.96-2.31 (m, 7 H), 2.74-2.80 (m, 4 H), 3.44 (d, J=3.03 Hz, 2 H), 7.35 (dd, J=8.08, 1.77 Hz, 1 H), 7.56 (s, 1 H), 7.70 (d, J=8.08, Hz 1 H). MS (ESI): 450 (M+H)$^+$.

Step 1: 244-Bromo-2-trifluoromethyl-phenyl)-2-ethyl-butyronitrile

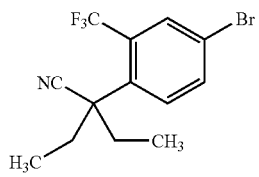

The title compound was prepared analogously to step 3 of example A(141) where iodoethane was substituted in place of methyl iodide in that example. $^1$H NMR (400 MHz, CDCl$_3$) δ 0.75 (t, J=7.2 Hz, 6 H), 1.3-1.4 (m, 4H), 7.46 (d, J=8.3 Hz, 1 H), 7.67 (d, J=8.3 Hz, 1 H), 7.78 (s, 1H).

Example A(147)

2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-ethylbutanenitrile

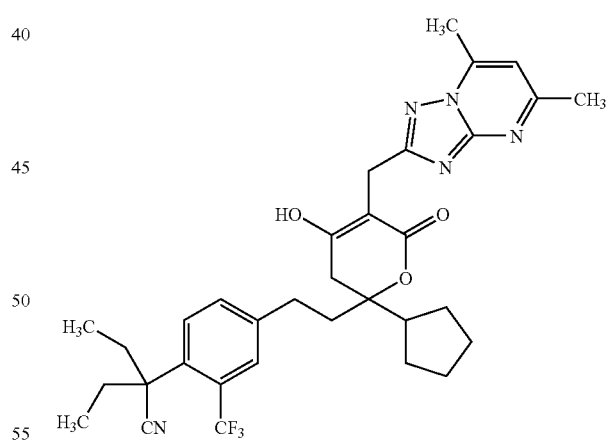

The title compound was prepared analogously to example A(1) where 2-[4-[2-(2-cyclopentyl-4,6-dioxotetrahydro-2H-pyran-2-yl)ethyl]-2-(trifluoromethyl)phenyl]-2-ethylbutanenitrile (example A(146))was substituted in place of 6-cyclopentyl-6-[2-(5-ethyl-4-hydroxy-2-propoxy-phenyl)-ethyl]-dihydro-pyran-2,4-dione of that example. $^1$H NMR (400 MHz, DMSO-d$_6$) δ: 0.77 (t, J=7.2 Hz, 6 H), 1.28-1.62 (m, 10 H), 1.90-2.10 (m, 5 H), 2.36-2.50 (m, 7 H), 2.58-2.74 (m, 3H), 3.62 (d, J=16 Hz, 1H), 3.74 (d, J=16 Hz, 1 H), 6.97 (s, 1 H), 7.58-7.67 (m, 3H), 10.77 (s, 1 H). MS (ESI): 610 (M+H)+

Example A(148)

Enantiomer 1 of 6-Cyclopentyl-6-(2-{4-[(dimethylamino)methyl]-3-ethylphenyl}ethyl)-3-[(5,7-dimethyl[1,2,4]triazolo[1,5-a]pyrimidin-2-yl)methyl]-4-hydroxy-5,6-dihydro-2H-pyran-2-one

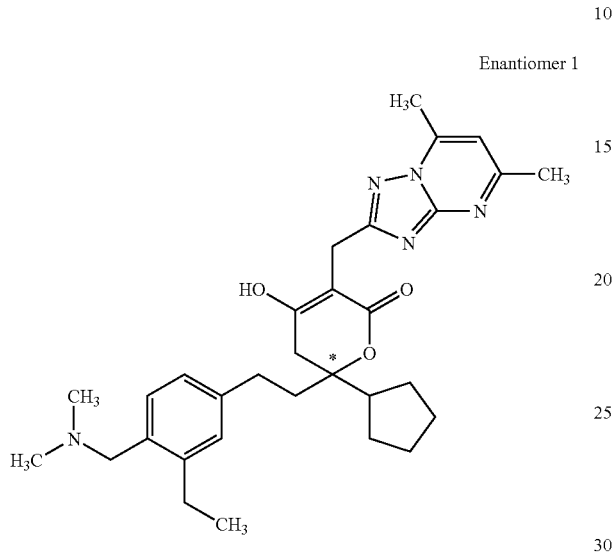

Enantiomer 1

The title compound was separated from racemic 6-cyclopentyl-6-(2-{4-[(dimethylamino)methyl]-3-ethylphenyl}ethyl)-3-[(5,7-dimethyl[1,2,4]triazolo[1,5-a]pyrimidin-2-yl)methyl]-4-hydroxy-5,6-dihydro-2H-pyran-2-one (238 mg, Example A(119)) using chiral HPLC (Chiralpak AS-H, 140 bar, 35% MeOH w/0.1% triethylamine). (31.7 mg, 2.108 min retention time, 100% ee).

Example A(149)

Enantiomer 2 of 6-Cyclopentyl-6-(2-{4-[(dimethylamino)methyl]-3-ethyl phenyl}ethyl)-3-[(5,7-dimethyl[1,2,4]triazolo[1,5-a]pyrimidin-2-yl)methyl]-4-hydroxy-5,6-dihydro-2H-pyran-2-one

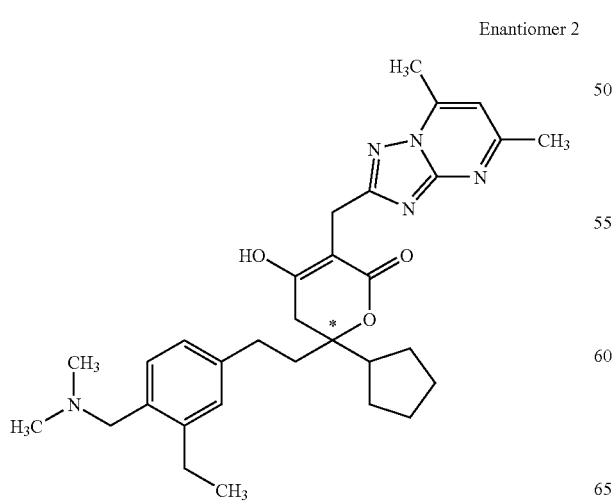

Enantiomer 2

The title compound was separated from racemic 6-cyclopentyl-6-(2-{4-[(dimethylamino)methyl]-3-ethylphenyl}ethyl)-3-[(5,7-dimethyl[1,2,4]triazolo[1,5-a]pyrimidin-2-yl)methyl]-4-hydroxy-5,6-dihydro-2H-pyran-2-one (238 mg, Example A(119)) using chiral HPLC (Chiralpak AS-H, 140 bar, 35% MeOH w/0.1% triethylamine). (20.7 mg, 3.754 min retention time, 100% ee).

Example A(150)

Enantiomer 1 of [4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]acetonitrile

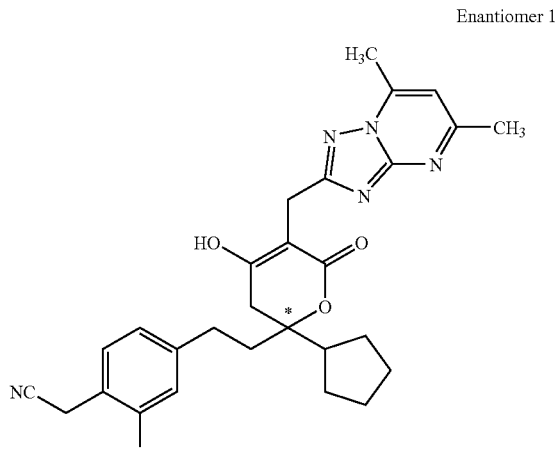

Enantiomer 1

The title compound was separated from racemic [4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]acetonitrile (490 mg, Example A(143)) using chiral HPLC (Chiralpak AS-H, 140 bar, 50% MeOH). (100 mg, 1.64 min retention time, 100% ee)

Example A(151)

Enantiomer 2 of [4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]acetonitrile

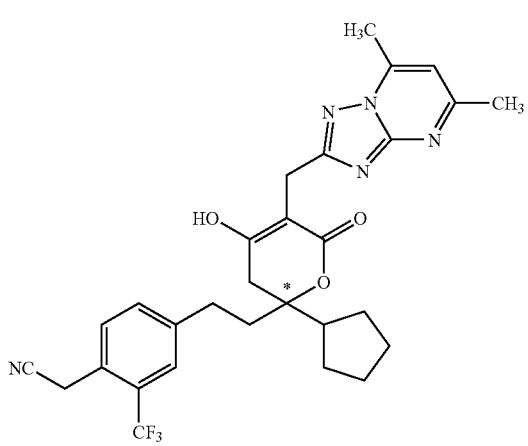

The title compound was separated from racemic [4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]acetonitrile (490 mg, Example A(143)) using chiral HPLC (Chiralpak AS-H, 140 bar, 50% MeOH). (75 mg, 3.67 min retention time, 100% ee)

Example A(152)

Enantiomer 1 of 1-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]cyclopropanecarbonitrile

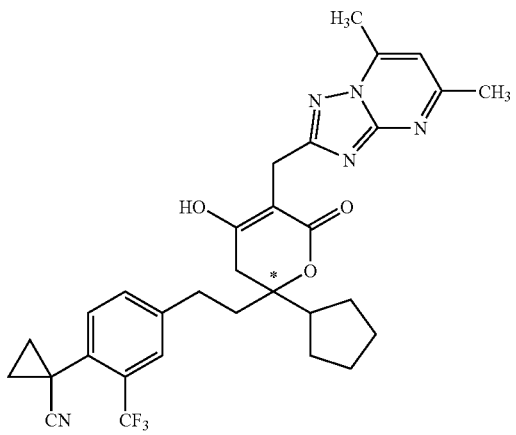

The title compound was separated from racemic 1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]cyclopropanecarbonitrile (250 mg, Example A(145)) using chiral HPLC (Chiralpak AS-H, 140 bar, 50% MeOH). (95 mg, 1.66 min retention time, 100% ee)

Example A(153)

Enantiomer 2 of 1-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]cyclopropanecarbonitrile

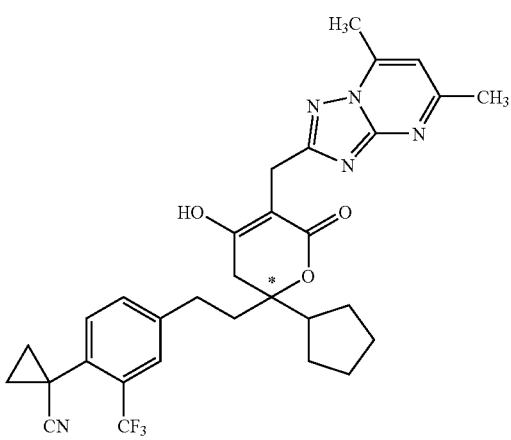

The title compound was separated from racemic 1-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]cyclopropanecarbonitrile (250 mg, Example A(145)) using chiral HPLC (Chiralpak AS-H, 140 bar, 50% MeOH). (67 mg, 5.36 min retention time, 100% ee)

Example A(154)

Enantiomer 1 of 2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-ethylbutanenitrile

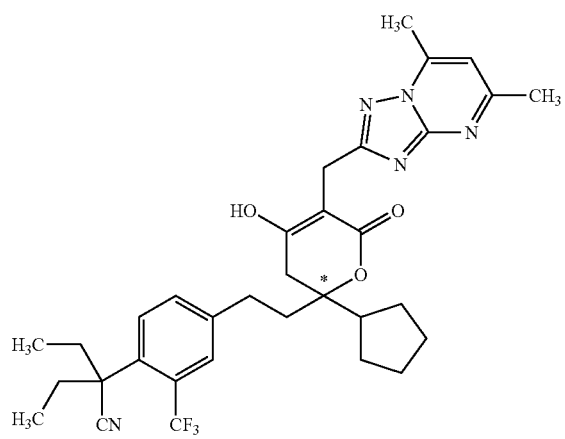

The title compound was separated from racemic 2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-ethylbutanenitrile (180 mg, Example A(147)) using chiral HPLC (Chiralpak AS-H, 140 bar, 30% MeOH). (62.27 mg, 2.47 min retention time, 100% ee)

Example A(155)

Enantiomer 2 of 2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-ethylbutanenitrile

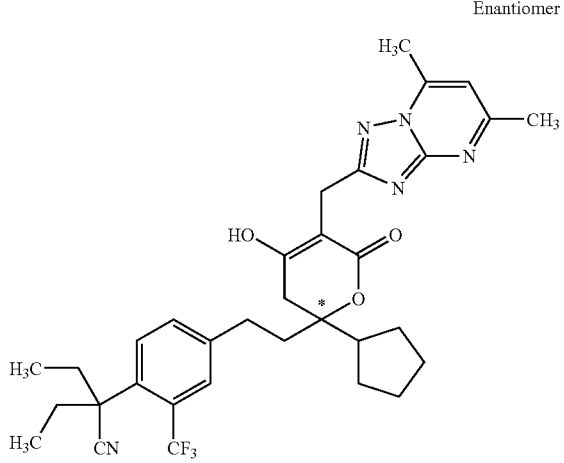

Enantiomer 2

The title compound was separated from racemic 2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-ethylbutanenitrile (180 mg, Example A(147)) using chiral HPLC (Chiralpak AS-H, 140 bar, 30% MeOH). (180 mg, 7.57 min retention time, 100% ee)

Example A(156)

Enantiomer 1 of 6-Cyclopentyl-3-[(5,7-dimethyl[1,2,4]triazolo[1,5-a]pyrimidin-2-yl)methyl]-6-{2-[3-ethyl-4-(morpholin-4-ylmethyl)phenyl]ethyl}-4-hydroxy-5,6-dihydro-2H-pyran-2-one

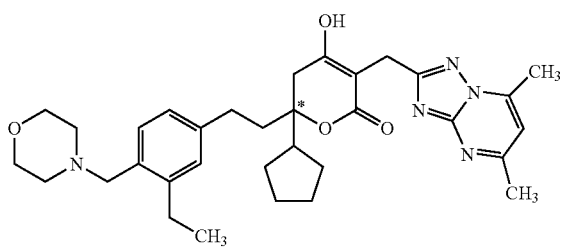

Enantiomer 1

The title compound was separated from racemic 6-cyclopentyl-3-[(5,7-dimethyl[1,2,4]triazolo[1,5-a]pyrimidin-2-yl)methyl]-6-{2-[3-ethyl-4-(morpholin-4-ylmethyl)phenyl]ethyl}-4-hydroxy-5,6-dihydro-2H-pyran-2-one (151 mg, Example A(123)) using chiral HPLC (Chiralpak AS-H, 140 bar, 40% MeOH). (32 mg, 3.302 min retention time, 100% ee)

Example A(157)

Enantiomer 2 of 6-Cyclopentyl-3-[(5,7-dimethyl[1,2,4]triazolo[1,5-a]pyrimidin-2-yl)methyl]-6-{2-[3-ethyl-4-(morpholin-4-ylmethyl)phenyl]ethyl}-4-hydroxy-5,6-dihydro-2H-pyran-2-one

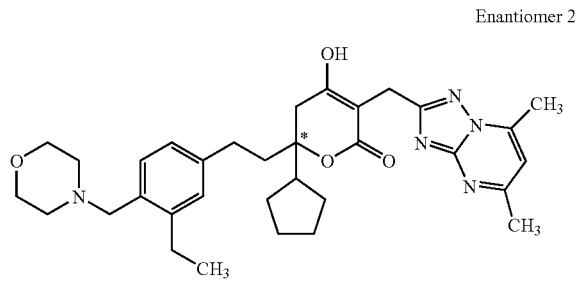

Enantiomer 2

The title compound was separated from racemic 6-cyclopentyl-3-[(5,7-dimethyl[1,2,4]triazolo[1,5-a]pyrimidin-2-yl)methyl]-6-{2-[3-ethyl-4-(morpholin-4-ylmethyl)phenyl]ethyl}-4-hydroxy-5,6-dihydro-2H-pyran-2-one (151 mg, Example A(123)) using chiral HPLC (Chiralpak AS-H, 140 bar, 40% MeOH). (34 mg, 9.004 min retention time, 100% ee)

Scheme 2: Heck Route

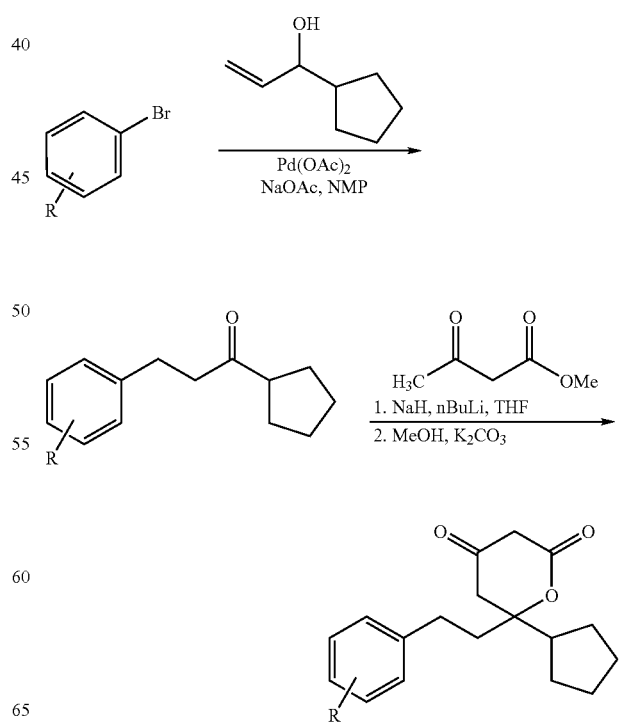

Example B(1)

6-{2-[3-Chloro-4-(methylsulfonyl)phenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one

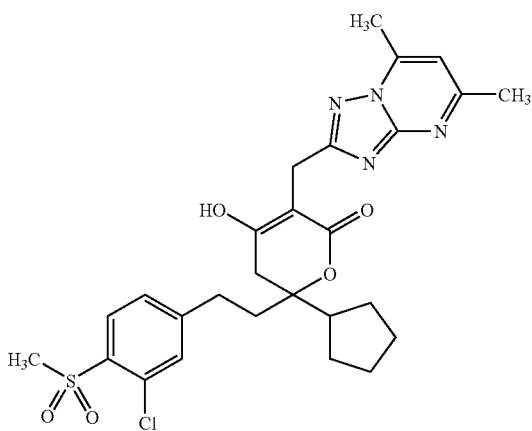

The title compound was prepared analogously to example A(1) where 6-{2-[3-chloro-4-(methylsulfonyl)phenyl]ethyl}-6-cyclopentyldihydro-2H-pyran-2,4(3H)-dione (Example B(2)) was substituted in place of 6-cyclopentyl-6-[2-(5-ethyl-4-hydroxy-2-propoxy-phenyl)-ethyl]-dihydro-pyran-2,4-dione in that example. $^1$H NMR (300 MHz, CDCl$_3$): δ 1.45-2.22 (m, 11 H), 2.56 (s, 3 H), 2.70-2.99 (m, 7 H), 3.02 (m, 2 H), 3.26 (s, 3H), 6.99 (s, 1 H), 7.01 (s, 1 H), 7.25 (s, 1 H), 7.36 (m, 2 H). Anal. Calcd. For C$_{27}$H$_{31}$N$_4$O$_5$S: C, 58.01; H, 5.59; N, 10.02. Found: C, 58.05; H, 5.50; N, 9.89.

Example B(2)

6-{2-[3-Chloro-4-(methylsulfonyl)phenyl]ethyl})cyclopentyldihydro-2H-pyran-2,4(3H)-dione

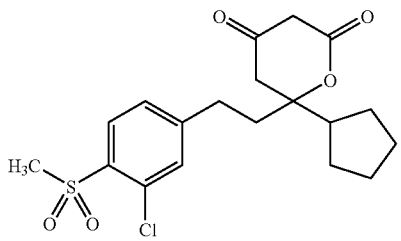

Methyl acetoacetate (1.03 mL, 9.5 mmol) was added to a cooled 0° C. suspension of NaH (0.38 g, 9.5 mmol, 60% dispersion in mineral oil) in THF (30 ml). After 15 min, n-BuLi (3.8 mL, 9.5 mmol, 2.5M in hexanes) was added. The resulting dianion was stirred for an additional 30 min and then treated with a solution of 3-(3-chloro-4-methanesulfonyl-phenyl)-1-cyclopentyl-propan-1-one (1.0 g, 3.18 mmol, from step 2 below) in THF (20 ml). After stirring for 30 mins at 0° C. and then at room temperature for 2 hours, the reaction mixture was quenched with 1N HCl and extracted with EtOAc. The organic layers were washed with brine, dried over Na$_2$SO$_4$ and concentrated to a yellow oil that was used without further purification. The oil was dissolved in methanol (100 mL), treated with potassium carbonate (1.0 g, 7.2 mmol), and refluxed under N$_2$ for 60 mins. The reaction mixture was partitioned between H$_2$O and IPE. The aqueous layer was made acidic with 1N HCl and extracted with EtOAc. The organic layers were washed with brine, dried over Na$_2$SO$_4$ and concentrated to give the product (0.9 g, 71% yield). $^1$H NMR (300 MHz, CDCl$_3$): δ 1.25-2.30 (m, 11 H), 2.75-3.16 (m, 6 H), 3.26 (s, 3H), 7.21 (s, 1 H), 7.40 (m, 2 H)

Step 1:
4-Bromo-2-chloro-1-methanesulfonyl-benzene

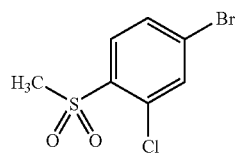

Hydrazine monohydrate (1.51 mL, 48 mmol) was added to a cooled 0° C. solution of 4-bromo-2-chlorobenzenesulfonyl chloride (5 g, 17.2 mmol) dissolved in THF (50 mL). The reaction was stirred at room temperature for 2 hours and then the solvent was removed in vacuo to give a white solid. The solid was dissolved in EtOH (100 mL) and treated with sodium acetate (6.56 g, 80 mmol) followed by methyl iodide (4.9 mL, 79 mmol). The reaction mixture was refluxed for 18 hours. The solvent was removed in vacuo to give a residue that was partitioned between 1 N HCl and EtOAc. The organic layer was dried over MgSO$_4$ and concentrated. The crude mixture was purified by flash column chromatography to give the product (1.5 g, 32%). $^1$H NMR (300 MHz, CDCl$_3$): δ 3.26 (s, 3H), 7.63 (dd, J=8.5, 1.9 Hz, 2 H), 7.74 (d, J=1.9 Hz, 1 H), 8.02 (d, J=8.5 Hz, 1 H).

Step 2: 343-Chloro-4-methanesulfonyl-phenyl)-1-cyclopentyl-propan-1-one

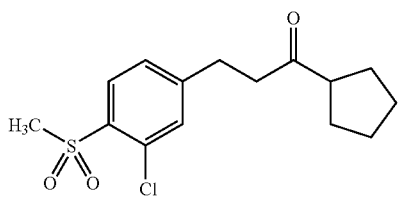

A mixture of 4-bromo-2-chloro-1-methanesulfonyl-benzene (1.5 g, 5.6 mmol), 1-cyclopentyl-2-propen-1-ol (0.88 g, 6.96 mmol) and sodium acetate (0.57 g, 6.9 mmol) in DMAC (20 mL) was purged with N$_2$ for 30 mins. Palladium (II) acetate (25 mg, 0.11 mmol) was added and the mixture was heated to 90° C. under N$_2$ for 16 hours. The reaction mixture was partitioned between 1N HCl and EtOAc. The organic layers were washed with saturated NaHCO$_3$, brine, dried over Na$_2$SO$_4$ and concentrated to a brown oil. Purification by flash column chromatography (0% to 20% EtOAc in hexanes) gave the desired product (1.2 g, 69%). $^1$H NMR (300 MHz, CDCl$_3$): δ 1.56-1.85 (br m, 8 H), 2.83 (m, 3 H), 2.96 (t, J=7.5

Hz, 2 H), 3.25 (s, 3 H), 7.29 (dd, J=8.1, 1.5 Hz, 1 H), 7.39 (d, J=1.5 Hz, 1 H), 8.04 (d, J=8.1 Hz, 1 H).

Example B(3)

6-Cyclopentyl-6-{2-[4-methylsulfonyl)-3-(trifluoromethyl)phenyl]ethyl}dihydro-2H-pyran-2,4(3H)-dione

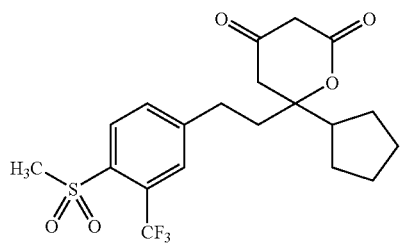

The title compound was prepared analogously to example B(2): where 4-bromo-1-methanesulfonyl-2-trifluoromethyl-benzene was substituted in place of 4-bromo-2-chlorobenzenesulfonyl chloride in step 1 of that example. ¹H NMR (300 MHz, CDCl₃): δ 1.50-2.40 (m, 11 H), 2.80-3.46 (m, 9 H), 7.52 (d, J=1.56 Hz, 1 H), 7.78 (s, 1 H), 7.90 (d, J=1.08 Hz, 1 H).

Example B(4)

6-Cyclopentyl-3-[(5,7-dimethyl[1,2,4]triazolo[1,5-a]pyrimidin-2-yl)methyl]-4-hydroxy-6-{2-[4-(methylsulfonyl)-3-(trifluoromethyl)phenyl]ethyl}-5,6-dihydro-2H-pyran-2-one

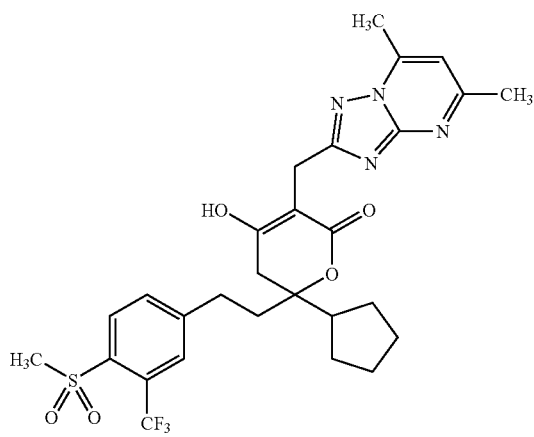

The title compound was prepared analogously to example A(1) where 6-cyclopentyl-6-{2-[4-(methylsulfonyl)-3-(trifluoromethyl)phenyl]ethyl}dihydro-2H-pyran-2,4(3H)-dione (Example B(3): was substituted in place of 6-cyclopentyl-6-[2-(5-ethyl-4-hydroxy-2-propoxy-phenyl)-ethyl]-dihydro-pyran-2,4-dione in that example. ¹H NMR (400 MHz, CDCl₃): δ 1.35-2.19 (m, 11 H), 2.40 (m, 5 H), 2.73 (m, 5 H), 3.04 (t, J=12.57 Hz, 2 H), 3.13 (s, 3 H), 7.03 (s, 1 H), 7.52 (d, J=1.52 Hz, 1 H), 7.80 (s, 1 H), 7.90 (d, J=2.56 Hz, 1 H) Anal. Calcd. For C₂₈H₃₁N₄O₅SF₃: C, 56.74; H, 5.27; N, 9.45. Found: C, 56.50; H, 5.40; N, 9.04.

Example B(5)

Methyl 4-[2-(2-cyclopentyl-4,6-dioxotetrahydro-2H-pyran-2-yl)ethyl]-2-fluorobenzoate

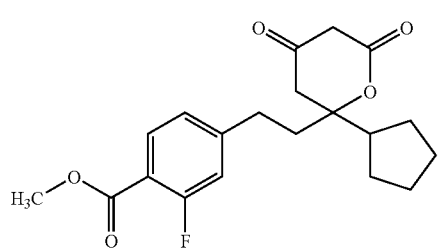

The title compound was prepared analogously to example B(2) where 4-bromo-2-fluoro-benzoic acid methyl ester was substituted in place of 4-bromo-2-chlorobenzenesulfonyl chloride in step 1 of that example. ¹H NMR (300 MHz, CDCl₃): δ 1.38-2.30 (m, 11 H), 2.80-3.15 (m, 6 H), 3.88 (s, 3 H), 6.91 (d, J=7.91 Hz, 1 H), 7.17 (m, 1 H), 7.93 (d, J=7.56 Hz, 1 H)

Example B(6)

4-[2-(2-Cyclopentyl-4,6-dioxotetrahydro-2H-pyran-2-yl)ethyl]-2-fluorobenzoic acid

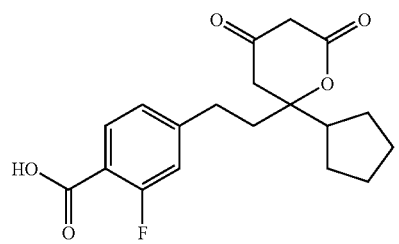

Methyl 4-[2-(2-cyclopentyl-4,6-dioxotetrahydro-2H-pyran-2-yl)ethyl]-2-fluorobenzoate (example B(5)) (300 mg) was treated with 4N NaOH (10 ml) and stirred for 4 hrs at room temperature. The mixture was then acidified with 1N HCl (20 ml) and the product was extracted with ethyl acetate (2×20 ml). The combined organic layers were dried over magnesium sulfate and concentrated to a solid. The solid was recrystallised from diethyl ether to afford the title compound as a white solid (120 mg). ¹H NMR (300 MHz, MeOD): δ

1.38-2.30 (m, 11 H), 2.80-3.12 (m, 6 H), 6.91 (d, J=7.19 Hz, 1 H), 7.17 (m, 1 H), 7.86 (d, J=719 Hz, 1 H)

Example B(7)

Methyl 2-chloro-4-[2-(2-cyclopentyl-4,6-dioxotetrahydro-2H-pyran-2-yl)ethyl]benzoate

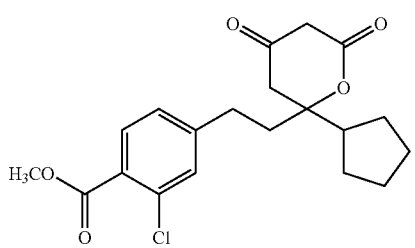

The title compound was prepared analogously to example B(2) where 4-bromo-2-chloro-benzoic acid methyl ester was substituted in place of .4-bromo-2-chlorobenzenesulfonyl chloride in step 1 of that example. $^1$H NMR (300 MHz, CDCl$_3$): δ 1.38-2.30 (m, 11 H), 2.78-3.15 (m, 6 H), 3.98 (s, 3 H), 7.10 (s, 1 H), 7.19 (d, J=1.58 Hz, 1 H), 7.62 (d, J=1.56 Hz, 1 H)

Example B(8)

Methyl 4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorobenzoate

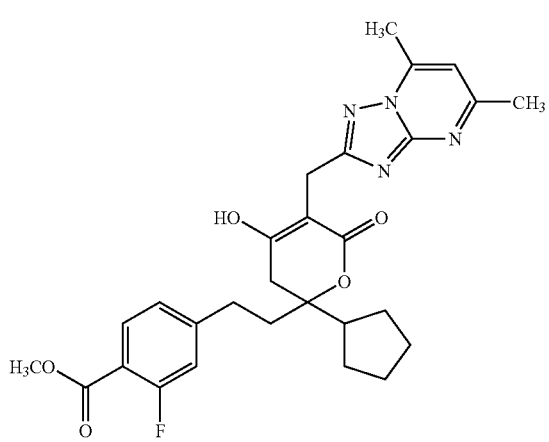

The title compound was prepared analogously to example A(1) where methyl 4-[2-(2-cyclopentyl-4,6-dioxotetrahydro-2H-pyran-2-yl)ethyl]-2-fluorobenzoate (example B(5)) was substituted in place of 6-cyclopentyl-6-[2-(5-ethyl-4-hydroxy-2-propoxy-phenyl)-ethyl]-dihydro-pyran-2,4-dione in that example. $^1$H NMR (300 MHz, CDCl$_3$): δ 1.25-1.85 (m, 8 H), 2.01-1.10 (m, 3 H), 2.58-2.80 (m, 10H), 3.10 (t, J=12.57 Hz, 1 H) 3.88 (s, 3 H), 6.91 (d, J=2.57 Hz, 1 H) 6.99 (s, 1 H), 7.15 (d, J=1.58 Hz, 1 H), 7.92 (m, 1 H) Anal. Calcd. For C$_{28}$H$_{31}$N$_4$O$_5$F: C, 64.36; H, 5.98; N, 10.72. Found: C, 64.50; H, 5.40; N, 10.70.

Example B(9)

Methyl 2-chloro-4-(2-{2-cyclopentyl-5-[(5,7-dimethyl[1,2,4]triazolo[1,5-a]pyrimidin-2-yl)methyl]-4-hydroxy-4-oxo-3,6-dihydro-2H-pyran-2-yl}ethyl)benzoate

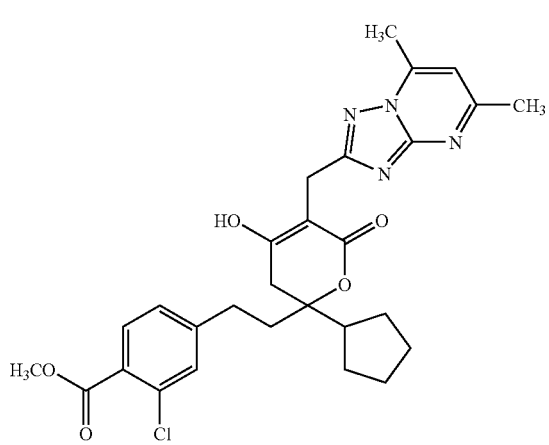

The title compound was prepared analogously to example A(1) where methyl 2-chloro-4-[2-(2-cyclopentyl-4,6-dioxotetrahydro-2H-pyran-2-yl)ethyl]benzoate (example B(7)) was substituted in place of 6-cyclopentyl-6-[2-(5-ethyl-4-hydroxy-2-propoxy-phenyl)-ethyl]-dihydro-pyran-2,4-dione in that example. $^1$H NMR (300 MHz, CDCl$_3$): δ 1.25-1.85 (m, 8 H), 2.01-1.10 (m, 3 H), 2.58-2.80 (m, 10 H), 3.10 (t, J=12.57 Hz, 1 H) 3.88 (s, 3 H), 6.91 (d, J=2.57 Hz, 1 H) 6.99 (s, 1 H), 7.10 (s, 1 H), 7.19 (d, J=1.8 Hz, 1 H), 7.62 (d, J=1.56 Hz, 1 H)

Example B(10)

2-Chloro-4-[2-(2-cyclopentyl-4,6-dioxotetrahydro-2H-pyran-2-yl)ethyl]benzoic acid

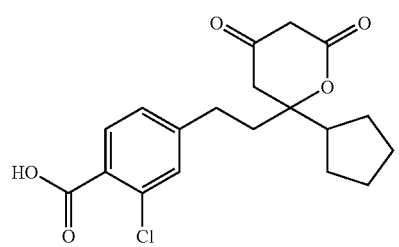

The title compound was prepared analogously to example B(6): where methyl 2-chloro-4-[2-(2-cyclopentyl-4,6-dioxotetrahydro-2H-pyran-2-yl)ethyl]benzoate (example B(7)) was substituted in place of methyl 4-[2-(2-cyclopentyl-4,6-dioxotetrahydro-2H-pyran-2-yl)ethyl]-2-fluorobenzoate in that example. $^1$H NMR (300 MHz, CDCl$_3$): δ 1.38-2.30 (m, 11 H), 2.78-3.15 (m, 6 H), 7.10 (s, 1 H), 7.19 (d, J=1.58 Hz, 1 H), 7.62 (d, J=1.56 Hz, 1 H) 12.30 (s, 1 H).

Example B(11)

4-(2-{2-Cyclopentyl-5-[(5,7-dimethyl[1,2,4]triazolo [1,5-a]pyrimidin-2-yl)methyl]-4-hydroxy-6-oxo-3,6-dihydro-2H-pyran-2-yl}ethyl)-2-fluorobenzoic acid

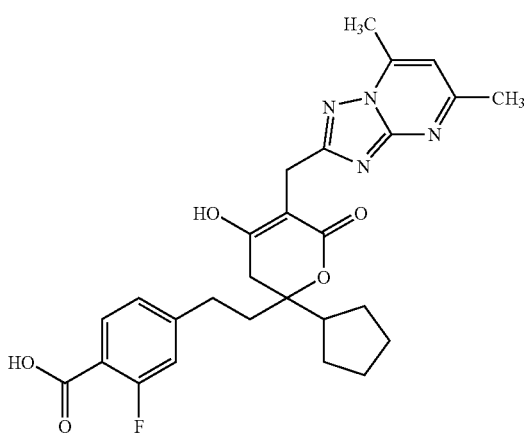

The title compound was prepared analogously to example A(1) where 4-[2-(2-cyclopentyl-4,6-dioxotetrahydro-2H-pyran-2-yl)ethyl]-2-fluorobenzoic acid (Example B(6): was substituted in place of 6-cyclopentyl-6-[2-(5-ethyl-4-hydroxy-2-propoxy-phenyl)-ethyl]-dihydro-pyran-2,4-dione in that example. $^1$H NMR (300 MHz, CDCl$_3$): δ 1.25-1.85 (m, 8 H), 2.01-1.10 (m, 3 H), 2.58-2.80 (m, 10 H), 3.10 (t, J=12.57 Hz, 1 H), 6.94 (d, J=2.57 Hz, 1 H) 6.99 (s, 1 H), 7.20 (d, J=8.29 Hz, 1 H), 7.90 (m, 1 H)

Example B(12)

2-Chloro-4-(2-{2-cyclopentyl-5-[(5,7-dimethyl[1,2, 4]triazolo[1,5-a]pyrimidin-2-yl)methyl]-4-hydroxy-6-oxo-3,6-dihydro-2H-pyran-2-yl}ethyl)benzoic acid

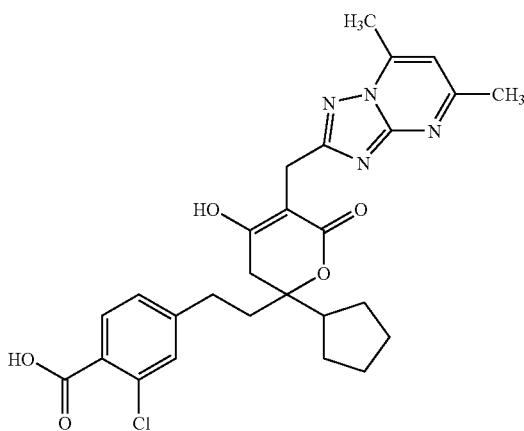

The title compound was prepared analogously to example A(1) where 2-chloro-4-[2-(2-cyclopentyl-4,6-dioxotetrahydro-2H-pyran-2-yl)ethyl]benzoic acid (example B(10)) was substituted in place of 6-cyclopentyl-6-[2-(5-ethyl-4-hydroxy-2-propoxy-phenyl)-ethyl]-dihydro-pyran-2,4-dione in that example. $^1$H NMR (300 MHz, CDCl$_3$): 1.25-1.85 (m, 8 H), 2.01-1.10 (m, 3 H), 2.58-2.80 (m, 10 H), 3.10 (t, J=12.57 Hz, 1 H), 6.99 (s, 1 H), 7.10 (s, 1 H), 7.22 (d, J=7.26 Hz, 1 H), 7.60 (d, J=7.56 Hz, 1H)

Example B(13)

Ethyl 2-[(6-{2-[3-chloro-4-(1-cyano-1-methylethyl) phenyl]ethyl}-6-cyclopentyl-4-hydroxy-2-oxo-5,6-dihydro-2H-pyran-3-yl)methyl][1,2,4]triazolo[1,5-a] pyrimidine-6-carboxylate

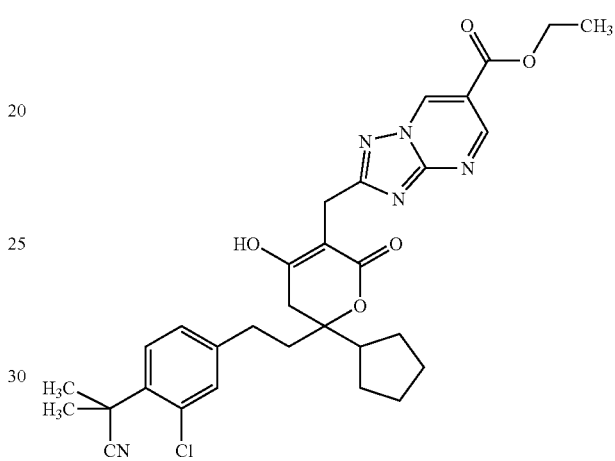

The title compound was prepared analogously to example A(1) where 2-{2-chloro-4-[2-(2-cyclopentyl-4,6-dioxo-tetrahydro-pyran-2-yl)-ethyl]-phenyl}-2-methyl-propionitrile from step 5 of example B(22) was substituted in place of 6-cyclopentyl-6-[2-(5-ethyl-4-hydroxy-2-propoxy-phenyl)-ethyl]-dihydro-pyran-2,4-dione and 2-formyl-[1,2,4]triazolo [1,5-]pyrimidine-6-carboxylic acid ethyl ester from step 2 below was substituted in place of 2,5-dimethyl-2H-[1,2,4] triazole-3-carbaldehyde in that example. $^1$H NMR (300 MHz, CDCl$_3$): δ 1.36 (t, J=7.56, Hz, 3 H) 1.42-1.68 (m, 8 H), 1.85 (s, 6 H), 2.00-2.25 (m, 5 H), 3.24-3.48 (m, 5 H), 4.24 (q, J=12.06 Hz, 2 H), 6.89-7.39 (m, 5 H). Anal. Calcd. For C$_{31}$H$_{34}$ClN$_5$O$_5$: C, 62.89; H, 5.79; N, 11.83. Found: C, 62.94; H, 5.73; N, 11.46.

Step 1: 2-Hydroxymethyl-[1,2,4]triazolo[1,5]pyrimidine-6-carboxylic acid ethyl ester

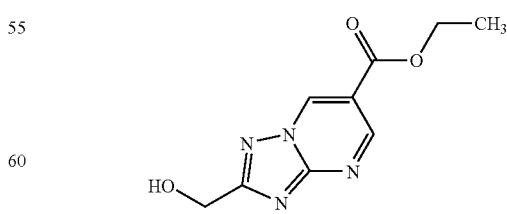

5-Amino-1H-[1,2,4]triazol-3-yl)-methanol (Bru-Magniez et al US (1995) U.S. Pat. No. 5,387,747 A19950207) (7.9 g, 41.6 mmol) was mixed with 2-formyl-3-oxo-propionic acid ethyl ester (Tori Sigeri et al Synthesis (1986) 5 pg 400-402), (6.0 g, 41.6 mmol) in acetic acid (30 ml). The reaction mixture was heated to 60° C. for 18 hrs. After which time the mixture was cooled to room temperature and diluted with diethyl ether (200 ml). Product crashes out of solution. The solids are then filtered and washed with diethyl ether (200 ml), product dried in vacc oven for 5 hrs. To afford title compound as a white solid (8.0 g). $^1$H NMR (300 MHz, CDCl$_3$): δ 1.47 (t, J=6.97, Hz, 3 H) 3.00 (bs, 1 H) 4.53 (q, J=7.16 Hz, 2 H), 5.00 (s, 2 H) 9.40 (d, J=2.07, Hz, 1 H) 9.50 (d, J=2.07, Hz, 1 H)

Step 2: 2-Formyl-[1,2,4]triazolo[1,5-]pyrimidine-6-carboxylic acid ethyl ester

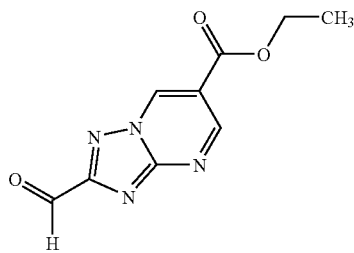

2-Hydroxymethyl-[1,2,4]triazolo[1,5]pyrimidine-6-carboxylic acid ethyl ester (1.0 g, 4.5 mmol) was mixed with TEMPO (75 mg, 7.5% by wt) and PhI(OAc)$_2$ (1.59 g, 4.95 mmol) in dichloromethane (7.5 ml). The reaction was stirred at room temperature for 18 hrs after which time the reaction was Purified by flash column chromatography (0% to 700% EtOAc in hexanes) gave the product as a white solid (800 mg.). $^1$H NMR (300 MHz, CDCl$_3$): δ 1.42 (t, J=6.97, Hz, 3 H), 4.48 (q, J=6.97 Hz, 2 H), 5.00 (s, 2 H) 9.39 (d, J=2.26, Hz, 1 H) 10.12 (d, J=2.26, Hz, 1 H), 10.20 (s, 1 H).

Example B(14)

2-(2-Chloro-4-{2-[2-cyclopentyl-4-hydroxy-5-(imidazo[1,2-b][1,2,4]triazin-6-ylmethyl)-6-oxo-3,6-dihydro-2H-pyran-2-yl]ethyl}phenyl)-2-methylpropanenitrile

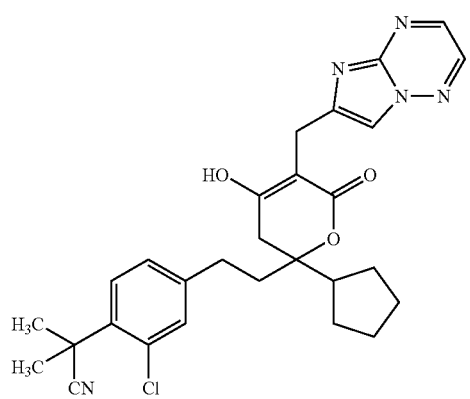

Prepared analogously to example A(1) substituting imidazo[1,2-b][1,2,4]triazine-6-carbaldehyde (47 mg, 0.34 mmol, from step 2 below) in place of 5,7-dimethyl-[1,2,4]triazolo[1,5-a]pyrimidine-2-carbaldehyde and 2-{2-chloro-4-[2-(2-cyclopentyl-4,6-dioxo-tetrahydro-pyran-2-yl)-ethyl]-phenyl}-2-methyl-propionitrile (87 mg, 0.22 mmol from step 5 of example B(22)) in place of 6-cyclopentyl-6-[2-(5-ethyl-4-hydroxy-2-propoxy-phenyl)-ethyl]-dihydro-pyran-2,4-dione. Yield: 10 mg, 8.7%. $^1$H NMR (400 MHz, CDCl$_3$) δ 1.24-1.74 (m, 8 H), 1.83 (s, 6 H), 1.98-2.02 (m, 2 H), 2.39 (t, J=8.84 Hz, 1 H), 2.50 (d, J=17.68 Hz, 1 H), 2.63-2.71 (m, 2 H), 2.76 (d, J=17.94 Hz, 1 H), 4.02 (d, J=3.03 Hz, 2 H), 7.06 (dd, J=8.08, 1.77 Hz, 1 H), 7.20 (d, J=1.77 Hz, 1 H), 7.34 (d, J=8.08 Hz, 1 H), 7.89 (s, 1 H), 8.44 (dd, J=21.73, 2.02 Hz, 2 H).

Step 1: Imidazo[1,2-b][1,2,4]triazine-6-carboxylic acid ethyl ester

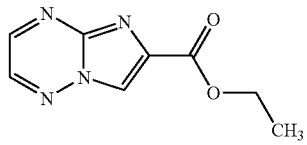

A solution of 3-amino-1,2,4-triazine (5.0 g, 52 mmol) and ethyl bromopyruvate (11 mL, 88 mmol) in ethanol (50 mL) was heated to reflux for 20 minutes. The reaction was cooled to room temperature, and then partitioned between 200 mL of EtOAc and 200 mL of water. The layers were separated, and the organic layer was dried over MgSO$_4$. The solids were removed by filtration, and then the solvent was removed by rotary evaporation. The residue was purified by chromatography (90 g SiO$_2$, 50 to 70% EtOAc in hexanes) to give the desired product (181 mg, 1.8%). MS (ESI): 192.4 (M+H)$^+$.

Step 2: Imidazo[1,2-b][1,2,4]triazine-carbaldehyde

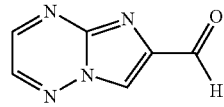

To a solution of imidazo[1,2-b][1,2,4]triazine-6-carboxylic acid ethyl ester (500 mg, 2.6 mmol, from step 1 above) in CH$_2$Cl$_2$ (15 mL) cooled to −78° C. was added diisobutylaluminum hydride (2.6 mL, 1.5 M in toluene). The reaction was stirred for one hour, and then extra diisobutylaluminum hydride (1 mL, 1.5 M) was added. After 20 more minutes, the cold reaction was quenched with EtOAc (10 mL), and then MeOH (10 mL). After the reaction had warmed to room temperature, 30 mL of 0.3 M HCl was added. The layers were separated. The aqueous phase was extracted three times with 10 mL of CH$_2$Cl$_2$. After the organic layers were combined and dried over MgSO$_4$, the solids were removed by filtration. The organic liquid was concentrated by rotary evaporation, and the resulting oil was chromatographed (40 g SiO$_2$, 50 to 100% EtOAc in hexanes) to give the desired product (47 mg, 12%). $^1$H NMR (400 MHz, CDCl$_3$) δ 8.48 (s, 2 H), 8.62 (d, J=1.77 Hz, 1 H), 10.25 (s, 1 H).

Example B(15)

6-[2-(5-Chloro-2,4-dimethoxyphenyl)ethyl]-6-cyclopentyl-4-hydroxy-3-[(1-methyl-3-pyrazin-2-yl-1H-1,2,4-triazol-5-yl)methyl]-5,6-dihydro-2H-pyran-2-one

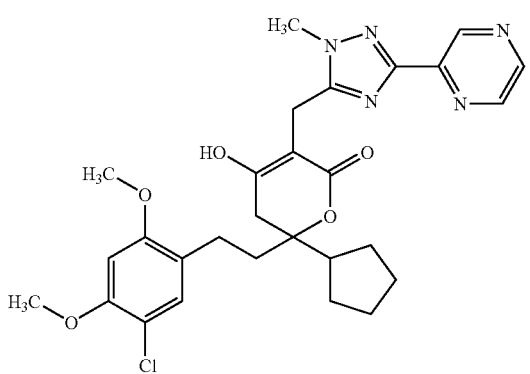

A solution of 6-[2-(5-chloro-2,4-dimethoxy-phenyl)-ethyl]-6-cyclopentyl-dihydro-pyran-2,4-dione (0.300 g, 0.78 mmol, from step 6 below) in hot isopropanol (5 mL) was treated with (CH$_3$)$_2$NHBH$_3$ (48 mg, 0.815 mmol, 1.04 equiv), then with a solution of 2-methyl-5-pyrazin-2-yl-2H-[1,2,4]triazole-3-carbaldehyde dihydrochloride monohydrate (229 mg, 0.819 mmol, 1.05 equiv, from step 3 below) in isopropanol (3 mL) containing triethylamine (0.230 mL, 2 equiv). The reaction mixture was stirred at room temperature, resulting in complete conversion after 1 h. The mixture was acidified with 1 M aqueous HCl to a pH of 2, stirred for 10 min, and concentrated in vacuo to afford a resin. This was diluted with water and extracted with dichloromethane containing 10% methanol (3×15 mL). The extract was dried over Na$_2$SO$_4$, filtered, and concentrated, affording the crude product (410 mg). This material was recrystallized from hot methylene chloride/ether, then the resulting solid triturated with acetone containing petroleum ether, filtered, and dried, affording the title product (107 mg, 24%). $^1$H NMR (300 MHz, DMSO-d$_6$): δ 1.26-1.75 (m, 8H), 1.78-2.13 (m, 2H), 2.37 (m, 1H), 2.45-2.50 (m, 2H, overlap with DMSO-d$_5$), 2.65 (d, J=17.9 Hz, 1H), 2.73 (d, J=17.9 Hz, 1H), 3.73 (s, m overlap, 5H), 3.80 (s, 3H), 3.95 (s, 3H), 6.63 (s, 1H), 7.05 (s, 1H), 8.6 (m, overlap, 2H), 8.93 (s, 1H), 11.07 (br s, 1H). LC-MS (APCI) calcd for C$_{28}$H$_{32}$ClN$_5$O$_5$: 553.21, found (M+H$^+$): 554.4 m/z.

Step 1: Ar-Methylpyrazine-2-carbohydrazonamide

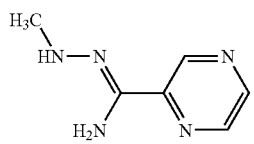

A 2-L flask was charged with molten 2-cyanopyrazine (50.0 g, 0.48 mol), methylhydrazine (80.0 g, 1.7 mol, 3.6 equiv), and ethanol (300 mL). The mixture was stirred at room temperature under nitrogen for 3 h, upon which time the reaction appeared complete by LC/MS. The yellow needles which had crystallized were filtered and washed with heptane to remove the unreacted methylhydrazine. The filtrate was concentrated in vacuo to a small volume, resulting in the formation of additional precipitate. The filtration, washing, and concentration process was repeated three times, affording additional batches of product. The combined batches were suspended in heptane (400 mL), stirred for 1 h, filtered, washed with heptane, and dried in vacuo at 50° C. overnight, affording the title amidrazone (55.4 g, 76%). $^1$H NMR (300 MHz, CDCl$_3$): δ 3.01 (s, 3H), 3.80 (br s, 1H), 5.04 (br s, 2H), 8.41 (s, 1H), 8.48 (s, 1H), 9.32 (s, 1H). MS (APCI) calcd for C$_6$H$_9$N$_5$: 151.09, found (M+H$^+$): 152.1

Step 2: 245-Diethoxymethyl-1-methyl-1H-[1,2,4]triazol-3-yl)-pyrazine

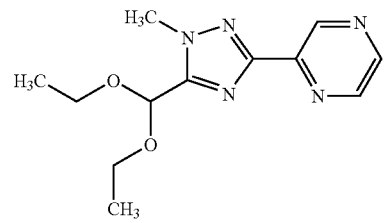

A 1-L flask was charged with diethoxyacetonitrile (25.0 g, 0.19 mol), a solution of sodium methoxide in methanol (4.32 g of 25 wt % solution, 0.02 mol, 10 mol %), and methanol (200 mL). The mixture was stirred at room temperature for 20 h, affording a solution of the imidate ester, 2,2-diethoxy-acetimidic acid methyl ester. The reaction mixture was treated with the amidrazone, N'-methylpyrazine-2-carbohydrazonamide (28.7 g, 0.19 mol, 1 equiv), from Step 1, and acetic acid (18.0 g, 0.30 mol, 1.5 equiv). The mixture was stirred at room temperature for 3 h, upon which time the reaction was complete by LC/MS. The volatiles were removed in vacuo, affording a viscous oil. This was basified with 20% Na$_2$CO$_3$ (100 mL) and saturated NaHCO$_3$ (200 mL), and extracted several times with ether (2 L total). The ether phase was washed with water (1×200 mL), dried over Na$_2$SO$_4$, filtered, and evaporated, affording the title acetal as a yellow oil (44.6 g, 89%). $^1$H NMR (300 MHz, CDCl$_3$): δ 1.24 (t, J=6 Hz, 6H), 3.62 (5-line pattern, J=6 Hz, 2H), 3.79 (5-line pattern, J=6 Hz, 2H), 4.08 (s, 3H), 5.68 (s, 1H), 8.56 (m, 1H), 8.63 (m, 1H), 9.34 (s, 1H). MS (APCI) calcd for C$_{12}$H$_{17}$N$_5$O$_2$: 263.14, found (M+H$^+$): 264.1

Step 3: 2-Methyl-5-pyrazin-2-yl-2H-[1,2,4]triazole-3-carbaldehyde dihydrochloride monohydrate

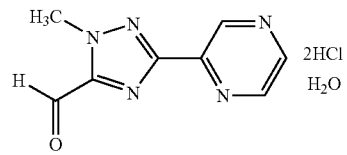

The acetal from step 2, 2-[5-(diethoxymethyl)-1-methyl-1H-1,2,4-triazol-3-yl]pyrazine (44.5 g, 0.17 mol) was dissolved in water (150 mL) and conc. HCl (30.0 mL of 12 M, 0.36 mol, ~2 equiv). The solution was degassed with nitrogen for 2 min and heated in an oil bath at a bath temperature of 60° C. for 2 h, resulting in complete hydrolysis of the acetal group. The volatiles were removed in vacuo, affording a yellow solid (49.8 g). This was suspended in dichloromethane (1 L), refluxed under nitrogen for 1 h, then filtered while still hot. The filter cake was washed with dichloromethane and dried in vacuo at 50° C. for 4 h, affording the title product (41.0 g, 81%) as a hygroscopic yellow solid. $^1$H NMR (300 MHz, DMSO-$d_6$): δ 4.21 (s, 3H), 8.50 (br s, 4H), 8.75 (m, 2H), 9.27 (s, 1H), 10.01 (s, 1H). MS (APCI) calcd for $C_8H_7N_5O$: 189.07, found (M+H$^+$): 190.1, 208.1 (hydrate); Anal. Calcd. For $C_8H_{11}Cl_2N_5O_2$: C, 34.30; H, 3.96; N, 25.00; O, 11.42; Cl, 25.31. Found: C, 33.43; H, 3.98; N, 24.70; O, 11.17; Cl, 25.44.

Step 4: 1-Cyclopentyl-3-(2,4-dimethoxy-phenyl)-propan-1-one

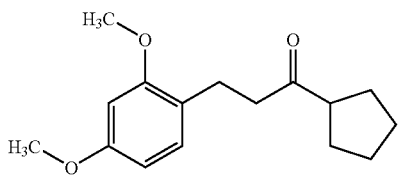

A solution of 2,4-dimethoxybenzaldehyde (10.27 g, 45 mmol) and methyl cyclopentyl ketone (6.06 g, 54 mmol) in anhydrous ethanol (81 mL) was treated with 5 M NaOH (aq) (18 mL, 90 mmol) and the mixture stirred at room temperature for 18 h. The volatiles were removed in vacuo. The residue was extracted with ether (100 mL) and the extract washed with water (3×60 mL), then with brine. The ethereal solution was dried over MgSO$_4$, filtered, and concentrated in vacuo, affording the intermediate chalcone in a crude yield of 14.63 g. The crude intermediate (14.52 g) was dissolved in 110 mL ethyl acetate, treated with platinum oxide (5 mole %) and stirred over 1 atm of H$_2$ at room temperature overnight. The Pt was filtered through a fine fritted funnel and the black residue washed with ethyl acetate. The filtrate was concentrated in vacuo to give a yellowish resin. The resin was chromatographed using silica gel and 6:1 hexanes/ethyl acetate, yielding 6.02 g (41%) of the ketone as a colorless oil. $^1$H NMR (CDCl$_3$): δ 1.48-1.81 (m, 8H), 2.67 (m, 2H), 2.80 (m, 3H), 3.76 (s, 3H), 3.75 (s, 3H), 6.37 (dd, J=8.1, 2.1 Hz, 1H), 6.41 (d, J=2.1 Hz, 1H), 7.00 (d, J=8.1 Hz, 1H). MS (APCI) calcd for $C_{16}H_{22}O_3$: 262.2; found (M+H$^+$): 263.1.

Step 5: 6-Cyclopentyl-6-[2-(2,4-dimethoxy-phenyl)-ethyl]-dihydro-pyran-2,4-dione

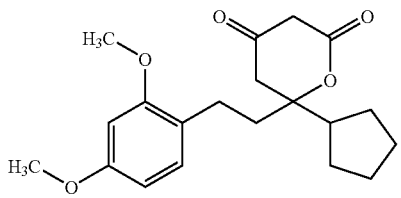

Methylacetoacetate (1.63 mL, 15.1 mmol) was dissolved in dry THF (42 mL) and cooled to 0° C. NaH (60% in mineral oil, 0.604 g, 15.1 mmol) were carefully added and the reaction mixture was stirred for 20 min. A solution of BuLi in hexanes (1.6 M, 9.44 mL, 15.1 mmol) was added dropwise and the resulting mixture was stirred an additional 20 min. A solution of 3-(2,4-dimethoxyphenyl)-1-cyclopentylpropan-1-one (2.33 g, 7.55 mmol) from Step 4 above in THF (37 mL) was added dropwise. After stirring 1 h, the reaction mixture was quenched with saturated aq NH$_4$Cl (100 mL) and extracted with Et$_2$O (600 mL). The organic phase was dried over MgSO$_4$ and evaporated. The residue was then stirred overnight in a mixture of 0.1 M NaOH (370 mL) and THF (37 mL). After the addition of solution of 10% aqueous KHSO$_4$ (50 mL), the resulting mixture was stirred 30 min and then extracted with Et$_2$O (600 mL). The organic phase was washed with brine, dried over MgSO$_4$ and evaporated. The residue was purified by flash column chromatography (50% EtOAc in hexanes) to give the product (1.54 g, 52%) as a white foam. $^1$H NMR (CDCl$_3$) δ 1.43 (m, 2 H), 1.78 (m, 8 H), 2.33 (m, 1H), 2.58 (m, 2H), 2.78 (s, 2H), 3.43 (s, 2H), 3.78 (s, 6H), 6.37 (s, 1H), 6.47 (s, 1H), 6.93 (d, J=7.93 Hz, 1H). MS (APCI) calcd for $C_{20}H_{26}O_5$: 346.2; found (M+1): 347.0.

Step 6. 6-[2-(5-Chloro-2,4-dimethoxy-phenyl)-ethyl]-6-cyclopentyl-dihydro-pyran-2,4-dione

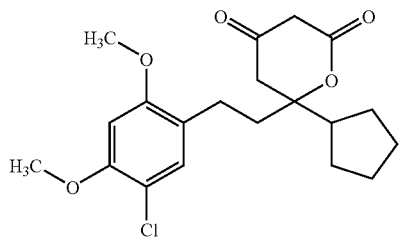

A solution of 6-[2-(2,4-dimethoxyphenyl)ethyl]-6-cyclopentyldihydro-2H-pyran-2,4(3H)-dione (from Step 5, above) (4.50 g, 13 mmol) in CH$_2$Cl$_2$ (20 mL) was cooled to −5° C. and treated with a solution of SO$_2$Cl$_2$ (1.94 g, 14.3 mmol) in CH$_2$Cl$_2$ (10 mL) dropwise under nitrogen. The reaction mixture was stirred for an additional 15 minutes at −5° C., then allowed to warm gradually to room temperature. After a total reaction time of 2 h, an aqueous solution of NaHCO$_3$ (5 wt %) was added to achieve a pH of 8 in the aqueous phase. The volatiles were removed in vacuo. The residue was treated with water and extracted with ethyl acetate (3×25 mL). The combined ethyl acetate extract was acidified to a pH 2 using 2 N HCl, then washed with water. The organic phase was dried over Na$_2$SO$_4$, filtered, and concentrated to a yellowish solid. Recrystallization from ether afforded the title product as a white solid (2.18 g, 44%). $^1$H NMR (CDCl$_3$) δ 1.74 (m, 8H), 2.32 (m, 1H), 2.58 (m, 2H), 2.78 (s, 2H), 3.43 (s, 2H), 3.82 (s, 3H), 3.92 (s, 3H), 6.44 (s, 1H), 7.07 (s, 1H). HRMS calcd for $C_{20}H_{25}O_5Cl$ (M+H$^+$): 381.1469, found 381.1475.

Example B(16)

6-[2-(5-Chloro-2,4-dimethoxyphenyl)ethyl]-6-cyclopentyl-4-hydroxy-3-[(1-methyl-3-pyridin-2-yl-1H-1,2,4-triazol-5-yl)methyl]-5,6-dihydro-2H-pyran-2-one

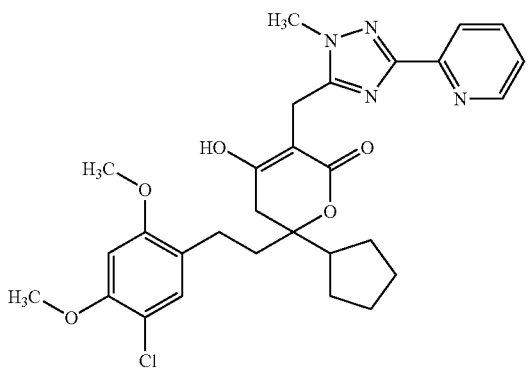

The title compound was prepared analogously to example B(15) using 2-methyl-5-pyridin-2-yl-2H-[1,2,4]triazole-3-carbaldehyde from step 3 below in place of 2-methyl-5-pyrazin-2-yl-2H-[1,2,4]triazole-3-carbaldehyde dihydrochloride monohydrate, and omitting the triethylamine. The crude material obtained after the aqueous workup (425 mg) was chromatographed on silica gel using a gradient of ethyl acetate containing 1% methanol to 15% methanol. The product-containing fractions were concentrated and the resulting solid recrystallized from hot dichloromethane/ether, affording 43 mg (10%) of the title product as a hydrated hydrochloride salt. $^1$H NMR (300 MHz, DMSO-d$_6$): δ 1.15-1.6 (m, 8H), 1.6-1.9 (m, 2H), 2.05 (m, 1H), 2.15-2.45 (m, 4H, overlap), 3.6-3.75 (s, m overlap, 5H), 3.80 (s, 3H), 3.95 (s, 3H), 6.67 (s, 1H), 6.92 (s, 1H), 7.3 (br m, 1H), 7.85 (br m, 2H), 8.92 (br m, 1H). LC-MS (APCI) calcd for $C_{29}H_{33}ClN_4O_5$: 552.21, found (M+H$^+$): 553.4 m/z. Anal. Calcd. For $C_{29}H_{36}Cl_2N_4O_6$: C, 57.33; H, 5.97; N, 9.22. Found: C, 57.46; H, 5.41; N, 8.12.

Step 1: N'-Methylpyridine-2-carbohydrazonamide

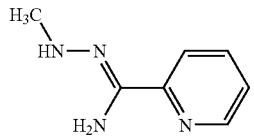

This compound was prepared by a modification of a reported procedure (J. Het Chem. 1975, 12, 855): A 2-L, 3-necked round bottom flask was charged with 2-cyanopyridine (40 g, 0.384 mol), methylhydrazine (93.7 g, 5.3 equiv, 2.035 mol), and ethanol (200 mL). The reaction was stirred under N$_2$, overnight at room temperature. An additional equiv of hydrazine was added (6.3 equiv cumulative total in reaction mixture) and stirred for an additional 2-3 h at room temperature. The EtOH and excess hydrazine were distilled off in vacuo to afford a yellow crystalline solid. The yellow solid was triturated with benzene, affording a slurry of white crystals. The crystals were filtered, washed with a minimal amount of benzene and dried overnight in a vacuum oven at 50° C. The reaction yielded 41.33 g (71.6%) of the product as white crystals. $^1$H NMR (300 MHz, CDCl$_3$): δ 2.97 (s, 3H), 4.02 (br s, 1H), 5.30 (br s, 1H), 7.20 (m, 1H), 7.66 (m, 1H), 8.08 (m, 1H), 8.45 (m, 1H). MS (APCI) calcd for $C_7H_{10}N_4$: 150.09, found (M+H$^+$): 151.3

Step 2: 2-(5-Diethoxymethyl-1-methyl-1H-[1,2,4]triazol-3-yl)-pyridine

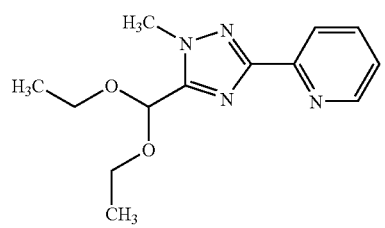

A 1-L, 3-necked round bottom flask was charged with a solution prepared from sodium methoxide (9.41 g, 0.174 mol, 0.9 equiv) in anhydrous methanol (150 mL). A solution of diethoxyacetonitrile (25 g, 0.193 mol) in anhydrous methanol (70 mL), was added to the methoxide solution, slowly, over 15 min, via an addition funnel. The reaction was then stirred overnight at room temperature, and the excess methanol was evaporated, in vacuo. The resulting oil was diluted with water and extracted into ethyl acetate (2×250 mL), then CH$_2$Cl$_2$ (2×250 mL). The organic phases were combined and dried over Na$_2$SO$_4$, filtered and concentrated in vacuo affording 9 g, (29%) of crude methyl 2,2-diethoxyethanimidoate having a purity of 80-85% by $^1$H NMR. This was used in the next step without further purification. A 500-mL round bottom flask was charged with a solution of the amidrazone from Step 1, N'-methylpyridine-2-carbohydrazonamide (22 g, 0.0548 mol) in methanol (75 mL), along with a solution of the crude imidate ester (8.84 g, 0.0548 mol) in methanol (75 mL). The mixture was treated with glacial acetic acid (4.75 mL, 1.5 equiv), and stirred at room temperature overnight while monitoring by LC/MS for disappearance of the amidrazone. The methanol was evaporated in vacuo, and the resulting oil was neutralized with saturated, aqueous NaHCO$_3$. The product was extracted into ethyl acetate (3×150 mL) and the organic phase dried over Na$_2$SO$_4$, filtered and concentrated, to give a yellow oil (11.06 g, 76% crude yield) of the acetal intermediate that was used in the next step without purification.

Step 3: 2-Methyl-5-pyridin-2-yl-2H-[1,2,4]triazole-3-carbaldehyde

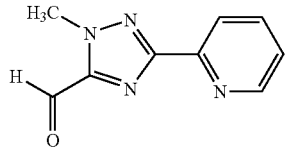

The acetal from step 2, 2-[5-(diethoxymethyl)-1-methyl-1H-1,2,4-triazol-3-yl]pyridine (11.06 g, 0.042 mol) was dissolved in 1.5 equiv of 2 N HCl (aq) and stirred at 40-50° C., overnight. The mixture was concentrated, yielding a viscous oil, which was then basified to pH 10 using saturated aqueous Na$_2$CO$_3$. The mixture was then extracted using ethyl acetate (4×200 mL), the organic layer dried over Na$_2$SO$_4$, filtered and concentrated, to a yellow solid. The solid was dissolved in a minimal amount of hot ethyl acetate, scratched and diluted with hexanes to recrystallize the product, affording 3.6 g (45%) of the desired aldehyde as a yellow powder. $^1$H NMR (300 MHz, CDCl$_3$): δ 4.28 (s, 3H), 7.46 (m, 1H), 7.82 (m, 1H), 8.15 (m, 1H), 8.78 (m, 1H), 10.08 (s, 1H). MS (APCI) calcd for C$_9$H$_8$N$_4$O: 188.07, found (M+H$^+$): 189.3.

Example B(17)

6-[2-(5-Chloro-2,4-dimethoxyphenyl)ethyl]-6-cyclopentyl-4-hydroxy-3-[(1-methyl-3-phenyl-1H-1,2,4-triazol-5-yl)methyl]-5,6-dihydro-2H-pyran-2-one

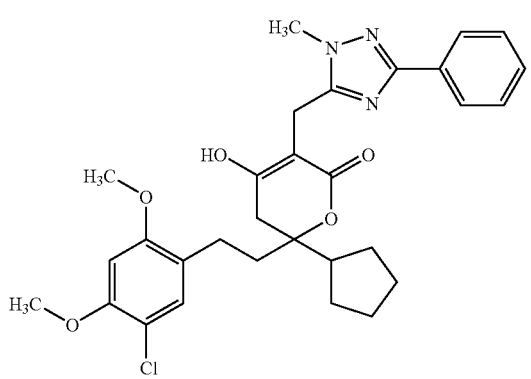

The title compound was prepared analogously to example B(15) using 2-methyl-5-phenyl-2H-[1,2,4]triazole-3-carbaldehyde hydrochloride hydrate from step 1 below in place of 2-methyl-5-pyrazin-2-yl-2H-[1,2,4]triazole-3-carbaldehyde dihydrochloride monohydrate, and using one equivalent of triethylamine instead of two. Yield: 100 mg (23%). $^1$H NMR (300 MHz, DMSO-d$_6$): δ 1.30-1.77 (m, 8H), 1.88 (m, 1H), 2.1 (m, 1H), 2.35 (m, 1H), 2.45-2.55 (m, 2H, overlap with DMSO-d$_5$), 2.68 (d, J=17.6 Hz, 1H), 2.73 (d, J=17.6 Hz, 1H), 3.65-3.7 (s, overlap with ABQ, J=16.7 Hz, total 5H), 3.82 (s, 3H), 3.86 (s, 3H), 6.65 (s, 1H), 7.12 (s, 1H), 7.28 (m, 3H), 7.71 (d, J=8 Hz, 2H), 10.98 (br s, 1H). LC-MS (APCI) calcd for C$_{30}$H$_{34}$ClN$_3$O$_5$: 551.22, found (M+H$^+$): 552.4 m/z.

Step 1: 2-Methyl-5-phenyl-2H-[1,2,4]triazole-3-carbaldehyde hydrochloride hydrate

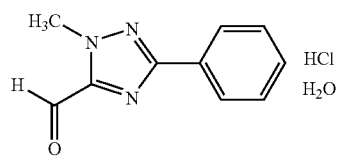

The title compound was prepared analogously to step 3 of example B(15): using N'-methylbenzene-carbohydrazonamide (the free base of the amidrazone reported in: Metz, H. J.; Neunhoeffer, H. Chem. Ber. 1982, 115, 2807) in place of N'-methylpyrazine-2-carbohydrazonamide in step 2 of that example. $^1$H NMR (300 MHz, DMSO-d$_6$): δ 4.17 (s, 3H), 7.30 (br m, 3H), 7.48 (m, 3H), 8.02 (d, J=9 Hz, 2H), 9.99 (s, 1H). MS (APCI) calcd for C$_{10}$H$_9$N$_3$O: 187.07, found (M+H$^+$): 188.3.

Example B(18)

6-[2-(5-Chloro-2,4-dimethoxyphenyl)ethyl]-6-cyclopentyl-3-[(1-ethyl-3,5-dimethyl-1H-pyrazol-4-yl)methyl]-4-hydroxy-5,6-dihydro-2H-pyran-2-one

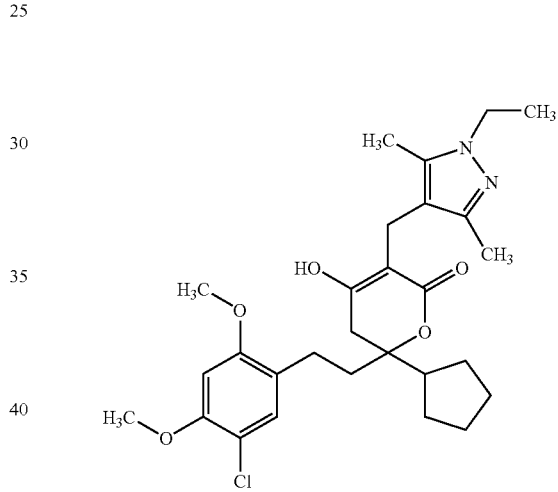

The title compound was prepared analogously to example B(15) using 1-ethyl-3,5-dimethyl-1H-pyrazole-4-carbaldehyde in place of 2-methyl-5-pyrazin-2-yl-2H-[1,2,4]triazole-3-carbaldehyde dihydrochloride monohydrate, and omitting the triethylamine. Following the aqueous workup, the product was recrystallized from a mixture of hot ethyl acetate, methanol and ether, affording 242 mg (60%) of the title product. $^1$H NMR (300 MHz, DMSO-d$_6$): δ 1.14 (t, J=7 Hz, 3H), 1.23-1.8 (m, overlap, 10H), 2.01 (s, 3H), 2.10 (s, 3H), 2.23 (m, 1H), 2.38 (m, 2H), 2.5 (d, 1H, overlap with DMSO-d$_5$ peak), 2.67 (d, J=17.9 Hz, 1H), 3.15 (ABQ, J=15.2 Hz, 2H), 3.74 (s, 3H), 3.82 (s, q overlap, total 5H), 6.7 (s, 1H), 7.0 (s, 1H), 10.58 (br s, 1H). LC-MS (APCI) calcd for $C_{28}H_{37}ClN_2O_5$: 516.24, found (M+H⁺): 517.4 m/z.

Example B(19)

6-[2-(3-chloro-4-isopropoxyphenyl)ethyl]-6-cyclopentyl-3-[(1-ethyl-3,5-dimethyl-1H-pyrazol-4-yl)methyl]-4-hydroxy-5,6-dihydro-2H-pyran-2-one

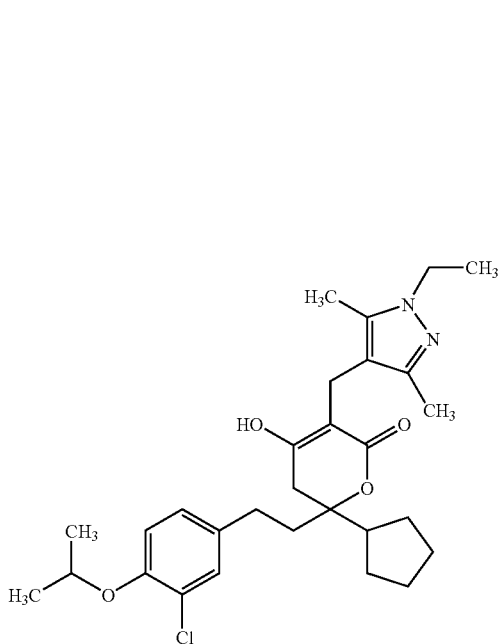

A solution of 6-[2-(3-chloro-4-isopropoxy-phenyl)-ethyl]-6-cyclopentyl-dihydro-pyran-2,4-dione (379 mg; 1.0 mmol from step 1 below) and 1-ethyl-3,5-dimethyl-1H-pyrazole-4-carbaldehyde (152 mg; 1.1 mmol) in methanol was heated at 40° C. overnight. The reaction mixture was treated with $(CH_3)_2NHBH_3$ (65 mg, 1.1 equiv), and heated at 40° C. overnight again. The reaction was partitioned between EtOAc and $H_2O$. The EtOAc layer was dried with $Na_2SO_4$, concentrated, and purified by reverse phase HPLC using 0.1% HOAc in $H_2O$ and $CH_3CN$. (Column: Water's Bondapak, C18, particle size: 37-55 micron column size: 47×300 mm; Flow rate: 70 ml/min; Detector: was set at 254 nm; Buffer A: 0.1% HOAc in $H_2O$; Buffer B: 0.1% HOAc in $CH_3CN$. The column was equilibrated in A for 20 minutes. The sample was dissolved in 5 ml of DMSO, filtered, and injected onto the column. The gradient was held at 75% A/25% for 5 minutes and then increased linearly to 55% A/45% B in 15 minutes and then continued isocratically at 45% B for another 25 minutes. The desired product eluted at 28 minutes.) The product-containing fractions were lyophilized to afford the title compound as a powder (196.2 mg, 40%). ¹H NMR (400 MHz, DMSO-d₆): δ 1.13 (t, 3H), 1.26 (d, m overlap, 8H), 1.35-1.63 (m, 6H), 1.75 (m, 2H), 2.02 (s, 3H), 2.10 (s, 3H), 2.21 (m, 1H), 2.39 (m, overlap, 3H), 2.61 (d, J=16.4 Hz, 1H), 3.1 (m, 2H, overlap with $H_2O$ peak), 3.81 (q, 2H), 4.56 (7 line pattern, 1H), 6.90 (d, J=8.8 Hz, 1H), 7.00 (d, J=8.8 Hz, 1H), 7.11 (s, 1H). LC-MS (APCI) calcd for $C_{29}H_{39}ClN_2O_4$: 514.26, found (M+H⁺): 515.3 m/z.

Step 1: 6-[2-(3-Chloro-4-isopropoxy-phenyl)-ethyl]-6-cyclopentyl-dihydro-pyran-2,4-dione

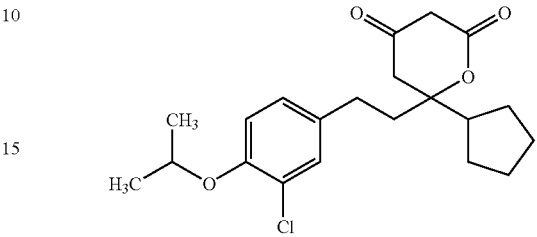

The title compound was prepared analogously to example B(2) where 4-bromo-2-chloro-1-isopropoxy-benzene was substituted in place of 4-bromo-2-chloro-1-methanesulfonyl-benzene in step 2 of that example. ¹H NMR (CDCl₃): δ 1.36 (d, J=6.0 Hz, 6H), 1.52-1.82 (brm, 8H), 1.94 (m, 2H), 2.27 (m, 1H), 2.60 (t, J=7.9 Hz, 2H), 2.76 (s, 2H), 3.43 (s, 2H), 4.50 (m, 1H), 6.86 (d, J=8.5 Hz, 1H), 6.94 (d, J=8.5 Hz, 1H), 7.14 (s, 1H) (m, 3H). Anal. Calcd. For $C_{21}H_{27}ClO_4$: C, 66.57; H, 7.18. Found: C, 66.33; H, 6.96.

Example B(20)

2-[4-(2-{2-Cyclopentyl-5-[(2-ethyl-5-oxo-5H-[1,3,4]thiadiazolo[3,2-a]pyrimidin-7-yl)methyl]-4-hydroxy-6-oxo-3,6-dihydro-2H-pyran-2-yl}ethyl)-2-fluorophenyl]-2-methylpropanenitrile

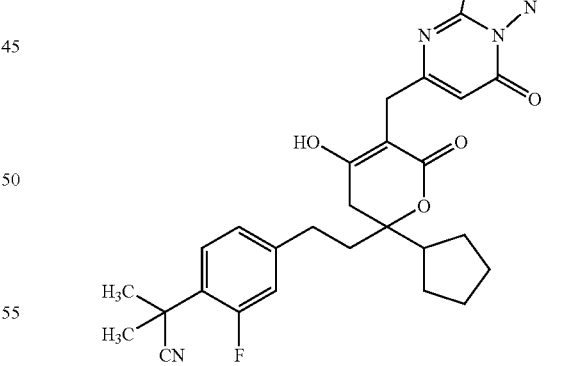

The title compound was prepared on a 0.5-mmol scale analogously to example B(19): except using 2-{4-[2-(2-cyclopentyl-4,6-dioxo-tetrahydro-pyran-2-yl)-ethyl]-2-fluoro-phenyl}-2-methyl-propionitrile from step 3 of example A(84) in place of 6-[2-(3-chloro-4-isopropoxy-phenyl)-ethyl]-6-cyclopentyl-dihydro-pyran-2,4-dione and 2-ethyl-5-oxo-5H-[1,3,4]thiadiazolo[3,2-a]pyrimidine-7-carbaldehyde from step 2 below in place of 1-ethyl-3,5-dimethyl-1H-pyrazole-4-carbaldehyde. Yield: 10 mg (4%). ¹H NMR (300 MHz, DMSO-d$_6$): δ 1.29 (t, 3H), 1.35-1.7 (s, m overlap, 14H), 1.99 (m, 2H), 2.38 (m, 1H), 2.63 (m, overlap, 3H), 2.75 (d, 1H), 3.03 (q, 2H), 3.48 (ABq, 2H), 6.06 (s, 1H), 7.10 (m, overlap, 2H), 7.35 (m, 1H), 10.98 (s, 1H). LC-MS (APCI) calcd for C$_{30}$H$_{33}$FN$_2$O$_4$S: 564.22, found (M+H$^+$): 565.2 m/z.

Step 1: 7-Chloromethyl-2-ethyl-[1,3,4]thiadiazolo[3,2-a]pyrimidin-5-one

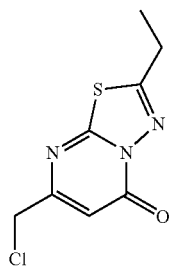

The title compound was prepared by a modification of a procedure described for analogs: (*J. Heterocyclic Chem.* 1983, 20, 1053). A 3-necked, 3-L flask with overhead stirring was charged with warm polyphosphoric acid (approx 250 g), 2-amino-5-ethyl-1,2,4-thiadiazole (45.2 g, 0.35 mol), and ethyl-4-chloroacetoacetate (86.4 g, 0.525 mol, 1.5 equiv). The mixture was heated to 110° C. with vigorous stirring. After 30 minutes, at exothermic reaction took place, resulting in an increase in the temperature to 140° C., an increase in the viscosity, and the appearance of a darker color. Heating was stopped, the reaction mixture cooled to 80° C., then treated slowly with water (300 mL) via an addition funnel. The resulting mixture was transferred to a 3-L beaker, cooled in an ice bath, and neutralized to pH 6 to 7 using aqueous NaOH (10%). The solid that precipitated was filtered, washed with water, ether, and petroleum ether, then dried in vacuo, affording 66.4 g (83%) of the title product as a sandy-colored crystalline solid. $^1$H NMR (300 MHz, CDCl$_3$): δ 1.46 (t, J=7.5 Hz, 3H), 3.09 (q, J=7.5 Hz, 2H), 4.42 (s, 2H), 6.61 (s, 1H). MS (APCI) calcd for C$_8$H$_8$ClN$_3$OS: 229.01, found (M+H$^+$): 230.0.

Step 2: 2-Ethyl-5-oxo-5H-[1,3,4]thiadiazolo[3,2-a]pyrimidine-7-carbaldehyde

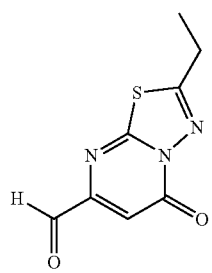

A mixture of 7-Chloromethyl-2-ethyl-[1,3,4]thiadiazolo[3,2-a]pyrimidin-5-one (11.48 g, 50 mmol), sodium iodide (15 g, 100 mmol, 2 equiv), sodium bicarbonate (12.6 g, 150 mmol, 3 equiv), water (25 mL) and DMSO (250 mL) was stirred and heated at 80° C. for 18 h. The volatiles were mostly removed on the rotary evaporator, then the residue treated with ethyl acetate to precipitate the salts, and the mixture filtered. The filtrate was lyophilized and chromatographed on silica gel using a gradient of ethyl acetate to 3% methanol in ethyl acetate, affording 2-ethyl-7-hydroxymethyl-[1,3,4]thiadiazolo[3,2-a]pyrimidin-5-one (4.24 g, 40%). This alcohol was dissolved in acetone (150 mL) and refluxed for 3 days with a total of 15 equivalents of MnO$_2$, added in 3-equiv portions over this time, affording complete conversion to the corresponding aldehyde. The reaction mixture was filtered through celite, the cake washed with acetone (3×100 mL), and the filtrate concentrated in vacuo, affording the title product (2.84 g, 67%). $^1$H NMR (300 MHz, CDCl$_3$): δ 1.55 (t, 3H), 3.10 (q, 2H), 6.98 (s, 1H), 9.90 (s, 1H). MS (APCI) calcd for C$_8$H$_7$ClN$_3$O$_2$S: 209.03, found (M+H$^+$): 210.2.

Example B(21)

3-[(2-Amino-7H-purin-6-yl)thio]-6-[2-(5-chloro-2,4-dimethoxyphenyl)ethyl]-6-cyclopentyldihydro-2H-pyran-2,4(3H)-dione

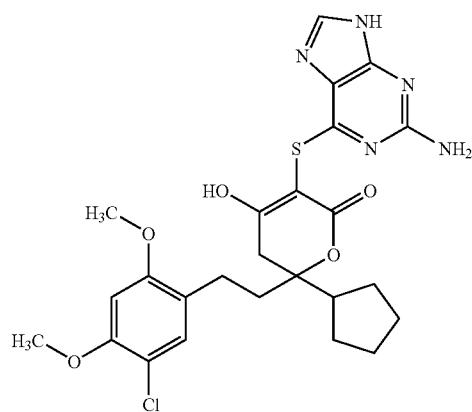

A mixture of 3-chloro-6-[2-(5-chloro-2,4-dimethoxy-phenyl)-ethyl]-6-cyclopentyl-4-hydroxy-5,6-dihydro-pyran-2-one (190 mg, 0.46 mmol, from step 1 below), 2-amino-9H-purine-6-thiol (90 mg, 0.5 mmol) and triethylamine (1 equiv) in DMF (3 mL) was heated at 50° C. overnight. The reaction mixture was partioned between water and ethyl acetate. The organic phase was concentrated, and the product was isolated by reverse-phase HPLC, affording 38 mg (14%). $^1$H NMR (300 MHz, DMSO-d$_6$): δ 1.35-1.75 (m, 8H), 2.0 (m, 1H), 2.18 (m, 1H), 2.35-2.55 (m, 3H, overlap with DMSO-d$_5$), 2.73 (d, J=17.3 Hz, 1H), 2.83 (d, J=17.3 Hz, 1H), 3.77 (s, 3H), 3.85 (s, 3H), 5.75 (br s, 2H), 6.71 (s, 1H), 7.15 (s, 1H), 7.81 (s, 1H); LC-MS (APCI) calcd for $C_{25}H_{28}ClN_5O_5S$: 545.15, found (M+H$^+$): 546.1 m/z.

Step 1. 3-Chloro-6-[2-(5-chloro-2,4-dimethoxy-phenyl)-ethyl]-6-cyclopentyl-4-hydroxy-5,6-dihydro-pyran-2-one

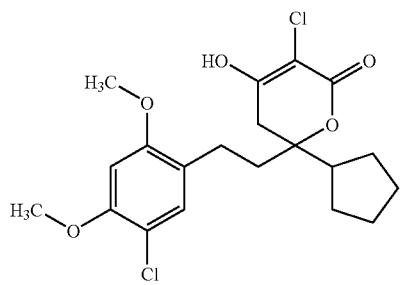

The title compound was prepared by chlorination of 6-[2-(5-chloro-2,4-dimethoxy-phenyl)-ethyl]-6-cyclopentyl-dihydro-pyran-2,4-dione from step 6 of example B(15) with sulfuryl chloride in dichloromethane at room temperature. $^1$H NMR (CDCl$_3$) δ 1.51 (m, 8H), 1.79 (m, 1H), 2.06, (m, 2H), 2.45 (m, 2H), 2.60 (m, 1H), 2.67 (d, J=17.75, 1H), 2.92 (d, J=17.75, 1H), 3.82 (s, 3H), 3.92 (s, 3H), 6.44 (s, 1H), 7.06 (s, 1H). HRMS calcd for $C_{20}H_{24}O_5Cl_2$ (M+H$^+$) 415.1079, found 415.1063.

Example B(22)

2-[2-Chloro-4-(2-{2-cyclopentyl-5-[(1,3-dimethyl-1H-1,2,4-triazol-5-yl)methyl]-4-hydroxy-6-oxo-3,6-dihydro-2H-pyran-2-yl}ethyl)phenyl]-2-methylpropanenitrile

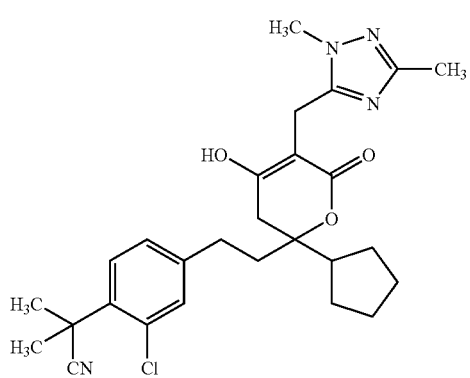

The title compound was prepared analogously to example A(1): where 2-{2-chloro-4-[2-(2-cyclopentyl-4,6-dioxo-tetrahydro-pyran-2-yl)-ethyl]-phenyl}-2-methyl-propionitrile from step 5 below, was substituted in place of 6-[2-(3-chloro-5-ethyl-4-methoxy-phenyl)-ethyl]-6-cyclopentyl-dihydro-pyran-2,4-dione and 2,5-dimethyl-2H-[1,2,4]triazole-3-carbaldehyde was substituted instead of 5,7-dimethyl-[1,2,4]triazolo[1,5-a]pyrimidine-2-carbaldehyde in that example. $^1$H NMR (300 MHz, DMSO-d$_6$): δ 1.47-1.74 (m, 8 H), 1.79 (s, 6 H), 2.01-2.11 (m, 8 H), 2.36-2.42 (m, 1 H), 2.56 (d, J=16 Hz, 1H), 2.60-2.66 (m, 2 H), 2.77 (d, J=16 Hz, 1 H), 3.53 (d, J=16 Hz, 1 H), 3.62 (d, J=16 Hz, 1 H), 7.25 (dd, J=8.2, 1.8 Hz, 1 H), 7.4 (d, J=1.8 Hz, 1 H), 7.45 (d, J=8.2 Hz, 1 H). Anal. Calcd. For $C_{27}H_{33}ClN_4O_3 \cdot 0.25H_2O$: C, 64.66; H, 6.73; N, 11.17. Found: C, 64.88; H, 6.74; N, 10.86. ESIMS (MH+): 498.

Step 1: (4-Bromo-2-chloro-phenyl)-methanol

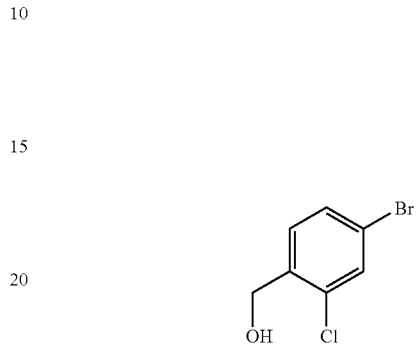

4-Bromo-2-chlorobenzoic acid (5 g, 21.23 mmol) was dissolved in dry THF (100 mL) and cooled to 0° C. A 1M solution of BH$_3$.THF in THF (31.85 mL, 31.85 mmol) was slowly added. The reaction was stirred overnight, allowing it to gradually reach room temperature. K$_2$CO$_3$ solid (1 g) and H$_2$O (100 mL) were added and the reaction was stirred for 30 minutes. THF was evaporated and residue extracted with EtOAc (30 mL). The organic phase was washed with 1N HCl (3×50 mL), brine (3×50 mL), dried over Na$_2$SO$_4$ and evaporated. The residue was purified by flash column chromatography (30% EtOAc in hexanes) to give the product (2.80 g, 50%) as a colorless oil. $^1$H NMR (400 MHz, CDCl$_3$): δ 4.73 (d, J=5.8 Hz, 2H), 7.37 (d, J=8.1 Hz, 1H), 7.42 (dd, J=8.1 Hz, 1.7), 7.52 (d, J=1.7 Hz, 1H)

Step 2: 4-Bromo-1-bromomethyl-2-chloro-benzene

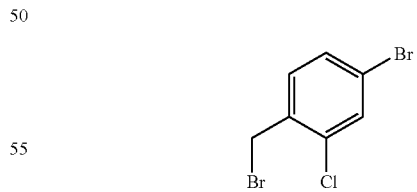

To a magnetically stirring solution of (4-bromo-2-chlorophenyl)-methanol (2.80 g, 12.67 mmol) from step 1 above in CH$_2$Cl$_2$ (60.0 mL) under argon at 0° C., was added carbon tetrabromide (4.41 g, 13.30 mmol) followed by triphenylphosphine (3.48 g, 13.30 mmol). The resulting mixture was stirred for 4 hours at room temperature. The resulting reaction mixture was concentrated in vacuo and the crude residue was purified by flash column chromatography (10% EtOAc in Hexanes) to yield the intermediate bromide as a clear oil (3.59 g, 100%). ¹H NMR (400 MHz, CDCl₃): δ 4.53 (s, 2H), 7.29 (d, J=8.2 Hz, 1H), 7.39 (dd, J=8.2, 1.9 Hz, 1 H), 7.56 (d, J=1.9 Hz, 1H).

Step 3: (4-Bromo-2-chloro-phenyl)-acetonitrile

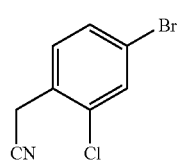

To a magnetically stirring solution of 4-bromo-1-bromomethyl-2-chloro-benzene (3.59 g, 12.67 mmol) from step 2 above and tetrabutylammonium bromide (0.41 g, 1.27 mmol) in CH₂Cl₂/H₂O 1:1 (60.0 mL), was added a solution of KCN (2.48 g, 38.01 mmol) in H₂O (30 mL). The resulting orange mixture was stirred at room temperature for 3 hours. The layers of the resulting reaction mixture were separated and the organic layer was washed with NaHCO₃ sat solution (3×50 mL), then dried over Na₂SO₄, filtered and concentrated in vacuo. The crude residue was purified by flash chromatography (30% EtOAc in Hexanes) to yield the intermediate as a clear oil (3.59 g, 100%). ¹H NMR (400 MHz, CDCl₃): δ 3.79 (s, 2H), 7.37-7.60 (m, 3H).

Step 4:
2-(4-Bromo-2-chloro-phenyl)-2-methyl-propionitrile

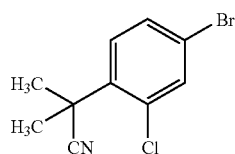

NaH (95%, 1.18 g, 49.35 mmol) was suspended in DMF (25 mL) and cooled to 0° C. 4-bromo-2-chloro-phenyl)-acetonitrile (2.27 g, 9.87 mmol) from step 3 above, was dissolved in THF (10 mL) and slowly added via cannula and the reaction mixture stirred 20 min. MeI (6.10 mL, 98 mmol) was added and the resulting mixture was stirred overnight at room temperature. Reaction was quenched with H₂O (50 mL). Solvents were removed in vacuo and residue partitioned between EtOAc and 1N HCl (50 mL). The organic phase was dried over Na₂SO₄ and evaporated. The crude organic product was purified by flash column chromatography (5% EtOAc in hexanes) to give the product (2.23 g, 87%) as a clear oil. ¹H NMR (400 MHz, CDCl₃): δ 7.34 (d, J=8.4 Hz, 1H), 7.43 (dd, J=8.4, 2.0 Hz, 1H), 7.61 (d, J=1.8 Hz, 1H).

Step 5: 2-{2-Chloro-4-[2-(2-cyclopentyl 4,6-dioxo-tetrahydro-pyran-2-yl)-ethyl]-phenyl}-2-methyl-propionitrile

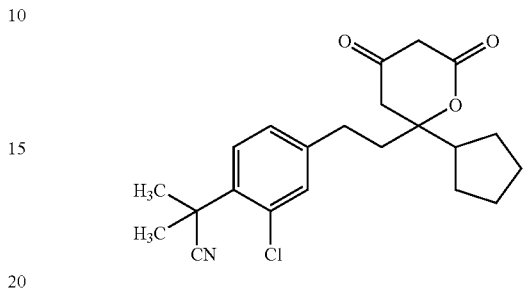

The title compound was prepared analogously to example A(1) where 2-(4-bromo-2-chloro-phenyl)-2-methyl-propionitrile from step 4 above was substituted in place of 1-benzyloxy-2-ethyl-4-iodo-5-propoxy-benzene in step 4 of that example. ¹H NMR (400 MHz, CDCl₃): δ 1.39-1.71 (m, 8H), 1.81-1.87 (m, 8H), 2.10-2.15 (m, 1H), 2.59-2.68 (m, 2H), 3.51 (s, 2H), 3.75 (s, 2H), 7.11 (dd, J=8.1 Hz, 1.8), 7.27 (d, J=1.8 Hz, 1H), 7.37 (d, J=8.1 Hz, 1H). MS (ESI): 388 (M+H)⁺.

Example B(23)

2-[2-Chloro-4-(2-{2-cyclopentyl-5-[(1-ethyl-1H-pyrazol-4-yl)methyl]-4-hydroxy-6-oxo-3,6-dihydro-2H-pyran-2-yl}ethyl)phenyl]-2-methylpropanenitrile

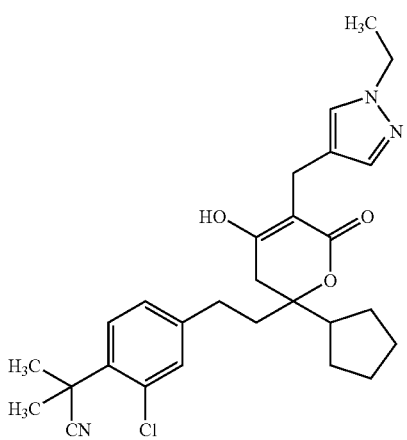

The title compound was prepared analogously to example B(22) where 1-ethyl-1H-pyrazole-4-carbaldehyde was substituted instead of 2,5-dimethyl-2H-[1,2,4]triazole-3-carbaldehyde in that example. ¹H NMR (300 MHz, DMSO-d₆): δ 1.43 (t, J=7.2 Hz, 3 H), 1.4-1.76 (m, 8 H), 1.78 (s, 6 H), 2.04-2.28 (m, 4 H), 2.63-2.65 (m, 2 H), 3.64-3.74 (m, 3H), 4.06-4.08 (m, 2 H), 6.91-7.6 (m, 5 H), 9.90 (s, 1 H). Anal.

Calcd. For C$_{28}$H$_{34}$ClN$_3$O$_3$.0.25H$_2$O: C, 67.19; H, 6.95; N, 8.39. Found: C, 67.30; H, 6.99; N, 8.50. ESIMS (MH+): 497.

Example B(24)

2-[2-Chloro-4-(2-{2-cyclopentyl-4-hydroxy-5-[(1-methyl-1H-pyrazolyl)methyl]-6-oxo-3,6-dihydro-2H-pyran-2-yl}ethyl)phenyl]-2-methylpropanenitrile

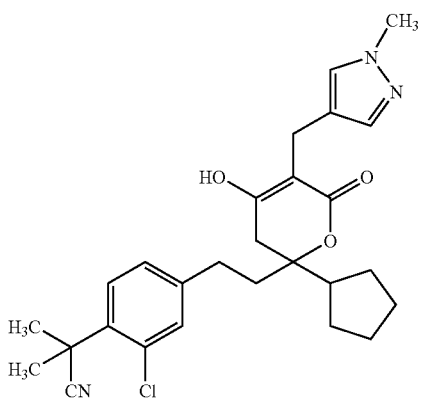

The title compound was prepared analogously to example B(22) where 1-methyl-1H-pyrazole-4-carbaldehyde was substituted instead of 2,5-dimethyl-2H-[1,2,4]triazole-3-carbaldehyde in that example. $^1$H NMR (300 MHz, CDCl$_3$): δ 1.42-1.68 (m, 8 H), 1.85 (s, 6 H), 2.29-2.79 (m, 5 H), 3.24-3.48 (m, 3 H), 3.61 (s, 2 H), 3.82 (s, 2 H), 6.89-7.39 (m, 5 H), 7.33-7.45 (m, 1 H). Anal. Calcd. For C$_{27}$H$_{32}$ClN$_3$O$_3$.0.5H$_2$O: C, 66.04; H, 6.77; N, 8.56. Found: C, 65.94; H, 6.73; N, 8.46. ESIMS (MH+): 483.

Example B(25)

2-[2-Chloro-4-(2-{2-cyclopentyl-4-hydroxy-6-oxo-5-[(1,3,5-trimethyl-1H-pyrazol-4-yl)methyl]-3,6-dihydro-2H-pyran-2-yl}ethyl)phenyl]-2-methylpropanenitrile

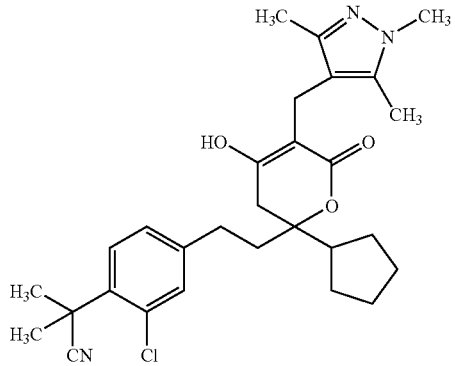

The title compound was prepared analogously to example B(22) where 1,3,5-trimethyl-1H-pyrazole-4-carbaldehyde was substituted instead of 2,5-dimethyl-2H-[1,2,4]triazole-3-carbaldehyde in that example. $^1$H NMR (300 MHz, DMSO-d$_6$): δ 1.40-1.67 (m, 8 H), 1.75 (s, 6 H), 1.70-1.83 (m, 2H), 1.99 (s, 3 H), 2.08 (s, 3 H), 2.21-2.25 (m, 1 H), 2.49-2.52 (m, 3 H), 2.64 (d, J=16 Hz, 1 H), 3.08 (d, J=14 Hz, 1 H), 3.20 (d, J=14 Hz, 1 H), 3.50 (s, 3 H), 7.05 (dd, J=8.2, 1.8 Hz, 1 H), 7.27 (d, J=1.8 Hz, 1 H), 7.39 (d, J=8.2 Hz 1 H), 10.7 (s, 1 H). Anal. Calcd. For C$_{29}$H$_{36}$ClN$_3$O$_3$.0.25H$_2$O: C, 67.69; H, 7.15; N, 8.17. Found: C, 67.72; H, 7.11; N, 8.02. ESIMS (MH+): 511.

Example B(26)

2-[2-Chloro-4-(2-{2-cyclopentyl-5-[(5,7-dimethyl[1,2,4]triazolo[1,5-a]pyrimidin-2-yl)(methyl)amino-4,6-dioxotetrahydro-2H-pyran-2-yl}ethyl)phenyl]-2-methylpropanenitrile A stirred suspension 2-{2-chloro-4-[2-(2-cyclopentyl-5-imino-4,6-dioxo-tetrahydro-pyran-2-yl)-ethyl]-phenyl}-2-methyl-propionitrile (0.63 g, 1.53 mmol, from step 1 below), N-methyl-4H-1,2,4-triazole-3,5-diamine (0.27 g, 1.53 mmol, from step 3 below), and Rh$_2$(OAC)$_2$ (0.00041 g, 0.00092 mmol), in hexafluorobenzene (7 mL) under argon was heated at 80° C. for 8 hours. The reaction was poured into water (10 mL) and extracted with EtOAc (3×5 mL). The organic layers were combined washed with saturated NaCl and dried over Na$_2$SO$_4$. The solvents were removed and the residue was purified by flash column chromatography (30-80% % EtOAc in hexanes, then 24% MeOH/CH$_2$Cl$_2$) to give the product as a yellow solid (0.086 g, 6%). $^1$H NMR (300 MHz, DMSO-d$_6$): δ 1.37-2.01 (m, 16H), 2.26-2.33 (m, 1H), 2.41-2.69 (m, 8H), 3.32 (s, 2H), 3.43 (d, J=2.5 Hz, 3H), 5.26-5.39 (m, 1H), 7.20-7.21 (m, 1H), 7.29-7.32 (m, 1H), 7.42-7.47 (m, 2H). ESIMS (MH+): 563.

Step 1: 2-{2-Chloro-4-[2-(2-cyclopentyl-5-imino-4, 6-dioxo-tetrahydro-pyran-2-yl)-ethyl]-phenyl}-2-methyl-propionitrile

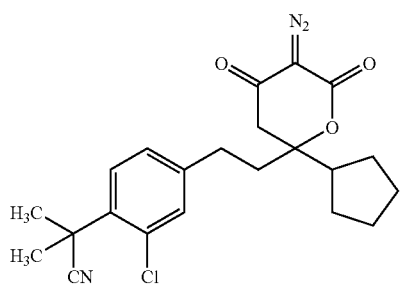

To a stirred solution of 2-{2-chloro-4-[2-(2-cyclopentyl-4, 6-dioxo-tetrahydro-pyran-2-yl)-ethyl]-phenyl}-2-methyl-propionitrile (0.5 g, 1.29 mmol) from step 5 of example B(22), and p-acetamidobenzenesulfonyl azide (0.46 g, 1.94 mmol) in THF (4 mL) under argon was added TEA (0.54 mL, 3.87 mmol). The resulting solution was stirred at 25° C. overnight. The solvents were removed and the residue was purified by flash column chromatography (25-60% % EtOAc in hexanes) to give the product as a yellow oil. ESIMS (MH+): 414.

Step 2: N-methyl-4H-1,2,4-triazole-3,5-diamine

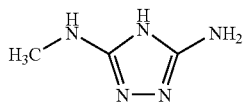

A mixture of N-cyano-N',S-dimethylisothiourea (100 g, 0.77 mol) and 85% hydrazine hydrate (91.2 g, 1.55 mol) in EtOH (380 mL) was refluxed for 2 hours. During the reaction, methanethiol was liberated. Once the reaction was complete (monitored by TLC: $CH_2Cl_2$/MeOH=20/1), the reaction mixture was evaporated to dryness. Petroleum ether was added, and the solid was filtered and washed with petroleum ether to give the product as a pink solid (77 g, 88%). $^1$H NMR (300 MHz, DMSO-$d_6$): δ 2.59 (s, 3 H), 4.52-6.20 (br m, 3 H), 10.67 (s, 1 H).

Step 3: N-methyl-4H-1,2,4-triazole-3,5-diamine

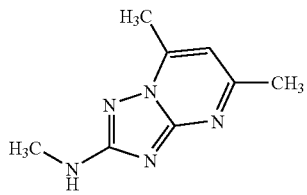

To a solution of N-methyl-4H-1,2,4-triazole-3,5-diamine (75 g, 0.66 mol, from step 2) in glacial acetic acid (375 mL) was added pentane 2,4-dione (66 g, 0.66 mol), and the mixture was refluxed for 8 hours. The reaction mixture was concentrated under reduced pressure. The residue was taken up into $CH_2Cl_2$ (1000 mL). The solution was washed with dilute aqueous sodium hydroxide and water. The combined aqueous layers were extracted with $CH_2Cl_2$ (1000 mL). The combined organic phases were dried over $Na_2SO_4$. Removal of $CH_2Cl_2$ under reduced pressure, a yellow precipitate was filtered and washed with petroleum ether to give the product (64 g, 55%). $^1$H NMR (300 MHz, DMSO-$d_6$): δ 2.43 (s, 3 H), 2.56 (s, 3 H), 2.80 (s, 3 H), 6.64 (s, 1 H), 6.80 (s, 1 H).

Example B(27)

2-[2-Chloro-4-(2-{2-cyclopentyl-5-[(5,7-dimethyl[1,2,4]triazolo[1,5-a]pyrimidin-2-yl)oxy]-4,6-dioxotetrahydro-2H-pyran-2-yl}ethyl)phenyl]-2-methylpropanenitrile

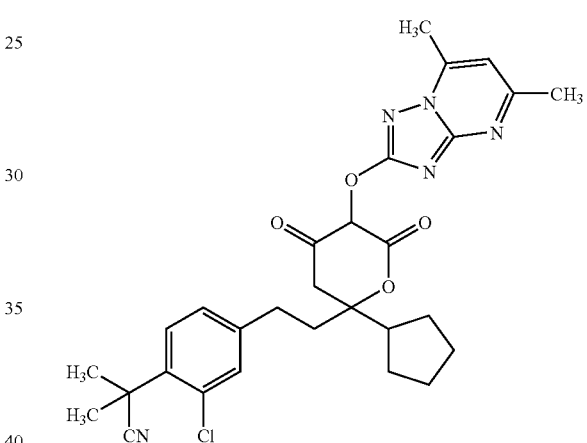

The title compound was prepared analogously to example B(26) where 5,7-dimethyl-[1,2,4]triazolo[1,5-a]pyrimidin-2-ol from step 3 below was substituted instead of (5,7-dimethyl-[1,2,4]triazolo[1,5-a]pyrimidin-2-yl)-methyl-amine in that example. $^1$H NMR (300 MHz, DMSO-$d_6$): δ 1.61-1.84 (m, 10 H), 1.88 9s, 6H), 2.12-2.18 (m, 1H), 2.41-2.78 (m, 8H), 3.43 (s, 2H), 3.25-5.30 (m, 1H), 6.53-6.54 (m, 1H), 7.4-7.54 (m, 1H), 7.55-7.57 (m, 1H), 7.63 (s, 1H). ESIMS (MH+): 551.

Step 1: N-(Anilinocarbonyl)-2-(1-methylethylidene) hydrazinecarboximidamide

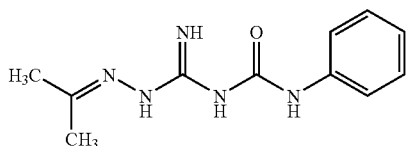

To a suspension of sodium (19 g, 0.82 mol) in acetone (1000 mL) and was added aminoguanidine hydrochloride (100 g, 0.91 mol) in portions. The mixture was refluxed for 60 minutes. The heating bath was removed, and phenyl isocyanate (78.4 g, 0.65 mol) was added dropwise during 30 minutes. The mixture was refluxed for another 30 minutes. The mixture was poured into ice water (2.5 L). The oil solidified at room temperature during an overnight stirring. The solid was filtered and washed with petroleum ether to afford the product as a yellow solid (150 g, 70%).

Step 2: 5-Amino-2,4-dihydro-3H-1,2,4-triazol-3-one

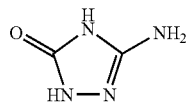

A solution of N-(anilinocarbonyl)-2-(1-methylethylidene)hydrazinecarboximidamide (150 g, 0.64 mol) in 2 N hydrochloric acid (200 mL) was refluxed for 30 minutes. The solution was made to pH=9 by 1 N aqueous sodium hydroxide. The mixture was concentrated until a precipitate was formed. The resultant mixture was cooled to room temperature and kept in the refrigerator over night. The precipitate was filtered to give the product (29 g, 45%).

Step 3: 5,7-Dimethyl[1,2,4]triazolo[1,5-a]pyrimidin-2-ol

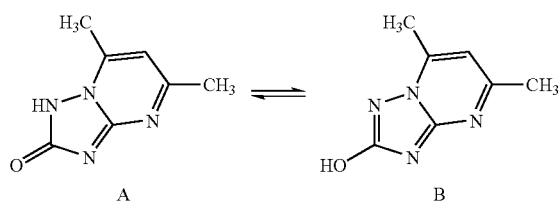

To a solution of 5-amino-2,4-dihydro-3H-1,2,4-triazol-3-one (29 g, 0.29 mol) in glacial acetic acid (140 mL) was added pentane-2,4-dione (29 g, 0.29 mol) and the solution was refluxed for 8 hours. The reaction mixture was concentrated under reduced pressure to afford a yellow solid. The solid was filtered and washed with ethanol (200 mL) to give the product (42 g, 80%).

Example B(28)

2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-trifluoromethyl)phenyl]-2-methylpropanenitrile

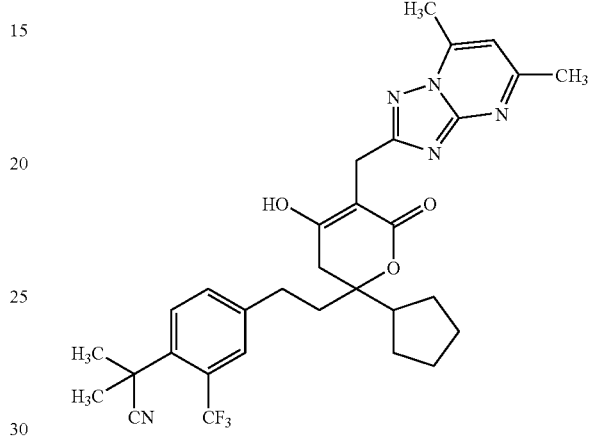

The title compound was prepared analogously to example A(1) where 2-[4-[2-(2-cyclopentyl-4,6-dioxotetrahydro-2H-pyran-2-yl)ethyl]-2-(trifluoromethyl)phenyl]-2-methylpropanenitrile (example A(141))) was substituted in place of 6-cyclopentyl-6-[2-(5-ethyl-4-hydroxy-2-propoxy-phenyl)-ethyl]-dihydro-pyran-2,4-dione in that example. $^1$H NMR (400 MHz, DMSO-$d_6$) δ: 1.44-1.76 (br m, 8 H), 1.87 (s, 6 H), 2.23 (m, 2 H), 2.48-2.61 (m, 8 H), 2.80 (m, 3 H), 3.76 (d, J=16.2 Hz, 1 H), 3.89 (d, J=16.2 Hz, 1 H), 7.10 (s, 1 H), 7.72 (s, 1 H), 7.77 (m, 2 H), 11.01 (s, 1 H). MS (ESI): 582.20 (M+H)$^+$ Example B(29)

2-{3-Chloro-5-[2-(2-cyclopentyl-4,6-dioxotetrahydro-2H-pyran-2-yl)ethyl]pyridin-2-yl}-2-methylpropanenitrile

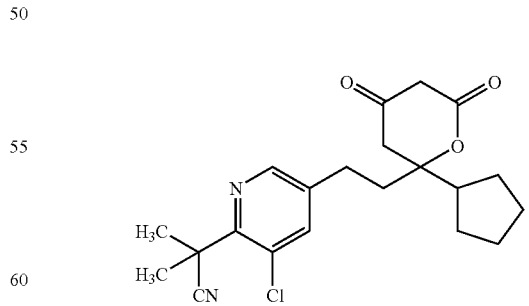

The title compound was prepared analogously to example B(2) where 2-[3-Chloro-5-(3-cyclopentyl-3-oxo-propyl)-pyridin-2-yl]-2-methyl-propionitrile, from step 7 below, was substituted in place of 3-(3-chloro-4-methanesulfonyl-phenyl)-1-cyclopentyl-propan-1-one of that example. $^1$H NMR (CDCl$_3$) δ: 1.43-1.79 (m, 8 H), 1.84 (s, 6 H), 1.93-1.98 (m, 2 H), 2.25-2.30 (m, 1 H), 2.69-2.84 (m, 4H), 3.39-3.59 (m, 2 H), 7.55 (s, 1 H), 8.29 (s, 1 H).

Step 1: 2-(3-Chloro-5-hydroxymethyl-pyridin-2-yl)-2-methyl-propionitrile

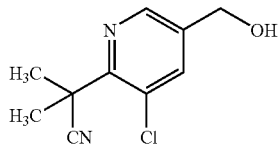

To a magnetically stirring solution of 5,6 dichloronicotinic acid (2.7 g, 14.06 mmol) in THF (70.0 mL), was added isobutyronitrile (6.37 mL, 69.66 mmol) followed by potassium hexamethyldisilazide 0.5 M in toluene (70 mL). The resulting orange mixture was stirred at 60° C. overnight. Solvents were removed and residue portioned between ethyl acetate (100 mL) and 1N HCl (100 mL). The layers of the resulting reaction mixture were separated and the aqueous layer was extracted three additional times with ethyl acetate. The organic layers were combined and dried over Na$_2$SO$_4$, filtered and concentrated in vacuo to a yellow solid (3.34 g). This crude residue was dissolved in THF (80 mL) and reaction cooled to 0° C. BH$_3$.THF 1M solution in THF (22.30 mL) was added and reaction stirred at 0° C. for 4 hours, then room temperature overnight. Solid K$_2$CO$_3$ (2 g) and water (100 mL) were added and the aqueous layer was extracted three additional times with ethyl acetate. The organics were combined dried over Na$_2$SO$_4$, filtered and concentrated in vacuo to a clear oil which was purified by silica gel chromatography (hexanes) to give the title compound as a white solid (0.95 g, 32%). ESIMS (MH+): 210.

Step 2: 2-(3-Chloro-5-formyl-pyridin-2-yl)-2-methyl-propionitrile

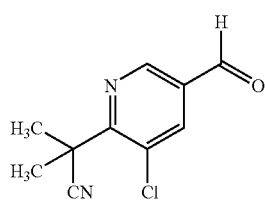

A solution of oxalyl chloride (0.45 mL, 5.21 mmol) and in dry CH$_2$Cl$_2$ (11 mL), was cooled to −50° C. Dimethyl sulfoxide (0.76 g, 10.87 mmol) was added drop wise at a rapid rate. After 5 minutes, 2-(3-chloro-5-hydroxymethyl-pyridin-2-yl)-2-methyl-propionitrile (0.95 g, 4.53 mmol) from step 1 above, in dry CH$_2$Cl$_2$ (5 mL) was added via cannula followed by triethylamine (3.16 g, 22.65 mmol). The reaction was stirred at −50° C. for 30 additional minutes and then allowed to reach room temperature. The reaction was poured into water (150 mL) and extracted with EtOAc (2×50 mL). The combined organics were washed with brine, dried over Na$_2$SO$_4$, filtered and concentrated. The residue was purified by flash column chromatography (0-20% EtOAc in hexanes) to give the product (0.58 g, 62% yield) as a clear oil. $^1$H NMR (400 MHz, CDCl$_3$): δ 1.90 (s, 6 H), 8.20 (s, 1 H), 8.93 (s, 1H), 10.12 (s, 1 H). ESIMS (MH+): 209.

Step 3: 3-[5-Chloro-6-(cyano-dimethyl-methyl)-pyridin-3-yl]-acrylic acid ethyl ester

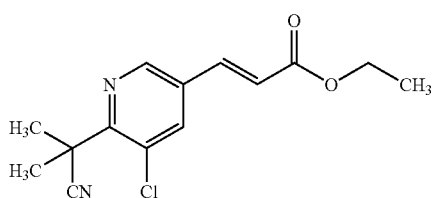

A solution of 2-(3-chloro-5-formyl-pyridin-2-yl)-2-methyl-propionitrile (0.58 g, 2.78 mmol) from step 3 above and (carbethoxymethylene)triphenylphosphorane (1.26 g, 3.61 mmol) in dry THF (12 mL) was heated to 55° C. and maintained at this temperature overnight. The solvents were removed and the residue was purified by flash column chromatography (0-20% EtOAc in hexanes) to give the product (0.74 g, 96% yield) as a white solid. $^1$H NMR (400 MHz, CDCl$_3$): δ 1.35 (t, J=7.7 Hz, 3 H), 1.87 (s, 6 H), 4.29 (q, J=14, 7.7 Hz, 2 H), 6.53 (d, J=16 Hz, 1 H), 7.65 (d, J=16 Hz, 1 H), 7.87 (d, J=2 Hz, 1 H), 8.58 (d, J=2 Hz, 1 H). ESIMS (MH+): 279.

Step 4: 3-[5-Chloro-6-(cyano-dimethyl-methyl)-pyridin-3-yl]-propionic acid ethyl ester

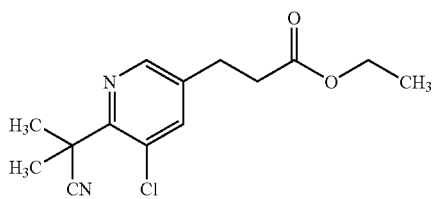

To a solution of 3-[5-chloro-6-(cyano-dimethyl-methyl)-pyridin-3-yl]-acrylic acid ethyl ester (0.74 g, 2.65 mmol) from step 3 above was added ethanol (10 mL) and Pd(OH)$_2$/C (0.37 g). The reaction was placed under a hydrogen atmosphere using a balloon filled with hydrogen. The slurry was stirred vigorously for 1 hour. The reaction was filtered to remove all of the solids, and the liquid was concentrated to an white solid which was used in next reaction without further purification. $^1$H NMR (400 MHz, CDCl$_3$): δ 1.25 (t, J=7.7 Hz, 3 H), 1.85 (s, 6 H), 2.62-2.66 (m, 2 H), 2.92-2.98 (m, 2H), 4.15 (q, J=14, 7.7 Hz, 2 H), 7.61 (d, J=2 Hz, 1 H), 8.3 (d, J=2 Hz, 1 H). ESIMS (MH+): 289.

Step 5: 3-[5-Chloro-6-(cyano-dimethyl-methyl)-pyridin-3-yl]-propionic acid

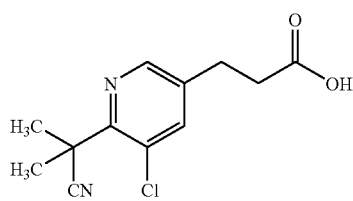

To a stirred solution of 3-[5-chloro-6-(cyano-dimethyl-methyl)-pyridin-3-yl]-propionic acid ethyl ester (0.68 g, 2.43 mmol) from step 4 above, in 1:1 THF/H$_2$O (4 mL) was added 2 N NaOH (2.43 mL). The resulting solution was stirred at 60° C. for 1 hour. Solvents were removed and residue was partitioned between ethyl acetate and 10% citric acid and extracted. The organic phase was washed with brine (50 mL), dried over Na$_2$SO$_4$ and evaporated. The residue solidified to a white solid and was used without further purification. (0.39 g, 64%) as a white solid. ESIMS (MH−): 251.

Step 6: 3-Cyclohexyl-thiopropionic acid S-pyridin-2-yl ester

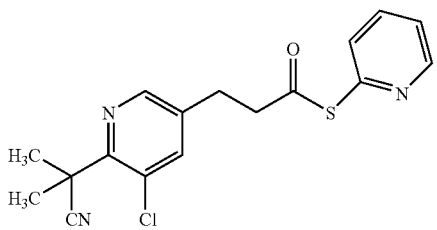

3-[5-Chloro-6-(cyano-dimethyl-methyl)-pyridin-3-yl]-propionic acid (0.39 g, 1.54 mmol) from step 5 above, triphenylphosphine (0.53 g, 2.01 mmol) and 2,2'-dipyridyl disulfide (0.44 g, 2.01 mmol) were combined successively in CH$_2$Cl$_2$ (7 mL). The reaction mixture was stirred 4 hours. The solvents were removed and the residue was purified by flash column chromatography (0-50% % EtOAc in hexanes) to give the product as a white solid. ESIMS (MH+): 346

Step 7: 2-[3-Chloro-5-(3-cyclopentyl-3-oxo-propyl)-pyridin-2-yl]-2-methyl-propionitrile

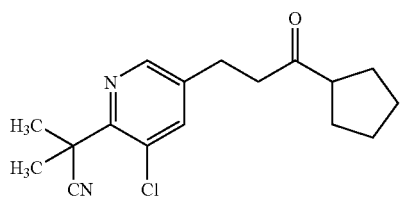

Cyclopentylmagnesium bromide 2.M solution in ether (0.54 mL, 1.10 mmol) was added to a cooled −78° C. solution of 3-cyclohexyl-thiopropionic acid S-pyridin-2-yl ester (0.38 g, 1.10 mmol), from step 6 above, dissolved in THF (5 mL). The reaction mixture was stirred for 2 min at −78° C. and then warmed up to room temperature. The reaction was quenched with 1N HCl and extracted with EtOAc. The organic layer was washed with saturated NaHCO$_3$, brine, dried over Na$_2$SO$_4$ and concentrated. The residue was purified by silica gel chromatography (0% to 30% EtOAc in hexanes) to give the title compound as a clear oil (0.25 g, 76%). $^1$H NMR (400 MHz, CDCl$_3$): δ 1.62-1.8 (m, 9 H), 1.84 (s, 6 H), 2.78-2.92 (m, 4 H), 7.58 (s, 1 H), 8.31 (s, 1 H). ESIMS (MH+): 305.

Example B(30)

5-Bromo-1-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2(1H)-one

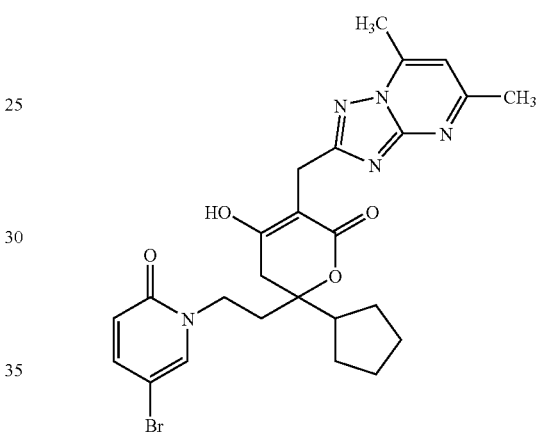

The title compound was prepared analogously to example A(101), where 5-bromo-1-[2-(2-cyclopentyl-4-hydroxy-6-oxo-3,6-dihydro-2H-pyran-2-yl)-ethyl]-1H-pyridin-2-one was substituted in place of {4-[2-(2-cyclopentyl-4,6-dioxo-tetrahydro-pyran-2-yl)-ethyl]-2-ethyl-phenyl}-acetonitrile. $^1$H NMR (300 MHz, DMSO-d$_6$): δ 1.33-1.70 (m, 9H), 2.07-2.25 (m, 2 H), 2.53 (s, 3 H), 2.56 (s, 3 H), 2.69 (s, 1 H), 3.68-3.82 (m, 2 H), 3.82-4.00 (m, 2 H), 6.32-6.35 (m, 1 H), 7.01 (s, 1 H), 7.47-7.51 (m, 1 H), 8.01-8.02 (m, 1 H). Anal. Calcd. For C$_{25}$H$_{28}$BrN$_5$O$_4$.1.2H$_2$O: C, 53.23; H, 5.43; N, 12.42. Found: C, 53.30; H, 5.32; N, 12.03.

Step 1: 5-Bromo-1-(3-cyclopentyl-3-oxo-propyl)-1H-pyridin-2-one

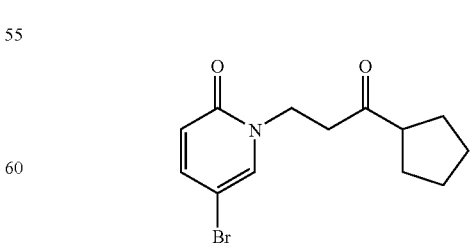

To a solution of 5-Bromo-1H-pyridin-2-one (0.53 g, 3 mmol) and 1-Cyclopentyl-propenone (0.38 g, 3 mmol) in anhydrous acetonitrile/DMF (10 mL/5 mL) was added CsF (46 mg, 0.3 mmol). The reaction was stirred at room temperature for 4.5 hours. The solvent was removed in vacuo and the mixture was purified by flash column chromatography (SiO$_2$, EtOAc in hexanes) to afford the desired product (400 mg, 45% yield). $^1$H NMR (300 MHz, CDCl$_3$): δ 1.56-1.80 (m, 9H), 2.98-3.02 (m, 2 H), 4.11-4.15 (m, 2 H), 6.44-6.47 (m, 1 H), 7.32-7.36 (m, 1 H), 7.61-7.62 (m, 1 H).

Step 2: 5-Bromo-1-[2-(2-cyclopentyl-4-hydroxy-6-oxo-3,6-dihydro-2H-pyran-2-yl)-ethyl]-1H-pyridin-2-one

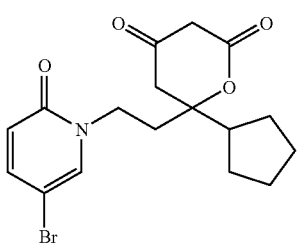

Methyl acetoacetate (0.44 mL, 4.04 mmol) dissolved in THF at 0° C. was treated with NaH (60%, 162 mg) and stirred at that temperature for 10 min before it was cooled further down to −40° C. n-BuLi (2.5 M in hexanes, 1.6 mL) was added slowly and stirring was continued for 10 min before 5-bromo-1-[2-(2-cyclopentyl-4-hydroxy-6-oxo-3,6-dihydro-2H-pyran-2-yl)-ethyl]-1H-pyridin-2-one (400 mg, 1.35 mmol) was added as a solution in THF. The solution was slowly warmed up to room temperature and stirred for additional 2 hours before it was quenched by the addition of H$_2$O. The mixture was extracted with EtOAc and the organic phase was washed with brine and dried over MgSO$_4$. The solvent was removed in vacuo and the crude was taken up directly into next step. The crude product from previous step was dissolved in THF and treated with 0.1 N NaOH (5 mL) for 15 hours. The reaction was acidified to pH 1 with 1.0 N HCl and the extracted with EtOAc. The organic phase was washed with brine, dried over MgSO$_4$ and concentrated in vacuo to afford the desired product (220 mg, 43% for two steps). $^1$H NMR (300 MHz, CDCl$_3$): δ 1.39-1.82 (m, 9 H), 2.10-2.24 (m, 2 H), 2.77-2.89 (m, 2 H), 3.41-3.57 (m, 2 H), 3.92-4.15 (m, 2 H), 6.46-6.49 (m, 1 H), 7.35-7.40 (m, 2 H).

Example B(31)

1-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-5-ethylpyridin-2(1H)-one

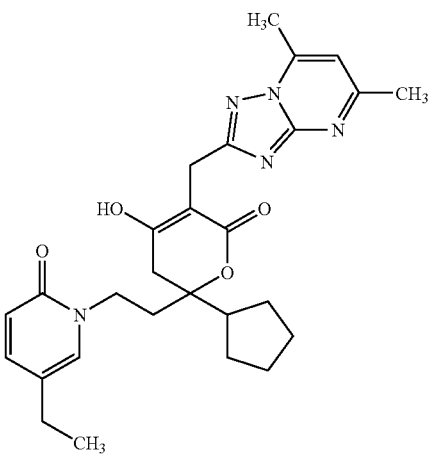

The title compound was prepared analogously to example B(30), where 5-ethyl-1H-pyridin-2-one was substituted in place of 5-bromo-1H-pyridin-2-one. $^1$H NMR (300 MHz, DMSO-d$_6$): δ 1.38 (t, J=7.5 Hz, 3H), 1.61-1.97 (m, 9H), 2.31-2.42 (m, 2H), 2.53-2.63 (m, 2H), 2.77 (s, 3 H), 2.79 (s, 3H), 2.88-3.01 (m, 2 H), 3.93-4.01 (m, 2H), 4.25 (s, 1 H), 6.54-6.57 (m, 1H), 7.29 (s, 1H), 7.55-7.59 (m, 1H), 7.70-7.71 (m, 1 H).

Step 1: 1-(6-Methoxy-pyridin-3-yl)-ethanol

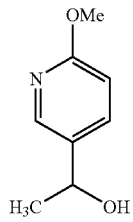

To a solution of 5-bromo-2-methoxy-pyridine (19.3 g, 193 mmol) in anhydrous Et$_2$O (200 mL) at −78° C. was added n-BuLi (2.5 M in hexanes, 50 mL) over 30 min. The resulting mixture was stirred at that temperature for addition 30 min before acetaldehyde (5 mL) was added. The reaction was slowly warmed up to room temperature and the solvent was removed in vacuo. The residue was purified by flash column chromatography to afford the desired product (14.3 g, 91% yield). $^1$H NMR (400 MHz, CDCl$_3$): δ 1.50 (d, J=8.0 Hz, 3 H), 3.93 (s, 3 H), 4.87-4.92 (m, 1 H), 6.75 (d, J=8.0 Hz, 3H), 7.63-7.66 (m, 1 H), 8.12-8.14 (m, 1 H).

Step 2: 2-Methoxy-5-vinyl-pyridine

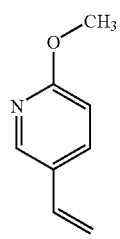

To a solution of 1-(6-methoxy-pyridin-3-yl)-ethanol (14.3 g, 93.5 mmol) in anhydrous THF was added triethylamine (32.3 mL), followed by MsCl (8.6 mL, 112 mmol). The resulting mixture was stirred at room temperature for 15 hours before it was filtered through a pad of celite. The filtrate was concentrated in vacuo and the residue was purified by flash column chromatography to afford the desired product (4.7 g, 37% yield). $^1$H NMR (300 MHz, CDCl$_3$): δ 3.94 (s, 3 H), 5.20-5.23 (m, 1H), 5.61-5.67 (m, 1 H), 6.60-6.78 (m, 2 H), 7.67-7.72 (m, 1 H), 8.12 (s, 1 H).

Step 3: 5-Ethyl-1H-pyridin-2-one

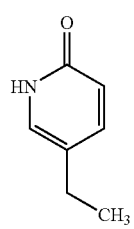

To a solution of 2-methoxy-5-vinyl-pyridine (2 g) in anhydrous MeOH was added Pd/C (10 wt %, 100 mg). The mixture was stirred under H2 atmosphere for 5 hours before it was filtered through a pad of celite. The solvent was removed in vacuo and the residue was taken directly into next step without further purification. The crude product from previous step was dissolved in anhydrous MeCN. To this solution was added NaI (3.3 g, 21.9 mmol) and TMSCl (2.8 mL, 21.9 mmol). The resulting mixture was heated to 65° C. for 5 hours before it was filtered through a pad of celite. The filtrate was concentrated in vacuo and the residue was purified by flash column chromatography to afford the desired product (1.5 g, 83% yield). $^1$H NMR (300 MHz, CDCl$_3$): δ 1.17 (t, J=7.5 Hz, 3 H), 2.39-2.49 (m, 2 H), 6.50-6.58 (m, 1 H), 7.15 (s, 1 H), 7.35-7.45 (m, 1 H).

Example B(32)

6-Cyclopentyl-3-[(5,7-dimethyl[1,2,4]triazolo[1,5-a]pyrimidin-2-yl)methyl]-4-hydroxy-6-{2-[4-(1-hydroxy-1-methylethyl)-3-methylphenyl]ethyl}-5,6-dihydro-2H-pyran-2-one

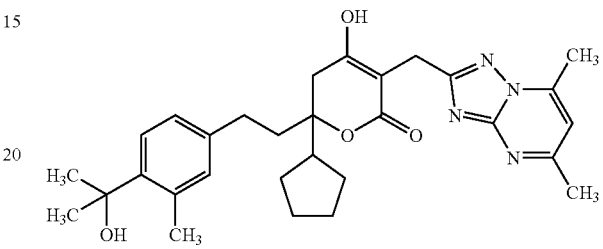

The title compound was prepared analogously to example B(1) where 2-(4-bromo-2-methyl-phenyl)-propan-2-ol was substituted in place of the bromide in step 2 of example B(2). $^1$H NMR (400 MHz, CDCl$_3$): δ ppm 1.51-1.60 (m, J=11.31, 5.94, 5.75 Hz, 6 H) 1.61 (s, 6 H) 1.63-1.65 (m, 2 H) 1.97-2.03 (m, J=6.95, 5.31, 5.18 Hz, 2 H) 2.34-2.40 (m, 1 H) 2.52 (s, 3 H) 2.55 (d, J=7.83 Hz, 1 H) 2.61 (dd, J=11.62, 5.81 Hz, 3 H) 2.66 (s, 3 H) 2.78 (s, 3 H) 4.03-4.12 (m, 2 H) 6.83 (s, 1 H) 6.90-6.94 (m, 2 H) 7.31 (d, J=7.83 Hz, 1 H). MS (ESI): 501 (M+H—H$_2$O)$^+$.

Step 1: 4-Bromo-2-methyl-benzoic acid methyl ester

To a solution of 4-bromo-2-methyl-benzoic acid 10.0 g, 46.5 mmol) in methanol (100 mL) at room temperature was added sulfuric acid (conc. 1 mL) dropwise. The solution was heated at reflux for 16 h. The solution was removed from heat and sulfuric acid (conc. 0.5 mL) was added. The solution was heated at reflux 2 h then cooled to room temperature and concentrated in vacuo. The residue was dissolved in ethyl acetate and washed with saturated sodium bicarbonate, then with saturated sodium chloride. The solution was dried (MgSO$_4$), filtered, and concentrated in vacuo to a crude colorless oil. Flash chromatography (SiO$_2$, 5% ethyl acetate/hexane) gave the title compound as a colorless oil (9.2 g, 87%). $^1$H NMR (400 MHz, CDCl$_3$): δ ppm 2.58 (s, 3 H) 3.88 (s, 3 H) 7.38 (dd, J=8.46, 1.89 Hz, 1 H) 7.42 (d, J=1.52 Hz, 1 H) 7.78 (d, J=8.34 Hz, 1 H).

Step 2: 2-(4-Bromo-2-methyl-phenyl)-propan-2-ol

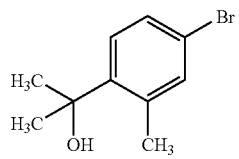

To 4-bromo-2-methyl-benzoic acid methyl ester (3.7 g, 15.9 mmol) in diethyl ether (10 mL) at 0° C. under N$_2$ was added 3N methylmagnesium bromide in diethyl ether (21 mL, 63 mmol). The mixture was stirred 16 h at room temperature. The mixture was poured into 1N hydrochloric acid (aq, 10 mL) and extracted with ethyl acetate. The organic layer was washed with saturated sodium chloride, dried (MgSO$_4$), filtered, and concentrated in vacuo to a crude colorless oil. Flash chromatography (SiO$_2$, 5% ethyl acetate/hexane) gave the title compound as a colorless oil (2.6 g, 72%). $^1$H NMR (300 MHz, CDCl$_3$): δ ppm 1.63 (s, 6 H) 2.56 (s, 3 H) 7.26-7.34 (m, 3 H).

Example B(33)

6-Cyclopentyl-3-[(5,7-dimethyl[1,2,4]triazolo[1,5-a]pyrimidin-2-yl)methyl]-6-{2-[3-ethyl-4-(hydroxymethyl)phenyl]ethyl}-4-hydroxy-5,6-dihydro-2H-pyran-2-one

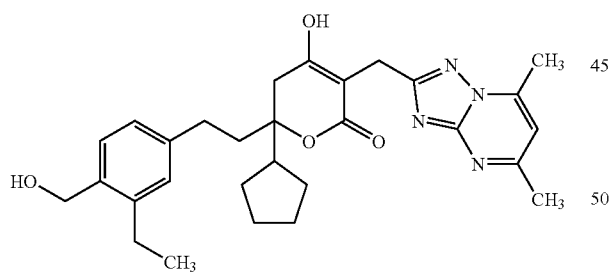

The title compound was prepared analogously to example B(1) where 6-cyclopentyl-6-{2-[3-ethyl-4-(hydroxymethyl)phenyl]ethyl}dihydro-2H-pyran-2,4(3 H)-dione (Example B(34)) was substituted in place of 6-[2-(3-chloro-4-methanesulfonyl-phenyl)-ethyl]-cyclopentyl-dihydro-pyran-2,4-dione in that example. Yield (50 mg, 23%). $^1$H NMR (300 MHz, CDCl$_3$): δ ppm 1.24 (t, J=7.25 Hz, 3 H) 1.53-1.64 (m, 8 H) 1.96-2.02 (m, 2 H) 2.32-2.42 (m, 1 H) 2.49-2.58 (m, 2 H) 2.65 (s, 3 H) 2.67-2.73 (m, 6 H) 2.78 (s, 3 H) 4.06 (s, 1 H) 4.66 (s, 2 H) 6.83 (s, 1 H) 6.94-7.01 (m, 2 H) 7.22 (d, J=7.54 Hz, 1 H). MS (ESI): 505 (M+H)$^+$.

Example B(34)

6-Cyclopentyl-6-{2-[3-ethyl-4-(hydroxymethyl)phenyl]ethyl}dihydro-2H-pyran-2,4(3H)-dione

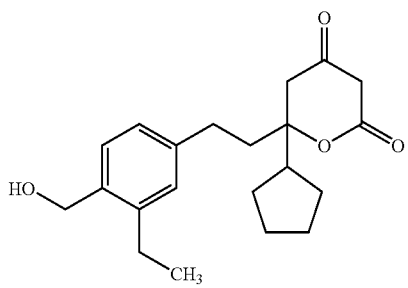

The title compound was prepared analogously to example B(2) where (4-bromo-2-ethyl-phenyl)-methanol was substituted in place of the bromide in that example. $^1$H NMR (300 MHz, CDCl$_3$): δ ppm 1.22 (t, J=7.54 Hz, 3 H) 1.60-1.75 (m, 8 H) 1.91-2.04 (m, 3 H) 2.22-2.33 (m, 1 H) 2.61-2.73 (m, 4 H) 2.76 (s, 2 H) 3.41 (s, 2 H) 4.68 (s, 2 H) 6.96-7.00 (m, 2 H) 7.28 (d, J=8.29 Hz, 1 H). MS (ESI): 367 (M+Na)$^+$.

Example B(35)

6-{2-[3-Chloro-4-(1-hydroxy-1-methylethyl)phenyl]ethyl}-6-cyclopentyl-4-hydroxy-3-([1,2,4]triazolo[1,5-a]pyrimidin-2-ylmethyl)-5,6-dihydro-2H-pyran-2-one

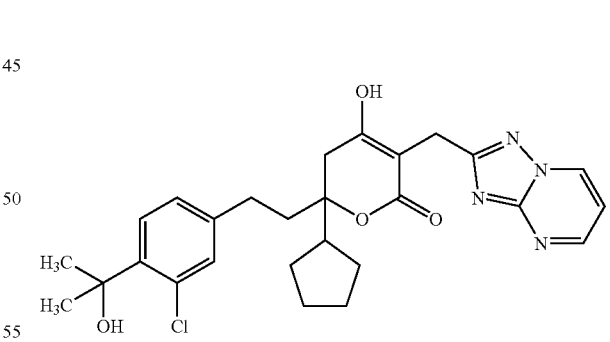

The title compound was prepared analogously to example B(1) where 2-(4-bromo-2-chloro-phenyl)-propan-2-ol was substituted in place of the bromide in step 2 of example B(2) that example and methoxy-[1,2,4]triazolo[1,5-a]pyrimidin-2-yl-methanol was substituted in place of 5,7-dimethyl-[1,2,4]triazolo[1,5-a]pyrimidine-2-carbaldehyde in Example A(1). $^1$H NMR (300 MHz, CDCl$_3$): δ ppm 1.58 (d, J=9.04 Hz, 8 H) 1.68 (s, 6 H) 1.94-2.05 (m, 2 H) 2.33-2.44 (m, 1 H) 2.46-2.55 (m, 1 H) 2.60-2.68 (m, 2 H) 2.70-2.80 (m, 1 H) 4.11 (d, J=2.45 Hz, 2 H) 7.01 (dd, J=8.19, 1.79 Hz, 1 H) 7.12 (d, J=1.70 Hz, 1 H) 7.14-7.21 (m, 1 H) 7.51 (d, J=8.10 Hz, 1 H) 8.81-8.85 (m, 2 H). MS (ESI): 533 (M+Na)⁺.

Step 1: 2-(4-Bromo-2-chloro-phenyl)-propan-2-ol

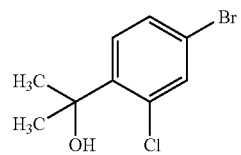

The title compound was prepared analogously to example B(32) (Step 2) where 4-bromo-2-chloro-benzoic acid was substituted in place of 4-bromo-2-methyl-benzoic acid. ¹H NMR (300 MHz, CDCl₃): δ ppm 1.71 (s, 6 H), 7.36-7.40 (m, 1 H), 7.52 (m, 1 H), 7.57-7.60 (m, 1 H).

Example B(36)

6-{2-[3-Chloro-4-(1-hydroxy-1-methylethyl)phenyl]ethyl}-6-cyclopentyl-4-hydroxy-3-[(6-methyl[1,2,4]triazolo[1,5-a]pyrimidin-2-yl)methyl]-5,6-dihydro-2H-pyran-2-one

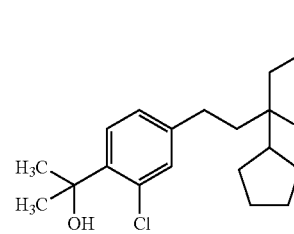

The title compound was prepared analogously to B(35) where 6-methyl-[1,2,4]triazolo[1,5-a]pyrimidine-2-carbaldehyde was substituted in place of methoxy-[1,2,4]triazolo[1,5-a]pyrimidin-2-yl-methanol in that example. ¹H NMR (400 MHz, CDCl₃): δ ppm 1.57 (m, 6 H) 1.62 (s, 3 H) 1.68 (s, 6 H) 1.70 (d, J=3.28 Hz, 3 H) 1.94-2.03 (m, 2 H) 2.34-2.43 (m, 1 H) 2.47 (s, 3 H) 2.59-2.67 (m, 2 H) 2.74 (d, J=17.94 Hz, 1 H) 4.08 (d, J=2.78 Hz, 1 H) 7.01 (dd, J=7.96, 1.64 Hz, 1 H) 7.12 (d, J=1.77 Hz, 1 H) 7.50 (d, J=8.08 Hz, 1 H) 8.60 (d, J=1.26 Hz, 1 H) 8.68 (d, J=2.27 Hz, 1 H). MS (ESI): 547 (M+Na)⁺.

Example B(37)

6-{2-[3-Chloro-4-(1-hydroxy-1-methylethyl)phenyl]ethyl}-6-cyclopentyl-3-[(5,7-dimethyl[1,2,4]triazolo[1,5-a]pyrimidin-2-yl)methyl]-4-hydroxy-5,6-dihydro-2H-pyran-2-one

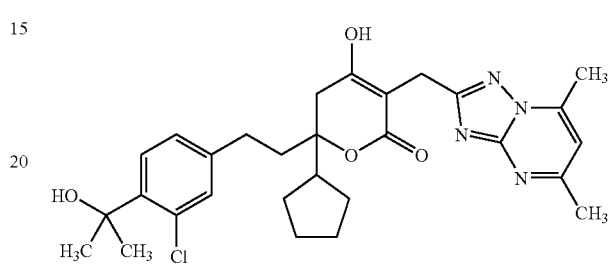

The title compound was prepared analogously to example B(1) where 2-(4-bromo-2-chloro-phenyl)-propan-2-ol was substituted in place of the bromide in step 2 of example B(2). ¹H NMR (300 MHz, CDCl₃): δ ppm 1.55 (s, 1 H) 1.64-1.71 (m, 12 H) 1.94-2.03 (m, 2 H) 2.30-2.43 (m, 2 H) 2.50 (d, J=17.90 Hz, 2 H) 2.58-2.64 (m, 2 H) 2.64-2.72 (m, 5 H) 2.78 (s, 3 H) 4.07 (s, 2 H) 6.83 (s, 1 H) 6.98-7.04 (m, 1 H) 7.11 (d, J=1.13 Hz, 1 H) 7.50 (d, J=8.10 Hz, 1 H). MS (ESI): 561 (M+Na)⁺. Anal. Calcd. For $C_{29}H_{35}ClN_4O_4$: 1.5 AcOH C, 61.09; H, 6.57; N, 8.91. Found: C, 61.22; H, 6.50; N, 8.65.

Example B(38)

6-{2-[3-Chloro-4-(1-hydroxy-1-methylethyl)phenyl]ethyl}-3-[(6-chloro[1,2,4]triazolo[1,5-a]pyrimidin-2-yl)methyl]-6-cyclopentyl-4-hydroxy-5,6-dihydro-2H-pyran-2-one

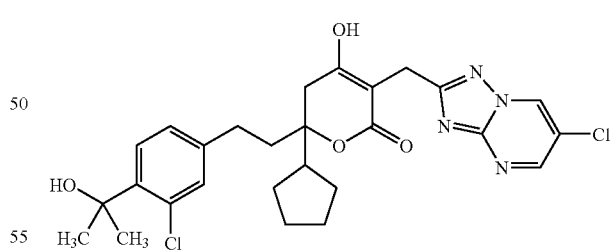

The title compound was prepared analogously to B(35) where 6-chloro-[1,2,4]triazolo[1,5-a]pyrimidine-2-carbaldehyde from step 2 below was substituted in place of methoxy-[1,2,4]triazolo[1,5-a]pyrimidin-2-yl-methanol in that example. ¹H NMR (400 MHz, DMSO-d₆): δ ppm 1.34 (s, 1 H) 1.48-1.59 (m, 10 H) 1.63-1.70 (m, 2 H) 2.03 (d, J=19.96 Hz, 2 H) 2.34-2.44 (m, J=8.84 Hz, 1 H) 2.52-2.61 (m, J=16.42 Hz, 3 H) 2.76 (d, J=17.43 Hz, 1 H) 3.29-3.41 (m, 3 H) 3.73-3.83 (m, 1 H) 5.19 (s, 1 H) 7.16 (dd, J=3.92, 2.40 Hz, 2 H) 7.70 (d, J=8.59 Hz, 1 H) 8.85 (d, J=2.53 Hz, 1 H) 9.57 (d, J=2.53 Hz, 1 H). Anal. Calcd. For $C_{27}H_{30}Cl_2N_4O_4 \cdot H_2O$ C, 57.55; H, 5.72; N, 9.94. Found: C, 57.57; H, 5.81; N, 9.72.

Step 1: (6-Chloro[1,2,4]triazolo[1,5-a]pyrimidin-2-yl)methanol

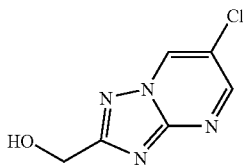

To a slurry of (5-amino-1H-[1,2,4]triazol-3-yl)-methanol (28.5 g, 150 mmol, from step 6 of example A(1)) in acetic acid was added chloromalonaldehyde (16 g, 150 mmol). The mixture was heated to 80° C. for 4 hours. Upon cooling of the reaction, the product crystallized out as a white solid (25.5 g, 92%). $^1$H NMR (300 MHz, DMSO-$d_6$): δ 4.67 (s, 2 H), 5.62 (s, 1 H), 8.94 (d, J=2.45 Hz, 1 H), 9.81 (d, J=2.45 Hz, 1 H).

Step 2: 6-Chloro[1,2,4]triazolo[1,5-a]pyrimidine-2-carbaldehyde

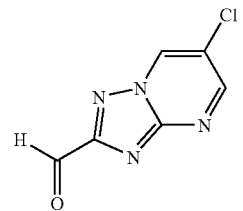

A mixture of (6-chloro[1,2,4]triazolo[1,5-a]pyrimidin-2-yl)methanol (9.86 g, 53.4 mmol), TEMPO (626 mg, 7.2 mmol), iodobenzene diacetate (18.9 g, 59 mmol) in $CH_2Cl_2$ (75 mL) was stirred at room temperature for 2 hours. Once the reaction was deemed complete, methyl-tert-butyl ether (50 mL) was added slowly to precipitate the product as a white solid (8.72 g, 90%). $^1$H NMR (300 MHz, CDCl$_3$) δ: 8.93 (d, J=2.45 Hz, 1 H), 8.99 (d, J=2.64 Hz, 1 H), 10.25 (s, 1 H). MS (APCI): 183.0, 195.0 (M+H$^+$).

Example B(39)

2-[3-Chloro-5-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2-yl]-2-methylpropanenitrile

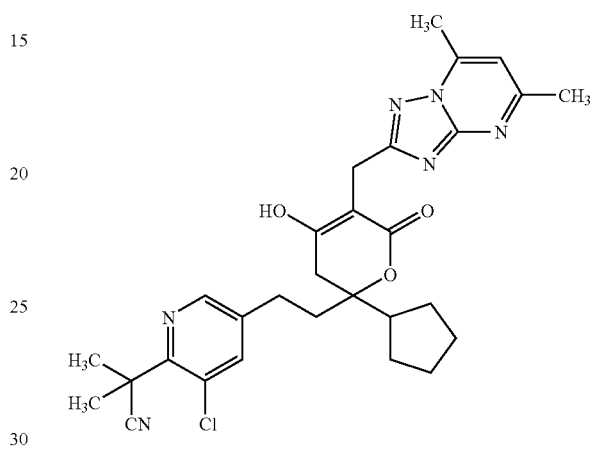

The title compound was prepared analogously to example A(1) where 2-{3-chloro-5-[2-(2-cyclopentyl-4,6-dioxotetrahydro-2H-pyran-2-yl)ethyl]pyridin-2-yl}-2-methylpropanenitrile (Example B(29)was substituted in place of 6-cyclopentyl-6-[2-(5-ethyl-4-hydroxy-2-propoxy-phenyl)-ethyl]-dihydro-pyran-2,4-dione of that example. $^1$H NMR (400 MHz, DMSO-$d_6$): δ 1.22-1.54 (m, 10 H), 1.59 (s, 6 H), 1.90-2.02 (m, 1 H), 2.30-2.35 (m, 8 H), 2.37-2.59 (m, 2 H), 3.54 (d, J=16 Hz, 1 H), 3.64 (d, J=16 Hz, 1 H), 6.85 (s, 1 H), 7.74 (s, 1 H), 8.27 (s, 1 H), 11 (s, 1 H). ESIMS (MH+): 549.

Example B(40)

tert-Butyl 4-[4-(2-cyclopentyl-4,6-dioxotetrahydro-2H-pyran-2-yl)butyl]piperidine-1-carboxylate

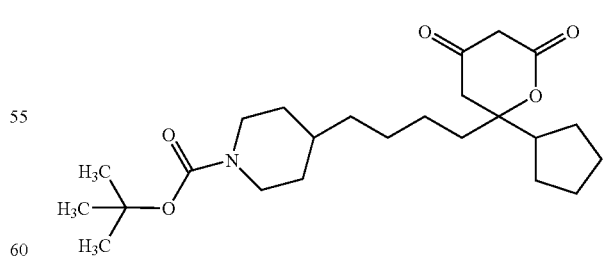

The title compound was prepared analogously to example B(2)where 4-(5-cyclopentyl-5-oxo-pentyl)-piperidine-1-carboxylic acid tert-butyl ester from step 6 below was substituted in place of 3-(3-chloro-4-methanesulfonyl-phenyl)-1-cyclopentyl-propan-1-one of that example. $^1$H NMR (400 MHz, CDCl₃): δ 1.06-1.69 (m, 29H), 2.05-2.22 (m, 2H), 2.58-2.78 (m, 4H), 3.40 (s, 2H), 4.0-4.11 (m, 2H). ESIMS (MH+): 422.

Step 1: 4-(3-Oxo-propyl)-piperidine-1-carboxylic acid tert-butyl ester

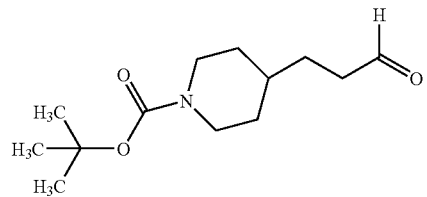

The title compound was prepared analogously to step 2 of example B(29) where 4-(3-hydroxy-propyl)-piperidine-1-carboxylic acid tert-butyl was substituted in place of 2-(3-chloro-5-hydroxymethyl-pyridin-2-yl)-2-methyl-propionitrile in that example. ¹H NMR (400 MHz, CDCl₃): δ 1.07-1.17 (m, 2H), 1.34-1.43 (m, 1H), 1.45 (s, 9H), 1.55-1.67 (m, 4H), 2.45-2.50 (m, 2H), 2.62-2.71 (m, 2H), 4.09-4.14 (m, 2H), 9.78 (s, 1H). ESIMS (MH+): 242.

Step 2: 4-(4-Ethoxycarbonyl-but-3-enyl)-piperidine-1-carboxylic acid tert-butyl ester

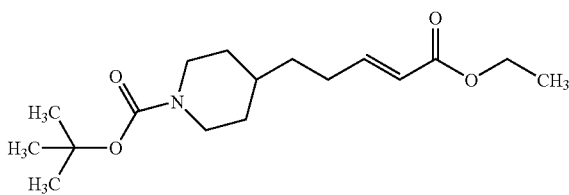

The title compound was prepared analogously to step 3 of example B(29) where 4-(3-oxo-propyl)-piperidine-1-carboxylic acid tert-butyl ester from step 1 above, was substituted in place of 2-(3-chloro-5-formyl-pyridin-2-yl)-2-methyl-propionitrile of that example. ¹H NMR (400 MHz, CDCl₃): δ 0.95-1.08 (m, 2H), 1.21 (t, J=7.2 Hz, 3H), 1.32-1.35 (m, 3H), 1.38 (s, 9H), 1.56-1.60 (m, 2H), 2.09-2.19 (m, 2H), 2.5-2.63 (m, 2H), 3.97-3.99 (m, 2H), 4.11 (q, J=7.2 Hz, 2 H), 5.74 (dd, J=15.6, 1.5 Hz, 1 H), 6.82-6.93 (m, 1H). ESIMS (MH+): 312.

Step 3: 4-(4-Ethoxycarbonyl-butyl)-piperidine-1-carboxylic acid tert-butyl ester

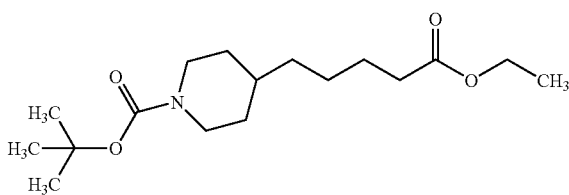

The title compound was prepared analogously to step 4 of example B(29) where 4-(4-ethoxycarbonyl-but-3-enyl)-piperidine-1-carboxylic acid tert-butyl ester from step 2 above, was substituted in place of 3-[5-chloro-6-(cyano-dimethyl-methyl)-pyridin-3-yl]-acrylic acid ethyl ester of that example. ¹H NMR (400 MHz, CDCl₃): δ 0.99-1.12 (m, 2H), 1.23-1.40 (m, 8H), 1.45 (s, 9H), 1.56-1.66 (m, 4H), 2.27-2.32 (m, 2H), 2.61-2.70 (m, 2H), 4.04-4.16 (m, 4H). ESIMS (MH+): 314.

Step 4: 4-(4-Carboxy-butyl)-piperidine-1-carboxylic acid tert-butyl ester

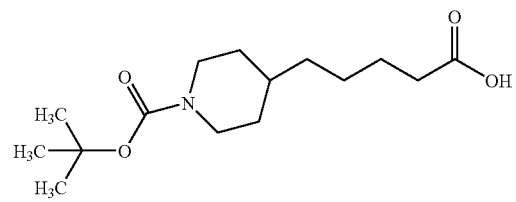

The title compound was prepared analogously to step 5 of example B(29) where 4-(4-ethoxycarbonyl-butyl)-piperidine-1-carboxylic acid tert-butyl ester from step 3 above, was substituted in place of 3-[5-chloro-6-(cyano-dimethyl-methyl)-pyridin-3-yl]-propionic acid ethyl ester in that example. ¹H NMR (400 MHz, CDCl₃): δ 1.07-1.39 (m, 7H), 1.45 (s, 9H), 1.59-1.70 (m, 4H), 2.33-2.38 (m, 2H), 2.64-2.68 (m, 2H), 4.09-4.12 (m, 2H). ESIMS (MH−): 284.

Step 5: 4-[4-(Pyridin-2-ylsulfanylcarbonyl)-butyl]-piperidine-1-carboxylic acid tert-butyl ester

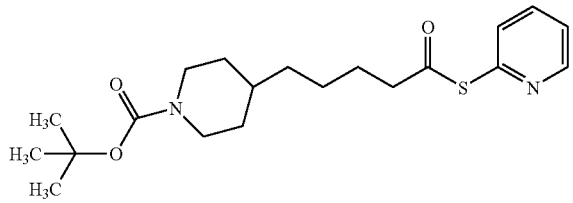

The title compound was prepared analogously to step 6 of example B(29) where 4-(4-carboxy-butyl)-piperidine-1-carboxylic acid tert-butyl ester from step 4 above, was substituted in place of 3-[5-chloro-6-(cyano-dimethyl-methyl)-pyridin-3-yl]-propionic acid of that example. ESIMS (MH+): 379.

Step 6: 4-(5-Cyclopentyl-5-oxo-pentyl)-piperidine-1-carboxylic acid tert-butyl ester

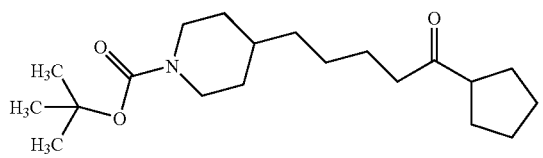

The title compound was prepared analogously to step 7 of example B(29) where 4-[4-(pyridin-2-ylsulfanylcarbonyl)-butyl]-piperidine-1-carboxylic acid tert-butyl ester from step 5 above, was substituted in place 3-cyclohexyl-thiopropionic acid S-pyridin-2-yl ester. ¹H NMR (400 MHz, CDCl₃): δ 1-1.42 (m, 8H), 1.45 (s, 9H), 1.50-1.84 (m, 14H), 2.42-2.46 (m, 2H), 2.62-2.7 (m, 2H), 2.82-2.87 (m, 1H). ESIMS (MH+): 337.

Example B(41)

tert-Butyl 4-(4-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}butyl)piperidine-1-carboxylate

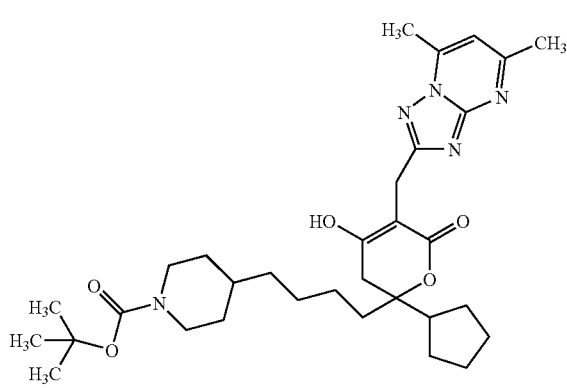

The title compound was prepared analogously to example A(1) where tert-butyl 4-[4-(2-cyclopentyl-4,6-dioxotetrahydro-2H-pyran-2-yl)butyl]piperidine-1-carboxylate (example B(40)) was substituted in place of 6-cyclopentyl-6-[2-(5-ethyl-4-hydroxy-2-propoxy-phenyl)-ethyl]-dihydro-pyran-2,4-dione of that example. ¹H NMR (400 MHz, DMSO-d₆): δ 0.76-1.50 (m, 29 H), 1.90-1.94 (m, 4 H), 2.27-2.6 (m, 8 H), 3.54-3.74 (m, 4H), 6.92 (s, 1H), 10.62 (s, 1H). ESIMS (MH+): 582.

Example B(42)

6-Cyclopentyl-3-[(5,7-dimethyl[1,2,4]triazolo[1,5-a]pyrimidin-2-yl)methyl]-4-hydroxy-6-(4-piperidin-4-ylbutyl)-5,6-dihydro-2H-pyran-2-one

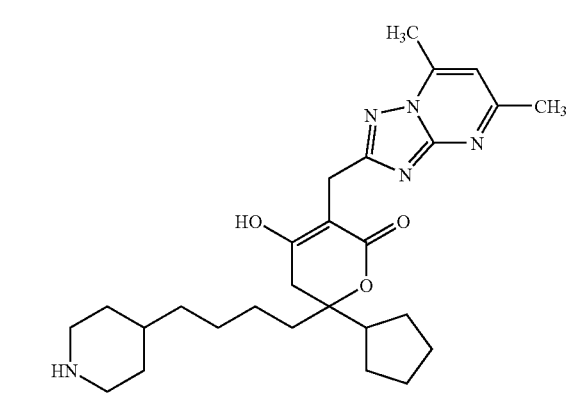

tert-Butyl 4-(4-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}butyl)piperidine-1-carboxylate (example B(41)) (0.47 g, 0.8 mmol) was dissolved in dioxane (1 mL) and 4N HCl in dioxane (1 mL). The reaction was stirred overnight at room temperature. Solvents were removed and the residue was purified using a Dionex system (30-70% CH₃CN/H₂O (0.1% AcOH). H NMR (400 MHz, DMSO-d₆): δ 1.37-1.70 (m, 20 H), 2.63-2.85 (m, 12 H), 3.69-3.95 (m, 4H), 7.98 (s, 1H), 11.12 (s, 1H). Anal. Calcd. For C₂₇H₃₉N₅O₃.1.0HCl. 1.5 H₂O: C, 59.49; H, 7.95; N, 12.85, Found: C, 59.60; H, 8.04; N, 12.95. ESIMS (MH+): 482.

Example B(43)

2-{4-[2-(2-Cyclopentyl-4-hydroxy-5-{[1-methyl-3-(6-methylpyridin-2-yl)-1H-1,2,4-triazol-5-yl]methyl}-6-oxo-3,6-dihydro-2H-pyran-2-yl)ethyl]-2-fluorophenyl}-2-methylpropanenitrile

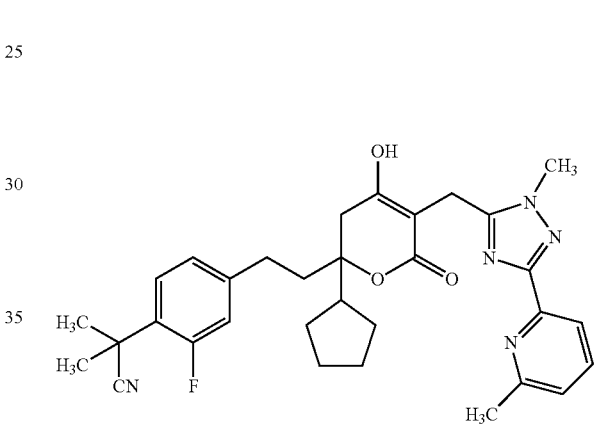

A solution of 2-{4-[2-(2-cyclopentyl-4,6-dioxo-tetrahydro-pyran-2-yl)-ethyl]-2-fluoro-phenyl}-2-methyl-propionitrile (1.0 g, 2.70 mmol, from step 3 of example A(84) in hot (50° C.) isopropanol (7 mL) was treated with (CH₃)₂NHBH₃ (175 mg, 2.97 mmol, 1.1 equiv), then with a solution of 1-methyl-3-(6-methylpyridin-2-yl)-1H-1,2,4-triazole-5-carbaldehyde hydrochloride hydrate (762 mg, 2.97 mmol, 1.1 equiv, from Step 4 below) in isopropanol (4 mL) containing triethylamine (301 mg, 2.97 mmol, 1.1 equiv). The reaction mixture was stirred heated at 47-50° C. for 18 h. The reaction mixture was treated with 1.1 equiv of 1 M aqueous HCl and concentrated in vacuo to afford an oily resin. This was diluted with water and extracted with dichloromethane containing 10% methanol (3×30 mL). The extract was dried over Na₂SO₄, filtered, and concentrated. The residue was triturated with hot ethyl acetate/methylene chloride, filtered, washed with cold ether, and dried, affording 584 mg (38%) of the title product. ¹H NMR (400 MHz, DMSO-d₆): δ 1.36-1.71 (m, 14 H), 2.05 (m, 2 H), 2.48 (m, 1 H), 2.46 (s, 3 H), 2.63 (m, 3 H), 2.78 (d, J=17.9 Hz, 1 H), 3.67 (d, J=15.7 Hz, 1 H), 3.74 (d, J=15.7 Hz, 1 H), 3.91 (s, 3 H), 6.99 (d, J=8.1 Hz, 1 H), 7.10-7.20 (m, 3 H), 7.57 (m, 2 H), 11.22 (s, 1 H). LC-MS (APCI) calcd for $C_{32}H_{36}FN_5O_3$: 557.28, found (M+H+): 558.40 m/z.

Step 1: N',6-Dimethylpyridine-2-carbohydrazonamide

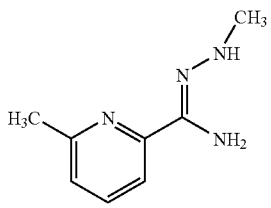

6-Methylpyridine-2-carbonitrile (45.3 g, 0.384 mol) and methylhydrazine (94 mL, 5.30 mol) were mixed with ethanol (200 mL). The mixture was stirred at room temperature overnight, and then an additional portion (18 mL, 1.00 mol) of methylhydrazine was added, and the mixture was stirred for a further 16 h. The mixture was then evaporated to give 58.0 g of crude N',6-dimethylpyridine-2-carbohydrazonamide (~92% yield), which was used for the next stage of the synthesis without additional purification.

Step 2: Methyl 2,2-diethoxyethanimidoate

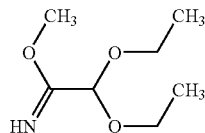

A solution of diethoxyacetonitrile (75 g, 0.579 mol) in methanol (210 mL) was added at room temperature to a solution of sodium methoxide (28.3 g, 0.522 mol) in methanol (450 mL). The mixture was stirred overnight, and then the methanol was carefully evaporated (volatile product). The residue was diluted with dichloromethane (200 mL) and water (300 mL). The organic layer was separated, and the aqueous one was extracted with dichloromethane (2×150 mL). The combined organic layer was dried over $Na_2SO_4$ and evaporated to give 83 g of crude methyl 2,2-diethoxyethanimidoate (~90% yield).

Step 3: 2-[5-(Diethoxymethyl)-1-methyl-1H-1,2,4-triazol-3-yl]-6-methylpyridine

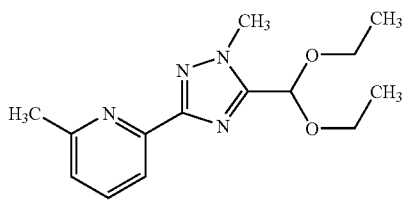

Methyl 2,2-diethoxyethanimidoate (42 g, 0.26 mol) was dissolved in methanol (200 mL), and a solution of compound N',6-dimethylpyridine-2-carbohydrazonamide (43 g, 0.25 mol) in methanol (200 mL) while cooling with a water bath, followed by the addition of acetic acid (22 mL, 0.37 mol). The mixture was stirred at room temperature for 3 h, and then $K_2CO_3$ (10 g, 0.071 mol) was added. The mixture was stirred for 10 min, and then the methanol was evaporated. The residue was stirred with a solution of $K_2CO_3$ (20 g) in water (200 mL), and extracted with ether (2×150 mL). The organic layer was washed with water and then saturated NaCl solution, dried over $Na_2SO_4$ and evaporated. The residue (62 g) was purified by chromatography on a silica gel column to afford 39.5 g (57%) of the title product.

Step 4: 1-Methyl-3-(6-methylpyridin-2-yl)-1H-1,2,4-triazole-5-carbaldehyde hydrochloride hydrate

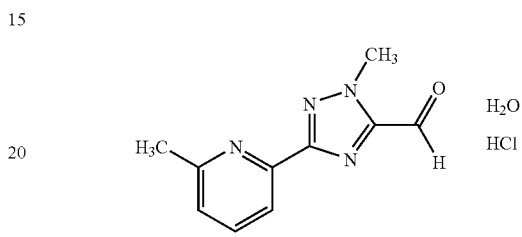

A mixture of 2-[5-(diethoxymethyl)-1-methyl-1H-1,2,4-triazol-3-yl]-6-methylpyridine (38 g, 0.1377 mol), water (92 mL) and concentrated HCl (23 mL, 0.276 mol) was heated at 70-80° C. for 2 h. The resulting solution was co-evaporated with water four times using a water aspirator vacuum, then dried in vacuo at 60° C. to give 33.5 g (94.5%) of the title product as a covalently-bound hydrate. Satisfactory C,H,N-analysis was obtained. $^1$H NMR (400 MHz, $D_2O$+TFA): δ 2.90 (s, 3H), 4.13 (s, 3H), 6.38 (s, 1H), 7.94 (d, J=8 Hz, 1H), 8.37 (d, J=8 Hz, 1H), 8.56 (t, J=8 Hz, 1H). LC-MS (API-ES) calcd for $C_{10}H_{10}N_4O$: 202.09, found (M+H+): 203.1; (M+18+H+) 221.1 m/z.

Example B(44)

2-[4-(2-{2-cyclopentyl-5-[(3-ethyl-1-methyl-1H-1,2,4-triazol-5-yl)methyl]-4-hydroxy-6-oxo-3,6-dihydro-2H-pyran-2-yl}ethyl)-2-fluorophenyl]-2-methylpropanenitrile

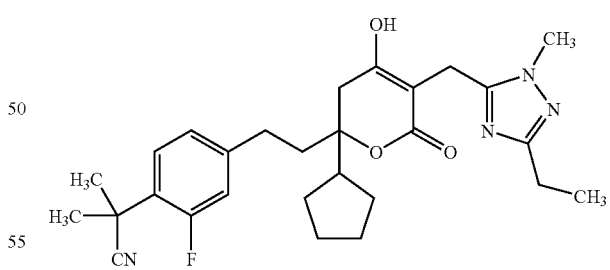

The title compound was prepared analogously to example B(43) where 3-ethyl-1-methyl-1H-1,2,4-triazole-5-carbaldehyde hydrochloride hydrate (step 4, below) was substituted in place of 1-methyl-3-(6-methylpyridin-2-yl)-1H-1,2,4-triazole-5-carbaldehyde. The product was isolated by trituration with ether. Yield 552 mg, 41%. $^1$H NMR (400 MHz, DMSO-$d_6$): δ 1.03 (d, J=7.6 Hz, 3 H), 1.34-1.76 (m, 14 H), 2.06 (m, 2 H), 2.38 (m, 3 H), 2.60 (m, 3 H), 2.76 (d, J=17.6 Hz, 1 H), 3.53 (d, J=15.9 Hz, 1 H), 3.61 (d, J=15.9 Hz, 1 H), 3.73 (s, 3 H), 7.07 (d, J=8.6 Hz, 1 H), 7.13 (d, J=13.1 Hz, 1 H), 7.35 (t, J=8.6 Hz, 1 H). LC-MS (APCI) calcd for $C_{28}H_{35}FN_4O_3$: 494.27, found (M+H$^+$): 495.40 m/z.

Step 1: Methyl propanimidoate hydrochloride

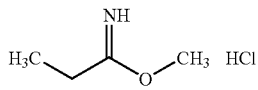

Propiononitrile (176 mL, 2.5 mol) was added at 0° C. to 4 M HCl in dioxane (690 mL). Absolute methanol (112 mL) was added dropwise at 0° C., and the mixture was left to stand at this temperature for 1 h, and then in a refrigerator overnight. The resulting crystalline slurry was treated with ether (700 mL). The crystalline precipitate was separated by filtration, washed with ether to removed residual HCl and dried to give the title product. Yield: 226 g (73%).

Step 2: N'-methylpropanehydrazonamide hydrochloride

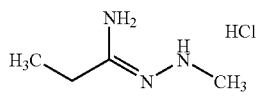

To a suspension of methyl propanimidoate hydrochloride (100 g, 0.803 mol) in methanol (400 mL) was added a solution of methylhydrazine (47 mL, 0.883 mol) dropwise at room temperature. The solution was allowed to stand at room temperature for 2 days, then evaporated. The resulting oil was washed with THF (3×150 mL) and dried to give 84.1 g (61%) of the crude title product.

Step 3: 5-(Diethoxymethyl)-3-ethyl-1-methyl-1H-1,2,4-triazole

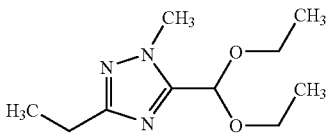

A solution of sodium methoxide (3.30 g, 0.0611 mol) in methanol (100 mL) was added at room temperature to a solution of diethoxyacetonitrile (78.9 g, 0.611 mol) in methanol (600 mL). The resulting mixture was stirred at room temperature overnight, and a solution of crude N'-methylpropanehydrazonamide hydrochloride from Step 2 (84.1 g, ~0.60 mol) in methanol (200 mL) was added. Anhydrous sodium acetate (50.0 g, 0.61 mol) was added, and the resulting mixture was refluxed under an atmosphere of Ar for 20 h. Then methanol was evaporated, and the dark oily residue was extracted with ether (3×250 mL). The ether solution was passed through a layer of silica gel, and the filtrate was evaporated. The residue was distilled in vacuo to give 35.0 g (27%) of the title product (bp 68° C. at 0.1 mm Hg). Note: There is a higher-boiling second fraction (15 g; bp 120° C. at 0.1 mm Hg) that is a triazole impurity containing two acetal groups.

Step 4: 3-Ethyl-1-methyl-1H-1,2,4-triazole-5-carbaldehyde hydrochloride hydrate

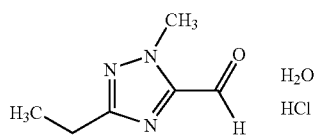

A solution of 5-(diethoxymethyl)-3-ethyl-1-methyl-1H-1,2,4-triazole from Step 3 (35.6 g, 0.167 mol) in 3.6 M HCl (150 mL) was heated (60° C.) for 10 h, then evaporated to dryness. The residual oil was washed with THF (3×100 mL), then treated with dry acetone (200 mL) causing crystallization. The product was filtered and dried, affording 18.8 g (59%) of the title product. Satisfactory C,H,N-analysis was obtained. The compound was observed by $^1$H NMR to be a 60:40 mixture of non-covalent (free aldehyde) and covalent hydrates, respectively. $^1$H NMR (400 MHz, DMSO-d$_6$): δ 1.22 (m, overlap, 3H), 2.67 (q, J=7.8 Hz, 0.6×2H), 2.79 (q, J=7.8 Hz, 0.4×2H), 3.96 (s, 0.4×3H), 4.04 (s, 0.6×3H), 6.21 (s, 0.4×1H), 8.35 (br s, 3H), 9.87 (s, 0.6×1H). LC-MS (APCI) calcd for $C_6H_9N_3O$: 139.07, found (M+H$^+$): 140.1; (M+18+H$^+$) 158.1 m/z.

Example B(45)

2-{4-[2-(2-cyclopentyl-5-{[1,3-dimethyl-5-(4-methylpiperazin-1-yl)-1H-pyrazol-4-yl]methyl}-4-hydroxy-6-oxo-3,6-dihydro-2H-pyran-2-yl)ethyl]-2-fluorophenyl}-2-methylpropanenitrile

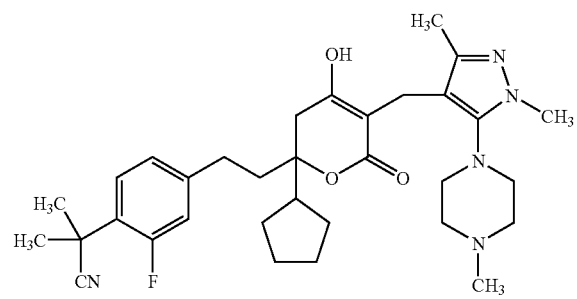

The title compound was prepared analogously to example B(43) where 1,3-dimethyl-5-(4-methylpiperazin-1-yl)-1H-pyrazole-4-carbaldehyde (step 3, below) was substituted in place of 1-methyl-3-(6-methylpyridin-2-yl)-1H-1,2,4-triazole-5-carbaldehyde, and the triethylamine was omitted. The product was isolated by trituration with ether. Yield 1.0 g (64%). $^1$H NMR (400 MHz, DMSO-d$_6$): δ 1.31-1.70 (m, 14 H), 1.90 (m, 2 H), 1.95 (s, 3 H), 2.25 (s, 3 H), 2.32 (m, 1 H), 2.43 (m, 4 H), 2.57 (m, 3 H), 2.67 (d, J=17.4 Hz, 1 H), 3.06 (m, 4 H), 3.25 (d, J=14.8 Hz, 1 H), 3.32 (d, J=14.6 Hz, 1 H), 3.48 (s, 3 H), 6.99 (d, J=8.1 Hz, 1 H), 7.08 (d, J=13.1 Hz, 1 H), 7.35

(t, J=8.3 Hz, 1 H). LC-MS (APCI) calcd for $C_{33}H_{44}FN_5O_3$: 577.34, found (M+H$^+$): 578.40 m/z.

Step 1: 1,3-Dimethyl-1H-pyrazol-5-ol

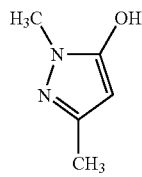

To a solution of ethyl acetoacetate (50 g, 0.3846 mol) in methanol (280 mL) was added a solution of methylhydrazine (17.5 g, 0.38 mol) in methanol (20 mL) dropwise over 20 min, resulting in an increase in temperature to 45° C. The reaction mixture was stirred overnight at room temperature. Methanol was removed under vacuum on a rotary evaporator to give 50 g of the crude title pyrazolone that was used in the next step without purification.

Step 2: 5-Chloro-1,3-dimethyl-1H-pyrazole-4-carbaldehyde

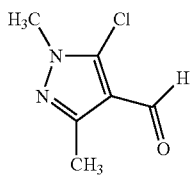

To DMF (33.29 mL, 0.456 mol) was carefully added POCl$_3$ (134.16 g, 81.5 mL 0.874 mol,) at 0° C. The reaction mixture was diluted with 1,2-dichloroethane (100 mL), then treated with a solution of crude 1,3-dimethyl-1H-pyrazol-5-ol (50 g, from Step 1) in dichloroethane (100 mL) under continued stirring at 0° C. The mixture was refluxed for 3 h, then left to stir overnight at room temperature. In order to decompose the formylating reagent, to the reaction mixture was added a solution of sodium hydroxide (91.2 g, 2.28 mol) in water (200 mL) dropwise at 0° C. The reaction mixture was diluted with water and extracted with dichloromethane (3×250 mL). The organic extracts were washed with water to neutral pH, washed with water, then dried with sodium sulfate. The solvent was removed under vacuum to afford the title product (31.1 g, 51% overall from methylhydrazine) as a yellow crystalline substance.

Step 3: 1,3-dimethyl-5-(4-methylpiperazin-1-yl)-1H-pyrazole-4-carbaldehyde

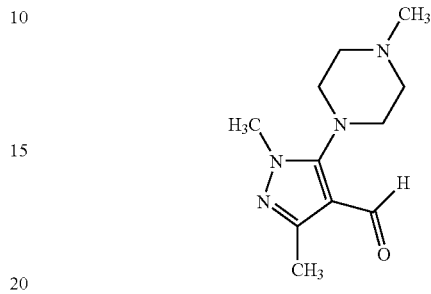

To a solution of 5-chloro-1,3-dimethyl-1H-pyrazole-4-carbaldehyde (25.4 g, 0.16 mol) in HMPA (25 mL) and water (25 mL) was added 1-methylpiperazine (40 g, 0.4 mol, 2.5 equiv), and the mixture was heated at 120-125° C. for 25 h. When the reaction was completed, the reaction mixture was poured into water (500 mL), and potassium carbonate was added to make the medium strongly alkaline. The mixture was extracted with dichloromethane (5×100 mL). The combined organic extracts were washed twice with water and dried with sodium sulfate, and the solvent evaporated. The residue was purified chromatographically on silica gel with gradient elution from dichloromethane to methanol, affording 10.2 g (29%) of the title product. Satisfactory C,H,N-analysis was obtained. $^1$H NMR (400 MHz, DMSO-d$_6$): δ 2.23 (s, 3H), 2.26 (s, 3H), 2.44 (m, 4H), 3.16 (m, 4H), 3.59 (s, 3H), 9.88 (s, 1H). LC-MS (API-ES) calcd for $C_{11}H_{18}N_4O$: 222.15, found (M+H$^+$): 223.1 m/z.

Example B(46)

2-[4-(2-{2-Cyclopentyl-4-hydroxy-5-[(1-methyl-3-pyrazin-2-yl-1H-1,2,4-triazol-5-yl)methyl]-6-oxo-3,6-dihydro-2H-pyran-2-yl}ethyl)-2-fluorophenyl]-2-methylpropanenitrile

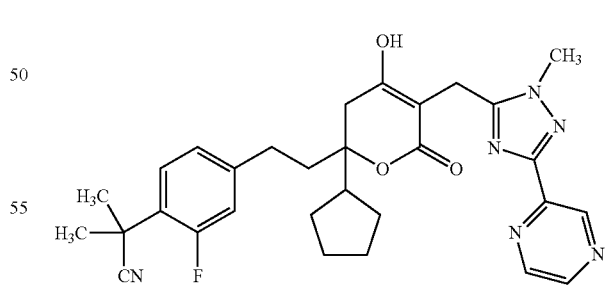

The title compound was prepared analogously to example B(15) where 2-{4-[2-(2-cyclopentyl-4,6-dioxo-tetrahydro-pyran-2-yl)-ethyl]-2-fluoro-phenyl}-2-methyl-propionitrile (from step 3 of example A(84)) was substituted in place of 6-[2-(5-chloro-2,4-dimethoxy-phenyl)-ethyl]-6-cyclopentyl-dihydro-pyran-2,4-dione. The product was chromatographed on silica gel and triturated with ether. Yield=201 mg (13%). $^1$H NMR (400 MHz, DMSO-d$_6$): δ 1.35-1.71 (m, 14

H), 2.02 (m, 2H), 2.39 (s, 1 H), 2.59 (m, 3 H), 2.75 (d, J=17.4 Hz, 1 H), 3.69 (d, J=17.1 Hz, 1 H), 3.76 (d, J=17.1 Hz, 1 H), 3.94 (s, 3 H), 6.99 (d, J=8.1 Hz, 1 H), 7.08 (d, J=13.1 Hz, 1 H), 7.20 (t, J=8.3 Hz, 1 H), 8.60 (s, 1 H), 8.64 (s, 1 H), 8.97 (s, 1 H). LC-MS (APCI) calcd for $C_{30}H_{33}FN_6O_3$: 544.63, found (M+H$^+$): 545.30 m/z.

Example B(47)

2-[4-(2-{2-Cyclopentyl-5-[(1-ethyl-3,5-dimethyl-1H-pyrazol-4-yl)methyl]-4-hydroxy-6-oxo-3,6-dihydro-2H-pyran-2-yl}ethyl)-2-fluorophenyl]-2-methylpropanenitrile

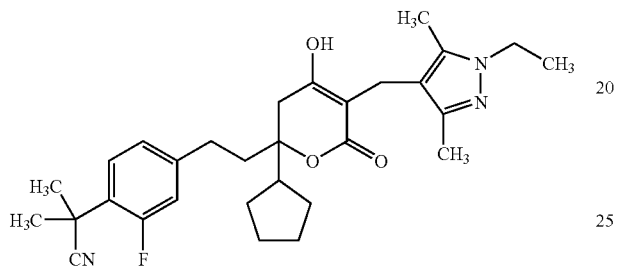

The title compound was prepared analogously to example B(43) where 1-ethyl-3,5-dimethyl-1H-pyrazole-4-carbaldehyde was substituted in place of 1-methyl-3-(6-methylpyridin-2-yl)-1H-1,2,4-triazole-5-carbaldehyde, and the triethylamine was omitted. The product was purified by chromatography on silica gel and trituration with ether. Yield: 795 mg, 58%. $^1$H NMR (400 MHz, DMSO-d$_6$): δ 1.14 (t, J=7.1 Hz, 3 H), 1.28-1.62 (m, 8 H), 1.70 (s, 6 H), 1.82 (m, 2 H), 2.04 (s, 3 H), 2.11 (s, 3 H), 2.26 (m, 1 H), 2.48-2.55 (m, 3 H), 2.69 (d, J=17.6 Hz, 1 H), 3.11 (d, J=14.6 Hz, 1 H), 3.22 (d, J=14.6 Hz, 1 H), 3.84 (q, J=7.3 Hz, 2 H), 6.93 (d, J=9.6 Hz, 1 H), 7.04 (d, J=11.6 Hz, 1 H), 7.34 (t, J=8.6 Hz, 1 H), 10.65 (s, 1 H). LC-MS (APCI) calcd for $C_{30}H_{38}FN_3O_3$: 507.29, found (M+H$^+$):
508.40 m/z.

Example B(48)

2-[4-(2-{2-Cyclopentyl-5-[(3-ethyl-1-methyl-5-morpholin-4-yl-1H-pyrazol-4-yl)methyl]-4-hydroxy-6-oxo-3,6-dihydro-2H-pyran-2-yl}ethyl)-2-fluorophenyl]-2-methylpropanenitrile

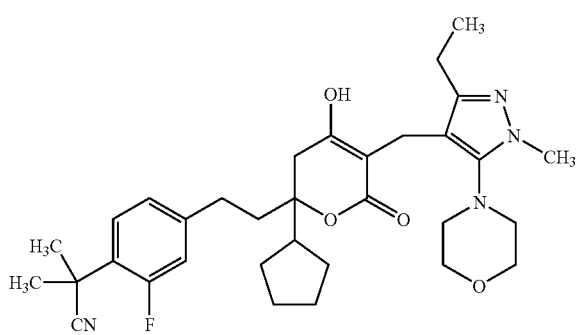

The title compound was prepared analogously to example B(43) where 3-ethyl-1-methyl-5-morpholin-4-yl-1H-pyrazole-4-carbaldehyde (Step 3, below) was substituted in place of 1-methyl-3-(6-methylpyridin-2-yl)-1H-1,2,4-triazole-5-carbaldehyde, and the triethylamine was omitted. The product was purified by chromatography on silica gel recrystallized from ethyl acetate/ether. Yield: 486 mg (31%). $^1$H NMR (400 MHz, DMSO-d$_6$): δ 1.01 (t, J=7.6 Hz, 3 H), 1.32-1.64 (m, 8 H), 1.70 (s, 6 H), 1.89 (m, 2 H), 2.36 (m, 2 H), 2.58 (m, 2 H), 2.67 (d, J=17.6 Hz, 1 H), 3.05 (s, 4 H), 3.26-3.41 (m, 4 H), 3.54 (s, 3 H), 3.63 (m, 4 H), 6.99 (d, J=9.3 Hz, 1 H), 7.09 (d, J=14.3 Hz, 1 H), 7.35 (t, J=8.3 Hz, 1 H), 10.70 (s, 1 H). LC-MS (APCI) calcd for $C_{33}H_{43}FN_4O_4$: 578.33, found (M+H$^+$): 579.40 m/z.

Step 1: 3-Ethyl-1-methyl-1H-pyrazol-5-ol

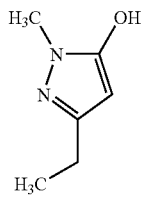

Methylhydrazine (31.6 g, 0.687 mol) in methanol (100 mL) was added dropwise to a solution of ethyl 3-oxopentanoate (100 g, 0.694 mol) in methanol (280 mL) over a period of 45 min, during which time the temperature increased to 45° C. The reaction mixture was then allowed to stir at room temperature overnight and then evaporated, affording 84.5 g (97%) of the crude title product.

Step 2: 5-Chloro-3-ethyl-1-methyl-1H-pyrazole-4-carbaldehyde

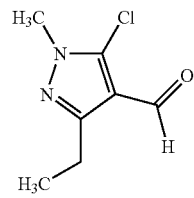

POCl$_3$ (236.88 g, 1.543 mol, 144 mL) was added dropwise at 0° C. to DMF (59 g, 0.808 mol). The reaction mixture was then diluted with dichloromethane (200 mL), and: 3-ethyl-1-methyl-1H-pyrazol-5-ol (84.5 g, from Step 1) was added while stirring at 0° C. The mixture was refluxed for 3 h and then stirred overnight at room temperature. After this, ice-cold water (500 mL) was added rapidly at 0° C. to the reaction mixture in order to decompose the formylation agent. The organic layer was separated, and the aqueous phase extracted with chloroform several times. The organic layers were then washed with K$_2$CO$_3$ solution to obtain a weak alkaline media, dried over Na$_2$SO$_4$ and evaporated to give 51.2 g of an oily substance. The residual reaction mass was neutralized with K$_2$CO$_3$ to obtain a weak acidic media and extracted with chloroform. The combined extracts were concentrated and the residue purified by chromatography (dichloromethane) on a silica gel to give 71.3 g (62%) of the title product.

Step 3: 3-Ethyl-1-methyl-5-morpholin-4-yl-1H-pyrazole-4-carbaldehyde

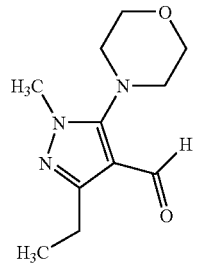

Morpholine (35.15 g, 0.4 mol) and water (30 mL) were added under stirring at room temperature to a mixture of 5-chloro-3-ethyl-1-methyl-1H-pyrazole-4-carbaldehyde from Step 2 (35 g, 0.202 mol) in HMPA (30 mL). The reaction mixture was heated at 90° C. for 8 h, then diluted with water and extracted with ethyl acetate (3×100 mL). The organic extracts were washed with water to obtain a weak alkaline media, dried over $Na_2SO_4$ and evaporated. The residue was purified by chromatography (hexane/ethyl acetate) on silica gel to afford 37.2 g (82.6%) of the title product. Satisfactory C,H,N-analysis was obtained.

$^1$H NMR (400 MHz, DMSO-$d_6$): δ 1.14 (t, J=7.6 Hz, 3H), 2.71 (q, J=7.6 Hz, 2H), 3.16 (m, 4H), 3.65 (s, 3H), 3.72 (m, 4H), 9.91 (s, 1H). LC-MS (API-ES) calcd for $C_{11}H_{17}N_3O_2$: 223.13, found (M+H$^+$): 224.1 m/z Example B(49)

2-[4-(2-{2-Cyclopentyl-5-[(1,3-dimethyl-5-morpholin-4-yl-1H-pyrazol-4-yl)methyl]-4-hydroxy-6-oxo-3,6-dihydro-2H-pyran-2-yl}ethyl)-2-fluorophenyl]-2-methylpropanenitrile

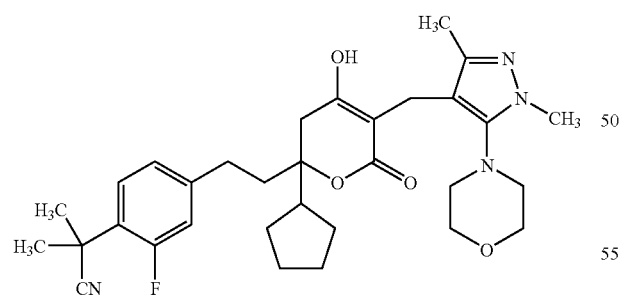

The title compound was prepared analogously to example B(43) where 1,3-dimethyl-5-morpholin-4-yl-1H-pyrazole-4-carbaldehyde was substituted in place of 1-methyl-3-(6-methylpyridin-2-yl)-1H-1,2,4-triazole-5-carbaldehyde. Yield: 448 (29%). $^1$H NMR (400 MHz, DMSO-$d_6$): δ 1.32-1.64 (m, 8 H), 1.70 (s, 6 H), 1.90 (m, 2 H), 1.95 (s, 3 H), 2.32 (m, 1 H), 2.58 (m, 3 H), 2.68 (d, J=17.6 Hz, 1 H), 3.04 (m, 4 H), 3.27 (d, J=14.9 Hz, 1 H), 3.30 (d, J=14.9 Hz, 1 H), 3.52 (s, 3 H), 3.62 (m, 4H), 6.99 (d, J=9.3 Hz, 1 H), 7.09 (d, J=14.3 Hz, 1 H), 7.35 (t, J=8.3 Hz, 1 H), 10.73 (s, 1 H). LC-MS (APCI) calcd for $C_{32}H_{41}FN_4O_4$: 564.31, found (M+H$^+$): 565.40 m/z.

Example B(50)

2-[4-(2-{2-Cyclopentyl-5-[(1-ethyl-5-methyl-1H-1,2,4-triazol-3-yl)methyl]-4-hydroxy-6-oxo-3,6-dihydro-2H-pyran-2-yl}ethyl)-2-fluorophenyl]-2-methylpropanenitrile

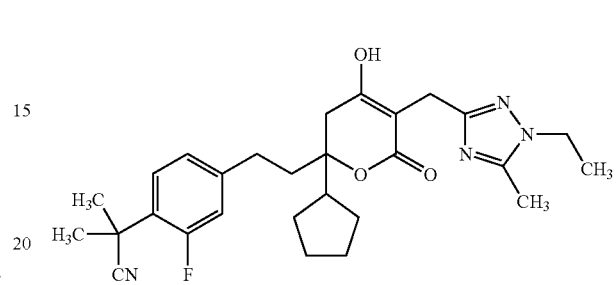

The title compound was prepared analogously to example B(43) where 1-ethyl-5-methyl-1H-1,2,4-triazole-3-carbaldehyde (step 2, below) was substituted in place of 1-methyl-3-(6-methylpyridin-2-yl)-1H-1,2,4-triazole-5-carbaldehyde, and the triethylamine omitted. Yield=195 mg (14%). $^1$H NMR (400 MHz, DMSO-$d_6$): δ 1.15 (t, J=7.3 Hz, 3 H), 1.37-1.71 (m, 14 H), 2.11 (m, 2 H), 2.24 (s, 3H), 2.40 (m, 1 H), 2.64 (m, 3 H), 2.74 (d, J=17.4 Hz, 1 H), 3.42 (d, J=15.8 Hz, 1 H), 3.52 (d, J=15.6 Hz, 1 H), 3.99 (q, J=7.3 Hz, 2 H), 7.11 (m, 2 H), 7.35 (t, J=8.3 Hz, 1 H), 10.81 (s, 1 H). LC-MS (APCI) calcd for $C_{28}H_{35}FN_4O_3$: 494.27, found (M+H$^+$): 495.30 m/z.

Step 1: 3-Diethoxymethyl-1-ethyl-5-methyl-1H-[1,2,4]triazole

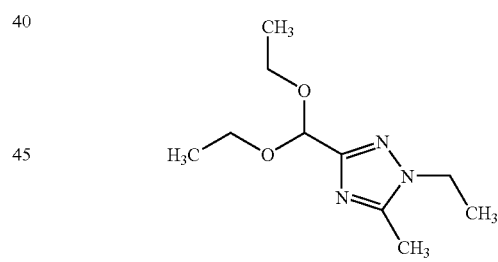

To a solution of NaOMe (24 mL, 25% wt in MeOH, 0.105 mol, 4.3 mol %) in MeOH (2.4 L) was added diethoxyacetonitrile (310 g, 2.40 mol), and the reaction mixture was stirred at room temperature for 24 h. The solvent was removed in vacuo (300 mbar, 44° C.) and the brown oily residue was dissolved into Et$_2$O (2.4 L). The organic solution was washed with water (3×500 mL) and brine (1×400 mL), and dried over Na$_2$SO$_4$. The solvent was removed in vacuo at 0° C. to yield methyl 2,2-diethoxyethanimidoate (333.32 g, 86%) as a clear liquid. To a solution of NaOMe (25% wt in MeOH, 424 g, 2 mol) and MeOH (2 L), was added ethylhydrazine oxalate (150.14 g, 1 mol), and the mixture was stirred for 10 min. Methyl 2,2-diethoxyethanimidoate (161.2 g, 1 mol) was added, and the mixture was stirred at room temperature for 3 h under a blanket of Nitrogen. The product, (1Z)-2,2-diethoxy-N-ethylethanehydrazonamide was used in situ. The crude (1Z)-2,2-diethoxy-N-ethylethanehydrazonamide was treated with acetimidate hydrochloride (109.6 g, 1 mol) and glacial acetic acid (90 g, 1.5 mol), and the mixture was stirred at room temperature for 24 h under nitrogen. LCMS indicated that no reaction had occurred after 24 h. The solvent was removed under vacuum from the reaction mixture and the residue was stored in the freezer. After 8 days the residue was removed from the freezer, warmed to room temperature, and treated with MeOH (1.5 L), acetic Acid (85.7 mL), and acetimidate HCl (98 g, 0.89 mol) from a new bottle, and this mixture was stirred at room temperature for 24 h. LCMS indicated that the starting materials had been consumed and that some of the desired product was present. The solvent was removed in vacuo and $H_2O$ (1.5 L) was added to the residue. The mixture was extracted with DCM (5×1 L), and the combined organic layers were dried over $Na_2SO_4$. The solvent was removed under vacuum to afford 163 g of a crude red oil. The product was purified by flash chromatography using 2% MeOH/DMC as eluent (RF=0.3) affording 56.86 g (23%) of 3-(diethoxymethyl)-1-ethyl-5-methyl-1H-1,2,4-triazole as a red oil, which was 96% pure by $^1$H NMR.

Step 2:
1-Ethyl-5-methyl-1H-[1,2,4]triazole-3-carbaldehyde

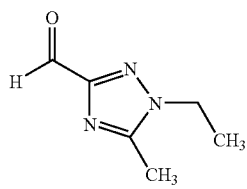

A mixture of 3-(diethoxymethyl)-1-ethyl-5-methyl-1H-[1,2,4]triazole from step 1 (56.86 g, 0.267 mol) and $H_2O$ (300 mL) was treated slowly with 35% aqueous HCl (55.61 g, 0.534 mol), and the reaction was stirred at room temperature for 24 h. The mixture was washed with DCM (2×200 mL). The aqueous phase was basified to pH 13 with NaOH, and washed with DCM (3×200 mL). The combined DCM extracts were discarded. The aqueous phase was neutralized to pH 7 with HCl, and extracted with DCM (3×200 mL). The organic phase from this last extraction, containing the product, was dried over $Na_2SO_4$, and the solvent was removed under vacuum, affording 9.8 g (26%) of 1-ethyl-5-methyl-1H-[1,2,4]triazole-3-carbaldehyde which was 96% pure by NMR. $^1$H NMR (500 MHz, $CDCl_3$): δ 1.49 (t, J=7.5 Hz, 3H), 2.51 (s, 3H), 4.20 (q, J=7.5 Hz, 2H), 9.91 (s, 1H). $^{13}$C NMR (125 MHz, $CDCl_3$): δ 12.1, 14.9, 44.4, 154.0, 159.2, 184.0. LC-MS (APCI) calcd for $C_6H_9N_3O$: 139.07, found (M+H$^+$): 140.1 m/z. Anal calcd for $C_6H_9N_3O$: C, 51.79; H, 6.52; N, 30.20. Found: C, 51.5; H, 6.38; N, 29.98.

Example B(51)

2-{4-[2-(2-Cyclopentyl-5-{[3-difluoromethyl)-5-(dimethylamino)-1-methyl-1H-pyrazol-4-yl]methyl}-4-hydroxy-6-oxo-3,6-dihydro-2H-pyran-2-yl)ethyl]-2-fluorophenyl}-2-methylpropanenitrile

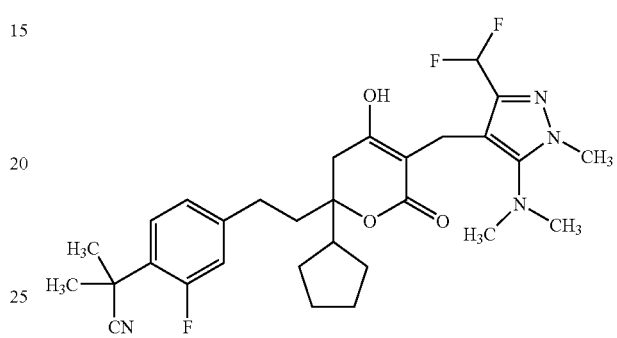

The title compound was prepared analogously to example B(43) where 3-(difluoromethyl)-5-(dimethylamino)-1-methyl-1H-pyrazole-4-carbaldehyde (step 3, below) was substituted in place of 1-methyl-3-(6-methylpyridin-2-yl)-1H-1,2,4-triazole-5-carbaldehyde, and the triethylamine was omitted. Yield: 142 mg (9%). $^1$H NMR (400 MHz, DMSO-$d_6$): δ 1.31-1.63 (m, 8 H), 1.70 (s, 6 H), 1.89 (m, 2H), 2.32 (m, 1 H), 2.57 (m, 3 H), 2.67 (m, 2 H), 2.74 (s, 6 H), 3.40 (d, J=15.1 Hz, 1 H), 3.44 (d, J=15.1 Hz, 1 H), 3.61 (s, 3 H), 6.98 (d, J=9.3 Hz, 1 H), 7.06 (d, J=13.1 Hz, 1 H), 7.34 (t, J=8.3 Hz, 1H), 10.92 (s, 1 H). LC-MS (APCI) calcd for $C_{30}H_{37}F_3N_4O_3$: 558.28, found (M+H$^+$): 559.30 m/z.

Step 1:
3-(Difluoromethyl)-1-methyl-1H-pyrazol-5-ol

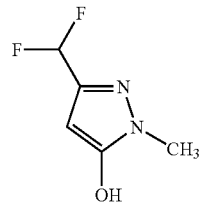

To a solution of methyl 4,4-difluoro-3-oxobutanoate (64 g, 0.38 mol) in methanol (500 mL) was added methylhydrazine (20.5 mL, 0.38 mol). The reaction mixture was left to stir overnight at room temperature. The volatiles were removed in vacuo, toluene was added (400 mL), the mixture was evaporated again, and this procedure was repeated. The resulting solid residue was purified chromatographically on silica gel using ethyl acetate/dichloromethane mixture (1:2, $R_f$=0.35). The resulting oil was crystallized from ether (200 mL) and dried under the vacuum of a membrane pump (10 mm Hg) for 3 h to give 28 g (49.8%) of the title product.

Step 2: 5-Chloro-3-(difluoromethyl)-1-methyl-1H-pyrazole-4-carbaldehyde

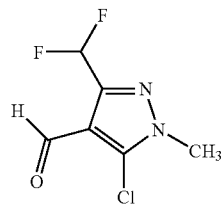

To DMF (40.84 g, 0.56 mol) was added POCl₃ (104.4 mL, 1.12 mol) at 0° C. After 30 min, to the resulting Vilsmier reagent was added 3-(difluoromethyl)-1-methyl-1H-pyrazol-5-ol from step 1 above (69.1 g, 0.46 mol), and the mixture was heated at 80° C. for 16 h. Then reaction was diluted with dichloromethane (400 mL), and treated with a solution of potassium carbonate (780 g) in water (2 L) at 0° C. The organic layer was separated, and the aqueous layer extracted with dichloromethane (3×100 mL). The combined organic extracts were washed with water (500 mL), passed through a layer of silica gel (10×10 cm), and evaporated. The residue was crystallized from ether (100 mL) and hexane (100 mL) to give 69 g (77%) of the title product.

Step 3: 3-(Difluoromethyl)-5-(dimethylamino)-1-methyl-1H-pyrazole-4-carbaldehyde

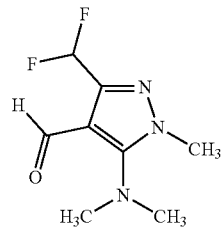

To mixture of 5-chloro-3-(difluoromethyl)-1-methyl-1H-pyrazole-4-carbaldehyde (34 g, 0.17 mol) and HMPA (50 mL) was added a 40% aqueous solution of dimethylamine (66.3 mL). The reaction mixture was stirred for at 50° C. for 12 h, diluted with water (1 L), and the product was extracted with dichloromethane (2×100 mL). The combined organic layers were dried with sodium sulfate and evaporated. The liquid residue was purified chromatographically on silica gel using dichloromethane/ethyl acetate as eluent (1:3, $R_f$=0.25) to give 17.81 g (51.6%) of the title product. Satisfactory C,H,N-analysis was obtained. ¹H NMR (400 MHz, DMSO-d₆): δ 2.93 (s, 6H), 3.72 (s, 6H), 7.07 (t, J=56 Hz, 1H), 9.94 (s, 1H). GC-MS calcd for $C_8H_{11}F_2N_3O$: 203.09, found (M⁺): 203 m/z.

Example B(52)

6-[2-(5-Chloro-2,4-dimethoxyphenyl)ethyl]-6-cyclopentyl-3-[(1,3-dimethyl-5-morpholin-4-yl-1H-pyrazol-4-yl)methyl]-4-hydroxy-5,6-dihydro-2H-pyran-2-one

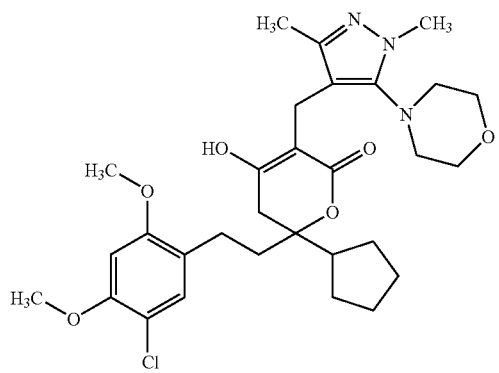

The title compound was prepared analogously to example B(15) using 1,3-dimethyl-5-morpholin-4-yl-1H-pyrazole-4-carbaldehyde in place of 2-methyl-5-pyrazin-2-yl-2H-[1,2,4]triazole-3-carbaldehyde dihydrochloride monohydrate, and omitting the triethylamine. The yield obtained on a 0.78-mmoL scale, was 34 mg (7%). ¹H NMR (400 MHz, CDCl₃): δ 1.18-1.83 (m, 8 H), 2.19 (s, 3 H), 2.28 (m, 1 H), 2.47 (m, 3 H), 2.68 (m, 1 H), 3.07 (m, 2 H), 3.21 (s, 3 H), 3.36 (s, 2 H), 3.69-3.81 (m, 14 H), 6.38 (s, 1 H), 6.94 (s, 1 H). LC-MS (APCI) calcd for $C_{30}H_{40}ClN_3O_6$: 573.26, found (M+H⁺): 574.20, 576.20 m/z.

Example B(53)

Enantiomer 1 of 2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-methylpropanenitrile Enantiomer 1

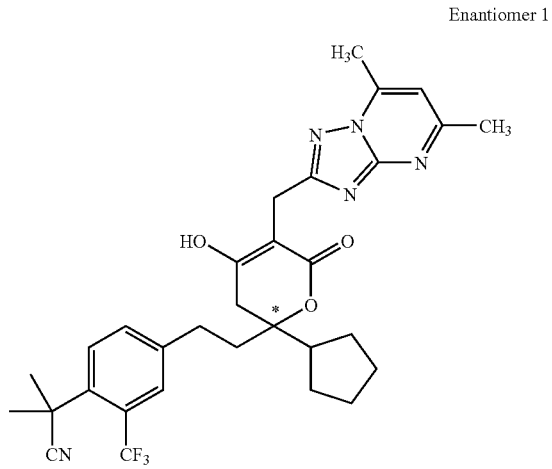

305

The title compound was separated from racemic 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-methylpropanenitrile (338 mg, Example B(28)) using chiral HPLC (Chiralpak AS-H, 140 bar, 50% MeOH). (151.32 mg, 1.84 min retention time, 100% ee).

Example B(54)

Enantiomer 2 of 2-[4-(2-{2-Cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-methylpropanenitrile Enantiomer 2

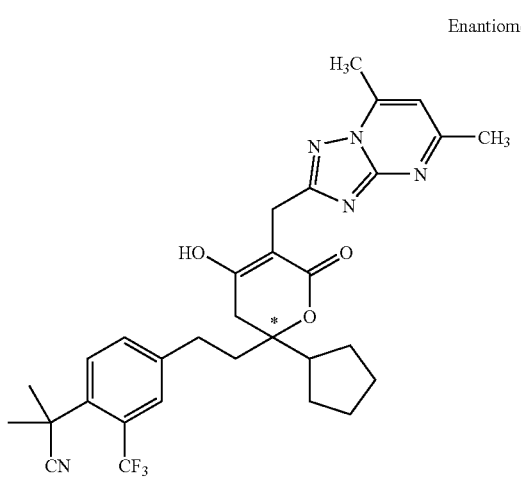

The title compound was separated from racemic 2-[4-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-(trifluoromethyl)phenyl]-2-methylpropanenitrile (338 mg, Example B(28)) using chiral HPLC (Chiralpak AS-H, 140 bar, 50% MeOH). (239.86 mg, 4.94 min retention time, 100% ee).

306

Example B(55)

Enantiomer 1 of 2-[3-Chloro-5-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2-yl]-2-methylpropanenitrile Enantiomer 1

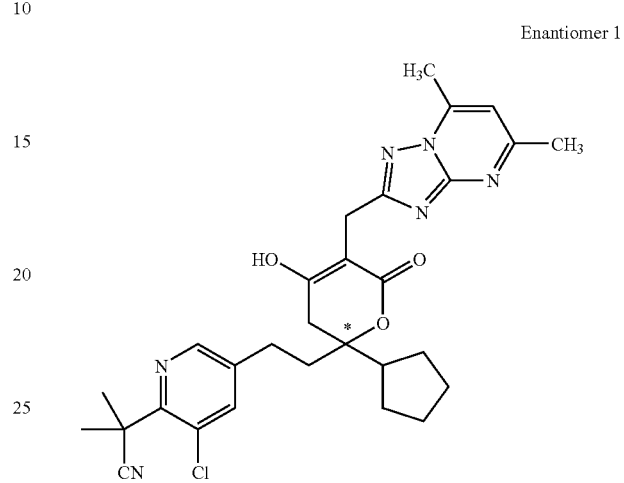

The title compound was separated from racemic 2-[3-chloro-5-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2-yl]-2-methylpropanenitrile (75 mg, Example B(39)) using chiral HPLC (Chiralpak AS-H, 140 bar, 55% MeOH). (11.37 mg, 1.93 min retention time, 91% ee).

Example B(56)

Enantiomer 2 of 2-[3-Chloro-5-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2-yl]-2-methylpropanenitrile Enantiomer 2

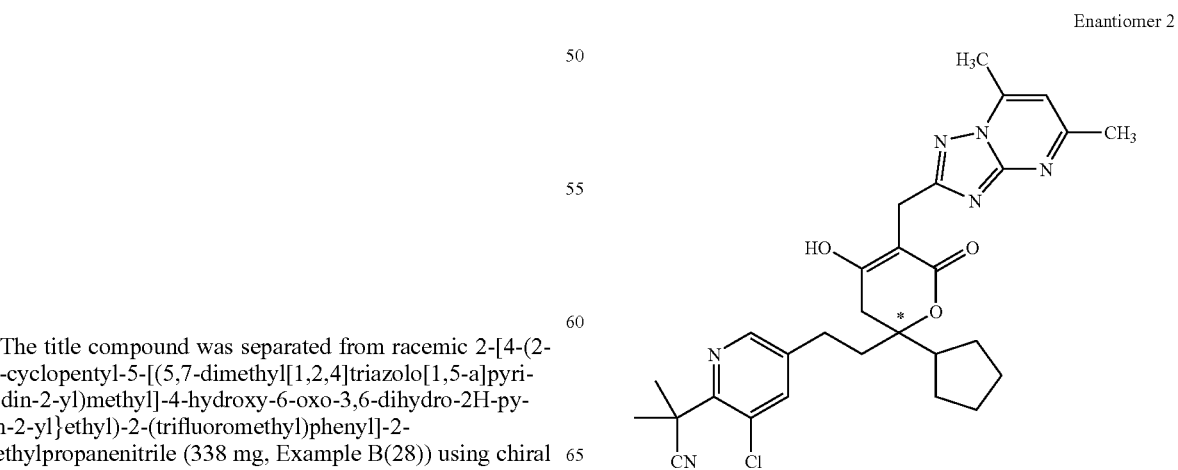

The title compound was separated from racemic 2-[3-chloro-5-(2-{2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)pyridin-2-yl]-2-methylpropanenitrile (75 mg, Example B(39)) using chiral HPLC (Chiralpak AS-H, 140 bar, 55% MeOH). (9.59 mg, 4.32 min retention time, 96% ee).

Example B(57)

2-(4-{2-[2-Cyclopentyl-4-hydroxy-5-({5-[(2-methoxyethyl)(methyl)amino]-1,3-dimethyl-1H-pyrazol-4-yl}methyl)-6-oxo-3,6-dihydro-2H-pyran-2-yl]ethyl}-2-fluorophenyl)-2-methylpropanenitrile

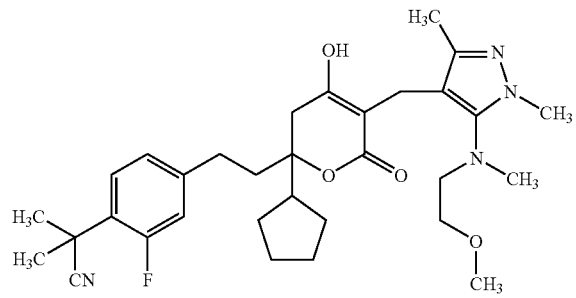

The title compound was prepared analogously to example B(43) where 5-[(2-methoxyethyl)(methyl)amino]-1,3-dimethyl-1H-pyrazole-4-carbaldehyde (step 1, below) was substituted in place of 1-methyl-3-(6-methylpyridin-2-yl)-1H-1,2,4-triazole-5-carbaldehyde, and the triethylamine was omitted. Yield: 132 mg (8%). $^1$H NMR (400 MHz, DMSO-$d_6$): δ 1.31-1.70 (m, 14H), 1.90 (m, 2 H), 1.95 (s, 3 H), 2.32 (m, 1 H), 2.57 (m, 3 H), 2.67 (d, J=17.6 Hz, 1 H), 2.72 (s, 3 H), 3.14 (m, 2 H), 3.21 (s, 3 H), 3.25 (d, J=5.5 Hz, 1 H), 3.31 (m, 3 H), 3.49 (s, 3 H), 6.99 (dd, J=8.2, 1.5 Hz, 1 H), 7.09 (dd, J=13.1, 1.5 Hz, 1 H), 7.35 (t, J=8.4 Hz, 1 H), 10.67 (s, 1 H). LC-MS (APCI) calcd for $C_{32}H_{43}FN_4O_4$: 566.71, found (M+H$^+$): 567.40 m/z.

Step 1: 5-[(2-Methoxyethyl)(methyl)amino]-1,3-dimethyl-1H-pyrazole-4-carbaldehyde

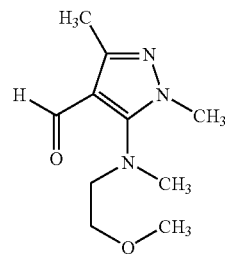

A mixture of 2-(methoxyethyl)methylamine (32.93 g, 40 mL, 0.37 mol), 5-chloro-1,3-dimethyl-1H-pyrazole-4-carbaldehyde (step 2 of example B(45)) (29.28 g, 0.185 mol), HMPA (25 mL) and water (25 mL) was heated at 120-125° C. for 17 h. The reaction mixture was poured into water (500 mL), and the resulting mixture basified with potassium carbonate. The mixture was extracted with ethyl acetate (5×100 mL). The combined organic extracts were washed twice with water, dried with sodium sulfate, filtered, and the solvent removed in vacuo. The residue was purified chromatographically on silica gel using hexane/ethyl acetate mixture as eluent, affording 35.35 g (90%) of the title product. $^1$H NMR (400 MHz, DMSO-$d_6$): δ 2.27 (s, 3H), 2.87 (s, 3H), 3.20 (s, 3H), 3.26 (m, 2H), 3.39 (m, 2H), 3.59 (s, 3H), 9.82 (s, 1H). GC-MS (API-ES) calcd for $C_{10}H_{17}N_3O_2$: 211.13, found (M+H$^+$): 212.1 m/z.

Example B(58)

2-{4-[2-(2-Cyclopentyl-5-{[1-(2-fluoroethyl)-3,5-dimethyl-1H-pyrazol-4-yl]methyl}-4-hydroxy-6-oxo-3,6-dihydro-2H-pyran-2-yl)ethyl]-2-fluorophenyl}-2-methylpropanenitrile

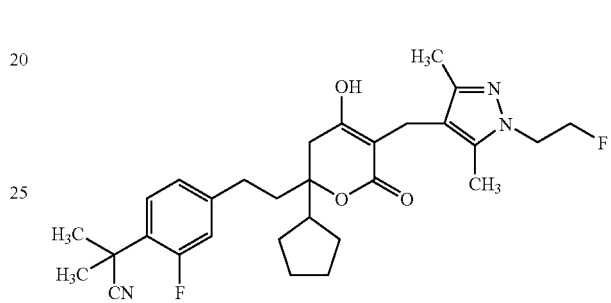

The title compound was prepared analogously to example B(43) where 1-(2-fluoroethyl)-3,5-dimethyl-1H-pyrazole-4-carbaldehyde (Step 2, below) was substituted in place of 1-methyl-3-(6-methylpyridin-2-yl)-1H-1,2,4-triazole-5-carbaldehyde, and the triethylamine was omitted. The product was purified by silica gel chromatography on a Biotage system. Yield: 843 mg (59%). $^1$H NMR (400 MHz, DMSO-$d_6$): δ 1.30-1.62 (m, 8H), 1.70 (s, 6H), 1.84 (m, 2H), 2.05 (s, 3H), 2.13 (s, 3H), 2.27 (m, 1H), 2.54 (m, 3H), 2.68 (d, J=19.8 Hz, 1 H), 3.14 (d, J=14.3 Hz, 1 H), 3.23 (d, J=14.3 Hz, 1 H), 4.15 (d, J=27.4 Hz, 2 H), 4.61 (d, J=47.3 Hz, 2 H), 6.94 (d, J=8.0, Hz, 1 H), 7.05 (d, J=11.5 Hz, 1 H), 7.34 (t, J=8.0 Hz, 1 H), 10.67 (s, 1 H). LC-MS (APCI) calcd for $C_{30}H_{37}F_2N_3O_3$: 525.28, found (M+H$^+$): 526.30 m/z.

Step 1: 1-(2-Fluoroethyl)-3,5-dimethyl-1H-pyrazole

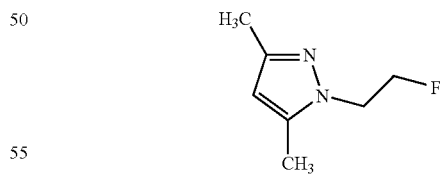

To a suspension of sodium hydride (1.37 mol, (60% in oil) in DMF (350 mL) was added 3,5-dimethyl-1H-pyrazole (120 g, 1.25 mol). After this, the reaction mixture was stirred for 1 h at room temperature and treated with 1-bromo-2-fluoroethane (175 g, 1.37 mol) in DMF (200 mL). The reaction mixture was left to stir overnight, diluted with water (2 L), and the product was extracted with ethyl acetate (3×300 mL). The combined organic extracts were washed with water (1 L), dried with sodium sulfate, and evaporated. The liquid residue (120 g) was chromatographed on a "Biotage" apparatus with Step 2: 1-(2-Fluoroethyl)-3,5-dimethyl-1H-pyrazole-4-carbaldehyde

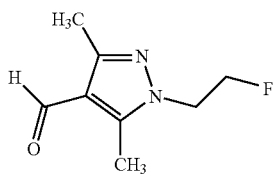

To DMF (56 g, 0.75 mol) was added POCl₃ (74.55 mL, 0.8 mol) at 0° C. After 30 minutes, to the formed Vilsmaier reagent was added 1-(2-fluoroethyl)-3,5-dimethyl-1H-pyrazole (88 g, 0.62 mol), and the reaction mixture was heated for 16 h at 80° C. The reaction mixture was diluted with dichloromethane (400 mL) and treated with potassium carbonate (600 g) in water (2 L) at 0° C. The organic layer was separated, passed through silica gel (10×10 cm), and evaporated. The liquid residue was crystallized from a mixture of hexane (100 mL) and ether (200 mL), separated by filtration, and dried in vacuo using an oil pump to give 26.3 g (24.9%) of the title product. Satisfactory C,H,N-analysis was obtained. $^1$H NMR (400 MHz, DMSO-$d_6$): δ 2.33 (s, 3H), 2.48 (s, 3H), 4.36 (dt, J=28 Hz, J=5 Hz, 2H), 4.74 (dt, J=44 Hz, J=5 Hz, 2H), 9.85 (s, 1H). GC-MS calcd for $C_8H_{11}FN_2O$: 170.09, found (M⁺): 170 m/z.

Example B(59)

2-{4-[2-(2-Cyclopentyl-5-{[3-(difluoromethyl)-1-methyl-1H-1,2,4-triazol-5-yl]methyl}-4-hydroxy-6-oxo-3,6-dihydro-2H-pyran-2-yl)ethyl]-2-fluorophenyl}-2-methylpropanenitrile

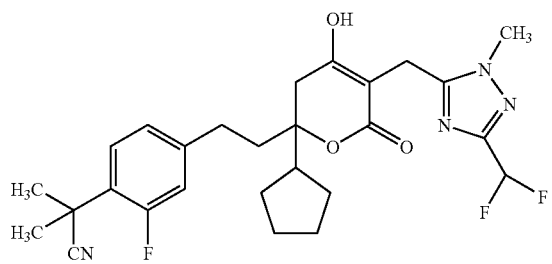

The title compound was prepared analogously to example B(43) where 3-(difluoromethyl)-1-methyl-1H-1,2,4-triazole-5-carbaldehyde (Step 3, below) was substituted in place of 1-methyl-3-(6-methylpyridin-2-yl)-1H-1,2,4-triazole-5-carbaldehyde, and the triethylamine was omitted. The product was purified by silica gel chromatography on a Biotage system. Yield: 335 mg (24%). $^1$H NMR (400 MHz, DMSO-$d_6$): δ 1.30-1.70 (m, 14 H), 1.91 (m, 2 H), 2.27 (m, 1 H), 2.65 (m, 4H), 3.62 (m, 2 H), 3.85 (s, 3 H), 5.70 (t, J=28 Hz, 1 H), 6.99-7.08 (m, 2 H), 7.33 (t, J=8.3 Hz, 1 H). LC-MS (APCI) calcd for $C_{27}H_{31}F_3N_4O_3$: 516.23, found (M+H⁺): 517.30 m/z.

Step 1: 2,2-Difluoro-N'-methylethanehydrazonamide Hydrochloride

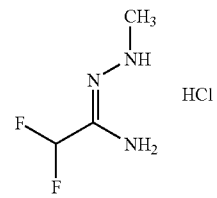

A stream of dry ammonia was passed through a solution of difluoroacetyl chloride (157 g, 1.37 mol) in ether (1.7 L) cooled to −5° C. in order to obtain an alkaline media. The reaction mixture was then filtered through a 4-cm silica gel layer, eluting with ether (~2.5 L). The ether was evaporated, affording to give 111.4 g (85.5%) of 2,2-difluoroacetamide as a crystalline solid. The 2,2-difluoroacetamide (111.4 g, 1.172 mol) was mixed under ice cooling with phosphorus pentoxide (183 g, 1.289 mol) in a 2-L flask. The flask was equipped with a reflux condenser and heated to 195° C. on an oil bath, in a using a trap cooled with dry ice/acetone mixture to collect 82.8 g (1.075 mol, 91.7%) of 2,2-difluoroacetonitrile. The resulting 2,2-difluoroacetonitrile was cooled to −78° C. and added to a solution of methanol (44.5 mL, 1.1 mol) in ether (400 mL) cooled to −78° C. The mixture was slowly added under stirring to a solution of HCl (1.183 mol) in ether cooled with dry ice/acetone and the mixture kept at −78° C. for 2 h, then at −20° C. for 24 h, and after that at 0° C. for 24 h. The precipitated crystals were separated by filtration, washed with ether (2×500 mL) and vacuum-dried to give 93.5 g (59.8%) of methyl 2,2-difluoroethanimidoate hydrochloride. Methylhydrazine (34.5 mL, 0.649 mol) was added under an atmosphere of Ar to a solution of methyl 2,2-difluoroethanimidoate hydrochloride (93.5 g, 0.6425 mol) in methanol (300 mL), and the mixture was stirred at room temperature for 4 days. The reaction mixture was then diluted with ethyl acetate, causing a partial crystallization of a hydrochloride salt. The crystals (12 g) were separated by filtration, and the mother liquors evaporated to give an additional quantity of product. The combined yield of crude 2,2-difluoro-N'-methylethanehydrazonamide hydrochloride was 104.9 g (0.6208 mol, 96.6%) yield. The compound was found to be 83% area % pure by LC/MS and was used without further purification.

Step 2: 5-(Diethoxymethyl)-3-(difluoromethyl)-1-methyl-1H-1,2,4-triazole

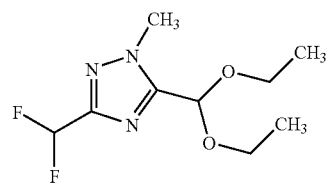

A solution of diethoxyacetonitrile (75 g, 0.579 mol) in methanol (210 mL) was added at room temperature to a solution of sodium methoxide (28.3 g, 0.522 mol) in methanol (450 mL). The mixture was stirred overnight, and then methanol was evaporated. The residue was diluted with dichloromethane (200 mL) and water (300 mL). The organic layer was separated, and the aqueous one was extracted with dichloromethane (2×150 mL). The combined organic layer was dried over $Na_2SO_4$ and evaporated to give 83 g of crude methyl 2,2-diethoxyacetimidate (~90% yield). A solution of methyl 2,2-diethoxyacetimidate prepared above (0.6208 mol, 125.1 g of 80% purity) in methanol (300 mL) was added to a solution of 2,2-difluoro-N'-methylethanehydrazonamide hydrochloride (0.6208 mol, obtained in Step 1) in methanol (700 mL). Anhydrous sodium acetate (61.1 g, 0.745 mol) was added, and the mixture was stirred at 30° C. for 3 days. The reaction mixture was then evaporated, and the residue subjected to chromatography (ethyl acetate/hexane 1:4→1:1) on a silica gel column, followed by vacuum distillation to give 47.6 g (32.6%) of 5-(diethoxymethyl)-3-(difluoromethyl)-1-methyl-1H-1,2,4-triazole.

Step 3: 3-(Difluoromethyl)-1-methyl-1H-1,2,4-triazole-5-carbaldehyde

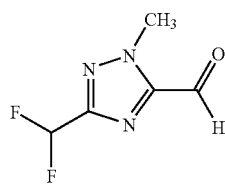

Water (190 mL) was added to 5-(diethoxymethyl)-3-(difluoromethyl)-1-methyl-1H-1,2,4-triazole (47.6 g, 0.2024 mol, from Step 2), and the mixture was degassed. Then concentrated HCl (73 mL, 0.81 mol, 11.1 M) was added, and the mixture was stirred at 55-60° C. for 24 h. After this, the reaction mixture was evaporated, and the residue was repeatedly (8-10 times) evaporated with THF until the water and HCl were completely removed. The final residue was distilled under vacuum to give the crude title product (bp 46-50° C. at 0.04 mm Hg), containing, according to LC-MS data, 7% of a dimerization side-product. Further purification on a silica gel (ethyl acetate/hexane 1:3) yielded 18.37 g (56.3%) of 3-(difluoromethyl)-1-methyl-1H-1,2,4-triazole-5-carbaldehyde. Satisfactory C,H,N-analysis was obtained. $^1$H NMR (400 MHz, $CDCl_3$): δ 4.25 (s, 3H), 6.74 (t, J=56 Hz, 1H), 10.01 (s, 1H). LC/MS (API-ES) calcd for $C_5H_5F_2N_3O$: 161.04, found (M+H$^+$): 162.1; (M+18+H$^+$): 180.1 m/z.

Example B(60)

2-{4-[2-(2-Cyclopentyl-5-{[3-(3-fluorophenyl)-1-methyl-1H-1,2,4-triazol-5-yl]methyl}-4-hydroxy-6-oxo-3,6-dihydro-2H-pyran-2-yl)ethyl]-2-fluorophenyl}-2-methylpropanenitrile

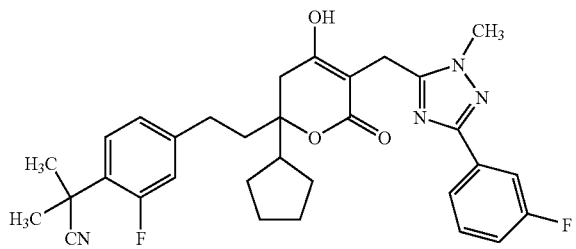

The title compound was prepared analogously to example B(43) where 3-(3-fluorophenyl)-1-methyl-1H-1,2,4-triazole-5-carbaldehyde hydrochloride dehydrate (Step 2, below) was substituted in place of 1-methyl-3-(6-methylpyridin-2-yl)-1H-1,2,4-triazole-5-carbaldehyde. The product was purified by silica gel chromatography on a Biotage system. Yield: 260 mg (17%). $^1$H NMR (400 MHz, DMSO-$d_6$): δ 1.38-1.70 (m, 14 H), 2.04 (m, 2 H), 2.42 (m, 1 H), 2.63 (m, 3 H), 2.75 (d, J=19.8 Hz, 1H), 3.65 (d, J=15.8 Hz, 1 H), 3.74 (d, J=15.8 Hz, 1 H), 3.89 (s, 3 H), 6.99 (d, J=7.8 Hz, 1 H), 7.09-7.20 (m, 3 H), 7.35 (m, 1 H), 7.48 (d, J=9.8 Hz, 1 H), 7.64 (d, J=8.1 Hz, 1 H), 11.18 (s, 1 H). LC-MS (APCI) calcd for $C_{32}H_{34}F_2N_4O_3$: 560.26, found (M+H$^+$): 561.30 m/z.

Step 1: 5-(Diethoxymethyl)-3-(3-fluorophenyl)-1-methyl-1H-1,2,4-triazole

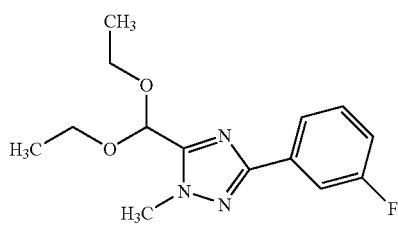

MeONa (2.35 g, 41 mmol) was added to a stirred solution of 3-fluorobenzonitrile (50.0 g, 413 mmol) in methanol (300 mL). The mixture was stirred at room temperature for 3 days and concentrated in vacuo. The residue was dissolved in ether (300 mL), washed with water (2×150 mL), brine (150 mL), dried with $Na_2SO_4$, and concentrated in vacuo to afford 62.8 g (99%) of methyl 3-fluorobenzenecarboximidoate. Methylhydrazine (21.8 mL, 410n mmol) was added to a stirred solution of methyl 3-fluorobenzenecarboximidoate (62.8 g, 410 mmol) in THF (350 mL). The mixture was stirred at room temperature for 3 days, then. Then methyl 2,2-diethoxyethanimidoate (66.1 g, 410 mmol) and acetic acid (37.5 mL, 656 mmol) were added. The mixture was stirred for 24 h. The reaction was diluted with $CH_2Cl_2$ (500 mL), and the formed precipitate was filtered off. The filtrate was washed with 10% citric acid (2×200 mL), water (300 mL), brine (200 mL), dried with Na₂SO₄, and concentrated in vacuo. The residue was subjected to flash chromatography on silica gel using 1% MeOH/CHCl₃ as eluent to give 24.0 g (21%) of the title product.

Step 2: 3-(3-Fluorophenyl)-1-methyl-1H-1,2,4-triazole-5-carbaldehyde hydrochloride dihydrate

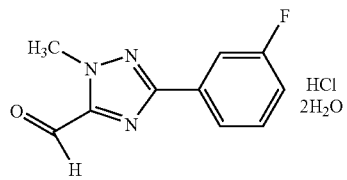

A solution of 5-(diethoxymethyl)-3-(3-fluorophenyl)-1-methyl-1H-1,2,4-triazole (24.0 g, 86 mmol) in 4M HCl (86 mL) was stirred at 60° C. for 2 h. The mixture was concentrated in vacuo, and the residue was recrystallized from MeOH/Et₂O mixture (1:1). The resulting solvate was dissolved in water/THF (1:2) and concentrated in vacuo to dryness to afford 11.33 g (47%) of the title product. Satisfactory C,H,N-analysis was obtained. ¹H NMR (400 MHz, D₂O+TFA): δ 4.16 (s, 3H), 6.47 (s, 1H), 7.42 (m, 1H), 7.62 (m, 1H), 7.70 (m, 1H), 7.77 (m, 1H). LC/MS (API-ES) calcd for C₁₀H₈FN₃O: 205.07, found (M+H⁺): 206.0; (M+18+H⁺): 224.0 m/z.

Example B(61)

2-{4-[2-(2-Cyclopentyl-4-hydroxy-5-{[1-methyl-5-(1-methyl-1H-pyrazol-5-yl)-1H-1,2,4-triazol-3-yl]methyl}-6-oxo-3,6-dihydro-2H-pyran-2-yl)ethyl]-2-fluorophenyl}-2-methylpropanenitrile

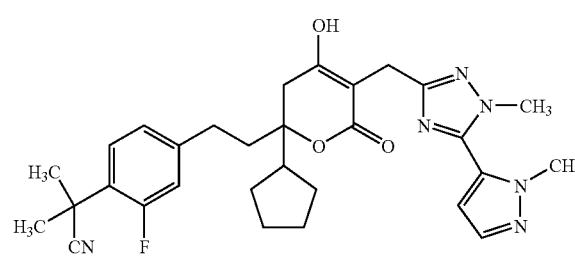

The title compound was prepared analogously to example B(43) where 1-methyl-5-(1-methyl-1H-pyrazol-5-yl)-1H-1,2,4-triazole-3-carbaldehyde (Step 3, below) was substituted in place of 1-methyl-3-(6-methylpyridin-2-yl)-1H-1,2,4-triazole-5-carbaldehyde, and the triethylamine omitted. The product was purified by silica gel chromatography on a Biotage system. Yield: 67 mg (4%). ¹H NMR (400 MHz, DMSO-d₆): δ 1.36-1.70 (m, 14 H), 2.07 (m, 2 H), 2.34 (m, 2 H), 2.63 (m, 3 H), 3.46-3.57 (m, 2 H), 3.74 (s, 3 H), 3.84 (s, 3 H), 6.76 (s, 1 H), 7.01-7.22 (m, 3 H), 7.59 (s, 1 H). LC-MS (APCI) calcd for C₃₀H₃₅FN₆O₃: 546.28, found (M+H⁺): 547.30 m/z.

Step 1: 1-Methyl-1H-pyrazole-5-carbonyl chloride

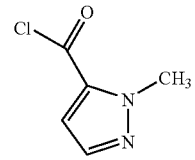

To a stirred solution of 1-methyl-1H-pyrazole (77.0 g 0.916 mol) in absolute ether (960 mL) under an atmosphere of argon was added a 1.6 M solution of n-BuLi in hexane (600 mL, 0.96 mol) dropwise at −40° C. over a period of 2 h. The reaction mixture was stirred at this temperature for a further 1 h, then siphoned into a mixture of solid carbon dioxide with ether. After heating to room temperature, the resulting mass was treated with water (1.5 L), the aqueous layer was separated, washed with ether (500 mL), concentrated to half volume under reduced pressure on a rotary evaporator, cooled to 2-3° C., and acidified while stirring with concentrated HCl to pH=3. The resulting precipitate was separated by filtration, washed with ice-cold water (25 mL), dried first in open air, and then in a vacuum desiccator over P₂O₅ to give 86.5 g (76%) of 1-methyl-1H-pyrazole-5-carboxylic acid as a white powder. To thionyl chloride (650 mL) was added 1-methyl-1H-pyrazole-5-carboxylic acid (86.5 g, 0.67 mol) in portions over a 35 min period, such that each portion was consumed before addition of the next. After this, the reaction mixture was refluxed for 4.5 h. The excess thionyl chloride was removed under vacuum at a bath temperature below 35° C. The residue was subjected to vacuum fractional distillation through a 15-cm Vigreux column. A fraction boiling at 71-72° C. at 15-16 mm Hg was collected to obtain the title product (49.0 g, 51%) as a colorless liquid.

Step 2: 3-(Diethoxymethyl)-1-methyl-5-(1-methyl-1H-pyrazol-5-yl)-1H-1,2,4-triazole

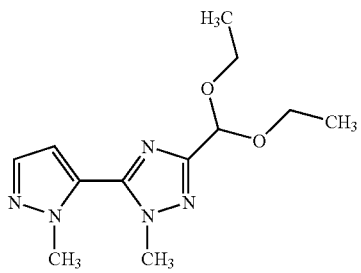

To a stirred solution of diethoxyacetonitrile (60 g, 0.465 mol) in absolute methanol (150 mL) under an atmosphere of argon was added a solution of sodium methylate (2.5 g; 0.047 mol) in absolute methanol (20 mL), and the reaction mixture was stirred at room temperature until the nitrile disappeared completely (70-75 h). The reaction was monitored by ¹H NMR. The reaction mixture was treated, while stirring, with CO₂ until the precipitate of sodium carbonate ceased to form. The latter was filtered off and washed with methanol (50 mL).

The filtrate was evaporated under on a rotary evaporator at a bath temperature less than 30° C. The resulting liquid was dissolved in ether (250 mL), filtered to remove the remaining inorganic salts, and evaporated again to give the crude methyl 2,2-diethoxyethanimidoate (71.0 g, 95%). It was distilled under vacuum through a 15-cm Vigreux column, affording 56.2 g (75%) of methyl 2,2-diethoxyethanimidoate (bp. 77-78° C. at 20-22 mm Hg) with a purity of more than 95% by $^1$H NMR. To a solution of the methyl 2,2-diethoxyethanimidoate (52.1 g, 0.321 mol) and triethylamine (49 mL, 0.353 mol) in absolute THF (300 mL) was added a solution of 1-methyl-1H-pyrazole-5-carbonyl Chloride (46.5 g, 0.321 mol, from Step 1) in absolute THF (150 mL) dropwise under an atmosphere of argon at 0-5° C. over a period of 2 h. The reaction mixture was stirred overnight at a room temperature. The residue the formed was filtered off, and the filtrate was evaporated on a rotary evaporator to give methyl (1Z)-2,2-Diethoxy-N-[(1-methyl-1H-pyrazol-5-yl)carbonyl]ethanimidoate (90 g) as a yellow viscous mass, which was used at the next stage without additional purification. The 90 g of the crude product N-acylated imidate ester obtained at the previous stage was dissolved in absolute dichloromethane (450 mL), and treated with methylhydrazine (17.1 mL, 0.321 mol) with stirring over a period of 10 min. The reaction mixture was stirred at room temperature for 3 h, washed with water (3×300 mL), and dried with anhydrous sodium sulfate. The solvent was removed under vacuum on a rotary evaporator, and the residue (56.5 g) was purified chromatographically on silica gel using hexane/ethyl acetate (1:2) as the eluent. The solvent was evaporated to give 40.1 g (47% based on 1-methyl-1H-pyrazole-5-carbonyl chloride) of the pure title product.

Step 3: 1-Methyl-5-(1-methyl-1H-pyrazol-5-yl)-1H-1,2,4-triazole-3-carbaldehyde

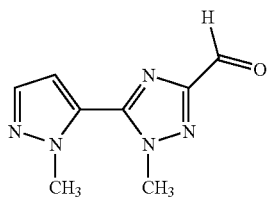

To a 4 N solution of HCl (185 mL, 0.74 mol) was added 3-(diethoxymethyl)-1-methyl-5-(1-methyl-1H-pyrazol-5-yl)-1H-1,2,4-triazole (40.1 g, 0.151 mol), and the reaction mixture was left to stir overnight. To the resulting mixture was added potassium carbonate (166 g) in portions under vigorous stirring, and the resulting mixture was extracted with ethyl acetate (5×300 mL). The organic layer was dried with anhydrous sodium sulfate, and the solvents were removed under vacuum on a rotary evaporator. To the residue was added absolute ether (4×100 mL) to give 27.3 g (94.5%) of the title product as a light-beige powder. Satisfactory C,H,N-analysis was obtained. $^1$H NMR (400 MHz, DMSO-d$_6$): δ 4.04 (s, 3H), 4.08 (s, 3H), 6.98 (d, J=2 Hz, 1H), 7.67 (d, J=2 Hz, 1H), 9.95 (s, 1H). LC/MS (API-ES) calcd for $C_8H_9N_5O$: 191.08, found (M+H$^+$): 192.0 m/z.

Example B(62)

2-[4-(2-{2-Cyclopentyl-5-[(5-cyclopropyl-1-methyl-1H-1,2,4-triazol-3-yl)methyl]-4-hydroxy-6-oxo-3,6-dihydro-2H-pyran-2-yl}ethyl)-2-fluorophenyl]-2-methylpropanenitrile

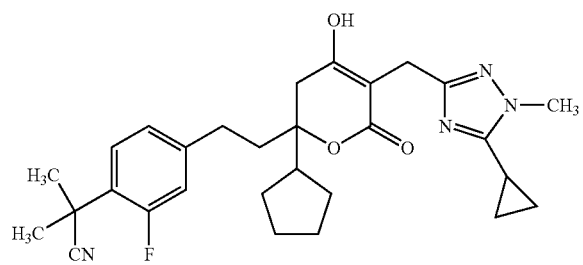

The title compound was prepared analogously to example B(43) where 5-cyclopropyl-1-methyl-1H-[1,2,4]triazole-3-carbaldehyde (Step 2, below) was substituted in place of 1-methyl-3-(6-methylpyridin-2-yl)-1H-1,2,4-triazole-5-carbaldehyde, and the triethylamine omitted. The product was purified by silica gel chromatography on a Biotage system. Yield: 326 mg (23%). $^1$H NMR (400 MHz, DMSO-d$_6$): δ 0.70 (m, 2 H), 0.90 (m, 2 H), 1.36-1.71 (m, 14 H), 1.97-2.12 (m, 3 H), 2.39 (m, 1 H), 2.52 (d, J=15.8 Hz, 1 H), 2.63 (m, 2 H), 2.72 (d, J=15.8 Hz, 1 H), 3.37 (d, J=15.8 Hz, 1 H), 3.47 (d, J=15.8 Hz, 1 H), 3.65 (s, 3 H), 7.10 (m, 2 H), 7.37 (t, J=8.3 Hz, 1 H), 10.70 (s, 1 H). LC-MS (APCI) calcd for $C_{29}H_{35}FN_4O_3$: 506.27, found (M+H$^+$): 507.30 m/z.

Step 1: 5-Cyclopropyl-3-diethoxymethyl-1-methyl-1H-[1,2,4]triazole

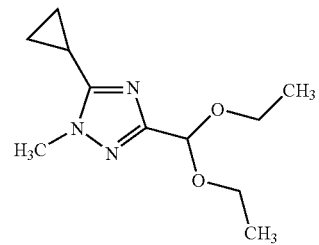

Cyclopropanecarbonitrile (100 g, 1.49 mol), methanol (59.7 g, 76 mL, 1.86 mol), and diethyl ether (184 mL) were charged to a 2 L three-necked flask. The mixture was cooled to −10° C. while stirring and HCl (g) (232 g, 6.36 mol) was then bubbled through the mixture solution such that the internal temperature was maintained below −5° C. Upon completion of gas addition, the mixture was stirred for 1.5 h at −10° C. Ether (685 mL) was added slowly over a 1-h period while continuing to maintain a the temperature below 0° C. The resulting solids were filtered and rinsed with diethyl ether (3×300 mL). The solids were further dried under vacuum, affording 181.5 g (89.8% yield) of methyl cyclopropanecarboximidoate hydrochloride. mp: 112-114° C.

In a 2 L three-neck flask, a solution of diethoxyacetonitrile (125 g, 968 mmol) in methanol (300 mL, anhydrous) was treated with a 25 wt % solution of sodium methoxide (21.0 g, 389 mmol) in methanol, producing a slightly exothermic reaction. After cooling, the mixture was stirred at room temperature for 15 h. Upon completion of the reaction, the solvent was slowly evaporated under vacuum. The remaining brown-colored residue was solvated with diethyl ether (1 L), then washed with water (3×500 mL), followed by brine (1×200 mL). The organic layer was dried using magnesium sulfate, the salts filtered, and the solvent evaporated carefully under vacuum to afford 132 g (85% yield) of methyl 2,2-diethoxyethanimidoate as a colorless liquid. Methyl 2,2-diethoxyethanimidoate (39.0 g, 242 mmol) was dissolved in tetrahydrofuran (345 mL), mixed with methylhydrazine (11.1 g, 242 mmol), then the mixture stirred at room temperature for 5 h, at which point LC/MS analysis confirmed the formation of the amidrazone intermediate. Methyl cyclopropanecarboximidoate hydrochloride (32.8 g, 242 mmol) was added to the reaction mixture, resulting in a suspension. Acetic acid (21.8 g, 363 mmol) was added slowly to the suspension, and the resulting exothermic reaction controlled with a cooling bath. After addition was completed, the reaction mixture was stirred at ambient temperature overnight. After LC/MS analysis indicated that the starting reactants had been consumed, the mixture was diluted with dichloromethane (500 mL) and stirred for 1 h. The solids were filtered and rinsed with dichloromethane (3×200 mL), and the filtrate concentrated in vacuo. The remaining oil was purified by column chromatography on silica gel (mobile phase: ethyl acetate, then with 1, 3, 5, 10% methanol, consecutively). The product-containing fractions were pooled and the solvent evaporated in vacuo. After further drying under high vacuum, 27.4 g of the title acetal was obtained as an oil containing 12.4 weight % of ethyl acetate as an impurity.

Step 2: 5-Cyclopropyl-1-methyl-1H-[1,2,4]triazole-3-carbaldehyde

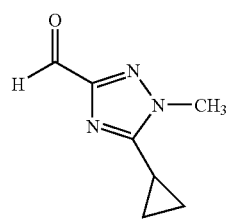

In a 2 L round-bottomed flask containing the crude 5-cyclopropyl-3-(diethoxymethyl)-1-methyl-1H-1,2,4-triazole from Step 2, a solution of 2 N HCl (125 mL) was added and the reaction was allowed to stir at room temperature for 23 h, at which point, LC/MS analysis confirmed the formation of the aldehyde. The mixture was then treated with solid sodium hydroxide until a pH of 13 was obtained. The aqueous mixture was extracted with dichloromethane (3×150 mL), and the combined organic layers dried over sodium sulfate, filtered and the solvent evaporated under vacuum. The crude material was distilled Kugel-Rhor distillation at 135° C.-146° C. to afford 11.4 g (61.9%) the title product as a yellow-colored oil. This material contained 4.8 wt % of the self-condensed side-product, 3,5-dicyclopropyl-1-methyl-1H-1,2,4-triazole, by $^1$H NMR. $^1$H NMR (300 MHz, DMSO-$d_6$): δ 0.96 (m, 2H), 1.10 (m, 2H), 2.22 (m, 1H), 4.00 (s, 3H), 9.78 (s, 1H). LC/MS (APCI) calcd for $C_7H_9N_3O$: 151.07, found (M+H$^+$): 152.1 m/z.

Example B(63)

2-{4-[2-(2-Cyclopentyl-5-{[1,3-dimethyl-5-(1,4-oxazepan-4-yl)-1H-pyrazol-4-yl]methyl}-4-hydroxy-6-oxo-3,6-dihydro-2H-pyran-2-yl)ethyl]-2-fluorophenyl}-2-methylpropanenitrile

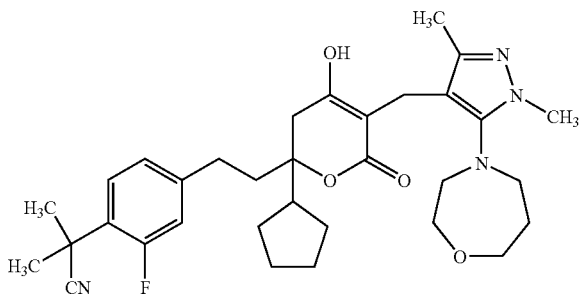

The title compound was prepared analogously to example B(43) where 1,3-dimethyl-5-(1,4-oxazepan-4-yl)-1H-pyrazole-4-carbaldehyde (step 1, below) was substituted in place of 1-methyl-3-(6-methylpyridin-2-yl)-1H-1,2,4-triazole-5-carbaldehyde, and the triethylamine omitted. The product was purified by silica gel chromatography on a Biotage system. Yield: 553 mg (35%). $^1$H NMR (400 MHz, DMSO-$d_6$): δ 1.32-1.64 (m, 8 H), 1.70 (s, 6 H), 1.82 (m, 2 H), 1.89 (m, 2 H), 1.94 (s, 3 H), 2.32 (m, 1 H), 2.57 (m, 3 H), 2.68 (d, J=17.6 Hz, 1 H), 3.17-3.27 (m, 6 H), 3.52 (s, 3 H), 3.64 (m, 2H), 3.78 (t, J=5.8 Hz, 2 H), 6.99 (d, J=8.1 Hz, 1 H), 7.08 (d, J=13.1 Hz, 1 H), 7.35 (t, J=8.6 Hz, 1 H), 10.69 (s, 1 H). LC-MS (APCI) calcd for $C_{33}H_{43}FN_4O_4$: 578.33, found (M+H$^+$): 579.40 m/z.

Step 2: 1,3-Dimethyl-5-(1,4-oxazepan-4-yl)-1H-pyrazole-4-carbaldehyde

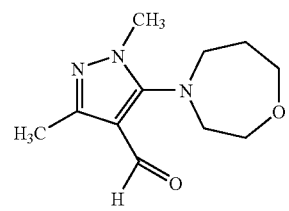

Homomorpholine hydrochloride (28.2 g, 200 mol) was added to a mixture of 5-chloro-1,3-dimethyl-1H-pyrazole-4-carbaldehyde (21.68 g, 0.1368 mol, Example B(45), Step 2), HMPA (30 mL), water (50 mL), and potassium carbonate (59 g, 0.6 mol) at constant stirring and room temperature. The reaction mixture was heated at 80° C. for 50 h, diluted with water, and extracted with ethyl acetate (3×100 mL). The organic extracts were washed with water to weakly alkaline pH and dried with sodium sulfate. The product was purified chromatographically using hexane/ethyl acetate mixture as eluent to afford the title product (18.7 g, 61%). Satisfactory C,H,N-analysis was obtained. $^1$H NMR (400 MHz, DMSO-$d_6$): δ 1.91 (m, 2H), 2.27 (s, 3H), 3.33 (m, 4H, overlap with H₂O peak), 3.62 (s, 3H), 3.72 (m, 2H), 3.81 (m, 2H), 9.83 (s, 1H). LC/MS (API-ES) calcd for C₁₁H₁₇N₃O₂: 223.13, found (M+H⁺): 224.1 m/z.

Example B(64)

6-Cyclopentyl-3-[(5,7-dimethyl[1,2,4]triazolo[1,5-a]pyrimidin-2-yl)methyl]-6-[2-(5-ethoxy-2-ethylpyridin-4-yl)ethyl]-4-hydroxy-5,6-dihydro-2H-pyran-2-one

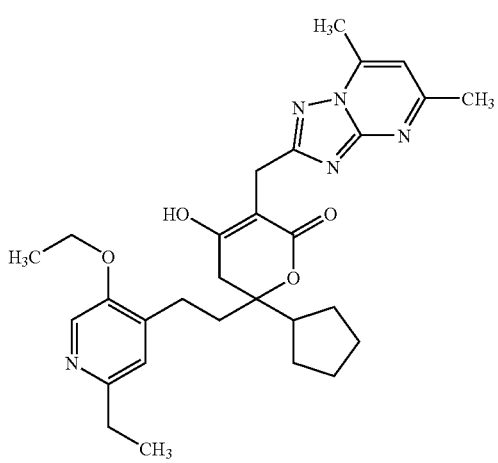

The title compound was prepared analogously to example A(1) where 6-cyclopentyl-6-[2-(5-ethoxy-2-ethylpyridin-4-yl)ethyl]dihydro-2H-pyran-2,4(3H)-dione from step 8 below was substituted in place of 6-cyclopentyl-6-[2-(5-ethyl-4-hydroxy-2-propoxy-phenyl)-ethyl]-dihydro-pyran-2,4-dione. ¹H NMR (400 MHz, DMSO-d₆) δ: 1.19 (t, J=7.6 Hz, 3 H), 1.31 (t, J=6.8 Hz, 3 H), 1.40-1.78 (br m, 8 H), 2.03-217 (m, 2 H), 2.48-2.72 (m, 12 H), 2.85 (d, J=17.4 Hz, 1 H), 3.76 (d, J=16.4 Hz, 1 H), 3.87 (d, J=16.2 Hz, 1 H), 4.08 (m, 2 H), 7.09 (m, 2 H), 8.13 (s, 1 H), 10.96 (s, 1 H). MS (ESI): 520.20 (M+H)⁺

Step 1: (6-Chloro-pyridin-3-yl)-carbamic acid tert-butyl ester

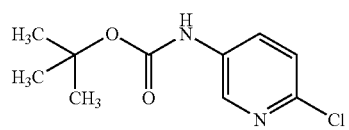

Di-tert-butyldicarbonate (41 g, 0.19 mol) was added to a solution of 5-amino-2-chloropyridine (20 g, 0.16 mol) dissolved in 1,4-dioxane (120 mL). The reaction mixture was heated to reflux for 16 hours. The reaction was cooled to room temperature and poured into H₂O and extracted with ether. The organics were dried over Na₂SO₄ and concentrated to a residue. Trituration with hexanes gave the product as a tan solid (31 g, 85%). ¹H NMR (400 MHz, CDCl₃): δ 1.52 (s, 9 H), 6.58 (s, 1 H), 7.26 (d, J=8.6 Hz, 1 H), 7.96 (m, 1 H), 8.23 (d, J=2.8 Hz, 1 H).

Step 2: (6-Chloro-4-iodo-pyridin-3-yl)-carbamic acid tert-butyl ester

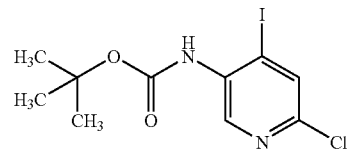

n-BuLi (52.4 mL, 0.12 mol, 2.5 M soln in hexanes) was added dropwise over 30 mins to a cooled −78° C. solution of (6-chloro-pyridin-3-yl)-carbamic acid tert-butyl ester (10.0 g, 43.7 mmol) and TMEDA (19.8 mL, 0.13 mol) dissolved in ether. The solution was warmed to −10° C., stirred for 2 hours and then recooled to −78° C. A solution of iodine (22.75 g, 90 mmol) in ether (100 mL) was added via an addition funnel and the reaction was warmed to room temperature and stirred for 16 hours. The reaction was quenched with sat NH₄Cl and sodium thiosulfite was added. The mixture was stirred for 30 mins and then extracted with ether. The organic extracts were washed with sodium thiosulfite, dried over MgSO₄, filtered and concentrated. Purification by silica gel chromatography (0% to 15% EtOAc in hexanes) gave the product (8.6 g, 56%). ¹H NMR (300 MHz, CDCl₃): δ 1.52 (s, 9 H), 6.58 (s, 1 H), 7.26 (d, J=8.6 Hz, 1 H), 7.96 (m, 1 H), 8.23 (d, J=2.8 Hz, 1 H).

Step 3: 6-Chloro-4-iodo-pyridin-3-ylamine

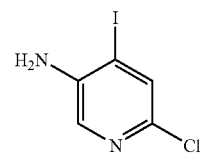

A solution of (6-chloro-4-iodo-pyridin-3-yl)-carbamic acid tert-butyl ester (8.6 g, 24.3 mmol) dissolved in CH₂Cl₂ was treated with 4 N HCl/dioxane (100 mL) and stirred at room temperature for 2 hours. The reaction mixture was diluted with CH₂Cl₂ and washed with 2 N NaOH. The organic layer was dried over MgSO₄ and concentrated to give the product as a solid (6.2 g, 100%).

Step 4: Acetic acid 6-chloro-4-iodo-pyridin-3-yl ester

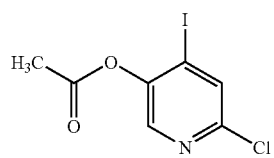

Boron trifluoride diethyl etherate (6.2 mL, 48.9 mmol) was slowly added to a cooled −15° C. solution of 6-chloro-4-iodo-pyridin-3-ylamine (5.82 g, 22.9 mmol) dissolved in DME (36 mL) and CH₂Cl₂ (12 mL). Tert-butyl nitrite (3.6 mL, 27.6 mmol) was slowly added maintaining the temperature below −5° C. The reaction was stirred at −10° C. for 25 minutes and then at 0° C. for 20 minutes. The mixture was diluted with pentanes (100 mL) and the tetrafluoroborate diazonium salt was collected by filtration. The salt was dissolved immediately by dissolving it in acetic anhydride (20 mL) and heated to 95° C. for 2 hours. The reaction was cooled to room temperature and partitioned between diethyl ether and saturated NaHCO₃. The organic layer was dried over MgSO₄ and concentrated. Purification by silica gel chromatography (0% to 60% EtOAc in hexanes) gave the product as a white solid (3.34 g, 49%). ¹H NMR (300 MHz, CDCl₃): δ 2.40 (s, 3 H), 7.82 (s, 1 H), 8.09 (s, 1 H).

Step 5: 2-Chloro-5-ethoxy-4-iodo-pyridine

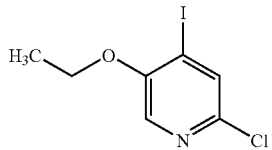

A mixture of acetic acid 6-chloro-4-iodo-pyridin-3-yl ester (3.58 g, 12.1 mmol), potassium carbonate (0.83 g, 6.0 mmol) in MeOH (20 mL) was stirred for 90 minutes. The solvent was removed in vacuo and the residue was partitioned between ether and 1 N citric acid. The organic layer was dried over MgSO₄ and concentrated to give an off white solid (2.86 g, 95%). The solid was dissolved in DMF (20 mL) and treated with potassium carbonate (4.63 g, 34 mmol) followed by ethyl iodide (2.73 mL, 33.6 mmol). The reaction mixture was heated to 60° C. for 2 hours and then cooled to room temperature. The mixture was poured into 20% citric acid and extracted with ether. The ether extracts were washed with H₂O, brine, dried over MgSO₄ and concentrated. Purification by silica gel chromatography (0% to 60% EtOAc in hexanes) gave the compound as a white solid (3 g, 95%). ¹H NMR (300 MHz, CDCl₃): δ 1.51 (t, J=7.0 Hz, 3 H), 4.17 (q, J=7.0 Hz, 2 H), 7.74 (s, 1 H), 7.81 (s, 1 H).

Step 6: 3-(2-Chloro-5-ethoxy-pyridin-4-yl)-1-cyclopentyl-propan-1-one

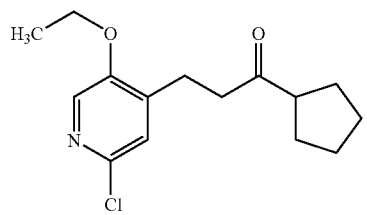

A mixture of 2-chloro-5-ethoxy-4-iodo-pyridine (1.5 g, 5.3 mmol), 1-cyclopentyl-2-propen-1-ol (0.83 g, 6.61 mmol), sodium acetate (0.54 g, 6.6 mmol), palladium (II) acetate (24 mg, 0.11 mmol) in DMAC (10 mL) was heated to 90° C. under N₂ for 16 hours. The reaction mixture was partitioned between 1N HCl and EtOAc. The organic layers were washed with saturated NaHCO₃, brine, dried over MgSO₄ and concentrated. Purification by silica gel chromatography (0% to 60% EtOAc in hexanes) gave the desired product (1.2 g, 58%). ¹H NMR (300 MHz, CDCl₃): δ 1.44 (t, J=7.0 Hz, 3H), 1.55-1.87 (m, 8 H), 2.75 (m, 2 H), 2.86 (m, 3 H), 4.11 (q, J=7.0 Hz, 2 H), 7.09 (s, 1 H), 7.89 (s, 1H).

Step 7: 1-Cyclopentyl-3-(5-ethoxy-2-ethyl-pyridin-4-yl)-propan-1-one

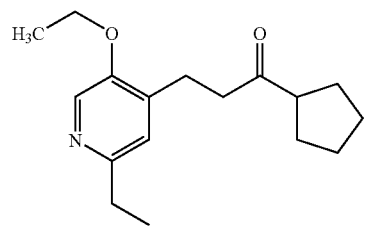

A solution of 3-(2-chloro-5-ethoxy-pyridin-4-yl)-1-cyclopentyl-propan-1-one (1.2 g, 4.3 mmol) dissolved in DMF (10 mL) was treated with potassium carbonate (0.88 g, 6.4 mmol), tetrakis(triphenylphosphine)palladium (0.12 g, 0.11 mmol), and triethylborane (4.5 mL, 4.5 mmol). The reaction was heated to 150° C. for 2 hours. The reaction was quenched with 1 N HCl and then made basic with 2 N NaOH. The mixture was extracted with ether and the organic layers were dried over MgSO₄ and concentrated. Purification by silica gel chromatography (0% to 60% EtOAc in hexanes) gave the product (0.8 g, 68%). ¹H NMR (300 MHz, CDCl₃): δ 1.26 (t, J=7.6 Hz, 3 H), 1.42 (t, J=6.9 Hz, 3 H), 1.55-1.87 (m, 8 H), 2.73 (m, 4 H), 2.86 (m, 3 H), 4.11 (q, J=6.9 Hz, 2 H), 6.93 (s, 1 H), 8.06 (s, 1 H).

Step 8: 6-Cyclopentyl-6-[2-(5-ethoxy-2-ethylpyridin-4-yl)ethyl]dihydro-2H-pyran-2,4(3H)-dione

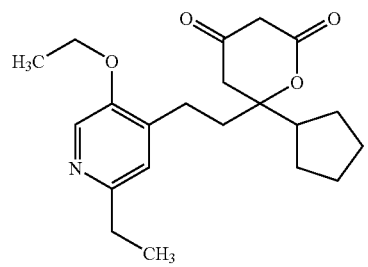

Methyl acetoacetate (1.2 mL, 10.9 mmol) was added to a cooled −50° C. suspension of LDA [prepared from diisopropylamine (3.0 mL, 21.8 mmol), and n-BuLi (8.7 mL, 21.8 mmol) dissolved in THF (30 mL)]. The reaction was stirred for 30 mins and then a solution of 1-cyclopentyl-3-(5-ethoxy-2-ethyl-pyridin-4-yl)-propan-1-one (1.0 g, 3.6 mmol) dissolved in THF (30 mL) was added. The reaction was warmed to room temperature and stirred for 2 hours. The reaction was poured into 1 N NaOH and extracted with EtOAc. The organic layers were dried over MgSO₄ and concentrated. The residue was dissolved in methanol (100 mL), treated with potassium carbonate (1.5 g, 10.9 mmol), and refluxed under N₂ for 120 mins. The reaction mixture was partitioned between H₂O and IPE. The aqueous layer was made neutral with 1N HCl and extracted with EtOAc. The organic layers were dried over MgSO₄ and concentrated to give the product (1.3 g, 99% yield). ¹H NMR (400 MHz, CDCl₃): δ 1.26 (t, J=7.6 Hz, 3 H), 1.43 (t, J=6.8 Hz, 3 H), 1.50-2.05 (br m, 9 H), 2.34 (m, 2 H), 2.62-2.77 (m, 6 H), 3.44 (m, 2 H), 4.11 (q, J=6.8 Hz, 2 H), 6.90 (s, 1 H), 8.08 (s, 1 H).

Example (C1)

Preparation of the glycolate salt of (5-amino-1H-1,2,4-triazol-3-yl)methanol

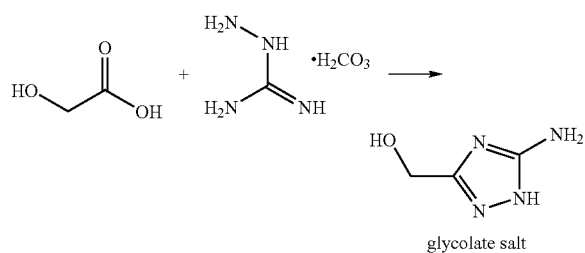

glycolate salt

Glycolic acid (1 L, 70% in water, 11.51 mol) was added to a 5 L flask. To the solution was slowly added aminoguanidine bicarbonate (783.33 g, 5.755 mol) in portions to control significant bubbling. As solids are added, the solution cools due to endothermic dissolution. The solution was gently heated to maintain an internal temp of 25° C. during addition. Ten minutes after complete addition of aminoguanidine bicarbonate, conc. nitric acid (6.8 mL) was carefully added. The solution was heated to an internal temperature of 104-108° C. (mild reflux) for 22 h. The heating was discontinued and the solution allowed to cool, with stirring. At an internal temp of ~81° C., solids began to crystallize. After the internal temperature was just below 80° C., ethanol (absolute, 375 mL) was slowly added to the mixture. After the internal temp had cooled to ~68° C., the cooling was sped up by the use of an ice/water bath. After cooling below rt, the solution became very thick but remained stirrable at all times. The slurry was stirred for 2 h at T<10° C., then filtered and the solids rinsed with ethanol (900 mL cold, then 250 mL rt). The solids were dried overnight in a vacuum oven (~25 mmHg, 45-50° C.) to provide 815.80 g (75%) of (5-amino-1H-1,2,4-triazol-3-yl)methanol as the glycolate salt. $^1$H (300 MHz, d$_6$-DMSO): 3.90 (s, 2), 4.24 (s, 2).

Example (C2)

Preparation of (5,7-dimethyl[1,2,4]triazolo[1,5-a]pyrimidin-2-yl)methanol

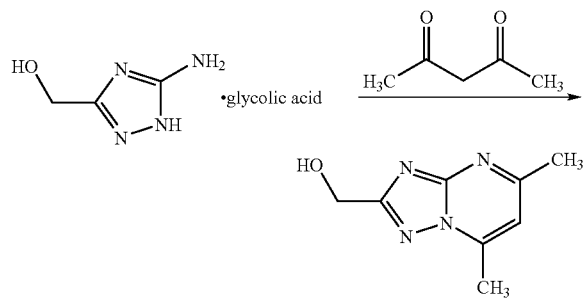

To a 10L reactor was charged HOAc (4.7 L), 2,4-Pentanedione (543 mL, 5.29 mol), and the glycolate salt of (5-amino-1H-1,2,4-triazol-3-yl)methanol (944 g, 4.96 mol). The mixture was heated to 100° C. until the solution was homogeneous. After reaching 100° C., the solution should be nearly homogeneous. The time at 100° C. should be ~15-30 min. After this time, if the solution remains cloudy heating should be discontinued. The resulting solution was cooled to ambient temperature, and MTBE (16 L) was added and the mixture stirred for 30 min. The mixture was filtered through a 14" Buchner, rinsed with MTBE (7 L), and dried in a vacuum oven overnight at 50° C. to provide 518 g (59%) of (5,7-dimethyl[1,2,4]triazolo[1,5-a]pyrimidin-2-yl)methanol as a white solid. The filtrate contained significant product, so a second crop was isolated by charging the MTBE filtrates to a 22L reactor and cooling to 0° C. MTBE (8 L) was added and stirred for 2 hours. The resulting slurry was filtered and dried to yield an additional 173.7 g (20%) of (5,7-dimethyl[1,2,4]triazolo[1,5-a]pyrimidin-2-yl)methanol as a grey solid. Both crops were carried forward. $^1$H NMR (300 MHz, d$_6$-DMSO): 2.57 (s, 3), 2.71 (d, 3, J=0.8), 4.63 (uneven d, 2, J=5.7), 5.49 (t, 1, J=6.2), 7.13 (d, 1, J=0.8).

Example (C3)

Preparation of 5,7-dimethyl[1,2,4]triazolo[1,5-a]pyrimidine-2-carbaldehyde

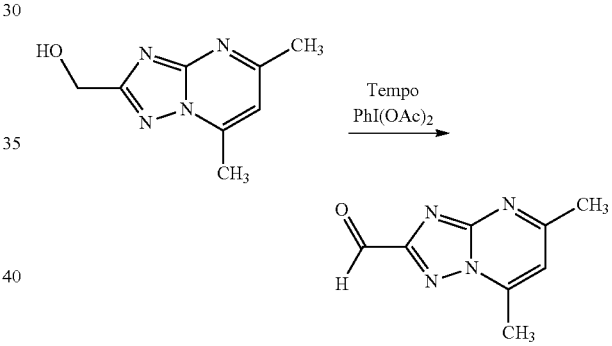

To a 10 L reactor was sequentially charged CH$_2$Cl$_2$ (5.1 L), (5,7-dimethyl[1,2,4]triazolo[1,5-a]pyrimidin-2-yl)methanol (680 g, 3.816 mol), and iodobenzene diacetate (1352 g, 4.197 mol). As the iodobenzene diacetate dissolves, there is a significant endotherm (typically down to 15-16° C.). The jacket was set to 23° C. The mixture was warmed to ambient temperature and Tempo (2,2,6,6-tetramethyl-1-piperidinyloxy, free radical, 43.75 g, 0.28 mol) added in a single charge. The reaction was stirred until 5% of the starting alcohol remained by HPLC. Once the starting material is adjudged to be less than about ~5%, the over-oxidized product begins to be observed. Allowing the reaction to run to further completion leads to an overall diminished yield of the desired product. For this reaction, the desired reaction completion was reached in 2.75 h. MTBE (5.1 L) was then slowly charged to the reactor, causing the product to precipitate, and the slurry stirred for an additional 30 mins. The mixture was filtered, washed twice with 1:1 DCM/MTBE (2×1 L), and dried in a vacuum oven overnight at 50° C. to provide 500.3 g (74%) of 5,7-dimethyl[1,2,4]triazolo[1,5-a]pyrimidine-2-carbaldehyde as an off-white solid. $^1$H NMR (300 MHz, d$_6$-DMSO): 2.64 (s, 3), 2.78 (d, 3, J=0.8), 7.36 (d, 1, J=0.9), 10.13 (s, 1).

Example (C4)

Preparation of 2-(4-bromo-2-fluorophenyl)-2-methylpropanenitrile

Step A:
2-(4-bromo-2-fluorophenyl)-2-methylpropanenitrile

A 5-L, 3-neck flask was sequentially charged with sodium cyanide (342.19 g, 6.982 moles), Bu₄Nor (49.29 g, 0.1529 mol), water (800 mL) and CH₂Cl₂ (800 mL). After dissolution, the solution was cooled to 10° C. In a separate vessel, CH₂Cl₂ (320 mL) was added to 4-bromo-2-fluorobenzyl bromide (1628.87 g, 6.080 mol) and the mixture stirred and heated to rt until dissolved The 4-bromo-2-fluorobenzyl bromide/CH₂Cl₂ solution was charged to an addition funnel, and added slowly to the stirred cyanide solution in order to control the reaction exotherm, maintaining the internal temperature between 25-30° C. After complete addition, an aliquot was removed and analyzed by HPLC, showing a 2.2:1 ratio of product to starting material. The bath temperature was adjusted to rt and the reaction stirred an additional 19 h. HPLC analysis showed no detectable starting material. The solution was added to a separatory funnel and the lower aqueous layer removed. To the organic phase was added an aqueous solution of 1% NaHCO₃ (8 g NaHCO₃ in 800 mL water) and isopropyl ether (IPE, 1600 mL) and the phases mixed well. The aqueous phase is now the top layer. The layers were separated and the lower organic phase added back to the separatory funnel and extracted again with an aq. 1% NaHCO₃ solution (800 mL). The phases were separated and the organic layer was added to a 5-L, 3-neck flask set up for distillation. The solution was distilled at atmospheric pressure down to an internal volume of ~1.6 L. To the solution was added IPE (800 mL) and the distillation continued until the internal volume was ~1.5 L. Additional IPE (500 mL) was added and the solution distilled down to an internal volume of 1.6 L. After the solvent displacement was complete, the solution was allowed to cool to 29° C. over 2 hours, and then seeded with crystalline 2-(4-bromo-2-fluorophenyl)-2-methylpropanenitrile causing an exotherm to 36° C. The solution was allowed to cool with vigorous stirring overnight. The slurry was then cooled in an ice/water bath to an internal temperature <10° C. for 1.5 h. The cold slurry was filtered and the solids rinsed with cold isopropyl ether (2×250 mL, <5° C.). The solids were dried under vacuum (no heating, solid melts <40° C.) to provide 1104.80 g (85%) of product as an off-white crystalline solid with purity of 99.8% by HPLC. ¹H NMR of (300 MHz, CDCl₃): 3.64 (s, 2), 7.27-7.42 (m, 3).

Step B

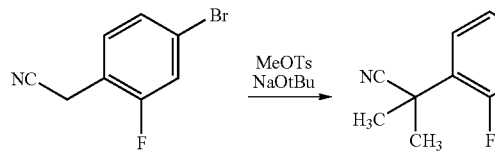

A 2-L, 3-neck flask was charged with (4-bromo-2-fluorophenyl)acetonitrile (100.91 g, 0.4715 mol), MeOTs (156 mL g, 1.034 mol), DMF (400 mL) and THF (400 mL). The headspace was purged with nitrogen and the solution was cooled to −10° C. The NaOtBu (96.58 g, 1.005 mol) was divided into 4 equal portions that were added separately to the reaction to control the exotherm. Five minutes after the fourth and final charge an aliquot was removed and analyzed by HPLC, verifying reaction completion. The cold bath was removed, and the reaction allowed to stir without cooling (internal temp=4° C.). The flask was then charged with DABCO (13.02 g, 0.116 mol) to consume the remaining MeOTs. After 30 min an aliquot was removed and analyzed by HPLC, showing no detectable MeOTs. The flask was charged with H₂O (400 mL) and hexanes (400 mL) and the mixture added to a separatory funnel. The phases were mixed well and then separated. The aqueous phase was re-charged to the separatory funnel and re-extracted with hexanes (200 mL). The organic phases from the first two extractions were combined and transferred back to the separatory funnel and washed twice with H₂O (200 mL). The phases were separated and the organic layer was added to a 2-L, 3-neck flask set up for distillation. The solution was distilled under vacuum (400 torr with an internal temperature of about 50° C.) until no significant solvent distillation occurred. An aliquot of the solution was removed and analyzed by ¹H NMR to record the amount of solvents present. The solution of product was held overnight and used without further processing in the next step.

For HPLC monitoring, aliquots were withdrawn and dissolved in CH₃CN/H₂O (70:30). HPLC conditions: Kromasil C4 column, 5 um, 4.6×150 mm, 40° C. column chamber, flow rate=1.0 mL/min, 70% CH₃CN/30% aqueous (1.0 mL 70% HClO₄ in 1 L H₂O) isocratic. Percentages reported are at 215 nm. Retention times: starting material=2.7 min, product=3.3 min, MeOTs=2.5 mins, mono-alkylated product=3.1 min. ¹H NMR (300 MHz, CDCl₃): 6.90-7.00 (m, 2), 7.33-7.39 (m, 1)

Example (C5)

Preparation of 2-[4-(3-cyclopentyl-3-oxopropyl)-2-fluorophenyl]-2-methylpropanenitrile

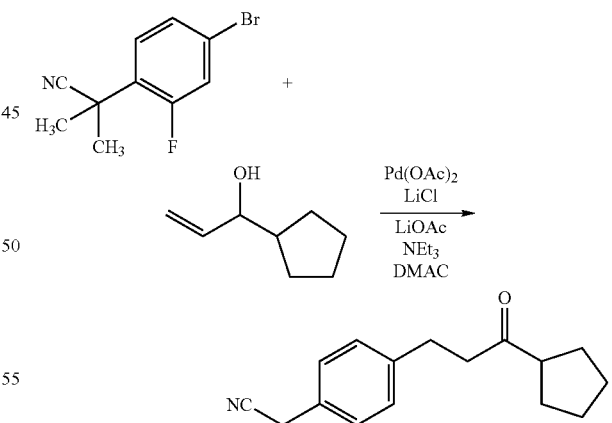

A nitrogen-purged, 2-L, 3-neck flask containing 2-(4-bromo-2-fluorophenyl)-2-methylpropanenitrile (114.14 g, 0.4715 mol) was sequentially charged (while stirring) with LiCl (39.62 g, 0.9347 mol), LiOAc (15.41 g, 0.2334 mol), DMAc (283 mL), and H₂O (28.3 mL). The solution was then purged (subsurface) with N₂ for 1 h. The flask was then charged with 1-cyclopentyl-prop-2-en-1-ol (73.70 g, 0.5808 mol), Et₃N (6.5 mL, 0.0466 mol, 10% of the total to be added), and Pd(OAc)₂ (5.2487 g, 0.0234 mol) followed by a careful purge of the headspace. The reaction was heated towards 75° C. Once the internal temperature reached 60° C. the reaction may exotherm. It took a total of 20 minutes to heat the reaction to 75° C. Fifteen minutes after the internal temp had reached 60° C., an aliquot was removed and analyzed by HPLC, showing a 3:1 ratio of starting material to product. At this point, a second addition of NEt₃ (13.0 mL, 0.0933 mol, 20% of the total to be added) was added to the reaction. Each addition of TEA causes additional exotherms.

was used directly in the next reaction without further processing. ¹H NMR (300 MHz, CDCl₃): 1.52-1.72 (m, 9), 1.77 (s, 6), 2.73-2.92 (m, 4), 6.90-7.00 (m, 1), 7.33-7.39 (m, 1)

Example (C6)

Preparation of 5-[4-(1-cyano-1-methylethyl)-3-fluorophenyl]-3-cyclopentyl-3-hydroxypentanoic acid dicyclohexylamine salt

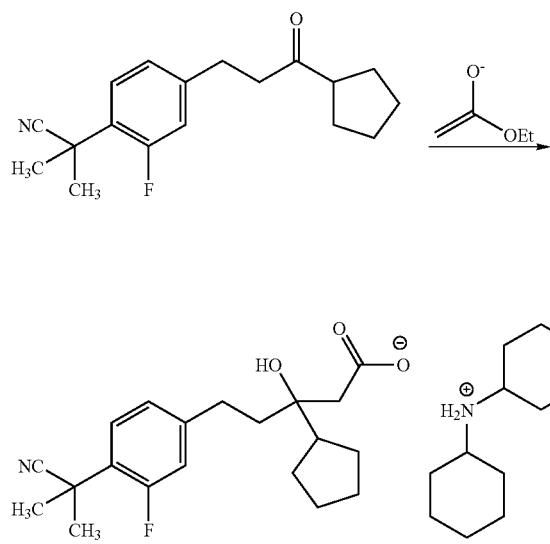
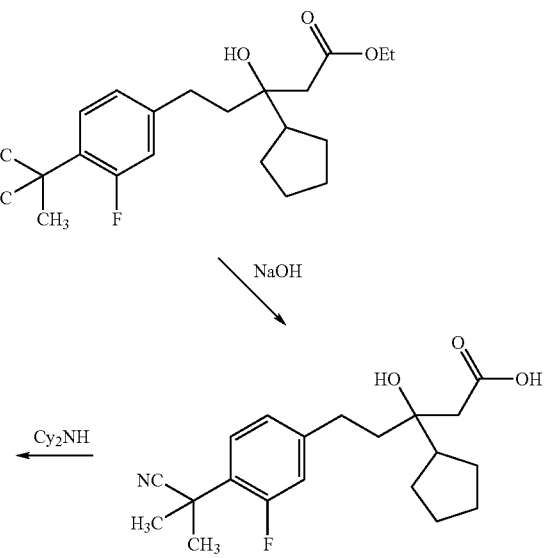

Twenty minutes after the second NEt₃ addition, an aliquot was removed and analyzed by HPLC, showing a 2:1 ratio of starting material to product. Ten minutes later, the third portion of NEt₃ (46.0 mL, 0.3300 mol, 70% of the total to be added) was added to the reaction. Thirty-five minutes after the final NEt₃ addition, an aliquot was removed and analyzed by HPLC, showing >70:1 ratio of product to starting material. The reaction was heated for 30 min more, then cooled to <30° C. over 15 min. The flask was charged with H₂O (500 mL), MTBE (500 mL), DARCO (28.5 g), and celite (28.5 g). The solution stirred well for 2 hours then filtered over a cake of celite (28.5 g packed in a 4" buchner funnel). This filtration of the bilayer through celite was slow, and the vacuum caused a significant portion of the organic solvent to boil away. The cake was washed with MTBE (250 mL followed by 125 mL). The filtrate was added to a separatory funnel with an additional portion of MTBE (200 mL), the phases mixed well, and the lower aqueous layer removed. The organic phase was extracted with H₂O (200 mL) and the phases mixed well. The lower aqueous layer was removed. The organic layer was extracted with a 5% NaCl/H₂O solution (200 mL). The phases were separated and the organic layer was added to a 1 L, 3-neck flask. The solution was concentrated by atmospheric distillation until the internal volume was ~2 volumes. After cooling below reflux, an aliquot was removed and analyzed by K-F titration, showing 0.35% H₂O. An additional portion of MTBE (150 mL) was added and distillation continued until the internal volume was again ~2 volumes. After cooling below reflux, an aliquot was removed and analyzed by K-F titration, showing 0.14% H₂O. The solution was cooled under nitrogen and held overnight at rt. The solution A 3-L, 3-neck flask was charged with LiHMDS (1.0 M in THF, 750 mL, 0.75 mol) and purged with nitrogen. The flask was cooled to −34° C. An addition funnel was then charged with EtOAc (74 mL, 0.7576 mol) and this reagent was slowly added to the reaction vessel. After complete EtOAc addition another addition funnel was charged with a 2-[4-(3-cyclopentyl-3-oxopropyl)-2-fluorophenyl]-2-methylpropanenitrile solution (crude MTBE soln from prior reaction, theor. 135.49 g, 0.4715 mol) and rinsed over with THF (anhydrous, 20 mL). The ketone solution was added to the reaction flask. Five minutes after complete addition a reaction aliquot was removed and analyzed by HPLC, showing 1% 2-[4-(3-cyclopentyl-3-oxopropyl)-2-fluorophenyl]-2-methylpropanenitrile. Ten minutes after complete ketone addition, the bath was switched to 0° C. Once the internal temperature had warmed to −10° C., 1M NaOH (860 mL) was slowly added. After complete NaOH soln addition, the reaction was heated to 50° C. After 21 hours an aliquot was removed from the top layer and analyzed by HPLC, showing no detectable ethyl 5-[4-(1-cyano-1-methylethyl)-3-fluorophenyl]-3-cyclopentyl-3-hydroxypentanoate. The reaction solution was cooled below 30° C. and added to a separatory funnel with MTBE (1265 mL). The phases were mixed well and separated. An aliquot of the aqueous phase was analyzed by HPLC, verifying no significant product, and this layer was discarded. Water (1265 mL) was added and the phases mixed well and separated. An aliquot of the organic phase was analyzed by HPLC, verifying very little product in this layer, and the organic phase was discarded. The aqueous phase was added to a flask. Concentrated aq. HCl (~49 mL) was added to the aqueous phase until the pH=2. The mixture was added back to a separatory funnel with IPE (1265 mL) and mixed well. An aliquot of the aqueous phase verified no significant product, and this layer was discarded. The organic layer was dried (MgSO$_4$, 25 g), filtered, and the cake rinsed with IPE (200 mL). The solution was analyzed by K-F titration, showing 0.93% water content. This solution was charged to a 3-L, 3-neck flask. While stirring well, dicyclohexylamine (188 mL, 0.9446 mol) was added. The amine addition caused an exotherm to 28° C. After 10 min, significant solids were observed. The solution was stirred at rt for 2.5 h. The solution was cooled in a 0° C. bath until the internal temp remains below 5° C. for 2 h. The slurry is filtered, and the solids rinsed with cold (5° C.) IPE (250 mL). The solids were dried to provide 189.68 g of 5-[4-(1-cyano-1-methylethyl)-3-fluorophenyl]-3-cyclopentyl-3-hydroxypentanoic acid dicyclohexylamine salt as a white powder. The solids had a 98.4% purity by HPLC and were clean by $^1$H NMR.

Example (C7)

Preparation of 5-[4-(1-cyano-1-methylethyl)-3-fluorophenyl]-3-cyclopentyl-3-hydroxypentanoic acid

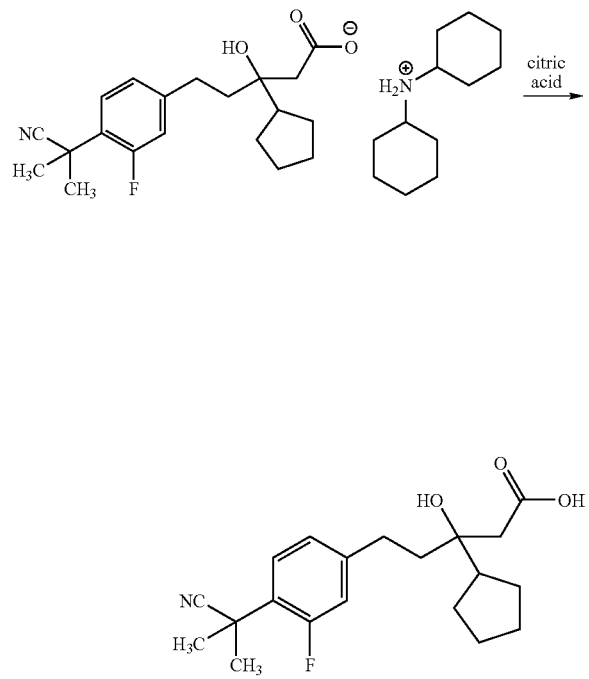

A 3-L, 3-neck flask was charged with 5-[4-(1-cyano-1-methylethyl)-3-fluorophenyl]-3-cyclopentyl-3-hydroxypentanoic acid dicyclohexylamine salt (166.0 g, 0.314 moles) and MTBE (1.7 L). The slurry was stirred at 22° C. and 10% aqueous citric acid was added. The mixture was stirred for 45 minutes. The mixture was added to a separatory funnel and the lower aqueous phase was removed. The organic solution was washed with H$_2$O (50 mL) and placed in a 2-L, 3-neck flask. The solution was distilled under atmospheric pressure to ~2.5 volumes, the distillate temperature starting at about 52° C. and stabilizing at ~56° C. The solution of 5-[4-(1-cyano-1-methylethyl)-3-fluorophenyl]-3-cyclopentyl-3-hydroxypentanoic acid (theoretical 0.314 mol) was used directly in the next step.

Example (C8)

Preparation of (1R,2S)-(+)-cis-1-amino-2-indanol salt of (3R)-5-[4-(1-cyano-1-methylethyl)-3-fluorophenyl]-3-cyclopentyl-3-hydroxypentanoic acid

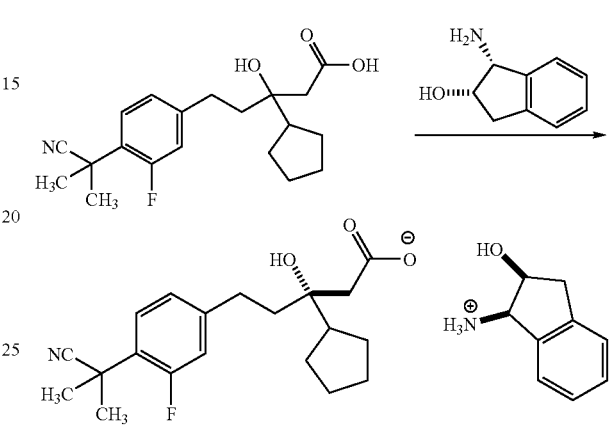

A 2-L, 3-neck flask was charged with (1R,2S)-(+)-cis-1-amino-2-indanol (23.40 g, 0.157 moles) and THF (580 mL). The mixture was stirred and heated to 50° C., at which point a homogeneous solution was observed. To the heated solution was added a solution of 5-[4-(1-cyano-1-methylethyl)-3-fluorophenyl]-3-cyclopentyl-3-hydroxypentanoic acid (109.10 g in MTBE, 0.314 moles, 425 mL total volume) at such a rate that the internal temperature was maintained above 47° C. After complete addition, MTBE (350 mL) was added at such a rate that the internal temperature was maintained above 47° C. The stirred mixture was seeded immediately after complete addition of the second portion of MTBE (crystallization progressed rapidly after seeding the mixture). After seeding, heating was discontinued and the mixture was allowed to gradually cool to rt. The mixture was stirred for 17 hours at 21° C. The mixture was filtered and the solids rinsed with 1:1 MTBE/THF (190 mL). The solids were dried in a vacuum oven (~25 mmHg, 50° C.) for 24 h to provide 66.10 g (42%) of (1R,2S)-(+)-cis-1-amino-2-indanol salt of (3R)-5-[4-(1-cyano-1-methylethyl)-3-fluorophenyl]-3-cyclopentyl-3-hydroxypentanoic acid as an off-white crystalline solid (yield represents an 85% recovery of the maximum yield of 50% for diastereomerically pure salt). Chiral HPLC analysis of the acid showed the product to be of 96% ee.

Recrystallization of (1R,2S)-(+)-cis-1-amino-2-indanol salt of (3R)-5-[4-(1-cyano-1-methylethyl)-3-fluorophenyl]-3-cyclopentyl-3-hydroxypentanoic acid: A 3-L, 3-neck flask was charged with (1R,2S)-(+)-cis-1-amino-2-indanol salt of (3R)-5-[4-(1-cyano-1-methylethyl)-3-fluorophenyl]-3-cyclopentyl-3-hydroxypentanoic acid (65.40 g, 0.132 moles) and IPA (1.7 L). The slurry was stirred and heated to 80° C. until all solids dissolved. At 80° C., the solution was seeded with (1R,2S)-(+)-cis-1-amino-2-indanol salt of (3R)-5-[4-(1-cyano-1-methylethyl)-3-fluorophenyl]-3-cyclopentyl-3-hydroxypentanoic acid and heating was discontinued. At 75° C., the solution was seeded again, at which point substantial crystallization began to occur. The stirred mixture was allowed to cool to rt and granulated for 22 h. The mixture was then filtered and the solids rinsed with IPA (60 mL). The solids were dried in a vacuum oven (~25 mmHg, 50° C.) for 48 h to provide 60.13 g (92%) of product as a white crystalline solid. Chiral HPLC analysis of the acid showed product with >99% ee.

For determination of e.e., the solid was dissolved in $CH_3CN/H_2O$ (70/30). HPLC conditions: Chiralcel OJ-RH column, 5 µm, 4.6×150 mm, 30° C. column chamber, flow rate=0.8 mL/min, 55% $H_2O$ (0.1% TFA)/45% $CH_3CN$ (0.1% TFA). Percentages reported are at 205 nm. Retention times: (1R,2S)-(+)-cis-1-amino-2-indanol=2.2 to 2.4 min; (3R)-5-[4-(1-cyano-1-methylethyl)-3-fluorophenyl]-3-cyclopentyl-3-hydroxypentanoic acid=6.4 min; undesired enantiomer=7.1 min. Chiral HPLC of filtrate indicated a 5:1 mixture of undesired enantiomer to desired enantiomer. $^1H$ NMR (300 MHz, $d_6$-DMSO): 1.36-1.62 (m, 8), 1.62-1.74 (m, 2), 1.70 (s, 6), 1.90-2.04 (m, 1), 2.17 (1, d, J=15.3), 2.23 (1, d, J=15.3), 2.58-2.68 (m, 2), 2.89 (dd, 1, J=3.3, 16.2), 3.07 (dd, 1, J=5.8, 16.2), 4.39 (d, 1, J=5.5), 4.52 (dt, 1, J=3.3, 5.6), 7.03-7.47 (m, 7).

Example (C9)

Preparation of (3R)-5-[4-(1-cyano-1-methylethyl)-3-fluorophenyl]-3-cyclopentyl-3-hydroxypentanoic acid

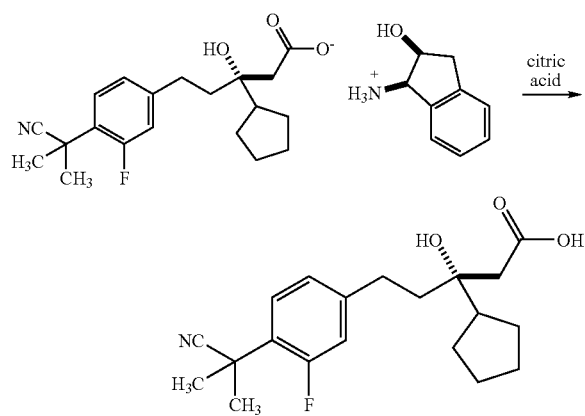

A 2-L, 3-neck flask was charged with (1R,2S)-(+)-cis-1-amino-2-indanol salt of (3R)-5-[4-(1-cyano-1-methylethyl)-3-fluorophenyl]-3-cyclopentyl-3-hydroxypentanoic acid (59.00 g, 0.119 moles) and MTBE. The mixture was stirred at rt and 10% aqueous citric acid solution was added. After stirring for three hours (if solids are still present, additional mixing time may be required), the mixture was added to a separatory funnel along with an MTBE rinse of the reactor (50 mL) and the lower aqueous layer was removed. The organic phase was washed with $H_2O$ (20 mL). The organic phase containing (3R)-5-[4-(1-cyano-1-methylethyl)-3-fluorophenyl]-3-cyclopentyl-3-hydroxypentanoic acid was >99% pure by HPLC. The wet organic solution was placed in a 1-L, 3-neck flask and the solution distilled under atmospheric pressure to remove $H_2O$ (starting volume=785 mL; volume after distillation=170 mL). The solution was filtered and charged to a 250 mL addition funnel. This solution was used directly in the next step.

HPLC analysis of aqueous and organic phases: aliquots were withdrawn and dissolved in $CH_3CN/H_2O$ (70/30). HPLC conditions: Kromasil C4 column, 5 µm, 4.6×150 mm, 40° C. column chamber, flow rate=1.0 mL/min, 70% $CH_3CN$/30% aqueous (1.0 mL 70% $HClO_4$ in 1 L $H_2O$) isocratic. Percentages reported are at 215 nm. Retention time: (3R)-5-[4-(1-cyano-1-methylethyl)-3-fluorophenyl]-3-cyclopentyl-3-hydroxypentanoic acid=2.7 min.

Example (C10)

Preparation of ethyl (5R)-7-[4-(1-cyano-1-methylethyl)-3-fluorophenyl]-5-cyclopentyl-5-hydroxy-3-oxoheptanoate

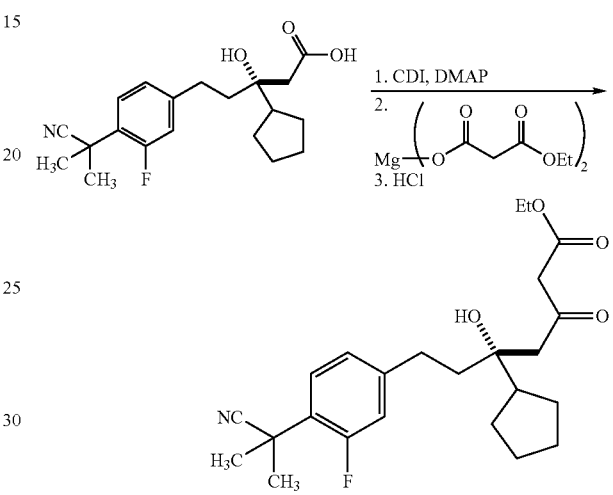

A 1-L, 3-neck flask was charged with CDI (29.00 g, 0.179 moles), DMAP (733 mg, 0.006 moles), and MTBE (70 mL) (notes 1, 2). An MTBE solution of (3R)-5-[4-(1-cyano-1-methylethyl)-3-fluorophenyl]-3-cyclopentyl-3-hydroxypentanoic acid (41.28 g, 0.119 moles, 170 mL) was added to the stirred mixture over a 30 minute period. The addition funnel was rinsed with THF (5 mL) and the rinse was added to the reaction mixture. The mixture was stirred for 30 min and an aliquot was removed and analyzed by HPLC. Once acyl-imidazole formation was complete, the solution was added to a 500 mL addition funnel. A separate 1-L, 3-neck flask was charged with ethyl magnesium malonate (51.30 g, 0.179 moles) and THF (100 mL) (the solids did not dissolve in THF, even after warming to 40° C.). The stirred mixture was heated to 40° C. and the acyl-imidazole solution was slowly added to the mixture. Stirring was continued at 40° C., and aliquots were periodically removed and analyzed by HPLC for completion. After the reaction was complete, heating was discontinued and the solution allowed to cool to rt. The solution was diluted with IPE (200 mL) and 1 N HCl (360 mL), the mixture was stirred for 15 minutes, and the phases were separated. The organic phase was extracted with $H_2O$ (10 mL), the phases separated, and the organic layer was added to a 1-L, 3-neck flask. The solution was distilled to a minimum of ~3.3 volumes to remove $H_2O$ (the distillate temperature was 48° C. during azeotrope distillation and the distillation was ended after the distillate temperature was steady at ~50° C.). The solution was used directly in the next step.

For HPLC monitoring of reaction, aliquots were withdrawn and dissolved in $CH_3CN/H_2O$ (70/30). HPLC conditions: Kromasil C4 column, 5 µm, 4.6×150 mm, 40° C. column chamber, flow rate=1.0 mL/min, 70% $CH_3CN$/30% aqueous (1.0 mL 70% $HClO_4$ in 1 L $H_2O$) isocratic. Percentages reported are at 215 nm. Retention time: Imidazole=1.4 min, acyl-imidazole=2.2 min, anhydride byproduct=2.4 min, ethyl (5R)-7-[4-(1-cyano-1-methylethyl)-3-fluorophenyl]-5-cyclopentyl-5-hydroxy-3-oxoheptanoate=2.7 min. $^1$H NMR (300 MHz, CDCl$_3$): 1.29 (t, 3, J=7.2), 1.40-1.55 (m, 3), 1.57-1.72 (m, 6), 1.86 (m, 6), 2.12 (m, 1), 2.65 (m, 2), 2.82 (d, 1, J=5.1), 3.66 (m, 2), 3.76 (m, 3), 4.22 (q, 2, J=7.2), 6.97 (m, 2), 7.38 (app. t, 1, J=8.1).

Example (C11)

Preparation of 2-(4-{2-[(2R)-2-cyclopentyl-4,6-dioxotetrahydro-2H-pyran-2-yl]ethyl}-2-fluorophenyl)-2-methylpropanenitrile

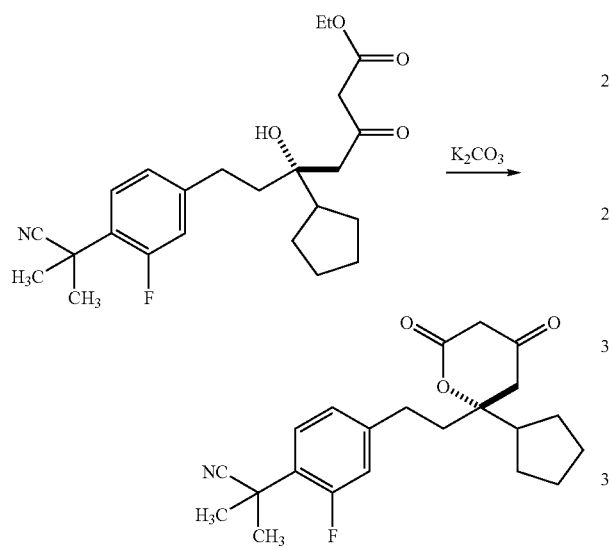

A solution of ethyl (5R)-7-[4-(1-cyano-1-methylethyl)-3-fluorophenyl]-5-cyclopentyl-5-hydroxy-3-oxoheptanoate (49.61 g, 0.1188 mol, 135 mL total volume) in a 1-L, 3-neck flask was charged with MeOH (120 mL) and K$_2$CO$_3$ (25.00 g, 0.1809 mol) and the stirred mixture was heated to 50° C. for 4 hours. An aliquot was removed and analyzed by HPLC and showed the reaction to be more than 99% complete. The solution was cooled to rt and charged with IPE (50 mL) and H$_2$O (200 mL). The mixture was stirred for 5 minutes and placed in a 2 L separatory funnel to separate phases. The reaction vessel was rinsed with H$_2$O (10 mL) and the rinse was added to the separatory funnel. The phases were separated and the product-containing aqueous phase was extracted with IPE (20 mL). The layers were separated and the aqueous phase added back to the funnel. To the aqueous phase was added 2-Me-THF (300 mL), MTBE (100 mL), and 1M HCl (~360 mL) until the pH of the aqueous phase was ~4.75. The phases were mixed well and the aqueous phase was removed. The organic phase was washed with H$_2$O (20 mL) and then placed in a 500-mL, 3-neck flask. The solution was concentrated by atmospheric distillation to ~3.3 vol. (the distillate temperature during azeotrope started at 38° C., then raised to 48° C., and finally stabilized at 57° C.). The solution was cooled to 25° C. and an aliquot was analyzed by Karl-Fischer titration. The solution was then reheated to 55° C. and heptane (50 mL) was added at such a rate that the internal temperature was kept above 53° C. (the addition of heptane when the internal temperature was less than 50° C. resulted in oiling). The solution was then seeded with solid 2-(4-{2-[(2R)-2-cyclopentyl-4,6-dioxotetrahydro-2H-pyran-2-yl] ethyl}-2-fluorophenyl)-2-methylpropanenitrile, followed by the addition of heptane (250 mL). The stirred mixture was allowed to gradually cool to rt. After stirring for 15 min at rt, the mixture was filtered and the solids rinsed with 1:1 IPE/heptane (75 mL). The solids were dried to provide 30.92 g (70%) of 2-(4-{2-[(2R)-2-cyclopentyl-4,6-dioxotetrahydro-2H-pyran-2-yl]ethyl}-2-fluorophenyl)-2-methylpropanenitrile as granular crystals. The solids were dried in a vacuum oven (~25 mmHg, 50° C.) for 20 h and were determined to be >98% pure by HPLC analysis.

HPLC conditions: aliquots were withdrawn and dissolved in CH$_3$CN/H$_2$O (80/20). HPLC conditions: Kromasil C4 column, 5 μm, 4.6×150 mm, 40° C. column chamber, flow rate=1.0 mL/min, 80% CH$_3$CN/20% aqueous (1.0 mL 70% HClO$_4$ in 1 L H$_2$O) isocratic. Percentages reported are at 215 nm. Retention time: 2-(4-{2-[(2R)-2-cyclopentyl-4,6-dioxotetrahydro-2H-pyran-2-yl]ethyl}-2-fluorophenyl)-2-methylpropanenitrile=2.2 min, ethyl (5R)-7-[4-(1-cyano-1-methylethyl)-3-fluorophenyl]-5-cyclopentyl-5-hydroxy-3-oxoheptanoate=2.7 min, by-product 1=2.8 min, by-product 2=2.9 min, by-product 3=3.1 min. $^1$H NMR (300 MHz, CDCl$_3$): 1.46-1.73 (m, 7), 1.77 (s, 7), 1.91 (m, 2), 2.27 (m, 1), 2.68 (t, 2, J=7.8), 2.77 (s, 2), 3.43 (d, 2, J=1.4), 6.92 (m, 2), 7.39 (app. t, 1, J=8.2).

Example (C12)

Preparation of 2-[4-(2{(2R)-2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorophenyl]-2-methylpropanenitrile

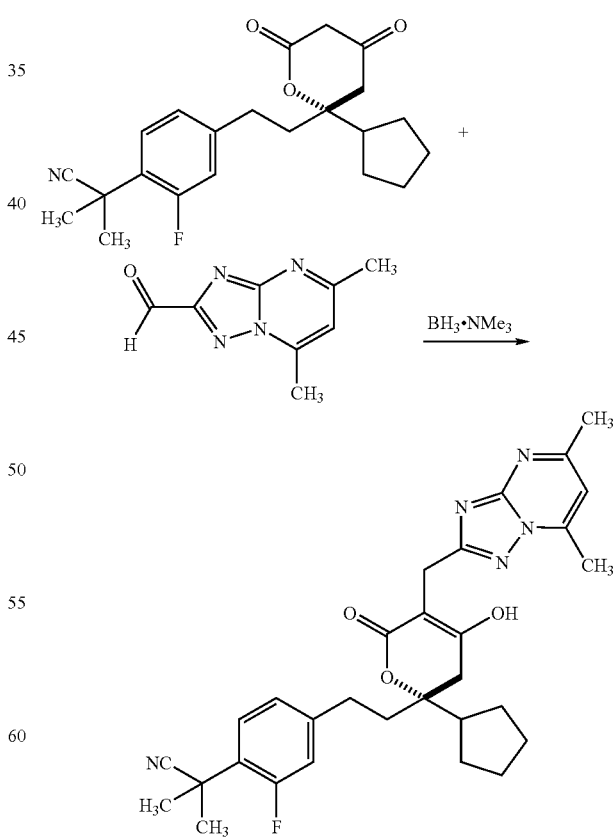

A 1-L, 3-neck flask was sequentially charged with 2-(4-{2-[(2R)-2-cyclopentyl-4,6-dioxotetrahydro-2H-pyran-2-yl]

ethyl}-2-fluorophenyl)-2-methylpropanenitrile (30.01 g, 0.0808 moles), and IPA (150 mL). After purging with N$_2$, the flask was charged with BH$_3$—NMe$_3$ (8.27 g, 0.113 moles) and 5,7-dimethyl[1,2,4]triazolo[1,5-a]pyrimidine-2-carbaldehyde (21.37 g, 0.121 moles). After 15 min an aliquot was removed and analyzed by HPLC (typically, the starting material is in the 5-8% range before quench). The flask was charged with isopropyl acetate (IPAc, 150 mL) and 1M HCl (150 mL). After 30 min an aliquot was removed and analyzed by HPLC to verify the decomplexation of boron. The reaction was transferred to a separatory funnel and the aqueous phase was removed. The organic phase was extracted with H$_2$O (150 mL) and the lower aqueous layer was removed. The organic layer was added to a 500 mL, 3-neck flask set up for distillation. The solution was distilled to a minimum level of 5 vols., IPAc (100 mL) was added, and the distillation was continued. This process was repeated until IPA was removed from the solution and the distillation was continued to achieve 5 vol. (the distillation was judged to be complete when the distillation head maintained a steady temperature of about 86-89° C.). The solution was slowly cooled to room temperature and stirred overnight. The mixture was filtered and the solids were washed with IPAc (2×25 mL). The solids were transferred to a 1-L, 3-neck flask with IPAc (150 mL) and IPA (150 mL) and heated to 50° C. The solution was cooled to an internal temperature of 30° C. and filtered through a 0.45 μm membrane filter. The flask was rinsed with an IPAc/IPA mixture (1:1, 100 mL). The filtrate was placed in a 500 mL, 3-neck flask set up for distillation. The solution was distilled to a minimum level of 5 vol. then IPAc (100 mL) was charged and the distillation was continued. The process was repeated until IPA was removed from the solution and the distillation was continued to achieve 5 vol. (the distillation was judged to be complete when the distillation head maintained a steady temperature of about 86-89° C.). The solution was slowly cooled to rt and stirred overnight. The mixture was filtered and the solids were washed with IPAc (2×25 mL) and dried in a vacuum oven (25 mmHg, 50° C.) overnight. The dry solids were charged to a flask with H$_2$O (500 mL HPLC grade), heated to 75° C., and stirred vigorously for 16 h. The slurry was cooled, filtered over polycloth, and the solids washed with H$_2$O (2×100 mL) and dried in a vacuum oven (25 mmHg, 50° C.) overnight to provide 23.58 g (55%) of 2-[4-(2-{(2R)-2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorophenyl]-2-methylpropanenitrile as a white crystalline solid.

For HPLC monitoring, aliquots were withdrawn and dissolved in CH$_3$CN/H$_2$O (70:30). HPLC conditions: Kromasil C4 column, 5 μm, 4.6×150 mm, 40° C. column chamber, flow rate=1.0 mL/min, 70% CH$_3$CN/30% aqueous (1.0 mL 70% HClO$_4$ in 1 L H$_2$O) isocratic. Percentages reported are at 215 nm. Retention times: 2-(4-{2-[(2R)-2-cyclopentyl-4,6-dioxotetrahydro-2H-pyran-2-yl]ethyl}-2-fluorophenyl)-2-methylpropanenitrile=2.67 min, 5,7-dimethyl[1,2,4]triazolo[1,5-a]pyrimidine-2-carbaldehyde=1.5 min, 2-[4-(2-{(2R)-2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorophenyl]-2-methylpropanenitrile 2.3 min, Boron/pdt. complex=2.6 min The product contained no detectable enantiomer by chiral HPLC analysis. For determination of e.e., the solid was dissolved in CH$_3$CN/H$_2$O (70/30). HPLC conditions: Chiralcel OJ-RH column, 5 μm, 4.6×150 mm, 30° C. column chamber, flow rate=0.8 mL/min, 55% H$_2$O (0.1% TFA)/45% CH$_3$CN (0.1% TFA). Percentages reported are at 205 nm. Retention times: undesired enantiomer=6.3 min, 2-[4-(2-{(2R)-2-cy-clopentyl-5-[(5,7-dimethyl[1,2,4]triazolo[1,5-a]pyrimidin-2-yl)methyl]-4-hydroxy-6-oxo-3,6-dihydro-2H-pyran-2-yl}ethyl)-2-fluorophenyl]-2-methylpropanenitrile=7.3 min.
$^1$H NMR (300 MHz, CDCl$_3$): 1.32-1.83 (m, 8), 1.80 (s, 6), 1.99-2.08 (m, 2), 2.33-2.48 (m, 1), 2.58 (d, 1, J=17.7), 2.63-2.76 (m, 2), 2.71 (s, 3), 2.82 (d, 1, J=17.7), 2.83 (s, 3), 4.14 (br s, 2), 6.87-6.98 (m, 3), 7.37 (app t, 1, J=8.2).

Example C(13)

3-Cyclopentyl-3-hydroxypent-4-enoic acid

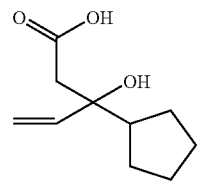

Ethyl 3-cyclopentyl-3-hydroxypent-4-enoate (22.12 g, 104.34 mmol), from step 2 below, was dissolved in MeOH (100 mL) and solution of NaOH (8.35 g) in H$_2$O (100 mL) was added. The reaction was stirred overnight at room temperature. The reaction mixture was partitioned between H$_2$O and IPE. The aqueous layer was made acidic with 4N HCl and extracted with EtOAc. The organic layers were washed with brine, dried over Na$_2$SO$_4$ and concentrated to give and off white solid that was recrystallized from hot hexanes. (18 g, 94% yield). $^1$H NMR (300 MHz, CDCl$_3$): δ 1.26-1.69 (m, 8H), 1.99-2.08 (m, 1H), 2.60 (d, J=15.6, 1H), 2.68 (d, J=15.6, 1H), 5.17-5.33 (m, 2H), 5.82-5.92 (m, 1H). ESIMS (MH–): 183.

Step 1: 1-Cyclopentyl-propenone

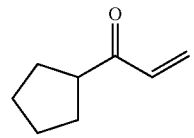

Cyclopentane carboxylic acid (15 mL, 138.41 mmol) was dissolved in CH$_2$Cl$_2$ (185 mL) and DMF (0.25 mL). The reaction was cooled to 0° C. and oxalyl chloride (13.9 mL, 159.19 mmol) was slowly added. After stirring for 1 hour at room temperature, it was cooled again to 0° C. and a solution of ALCl$_3$ (20.30 g, 152.28 mmol) and vinyltrimethylsilane (21.38 mL, 138.44 mmol) in CH$_2$Cl$_2$ (190 mL) was added slowly via addition funnel. The reaction mixture was stirred for 10 minutes and then poured over ice. Concentrated HCl was added until the precipitate of Al(OH)$_3$ dissolved and the layers were separated. The organic layer was washed with brine, dried over Na$_2$SO$_4$ and concentrated to a yellow oil that was used without further purification.

The oil was dissolved in CH$_3$CN (100 mL), treated with triethyl amine (24 mL), and stirred at 5° C. for 1 hour. The reaction mixture was poured into 5% KHSO$_4$ (100 mL) and extracted with ethyl acetate (3×100 mL). The organic layers were washed with brine, dried over Na$_2$SO$_4$ and carefully Step 2: Ethyl 3-cyclopentyl-3-hydroxypent-4-enoate

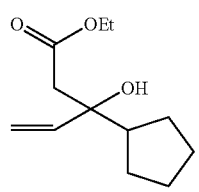

A magnetically stirring solution of lithium hexamethyldisilazine 1 M in THF (253.23 mL) was cooled to −78° C. Ethyl acetate (24.74 mL, 253.23 mmol) was slowly added and reaction stirred for 20 min at this temperature. 1-Cyclopentyl-propenone, from step 1 above, was dissolved in THF (40 mL) and added to lithium anion via cannula over a period of 30 minutes. The reaction was stirred at −78° C. for 1 hour. The reaction mixture was partitioned between 1N HCl and IPE. The layers of the resulting reaction mixture were separated and the organic layer was washed with brine (1×10 mL), then dried over $Na_2SO_4$, filtered and concentrated in vacuo. The crude residue was purified by flash column chromatography (20% EtOAc in Hexanes) to give the desired product as a yellow oil (22.12 g, 81%). $^1$H NMR (400 MHz, $CDCl_3$): δ 1.25 (t, J=7.2, 3H), 1.36-1.68 (m, 8H), 1.96-2.03 (m, 1H), 2.53 (d, J=15.2, 1H), 2.60 (d, J=15.2, 1H), 4.13 (q, J=7.2, 2H), 5.11-5.32 (m, 2H), 5.80-5.90 (m, 1H). ESIMS (MH+): 213.

Example C(14)

(3R)-3-cyclopentyl-3-hydroxypent-4-enoic acid (ENANTIOMER 1)

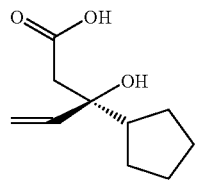

To a solution of 3-cyclopentyl-3-hydroxypent-4-enoic acid (1 g, 5.43 mmol) in EtOAc (27 mL) from example C(13) under stirring was added a solution of (S)-1,2,3,4-tetrahydro-1-naphtylamine (0.399 g, 2.71 mmol) in EtOAc (13 mmol). After 10 minutes a white precipitate formed. This precipitate was collected on paper and recrystallized from hot EtOAc. The precipitate was partitioned between EtOAc (5 mL) and 1N HCl (5 mL) and the organic layer was separated, dried over $Na_2SO_4$ and concentrated in vacuo to an oil which solidified upon standing (0.43 g, 43%).
$^1$H NMR (300 MHz, $CDCl_3$): δ 1.26-1.69 (m, 8H), 1.99-2.08 (m, 1H), 2.60 (d, J=15.6, 1H), 2.68 (d, J=15.6, 1H), 5.17-5.33 (m, 2H), 5.82-5.92 (m, 1H). ESIMS (MH−): 183.96% ee, Retention time 25.02 min (Chiralpack OD-RH, 150×4.6 mm, 0.6 mL/min, 15% B and 85% buffer for 30 min).
*Other amines suitable for the resolution are: (S)-(−)-1-(2-naphthyl)ethylamine and (R)-(−)-1-(2-naphthyl)ethylamine and (1R,2S)-(−)-norephedrine and (1S,2R)-(+)-norephedrine.

Example C(15)

(3S)-3-cyclopentyl-3-hydroxypent-4-enoic acid (ENANTIOMER 2)

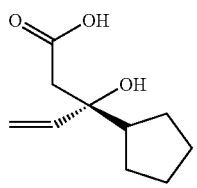

The title compound is prepared analogously to example C(14) (enantiomer 1) above where (R)-1,2,3,4-tetrahydro-1-naphtylamine is substituted in place of (S)-1,2,3,4-tetrahydro-1-naphtylamine of that example. Other amines suitable for the resolution are: (S)-(−)-1-(2-naphthyl)ethylamine and (R)-(−)-1-(2-naphthyl)ethylamine and (1R,2S)-(−)-norephedrine and (1S,2R)-(+)-norephedrine.

Example C(16)

2-[2-chloro-4-(2-(2S)-2-cyclopentyl-5-[(5,7-dimethyl[1,2,4]triazolo[1,5-a]pyrimidin-2-yl)methyl]-4-hydroxy-6-oxo-3,6-dihydro-2H-pyran-2-yl)ethyl)phenyl]-2-methylpropanenitrile

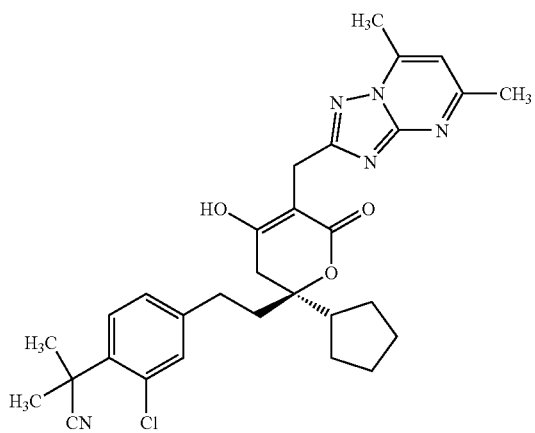

The title compound was prepared analogously to example A(1) where 2-{2-chloro-4-[2-(2-cyclopentyl-4,6-dioxo-tetrahydro-pyran-2-yl)-ethyl]-phenyl}-2-methyl-propionitrile, from step 2 below was substituted in place of 6-cyclopentyl-6-[2-(5-ethyl-4-hydroxy-2-propoxy-phenyl)-ethyl]-dihydro-pyran-2,4-dione in that example. $^1$H NMR (400 MHz, DMSO-$d_6$): δ 1.39-1.64 (m, 8H), 1.67 (s, 6H), 2.01-2.05 (m, 2H), 2.36-2.46 (m, 7H), 2.51-2.57 (m, 2H), 2.69 (d, J=17 Hz, 2H), 3.61 (d, J=16 Hz, 1H), 3.72 (d, J=16 Hz, 1H), 6.94 (s, 1H), 7.25 (s, 1H), 7.28 (s, 1H), 7.35 (d, J=8 Hz, 1H), 10.75 (s, 1H). IR (neat): 2243, 2355 (CN), 1666, 1625, 1543, 1390. MS

Step 1: 5-[3-Chloro-4-(cyano-dimethyl-methyl)-phenyl]-3-cyclopentyl-3-hydroxy-pent-4-enoic acid

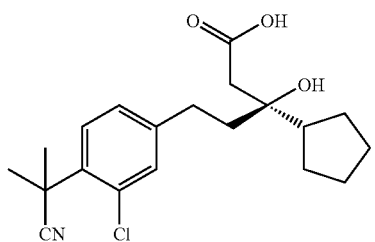

A mixture of 2-(4-bromo-2-chloro-phenyl)-2-methyl-propionitrile (0.61 g, 2.34 mmol), from step 4 of example B(22), (3R)-3-cyclopentyl-3-hydroxypent-4-enoic acid (0.43 g, 2.34 mmol, example C(14), Pd(OAc)$_2$ (0.01 g, 5 mol %) and NaOAc (0.24 g, 2.93 mmol). in DMAC (5 mL) was heated at 90° C. overnight. The reaction mixture was cooled to room temperature and partitioned between 1N HCl and EtOAc. The organic layer was washed with brine, dried over Na$_2$SO$_4$ and concentrated to dark brown oil. Flash column chromatography (0% to 40% EtOAc in hexanes) gave a light brown oil. The oil was dissolved in EtOH (10 mL) and treated with Pd(OH)$_2$ (0.23 g) The mixture was stirred under a balloon of hydrogen for 1 hour. The reaction mixture was filtered through a pad of celite washing with EtOAc. The filtrate was concentrated to an orange oil and purified by flash column chromatography to give the product as a yellow solid (0.47 g, 100%). $^1$H NMR (300 MHz, CDCl$_3$): δ 1.4-1.72 (m, 10 H), 1.85 (s, 6 H), 2.11-2.18 (m, 1 H), 2.56-2.73 (m, 4 H), 7.10 (d, J=7.9 Hz, 1 H), 7.26 (s, 1 H), 7.36 (d, J=7.9 Hz, 1 H). ESIMS (MNa+): 364.

Step 2: 2-{2-Chloro-4-[2-(2-cyclopentyl-4,6-dioxo-tetrahydro-pyran-2-yl)-ethyl]-phenyl}-2-methyl-propionitrile

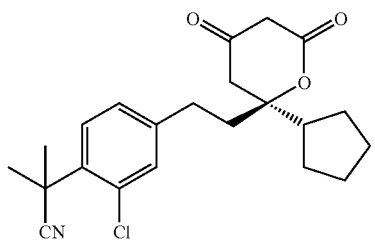

5-[3-Chloro-4-(cyano-dimethyl-methyl)-phenyl]-3-cyclopentyl-3-hydroxy-pent-4-enoic acid, from step 1 above, was dissolved in methyl tert-butyl ethylmalonate (3 mL). 4-DMAP (0.16 g, 0.13 mmol) and CDI (0.27 g, 1.68 mmol) were added and the reaction mixture was stirred under argon for 2 hours. In a separate flask was placed magnesium-bis-monoethyl malonate (0.74 g, 2.58 mmol) was suspended in THF (3 mL) and the mixture was heated to 42° C. The acylimidazole solution was added via cannula to the malonate mixture and the reaction was heated to 42° C. for 2 hours. The solvent was removed in vacuo to give a residue that was partitioned between 1N HCl and EtOAc. The organic layer was dried over MgSO$_4$ and concentrated to a clear oil (0.56 g, 100%). The oil was dissolved in a 0.3 M NaOH solution in MeOH/H$_2$O 1:1 (6 mL), and stirred overnight at room temperature. The reaction mixture was partitioned between H$_2$O and IPE. The aqueous layer was made acidic with 1N HCl and extracted with EtOAc. The organic layers were washed with brine, dried over Na$_2$SO$_4$ and concentrated to give the product (0.45 g, 90% yield). $^1$H NMR (400 MHz, CDCl$_3$): δ 1.39-1.71 (m, 8H), 1.81-1.87 (m, 8H), 2.10-2.15 (m, 1H), 2.59-2.68 (m, 2H), 3.51 (s, 2H), 3.75 (s, 2H), 7.11 (dd, J=8.1 Hz, 1.8), 7.27 (d, J=1.8 Hz, 1H), 7.37 (d, J=8.1 Hz, 1H). ESIMS (MH+): 388.

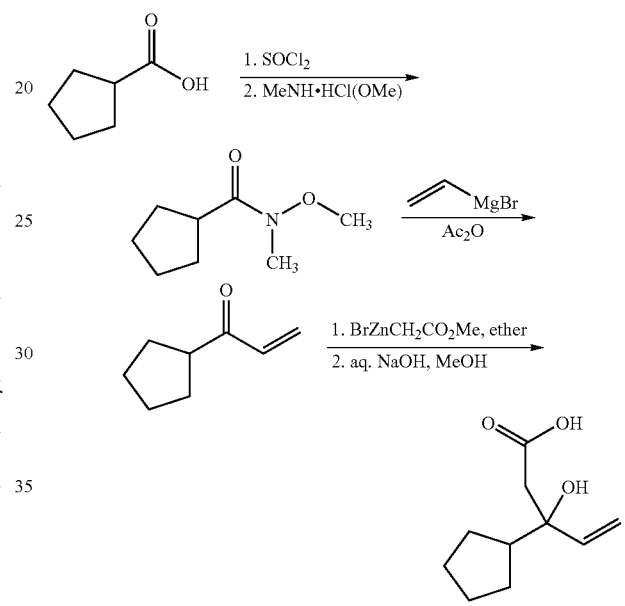

Example C(17)

3-Cyclopentyl-3-hydroxypent-4-enoic acid

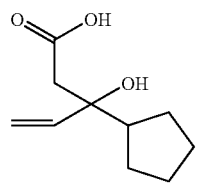

A solution of NaOH (30 g in 300 ml water, 0.75 mol) was added into a mixture of methyl 3-cyclopentyl-3-hydroxy-pent-4-enoate (74 g, 0.37 mol, from step 4 below) in methanol (300 ml) at 15° C. After addition, the mixture was stirred at room temperature overnight. Methanol was removed in vacuo and the aqueous solution was extracted with Et$_2$O (200 mL×2) and ethyl acetate (200 mL×2) to remove neutral impurities. The aqueous phase was acidified to pH=2 with 4N of HCl and extracted with CH$_2$Cl$_2$ (200 mL×2+100 mL). The combined organic layers were washed with water, brine and dried over Na$_2$SO$_4$. After evaporation, the obtained crude compound was re-crystallized from hexane (about 100 ml) to afford 44.3 g of pure product and 7 g of crude material was recovered.

$^1$H NMR (300 MHz, CDCl$_3$): δ 1.26-1.69 (m, 8H), 1.99-2.08 (m, 1H), 2.60 (d, J=15.6, 1H), 2.68 (d, J=15.6, 1H), 5.17-5.33 (m, 2H), 5.82-5.92 (m, 1H). ESIMS (MH-): 183.

Step 1: Cyclopentanecarbonyl chloride

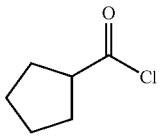

Cyclopentane carboxylic acid (100 g) was dissolved in 250 mL of SOCl$_2$ and heated to reflux for about 3 h. The excess SOCl$_2$ was removed under reduced pressure. The acid chloride was obtained via distillation in high vacuum (102 g).

Step 2: N-methoxy-N-methylcyclopentanecarboxamide

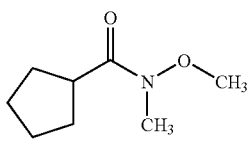

Cyclopentane carbonyl chloride (65 g, 0.49 mol) was added dropwise into a mixture of Et$_3$N (180 mL, 1.3 mol) and N,O-dimethyl hydroxylamine hydrochloride (50 g, 0.52 mol) in anhydrous CH$_2$Cl$_2$ at 0° C. After the addition, the reaction mixture was allowed to stir at ambient temperature overnight. To the reaction mixture was added about 100 g of crushed ice followed 100 g of water. The mixture was separated, and the aqueous layer was extracted with CH$_2$Cl$_2$ (100 mL×2). The combined organic layers were washed with 1N HCl, water, brine and dried over Na$_2$SO$_4$. The solvent was removed under reduced pressure to afford 61 g of desired product as oil in 78.8% of yield.

Step 3: 1-Cyclopentyl-propenone

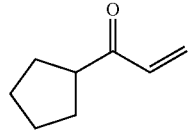

To a solution of N-methoxy-N-methylcyclopentanecarboxamide (40 g, 0.25 mol) in 200 mL of anhydrous THF was added dropwise a solution of vinylmagnesium bromide (1.0 M solution in THF, 300 mL, 0.3 mol) at −30° C. under nitrogen. The reaction mixture was then stirred at room temperature overnight. The reaction was quenched by addition of acetic anhydride (48 mL) followed by methanol (48 mL). The solution was concentrated under reduced pressure, and 300 mL of ether was added followed by 300 mL of 1N HCl. The mixture was separated, and the aqueous layer was extracted with ether (100 mL×2). The organic layers were combined, washed with water, brine and dried over Na$_2$SO$_4$. After evaporation, 31 g of crude compound were obtained and used in the next step without further purification.

Step 4: Methyl 3-cyclopentyl-3-hydroxypent-4-enoate

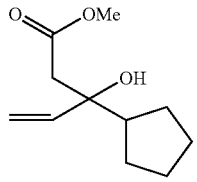

To a suspension of activated zinc (27 g, 0.4 mol) in anhydrous ethyl ether (200 mL) was added dropwise a solution of methyl bromoacetate (24 ml, 0.24 mol) and 1-cyclopentyl-propenone (31 g, 0.24 mol) in 100 mL anhydrous ethyl ether. Once the reaction had commenced, the remainder of the solution was added at such a rate as allowing a gentle refluxing. When the addition was complete, the mixture was heated under reflux for another 3 h. The mixture was cooled and quenched with 10% of aq. AcOH. Excess zinc was removed by filtration. The filtrate was treated with saturated ammonium chloride. The ether layer was separated and the aqueous phase was extracted with ether (100 ml×2). The combined extracts were washed with water, brine, dried over Na$_2$SO$_4$ and concentrated to give the product (36.4 g).

Example (C18)

4-bromo-2,6-diethyl-pyridine

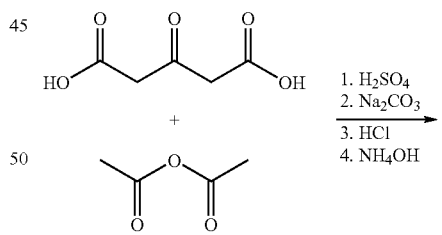

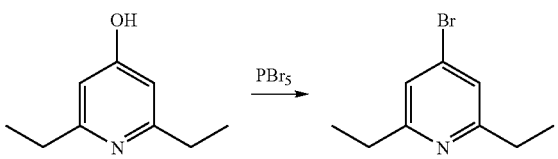

4-Bromo-2,6-diethyl-pyridine

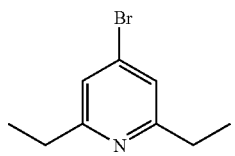

2,6-Diethyl-pyridin-4-ol from step 1 below (4 g, 26.45 mol) was dissolved in CHCl$_3$ (40 mL) and PBr$_5$ (11.43 g, 26.45 mmol). The reaction was heated at 60° C. for 1 hours and the CHCl$_3$ was evaporated. The residue was heated at 120° C. for 8 hours. After cooling, the reaction mixture was carefully added to a solution made with water (500 mL) and NaOH pellets (45 g) then extracted 3×EtOAc (100 mL). The combined organic layers were dried over sodium sulfate and concentrated to a brown oil which was purified via short plug of silica gel with 10% EtOAc/Hexanes (×1000 mL).

Step 1: 2,6-Diethyl-pyridin-4-ol

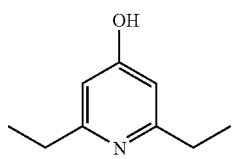

Acetonedicarboxylic acid (Aldrich, 165115) (60 g, 0.41 mol) was added rapidly to propionic anhydride (Aldrich, 240311) (170 mL, 1.3 mol) containing concentrated sulfuric acid (2 mL), and the reaction mixture was heated at 100° C. for 30 minutes with stirring. The solution was cooled rapidly in an ice-salt mixture, and just when a white solid mass was forming, the reaction was added to cold water (500 mL), stirred and filtered immediately. The product was air-dried and placed in a 3 L flask and treated with aqueous 10% sodium carbonate (600 mL). The resulting paste was stirred with a stirrer and heated at 100° C. for 30 min. Carbon dioxide evolved and a light yellow solution was obtained which was heated at 85-90° C. for further 80 min. The solution was cooled and acidified with aqueous 30% acetic acid until no more carbon dioxide was evolved. The white precipitate was filtered, washed with water, air-dried and then added to concentrate hydrochloric acid (120 mL) in a 2 L round-bottomed flask, and the mixture was heated under reflux for 4 hours. The solution was cooled in ice and neutralized by adding it to a stirred solution of sodium carbonate (about 115 g) in water (about 500 mL). The neutral solution was extracted thoroughly with EtOAc. The extract was dried and stripped of solvent to give product 2,6-Diethyl-4-pyrone as a brown oil. (Yates et al, JOC, vol. 34, No, 12, 1969, p 4046-4052)

The above product was dissolved in 28% NH$_3$ in H$_2$O (10 equivalents) and the reaction was heated at 50° C. overnight. The next morning, the solvents were completely removed to yield the title compound as a brown oil, which was submitted crude to the bromination reaction.

Example (C19)

2-chloro-5-ethoxy-4-iodo-pyridine

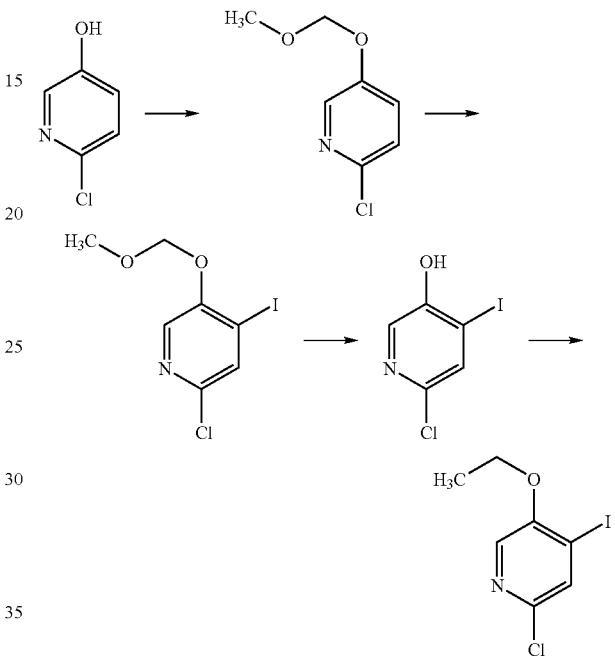

Step 1: 2-Chloro-5-methoxymethoxy-pyridine

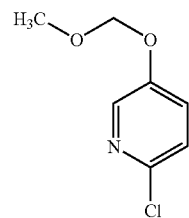

Sodium hydride (60% dispersion in oil, 1.83 g, 46.0 mmol) was suspended in anhydrous DMF (50 mL) at under N$_2$ at room temperature with stirring. A solution of 2-chloro-5-hydroxy-pyridine (5.0 g, 38.2 mmol) in anhydrous DMF (20 mL) was added dropwise over 30 min. Stirring at room temperature was continued for 1.5 hours. Chloromethyl methyl-ether (3.32 mL, 44.1 mmol) was next added neat over 20 min. Stirring was continued at room temperature for 12 hours. The mixture was partitioned between water and EtOAc. The organics were washed with brine, dried over Na2SO4, filtered and concentrated. The crude residue was chromatographed on silica gel, eluting with 20% EtOAc in Hexanes to provide the desired product as a clear oil (6.4 g, 96%). $^1$H NMR (400

MHz, CDCl$_3$): δ 8.18 (s, 1H), 7.36 (d, J=8.6 Hz, 1H), 7.23 (d, J=8.6 Hz, 1H), 5.19 (s, 2H), 3.50 (s, 3H).

Step 2:
2-Chloro-4-iodo-5-methoxymethoxy-pyridine

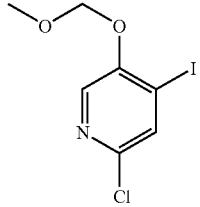

2-Chloro-5-methoxymethyl-pyridine (1 g, 5.8 mmol) was dissolved in anhydrous THF (30 mL) and cooled to −78° C. with magnetic stirring under N$_2$. Next, t-BuLi (1.7M in pentane (5.76 mL, 11.5 mmol) was added over 10 min. The resulting brown solution was allowed to stir at −78° C. for 30 min. Iodine (2.19 g, 8.6 mmol) was added as a solution in THF (15 mL) dropwise over 20 min. The mixture was stirred at −78° C. for 1 hour. The reaction was quenched at −78° C. with water and allowed to warm to room temperature. The mixture was partitioned between EtOAc and water. The aqueous was extracted with EtOAc (2×100 mL). The combined organics were washed with saturated aqueous sodium thiosulfate (2×100 mL) and brine (100 mL). The organics were dried over Na$_2$SO$_4$, filtered, and concentrated. The yellow/orange residue was triturated with hexanes to provide a yellow solid (0.88 g, 51%). $^1$H NMR (400 MHz, CDCl$_3$): δ 8.09 (s, 1H), 7.75 (s, 1H), 5.25 (s, 2H), 3.50 (s, 3H).

Step 3: 6-Chloro-4-iodo-pyridin-3-ol

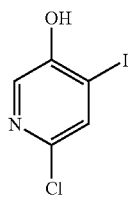

2-Chloro-4-iodo-5-methoxymethoxy-pyridine (0.8 g, 2.7 mmol) was dissolved in THF (4 mL) and 3N HCl (6 mL). The mixture was heated to 60° C. with magnetic stirring. Heating was maintained for 3 hours. The mixture was cooled to room temperature and the pH was adjusted to 7 with the slow addition of saturated aqueous sodium bicarbonate. The result was extracted with EtOAc (3×50 mL) dried over Na$_2$SO$_4$, filtered and concentrated. The solid was suspended in EtOAc and stirred for 12 hours at room temperature. The mixture was filtered and the filtrate was concentrated to yield an off white solid (0.63 g, 93%). $^1$H NMR (400 MHz, DMSO-d$_6$): δ11.10 (br s, 1H), 7.89 (s, 2H).

Step 4: 2-Chloro-5-ethoxy-4-iodo-pyridine

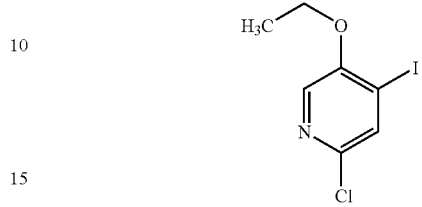

6-Chloro-4-iodo-pyridin-3-ol (0.41 g, 1.62 mmol) was dissolved in anhydrous DMF (4 mL) and stirred at room temperature. Potassium carbonate (0.67 g, 4.9 mmol) and iodoethane (0.40 mL, 4.9 mmol) were added sequentially. The mixture was heated to 60° C. and maintained for 2 hours. The mixture was cooled to room temperature and filtered. The filtrate was diluted with diethyl ether (25 mL) and washed with 20% aqueous citric acid (25 mL). The aqueous was extracted with diethyl ether (2×20 mL). The combined organics were washed with brine, dried over Na$_2$SO$_4$, filtered and concentrated. The residue was triturated with hexane resulting in a tan solid (0.42 g, 91%). $^1$H NMR (400 MHz, CDCl$_3$): δ 7.80 (s, 1H), 7.74 (s, 1H) 4.18 (q, J=7.1 Hz, 2H), 1.51 (t, J=7.1 Hz, 3H).

Example D1

Antiviral Activity

The compounds described herein were tested for activity with HCV polymerase. Recombinant HCV polymerase was tested for its ability to perform primer/template-directed transcription in assays that contained 30 mM tris-HCl pH 7.2, 10 mM MgCl$_2$, 20 mM NaCl, 1 mM Dithiothreitol (DTT), 0.05% Tween-20, 1% glycerol, 5 pmoles biotin-dG$_{12}$ (primer), 0.5 pmoles poly(rC)$_{300}$ (template), 1 μM GTP, 0.1-0.3 uCi α-$^{32}$P-GTP, and 2.5 pmoles (0.15 μg) HCV polymerase protein in a final volume of 75 μL. Reactions were initiated by addition of enzyme and incubated 30 minutes at 30° C. Reactions were stopped by addition of 33 mM EDTA, and polynucleotide products were collected by filtration through Diethylaminoethyl (DE) Filtermat papers (Wallac). Unincorporated triphosphate was removed by washing the filters with 5% dibasic sodium phosphate. The filters were counted in a Packard Tri-Lux Microbeta scintillation counter (Packard Bioscience, Meriden, Conn.). Compounds to be tested were added at various concentrations, e.g., 1 μm to 50 μm, from stocks in 10% DMSO-water (final DMSO is 1% in reaction).

IC$_{50}$ values were estimated from the primary cpm data (collected in triplicate) using the formula: cpm (I)=cpm (no inhibitor)(1−([I]/([I]+IC$_{50}$))). An IC$_{50}$ value represents the concentration (in μM) of a compound that provides 50% inhibition of polymerase-directed transcription in the above assay. A percent inhibition value is expressed for a compound where it was impractical to calculate an IC$_{50}$ value with available data. If the IC$_{50}$ estimated by the above equation was less than 200 nM, it was recalculated using the following equation, which takes into account the enzyme concentration (30 nM) in the assay: cpm(I)=cpm(no inhibitor)(1−((((I+IC$_{50}$+

30e−9)−sqrt(((I+IC$_{50}$+30e−9)$^2$)−4×30e−9×I)))/((2)(30e−9))). Curve fitting was performed using the program KaleidaGraph (Synergy Software, Reading, Pa.).

Inhibition concentration (IC$_{50}$) data as determined for exemplary compounds of the invention are presented in Table 1 below.

TABLE 1

| Example No. | IC50 (μM) |
|---|---|
| A(1) | 0.003 |
| A(101) | 0.008 |
| A(111) | 0.005 |
| A(116) | 0.005 |
| A(117) | 0.005 |
| A(12) | 0.002 |
| A(21) | 0.001 |
| A(22) | 0.004 |
| A(23) | 0.006 |
| A(13) | 0.001 |
| A(24) | 0.014 |
| A(26) | 0.004 |
| A(30) | 0.004 |
| A(31) | 0.006 |
| A(37) | 0.003 |
| A(47) | 0.005 |
| A(49) | 0.007 |
| A(50) | 0.004 |
| A(57) | 0.003 |
| A(58) | 0.001 |
| A(59) | 0.003 |
| A(74) | 0.003 |
| A(75) | 0.005 |
| A(76) | 0.005 |
| A(77) | 0.005 |
| A(78) | 0.012 |
| A(84) | 0.072 |
| A(85) | 0.083 |
| A(86) | 0.086 |
| A(89) | 0.009 |
| A(94) | 0.027 |
| A(95) | 0.04 |
| A(96) | 0.006 |
| A(97) | 0.011 |
| B(14) | 0.026 |
| B(18) | 0.17 |
| B(19) | 1.1 |
| B(20) | 0.005 |
| B(22) | 0.042 |
| B(23) | 0.14 |
| B(24) | 0.1 |
| B(25) | 0.033 |
| B(28) | 0.005 |
| A(28) | 0.002 |
| A(79) | 0.012 |
| A(103) | 0.003 |
| A(104) | 0.006 |
| A(106) | 0.004 |
| A(107) | 0.006 |
| A(108) | 0.006 |
| A(109) | 0.006 |
| A(114) | 0.005 |
| A(115) | 0.006 |
| A(118) | 0.007 |
| A(119) | 0.01 |
| A(120) | 0.007 |
| A(121) | 0.006 |
| A(125) | 0.01 |
| A(126) | 0.006 |
| A(127) | 0.13 |
| A(128) | 0.006 |
| A(129) | 0.004 |
| A(130) | 0.003 |
| A(131) | 0.002 |
| A(132) | 0.035 |
| A(133) | 0.005 |
| A(19) | 0.012 |
| A(20) | 0.009 |
| A(25) | 0.1 |
| A(29) | 0.017 |
| A(64) | |
| A(65) | 0.25 |
| A(69) | 0.015 |
| A(70) | 0.014 |
| A(71) | 0.009 |
| A(72) | 0.008 |
| A(80) | 0.022 |
| A(81) | 0.12 |
| A(82) | 0.065 |
| A(83) | 0.038 |
| A(91) | 0.16 |
| A(92) | 0.3 |
| A(98) | 0.011 |
| B(1) | 0.06 |
| B(11) | 0.26 |
| B(12) | 0.11 |
| B(32) | 0.091 |
| B(33) | 0.028 |
| B(35) | 0.01 |
| B(36) | 0.019 |
| B(37) | 0.022 |
| B(38) | 0.067 |
| B(4) | 0.006 |
| B(8) | 0.029 |
| B(9) | 0.006 |
| A(102) | 0.84 |
| A(105) | 0.25 |
| A(135) | 0.21 |
| A(37) | 6.6 |
| A(63) | 18.5 |
| A(66) | 31 |
| A(67) | 47 |
| A(68) | 12 |
| A(73) | 19% inh @ 50 uM |
| A(88) | 27 |
| A(90) | 43 |
| A(99) | 8.4 |
| B(10) | 30 |
| B(2) | 48 |
| B(3) | 6.4 |
| B(34) | 1.3 |
| B(5) | 22 |
| B(6) | 12 |
| B(7) | 7 |
| A(10) | 0.003 |
| A(11) | 0.008 |
| A(124) | 0.008 |
| A(14) | 0.008 |
| A(15) | 0.007 |
| A(16) | 0.055 |
| A(17) | 0.016 |
| A(18) | 0.17 |
| A(2) | 0.62 |
| A(27) | 0.003 |
| A(3) | 0.001 |
| A(33) | 0.007 |
| A(34) | 0.012 |
| A(35) | 0.009 |
| A(36) | 0.03 |
| A(38) | 0.003 |
| A(39) | 0.006 |
| A(4) | 0.007 |
| A(40) | 0.012 |
| A(41) | 0.008 |
| A(42) | 0.004 |
| A(43) | 0.008 |
| A(44) | 0.007 |
| A(45) | 0.014 |
| A(46) | 0.006 |
| A(48) | 0.023 |
| A(5) | 8.6 |
| A(51) | 0.003 |
| A(52) | 0.003 |
| A(53) | 0.003 |
| A(54) | 0.003 |
| A(55) | 0.002 |
| A(56) | 0.004 |

TABLE 1-continued

| Example No. | IC50 (µM) |
|---|---|
| A(6) | 0.039 |
| A(61) | 0.14 |
| A(62) | 0.06 |
| A(7) | 11.3 |
| A(8) | 0.099 |
| A(9) | 0.005 |
| B(29) | 5.2 |
| B(30) | 1.2 |
| B(31) | 0.18 |
| B(39) | 0.012 |
| A(100) | 0.079 |
| A(110) | 0.006 |
| A(112) | 0.007 |
| A(113) | 0.007 |
| A(122) | 0.004 |
| A(123) | 0.039 |
| A(134) | 0.003 |
| A(136) | 0.003 |
| A(137) | 0.3 |
| A(138) | 0.01 |
| A(139) | 0.004 |
| A(32) | 0.005 |
| A(60) | 0.003 |
| A(93) | 0.006 |
| B(13) | 0.004 |
| B(15) | 0.019 |
| B(16) | 0.053 |
| B(17) | 0.026 |
| B(21) | 0.178 |
| B(26) | 18 |
| B(27) | 10 |
| B(50) | 0.043 |
| B(51) | 0.024 |
| A(156) | 0.005 |
| A(157) | 0.01 |
| A(154) | 0.011 |
| A(155) | 0.054 |

We claim:

1. A compound of formula (4a),

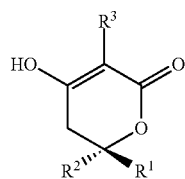

(4a)

wherein:
$R^1$ is cyclopentyl;
$R^2$ is —$(CR^6R^7)_n$(5-6 membered heterocyclic), wherein said 5-6 membered heterocyclic group is optionally substituted with at least one $R^4$ group;
$R^3$ is —$(CR^6R^7)_t(C_6-C_{10}$ aryl) or —$(CR^6R^7)_t$(4-10 membered heterocyclic), wherein each of said $C_6-C_{10}$ aryl and 4-10 membered heterocyclic moieties of said $R^3$ groups are optionally substituted with at least one $R^5$ group;
each $R^4$ is independently selected from halo, —$OR^6$, oxo, —$NR^6R^7$, —$CF_3$, —CN, —$C(O)R^6$, —$C(O)OR^6$, —$OC(O)R^6$, —$NR^6C(O)R^7$, —$NR^6C(O)OR^7$, —$NR^6C(O)NR^6R^7$, —$C(O)NR^6R^7$, —$SO_2NR^6R^7$, —$NR^6SO_2R^7$, $C_1-C_6$ alkyl, $C_2-C_6$ alkenyl, and $C_2-C_6$ alkynyl, wherein said $C_1-C_6$ alkyl, $C_2-C_6$ alkenyl, and $C_2-C_6$ alkynyl groups are optionally substituted with at least one $R^5$;
each $R^5$ is independently selected from $C_1-C_6$ alkyl, halo, —$OR^6$, —$CF_3$, and —CN;
each $R^6$ and $R^7$ is independently selected from hydrogen and $C_1-C_6$ alkyl;
n is 0, 1, 2, 3, 4, or 5; and
t is 0, 1, 2, 3, 4, or 5; or
a pharmaceutically acceptable salt thereof, with the proviso that the compound of formula (4a) is not 6-cyclopentyl-3-[(5,7-dimethyl[1,2,4]triazolo[1,5-a]pyrimidin-2-yl)methyl]-6-[2-(2-ethylpyridin-4-yl)ethyl]-4-hydroxy-5,6-dihydro-2H-pyran-2-one, 3-[(6-chloro[1,2,4]triazolo[1,5-a]pyrimidin-2-yl)methyl]-6-cyclopentyl-6-[2-(2-ethylpyridin-4-yl)ethyl]-4-hydroxy-5,6-dihydro-2H-pyran-2-one, or 6-cyclopentyl-3-[(5,7-dimethyl[1,2,4]triazolo[1,5-a]pyrimidin-2-yl)methyl]-6-[2-(5-ethylpyridin-3-yl)ethyl]-4-hydroxy-5,6-dihydro-2H-pyran-2-one.

2. A compound according to claim 1, wherein n is 1 or 2 and t is 1 or 2.

3. A compound according to claim 2, wherein n is 2.

4. A compound according to claim 3, wherein $R^3$ is —$(CR^6R^7)_t$(4-10 membered heterocyclic), optionally substituted with at least one $R^5$ group.

5. A compound according to claim 4, wherein t is 1.

6. A compound according to claim 5, wherein $R^2$ is a —$(CH_2)_2$(pyridyl), —$(CH_2)_2$(pyrazolyl), —$(CH_2)_2$(pyrrolyl), —$(CH_2)_2$(oxazolyl), —$(CH_2)_2$(thiazolyl), —$(CH_2)_2$(imidazolyl), —$(CH_2)_2$(isoxazolyl), —$(CH_2)_2$(isothiazolyl), —$(CH_2)_2$(1,2,3-triazolyl), —$(CH_2)_2$(1,3,4-triazolyl), —$(CH_2)_2$(1,3,4-thiadiazolyl), —$(CH_2)_2$(pyridazinyl), —$(CH_2)_2$(pyrimidinyl), —$(CH_2)_2$(pyrazinyl), or —$(CH_2)_2$(1,3,5-triazinyl) group, each of which is optionally substituted with at least one $R^4$ group.

7. A compound according to claim 6, wherein $R^3$ is —$(CH_2)$([1,2,4]triazolo[1,5-a]pyrimidin-2-yl), optionally substituted with at least one $R^5$ group.

8. A compound according to claim 7, wherein $R^2$ is —$(CH_2)_2$(pyridyl), —$(CH_2)_2$(pyrazolyl), or —$(CH_2)_2$(pyrrolyl), each of which is optionally substituted with at least one $R^4$ group.

9. A compound according to claim 8, wherein $R^2$ is —$(CH_2)_2$(pyridyl) or —$(CH_2)_2$(pyrazolyl), each of which is optionally substituted with at least one $R^4$ group.

10. A compound according to claim 9, wherein:
$R^2$ is —$(CH_2)_2$(pyridyl) or —$(CH_2)_2$(pyrazolyl), each of which is optionally substituted with at least one substituent selected from halo, $C_1-C_6$ alkyl, —$OR^6$, and —$NR^6R^7$; and
$R^3$ is —$(CH_2)$([1,2,4]triazolo[1,5-a]pyrimidin-2-yl), optionally substituted with at least one substituent selected from halo and $C_1-C_6$ alkyl.

11. A compound according to claim 10, wherein $R^2$ is —$(CH_2)_2$(pyridyl) optionally substituted with at least one substituent selected from halo, $C_1-C_6$ alkyl, —$OR^6$, and —$NR^6R^7$.

12. A pharmaceutical composition, comprising a therapeutically effective amount of a compound according to claim 1 and a pharmaceutically acceptable carrier.

* * * * *